US011793841B2

(12) United States Patent
Toledo et al.

(10) Patent No.: US 11,793,841 B2
(45) **Date of Patent: *Oct. 24, 2023**

(54) MICROBIAL COMPOSITIONS AND METHODS FOR TREATING TYPE 2 DIABETES, OBESITY, AND METABOLIC SYNDROME

(71) Applicant: Solarea Bio, Inc., Cambridge, MA (US)

(72) Inventors: Gerardo V. Toledo, Hopkinton, MA (US); Tracy Mincer, Jupiter, FL (US); Jahir Mauricio Gutierrez Bugarin, Montreal (CA); Jillian DeWalt, Salem, NC (US); Eric Schott, Charlestown, MA (US); Maria Juliana Soto Giron, Cambridge, MA (US)

(73) Assignee: SOLAREA BIO, INC., Cambridge, MA (US)

( * ) Notice: Subject to any disclaimer, the term of this patent is extended or adjusted under 35 U.S.C. 154(b) by 156 days.

This patent is subject to a terminal disclaimer.

(21) Appl. No.: 16/826,078

(22) Filed: Mar. 20, 2020

(65) Prior Publication Data

US 2020/0376049 A1 Dec. 3, 2020

Related U.S. Application Data

(63) Continuation of application No. 16/235,858, filed on Dec. 28, 2018, now Pat. No. 10,596,209, which is a continuation of application No. PCT/US2018/066088, filed on Dec. 17, 2018.

(60) Provisional application No. 62/727,497, filed on Sep. 5, 2018, provisional application No. 62/607,149, filed on Dec. 18, 2017, provisional application No. 62/599,647, filed on Dec. 15, 2017.

(51) Int. Cl.

| | |
|---|---|
| ***A61P 3/04*** | (2006.01) |
| ***A61P 3/10*** | (2006.01) |
| ***A61K 35/74*** | (2015.01) |
| ***A61K 35/741*** | (2015.01) |
| ***A23L 29/00*** | (2016.01) |
| ***A61K 35/747*** | (2015.01) |
| ***A61K 45/06*** | (2006.01) |

(52) U.S. Cl.

CPC .......... *A61K 35/747* (2013.01); *A23L 29/065* (2016.08); *A61K 35/74* (2013.01); *A61K 35/741* (2013.01); *A61K 45/06* (2013.01); *A61P 3/04* (2018.01); *A61P 3/10* (2018.01)

(58) Field of Classification Search

CPC .... A61K 35/74; A61K 35/747; A61K 35/741; A61K 45/06; A61K 2300/00; A61P 3/10; A61P 3/04; A23L 29/065

See application file for complete search history.

(56) References Cited

U.S. PATENT DOCUMENTS

| | | | |
|---|---|---|---|
| 3,048,526 | A | 8/1962 | Boswell |
| 3,108,046 | A | 10/1963 | Harbit |
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,478,822 | A | 10/1984 | Haslam et al. |
| 4,532,126 | A | 7/1985 | Ebert et al. |
| 4,625,494 | A | 12/1986 | Iwatschenko |
| 4,671,953 | A | 6/1987 | Stanley et al. |
| 4,786,505 | A | 11/1988 | Lovgren et al. |
| 4,800,083 | A | 1/1989 | Hom et al. |
| 4,904,479 | A | 2/1990 | Illum |
| 4,919,939 | A | 4/1990 | Baker |
| 4,935,243 | A | 6/1990 | Borkan et al. |
| 4,950,484 | A | 8/1990 | Olthoff et al. |
| 5,013,726 | A | 5/1991 | Ivy et al. |
| 5,059,595 | A | 10/1991 | Grazie |

(Continued)

FOREIGN PATENT DOCUMENTS

| | | |
|---|---|---|
| AU | 2008231930 | 10/2008 |
| EP | 1495109 | 12/2005 |

(Continued)

OTHER PUBLICATIONS

Abuajah et al (2015) Functional components and medicinal properties of food: a review. J Food Sci Technol 52(5): 2522-2529.

(Continued)

*Primary Examiner* — Satyendra K Singh
(74) *Attorney, Agent, or Firm* — Goodwin Procter LLP

(57) ABSTRACT

The present invention relates to the identification of a group of microorganisms, which are relatively abundant in the microbial communities associated with fruits and vegetables typically consumed raw and therefore transient or permanent members of the human microbiota. The consumption of mixtures of these microbes at relevant doses will produce a beneficial effect in the host by reducing the propensity to diabetes, obesity and metabolic syndrome mediated in part by production of short chain fatty acids to enhance colonic butyrate production. Therapeutic methods of the invention involve the use of live microorganisms or metabolites derived from said microorganisms to establish a microbial composition in the mammalian host that will improve significantly the ability to control weight, reduce the onset of diabetes, obesity and metabolic syndrome, and improve overall health.

10 Claims, 23 Drawing Sheets

Specification includes a Sequence Listing.

(56) References Cited

U.S. PATENT DOCUMENTS

| | | | |
|---|---|---|---|
| 5,073,543 A | 12/1991 | Marshall et al. | |
| 5,120,548 A | 6/1992 | McClelland et al. | |
| 5,225,202 A | 7/1993 | Hodges et al. | |
| 5,354,556 A | 10/1994 | Sparks et al. | |
| 5,591,767 A | 1/1997 | Mohr et al. | |
| 5,610,184 A | 3/1997 | Shahinian et al. | |
| 5,639,476 A | 6/1997 | Oshlack et al. | |
| 5,674,533 A | 10/1997 | Santus et al. | |
| 5,733,556 A | 3/1998 | Schrier et al. | |
| 5,733,575 A | 3/1998 | Mehra et al. | |
| 5,837,284 A | 11/1998 | Mehta | |
| 5,871,776 A | 2/1999 | Mehta | |
| 5,902,632 A | 5/1999 | Mehta | |
| 6,139,875 A | 10/2000 | Adams et al. | |
| 6,258,380 B1 | 7/2001 | Overholt | |
| 6,420,473 B1 | 7/2002 | Chittamuru et al. | |
| 6,455,052 B1 | 9/2002 | Marcussen et al. | |
| 6,482,435 B1 | 11/2002 | Stratton et al. | |
| 6,544,510 B2 | 4/2003 | Olshenitsk et al. | |
| 6,569,457 B2 | 5/2003 | Ullah et al. | |
| 6,572,871 B1 | 6/2003 | Church et al. | |
| 6,750,331 B1 | 6/2004 | Takaichi et al. | |
| 7,214,370 B2 | 5/2007 | Naidu et al. | |
| 8,318,151 B2 | 11/2012 | Darimont-Nicolau et al. | |
| 8,460,726 B2 | 6/2013 | Harel et al. | |
| 8,802,158 B2 | 8/2014 | Boileau et al. | |
| 8,871,266 B2 | 10/2014 | Sanguansri et al. | |
| 8,877,178 B2 | 11/2014 | Boileau et al. | |
| 9,040,101 B2 | 5/2015 | Heiman et al. | |
| 9,095,604 B2 | 8/2015 | Ikegami et al. | |
| 9,173,910 B2 | 11/2015 | Kaplan et al. | |
| 9,301,983 B2 | 4/2016 | Huang et al. | |
| 9,371,510 B2 | 6/2016 | Moore et al. | |
| 9,386,793 B2 | 7/2016 | Blaser et al. | |
| 9,487,764 B2 | 11/2016 | Falb et al. | |
| 9,549,955 B2 | 1/2017 | Rittmann et al. | |
| 9,636,367 B2 | 5/2017 | Garcia-Rodenas et al. | |
| 9,937,211 B2 | 4/2018 | Kelly et al. | |
| 10,064,895 B2 | 9/2018 | Vincent et al. | |
| 2004/0213828 A1 | 10/2004 | Smith | |
| 2005/0147710 A1 | 7/2005 | Teckoe et al. | |
| 2010/0172874 A1 | 7/2010 | Turnbaugh et al. | |
| 2011/0177976 A1 | 7/2011 | Gordon et al. | |
| 2011/0111094 A1 | 11/2011 | Lavermicocca et al. | |
| 2012/0015075 A1 | 1/2012 | Davis et al. | |
| 2012/0040387 A1 | 2/2012 | Matsuoka | |
| 2014/0044858 A1 | 2/2014 | Quevedo | |
| 2014/0065209 A1 | 3/2014 | Putaala et al. | |
| 2014/0147425 A1* | 5/2014 | Henn et al. ............ | A61K 35/74 424/93.41 |
| 2014/0179726 A1 | 6/2014 | Bajaj et al. | |
| 2014/0314719 A1 | 10/2014 | Smith et al. | |
| 2015/0126463 A1 | 5/2015 | Hsiao et al. | |
| 2015/0259728 A1 | 9/2015 | Cutcliffe et al. | |
| 2015/0366941 A1 | 12/2015 | Menear et al. | |
| 2016/0081309 A1 | 3/2016 | Newton et al. | |
| 2016/0199424 A1 | 7/2016 | Berry et al. | |
| 2016/0206666 A1 | 7/2016 | Falb et al. | |
| 2016/0235792 A1 | 8/2016 | Berry et al. | |
| 2016/0263166 A1 | 9/2016 | Elinav et al. | |
| 2016/0271189 A1 | 9/2016 | Cutcliffe et al. | |
| 2016/0302464 A1 | 10/2016 | Egli et al. | |
| 2017/0326190 A1 | 11/2017 | Ansell et al. | |

FOREIGN PATENT DOCUMENTS

| | | | |
|---|---|---|---|
| EP | 1794283 | 10/2016 | |
| WO | WO 2004/080200 | 9/2004 | |
| WO | WO 2010/099617 | 9/2010 | |
| WO | WO 2012/098254 | 7/2012 | |
| WO | WO 2012/170047 | 12/2012 | |
| WO | WO 2013/067146 | 10/2013 | |
| WO | WO 2013/176774 | 11/2013 | |
| WO | WO 2014/068338 | 8/2014 | |
| WO | 2014/145958 A2 | 9/2014 | |
| WO | WO-2015/172191 A1 | 11/2015 | |
| WO | WO 2015/177246 | 11/2015 | |
| WO | WO 2015200842 A1 * | 12/2015 | .............. A23L 1/29 |
| WO | WO 2016/065075 | 4/2016 | |
| WO | WO 2016/086205 | 6/2016 | |
| WO | WO 2016/124940 | 8/2016 | |
| WO | WO-2017/160711 A1 | 9/2017 | |

OTHER PUBLICATIONS

Alcock et al (2014) Is eating behavior manipulated by the gastrointestinal microbiota? Evolutionary pressures and potential mechanisms. Bioessays 36: 940-949.
Allgeier, RJ et al (1929) A colorimetric method for the determination of butyric acid. J Bacteriol 17(2): 79-87.
Aron-Wisnewsky, J et al (2012) The importance of the gut microbiota after bariatric surgery. Nature 9(10): 590-598.
Arumugam et al (2011) Enterotypes of the human gut microbiome. Nature 473(7346): 174-180.
Backhed et al (2004) The Gut microbiota as an environmental factor that regulates fat storage. PNAS 101(44): 15718-15723.
Backhed et al (2007) Mechanisms underlying the resistance to diet-induced obesity in germ-free mice. PNAS 104(3): 979-984.
Bahr et al (2015) Risperidone-induced weight gain is mediated through shifts in the gut microbiome and suppression of energy expenditure. EBioMedicine 2: 1725-1734.
Bai et al (2016) Response of gut microbiota and inflammatory status to bitter melon (*Momordica charantia* L.) in high fat diet induced obese rats. J Ethnopharmacol 194: 717-726.
Bakker-Zierikzee et al (2005) Effects of infant formula containing a mixture of galacto- and fructo-oligosaccharides or viable Bifidobacterium animalis on the intestinal microflora during the first 4 months of life. Br J Nutr 94: 783-790.
Basu, A et al (2010) Blueberries decrease cardiovascular risk factors in obese men and women with metabolic syndrome. J Nutr 140(9):1582-1587.
Berg.G et al (2015) The Edible plant microbiome: importance and health issues. In: Lugtenberg B. (eds) Principles of plant-microbe interactions. Springer, Cham.
Bernini et al (2016) Beneficial effects of Bifidobacterium lactis on lipid profile and cytokines in patients with metabolic syndrome. Nutrition 32: 716-719.
Bleau et al (2015) Crosstalk between intestinal microbiota, adipose tissue and skeletal muscle as an early event in systemic low-grade inflammation and the development of obesity and diabetes. Diabetes Metab Res Rev 31 (6): 545-61.
Boden, G (2011) Obesity, Insulin Resistance and Free Fatty Acids. Curr Opin Endocrinol Diabetes Obes 18(2): 139-143.
Brahe, LK et al (2013) Is butyrate the link between diet, intestinal microbiota and obesity-related metabolic diseases? Obes Rev 14: 950-959.
Bron et al (2012) Emerging molecular insights into the interaction between probiotics and the host intestinal mucosa. Nat Rev Microbiol 10: 66-78.
Brunkwell, L and Orho-Melander, M. (2017) The gut microbiome as a target for prevention and treatment of hyperglycaemia in type 2 diabetes: from current human evidence to future possibilities. Diabetalogia 60: 943-951.
Camacho, L et al (2015) Metformin in breast cancer-an evolving mystery. Breast Cancer Res 17(88): 1-4.
Campbell, T.C. et al., "The China Study: The most comprehensive study of nutrition ever conducted and startling implications for diet, weight loss, and long term health," Benbella, 2006, 1-425.
Cani et al (2006) Improvement of glucose tolerance and hepatic insulin sensitivity by oligofructose requires a functional glucagon-like peptide 1 receptor. Diabetes 55:1484-1490.
Cani et al (2007) Metabolic endotoxemia initiates obesity and insulin resistance. Diabetes 56:1761-1772.
Cani et al (2007) Selective increases of bifidobacteria in gut microflora improve high-fat-diet-induced diabetes in mice through a mechanism associated with endotoxaemia. Diabetologica 50: 2374-2383.

(56) References Cited

OTHER PUBLICATIONS

Cani et al (2008) Changes in gut microbiota control metabolic endotoxemia-induced inflammation in high-fat diet-induced obesity and diabetes in mice. Diabetes 57:1470-1481.
Chambers, et al (2015) Effects of targeted delivery of propionate to the human colon on appetite regulation, body weight maintenance and adiposity in overweight adults. Gut 64: 1744-1754.
Chanclud, E and Lacombe, B (2017) Plant hormones: key players in gut microbiota and human diseases? Trends Plant Sci 22(9): 754-758.
Chaudhury et al (2017) Clinical review of antidiabetic drugs: implications for type 2 diabetes mellitus management. Front endocrinol8(6): 1-12.
Chen et al (2015) Metabolism of fructooligosaccharides in Lactobacillus plantarum ST-III via differential gene transcription and alteration of cell membrane fluidity. Appl Environ Microbiol 81(22): 7697-7707.
Cockburn, DW and Koropatkin, NM (2016) Polysaccharide degradation by the intestinal microbiota and its influence on human health and disease. J Mol Biol 428: 3230-3252.
Codella, R et al (2018) Exercise has the guts: how physical activity may positively modulate gut microbiota in chronic and immune-based diseases. Digest Liv Dis 50: 331-341.
Coyle, C et al (2016) Metformin as an adjuvant treatment for cancer: a systematic review and meta analysis. Ann Onc 27:2184-2195.
Dalby et al (2017) Dietary uncoupling of gut microbiota and energy harvesting from obesity and glucose tolerance in mice. Cell Reports 21: 1521-1533.
Das, S (2013) Prevention of Diabetes—a historical note. IJHS 48.4: 625-642.
David, LA et al (2014) Diet rapidly and reproducibly alters the human gut microbiome. Nature 505: 559-563.
Davies et al (2017) Effect of an oral semaglutide compared with placebo and subcutaneous semaglutide on glycemic control in patients with type 2 diabetes. JAMA 318(15):1460-1470.
De Jesus Raposo et al (2016) Emergent Sources of prebiotics: seaweed and microalgae. Mar. Drugs 14(2): doi: 10.3390/md14020027.
De la Cuesta-Zuluaga (2017) Metformin is associated with higher relative abundance of mucin-degrading Akkermansia muciniphila and several short chain fatty acid-producig microbiota in the gut. Diabetes Care 40:54-62.
De Vadder, F et al (2016) Microbiota-produced succinate improves glucose homeostasis via intestinal gluconeogenesis. Cell Metab 24: 151-157.
Delzenne, NM (2015) Gut microorganisms as promising targets for the management of type 2 diabetes. Diabetalogia 58: 2206-2217.
Derrien, M and van Hylckama Vlieg, JET (2015) Fate, activity, and impact of ingested bacteria within the human gut microbiota. Trends in Microbiol 23(6): 354-366.
Devaraj, S et al (2013) The Human gut microbiome and body metabolism: implications for obesity and diabetes. Clin Chem 59(4): 617-628.
Di Francesco et al (2018) a time to fast. Science 362: 770-775.
Drew, L (2016) Reseeding the gut. Nature 540:s109-s112.
Duncan, SH et al (2004) Contribution of acetate to butyrate formation by human faecal bacteria. Br J Nutr 91: 915-923.
Ericsson et al (2017) Variable colonization after reciprocal fecal microbiota transfer between mice with low and high richness microbiota. Front Microbiol 8(196): 1-13.
Everard et al (2013) Cross-talk between Akkermansia muciniphila and intestinal epithelium controls diet-induced obesity. PNAS 11(22):9066-9071.
Everard et al (2014) Microbiome of prebiotic-treated mice reveals novel targets involved in host response during obesity. ISME 8:2116-2130.
Everard, A and Cani, P (2013) Diabetes, obesity and gut microbiota. Best Pract Res Clin Gastroenterol 27: 73-83.
Famouri et al (2017) Effects of probiotics on nonalcoholic fatty liver disease in obese children and adolescents. JPGN 64(3): 413-417.
Fang et al (2015) Intestinal FXR agonism promotes adipose tissue browning and reduces obesity and insulin resistance. Nature 21(2):159-167.
Forslund et al (2015) Corrigendum: Disentangling type 2 diabetes and metformin treatment signatures in the human gut microbiota. Nature 528: 262-266.
Forslund et al (2015) Disentangling type 2 diabetes and metformin treatment signatures in the human gut microbiota. Nature 528(7581): 262-266.
Frost, G et al (2014) The short-chain fatty acid acetate reduces appetite via a central homeostatic mechanism. Nat Commun. 5(3611): 1-11.
Garidou et al (2015) The Gut microbiota regulates intestinal CD4 T cells expressing RORgammat and controls metabolic disease. Cell metab 22:100-112.
Gentile and Weir (2018) The gut microbiota at the intersection of diet and human health. Science 362: 776-780.
Gibson, G and Roberfroid M (1995) Dietary modulation of the human colonic microbiota: introducing the concept of prebiotics. J Nutr 125(6):1401-1412.
Gonzalez-Garcia, RA et al (2017) Microbial propionic acid production. Fermentation 3(21): 1-20.
Graessler et al (2013) Metagenomic sequencing of the human gut microbiome before and after bariatric surgery in obese patients with type 2 diabetes: correlation with inflammatory and metabolic parameteres. Pharmacogenetics J 13: 514-522.
Gu et al (2017) Analyses of gut microbiota and plasma bile acids enable stratification of patients for antidiabetic treatment. Nature Commun 8:1785.
Guo et al (2017) Secretions of Bifidobacterium infantis and Lactobacillus acidophilus protect intestinal epithelial barrier function. JPGN 64(3): 404-412.
Hacquard et al (2015) Microbiota and host nutrition across plant and animal kingdoms. Cell host & microbe 17: 603-616.
Harley and Karp (2012) Obesity and the gut microbiome: striving for causality. Mol Metab 1: 21-31.
Hehemann et al (2010) Transfer of carbohydrate-active enzymes from marine bacteria to Japanese gut microbiota. Nature 464: 908-914.
Heineken, A et al (2013) Systems-level characterization of a host-microbe metabolic symbiosis in the mammalian gut. Gut microbes 4(1):28-40.
Henao-Mejia et al (2012) Inflammasome-mediated dysbiosis regulates progression of NAFLD and obesity. Nature 482 (7384): 179-185.
Hildebrandt et al (2009) High fat diet determines the composition of the murine gut microbiome independently of obesity. Gastroenterology 137(5): 1716.
Holmes, AJ et al (2017) Diet-Microbiome interactions in health are controlled by intestinal nitrogen source constraints. Cell Metab 25: 140-151.
Hooper et al (2012) Interactions between the microbiota and the immune system. Science 336(6086): 1268-1273.
Ilhan, ZE et al (2017) Distinctive microbiomes and metabolites linked with weight loss after gastric bypass, but not gastric banding. ISME J 11 (9): 2047-2058.
Imaoka et al (2008) Anti-inflammatory activity of probiotic Bifidobacterium: enhancement of IL-10 production in peripheral blood mononuclear cells from ulcerative colitis patients and inhibition of IL-8 secretion in HT-29 cells. World J Gastroenterol 14(16): 2511-2516.
Jackson, CR et al (2013) Culture dependent and independent analysis of bacterial communities associated with commercial salad leaf vegetables. BMC Microbiol 13 (274): 1-12.
Jackson, CR et al (2015) Emerging perspectives on the natural microbiome of fresh produce vegetables. Agriculture 5: 170-187.
Jahangir, et al (2017) Type 2 diabetes current and future medications: a short review. Int J Pharm Pharmacol 1(1): 101.
Jain, C et al (2018) High throughput ANI analysis of 90K prokaryotic genomes reveals clear species boundaries. Nat Commun 9(5114): 1-8.

(56) References Cited

OTHER PUBLICATIONS

Jain, M. et al. "Nanopore sequencing and assembly of a human genome with ultra-long reads," Nature Biotechnology, 2018, vol. 36, No. 4, p. 338.
Jarvis, KG et al (2018) Microbiomes associated with foods from plant and animal sources. Front Microbiol 9:2540.
Jia, B et al (2017) CARD 2017: expansion and model-centric curation of the comprehensive antibiotic resistance database. Nucleic Acids Res 45: D566-D573.
Kaluzna-Czaplinska et al (2017) Is there a relationship between intestinal microbiota, dietary compounds, and obesity? Trends Food Sci Technol 70: 105-113.
Kapitza et al (2017) Effects of semaglutide on beta cell function and glycaemic control in particpants with type 2 diabetes: a randomized , double-blind , placebo-controlled trial. Diabetalogia 60: 1390-1399.
Kaplan, H and Hutkins, RW (2000) Fermentation of fructooligosaccharides by lactic acid bacteria and bifidobacteria. Appl Environ Microbiol 66(6): 2682-2684.
Kasubuchi, M et al (2015) Dietary gut microbial metabolites, short-chain fatty acids, and host metabolic regulation. Nutrients 7: 2839-2849.
Kau et al (2011) Human nutrition, the gut microbiome and the immune system. Nature 474: 327-336.
Kimura et al (2013) The Gut microbiota suppresses insulin-mediated fat accumulation via the short-chain fatty acid receptor GPR43. Nat Commun 4(1829): 1-12.
Kishida et al (2017) Effect of miglitol on the suppression of nonalcoholic steatohepatitis development and improvement of thegut environment in a rodent model. J Gastroenterol 52(11): 1180-1191.
Koh et al (2016) From Dietary fiber to host physiology: short chain fatty acids as key bacterial metabolites. Cell 165: 1332-1345.
Kreznar et al (2017) Host genotype and gut microbiome modulate insulin secretion and diet-induced metabolic phenotypes. Cell Rep 18: 1739-1750.
Lang, JM et al (2014) The microbes we eat: abundance and taxonomy of microbes consumed in a day's worth of meals for three diet types. PeerJ 2:e659; doi 10.7717/peerj.659.
Lee and Hase (2014) Gut microbiota-generated metabolites in animal health and disease. Nat Chem Biol 10:416-424.
Lee, H and Ko, G (2014) Effect of Metformin on Metabolic Improvement and Gut Microbiota. Appl Environ Microbiol 80 (19): 59355943.
Lee, S et al (2018) Blueberry supplementation influences the gut microbiota, inflammation, and insulin resistance in high-fat-diet-fed rats. J Nutr 148(2): 209-219.
Ley et al (2005) Obesity alters gut microbial ecology. PNAS 102(31): 11070-11075.
Li et al (2011) Metabolic surgery profoundly influences gut microbial-host metabolic crosstalk. Gut 60(9): 1214-1223.
Li et al (2017) Butyrate reduces appetite and activates brown adipose tissue via the gut-brain neural circuit. Gut 0:1-11.
Li et al (2017) Intermittent fasting promotes white adipose browning and decreases obesity by shaping the gut microbiota. Cell Metab 26: 672-685.
Lin, H et al (2012) Butyrate and propionate protect against diet-induced obesity and regulate gut hormones via free fatty acid receptor 3-independent mechanisms. PLoS One 7(4): 1-9.
Lin, H et al (2016) Correlations of fecal metabonomic and microbiomic changes induced by high-fat diet in the pre-obesity state. Sci Rep 6(21618):1-14.
Liu, B et al (2019) VFDB 2019: a comparative pathogenomic platform with an interactive web interface. Nucleic Acids Res 47: D687-D692.
Louis, P and Flint, HJ (2017) Formation of propionate and butyrate by the human colonic microbiota. Environ Microbiol. 19(1): 29-41.
Lu, Y et al (2016) Short chain fatty acids prevent high-gat-diet-induced obesity in mice by regulating G protein coupled receptors and gut microbiota. Sci Rep. 6(37589): 1-13.
Lyu, M et al (2017) Balancing herbal medicine and functional food for prevention and treatment of cardiometabolic diseases through modulating gut microbiota. Front Microbiol 8(2146): 1-21.
Madiraju, A et al (2014) Metformin suppresses gluconeogenesis by inhibiting mitochondrial glycerophosphate dehydrogenase. Nature 510: 542-546.
Magnusdottir, S et al (2017) Generation of genome-scale metabolic reconstructions for 773 members of the human gut microbiota. Nature biotechnol 35(1):81-89.
Maier, L et al (2018) Extensive impact of non-antibiotic drugs on human gut bacteria. Nature 000: 1 -6.
Martinez-Lopez et al. (2017) System-wide benefits of intermeal fasting by autophagy. Cell Metab 26:856-871.
McCabe, L et al (2018) Exercise prevents high fat diet induced bone loss, marrow adiposity and dysbiosis in male mice. Bone https://doi.org/10.1016/j.bone.2018.03.024.
Meng, D et al (2016) Anti-inflammatory effects of Bifidobacterium longum subsp infantis secretions on fetal human enterocytes are mediated by TLR-4 receptors. Am J Physiol Gastrointest Liver Physiol 311:G744-G753.
Milani, C et al (2015) Bifidobacteria exhibit social behavior through carbohydrate resource sharing in the gut. Sci Rep 5 (15782): 1-14.
Montandon, S and Jornayvaz, F (2017) Effects of antidiabetic drugs on gut microbiota composition. Genes 8(250): 1-12.
Morrison, D and Preston, T (2016) Formation of short chain fatty acids by the gut microbiota and their impact on human metabolism. Gut Microbes 7(3):189-200.
Moslehi-Jenabian, S et al (2010) Beneficial effects of probiotic and food borne yeasts on human health. Nutrients 2: 449-473.
Napolitano et al (2014) Novel Gut-Based Pharmacology of Metformin in Patients with Type 2 Diabetes Mellitus. PLoS One 9(7): e100778.
Ni et al (2015) A Molecular-level landscape of diet-gut microbiome interactions: toward dietary interventions targeting bacterial genes. mBio 6(6): e01263-15.
Okeke, F et al (2014) The role of the gut microbiome in the pathogenesis and treatment of obesity. GAHMJ 3(3): 44-57.
Olar, R et al (2010) Prospects for new antimicrobials based on N,N-dimethylbiguanide complexes as effective agents on both planktonic and adhered strains. Eur J Med Chem 45: 2868-2875.
Olson, O et al (2017) Obesity and the tumor microenvironment. Science 358(6367): 1130-1131.
Ozcan, E et al (2017) A Human gut commensal ferments cranberry carbohydrates to produce formate. Appl Environ Microbiol 83(17): 1-16.
Palacios, T et al (2017) The effect of a novel probiotic on metabolic biomarkers in adults with prediabetes and recently diagnosed type 2 diabetes mellitus: study protocol for a randomized controlled trial. Trials 18(7): 1-8.
Parekh, P et al (2014) The role and influence of gut microbiota in pathogenesis and management of obesity and metabolic syndrome. Front Endocrinol 5(47):1-7.
Perry, R et al (2016) Acetate mediates a microbiome-brain-beta-cell axis to promote metabolic syndrome. Nature 534: 213-217.
Plovier, H et al (2017) A purified membrane protein from Akkermansia muciniphila or the pasteurized bacterium improves metabolism in obese and diabetic mice. Nat. Med. 23(1): 107-113.
Postler, TS and Ghosh, S (2017) Understanding the holobiont: how microbial metabolites affect human health and shape the immune system. Cell 26: 110-130.
Pryor, R and Cabriero, F (2015) Repurposing metformin: an old drug with new tricks in its binding pockets. Biochem J 471: 307-322.
Psichas et al (2015) The short chain fatty acid propionate stimulates GLP-1 and PYY secretion via free fatty acid receptor 2 in rodents. Int J Obes 39: 424-429.
Puertollano, E et al (2014) Biological significance of short-chain fatty acid metabolism by the intestinal microbiome. Curr Opin Clin Nutr Metab Care 17(2): 139-144.
Pyra, K et al (2012) Prebiotic fiber increases hepatic acetyl CoA carboxylase phosphorylation and suppresses glucose-dependent insulinotropic polypeptide secretion more effectively when used with metformin in obese rats. J Nutr 142(2): 213-220.

(56) References Cited

OTHER PUBLICATIONS

Qin et al (2010) A human gut microbial gene catalogue established by metagenomic sequencing. Nature 464: 59-65.
Ramirez-Puebla et al (2013) Gut and Root Microbiota Commonalities. App Environ Microbiol 79(1): 2-9.
Rastall RA and Gibson GR (2015) Recent developments in prebiotics to selectively impact beneficial microbes and promote intestinal health. Curr Opin Biotechnol 32: 42-46.
Rastogi, G et al (2012) Leaf microbiota in an agroecosystem: spatiotemporal variation in bacterial community composition on field-grown lettuce. ISME J 6: 1812-1822.
Ravussin et al (2012) Responses of gut microbiota to diet composition and weight loss in lean and obese mice. Obesity 20(4): 738-747.
Reichardt, N et al (2014) Phylogenetic distribution of three pathways for propionate production within the human gut microbiota. ISME J 8:1323-1335.
Reichold et al (2014) Bifidobacterium adolescentis protects from the development of nonalcoholic steatohepatitis in a mouse model. J Nutr Biochem 25: 118-125.
Rios-Covain, D et al (2015) Enhanced butyrate formation by cross-feeding between Faecalibacterium prausnitzii and Bifidobacterium adolescentis. FEMS Microbiol Lett 362(21): 1-7.
Rodriguez-R, LM and Konstantinidis, KT (2016) The enveomics collection: a toolbox for specialized analyses of microbial genomes and metagenomes. PeerJ Preprints 4: e1900v1.
Rosario, D et al (2018) Gut microbiota dysbiosis in metformin-treated type 2 diabetes patients using genome-scale metabolic modeling. Front Physiol 9: 775.
Rosenbaum, M (2015) The Gut microbiota in human energy homeostasis and obesity. Trends Endocrinol Metab 26(9): 493-501.
Rosenberg and Zilber-Rosenberg (2016) Interaction between the microbiome and diet: the hologenome concept. J Nutr Food Sci 6(5): 1000545.
Rothschild, D et al (2018) Environment dominates over host genetics in shaping human gut microbiota. Nature 000: 1-6.
Round and Mazmanian (2009) The gut microbiota shapes intestinal immune responses during health and disease. Nat Rev Immunol 9: 313-324.
Saltiel, AR (2016) New therapeutic approaches for the treatment of obesity. Sci Transl Med 8 (323): 1-12.
Saltiel, AR and Olefsky JM (2017) Inflammatory mechanisms linking obesity and metabolic disease. J Clin Invest 127 (1): 1-4.
Sam, QH et al (2017) The Fungal mycobiome and its interaction with gut bacteria in the host. Int J Mol Sci 18(330): 1-11.
Samah, S et al (2016) Probiotics for the management of type 2 diabetes mellitus: a systematic review and meta-analysis. Diabetes res clin pract 118: 172-182.
Samuel and Gordon (2006) A Humanized gnotobiotic mouse model of host-archaeal-bacteria mutualism. PNAS 103 (26): 10011-10016.
Samuel et al (2008) Effects of the gut microbiota on host adiposity are modulated by the short-chain fatty-acid binding G protein-coupled receptor, Gpr41. PNAS 105(43): 16767-16772.
Sawin, EA (2015) Glycomacropeptide is a prebiotic that reduces Desulfovibrio bacteria, increases cecal short-chain fatty acids, and is anti-inflammatory in mice. Am J Physiol Gastrointest Liver Physiol 309: G590-G601.
Schirmer et al (2016) Linking the human gut microbiome to inflammatory cytokine production capacity. Cell 167(4): 1125-1136.
Schoch, C.L. et al., "Nuclear ribosomal internal transcribed spacer (ITS) region as a universal DNA barcode marker for Fungi," Proceedings of the National Academy of Sciences, 2012, vol. 109, No. 16, pp. 6241-6246.
Schroeder, B and Backhed, F (2016) Signals from the gut microbiota to distant organs in physiology and disease. Nat Med 22(10): 1079-1089.
Schroeder, B et al (2018) Bifidobacteria or Fiber protects against diet-induced microbiota-mediated colonic mucus deterioration. Cell host microbe 23:27-40.
Scott, KP et al (2015) Manipulating the gut microbiota to maintain health and treat disease. Micro Ecol Health Dis 26 (25877): 1-10.
Serino et al (2012) Metabolic adaptation to a high-fat diet is associated with a change in the gut microbiota. Gut 61: 543-553.
Sheikhi, A (2016) Probiotic yogurt culture Bifidobacterium animalis subsp lactis BB-12 and Lactobacillus acidophilus LA-5 modulate the cytokine secretion by peripheral blood mononuclear cells from patients with ulcerative colitis. Drug Res 66: 300-305.
Shin et al (2014) An increase in the *Akkermansia* spp population induced by metformin treatment improves glucose homeostasis in diet-induced obese mice. Gut 63: 727-735.
Shoaie, S et al (2015) Quantifying diet-induced metabolic changes of the human gut microbiome. Cell metab 22: 320-331.
Simpson, HL and Campbell, BJ (2015) Review article: dietary fibre-microbiota interactions. Aliment Pharmacol Ther 42: 158-179.
Singer and Lumeng (2017) The initiation of metabolic inflammation in childhood obesity. J Clin Invest 127(1):65-73.
Singh et al (2018) Dysregulated microbial fermentation of soluble fiber induces cholestatic liver cancer. Cell 175: 679-694.
Slavin, J (2013) Fiber and Prebiotics: Mechanisms and health benefits. Nutrients 5: 1417-1435.
Smith, IM et al (2014) Yeast modulation of human dendritic cell cytokine secretion: an in vitro study. PLoS One 9(5): 1-14.
Sonnenburg, JL and Backhed, F (2016) Diet-microbiota interactions as moderators of human metabolism. Nature 535: 56-64.
Strorelli et al (2013) Metformin, microbes, and aging. Cell Metab 17: 809-811.
Stull, AJ (2016) Blueberries' impact on insulin resistance and glucose intolerance. Antioxidants 5(44): 1-11.
Stull, AJ et al (2010) Bioactives in blueberries improve insulin sensitivity in obese, insulin-resistant men and women. J Nutr 140(10): 1764-8.
Suez, J et al (2018) Post-antibiotic gut mucosal microbiome reconstitution is impaired by probiotics and improved by autologous FMT. Cell 174: 1406-1423.
Sun, et al (2018) Gut Mirobiota and intestinal fxr mediate the clinical benefits of metformin. Nat Med 24: 1919-1929.
Sweeney, T et al (2014) Metabolic surgery: action via hormonal milieu changes, changes in bile acids or gut microbiota? A summary of the literature. Best Pract Res Clin Gastroenterol 28: 727-740.
Terrapon, N and Henrissat, B (2014) How do gut microbes break down dietary fiber? Trends Biochem Sci 39(4):156-158.
Tolhurst, G et al (2012) Short-chain fatty acids stimulate glucagon-like peptide-1 secretion via the G-protein-coupled receptor FFAR2. Diabetes 61: 364-371.
Truong, DT et al (2015) MetaPhlAn2 for enhanced metagenomic taxonomic profiling. Nature Methods 12(10): 902-904.
Tuohy, KM et al (2012) Up-regulating the human intestinal microbiome using whole plant foods, polyphenols, and/or fiber. J Agric Food Chem 60: 8776-8782.
Turnbaugh et al (2009) A Core gut microbiome in obese and lean twins. Nature 457(7228): 480-484.
Turnbaugh, PJ et al (2006) An Obesity-associated gut microbiome with increased capacity for energy harvest. Nature 444: 1027-1031.
Turnbaugh, PJ et al (2008) Diet-induced obesity is linked to marked but reversible alterations in the mouse distal gut microbiome. Cell Host Microbe 3: 213-223.
Turnbaugh, PJ et al (2009) Supplement: The effect of diet on the human gut microbiome: a metagenomic analysis in humanized gnotobiotic mice. Sci Transl Med 1(6ra14)1-23.
Van Hui et al (2017) Reduced obesity, diabetes and steatosis upon cinnamon and grape pomace are associated with changes in gut microbiota and markers of gut barrier. Am J Physiol Endocrinol Metab 314(4): E3340E352.G.
Vatanen, T et al (2016) Variation in microbiome LPS immunogenicity contributes to autoimmunity in humans. Cell 165: 842-853.
Verma et al (2018) Cell Surface polysaccharides of Bifidobacterium bifidum induce the generation of Foxp3+ regulatory T cells. Sci Immunol 3 , eaat6975.
Vijay-Kumar et al (2010) Metabolic syndrome and altered gut microbiota in mice lacking toll-like receptor 5. Science 328(5975): 228-231.

(56) References Cited

OTHER PUBLICATIONS

Vital, M et al (2013) A gene-targeted approach to investigate the intestinal butyrate-producing bacterial community. Microbiome 1(8): 1-14.
Voreades et al (2014) Diet and the development of the human intestinal microbiome. Front Microbiol 5(494): 1-9.
Wahlstrom et al (2016) Intestinal crosstalk between bile acids and microbiota and its impact on host metabolism. Cell Metab 24: 41-50.
Wallace, T et al (2004) Use and abuse of HOMA modeling. Diabetes Care 27(6): 1487-1495.
Wang, J (2015) Modulation of gut microbiota during probiotic-mediated attenuation of metabolic syndrome in high fat diet-fed mice. ISME J 9: 1-15.
Wassermann, B et al (2017) Harnessing the microbiomes of *Brassica* vegetables for health issues. Sci Rep 7: 17649.
Weitkunat, K et al (2017) Short-chain fatty acids and inulin, but not guar gum, prevent diet-induced obesity and insulin resistance through differential mechanisms in mice. Sci Rep 7(6109): 1-13.
White, J (2014) A Brief history of the development of diabetes medications. Diabetes Spectr 27(2): 82-86.
Winer et al (2016) The Intestinal immune system in obesity and insulin resistance. Cell Metab 23: 413-426.
Winer et al (2017) Immunologic impact of the intestine in metabolic disease. J Clin Invest 127(1):33-42.
Woo, S-L et al (2014) Metformin ameliorates hepatic steatosis and inflammation without altering adipose phenotype in diet-induced obesity. PLoS One 9(3): e91111.
Wu, H et al (2017) Metformin alters the gut microbiome of individuals with treatment-naïve type 2 diabetes, contributing to the therapeutic effects of the drug. Nat Med. 23(7): 850-858.
Wu, H et al (2017) Metformin alters the gut microbiome of individuals with treatment-naïve type 2 diabetes, contributing to the therapeutic effects of the drug. Nat Med. 23(7): supplement.
Yang, JH et al (2017) Potent anti-inflammatory and antiadipogenic properties of bamboo (*Sasa coreana* Nakai) leaves extract and its major constituent flavonoids. J Agric Food Chem 65: 6665-6673.
Yassour, M et al (2016) Natural history of the infant gut microbiome and impact of antibiotic treatment on bacterial strain diversity and stability. Sci Transl Med 8(343): 1-12.
Yousef, N et al (2017) Metformin: a unique herbal origin medication. GJMR-B: Pharma, Drug Discovery, Toxicology, and Medicine 17(3): 31-37.
Zhang et al (2009) Human gut microbiota in obesity and after gastric bypass. PNAS 106(7): 2365-2370.
Zhang, Q et al (2016) Effect of probiotics on glucose metabolism in patients with type 2 diabetes mellitus: a meta-analysis of randomized controlled trials. Medicina 52: 28-34.
Zhang, X et al (2012) Structural changes of gut microbiota during berberine-mediated prevention of obesity and insulin resistance in high-fat diet-fed rats. PLoS One 7(8): e42529.
Zhang, X et al (2015) Modulation of gut microbiota by berberine and metformin during the treatment of high-fat diet-induced obesity in rats. Sci Rep 5(14405): 1-10.
Zhang, X et al (2017) Effects of Acarbose on the gut microbiota of prediabetic patients: a randomized, double-blind, controlled crossover trial. 8: 293-307.
Zhao, L et al (2018) Gut bacteria selectively promoted by dietary fibers alleviate type 2 diabetes. Science 359: 1151-1156.
Zheng, J et al (2018) Prebiotic Mannan-oligosaccharides augment the hypoglycemic effects of metformin in correlation with modulating gut microbiota. J Agric Food Chem 66(23): 5821-5831.
Zmora, N et al (2018) Personalized gut mucosal colonization resistance to empiric probiotics is associated with unique host and microbiome features. Cell 174: 1388-1405.
Gouda et al.., Endophytes: A Treasure House of Bioactive Compounds of Medicinal Importance, Frontiers in Microbiology, Mini Review, Sep. 29, 2016, vol. 7, article 1538, total pp. 1-8. (Front. Microbiol. 7:1538. doi: 10. 3389/fmicb.2016.01538). (Year: 2016).
U.S. Appl. No. 16/694,876, filed Nov. 25, 2019, Pending.
U.S. Appl. No. 17/816,371, filed Jul. 29, 2022, Pending.
U.S. Appl. No. 18/053,262, filed Nov. 7, 2022, Pending.
U.S. Appl. No. 16/235,858, filed Dec. 28, 2018, U.S. Pat. No. 10,596,209, Mar. 24, 2020, Issued.
U.S. Appl. No. 17/555,261, filed Dec. 17, 2021, Pending.
U.S. Appl. No. 17/816,932, filed Aug. 2, 2022, Pending.
U.S. Appl. No. 18/304,264, filed Apr. 20, 2023, Pending.
U.S. Appl. No. 18/181,495, filed Mar. 9, 2023, Pending.
EP 18887397.0—Extended European Search Report, dated Mar. 14, 2022, 11 pages.

* cited by examiner

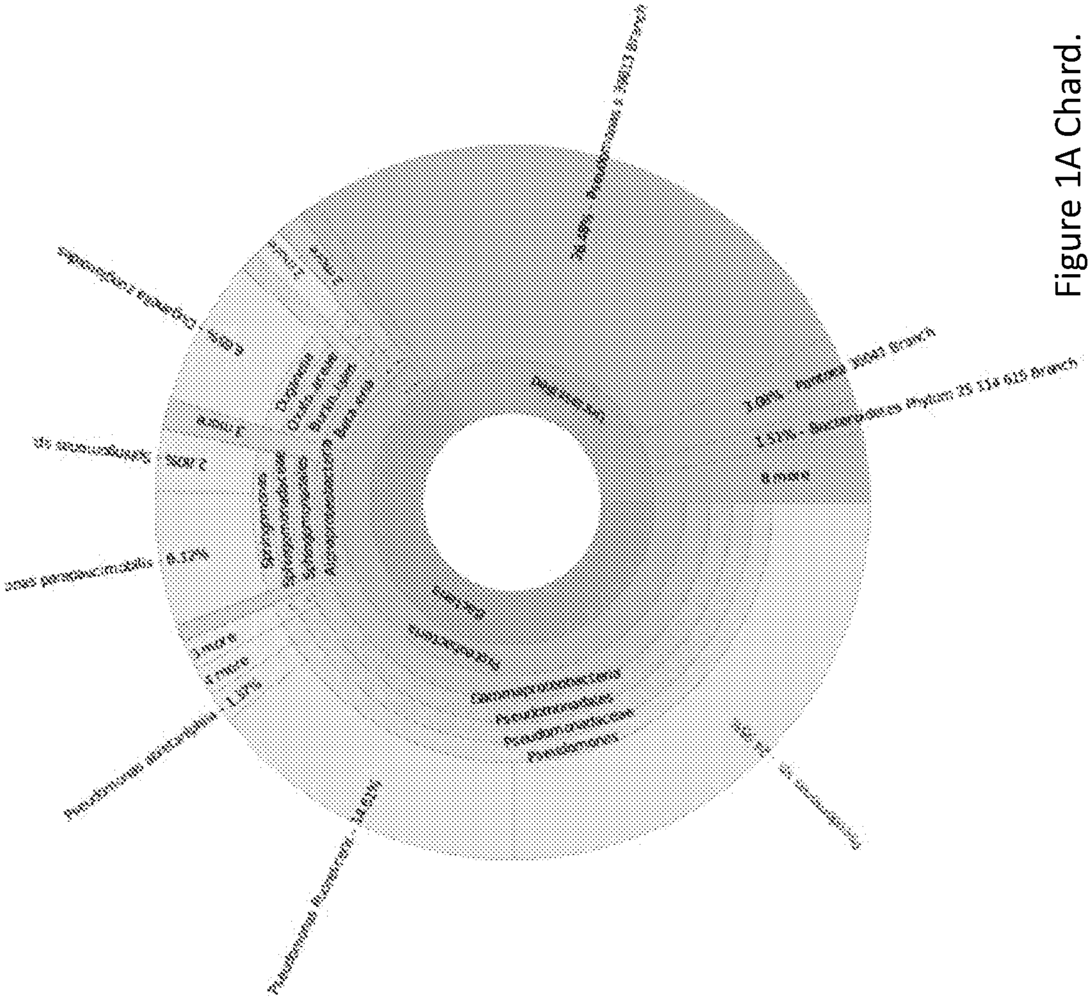
Figure 1A Chard.

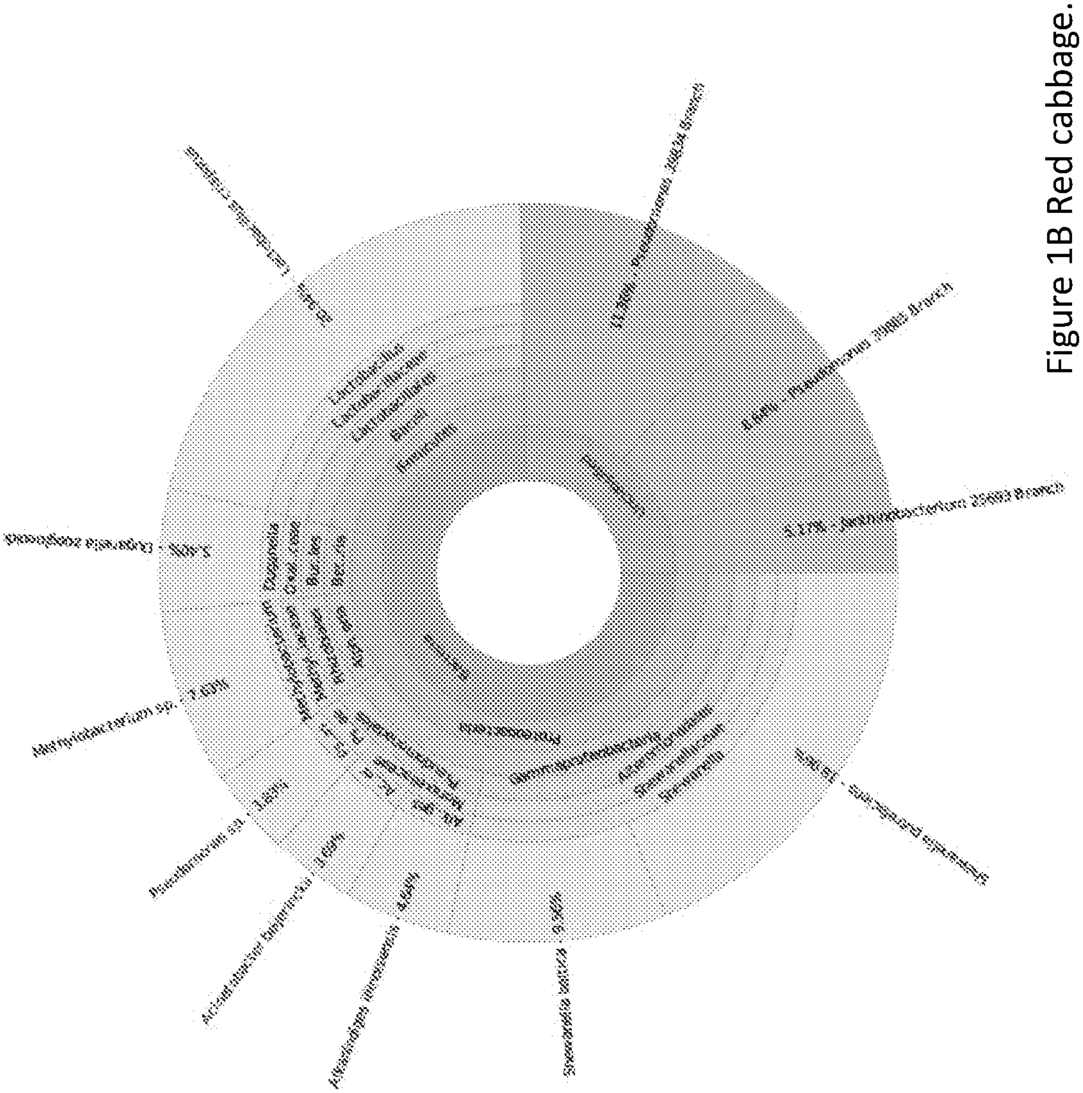
Figure 1B Red cabbage.

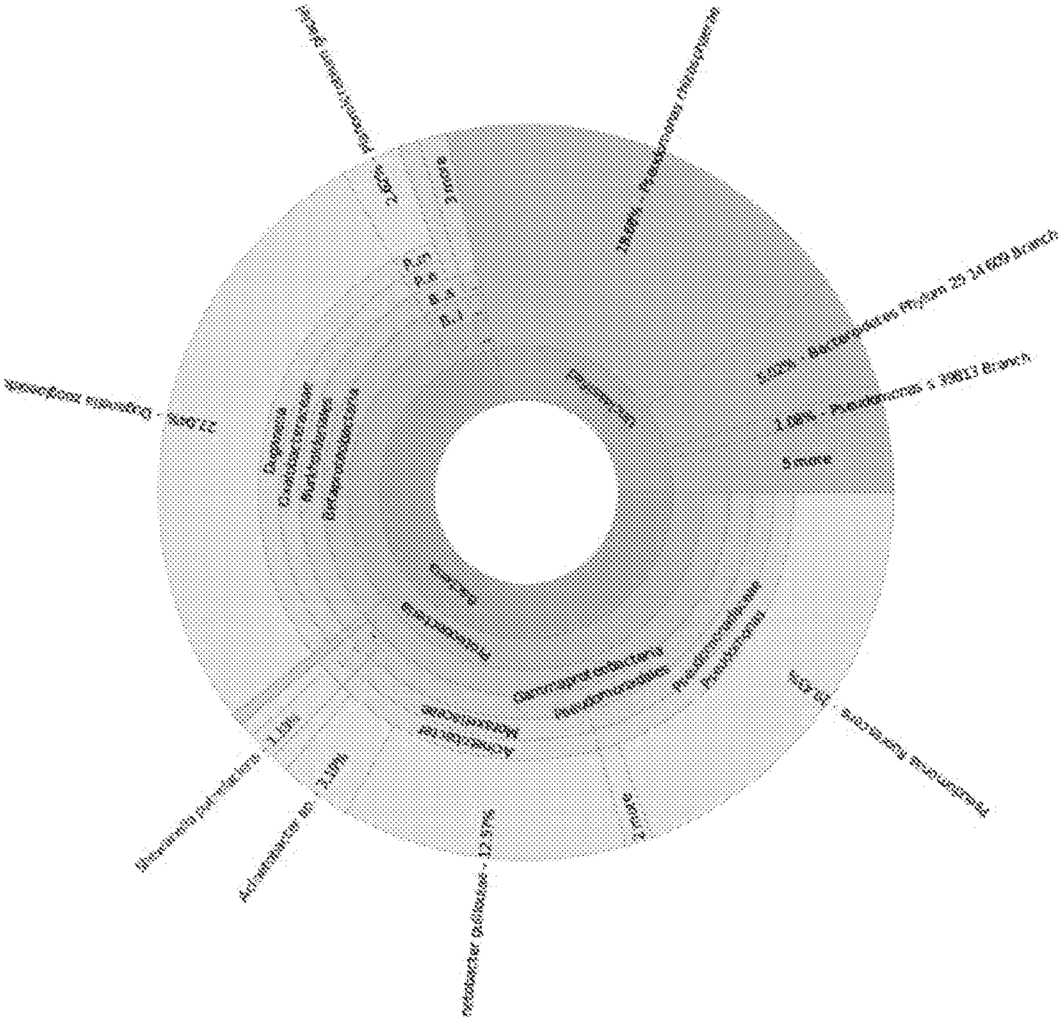
Figure 1C Romaine lettuce.

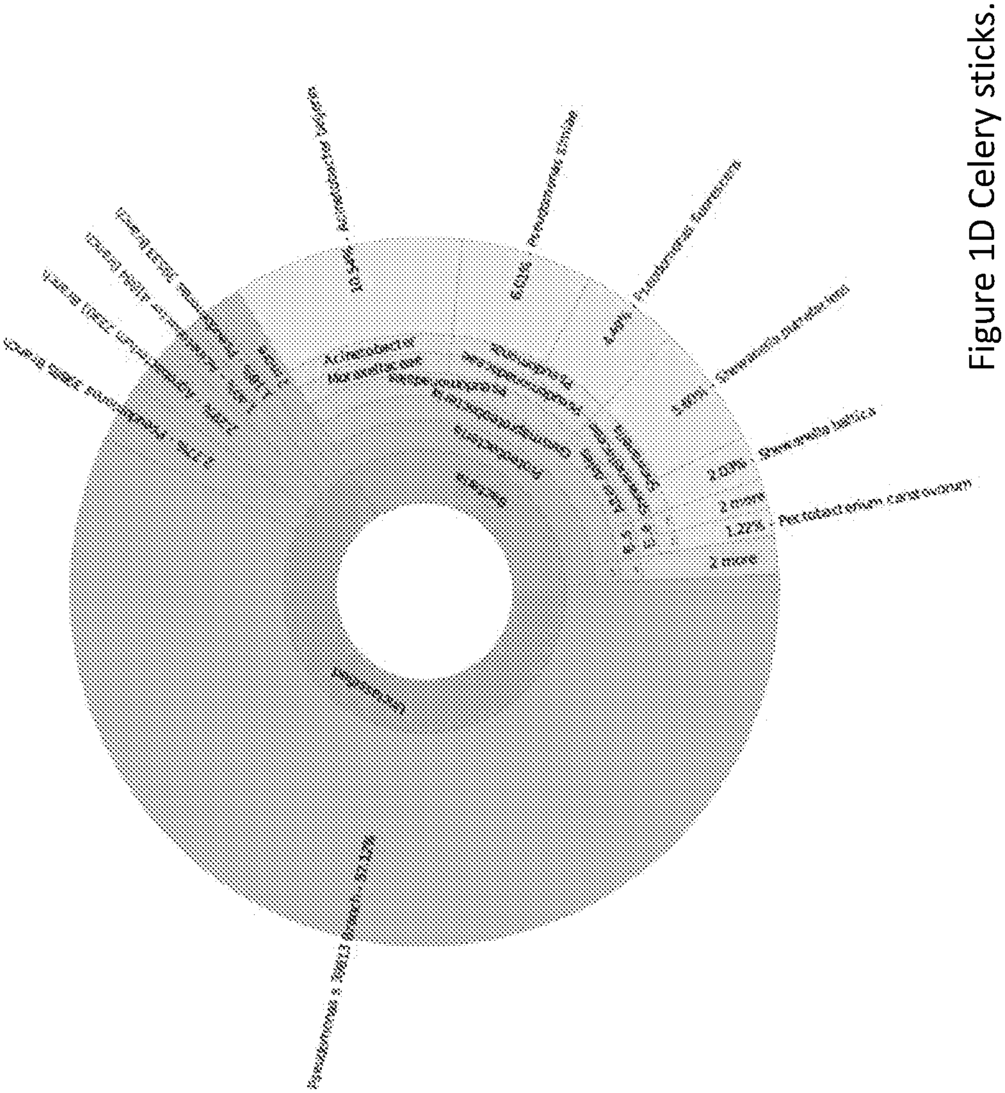
Figure 1D Celery sticks.

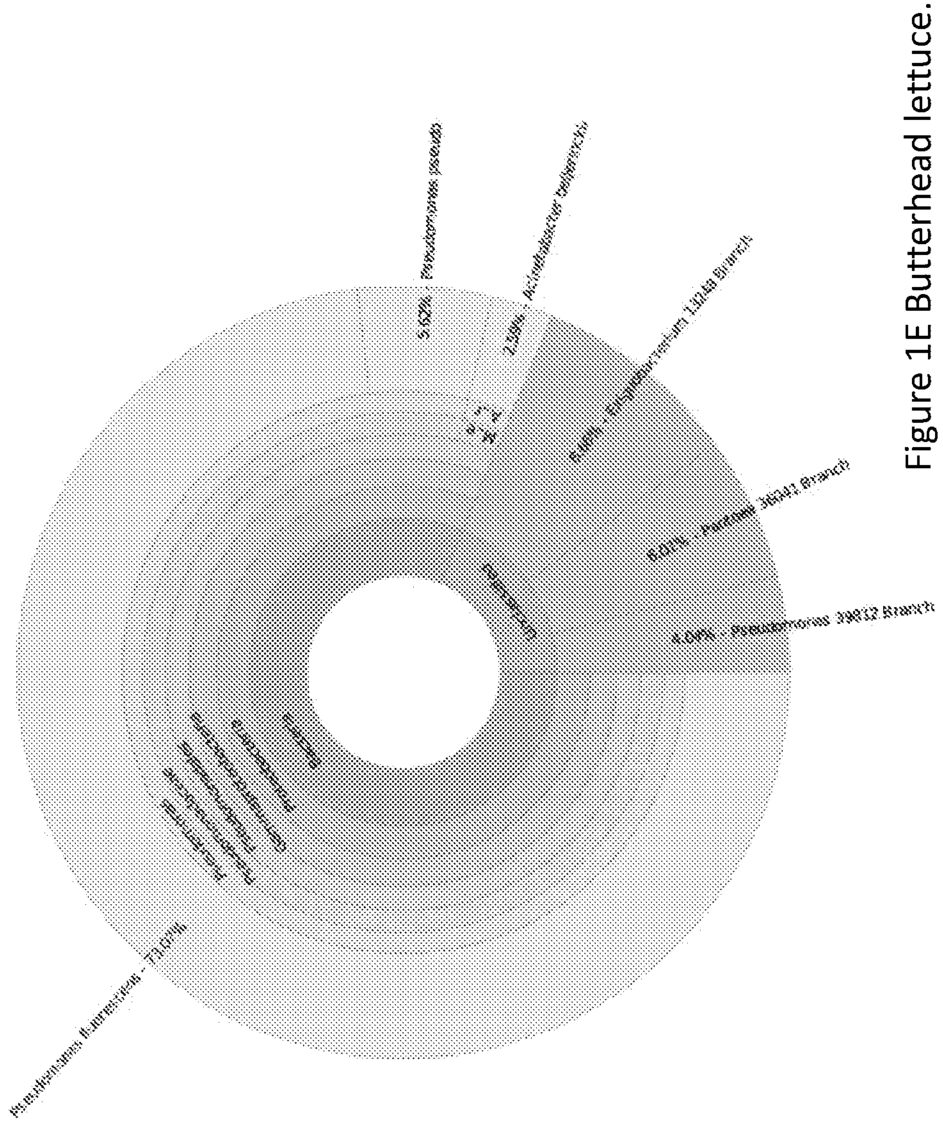
Figure 1E Butterhead lettuce.

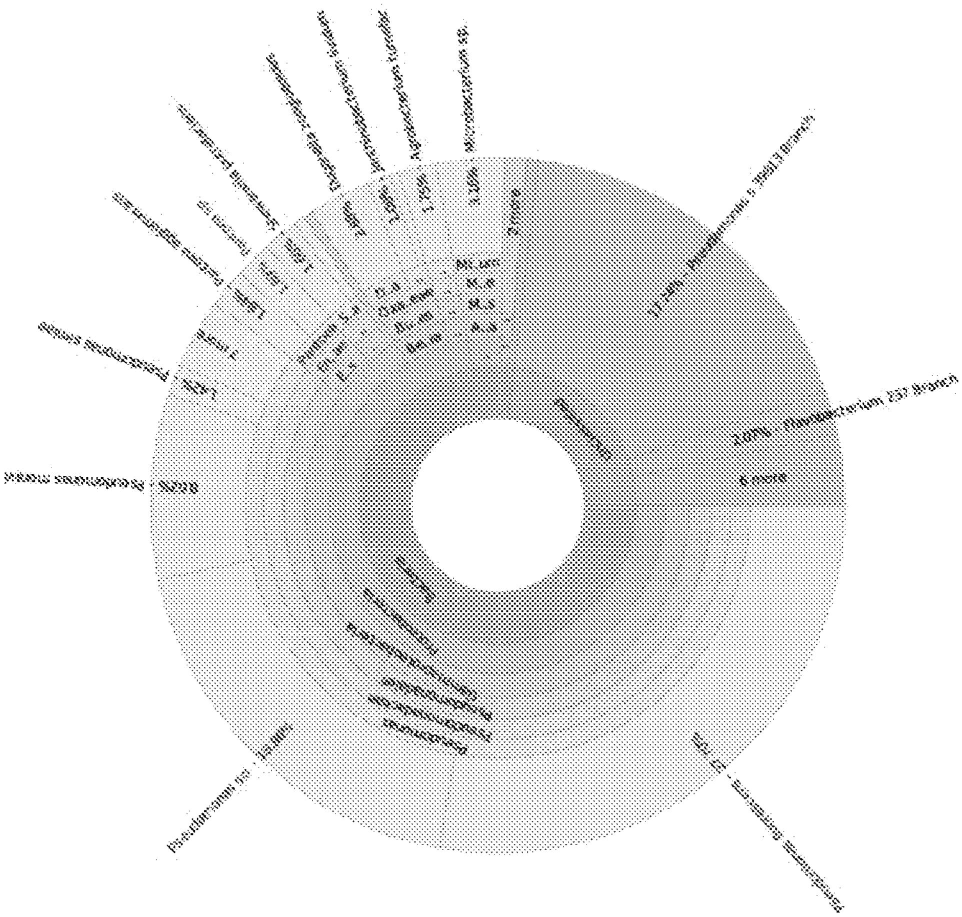
Figure 1F Baby spinach.

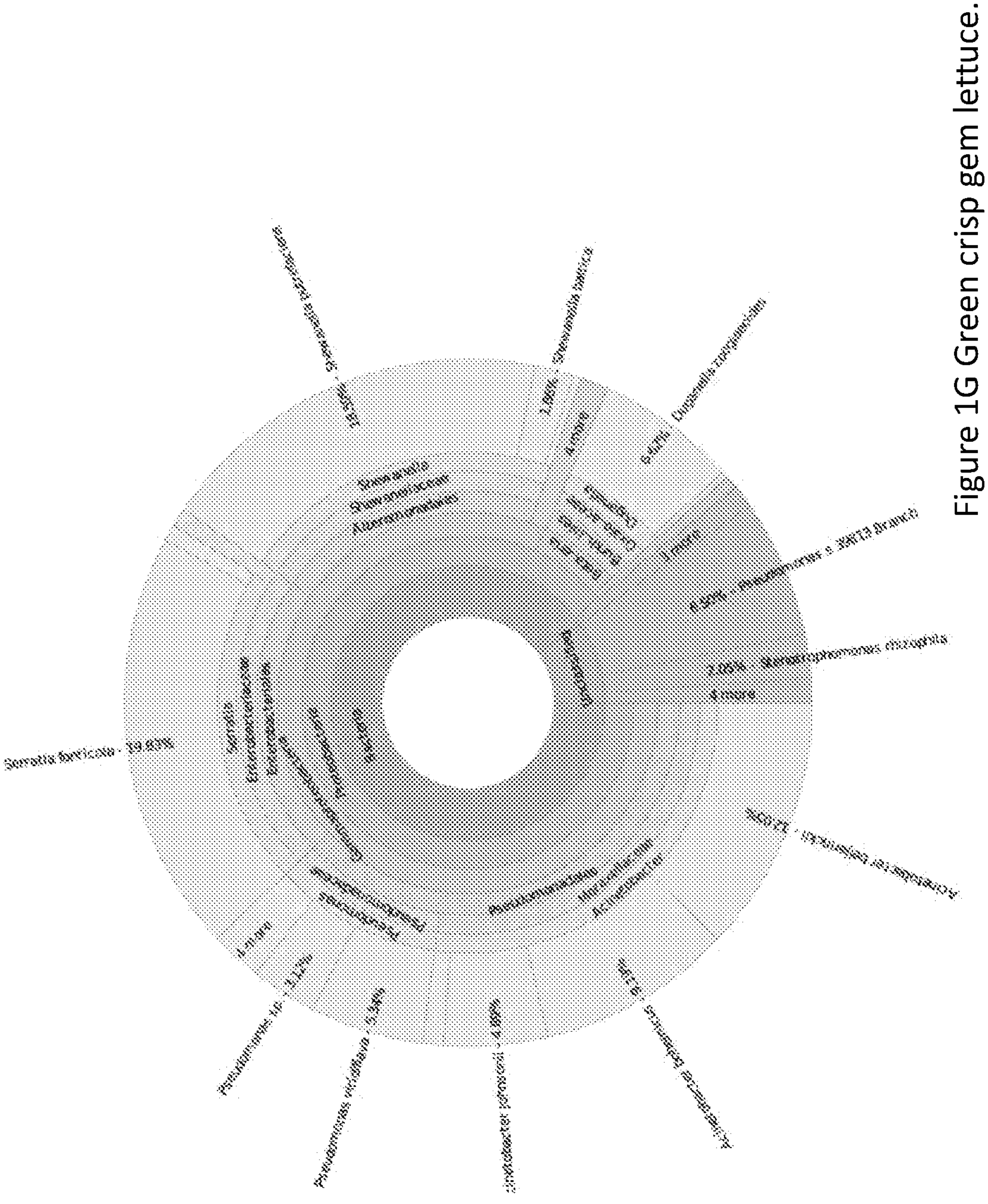
Figure 1G Green crisp gem lettuce.

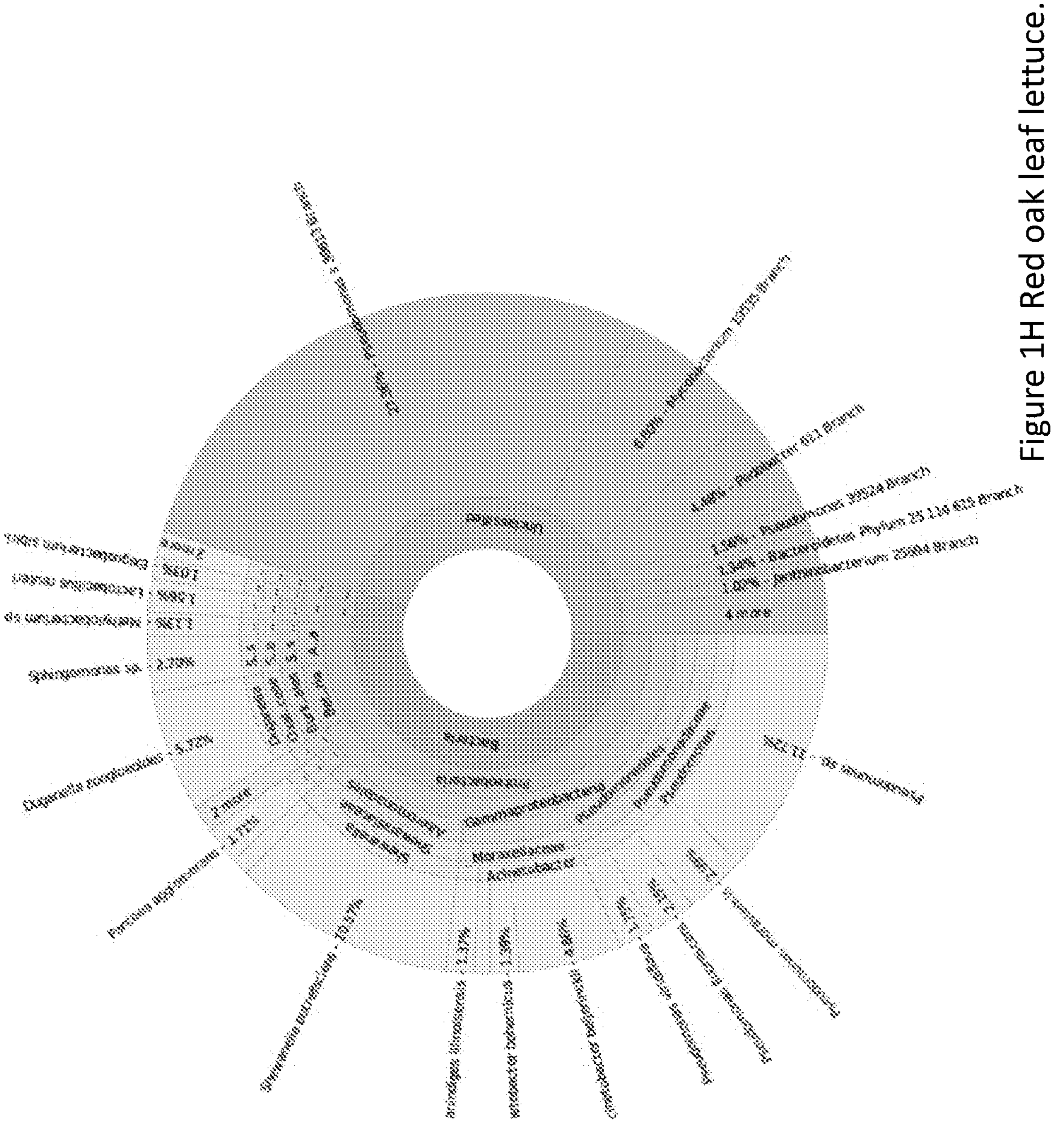
Figure 1H Red oak leaf lettuce.

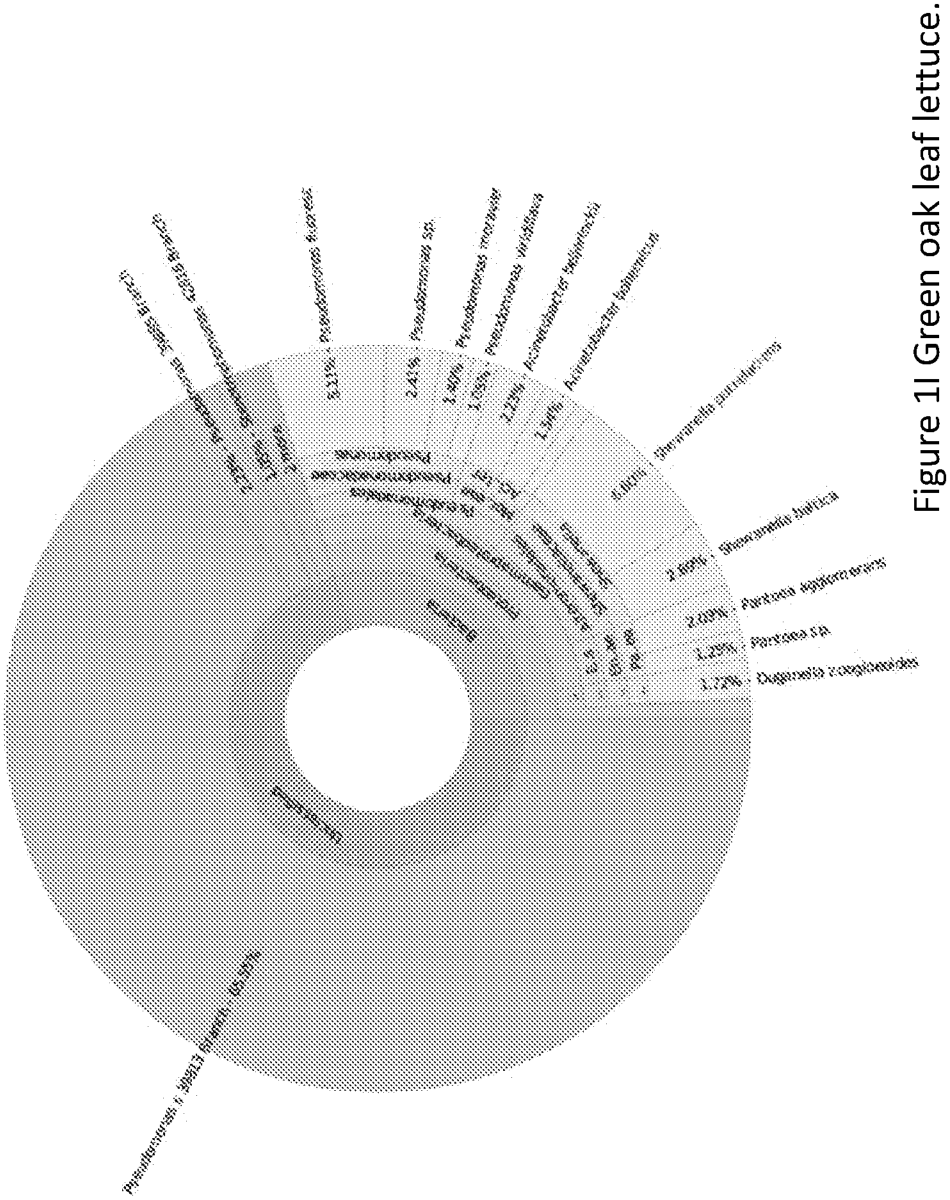
Figure 1I Green oak leaf lettuce.

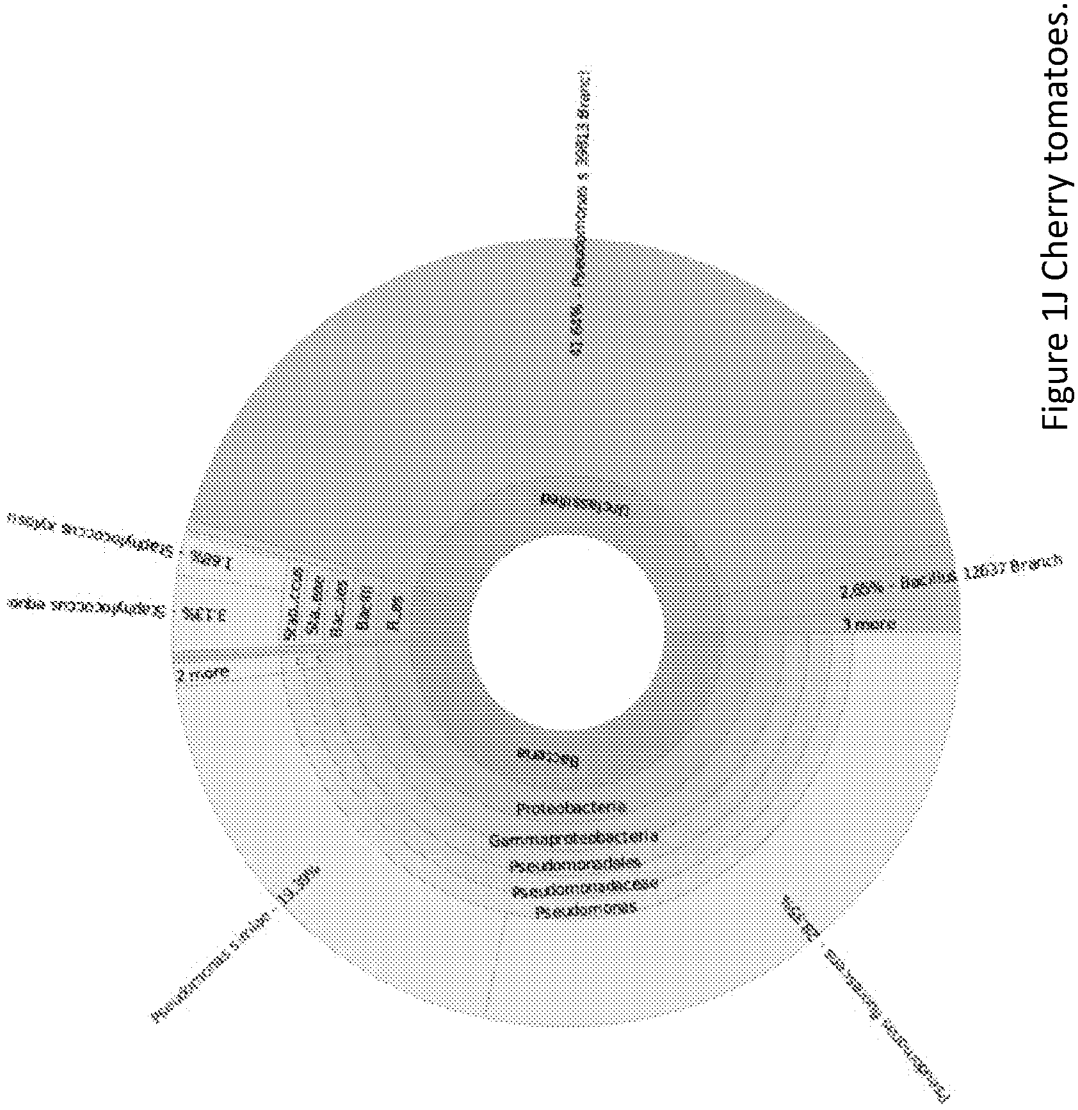
Figure 1J Cherry tomatoes.

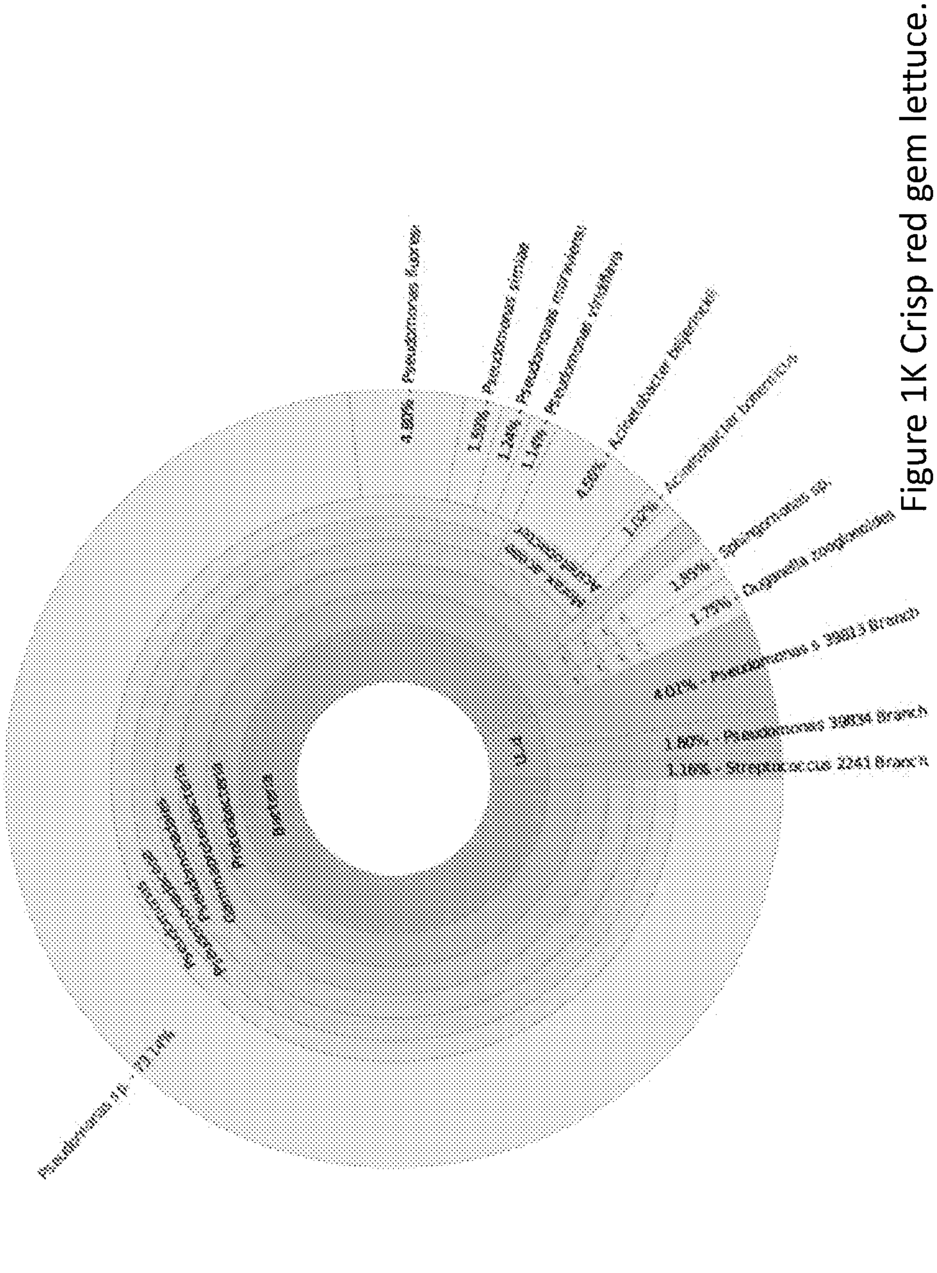
Figure 1K Crisp red gem lettuce.

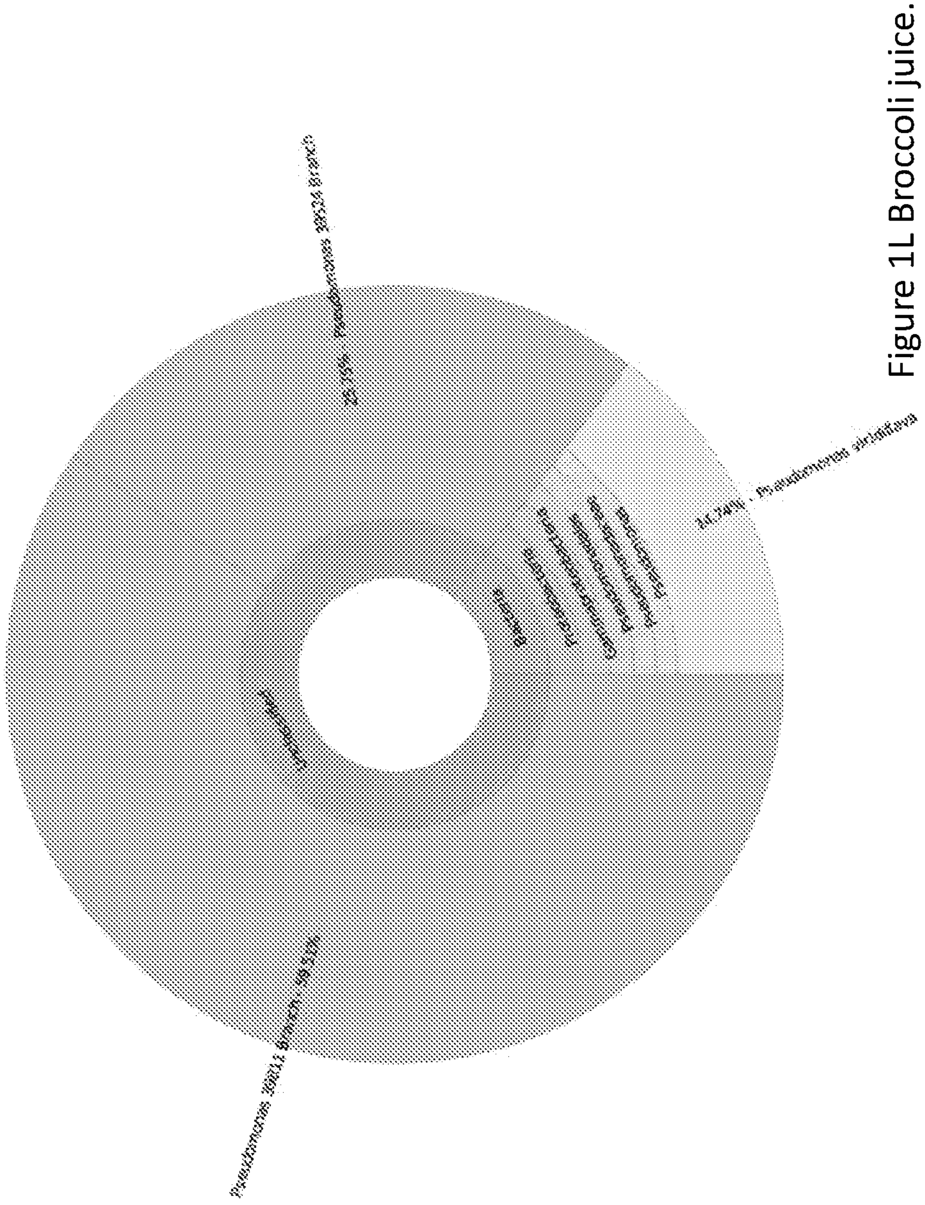
Figure 1L Broccoli juice.

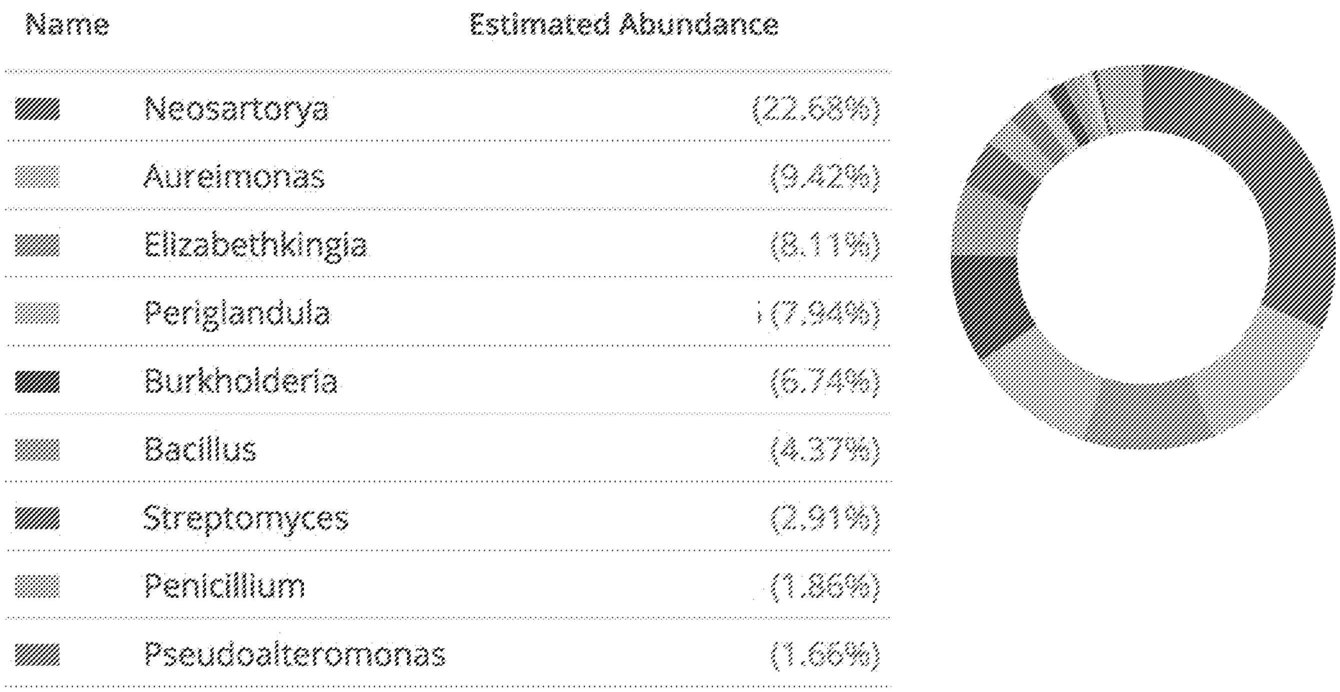
Figure 2A Broccoli head.

| Name | Estimated Abundance |
|---|---|
| Pseudomonas fluorescens | 53.94% |
| Pseudomonas sp. DSM 29167 | 10.99% |
| Propionibacterium acnes | 6.10% |
| Acinetobacter soli | 4.97% |
| Aureobasidium pullulans | 2.96% |
| Pseudomonas syringae | 2.76% |
| Pseudomonas sp. Leaf15 | 1.84% |
| Acinetobacter baumannii | 1.58% |
| Pantoea sp. SL1_M5 | 1.43% |
| Raoultella ornithinolytica | 1.32% |
| Sphingomonas sp. Ant20 | 1.27% |
| Comamonas testosteroni | 1.18% |
| Rahnella sp. WP5 | 1.18% |
| Enterobacter sp. 940_PEND | 1.06% |
| Pseudomonas sp. FH1 | 0.73% |
| Rothia dentocariosa | 0.54% |
| Pectobacterium carotovorum | 0.54% |
| Enhydrobacter aerosaccus | 0.54% |
| Bacillus sp. LL01 | 0.42% |
| Pseudomonas trivialis | 0.39% |

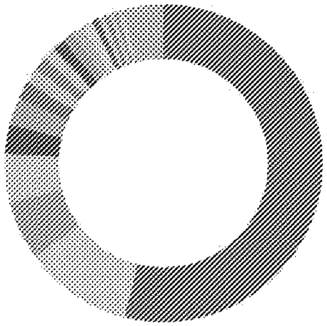

Figure 2B Blueberry.

| | Name | Estimated Abundance |
|---|---|---|
| | Lactobacillus acetotolerans | 60.98% |
| | Lactobacillus buchneri | 12.34% |
| | Pediococcus ethanolidurans | 5.47% |
| | Lactobacillus parafarraginis | 4.32% |
| | Lactobacillus rapi | 2.91% |
| | Lactobacillus plantarum | 1.52% |
| | Lactobacillus kefiranofaciens | 1.40% |
| | Lactobacillus futsaii | 1.38% |
| | Lactobacillus brevis | 1.25% |
| | Lactobacillus panis | 1.16% |
| | (Remaining) | 7.26% |
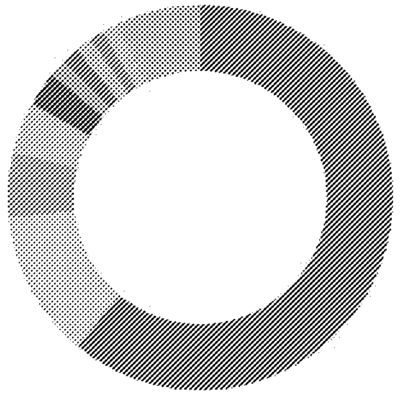
Figure 2C Pickled green olives.

MICROBIAL COMPOSITIONS AND METHODS FOR TREATING TYPE 2 DIABETES, OBESITY, AND METABOLIC SYNDROME

CROSS REFERENCE TO RELATED APPLICATIONS

This application is a continuation of U.S. application Ser. No. 16/235,858, filed Dec. 28, 2018, allowed, which is a continuation of PCT Application No. PCT/US2018/066088, filed Dec. 17, 2018, which claims the benefit of U.S. Provisional Application Nos. 62/599,647, filed Dec. 15, 2017; 62/607,149, filed Dec. 18, 2017; and 62/727,497, filed Sep. 5, 2018, each of which is hereby incorporated by reference in its entirety.

SEQUENCE LISTING

The instant application contains a Sequence Listing which has been submitted via EFS-Web and is hereby incorporated by reference in its entirety. Said ASCII copy, created on Feb. 6, 2020, is named SBI002C2_SequenceListing.txt, and is 321,953 bytes in size.

BACKGROUND OF THE INVENTION

The invention relates to methods and compositions useful for treating type 2 diabetes, obesity, and metabolic syndrome.

Daily consumption of fresh fruits, vegetables, seeds and other plant-derived ingredients of salads and juices is recognized as part of a healthy diet and associated with weight loss, weight management and overall healthy life styles. This is demonstrated clinically and epidemiologically in the "China Study" (Campbell, T. C. and Campbell T. M. 2006. The China Study: startling implications for diet, weight loss and long-term health. Benbella books. pp 419) where a lower incidence of cardiovascular diseases, cancer and other inflammatory-related indications were observed in rural areas where diets are whole food plant-based. The benefit from these is thought to be derived from the vitamins, fiber, antioxidants and other molecules that are thought to benefit the microbial flora through the production of prebiotics. These can be in the form of fermentation products from the breakdown of complex carbohydrates and other plant-based polymers. There has been no clear mechanistic association between microbes in whole food plant-based diets and the benefits conferred by such a diet. The role of these microbes as probiotics, capable of contributing to gut colonization and thereby influencing a subject's microbiota composition in response to a plant-based diet, has been underappreciated. In contrast to a plant-based diet, diets deficient in microbes such as the Western diet are associated with chronic inflammation, obesity, metabolic syndrome, type 2 diabetes (T2D) and sequelae.

Type 2 diabetes (T2D) is a systemic inflammatory condition where loss of insulin sensitivity leads to hyperglycemia and dyslipidemia, culminating in cell and tissue damage. Numerous studies have identified dysbiosis of the gut microbiome as a primary factor in the development of obesity and T2D, leading to a robust effort to develop microbiome-based therapeutic candidates for these conditions. In obesity and T2D, the gut microbiome is characterized by reduced microbial diversity and a shift in the equilibrium of Firmicutes and Bacteroidetes, the two most prevalent bacterial phyla residing in the colon. This altered microbial environment can result in increased energy harvest and intestinal permeability, as well as reduced production of enteroendocrine peptides and short chain fatty acids (SCFA), all of which can promote the inflammation and insulin resistance associated with obesity and T2D. Recent evidence indicates oral anti-diabetic drugs such as metformin may in part exert their effects through modulation of the gut microbiome.

What is needed are compositions and methods that treat T2D, obesity and metabolic syndrome by modulating a subject's microbiota composition away from that associated with a Western diet and toward one conferring the benefits of a plant-based diet.

SUMMARY OF THE INVENTION

In one aspect, provided herein are pharmaceutical compositions comprising a plurality of purified microbes, wherein at least two microbes have at least 97 percent identity to any of Seq ID Nos. 1-66 at the 16S rRNA or fungal ITS locus.

In some embodiments, at least two microbes have 100 percent identity to one of Seq ID Nos 1-66 at the 16S rRNA or fungal ITS locus, or 100 percent identity to a diagnostic sequence thereof.

In some embodiments, the pharmaceutical composition comprises microbial entities DP5 and DP1. In some embodiments, the pharmaceutical composition comprises microbial entities DP9, DP5, and DP22. In some embodiments, the pharmaceutical composition comprises microbial entities DP9, DP2, and DP3. In some embodiments, the pharmaceutical composition comprises microbial entities DP9, DP2, and DP53.

In some embodiments, the pharmaceutical composition comprises microbes with 16S sequences that are individually at least 97% identical to SEQ ID Nos 9, 5, and 22. In some embodiments, the pharmaceutical composition comprises microbes with 16S sequences that are individually at least 98% identical to SEQ ID Nos 9, 5, and 22. In some embodiments, the pharmaceutical composition comprises microbes with 16S sequences that are individually at least 99% identical to SEQ ID Nos 9, 5, and 22. In some embodiments, the pharmaceutical composition comprises microbes with 16S sequences that are individually 100% identical to SEQ ID Nos 9, 5, and 22. In some embodiments, the pharmaceutical composition comprises microbes with 16S sequences that are individually at least 97% identical to SEQ ID Nos 9, 2, and 3. In some embodiments, the pharmaceutical composition comprises microbes with 16S sequences that are individually at least 98% identical to SEQ ID Nos 9, 2, and 3. In some embodiments, the pharmaceutical composition comprises microbes with 16S sequences that are individually at least 99% identical to SEQ ID Nos 9, 2, and 3. In some embodiments, the pharmaceutical composition comprises microbes with 16S sequences that are individually 100% identical to SEQ ID Nos 9, 2, and 3. In some embodiments, the pharmaceutical composition comprises microbes with 16S sequences that are individually at least 97% identical to SEQ ID Nos 9, 2, and 53. In some embodiments, the pharmaceutical composition comprises microbes with 16S sequences that are individually at least 98% identical to SEQ ID Nos 9, 2, and 53. In some embodiments, the pharmaceutical composition comprises microbes with 16S sequences that are at individually least 99% identical to SEQ ID Nos 9, 2, and 53. In some embodiments, the pharmaceutical composition comprises microbes with 16S sequences that are individually 100% identical to SEQ ID Nos 9, 2, and 53. In some embodiments, the pharmaceutical composition comprises microbes with 16S sequences that are individually at least 97% identical to SEQ ID Nos 5 and 1. In some embodiments, the pharmaceutical composition comprises microbes with 16S sequences that are individually at least 98% identical to SEQ ID Nos 5 and 1. In some embodiments, the pharmaceutical composition comprises microbes with 16S sequences that are individually at least 99% identical to SEQ ID Nos 5 and 1. In some embodiments, the pharmaceutical composition comprises microbes with 16S sequences that are individually 100% identical to SEQ ID Nos 5 and 1.

In another aspect, provided herein are pharmaceutical compositions comprising a plurality of purified viable microbes comprising at least one microbial entity classified as a gamma proteobacterium, and at least one prebiotic fiber.

In some embodiments, the pharmaceutical composition further comprising at least one additional probiotic microbial species.

In some embodiments, the pharmaceutical composition further comprising at least one microbial entity classified as a fungus or yeast.

In some embodiments, the prebiotic fiber is oligofructose, or derived from a fiber source yielding a prebiotic fiber rich in oligofructose.

In another aspect, provided herein are methods for treating diabetes or metabolic syndrome, comprising administering to a patient in need thereof the pharmaceutical composition of any of the previous claims in concert with an appropriate regimen of any suitable anti-diabetic therapy.

In another aspect, provided herein are pharmaceutical compositions comprising a plurality of purified viable microbes and a prebiotic fiber, wherein the microbes produce more short chain fatty acids (SCFAs) when grown together than when cultured separately, and wherein growth on the chosen prebiotic sugar results in increased synergy compared to growth on rich medium, and wherein at least one of the microbes has at least 97 percent identity at the 16S rRNA locus or the ITS locus to any of Seq ID No 1-66.

In some embodiments, at least one of the microbes has at least 97 percent identity at the 16S rRNA locus to Seq ID No 1. In some embodiments, at least one of the microbes has at least 97 percent identity at the ITS locus to Seq ID No 2. In some embodiments, at least one of the microbes has at least 97 percent identity at the 16S rRNA to Seq ID No 3. In some embodiments, at least one of the microbes has at least 97 percent identity at the ITS locus to Seq ID No 5. In some embodiments, at least one of the microbes has at least 97 percent identity at the 16S rRNA locus to Seq ID No 9. In some embodiments, at least one of the microbes has at least 97 percent identity at the 16S rRNA locus to Seq ID No 22. In some embodiments, at least one of the microbes has at least 97 percent identity at the 16S rRNA locus to Seq ID No 53. In some embodiments, at least one of the microbes has 100 percent identity at the 16S rRNA locus or the ITS locus to any of Seq ID No 1-63, or 100 percent identity to a diagnostic sequence thereof. In some embodiments, at least one of the microbes has 100 percent identity at the 16S rRNA locus or the ITS locus to any of Seq ID No 1, 2, 3, 5, 9, 22, and 53, or 100 percent identity to a diagnostic sequence thereof.

In another aspect, provided herein are methoda for altering relative abundance of microbiota in a subject, comprising administering to the subject an effective dose of a composition consisting of a substantially purified plant-derived microbial assemblage, comprising at least 2 microbes from Table 4 as identified by 16S rRNA sequence or ITS sequence, wherein the subject has a disorder selected from the group consisting of obesity, metabolic syndrome, insulin deficiency, insulin-resistance related disorders, elevated fasting blood glucose, glucose intolerance, diabetes, non-alcoholic fatty liver, and abnormal lipid metabolism.

In another aspect, provided herein are methods to formulate a defined microbial assemblage comprising a purified microbial population isolated from a first plant-based sample selected from samples in Table 3 artificially associated with a purified microbial population isolated from a second plant-based sample from selected from samples Table 3, wherein the purified bacterial population is predicted using a computational simulation and is capable of modulating production of one or more branched chain fatty acids, short chain fatty acids, and/or flavones in a mammalian gut.

In another aspect, provided herein are a defined microbial assemblage comprising a purified microbial population isolated from a first plant-based sample selected from samples in Table 3 artificially associated with a purified microbial population isolated from a second plant-based sample from selected from samples Table 3, wherein the synthetic microbial consortia is capable of modulating the diabetic symptoms of a mammal treated with the synthetic microbial consortia, as compared to a reference mammal.

In another aspect, provided herein are a defined microbial assemblage comprising a purified microbial population that, when combined with an anti-diabetic regimen, lowers fasting blood glucose to levels found in a low fat diet control subject and wherein at least one of the microbes has at least 97 percent identity at the 16S rRNA locus or the ITS locus to any of Seq ID No 1-66.

In another aspect, provided herein are a fermented probiotic composition for the treatment of diabetes comprising a mixture of *Pediococcus pentosaceus* and/or *Leuconostoc mesenteroides* combined with non-lactic acid bacteria from Table 4 or Table 7, the fermented probiotic being in a capsule or microcapsule adapted for enteric delivery.

In another aspect, provided herein are methoda for treatment of diabetes in a mammal comprising the steps of administering a composition comprising an effective amount of organisms described in Table 4 to a mammal in need of treatment for diabetes.

In another aspect, provided herein are methods of treating diabetes, comprising administering to a subject a pharmaceutical composition comprising a plurality of purified microbes, wherein at least two microbes have at least 97 percent identity to any of Seq ID Nos. 1-66 at the 16S rRNA or fungal ITS locus.

In another aspect, provided herein are methods of treating diabetes, comprising administering to a subject a pharmaceutical composition comprising a plurality of strains having at least 97 percent identity to DP5 or DP1.

In another aspect, provided herein are methods of treating diabetes, comprising administering to a subject a pharmaceutical composition comprising a plurality of strains having at least 97 percent identity to DP9, DP22, and DP2.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms comprise genes encoding metabolic functions related to desirable health outcomes such as BMI, low inflammatory metabolic indicators, and ameliorated diabetic symptoms, and wherein at least one of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms comprise genes encoding metabolic functions related to desirable health outcomes such as BMI, low inflammatory metabolic indicators, and ameliorated diabetic symptoms, and wherein at least two of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms comprise genes encoding metabolic functions related to desirable health outcomes such as BMI, low inflammatory metabolic indicators, and ameliorated diabetic symptoms, and wherein at least three of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms are identified to a whole genome sequence in public databases by using a k-mer method, and wherein at least one of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms are identified to a whole genome sequence in public databases by using a k-mer method, and wherein at least two of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms are identified to a whole genome sequence in public databases by using a k-mer method, and wherein at least three of the microorganisms has a 16S rRNA sequence that is 97 percent identical to one of Seq ID Nos 1-66.

In another aspect, provided herein are methods for treating diabetes in a mammal in need thereof comprising administering to the mammal a therapeutically effective amount of a probiotic composition comprising at least one strain classified as gamma proteobacteria by 16S rRNA gene sequence.

In another aspect, provided herein are methods for treating diabetes in a mammal in need thereof comprising administering to the mammal a therapeutically effective amount of a probiotic composition comprising at least two strain classified as gamma proteobacteria by 16S rRNA gene sequence.

In another aspect, provided herein are methods for treating diabetes in a mammal in need thereof comprising administering to the mammal a therapeutically effective amount of a probiotic composition comprising at least three strain classified as gamma proteobacteria by 16S rRNA gene sequence.

In another aspect, provided herein are methods for reducing body weight of a high fat diet subject, comprising administering a probiotic composition, wherein the probiotic bacterial assemblage comprises at least one strain classified as gamma proteobacteria by 16S rRNA gene sequence, formulated as a defined microbial assemblage with at least one other plant-derived microbe listed in Table 4 or Table 7.

In some embodiments, the at least one other plant-derived microbe is listed in Table 4. In some embodiments, the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, the at least two other plant-derived microbe are listed in Table 7.

In another aspect, provided herein are methods for reducing body weight of a high fat diet subject, comprising administering a probiotic composition, wherein the probiotic bacterial assemblage comprises at least two strain classified as gamma proteobacteria by 16S rRNA gene sequence, formulated as a defined microbial assemblage with at least one other plant-derived microbe listed in Table 4 or Table 7.

In some embodiments, the at least one other plant-derived microbe is listed in Table 4.

In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, the at least two other plant-derived microbe are listed in Table 7.

In another aspect, provided herein are methods for reducing body weight of a high fat diet subject, comprising administering a probiotic composition, wherein the probiotic bacterial assemblage comprises at least three strain classified as gamma proteobacteria by 16S rRNA gene sequence, formulated as a defined microbial assemblage with at least one other plant-derived microbe listed in Table 4 or Table 7.

In some embodiments, the at least one other plant-derived microbe is listed in Table 4. In some embodiments, the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, the at least two other plant-derived microbe are listed in Table 7.

In another aspect, provided herein are methods for treatment of diabetes and its complications for a high fat diet subject, comprising administering a probiotic composition, wherein the probiotic bacterial assemblage comprises at least one strain classified as gamma proteobacteria by 16S rRNA gene sequence, and wherein the probiotic is formulated as a defined microbial assemblage with at least one other plant-derived microbe from Table 4 or Table 7. In some embodiments, the at least one other plant-derived microbe is listed in Table 4. In some embodiments, the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, wherein the at least two other plant-derived microbe are listed in Table 7.

In another aspect, provided herein are methods for treatment of diabetes and its complications for a high fat diet subject, comprising administering a probiotic composition, wherein the probiotic bacterial assemblage comprises at least one strain classified as gamma proteobacteria by 16S rRNA gene sequence, and wherein the probiotic is formulated as a defined microbial assemblage with at least two other plant-derived microbe from Table 4 or Table 7. In some embodiments, the at least one other plant-derived microbe is listed in Table 4. In some embodiments, the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, the at least two other plant-derived microbe are listed in Table 7.

In another aspect, provided herein are methods of the treatment of inhibition of the biosynthesis of lipids, high total body fat, high visceral fat, high gonadal fat, high total cholesterol, high triglyceride concentration, or high LDL/HDL ratio for a high fat diet subject, comprising administrating a probiotic composition, wherein the probiotic bacterial assemblage comprises at least one strain classified as gamma proteobacteria by 16S rRNA gene sequence.

In another aspect, provided herein are microbial compositions comprised of bacterial assemblages present in whole food plant-based diets that bear taxonomic resemblance to microbial species present in human microbiome as detected by stool from individuals with desirable phenotypic attributes such as BMI, low levels of inflammatory signaling molecules or diabetic symptoms.

In another aspect, provided herein are microbial compositions comprised of bacterial assemblages present in whole food plant-based diets that bear taxonomic resemblance to microbial species present in companion animal, or livestock microbiome as detected by stool from individuals with desirable phenotypic attributes such as BMI, low levels of inflammatory signaling molecules or diabetes symptoms.

In some embodiments, the composition comprises at least one microbe from Table 4, as determined by 97 percent or higher sequence identity at the 16S rRNA or ITS locus.

In another aspect, provided herein are methods for treating diabetes, the method comprising administration of a known anti-diabetic medication and the microbial composition of any of the preceding claims.

In another aspect, provided herein are methods for treating diabetes comprising administration of metformin and the microbial composition of any of the preceding claims.

In another aspect, provided herein are methods for treating diabetes comprising administration of a known anti-diabetic medication and a composition of metabolites derived from the microbial community of any of the preceding claims.

In another aspect, provided herein are methods for improving the efficacy of a known anti-diabetic drug, said method comprising administration of the anti-diabetic drug along with the microbial composition of any of the preceding claims.

In another aspect, provided herein are methods for treating diabetes, the method comprising administration of a known anti-diabetic medication and the pharmaceutical composition of any of the preceding claims.

In an aspect, the disclosure describes an oral or rectal pharmaceutical composition in a capsule or microcapsule, solution, or slurry adapted for enteric delivery comprising a plurality of viable gammaproteobacteria and other microbes from Table 4 or Table 7, wherein said pharmaceutical comprises between about 10^5 and 10^10 viable microbes. In another aspect, the oral pharmaceutical composition comprises at least *Pseudomonas, Rahnella*, other gammaproteobacteria, or other microbial species. In another aspect, the pharmaceutical composition comprises an isolated population of bacterial cells comprising three or more strains present in whole food plant-based diets, wherein each strain is capable of modulating production of one or more short chain fatty acids. In another aspect, the disclosure describes a pharmaceutical composition for treatment of obesity and obesity related metabolic syndrome, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms comprise genes encoding metabolic functions related to desirable health outcomes such as BMI or low inflammatory metabolic indicators. Metabolic indicators of relevance would be related to microbial production of short chain fatty acids (SCFA) including: Glycoside Hydrolase, Polysaccharide lyase, beta-fructofuranosidase, Phosphotransferase (PTS), Beta-fructofuranosidase (SacA), fructokinase (SacK), pyruvate formate lyase (PFL), Pyruvate Dehydrogenase (PDH), Lactate Dehydrogenase (LDH), Pyruvate Oxidase (PDX), Phosphotransacetylase (PTA), Acetate Kinase (ACK), Butyryl-CoA:Acetate CoA-transferase (But1, But2, But3) Butyrate inase (Buk1, Buk2, Buk3, ect) Phosphotransbutyrylase, propionaldehyde dehydrogenase (pduP) methylmalonyl-CoA (mmdA, mmdB), Lactoyl-CoA (lcdA, lcdB, lcdC), Succinate pathway, and the propanediol pathway.

In another aspect, the pharmaceutical composition comprises a treatment for T2D. In an aspect, the pharmaceutical composition may be administered with an anti-diabetic drug, either simultaneously or according to a sequence.

In another aspect, the disclosed invention pertains to methods of treating diabetes.

BRIEF DESCRIPTION OF THE SEVERAL VIEWS OF THE DRAWINGS

These and other features, aspects, and advantages of the present invention will become better understood with regard to the following description, and accompanying drawings, where:

FIGS. 1A-L show plots depicting the diversity of microbial species detected in samples taken from 12 plants usually consumed raw by humans.

FIGS. 2A-C show graphs depicting the taxonomic composition of microbial samples taken from broccoli heads (FIG. 2A), blueberries (FIG. 2B), and pickled olives (FIG. 2C).

DETAILED DESCRIPTION

Advantages and Utility

Figure 3:
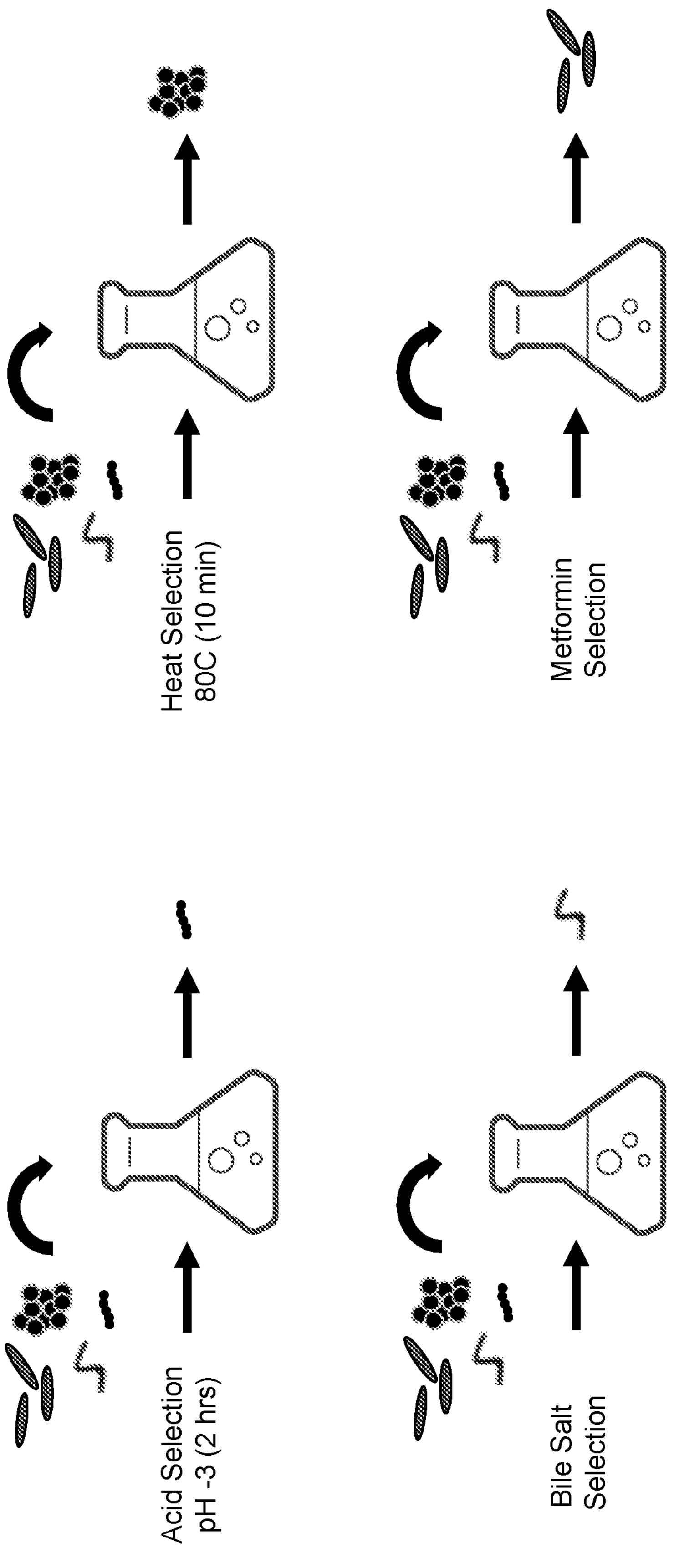
FIG. 3 shows a schematic describing a gut simulator experiment. The experiment comprises an in vitro system that represents various sections of the gastrointestinal tract. Isolates of interest are incubated in the presence of conditions that mimic particular stresses in the gastro-intestinal tract (such as low pH or bile salts), heat shock, or metformin. After incubation, surviving populations are recovered. Utilizing this system, the impact of various oral anti-diabetic therapies alone or in combination with probiotic cocktails of interest on the microbial ecosystem is tested.

Briefly, and as described in more detail below, described herein are methods and compositions for using microbial agents (probiotics) and agents that promote growth of certain microbes (prebiotics) for management (including prevention and treatment) of T2D, obesity and metabolic syndrome. Diabetes Mellitus is a feared and complex disorder. It has been a most distressing disease that can develop to a seriously life-threatening condition. For ages, society was resigned to accepting various methods and medications that became a standard with no real hope for a cure, or drastic eradication of the disease. In fact, many of the drugs used cause serious side effects.

An important indicator of the ability of the body to deal with the complications of diabetes is the glycated hemoglobin (HbAlc), that gives an integrated reading of the level of blood glucose. While all other known methods and medications help lower the glucose level at limited periods of the day or night time, the HbAlC remains higher than the normal 4.3 to 6.7 range regardless of the insulin dosage and other medicines. No full cure is expected by the present regimens. Thus, in an aspect, the present disclosure provides compositions and methods for treatment of T2D that result in reductions of HbAlC toward more normal levels.

Several features of the current approach should be noted. It is based on development of synergistic combinations of microbes based on those found in fruits and vegetables consumed as part of a plant-based diet. The combinations are based, in part, on analyses of biochemical pathways catalyzed by genes in these microbes and selection of microbial combinations that promote beneficial metabolic changes in a subject through the biochemical reactions they catalyze such as the production of SCFA.

Advantages of this approach are numerous. They include reduction of the morbidity associated with T2D, obesity and metabolic syndrome without the use of traditional drugs, or with lower doses of traditional drugs, and thus reduced levels of the side effects they can sometimes cause. Typical treatment regimens for T2D involve use of drugs such as metformin or acarbose. These drugs can be efficacious but are not without side effects. Prior art approaches are, additionally, not recommended for all patients. The disclosed methods and compositions provided in this application augment the efficacy of traditional drugs and additionally can serve patient populations for whom current methodologies are not recommended, by providing health benefits associated with consumption of a plant-based diet.

Definitions

Terms used in the claims and specification are defined as set forth below unless otherwise specified.

The term "ameliorating" refers to any therapeutically beneficial result in the treatment of a disease state, e.g., a metabolic disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and includes but is not limited to humans, non-human primates, canines, felines, murines, bovines, equines, and porcines.

As used herein, the term "derived from" includes microbes immediately taken from an environmental sample and also microbes isolated from an environmental source and subsequently grown in pure culture.

The term "percent identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. In some aspects, percent identity is defined with respect to a region useful for characterizing phylogenetic similarity of two or more organisms, including two or more microorganisms.

Percent identity, in these circumstances can be determined by identifying such sequences within the context of a larger sequence, that can include sequences introduced by cloning or sequencing manipulations such as, e.g., primers, adapters, etc., and analyzing the percent identity in the regions of interest, without including in those analyses introduced sequences that do not inform phylogenetic similarity.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

The term "sufficient amount" means an amount sufficient to produce a desired effect, e.g., an amount sufficient to alter the microbial content of a subject's microbiota.

The term "therapeutically effective amount" is an amount that is effective to ameliorate a symptom of a disease. A therapeutically effective amount can be a "prophylactically effective amount" as prophylaxis can be considered therapy.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, inhibiting substantially, slowing, or reversing the progression of a condition, substantially ameliorating clinical or aesthetical symptoms of a condition.

As used herein, the term "preventing" includes completely or substantially reducing the likelihood or occurrence or the severity of initial clinical or aesthetical symptoms of a condition.

As used herein, the term "about" includes variation of up to approximately +/−10% and that allows for functional equivalence in the product.

As used herein, the term "colony-forming unit" or "cfu" is an individual cell that is able to clone itself into an entire colony of identical cells.

As used herein all percentages are weight percent unless otherwise indicated.

As used herein, "viable organisms" are organisms that are capable of growth and multiplication. In some embodiments, viability can be assessed by numbers of colony-forming units that can be cultured. In some embodiments viability can be assessed by other means, such as quantitative polymerase chain reaction.

The term "derived from" includes material isolated from the recited source, and materials obtained using the isolated materials (e.g., cultures of microorganisms made from microorganisms isolated from the recited source).

"Microbiota" refers to the community of microorganisms that occur (sustainably or transiently) in and on an animal subject, typically a mammal such as a human, including eukaryotes, archaea, bacteria, and viruses (including bacterial viruses i.e., phage).

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

The term "subject" refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a dysbiosis, including, but not limited to, an infection due to a gastrointestinal pathogen or may be at risk of developing or transmitting to others an infection due to a gastrointestinal pathogen.

The "colonization" of a host organism includes the non-transitory residence of a bacterium or other microscopic organism. As used herein, "reducing colonization" of a host subject's gastrointestinal tract (or any other microbiotal niche) by a pathogenic bacterium includes a reduction in the residence time of the pathogen in the gastrointestinal tract as well as a reduction in the number (or concentration) of the pathogen in the gastrointestinal tract or adhered to the luminal surface of the gastrointestinal tract. Measuring reductions of adherent pathogens may be demonstrated, e.g., by a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

As used herein "heterologous" designates organisms to be administered that are not naturally present in the same proportions as in the therapeutic composition as in subjects to be treated with the therapeutic composition. These can be organisms that are not normally present in individuals in need of the composition described herein, or organisms that are not present in sufficient proportion in said individuals. These organisms can comprise a synthetic composition of organisms derived from separate plant sources or can comprise a composition of organisms derived from the same plant source, or a combination thereof.

Compositions disclosed herein can be used to treat obesity and metabolic syndrome. As defined herein "obesity" indicates a condition where the subject's body mass index is 30 or higher.

As used herein "metabolic syndrome" indicates a syndrome whose characterizing symptoms include high blood pressure, high blood sugar, excess body fat around the waist, and abnormal cholesterol levels.

As used herein, "diabetes" indicates diabetes mellitus.

Controlled-release refers to delayed release of an agent, from a composition or dosage form in which the agent is released according to a desired profile in which the release occurs after a period of time.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable subcombination or as suitable in any other described embodiment of the invention. Certain features described in the context of various embodiments are not to be considered essential features of those embodiments, unless the embodiment is inoperative without those elements.

It must be noted that, as used in the specification and the appended claims, the singular forms "a," "an" and "the" include plural referents unless the context clearly dictates otherwise.

As used herein GOS indicates one or more galacto-oligosaccharides and FOS indicates one or more fructo-oligosaccharide.

The following abbreviations are used in this specification and/or Figures: ac=acetic acid; but=butyric acid; ppa=propionic acid.

Prebiotic and Probiotic Compositions

In certain embodiments, compositions of the invention comprise probiotic compositions formulated for administration or consumption, with a prebiotic and any necessary or useful excipient. In other embodiments, provided herein are probiotic compositions formulated for consumption without a prebiotic. Probiotic compositions are preferably isolated from foods normally consumed raw and isolated for cultivation. Preferably, microbes are isolated from different foods normally consumed raw, but multiple microbes from the same food source may be used.

It is known to those of skill in the art how to identify microbial strains. Bacterial strains are commonly identified by 16S rRNA gene sequence. Fungal species can be identified by sequence of the internal transcribed space (ITS) regions of rDNA.

One of skill in the art will recognize that the 16S rRNA gene and the ITS region comprise a small portion of the overall genome, and so sequence of the entire genome (whole genome sequence) may also be obtained and compared to known species.

Additionally, multi-locus sequence typing (MLST) is known to those of skill in the art. This method uses the sequences of 7 known bacterial genes, typically 7 housekeeping genes, to identify bacterial species based upon sequence identity of known species as recorded in the publically available PubMLST database. Housekeeping genes are genes involved in basic cellular functions. Examples of MLST gene sequences are provided for DP1, DP3, DP9, DP22, DP53, and DP67-DP71.

In certain embodiments, bacterial entities of the invention are identified by comparison of the 16S rRNA sequence to those of known bacterial species, as is well understood by those of skill in the art. In certain embodiments, fungal species of the invention are identified based upon comparison of the ITS sequence to those of known species (Schoch et al PNAS 2012). In certain embodiments, microbial strains of the invention are identified by whole genome sequencing and subsequent comparison of the whole genome sequence to a database of known microbial genome sequences. While microbes identified by whole genome sequence comparison, in some embodiments, are described and discussed in terms of their closest defined genetic match, as indicated by 16S rRNA sequence, it should be understood that these microbes are not identical to their closest genetic match and are novel microbial entities. This can be shown by examining the Average Nucleotide Identity (ANI) of microbial entities of interest as compared to the reference strain that most closely matches the genome of the microbial entity of interest. ANI is further discussed in example 6.

In other embodiments, microbial entities described herein are functionally equivalent to previously described strains with homology at the 16S rRNA or ITS region. In certain embodiments, functionally equivalent bacterial strains have 95% identity at the 16S rRNA region and functionally equivalent fungal strains have 95% identity at the ITS region. In certain embodiments, functionally equivalent bacterial strains have 96% identity at the 16S rRNA region and functionally equivalent fungal strains have 96% identity at the ITS region. In certain embodiments, functionally equivalent bacterial strains have 97% identity at the 16S rRNA region and functionally equivalent fungal strains have 97% identity at the ITS region. In certain embodiments, functionally equivalent bacterial strains have 98% identity at the 16S rRNA region and functionally equivalent fungal strains have 98% identity at the ITS region. In certain embodiments, functionally equivalent bacterial strains have 99% identity at the 16S rRNA region and functionally equivalent fungal strains have 99% identity at the ITS region. In certain embodiments, functionally equivalent bacterial strains have 99.5% identity at the 16S rRNA region and functionally equivalent fungal strains have 99.5% identity at the ITS region. In certain embodiments, functionally equivalent bacterial strains have 100% identity at the 16S rRNA region and functionally equivalent fungal strains have 100% identity at the ITS region.

16S rRNA sequences for strains tolerant of metformin (described in table 7) are found in seq ID No.s 1-63. 16S rRNA is one way to classify bacteria into operational taxonomic units (OTUs). Bacterial strains with 97% sequence identity at the 16S rRNA locus are considered to belong to the same OTU. A similar calculation can be done with fungi using the ITS locus in place of the bacterial 16S rRNA sequence.

In some embodiments, the invention provides a fermented probiotic composition for the treatment of diabetes, obesity, and metabolic syndrome comprising a mixture of *Pediococcus pentosaceus* and/or *Leuconostoc mesenteroides*, combined with non-lactic acid bacteria isolated or identified from samples described in Table 3 or described in Table 4. In some embodiments, the invention provides a fermented probiotic composition for the treatment of diabetes, obesity, and metabolic syndrome comprising a mixture of *Pediococcus pentosaceus* and/or *Leuconostoc mesenteroides* and at least one non-lactic acid bacterium, preferably a bacterium classified as a gamma proteobacterium or a filamentous fungus or yeast. Some embodiments comprise the fermented probiotic being in a capsule or microcapsule adapted for enteric delivery. In some embodiments, the probiotic regimen complements an anti-diabetic regimen.

The compositions disclosed herein are derived from edible plants and can comprise a mixture of microorganisms, comprising bacteria, fungi, archaea, and/or other indigenous or exogenous microorganisms, all of which work together to form a microbial ecosystem with a role for each of its members.

In some embodiments, species of interest are isolated from plant-based food sources normally consumed raw. These isolated compositions of microorganisms from individual plant sources can be combined to create a new mixture of organisms. Particular species from individual plant sources can be selected and mixed with other species cultured from other plant sources, which have been similarly isolated and grown. In some embodiments, species of interest are grown in pure cultures before being prepared for consumption or administration. In some embodiments, the organisms grown in pure culture are combined to form a synthetic combination of organisms.

In some embodiments, the microbial composition comprises proteobacteria or gamma proteobacteria. In some embodiments, the microbial composition comprises several species of *Pseudomonas*. In some embodiments, species from another genus are also present. In some embodiments, a species from the genus *Duganella* is also present. In some embodiments of said microbial composition, the population comprises at least three unique isolates selected from the group consisting of *Pseudomonas, Acinetobacter, Aeromonas, Curtobacterium, Escherichia, Lactobacillus, Leuconostoc, Pediococcus, Serratia, Streptococcus*, and *Stenotrophomonas*. In some embodiments, the bacteria are selected based upon their ability to modulate production of one or more branch chain fatty acids, short chain fatty acids, and/or flavones in a mammalian gut.

In some embodiments, microbial compositions comprise isolates that are capable of modulating production or activity of the enzymes involved in fatty acid metabolism, such as acetolactate synthase I, N-acetylglutamate synthase, acetate kinase, Acetyl-CoA synthetase, acetyl-CoA hydrolase, Glucan 1,4-alpha-glucosidase, or Bile acid symporter Acr3.

In some embodiments, the administered microbial compositions colonize the treated mammal's digestive tract. In some embodiments, these colonizing microbes comprise bacterial assemblages present in whole food plant-based diets. In some embodiments, these colonizing microbes comprise *Pseudomonas* with a diverse species denomination that is present and abundant in whole food plant-based diets. In some embodiments, these colonizing microbes reduce free fatty acids absorbed into the body of a host by absorbing the free fatty acids in the gastrointestinal tract of mammals. In some embodiments, these colonizing microbes comprise genes encoding metabolic functions related to desirable health outcomes such as increased efficacy of anti-diabetic treatments, lowered BMI, lowered inflammatory metabolic indicators, etc.

Some embodiments comprise bacteria that are not completely viable but act by releasing metabolites that act in the gastro-intestinal tract of a patient promoting weight loss, increased efficacy of diabetic regimens, or other desirable outcome. Some embodiments comprise a prebiotic composition derived from metabolites present in whole food plant-based materials, identified and enriched as part of the formula for oral delivery.

Prebiotics

Prebiotics, in accordance with the teachings of this disclosure, comprise compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect a subject's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

Prebiotics help probiotics flourish in the gastrointestinal tract, and accordingly, their health benefits are largely indirect. Metabolites generated by colonic fermentation by intestinal microflora, such as short-chain fatty acids, can play important functional roles in the health of the host. Prebiotics can be useful agents for enhancing the ability of intestinal microflora to provide benefits to their host.

Prebiotics, in accordance with the embodiments of this invention, include, without limitation, mucopolysaccharides, oligosaccharides, polysaccharides, amino acids, vitamins, nutrient precursors, proteins, and combinations thereof.

According to particular embodiments, compositions comprise a prebiotic comprising a dietary fiber, including, without limitation, polysaccharides and oligosaccharides. These compounds have the ability to increase the number of probiotics, and augment their associated benefits. For example, an increase of beneficial Bifidobacteria likely changes the intestinal pH to support the increase of Bifidobacteria, thereby decreasing pathogenic organisms.

Non-limiting examples of oligosaccharides that are categorized as prebiotics in accordance with particular embodiments include galactooligosaccharides, fructooligosaccharides, inulins, isomalto-oligosaccharides, lactilol, lactosucrose, lactulose, pyrodextrins, soy oligosaccharides, transgalacto-oligosaccharides, and xylo-oligosaccharides.

According to other particular embodiments, compositions comprise a prebiotic comprising an amino acid.

Prebiotics are found naturally in a variety of foods including, without limitation, cabbage, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans). Generally, according to particular embodiments, compositions comprise a prebiotic present in a sweetener composition or functional sweetened composition in an amount sufficient to promote health and wellness.

In particular embodiments, prebiotics also can be added to high-potency sweeteners or sweetened compositions. Non-limiting examples of prebiotics that can be used in this manner include fructooligosaccharides, xylooligosaccharides, galactooligosaccharides, and combinations thereof.

Many prebiotics have been discovered from dietary intake including, but not limited to: antimicrobial peptides, polyphenols, Okara (soybean pulp by product from the manufacturing of tofu), polydextrose, lactosucrose, malto-oligosaccharides, gluco-oligosaccharides (GOS), fructo-oligosaccharides (FOS), xantho-oligosaccharides, soluble dietary fiber in general. Types of soluble dietary fiber include, but are not limited to, *psyllium*, pectin, or inulin. Phytoestrogens (plant-derived isoflavone compounds that have estrogenic effects) have been found to have beneficial growth effects of intestinal microbiota through increasing microbial activity and microbial metabolism by increasing the blood testosterone levels, in humans and farm animals. Phytoestrogen compounds include but are not limited to: Oestradiol, Daidzein, Formononetin, Biochainin A, Genistein, and Equol.

Dosage for the compositions described herein are deemed to be "effective doses," indicating that the probiotic or prebiotic composition is administered in a sufficient quantity to alter the physiology of a subject in a desired manner. In some embodiments, the desired alterations include reducing obesity, and or metabolic syndrome, and sequelae associated with these conditions. In some embodiments, the desired alterations are promoting rapid weight gain in livestock. In some embodiments, the prebiotic and probiotic compositions are given in addition to an anti-diabetic regimen.

FOS, GOS, and Other Appropriate Polysaccharide Formulations

Formulations

In an aspect, prebiotic compositions for the treatment of T2D, obesity and metabolic syndrome are provided. In an embodiment a prebiotic composition comprises inulin, FOS, lactulose, GOS, raffinose, stachyose, or a combination thereof. In addition, other plant-derived polysaccharides such as xylan, pectin, isomalto-oligosaccharides, gentio-oligosaccharides, 4-O-methyl glucuronoxylan (GX), neutral arabinoxylan (AX), heteroxylan (HX) can be combined with the probiotics to enhance bacterial metabolic function. Some of these can be derived from plant material found in the plant host from which the probiotics were isolated (i.e., the "cognate" plant). In some embodiments the prebiotics are thus adapted to be assimilated and digested by the accompanying probiotics in a manner that recapitulates the rich complexity and variety of polysaccharides present in the cognate plant and which play a role during digestion following its consumption of an animal.

In an embodiment a prebiotic composition comprises or consists of FOS, GOS, or other appropriate polysaccharide. In another embodiment a prebiotic composition comprises FOS, GOS, or other appropriate polysaccharide, in combination with one or more digestible saccharides. Digestible saccharides are saccharides that are digestible by humans and include, but are not limited to lactose, glucose, and galactose. In an embodiment a prebiotic composition comprises FOS, GOS, or other appropriate polysaccharide, and less than 20% weight/weight of one or more digestible saccharides (e.g. lactose, glucose, or galactose). In an embodiment a prebiotic composition comprises FOS, GOS, or other appropriate polysaccharide, and less than 10% of one or more digestible saccharides. In an embodiment a prebiotic composition comprises FOS, GOS, or other appropriate polysaccharide, and less than 5% of one or more digestible saccharides. In another embodiment a prebiotic composition contains less than 5% lactose. In another embodiment a prebiotic composition contains less than 4% lactose. In another embodiment a prebiotic composition contains less than 3% lactose. In another embodiment a prebiotic composition contains less than 2% lactose. In another embodiment a prebiotic composition contains less than 1% lactose. In another embodiment a prebiotic composition contains less than 0.5% lactose. In another embodiment a prebiotic composition contains less than 0.4% lactose. In another embodiment a prebiotic composition contains less than 0.3% lactose. In another embodiment a prebiotic composition contains less than 0.2% lactose. In another embodiment a prebiotic composition contains less than 0.1% lactose. In another embodiment a prebiotic composition contains less than 0.05% lactose. In another embodiment a prebiotic composition contains less than 0.01% lactose. In another embodiment a prebiotic composition contains less than 0.005% lactose. In an embodiment a prebiotic composition comprises FOS, GOS, or other appropriate polysaccharide, and essentially no lactose. In an embodiment a prebiotic composition does not contain any lactose. In another embodiment a prebiotic composition contains FOS, GOS, or other appropriate polysaccharide, and at least one probiotic bacteria strain. In another embodiment a prebiotic composition comprises FOS, GOS, or other appropriate polysaccharide, and optionally one or more of lactose, at least one probiotic bacteria strain, or a buffer. Additional ingredients include ingredients to improve handling, preservatives, antioxidants, flavorings and the like.

In an embodiment, a prebiotic composition comprises FOS, GOS, or other appropriate polysaccharide, or a probiotic. In other embodiment, a prebiotic composition is in the form of a powder, tablet, capsule, or liquid. In an embodiment, a prebiotic composition can be administered with a dairy product and is in the form of milk or other common dairy product such as a yogurt, shake, smoothie, cheese, and the like.

In embodiments where a prebiotic composition comprises less than 100% by weight of FOS, GOS, or other appropriate polysaccharide, the remaining ingredients can be any suitable ingredients intended for the consumption of the subject in need thereof, e.g., human, including, but not limited to, other prebiotics (e.g., FOS), a buffer, one or more digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings, and the like.

Buffer Components

One or more buffers, optionally with a calcium counter ion, can also be administered in methods and compositions described herein. Any buffer suitable for consumption by the subject being treated, e.g., human, are useful for the compositions herein. The buffer can partially or wholly neutralize stomach acidity, which can, e.g., allow live bacteria to reach the gut. Buffers include citrates, phosphates, and the like. One embodiment utilizes a buffer with a calcium counter ion, such as Calcium Phosphate Tribasic. The calcium can serve to restore the calcium that many lactose intolerant subjects are missing in their diet. Calcium phosphate can protect *Lactobacillus acidophilus* from bile.

In an embodiment, a buffer such as calcium phosphate is given prior to beginning treatment with a prebiotic composition (such as a composition comprising or consisting essentially of FOS, GOS, or other appropriate polysaccharide), optionally in conjunction with administration of bacteria. In an embodiment, a buffer such as calcium phosphate is given in conjunction with treatment with a prebiotic composition (e.g., a composition comprising or consisting essentially of FOS, GOS, or other appropriate polysaccharide), for part or all of the treatment with lactose. Thus, in an embodiment, some or all doses of a prebiotic composition are accompanied by a dose of a buffer such as calcium phosphate. In an embodiment, a buffer such as calcium phosphate is given initially with a prebiotic composition (such as a composition comprising or consisting essentially of FOS, GOS, or other appropriate polysaccharide), but then the buffer use is discontinued. For example, the initial one, two, three, four, five, six, seven, eight, nine, ten, or more than ten days of treatment with a prebiotic composition can include doses of a buffer such as calcium phosphate, with the use of the buffer discontinued after that time. In an embodiment, a buffer such as calcium phosphate can be given for the first two days of treatment, and then the administration of buffer is discontinued. In an embodiment, a buffer such as calcium phosphate, either alone or in combination with other substances or treatments is used after the treatment with a prebiotic composition is terminated. A buffer such as calcium phosphate can be taken for any suitable period after the termination of treatment with lactose, and can be taken daily or at regular or irregular intervals. Doses can be as described below.

Numerous buffers suitable for human consumption are known in the art, and any suitable buffer can be used in the methods and compositions described herein. Calcium triphosphate is an exemplary buffer, and its counterion supplies a nutrient that is often lacking in lactose-intolerant subjects, i.e., calcium. In an embodiment a buffer can be used in a dose from about 2 mg to about 2000 mg, or about 4 mg to about 400 mg, or about 4 mg to about 200 mg, or about 4 mg to about 100 mg, or about 8 mg to about 50 mg, or about 10 mg to about 40 mg, or about 20 mg to about 30 mg, or about 20, 21, 22, 23, 24, 25, 26, 27, 28, 29, or 30 mg. In another embodiment a prebiotic composition further comprises an amount of a buffer from 1-50 mg, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg. In an embodiment, buffer is used in a dose of about 25 mg. In an embodiment, calcium phosphate is used in a dose of about 25 mg. The dose can be given in combination with a prebiotic composition (e.g., a composition comprising or consisting essentially of FOS, GOS, or other appropriate polysaccharide). In an embodiment, as a prebiotic composition dose increases, the dose of buffer increases as well. For example, an initial dose of a prebiotic composition can be about 0.6 g to 1.0 g, e.g., 0.8 g, given in combination with about 20-30 mg, e.g., about 25 mg, of buffer, e.g., calcium phosphate. The dose of a prebiotic composition can be increased incrementally by about 0.6 g to 1.0 g, e.g., 0.8 g, and the accompanying dose of buffer, e.g., calcium phosphate, can be increased by about 20-30 mg, e.g., about 25 mg, of buffer, e.g., calcium phosphate.

Compositions Comprising GOS and at Least One Probiotic Bacteria Strain

In an embodiment, a prebiotic composition comprises FOS, GOS, or other appropriate polysaccharide, and at least one probiotic bacteria strain. The FOS, GOS, or other appropriate polysaccharide can comprise more than 1% of the weight of the composition while the at least one probiotic bacteria strain will typically comprise less than about 10%, 5%, 4%, 3%, or 2% by weight of the compositions. For example, the FOS, GOS, or other appropriate polysaccharide can be present at about 1-99.75% by weight and the at least one probiotic bacteria strain at about 0.25-2% by weight, or the FOS, GOS, or other appropriate polysaccharide can be present at about 89-96% by weight and the bacteria at about 1.2-3.7% by weight. In an embodiment, FOS, GOS, or other appropriate polysaccharide are present at about 92% by weight and at least one probiotic bacteria strain, (e.g., *L. mesenteroides, P. pentosaceus*, or other members from Table 4), is present at about 1.5% by weight. In an embodiment, FOS, GOS, or other appropriate polysaccharide are present at about 92% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 93% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 94% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 95% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 96% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 97% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 98% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 98.5% by weight and at least one probiotic bacteria strain, (e.g., *L. mesenteroides, P. pentosaceus*, or other members from Table 4), is present at about 1.5% by weight. If the at least one probiotic bacteria strain and FOS, GOS, or other appropriate polysaccharide do not make up 100% by weight of the prebiotic composition, the remaining ingredients can be any suitable ingredients intended for consumption by the subject in need thereof, e.g., human, including, but not limited to, other prebiotics (e.g., FOS), one or more buffers, digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising FOS, GOS, or Other Appropriate Polysaccharide and a Buffer In another embodiment, a prebiotic composition comprises FOS, GOS, or other appropriate polysaccharide and a buffer (e.g., calcium phosphate tribasic). For example, FOS, GOS, or other appropriate polysaccharide can be present at about 1-100% by weight and the buffer at about 0.50-4% by weight, or FOS, GOS, or other appropriate polysaccharide can be present at about 1-96% by weight and the buffer at about 1 to about 3.75% by weight. In an embodiment, FOS, GOS, or other appropriate polysaccharide are present at about 1% by weight and buffer is present at about 3% by weight. In an embodiment, FOS, GOS, or other appropriate polysaccharide are present at about 5% by weight and buffer is present at about 3% by weight. In an embodiment, FOS, GOS, or other appropriate polysaccharide are present at about 10% by weight and buffer is present at about 3% by weight. In an embodiment, FOS, GOS, or other appropriate polysaccharide are present at about 15% by weight and buffer is present at about 15% by weight. In an embodiment, FOS, GOS, or other appropriate polysaccharide are present at about 20% by weight and buffer is present at about 3% by weight. In an embodiment, FOS, GOS, or other appropriate polysaccharide are present at about 25% by weight and buffer is present at about 3% by weight. In an embodiment, FOS, GOS, or other appropriate polysaccharide are present at about 30% by weight and buffer is present at about 3% by weight. In an embodiment, FOS, GOS, or other appropriate polysaccharide are present at about 35% by weight and buffer is present at about 3% by weight. In an embodiment, FOS, GOS, or other appropriate polysaccharide are present at about 40% by weight and buffer is present at about 3% by weight. In an embodiment, FOS, GOS, or other appropriate polysaccharide are present at about 50% by weight and buffer is present at about 3% by weight. In an embodiment, FOS, GOS, or other appropriate polysaccharide are present at about 60% by weight and buffer is present at about 3% by weight. In an embodiment, FOS, GOS, or other appropriate polysaccharide are present at about 70% by weight and buffer is present at about 3% by weight. In another embodiment, FOS, GOS, or other appropriate polysaccharide are present at about 90% by weight and buffer is present at about 3% by weight. In another embodiment, FOS, GOS, or other appropriate polysaccharide are present at about 92% by weight and buffer is present at about 3% by weight. In another embodiment, FOS, GOS, or other appropriate polysaccharide are present at about 93% by weight and buffer is present at about 3% by weight. In another embodiment, FOS, GOS, or other appropriate polysaccharide are present at about 94% by weight and buffer is present at about 3% by weight. In another embodiment, FOS, GOS, or other appropriate polysaccharide are present at about 95% by weight and buffer is present at about 3% by weight. In another embodiment, FOS, GOS, or other appropriate polysaccharide are present at about 96% by weight and buffer is present at about 3% by weight. In another embodiment, FOS, GOS, or other appropriate polysaccharide are present at about 97% by weight and buffer is present at about 2% by weight. In another embodiment, FOS, GOS, or other appropriate polysaccharide are present at about 98% by weight and buffer is present at about 1% by weight. In another embodiment, FOS, GOS, or other appropriate polysaccharide are present at about 99% by weight and buffer is present at about 1% by weight. In another embodiment, FOS, GOS, or other appropriate polysaccharide are present at about 100% by weight and buffer is present at less than about 1% by weight. If the buffer and FOS, GOS, or other appropriate polysaccharide do not make up 100% by weight of the composition, the remaining ingredients can be any suitable ingredients intended for consumption by the subject (e.g., a human) including, but not limited to, probiotics (e.g., beneficial bacteria) or other prebiotics (e.g., FOS), but also including ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising a Digestible Saccharide, a Probiotic Bacteria, and FOS, GOS, or Other Appropriate Polysaccharide In an embodiment, a prebiotic composition comprises a digestible saccharide (e.g. lactose, glucose, or galactose), a probiotic bacteria (e.g., *L. mesenteroides, P. pentosaceus*, or other members from Table 4), and FOS, GOS, or other appropriate polysaccharide. In an embodiment, lactose can be present at about 1-20% by weight, bacteria at about 0.25-20.10% by weight, and FOS, GOS, or other appropriate polysaccharide at about 1-98.75% by weight. In another embodiment lactose can be present at about 5-20% by weight, bacteria at about 0.91-1.95% by weight, and FOS, GOS, or other appropriate polysaccharide at about 1 to about 96% by weight. In another embodiment, lactose is present at about 20% by weight, bacteria at about 1.5% by weight, and FOS, GOS, or other appropriate polysaccharide are present at about 1% by weight. In another embodiment, lactose is present at about 20% by weight, bacteria at about 1.5% by weight, and FOS, GOS, or other appropriate polysaccharide are present at about 50% by weight. In another embodiment, lactose is present at about 20% by weight, bacteria at about 1.5% by weight, and FOS, GOS, or other appropriate polysaccharide are present at about 60% by weight. In another embodiment, lactose is present at about 20% by weight, bacteria at about 1.5% by weight, and FOS, GOS, or other appropriate polysaccharide are present at about 70% by weight. In another embodiment, lactose is present at about 5% by weight, bacteria at about 1.5% by weight, and FOS, GOS, or other appropriate polysaccharide are present at about 90% by weight. In another embodiment, lactose is present at about 5% by weight, bacteria at about 1.5% by weight, and FOS, GOS, or other appropriate polysaccharide are present at about 92% by weight. In another embodiment, lactose is present at about 5% by weight, bacteria at about 1.5% by weight, and FOS, GOS, or other appropriate polysaccharide are present at about 93% by weight. In another embodiment, lactose is present at about 5% by weight, bacteria at about 1% by weight, and FOS, GOS, or other appropriate polysaccharide are present at about 94% by weight. In another embodiment, lactose is present at about 4.5% by weight, bacteria at about 1.5% by weight, and FOS, GOS, or other appropriate polysaccharide are present at about 94% by weight. In another embodiment, lactose is present at about 4.5% by weight, bacteria at about 0.5% by weight, and FOS, GOS, or other appropriate polysaccharide are present at about 95% by weight. In another embodiment, lactose is present at about 3.5% by weight, bacteria at about 0.5% by weight, and FOS, GOS, or other appropriate polysaccharide are present at about 96% by weight. In another embodiment, lactose is present at about 2.5% by weight, bacteria at about 0.5% by weight, and FOS, GOS, or other appropriate polysaccharides are present at about 97% by weight. In another embodiment, lactose is present at about 1.5% by weight, bacteria at about 0.5% by weight, and FOS, GOS, or other appropriate polysaccharide are present at about 98% by weight. In another embodiment, lactose is present at about 0.5% by weight, bacteria at about 0.5% by weight, and FOS, GOS, or other appropriate polysaccharide are present at about 99% by weight. If the bacteria, FOS, GOS, or other appropriate polysaccharide and lactose do not make up 100% of the composition, the remaining ingredients can be any suitable ingredients intended for consumption by the subject, e.g., a human, including, but not limited to a buffer, digestible saccharides (e.g., lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising FOS, GOS, or Other Appropriate Polysaccharide, a Probiotic Bacteria, and Buffer In an embodiment, a prebiotic composition comprises FOS, GOS, or other appropriate polysaccharide, a probiotic bacteria strain, and buffer. In an embodiment, FOS, GOS, or other appropriate polysaccharide can be present at about 1-100% by weight, a probiotic bacteria strain at about 0.25-2% by weight, and the buffer at about 0.50-4% by weight. In another embodiment, FOS, GOS, or other appropriate polysaccharide can be present at about 1-95% by weight, a probiotic bacteria strain at about 0.91-1.95% by weight, and the buffer at about 1.2-30.75% by weight. In another embodiment, FOS, GOS, or other appropriate polysaccharide are present at about 1% by weight, a probiotic bacteria strain at about 1.5% by weight, and buffer is present at about 3% by weight. In another embodiment, FOS, GOS, or other appropriate polysaccharide are present at about 5% by weight, a probiotic bacteria strain at about 1.5% by weight, and buffer is present at about 3% by weight. In another embodiment, FOS, GOS, or other appropriate polysaccharide are present at about 10% by weight, a probiotic bacteria strain at about 1.5% by weight, and buffer is present at about 3% by weight. In another embodiment, FOS, GOS, or other appropriate polysaccharide are present at about 15% by weight, a probiotic bacteria strain at about 1.5% by weight, and buffer is present at about 3% by weight. In another embodiment, FOS, GOS, or other appropriate polysaccharide are present at about 20% by weight, a probiotic bacteria strain at about 1.5% by weight, and buffer is present at about 3% by weight. In another embodiment, FOS, GOS, or other appropriate polysaccharide are present at about 25% by weight, a probiotic bacteria strain at about 1.5% by weight, and buffer is present at about 3% by weight. In another embodiment, FOS, GOS, or other appropriate polysaccharide are present at about 30% by weight, a probiotic bacteria strain at about 1.5% by weight, and buffer is present at about 3% by weight. In another embodiment, FOS, GOS, or other appropriate polysaccharide are present at about 35% by weight, a probiotic bacteria strain at about 1.5% by weight, and buffer is present at about 3% by weight. In another embodiment, FOS, GOS, or other appropriate polysaccharide are present at about 40% by weight, a probiotic bacteria strain at about 1.5% by weight, and buffer is present at about 3% by weight. In another embodiment, FOS, GOS, or other appropriate polysaccharide are present at about 50% by weight, a probiotic bacteria strain at about 1.5% by weight, and buffer is present at about 3% by weight. In another embodiment, FOS, GOS, or other appropriate polysaccharide are present at about 60% by weight, a probiotic bacteria strain at about 1.5% by weight, and buffer is present at about 3% by weight. In another embodiment, FOS, GOS, or other appropriate polysaccharide are present at about 70% by weight, a probiotic bacteria strain at about 1.5% by weight, and buffer is present at about 3% by weight. In another embodiment, FOS, GOS, or other appropriate polysaccharide are present at about 90% by weight, a probiotic bacteria strain at about 1.5% by weight, and buffer is present at about 3% by weight. In another embodiment, FOS, GOS, or other appropriate polysaccharide are present at about 92% by weight, a probiotic bacteria strain at about 1.5% by weight, and buffer is present at about 3% by weight. In another embodiment, FOS, GOS, or other appropriate polysaccharide are present at about 93% by weight, a probiotic bacteria strain at about 1.5% by weight, and buffer is present at about 3% by weight. In another embodiment, FOS, GOS, or other appropriate polysaccharide are present at about 94% by weight, a probiotic bacteria strain at about 1.5% by weight, and buffer is present at about 3% by weight. In another embodiment, FOS, GOS, or other appropriate polysaccharide are present at about 95% by weight, a probiotic bacteria strain at about 1.5% by weight, and buffer is present at about 3% by weight. In another embodiment, FOS, GOS, or other appropriate polysaccharide are present at about 96% by weight, a probiotic bacteria strain at about 1.5% by weight, and buffer is present at about 2% by weight. In another embodiment, FOS, GOS, or other appropriate polysaccharide are present at about 97% by weight, a probiotic bacteria strain at about 1.5% by weight, and buffer is present at about 1.5% by weight. In another embodiment, FOS, GOS, or other appropriate polysaccharide are present at about 99% by weight, a probiotic bacteria strain at about 0.5% by weight, and buffer is present at about 0.5% by weight. In another embodiment, FOS, GOS, or other appropriate polysaccharide are present at about 100% by weight, a probiotic bacteria strain at less than about 0.5% by weight, and buffer is present at less than about 0.5% by weight. If the probiotic bacteria strain, buffer, and FOS, GOS, or other appropriate polysaccharide do not make up 100% of the composition, the remaining ingredients can be any suitable ingredients intended for the consumption of a subject (e.g., human) including, but not limited to, other prebiotics (e.g., FOS), digestible saccharides (e.g., lactose, glucose or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising a Digestible Saccharide, FOS, GOS, or Other Appropriate Polysaccharide, and a Buffer.

In an embodiment, a prebiotic composition comprises a digestible saccharide (e.g. lactose, glucose, or galactose), FOS, GOS, or other appropriate polysaccharide, and a buffer. For example, lactose can be present at about 1-20% by weight, FOS, GOS, or other appropriate polysaccharide at about 1-100% by weight, and the buffer at about 0.50-4% by weight, or the lactose can be present at about 5-20% by weight, FOS, GOS, or other appropriate polysaccharide at about 1-96% by weight, and the buffer at about 1.2-30.75% by weight. In an embodiment, lactose is present at about 20% by weight, FOS, GOS, or other appropriate polysaccharide at about 1% by weight, and buffer is present at about 3% by weight. In an embodiment, lactose is present at about 5% by weight, FOS, GOS, or other appropriate polysaccharide at about 1% by weight, and buffer is present at about 3% by weight. In an embodiment, lactose is present at about 20% by weight, FOS, GOS, or other appropriate polysaccharide at about 10% by weight, and buffer is present at about 3% by weight. In an embodiment, lactose is present at about 20% by weight, FOS, GOS, or other appropriate polysaccharide at about 15% by weight, and buffer is present at about 3% by weight. In an embodiment, lactose is present at about 20% by weight, FOS, GOS, or other appropriate polysaccharide at about 20% by weight, and buffer is present at about 3% by weight. In an embodiment, lactose is present at about 20% by weight, FOS, GOS, or other appropriate polysaccharide at about 25% by weight, and buffer is present at about 3% by weight. In an embodiment, lactose is present at about 20% by weight, FOS, GOS, or other appropriate polysaccharide at about 30% by weight, and buffer is present at about 3% by weight. In an embodiment, lactose is present at about 20% by weight, FOS, GOS, or other appropriate polysaccharide at about 35% by weight, and buffer is present at about 3% by weight. In an embodiment, lactose is present at about 20% by weight, FOS, GOS, or other appropriate polysaccharide at about 40% by weight, and buffer is present at about 3% by weight. In an embodiment, lactose is present at about 20% by weight, FOS, GOS, or other appropriate polysaccharide at about 50% by weight, and buffer is present at about 3% by weight. In an embodiment, lactose is present at about 20% by weight, FOS, GOS, or other appropriate polysaccharide at about 60% by weight, and buffer is present at about 3% by weight. In an embodiment, lactose is present at about 20% by weight, FOS, GOS, or other appropriate polysaccharide at about 70% by weight, and buffer is present at about 3% by weight. In another embodiment, lactose is present at about 5% by weight, FOS, GOS, or other appropriate polysaccharide at about 90% by weight, and buffer is present at about 3% by weight. In another embodiment, lactose is present at about 5% by weight, FOS, GOS, or other appropriate polysaccharide at about 92% by weight, and buffer is present at about 3% by weight. In another embodiment, lactose is present at about 4% by weight, FOS, GOS, or other appropriate polysaccharide at about 93% by weight, and buffer is present at about 3% by weight. In another embodiment, lactose is present at about 3% by weight, FOS, GOS, or other appropriate polysaccharide at about 94% by weight, and buffer is present at about 3% by weight. In another embodiment, lactose is present at about 2% by weight, FOS, GOS, or other appropriate polysaccharide at about 95% by weight, and buffer is present at about 3% by weight. In another embodiment, lactose is present at about 1% by weight, FOS, GOS, or other appropriate polysaccharide at about 96% by weight, and buffer is present at about 3% by weight. If a suitable prebiotic, buffer and lactose do not make up 100% of the composition by weight, the remaining ingredients can be any suitable ingredients intended for consumption by a subject (e.g., human) including, but not limited to, bacteria, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising a Digestible Saccharide, Bacteria, GOS, and a Buffer

In an embodiment, a composition comprises a digestible saccharide (e.g. lactose, glucose, or galactose), bacteria, FOS, GOS, or other appropriate polysaccharide, and buffer. For example, lactose can be present at about 1-20% by weight, bacteria at about 0.25-2.10% by weight, FOS, GOS, or other appropriate polysaccharide at about 1-100% by weight, and the buffer at about 0.50-4% by weight, or the lactose can be present at about 5-20% by weight, bacteria at about 0.91-1.95% by weight, FOS, GOS, or other appropriate polysaccharide at about 70-95% by weight, and the buffer at about 1.2-30.75% by weight. In an embodiment, lactose is present at about 20% by weight, bacteria at about 1.47% by weight, FOS, GOS, or other appropriate polysaccharide at about 1% by weight, and buffer is present at about 3% by weight. In an embodiment, lactose is present at about 20% by weight, bacteria at about 1.47% by weight, FOS, GOS, or other appropriate polysaccharide at about 10% by weight, and buffer is present at about 3% by weight. In an embodiment, lactose is present at about 20% by weight, bacteria at about 1.47% by weight, FOS, GOS, or other appropriate polysaccharide at about 15% by weight, and buffer is present at about 3% by weight. In an embodiment, lactose is present at about 20% by weight, bacteria at about 1.47% by weight, FOS, GOS, or other appropriate polysaccharide at about 20% by weight, and buffer is present at about 3% by weight. In an embodiment, lactose is present at about 20% by weight, bacteria at about 1.47% by weight, FOS, GOS, or other appropriate polysaccharide at about 25% by weight, and buffer is present at about 3% by weight. In an embodiment, lactose is present at about 20% by weight, bacteria at about 1.47% by weight, FOS, GOS, or other appropriate polysaccharide at about 30% by weight, and buffer is present at about 3% by weight. In an embodiment, lactose is present at about 20% by weight, bacteria at about 1.47% by weight, FOS, GOS, or other appropriate polysaccharide at about 35% by weight, and buffer is present at about 3% by weight. In an embodiment, lactose is present at about 20% by weight, bacteria at about 1.47% by weight, FOS, GOS, or other appropriate polysaccharide at about 40% by weight, and buffer is present at about 3% by weight. In an embodiment, lactose is present at about 20% by weight, bacteria at about 1.47% by weight, FOS, GOS, or other appropriate polysaccharide at about 50% by weight, and buffer is present at about 3% by weight. In an embodiment, lactose is present at about 20% by weight, bacteria at about 1.47% by weight, FOS, GOS, or other appropriate polysaccharide at about 60% by weight, and buffer is present at about 3% by weight. In an embodiment, lactose is present at about 20% by weight, bacteria at about 1.47% by weight, FOS, GOS, or other appropriate polysaccharide at about 70% by weight, and buffer is present at about 3% by weight. In an embodiment, lactose is present at about 5% by weight, bacteria at about 1.47% by weight, FOS, GOS, or other appropriate polysaccharide at about 90% by weight, and buffer is present at about 3% by weight. In an embodiment, lactose is present at about 3% by weight, bacteria at about 1.47% by weight, FOS, GOS, or other appropriate polysaccharide at about 92% by weight, and buffer is present at about 3% by weight. In an embodiment, lactose is present at about 2% by weight, bacteria at about 1.47% by weight, FOS, GOS, or other appropriate polysaccharide at about 93% by weight, and buffer is present at about 3% by weight. In an embodiment, lactose is present at about 1% by weight, bacteria at about 1.47% by weight, FOS, GOS, or other appropriate polysaccharide at about 94% by weight, and buffer is present at about 3% by weight. In an embodiment, lactose is present at about 0.5% by weight, bacteria at about 1.47% by weight, FOS, GOS, or other appropriate polysaccharide at about 95% by weight, and buffer is present at about 3% by weight. If the bacteria, FOS, GOS, or other, buffer and lactose do not make up 100% of the composition by weight, the remaining ingredients can be any suitable ingredients intended for consumption by a subject, e.g., human, including, but not limited to, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Additional Ingredients

Additional ingredients include ingredients to improve handling, preservatives, antioxidants, flavorings and the like. For example, in an embodiment, a prebiotic composition in powdered form can include flavorings such that when mixed in a liquid (e.g., water), the powder can flavor the liquid with various flavors such as grape, strawberry, lime, lemon, chocolate, and the like. In an embodiment, the compositions include microcrystalline cellulose or silicone dioxide. Preservatives can include, for example, benzoic acid, alcohols, for example, ethyl alcohol, and hydroxybenzoates. Antioxidants can include, for example, butylated hydroxyanisole (BHA), butylated hydroxytoluene (BHT), tocopherols (e.g., Vitamin E), and ascorbic acid (Vitamin C).

Methods of Use

Included within the scope of this disclosure are methods for treatment of diabetes, obesity, and/or metabolic syndrome.

These methods include treatment with a prebiotic composition (e.g., a composition comprising or consisting of FOS, GOS, or other appropriate polysaccharide), optionally in conjunction with a probiotic composition, one or more digestible saccharides (e.g. lactose, glucose, or galactose), a buffer, or a combination thereof. These methods optionally are used in combination with other treatments to reduce diabetes, obesity, and/or metabolic syndrome. Any suitable treatment for the reduction of diabetes, obesity and/or metabolic syndrome can be used. In some embodiments the additional treatment is administered before, during, or after treatment with a prebiotic composition, or any combination thereof. In an embodiment, when diabetes, obesity and/or metabolic syndrome are not completely or substantially completely eliminated by treatment with a prebiotic composition, the additional treatment is administered after prebiotic treatment is terminated. The additional treatment is used on an as-needed basis.

In an embodiment, treating diabetes further involves administration of any one or combination of known anti-diabetic medications. These include, but are not limited to, metformin, Acarbose, Miglitol, Voglibose, Sitagliptin, Saxagliptin, Liraglutide, Pioglitazone, dipeptidyl peptidase-4 (DPP4)-inhibitors, glucagon-like peptide-1 (GLP-1) receptor analogs, alpha glucosidase inhibitors, thiazolidinedione, and sodium/glucose cotransporter 2 (SGLT2) inhibitors.

In an embodiment a subject to be treated for one or more symptoms of obesity and/or metabolic syndrome is a human. In an embodiment the human subject is a preterm newborn, a full-term newborn, an infant up to one year of age, a young child (e.g., 1 yr to 12 yrs), a teenager, (e.g., 13-19 yrs), an adult (e.g., 20-64 yrs), a pregnant woman, or an elderly adult (65 yrs and older).

The administration of the microbial composition can be accomplished orally or rectally, although administration is not limited to these methods. In some embodiments, the microbial composition is administered orally. In some embodiments, the microbial composition is delivered rectally. In some embodiments, the administration of the microbial composition occurs at regular intervals. In some embodiments, the administration occurs daily.

The microbial composition can be administered via typical pharmacological means, such as slurries, capsules, microcapsules, or solutions, although means of administration are not limited to these methods. In some embodiments, an enteric capsule or enteric microcapsule is used. In some embodiments the pharmaceutical composition involving the microbial composition described herein will be fresh or frozen prior to application. In some embodiments, said pharmaceutical composition will be lyophilized or otherwise treated to increase stability or otherwise obtain a benefit from said treatment.

In some embodiments, the microbial composition is administered with an effective amount of an anti-diabetic drug or along with an effective anti-diabetic drug regimen.

Timing and Dose of Probiotics and Prebiotics

In an embodiment, probiotic bacteria, such as *Lactobacillus, Leuconostoc*, or *Pediococcus* are given prior to beginning treatment with a prebiotic. In an embodiment, probiotic bacteria, such as *L. mesenteroides*, are given in conjunction with treatment with a prebiotic (e.g., comprising or consisting essentially of FOS, GOS, or other appropriate polysaccharide), for part or all of the duration of treatment with the prebiotic. Thus, in an embodiment, some or all doses of a prebiotic (e.g., comprising or consisting essentially of FOS, GOS, or other appropriate polysaccharide) are accompanied by a dose of bacteria, e.g., live cultured bacteria, e.g., *L. mesenteroides*. In an embodiment, bacteria, e.g., *L. mesenteroides*, are given initially with a prebiotic (e.g., comprising or consisting essentially of FOS, GOS, or other appropriate polysaccharide), but then use of the bacteria is discontinued. For example, the initial one, two, three, four, five, six, seven, eight, nine, ten, or more than ten days of treatment with a prebiotic (e.g., comprising or consisting essentially of FOS, GOS, or other appropriate polysaccharide) further comprises doses of bacteria, with the use of bacteria discontinued after that time. In an embodiment, bacteria, (e.g., bacteria in yogurt), or bacteria by themselves, can be given for the first two days of treatment; then the administration of bacteria is discontinued. In another embodiment, probiotic bacteria, either alone or in combination with other substances or treatments are used after the treatment with a prebiotic (comprising or consisting essentially of FOS, GOS, or other appropriate polysaccharide) is terminated. The bacteria can be taken for any suitable period after the termination of treatment with prebiotic and can be taken daily or at regular or irregular intervals. Doses can be as described below.

Any suitable amount of probiotic per serving can be used that allows an effective microbiota in the GI as demonstrated by a reduction in weight or amelioration of other signs of metabolic syndrome measured by insulin resistance, HbAlc, body mass index (BMI), visceral adiposity, and dyslipidemia. Typically, probiotics are given as live cultured bacteria. Herein measurement is mg indicate dry weight of purified bacteria. The dose can be about 0.001 mg to about 1 mg, or about 0.5 mg to about 5 mg, or about 1 mg to about 1000 mg, or about 2 mg to about 200 mg, or about 2 mg to about 100 mg, or about 2 mg to about 50 mg, or about 4 mg to about 25 mg, or about 5 mg to about 20 mg, or about 10 mg to about 15 mg, or about 50 mg to about 200 mg, or about 200 mg to about 1000 mg, or about 10, 11, 12, 12.5, 13, 14, or 15 mg per serving. In an embodiment, *L. mesenteroides* used in a dose of about 12.5 mg per serving. The probiotic bacteria can also be about 0.5% w/w to about 20% w/w of the final composition. The dose of probiotics can be given in combination with one or more prebiotics. Another common way of specifying the amount of probiotics is as a colony forming unit (cfu). In an embodiment, one or more strains of probiotic bacteria are ingested in an amount of about 1×10^6 to about 1×10^9 cfu's, or about 1×10^6 cfu's to about 1×10^9 cfu's, or about 10×10^6 cfu's to about 0.5×10^9 cfu's, or about 113×10^5 cfu's to about 113×10^6 cfu's, or about 240×10^5 cfu's to about 240×10^6 cfu's, or about 0.3×10^9 cfu's per serving. In another embodiment, one or more strains of probiotic bacteria are administered as part of a dairy product. In an embodiment, a typical serving size for a dairy product such as fluid milk is about 240 g. In other embodiments, a serving size is about 245 g, or about 240 g to about 245 g, or about 227 to about 300 g. In an embodiment the dairy product is yogurt. Yogurt can have a serving size of about 4 oz, or about 6 oz, or about 8 oz, or about 4 oz to 10 oz, or about half cup, or about 1 cup, or about 113 g, or about 170 g, or about 227 g, or about 245 g or about 277 g, or about 100 g to about 350 g.

In an embodiment, probiotic bacteria are given as live cultured bacteria, e.g., in combination with a prebiotic (e.g., comprising or consisting essentially of FOS, GOS, or other appropriate polysaccharide) and, optionally, other substances. The dose can be about 1 mg to about 1000 mg, or about 2 mg to about 200 mg, or about 2 mg to about 100 mg, or about 2 mg to about 50 mg, or about 4 mg to about 25 mg, or about 5 mg to about 20 mg, or about 10 mg to about 15 mg, or about 10, 11, 12, 12.5, 13, 14, or 15 mg of probiotic bacterial cell culture dry weight. In an embodiment, *Lactobacillus* (i.e. *L. acidophilus*), *Leuconostoc* (i.e. *L. mesenteroides*), or *Pediococcus* (i.e. *P. pentosaceus*), is used in a dose of about 12.5 mg. In an embodiment, as the administration of a prebiotic (e.g., comprising or consisting essentially of FOS, GOS, or other appropriate polysaccharide)

dose to a subject increases, the dose of bacteria increases as well. For example, an initial dose of a prebiotic (e.g., comprising or consisting essentially of FOS, GOS, or other appropriate polysaccharides) can be about 0.6 g to 1.0 g, e.g., 0.8 g, given in combination with about 10-15 mg, e.g., about 12.5 mg, of *L. mesenteroides*. The dose of a prebiotic (e.g., comprising or consisting essentially of FOS, GOS, or other appropriate polysaccharide) can be increased incrementally by about 0.6 g to 1.0 g, e.g., 0.8 g, and the accompanying dose of *L. mesenteroides* can be increased by about 10-15 mg, e.g., about 12.5 mg, of *L. mesenteroides*.

Timing and Dosage of Probiotic and Anti-Diabetic Drugs

In an embodiment, probiotic bacteria, such as *L. mesenteroides, P. pentosaceus*, are given prior to beginning treatment with an anti-diabetic drug. In an embodiment, probiotic bacteria, such as *L. mesenteroides, P. pentosaceus*, are given in conjunction with treatment with an anti-diabetic drug, such as metformin, for part or all of the treatment with the anti-diabetic drug. Thus, in an embodiment, some or all doses of an anti-diabetic drug are accompanied by a dose of bacteria, e.g., live cultured bacteria, e.g., *L. mesenteroides, P. pentosaceus*. In an embodiment, bacteria, e.g., *L. mesenteroides, P. pentosaceus*, are given initially with an anti-diabetic therapy, but then use of the bacteria is discontinued. For example, the initial one, two, three, four, five, six, seven, eight, nine, ten, or more than ten days of treatment with an anti-diabetic drug further comprises doses of bacteria, with the use of bacteria discontinued after that time. In an embodiment, bacteria, (e.g., bacteria in yogurt), or bacteria by themselves, can be given for the first two days of treatment; then the administration of bacteria is discontinued. In another embodiment, probiotic bacteria, either alone or in combination with other substances or treatments are used after the treatment with an anti-diabetic drug is terminated. The bacteria can be taken for any suitable period after the termination of treatment with the anti-diabetic drug and can be taken daily or at regular or irregular intervals. Doses can be as described below. Any suitable amount of probiotic per serving can be used that allows an effective microbiota in the GI as demonstrated by a reduction in weight or amelioration of other signs of metabolic syndrome measured by one or more of: insulin resistance, HbA1c, body mass index (BMI), visceral adiposity, and dyslipidemia.

Examples of antidiabetic combination partners are metformin; sulphonylureas such as glibenclamide, tolbutamide, glimepiride, glipizide, gliquidon, glibornuride and gliclazide; nateglinide; repaglinide; thiazolidinediones such as rosiglitazone and pioglitazone; PPAR gamma modulators such as metaglidases; PPAR-gamma agonists such as GI 262570; PPAR-gamma antagonists; PPAR-gamma/alpha modulators such as tesaglitazar, muraglitazar, aleglitazar, indeglitazar, AVE0897 and KRP297; PPAR-gamma/alpha/delta modulators; AMPK-activators such as AICAR; acetyl-CoA carboxylase (ACC1 and ACC2) inhibitors; diacylglycerol-acetyltransferase (DGAT) inhibitors; pancreatic beta cell GPCR agonists other than GPR119 agonists; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin zinc suspension and insulin glargin; Gastric inhibitory Peptide (GIP); pramlintide, davalintide; amylin and amylin analogues or GLP-1 and GLP-1 analogues such as Exendin-4, e.g. exenatide, exenatide LAR, liraglutide, taspoglutide, AVE-0010, LY-2428757, LY-2189265, semaglutide or albiglutide; SGLT2-inhibitors such as KGT-1251; inhibitors of protein tyrosine-phosphatase (e.g., trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors, such as e.g. dapagliflozin, sergliflozin, atigliflozin, larnagliflozin or canagliflozin (or compound of formula (I-S) or (I-K) from WO 2009/035969); KV 1.3 channel inhibitors; GPR40 modulators; SCD-1 inhibitors; dopamine receptor agonists (bromocriptine mesylate [Cycloset]); and CCR-2 antagonists.

Metformin is usually given in doses varying from about 250 mg to 3000 mg, particularly from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day.

Particular dosage strengths may be 250, 500, 625, 750, 850 and 1000 mg of metformin hydrochloride.

Dosage Forms

Compositions described herein include any suitable form, including liquid or powder. Powdered compositions can be as pure powder, or can be in the form of capsules, tablets, or the like. Powder can be packaged in bulk (e.g., in a container containing sufficient prebiotic or other substances for a subject to follow for an entire course of treatment with increasing doses of prebiotic, or a portion of a course of treatment), or as individual packets (e.g., packets containing a single dose of prebiotic plus other components, or packets containing the dose of prebiotic and other components needed for a particular day of a prebiotic treatment regimen). If packaged in bulk, the powder can be in any suitable container, such as a packet, sachet, canister, ampoule, ramekin, or bottle. The container can also include one or more scoops or similar serving devices of a size or sizes appropriate to measure and serve one or more doses of prebiotic and, optionally, other ingredients included in the powder. Liquid compositions contain prebiotic and, optionally, other ingredients, in a suitable liquid, e.g., water or buffer. Liquid compositions can be provided in bulk (e.g., in a container containing sufficient prebiotic or other substances for one subject in need thereof to follow an entire course of treatment with increasing doses of prebiotic, or a portion of a course of treatment), or as individual containers, such as cans, bottles, soft packs, and the like (e.g., containers containing a single dose of prebiotic plus other components in suitable liquid, or containers containing the dose of prebiotic and other components needed for a particular day of a prebiotic treatment regimen). The container can also include one or more measuring cups or similar serving devices of a size or sizes appropriate to measure and serve one or more doses of prebiotic and, optionally, other ingredients included in the liquid.

In an embodiment, compositions described herein comprise one or more excipients. In an embodiment, the one or more excipients comprise one or more antiadherents, one or more binders, one or more coatings, one or more disintegrants, one or more fillers, one or more flavors, one or more colors, one or more lubricants, one or more glidants, one or more sorbents, one or more preservatives, one or more sweeteners, or a combination thereof. In an embodiment, the antiadherent is magnesium stearate. In an embodiment, the one or more binders are cellulose, microcrystalline cellulose, hydroxypropyl cellulose, xylitol, sorbitol, maltitiol, gelatin, polyvinylpyrrolidone, polyethylene glycol, methyl cellulose, hydroxypropyl methylcellulose, or a combination thereof. In an embodiment, the one or more coatings are a hydroxypropyl methylcellulose film, shellac, corn protein zein, gelatin, methyl acrylate-methacrylic acid copolymers, cellulose acetate succinate, hydroxy propyl methyl cellulose phthalate, hydroxy propyl methyl cellulose acetate succinate, polyvinyl acetate phthalate, methyl methacrylate-methacrylic acid copolymers, sodium alginate, stearic acid, or a combination thereof. In an embodiment, the one or more disintegrants are crosslinked polyvinylpyrrolidone (crospovidone), crosslinked sodium carboxymethyl cellulose (croscarmellose sodium), sodium starch glycolate, or a combination thereof. In an embodiment, the one or more fillers are calcium carbonate, magnesium stearate, dibasic calcium phosphate, cellulose, vegetable oil, vegetable fat, or a combination thereof. In an embodiment, the one or more flavors are mint, cherry, anise, peach, apricot, licorice, raspberry, vanilla, or a combination thereof. In an embodiment, the one or more lubricants are talc, silica, vegetable stearin, magnesium stearate, stearic acid, or a combination thereof. In an embodiment, the one or more glidants are fumed silica, talc, magnesium carbonate, or a combination thereof. In an embodiment, the one or more sorbents are fatty acids, waxes, shellac, plastics, plant fibers, or a combination thereof. In an embodiment, the one or more preservatives are vitamin A, vitamin E, vitamin C, retinyl palmitate, selenium, cysteine, methionine, citric acid, sodium citrate, methyl paraben, propyl paraben, or a combination thereof. In an embodiment, the one or more sweeteners are stevia, sparame, sucralose, neotame, acesulfame potassium, saccharin or a combination thereof.

Oral Dosage Forms and Components

In one aspect provided herein are methods and compositions formulated for oral delivery to a subject in need thereof. In an embodiment a composition is formulated to deliver a composition comprising a prebiotic to a subject in need thereof. In another embodiment, a pharmaceutical composition is formulated to deliver a composition comprising a prebiotic to a subject in need thereof. In another embodiment a composition is formulated to deliver a composition comprising prebiotic and a probiotic to a subject in need thereof 1. Forms In an embodiment, a composition is administered in solid, semi-solid, micro-emulsion, gel, or liquid form. Examples of such dosage forms include tablet forms disclosed in U.S. Pat. Nos. 3,048,526, 3,108,046, 4,786,505, 4,919,939, and 4,950,484; gel forms disclosed in U.S. Pat. Nos. 4,904,479, 6,482,435, 6,572,871, and 5,013,726; capsule forms disclosed in U.S. Pat. Nos. 4,800,083, 4,532,126, 4,935,243, and 6,258,380; or liquid forms disclosed in U.S. Pat. Nos. 4,625,494, 4,478,822, and 5,610,184; each of which is incorporated herein by reference in its entirety.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients including freeze-dried plant material serving both as prebiotic and as a filler. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds (prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Oral liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydoxybenzoate or sorbic acid, and, if desired, conventional flavoring or coloring agents.

In an embodiment, a provided composition includes a softgel formulation. A softgel can contain a gelatin-based shell that surrounds a liquid fill. The shell can be made of gelatin, plasticiser (e.g., glycerin and/or sorbitol), modifier, water, color, antioxidant, or flavor. The shell can be made with starch or carrageenan. The outer layer can be enteric coated. In an embodiment, a softgel formulation can include a water or oil soluble fill solution, or suspension of a composition, for example, a prebiotic composition, covered by a layer of gelatin.

An enteric coating can control the location of where a prebiotic composition is absorbed in the digestive system. For example, an enteric coating can be designed such that a prebiotic composition does not dissolve in the stomach, but rather, travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade name aquacoat CPD®, Sepifilm™ LP, Klucel®, Aquacoat® ECD, and Metolose®); polyvinylacetate phthalate (trade name Sureteric®); and methacrylic acid (trade name Eudragit®).

In an embodiment, an enteric coated prebiotic composition is administered to a subject. In another embodiment, an enteric coated probiotic composition is administered to a subject. In another embodiment, an enteric coated probiotic and prebiotic composition is administered to a subject. In an embodiment, probiotic bacteria can be administered to a subject using an enteric coating. The stomach has an acidic environment that can kill probiotics. An enteric coating can protect probiotics as they pass through the stomach and small intestine.

Enteric coatings can be used to (1) prevent the gastric juice from reacting with or destroying the active substance, (2) prevent dilution of the active substance before it reaches the intestine, (3) ensure that the active substance is not released until after the preparation has passed the stomach, and (4) prevent live bacteria contained in the preparation from being killed because of the low pH-value in the stomach.

Enteric coatings can also be used for avoiding irritation of or damage to the mucous membrane of the stomach caused by substances contained in the oral preparation, and for counteracting or preventing formation or release of substances having an unpleasant odor or taste in the stomach. Finally, such coatings can be used for preventing nausea or vomiting on intake of oral preparations.

In an embodiment a prebiotic composition is provided as a tablet, capsule, or caplet with an enteric coating. In an embodiment the enteric coating is designed to hold the tablet, capsule, or caplet together when in the stomach. The enteric coating is designed to hold together in acid conditions of the stomach and break down in non-acid conditions and therefore release the drug in the intestines.

Softgel delivery systems can also incorporate phospholipids or polymers or natural gums to entrap a composition, for example, a prebiotic composition, in the gelatin layer with an outer coating to give desired delayed/control release effects, such as an enteric coating.

Formulations of softgel fills can be at pH 2.5-7.5.

A softgel formulation can be sealed tightly in an automatic manner. A softgel formulation can easily be swallowed, allow for product identification using colors and several shapes, allow uniformity, precision and accuracy between dosages, be safe against adulteration, provide good availability and rapid absorption, and offer protection against contamination, light and oxidation. Furthermore, softgel formulations can avoid unpleasant flavors due to content encapsulation.

A composition comprising a softgel formulation can be in any of number of different sizes, including, for example, round, oblong, oval, tube, droplet, or suppositories.

In an embodiment a composition is provided in a dosage form which comprises an effective amount of prebiotic and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. In an embodiment the dosage form is a tablet, caplet, capsule or lollipop. In another embodiment, the dosage form is a liquid, oral suspension, oral solution, or oral syrup. In yet another embodiment, the dosage form is a gel capsule, soft gelatin capsule, or hard gelatin capsule.

In an embodiment, the dosage form is a gelatin capsule having a size indicated in Table 1.

Gel Cap Sizes Allowable for Human Consumption

Empty Gelatin Capsule Physical Specifications. Note: sizes and volumes are approximate.

TABLE 1

| Outer Diameter Size (mm) | Height or Locked Length (mm) | Actual Volume (ml) |
|---|---|---|
| 9.97 | 26.14 | 1.37 |
| 8.53 | 23.30 | 0.95 |
| 7.65 | 21.7 | 0.68 |
| 6.91 | 19.4 | 0.50 |
| 6.35 | 18.0 | 0.37 |
| 5.82 | 15.9 | 0.3 |
| 5.31 | 14.3 | 0.21 |
| 4.91 | 11.1 | 0.13 |

In another embodiment a composition comprising a prebiotic is provided in effervescent dosage forms. The compositions can also comprise non-release controlling excipients.

In another embodiment, a composition comprising a prebiotic is provided in a dosage form that has at least one component that can facilitate release of the prebiotic. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances.

In another embodiment the prebiotic mixture is a plant or plant extract, either in solid or liquid form.

In another embodiment a composition comprising a prebiotic is provided in an enteric coated dosage form. The composition can also comprise non-release controlling excipients.

In another embodiment a composition comprising a prebiotic is provided in a dosage form for oral administration to a subject in need thereof, which comprises one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In an embodiment a composition comprising a prebiotic is provided in the form of enteric-coated granules, for oral administration. The compositions can further comprise cellulose, disodium hydrogen phosphate, hydroxypropyl cellulose, hypromellose, lactose, mannitol, and sodium lauryl sulfate.

In another embodiment a composition comprising a prebiotic is provided in the form of enteric-coated pellets, for oral administration. The compositions can further comprise glyceryl monostearate 40-50, hydroxypropyl cellulose, hypromellose, magnesium stearate, methacrylic acid copolymer type C, polysorbate 80, sugar spheres, talc, and triethyl citrate.

In an embodiment a composition comprising a prebiotic is provided in the form of enteric-coated granules, for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In another embodiment a composition comprising a prebiotic can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The compositions provided herein can be in unit-dosage forms or multiple-dosage forms. Unit-dosage forms, as used herein, refer to physically discrete units suitable for administration to human or non-human animal subject in need thereof and packaged individually. Each unit-dose can contain a predetermined quantity of an active ingredient(s) sufficient to produce the desired therapeutic effect, in association with other pharmaceutical carriers or excipients. Examples of unit-dosage forms include, but are not limited to, ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents. For example, a multiple dosage form can be provided which comprises a first dosage element comprising a composition comprising a prebiotic and a second dosage element comprising lactose or a probiotic, which can be in a modified release form.

In this example a pair of dosage elements can make a single unit dosage. In an embodiment a kit is provided comprising multiple unit dosages, wherein each unit comprises a first dosage element comprising a composition comprising a prebiotic and a second dosage element comprising probiotic, lactose or both, which can be in a modified release form. In another embodiment the kit further comprises a set of instructions.

In an embodiment, compositions can be formulated in various dosage forms for oral administration. The compositions can also be formulated as a modified release dosage form, including immediate-, delayed-, extended-, prolonged-, sustained-, pulsatile-, controlled-, extended, accelerated-, fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which is herein incorporated by reference in its entirety).

In an embodiment, the compositions are in one or more dosage forms. For example, a composition can be administered in a solid or liquid form. Examples of solid dosage forms include but are not limited to discrete units in capsules or tablets, as a powder or granule, or present in a tablet conventionally formed by compression molding. Such compressed tablets can be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of a composition comprising a prebiotic. Furthermore, dosage forms of the invention can comprise acceptable carriers or salts known in the art, such as those described in the Handbook of Pharmaceutical Excipients, American Pharmaceutical Association (1986), incorporated by reference herein in its entirety.

In an embodiment, an effective amount of a composition comprising a prebiotic is mixed with a pharmaceutical excipient to form a solid preformulation composition comprising a homogeneous mixture of compounds described herein. When referring to these compositions as "homogeneous," it is meant that the agents are dispersed evenly throughout the composition so that the composition can be subdivided into unit dosage forms such as tablets, caplets, or capsules. This solid preformulation composition can then be subdivided into unit dosage forms of the type described above comprising from, for example, about 1 g to about 20 mg of a prebiotic composition. A prebiotic composition can be formulated, in the case of caplets, capsules or tablets, to be swallowed whole, for example with water.

The compositions described herein can be in liquid form. The liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for oral administration. Examples of such vehicles and additives can be found in Remington's Pharmaceutical Sciences, 17th edition (1985).

Manufacturing

The dosage forms described herein can be manufactured using processes that are well known to those of skill in the art. For example, for the manufacture of tablets, an effective amount of a prebiotic can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers," can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

In an embodiment, a softgel formulation is made with a gelatin mass for the outer shell, and a composition including one or more substances, for example prebiotics and/or probiotics, for the capsule fill can be prepared. To make the gelatin mass, gelatin powder can be mixed with water and glycerin, heated, and stirred under vacuum. Additives, for example, flavors or colors, can be added to molten gelatin using a turbine mixer and transferred to mobile vessels. The gelatin mass can be kept in a steam-jacketed storage vessel at a constant temperature.

The encapsulation process can begin when the molten gel is pumped to a machine and two thin ribbons of gel are formed on either side of machine. These ribbons can then pass over a series of rollers and over a set of die that determine the size and shapes of capsules. A fill composition, for example a prebiotic and/or probiotic fill composition, can be fed to a positive displacement pump, which can dose the fill and inject it between two gelatin ribbons prior to sealing them together through the application of heat and pressure. To remove excess water, the capsules can pass through a conveyer into tumble dryers where a portion of the water can be removed. The capsules can then be placed on, for example, trays, which can be stacked and transferred into drying rooms. In the drying rooms, dry air can be forced over capsules to remove any excess moisture.

3. Release Formulations

Immediate-release formulations of an effective amount of a prebiotic composition can comprise one or more combinations of excipients that allow for a rapid release of a pharmaceutically active agent (such as from 1 minute to 1 hour after administration). In an embodiment an excipient can be microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, Avicel PH200, and combinations of such excipients.

"Controlled-release" formulations (also referred to as sustained release (SR), extended-release (ER, XR, or XL), time-release or timed-release, controlled-release (CR), or continuous-release) refer to the release of a prebiotic composition from a dosage form at a particular desired point in time after the dosage form is administered to a subject. Controlled-release formulations can include one or more excipients, including but not limited to microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, or Avicel PH200. Generally, controlled-release includes sustained but otherwise complete release. A sudden and total release in the large intestine at a desired and appointed time or a release in the intestines such as through the use of an enteric coating are both considered controlled-release. Controlled-release can occur at a predetermined time or in a predetermined place within the digestive tract. It is not meant to include a passive, uncontrolled process as in swallowing a normal tablet. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,556; 5,871,776; 5,902,632; and 5,837,284 each of which is incorporated herein by reference in its entirety.

In an embodiment a controlled release dosage form begins its release and continues that release over an extended period of time. Release can occur beginning almost immediately or can be sustained. Release can be constant, can increase or decrease over time, can be pulsed, can be continuous or intermittent, and the like. Generally, however, the release of at least one pharmaceutically active agent from a controlled-release dosage form will exceed the amount of time of release of the drug taken as a normal, passive release tablet. Thus, for example, while all of at least one pharmaceutically active agent of an uncoated aspirin tablet should be released within, for example, four hours, a controlled-release dosage form could release a smaller amount of aspirin over a period of six hours, 12 hours, or even longer. Controlled-release in accordance with the compositions and methods described herein generally means that the release occurs for a period of six hours or more, such as 12 hours or more.

In another embodiment a controlled release dosage refers to the release of an agent, from a composition or dosage form in which the agent is released according to a desired profile over an extended period of time. In an embodiment, controlled-release results in dissolution of an agent within 20-720 minutes after entering the stomach. In another embodiment, controlled-release occurs when there is dissolution of an agent within 20-720 minutes after being swallowed. In another embodiment, controlled-release occurs when there is dissolution of an agent within 20-720 minutes after entering the intestine. In another embodiment, controlled-release results in substantially complete dissolution after at least 1 hour following administration. In another embodiment, controlled-release results in substantially complete dissolution after at least 1 hour following oral administration. For example, controlled-release compositions allow delivery of an agent to a subject in need thereof over an extended period of time according to a predetermined profile. Such release rates can provide therapeutically effective levels of agent for an extended period of time and thereby provide a longer period of pharmacologic or diagnostic response as compared with conventional rapid release dosage forms. Such longer periods of response provide for many inherent benefits that are not achieved with immediate-release dosages. When used in connection with the dissolution profiles discussed herein, the term "controlled-release" refers to wherein all or less than all of the total amount of a dosage form, made according to methods and compositions described herein, delivers an active agent over a period of time greater than 1 hour.

When present in a controlled-release oral dosage form, the compositions described herein can be administered at a substantially lower daily dosage level than immediate-release forms.

In an embodiment, the controlled-release layer is capable of releasing about 30 to about 40% of the one or more active agents (e.g., prebiotic and/or probiotic) contained therein in the stomach of a subject in need thereof in about 5 to about 10 minutes following oral administration. In another embodiment, the controlled-release layer is capable of releasing about 90% of the one or more active agents (e.g., prebiotic and/or probiotic) is released in about 40 minutes after oral administration.

In some embodiments, the controlled-release layer comprises one or more excipients, including but not limited to silicified microcrystalline cellulose (e.g., HD90), croscarmellose sodium (AC-Di-Sol), hydroxyl methyl propyl cellulose, magnesium stearate, or stearic acid. In an embodiment, a controlled release formulation weighs between about 100 mg to 3 g.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action.

In another embodiment, an effective amount of the prebiotic is formulated in an immediate release form. In this embodiment the immediate-release form can be included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing," which is incorporated herein in its entirety by reference.

The dosage forms described herein can also take the form of pharmaceutical particles manufactured by a variety of methods, including but not limited to high-pressure homogenization, wet or dry ball milling, or small particle precipitation (nano spray). Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size.

In a further aspect the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a prebiotic). The acid sources can be any which are safe for human consumption and can generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included. In an embodiment citric acid and sodium bicarbonate are used.

In another aspect the dosage form can be in a candy form (e.g., matrix), such as a lollipop or lozenge. In an embodiment an effective amount of a prebiotic is dispersed within a candy matrix. In an embodiment the candy matrix comprises one or more sugars (such as dextrose or sucrose). In another embodiment the candy matrix is a sugar-free matrix. The choice of a particular candy matrix is subject to wide variation. Conventional sweeteners such as sucrose can be utilized, or sugar alcohols suitable for use with diabetic patients, such as sorbitol or mannitol can be employed. Other sweeteners, such as the aspartames, can also be easily incorporated into a composition in accordance with compositions described herein. The candy base can be very soft and fast dissolving, or can be hard and slower dissolving. Various forms will have advantages in different situations.

A candy mass composition comprising an effective amount of the prebiotic can be orally administered to a subject in need thereof so that an effective amount of the prebiotic will be released into the subject's mouth as the candy mass dissolves and is swallowed. A subject in need thereof includes a human adult or child.

In an embodiment a candy mass is prepared that comprises one or more layers which can comprise different amounts or rates of dissolution of the prebiotic. In an embodiment a multilayer candy mass (such as a lollipop) comprises an outer layer with a concentration of the prebiotic differing from that of one or more inner layers. Such a drug delivery system has a variety of applications.

The choices of matrix and the concentration of the drug in the matrix can be important factors with respect to the rate of drug uptake. A matrix that dissolves quickly can deliver drug into the subject's mouth for absorption more quickly than a matrix that is slow to dissolve. Similarly, a candy matrix that contains the prebiotic in a high concentration can release more of the prebiotic in a given period of time than a candy having a low concentration. In an embodiment a candy matrix such as one disclosed in U.S. Pat. No. 4,671,953 or US Application Publication No. 2004/0213828 (which are herein incorporated by reference in their entirety) is used to deliver the prebiotic.

The dosage forms described herein can also take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In an embodiment the pharmaceutical particles have a final size of 3-1000 μM, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 μM. In another embodiment the pharmaceutical particles have a final size of 10-500 μM. In another embodiment the pharmaceutical particles have a final size of 50-600 μM. In another embodiment the pharmaceutical particles have a final size of 100-800 μM.

In an embodiment an oral dosage form (such as a powder, tablet, or capsule) is provided comprising a prebiotic composition comprising about 0.7 g of FOS, GOS, or other FOS, GOS, or other appropriate polysaccharide, about 0.2 g of lactose, about 0.01 g of glucose, about 0.01 g of galactose, about 0.1-0.2 g of a binder, about 0.1-0.2 g of a dispersant, about 0.1-0.2 g of a solubilizer, wherein the FOS, GOS, or other FOS, GOS, or other appropriate polysaccharide are composed of about 1-25% disaccharides, about 1-25% trisaccharides, about 1-25% tetrasaccharides, and about 1-25% pentasaccharides. The oral dosage form can be in the form of a powder, capsule, or tablet. Suitable amounts of binders, dispersants, and solubilizers are known in the art for preparation of oral tablets or capsules.

In another embodiment an oral dosage form (such as a powder, tablet or capsule) is provided comprising a prebiotic composition comprising about 1-99.9% by weight of FOS, GOS, or other FOS, GOS, or other appropriate polysaccharide about 0.5-20% by weight of lactose, about 0.1-2% by weight of glucose, about 0.1-2% by weight of galactose, about 0.05-2% by weight of a binder, about 0.05-2% by weight of a dispersant, about 0.05-2% by weight of a solubilizer, wherein the FOS, GOS, or other FOS, GOS, or other appropriate polysaccharide are composed of about 1-25% by weight disaccharides, about 1-25% by weight trisaccharides, about 1-25% by weight tetrasaccharides, and about 1-25% by weight pentasaccharides.

In another embodiment an oral dosage form (such as a powder, tablet, or capsule) is provided comprising a prebiotic composition comprising about 1, 10, 20, 30, 40, 50, 60, 70, 80, 90, 95, 99.5, 100% by weight of FOS, GOS, or other FOS, GOS, or other appropriate polysaccharide about 0, 5, 10, 15, or 20% by weight of lactose, about 0.1, 0.5, 1, or 2% by weight of glucose, about 0.1, 0.5, 1, or 2% by weight of galactose, about 0.05, 0.1, 0.5, 1, or 2% by weight of a binder, about 0.05, 0.1, 0.5, 1, or 2% by weight of a dispersant, about 0.05, 0.1, 0.5, 1, or 2% by weight of a solubilizer, wherein the FOS, GOS, or other FOS, GOS, or other appropriate polysaccharide are composed of about 1, 5, 10, 15, 20, or 25% by weight disaccharides, about 1, 5, 10, 15, 20, or 25% by weight trisaccharides, about 1, 5, 10, 15, 20, or 25% by weight tetrasaccharides, and about 1, 5, 10, 15, 20, or 25% by weight pentasaccharides.

In another embodiment, an oral dosage form is provided comprising a prebiotic composition, wherein the oral dosage form is a syrup. The syrup can comprise about 1%, 5%, 10%, 15%, 20%, 25%, 30%, 35%, 40%, 45%, 50%, 55%, 60%, 65%, 70%, 75%, 80%, or 85% solid. The syrup can comprise about 15%, 20%, 25%, 30%, 35%, 40%, 45%, or 50% liquid, for example, water. The solid can comprise a prebiotic composition. The solid can be, for example, about 1-96%, 10-96%, 20-96%, 30-96%, 40-96%, 50-96%, 60-96%, 70-96%, 80-96%, or 90-96% prebiotic composition. The solid can be, for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96% prebiotic composition. In an embodiment a prebiotic composition comprises FOS, GOS, or other FOS, GOS, or other appropriate polysaccharide. In another embodiment a prebiotic composition comprises FOS, GOS, or other FOS, GOS, or other appropriate polysaccharide and another prebiotic. In another embodiment a prebiotic composition comprises FOS, GOS or other and inulin or GOS and FOS.

In an embodiment, the softgel capsule is about 0.25 mL, 0.5 mL, 1.0 mL, 1.25 mL, 1.5 mL, 1.75 mL, or 2.0 mL. In another embodiment, a softgel capsule comprises about 0.1 g to 2.0 g of prebiotic composition. In another embodiment, a softgel capsule comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 g of a prebiotic composition. In an embodiment the prebiotic composition comprises FOS, GOS, or other FOS, GOS, or other appropriate polysaccharide. In another embodiment the prebiotic composition consists essentially of FOS, GOS, or other FOS, GOS, or other appropriate polysaccharide. In another embodiment, a softgel capsule comprises FOS, GOS, or other FOS, GOS, or other appropriate polysaccharide and inulin or FOS.

In another embodiment, the prebiotic composition is delivered in a gelatin capsule containing an amount of FOS, GOS, or other FOS, GOS, or other appropriate polysaccharide within the ranges listed in Table 2. In another embodiment, the number of pills taken per day is within the ranges listed in Table 2.

TABLE 2

Exemplary GOS Dosing Units
Exemplary GOS Composition
Dosages in Gel Caps
Table 2

| Size | GOS/Pill (g) | # pills per day |
|---|---|---|
| 000 | 1-2 | 1-15 |
| 00 | 0.6-1.5 | 1-25 |
| 0 | 0.4-1.1 | 1-38 |
| 1 | 0.3-0.8 | 1-50 |
| 2 | 0.25-0.6 | 1-60 |
| 3 | 0.2-0.5 | 1-75 |
| 4 | 0.14-0.3 | 1-107 |

In another embodiment, a prebiotic composition is provided that does not contain a preservative. In another embodiment, a prebiotic composition is provided that does not contain an antioxidant. In another embodiment, a prebiotic composition is provided that does not contain a preservative or an antioxidant. In an embodiment a prebiotic composition comprising FOS, GOS, or other FOS, GOS, or other appropriate polysaccharide does not contain a preservative or an antioxidant.

In another embodiment, a prebiotic composition is formulated as a viscous fluid. In another embodiment, a prebiotic composition is formulated such that its water content is low enough that it does not support microbial growth. In an embodiment, this composition is an intermediate-moisture food, with a water activity between 0.6 and 0.85; in another embodiment this composition is a low-moisture food, with a water activity less than 0.6. Low-moisture foods limit microbial growth significantly and can be produced by one of ordinary skill in the art. For example, these products could be produced similarly to a liquid-centered cough drop. In another embodiment, a prebiotic composition is formulated as a viscous fluid without a preservative in a gel capsule. In another embodiment, a prebiotic composition comprising FOS, GOS, or other FOS, GOS, or other appropriate polysaccharide is a viscous fluid. In another embodiment, a prebiotic composition comprises a high percentage of FOS, GOS, or other FOS, GOS, or other appropriate polysaccharide that does not support microbial growth. In another embodiment, the prebiotic composition comprises FOS, GOS, or other FOS, GOS, or other appropriate polysaccharide and inulin or FOS.

In another embodiment, an oral dosage form is provided comprising a prebiotic composition, wherein the oral dosage form is a softgel. In an embodiment the softgel comprises a syrup. In an embodiment the syrup comprises a prebiotic composition. In an embodiment the prebiotic composition comprises FOS, GOS, or other FOS, GOS, or other appropriate polysaccharide. In another embodiment the prebiotic composition comprises more than 80% FOS, GOS, or other FOS, GOS, or other appropriate polysaccharide. In another embodiment the prebiotic composition comprises between 80-99.9% FOS, GOS, or other. In another embodiment the prebiotic composition comprises more than 80% FOS, GOS, or other FOS, GOS, or other appropriate polysaccharide. In another embodiment the prebiotic composition comprises about 80, 81, 82, 83, 84, 85, 86, 87, 88, 89, 90, 91, 92, 93, 94, 95, 96, 97, 98, 99, or 99.9% FOS, GOS, or other FOS, GOS, or other appropriate polysaccharide.

In an embodiment a FOS, GOS, or other FOS, GOS, or other appropriate polysaccharide composition is formulated for delivery in a soft gel capsule. In an embodiment a FOS, GOS, or other FOS, GOS, or other appropriate polysaccharide composition formulated for delivery in a soft gel capsule is a high percentage FOS, GOS, or other FOS, GOS, or other appropriate polysaccharide composition, such as a 90-100% FOS, GOS, or other FOS, GOS, or other appropriate polysaccharide composition (e.g., 90, 91, 92, 93, 94, 95, 96, 97, 98, 99 or 100% FOS, GOS, or other FOS, GOS, or other appropriate polysaccharide composition by weight). In another embodiment a FOS, GOS, or other FOS, GOS, or other appropriate polysaccharide composition formulated for delivery in a soft gel capsule comprises about 95% FOS, GOS, or other FOS, GOS, or other appropriate polysaccharide. In another embodiment a FOS, GOS, or other FOS, GOS, or other appropriate polysaccharide composition formulated for delivery in a soft gel capsule comprises about 96% FOS, GOS, or other FOS, GOS, or other appropriate polysaccharide. In another embodiment, the FOS, GOS, or other FOS, GOS, or other appropriate polysaccharide composition is formulated such that its water content is low enough that it does not support microbial growth. In another embodiment, the FOS, GOS, or other FOS, GOS, or other appropriate polysaccharide composition is formulated as a viscous fluid without a preservative in a gel capsule. In another embodiment, the FOS, GOS, or other FOS, GOS, or other appropriate polysaccharide composition is formulated as a viscous fluid without an antioxidant in a gel capsule. In another embodiment the soft gel capsule comprises about 0.1-2 g of a FOS, GOS, or other FOS, GOS, or other appropriate polysaccharide composition.

In another embodiment a prebiotic composition can be formulated as described, in U.S. Pat. No. 6,750,331, which is herein incorporated by reference in its entirety. A prebiotic composition can be formulated to comprise an oligosaccharide, a foaming component, a water-insoluble dietary fiber (e.g., cellulose or lignin), or a neutralizing component. In an embodiment a prebiotic composition can be in the form of a chewable tablet.

In an embodiment a foaming component can be at least one member selected from the group consisting of sodium hydrogencarbonate, sodium carbonate, and calcium carbonate. In an embodiment a neutralizing component can be at least one member selected from the group consisting of citric acid, L-tartaric acid, fumaric acid, L-ascorbic acid, DL-malic acid, acetic acid, lactic acid, and anhydrous citric acid. In an embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

Formulations of the provided invention can include additive components selected from various known additives. Such additives include, for example, saccharides (excluding oligosaccharides), sugar alcohols, sweeteners and like excipients, binders, disintegrators, lubricants, thickeners, surfactants, electrolytes, flavorings, coloring agents, pH modifiers, fluidity improvers, and the like. Specific examples of the additives include wheat starch, potato starch, corn starch, dextrin and like starches; sucrose, glucose, fructose, maltose, xylose, lactose and like saccharides (excluding oligosaccharides); sorbitol, mannitol, maltitol, xylitol and like sugar alcohols; calcium phosphate, calcium sulfate and like excipients; starch, saccharides, gelatine, gum arabic, dextrin, methyl cellulose, polyvinylpyrrolidone, polyvinyl alcohol, hydroxypropylcellulose, xanthan gum, pectin, gum tragacanth, casein, alginic acid and like binders and thickeners; leucine, isoleucine, L-valine, sugar esters, hardened oils, stearic acid, magnesium stearate, talc, macrogols and like lubricants; CMC, CMC-Na, CMC-Ca and like disintegrators; polysorbate, lecithin and like surfactants; aspartame, alitame and like dipeptides; silicon dioxide and like fluidity improvers; and stevia, saccharin, and like sweeteners. The amounts of these additives can be properly selected based on their relation to other components and properties of the preparation, production method, etc.

In an embodiment, a FOS, GOS, or other FOS, GOS, or other appropriate polysaccharide composition is a chewable oral dosage formulation. In an embodiment the chewable formulation can comprises between about 1-99.9% FOS, GOS, or other FOS, GOS, or other appropriate polysaccharide. In an embodiment, a FOS, GOS, or other FOS, GOS, or other appropriate polysaccharide composition comprises about 80% FOS, GOS, or other FOS, GOS, or other appropriate polysaccharide about 5% L-ascorbic acid, about 2% anhydrous citric acid, about 3% sodium hydrogencarbonate, about 3% calcium carbonate, about 2% sucrose fatty acid, about 3% fruit juice powder, and about 2% potassium carbonate.

In another embodiment, a FOS, GOS, or other FOS, GOS, or other appropriate polysaccharide composition comprises about 85% FOS, GOS, or other FOS, GOS, or other appropriate polysaccharide, about 5% L-ascorbic acid, about 3% sodium hydrogencarbonate, about 2% sodium carbonate, about 2% sucrose fatty acid ester, about 2% fruit juice powder, and about 1% potassium carbonate.

In another embodiment, a FOS, GOS, or other FOS, GOS, or other appropriate polysaccharide composition comprises about 90% FOS, GOS, or other FOS, GOS, or other appropriate polysaccharide, about 2% L-ascorbic acid, about 1% anhydrous citric acid, about 2% sodium hydrogencarbonate, about 2% sodium carbonate, about 2% sucrose fatty acid ester, and about 1% potassium carbonate.

In another embodiment, a FOS, GOS, or other FOS, GOS, or other appropriate polysaccharide composition comprises about 95% FOS, GOS, or other FOS, GOS, or other appropriate polysaccharide, about 2% L-ascorbic acid, about 1% sodium hydrogencarbonate, and about 2% fruit juice powder. In another embodiment, a FOS, GOS, or other FOS, GOS, or other appropriate polysaccharide composition comprises about 95% FOS, GOS, or other FOS, GOS, or other appropriate polysaccharide and about 5% of L-ascorbic acid, anhydrous citric acid, sodium hydrogencarbonate, calcium carbonate, sucrose fatty acid, fruit juice powder, or potassium carbonate.

In another embodiment, a FOS, GOS, or other FOS, GOS, or other appropriate polysaccharide composition comprises about 95% FOS, GOS, or other FOS, GOS, or other appropriate polysaccharide and about 5% of L-ascorbic acid, anhydrous citric acid, sodium hydrogencarbonate, calcium carbonate, sucrose fatty acid, fruit juice powder, and potassium carbonate.

Medical Foods

An alternate embodiment of the present invention is a formulation as a medical food.

The consuming public has come to understand that foods possess more than basic nutrition (protein, carbohydrate, fat, etc). For example, 95% of consumers agree that "certain foods have health benefits that go beyond basic nutrition and may reduce the risk of disease or other health concerns." More than 50% of consumers believe that foods can replace the use of drugs. Replacing the use of drugs may have the benefit of reducing the incidence of adverse side effects suffered by patients following a pharmaceutical drug treatment regimen. In fact, medical foods are assumed to be generally safe, as people have historically consumed these foods safely in non-medical contexts.

The compositions of the invention may be administered under the supervision of a medical specialist, or may be self-administered. Medical foods could take the form of nutritional shakes or other liquids or meal replacements. Medical foods of the present invention could also take the form of a powder capable of being consumed upon addition to suitable food or liquid.

For treatment of metabolic syndrome, obesity or diabetes under clinical supervision it is possible to combine the nutritional approach with conventional pharmaceutical therapies such as weight-control drugs or diabetes medicines. For example, the composition of the invention may be provided in the form of a kit for separate, sequential or simultaneous administration in conjunction with weight-control drugs or diabetes medicines as defined hereinabove.

A medical food formulation of the present invention could confer benefits of a synthetic composition of microbes isolated from nutritionally beneficial plants, as well as the benefits of prebiotics, or other nutritionally beneficial inclusions, but not consumed to obtain nutrition from them but rather to provide a metabolic function different than a foodstuff. For example, medical foods of the invention may also include at least one vitamin, or vitamin precursor. Preferred vitamins possess antioxidant properties and include vitamins A, C and E, and/or their biochemical precursors. Another embodiment of the medical foods of the invention also includes at least one trace element, preferably selected from the group consisting of zinc, manganese and selenium. Medical foods of the invention also may include at least one additional antioxidant selected from the group consisting of carotenoids, N-acetylcysteine and L-glutamine. It is known to those of skill in the art how to construct medical foods containing these elements.

Medical foods of the present invention would include effective doses of microbes deemed useful for the indication and effective doses of any vitamin, prebiotic, or other beneficial additive not consumed to obtain nutrition but to add a therapeutic benefit mediated by the production of SCFA or other immuno-stimulant molecules when passing through the GI tract.

Typically, the dietary supplements and medical foods of the present invention are consumed at least once daily, and preferably administered two times per day, preferably once in the morning and once in the afternoon. A typical treatment regime for the dietary supplements or medical foods will continue for four to eight weeks. Depending on such factors as the medical condition being treated and the response of the patient, the treatment regime may be extended. A medical food of the present invention will typically be consumed in two servings per day as either a meal replacement or as a snack between meals.

Anyone perceived to be at risk from metabolic syndrome, obesity, T2D, or already suffering from these or associated disorders, can potentially benefit from ingesting the compositions of the invention. According to the invention it is believed to be possible to effectively ameliorate symptoms and conditions associated with T2D, metabolic syndrome, or obesity with natural compounds, which do not show any severe side effects. Furthermore, the present methods are expected to be well-tolerated, for example without causing any discomfort or nausea, and simple to apply.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Microbial Preparations and Metagenomic Analyses

A sample set of 15 vegetables typically eaten raw was selected to analyze the microbial communities by whole genome shotgun sequencing and comparison to microbial databases. The 15 fruits and vegetable samples are shown in Table 3 and represent ingredients in typical salads or eaten fresh. The materials were sourced at the point of distribution in supermarkets selling both conventional and organic farmed vegetables, either washed and ready to eat or without washing.

The samples were divided into 50 g portions, thoroughly rinsed with tap water and blended for 30 seconds on phosphate buffer pH 7.4 (PBS) in a household blender. The resulting slurry was strained by serial use of a coarse household sieve and then a fine household sieve followed by filtration through a 40 μm sieve. The cell suspension containing the plant microbiota, chloroplasts and plant cell debris was centrifuged at slow speed (100×g) 5 minutes for removing plant material and the resulting supernatant centrifuged at high speed (4000×g) 10 minutes to pellet microbial cells. The pellet was resuspended in a plant cell lysis buffer containing a chelator such as EDTA 10 mM to reduce divalent cation concentration to less than, and a non-ionic detergent to lyse the plant cells without destroying the bacterial cells. The lysed material was washed by spinning down the microbial cells at 4000×g for 10 minutes, and then resuspended in PBS and repelleted as above. For sample #12 (broccoli) the cell pellet was washed and a fraction of the biomass separated and only the top part of the pellet collected. This was deemed "broccoli juice" for analyses. The resulting microbiota prep was inspected under fluorescence microscopy with DNA stains to visualize plant and microbial cells based on cell size and DNA structure (nuclei for plants) and selected for DNA isolation based on a minimum ratio of 9:1 microbe to plant cells. The DNA isolation was based on the method reported by Marmur (Journal of Molecular Biology 3, 208-218; 1961), or using commercial DNA extraction kits based on magnetic beads such as Thermo Charge Switch resulting in a quality suitable for DNA library prep and free of PCR inhibitors.

The DNA was used to construct a single read 150 base pair libraries and a total of 26 million reads sequenced per sample according to the standard methods done by CosmosID (www.cosmosid.com) for samples #1 to #12 or 300 base pair-end libraries and sequenced in an Illumina NextSeq instrument covering 4 Gigabases per sample for samples #13 to #15. The unassembled reads were then mapped to the CosmosID for first 12 samples or OneCodex for the last 3 samples databases containing 36,000 reference bacterial genomes covering representative members from diverse taxa. The mapped reads were tabulated and represented using a "sunburst" plot to display the relative abundance for each genome identified corresponding to that bacterial strain and normalized to the total of identified reads for each sample. In addition, phylogenetic trees were constructed based on the classification for each genome in the database with a curated review. There are genomes that have not been updated in the taxonomic classifier and therefore reported as unclassified here but it does not reflect a true lack of clear taxonomic position, it reflects only the need for manual curation and updating of those genomes in the taxonomic classifier tool.

Figure 4:
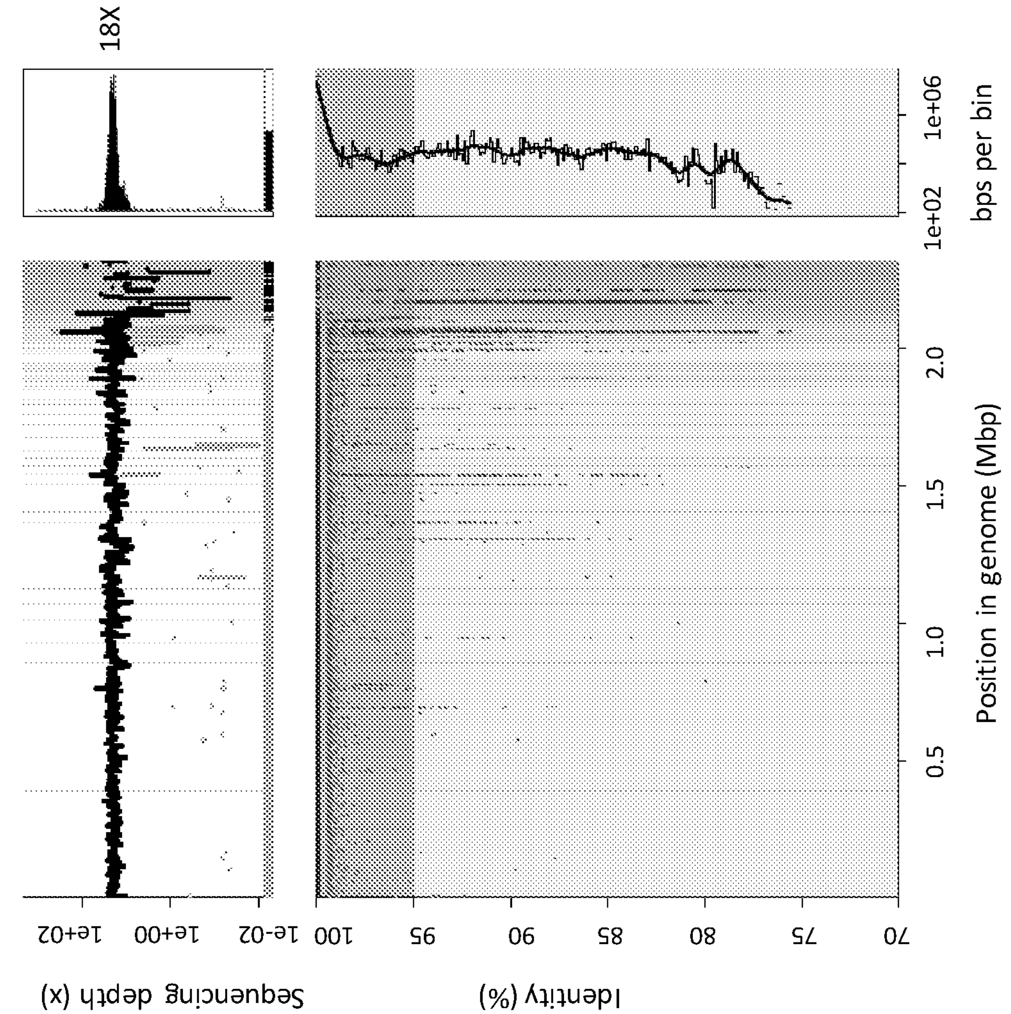
FIG. 4. Shows a fragment recruitment plot sample for the shotgun sequencing on sample 22 (fermented cabbage) comparing to the reference genome of strain DP3 *Leuconostoc mesenteroides*-like and the 18× coverage indicating the isolated strain is represented in the environmental sample and it is relatively clonal.

FIG. 4 shows a fragment recruitment plot sample for the shotgun sequencing on sample 22 (fermented cabbage) comparing to the reference genome of strain DP3 *Leuconostoc mesenteroides*-like and the 18×coverage indicating the isolated strain is represented in the environmental sample and it is relatively clonal.

In addition to the shotgun metagenomics survey relevant microbes were isolated from fruits and vegetables listed in Table 3 using potato dextrose agar or nutrient agar and their genomes sequenced to cover 50× and analyzed their metabolic potential by using genome-wide models. For example, a yeast isolated from blueberries was sequenced and its genome showed identity to *Aureobasidium subglaciale* assembled in contigs with an N50 of 71 Kb and annotated to code for 10, 908 genes. Similarly, bacterial genomes from the same sample were sequenced and annotated for strains with high identity to *Pseudomonas* and *Rahnella.*

The microbial cocktail with the combined individual strains is then adjusted to the correct dose to be fed to mice to validate the efficacy using a laboratory animal model to demonstrate the biological effect in obesity, or metabolic syndrome. For this, a mouse model recapitulating the onset and symptoms on obesity and prediabetes are generated by either feeding a high fat diet to lean mice to induce weight gain and sequelae. This is observed by insulin resistance and increase on BMI. In addition, other mice models such as ob/ob, db/db recapitulating some of the late stages in diabetes seen as hyperglycemia, and observed in the islet cells, n-cells and insulin resistance or not producing insulin at all. For the diet-induced obese and pre-diabetic mice the test animals are subject to a 12-week high fat diet to observe an approximate doubling in weight vs low fat diet control. The subject arm of the mice cohort is then fed with a high fat, diet simulating the Western diet and a range of doses with the candidate assemblage fed daily. The high fat diet is 60% kcal of fat (lard), 20% protein, and 20% carb (https://researchdiets.com/formulas/d12492). The low fat diet control is 10% kcal from fat, 20% protein, and 70% carbohydrate (https://researchdiets.com/formulas/d12450J).

The mice response is measured daily during the treatment period of 4 weeks for acetate in blood, insulin response, weight, BMI and other chronic inflammation indicators.

The optimal dose for the feeding experiment is determined experimentally by providing a range between 10^8 and 10^11 CFU per gram of chow in a feeding experiment that will elicit a response in the mice. The dose, once determined in the animal model is then normalized to a person on an equivalent biomass and food intake.

TABLE 3

Table 3. Samples analyzed.

| Sample # | FIG. 1 Legend | Description |
|---|---|---|
| 1 | 1A | Chard |
| 2 | 1B | Red cabbage |
| 3 | 1C | Organic romaine |
| 4 | 1D | Organic celery |
| 5 | 1E | Butterhead organic lettuce |
| 6 | 1F | Organic baby spinach |
| 7 | 1G | Crisp green gem lettuce |
| 8 | 1H | Red oak leaf lettuce |
| 9 | 1I | Green oak leaf lettuce |
| 10 | 1J | Cherry tomato |
| 11 | 1K | Crisp red gem lettuce |
| 12 | 1L | Broccoli juice |
| 13 | 2A | Broccoli head |
| 14 | 2B | blueberries |
| 15 | 2C | Pickled olives |

Results

For most samples, bacterial abundances of fresh material contain 10^7 to 10^8 microbes per gram of vegetable as estimated by direct microscopy counts. Diverse cell morphologies were observed including rods, elongated rods, cocci and fungal hyphae. Microorganisms were purified from host cells, DNA was isolated and sequenced using a shotgun approach mapping reads to 35,000 bacterial genomes using a k-mer method. All samples were dominated by gamma proteobacteria, primarily Pseudomonadacea, presumably largely endophytes as some samples were triple washed before packaging. *Pseudomonas* cluster was the dominant genera for several samples with 10-90% of the bacterial relative abundance detected per sample and mapped to a total of 27 different genomes indicating it is a diverse group. A second relevant bacterial strain identified was *Duganella zoogloeoides* ATCC 25935 as it was present in almost all the samples ranging from 1-6% of the bacterial relative abundance detected per sample or can reach 29% of the bacterial relative abundance detected per sample in organic romaine. Red cabbage was identified to contain a relatively large proportion of lactic acid bacteria as it showed 22% *Lactobacillus crispatus*, a species commercialized as probiotic and recognized relevant in vaginal healthy microbial community. Another vegetable containing lactic acid bacteria was red oak leaf lettuce containing 1.5% of the bacterial relative abundance detected per sample *Lactobacillus reuteri*. Other bacterial species recognized as probiotics included *Bacillus, Bacteroidetes, Propionibacterium* and *Streptococcus*. A large proportion of the abundant taxa in most samples was associated with plant microbiota and members recognized to act as biocontrol agents against fungal diseases or growth promoting agents such as *Pseudomonas fluorescens*. The aggregated list of unique bacteria detected by the k-mer method is 318 (Table 4).

Blueberries contain a mixture of bacteria and fungi dominated by *Pseudomonas* and *Propionibacterium* but the yeast *Aureobasidium* was identified as a relevant member of the community. A lesser abundant bacterial species was *Rahnella*. Pickled olives are highly enriched in lactic acid bacteria after being pickled in brine allowing the endogenous probiotic populations to flourish by acidifying the environment and eliminating most of the acid-sensitive microbes including bacteria and fungi. This resulted in a large amount of *Lactobacillus* species and *Pediococcus* recognized as probiotics and related to obesity treatment.

The shotgun sequencing method allows for the analysis of the metagenome including genes coding for metabolic reactions involved in the assimilation of nutrient, fermentative processes to produce short chain fatty acids, flavonoids and other relevant molecules in human nutrition.

TABLE 4

Table 4. Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Acinetobacter baumannii* | — | |
| *Acinetobacter soli* | — | |
| *Acinetobacter* 41764 Branch | — | |
| *Acinetobacter* 41930 Branch | — | |
| *Acinetobacter* 41981 Branch | — | |
| *Acinetobacter* 41982 Branch | — | |
| *Acinetobacter baumannii* 348935 | — | |
| *Acinetobacter baumannii* 40298 Branch | — | |
| *Acinetobacter beijerinckii* 41969 Branch | — | |
| *Acinetobacter beijerinckii* CIP 110307 | CIP 110307 | WFCC |
| *Acinetobacter bohemicus* ANC 3994 | — | |
| *Acinetobacter guillouiae* 41985 Branch | — | |
| *Acinetobacter guillouiae* 41986 Branch | — | |
| *Acinetobacter gyllenbergii* 41690 Branch | — | |
| *Acinetobacter haemolyticus* TG19602 | — | |
| *Acinetobacter harbinensis* strain HITLi 7 | — | |
| *Acinetobacter johnsonii* 41886 Branch | — | |
| *Acinetobacter johnsonii* ANC 3681 | — | |
| *Acinetobacter junii* 41994 Branch | — | |
| *Acinetobacter lwoffii* WJ10621 | — | |
| *Acinetobacter* sp 41945 Branch | — | |
| *Acinetobacter* sp 41674 Branch | — | |
| *Acinetobacter* sp 41698 Branch | — | |
| *Acinetobacter* sp ETR1 | — | |
| *Acinetobacter* sp NIPH 298 | — | |
| *Acinetobacter tandoii* 41859 Branch | — | |
| *Acinetobacter tjernbergiae* 41962 Branch | — | |
| *Acinetobacter towneri* 41848 Branch | — | |
| *Acinetobacter venetianus* VE C3 | — | |
| *Actinobacterium* LLX17 | — | |
| *Aeromonas bestiarum* strain CECT 4227 | CECT 4227 | CECT |
| *Aeromonas caviae* strain CECT 4221 | CECT 4221 | CECT |
| *Aeromonas hydrophila* 4AK4 | — | |
| *Aeromonas media* 37528 Branch | — | |
| *Aeromonas media* strain ARB 37524 Branch | — | |
| *Aeromonas salmonicida* subsp 37538 Branch | — | |
| *Aeromonas* sp ZOR0002 | — | |
| *Agrobacterium* 22298 Branch | — | |
| *Agrobacterium* 22301 Branch | — | |
| *Agrobacterium* 22313 Branch | — | |
| *Agrobacterium* 22314 Branch | — | |
| *Agrobacterium* sp ATCC 31749 | ATCC 31749 | ATCC |
| *Agrobacterium tumefaciens* 22306 Branch | | |
| *Agrobacterium tumefaciens* strain MEJ076 | — | |
| *Agrobacterium tumefaciens* strain S2 | — | |
| *Alkanindiges illinoisensis* DSM 15370 | DSM 15370 | WFCC |
| alpha proteobacterium L41A | — | |
| *Arthrobacter* 20515 Branch | — | |
| *Arthrobacter arilaitensis* Re117 | — | |
| *Arthrobacter chlorophenolicus* A6 | — | |
| *Arthrobacter nicotinovorans* 20547 Branch | — | |
| *Arthrobacter phenanthrenivorans* Sphe3 | — | |
| *Arthrobacter* sp 20511 Branch | — | |
| *Arthrobacter* sp PAO19 | — | |
| *Arthrobacter* sp W1 | — | |
| *Aureimonas* sp. Leaf427 | — | |
| *Aureobasidium pullulans* | — | |
| Bacillaceae Family 24 4101 12691 Branch | — | |
| *Bacillus* sp. LL01 | — | |
| *Bacillus* 12637 Branch | — | |
| *Bacillus aerophilus* strain C772 | — | |
| *Bacillus thuringiensis* serovar 12940 Branch | — | |
| *Brevundimonas nasdae* strain TPW30 | — | |
| *Brevundimonas* sp 23867 Branch | — | |

TABLE 4-continued

Table 4. Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Brevundimonas* sp EAKA | — | |
| *Buchnera aphidicola* str 28655 Branch | — | |
| Burkholderiales Order 15 6136 Node 25777 | — | |
| *Buttiauxella agrestis* 35837 Branch | — | |
| *Candidatus* Burkholderia verschuerenii | — | |
| *Carnobacterium* 5833 Branch | — | |
| *Carnobacterium maltaromaticum* ATCC 35586 | ATCC 35586 | ATCC |
| *Chryseobacterium* 285 Branch | — | |
| *Chryseobacterium daeguense* DSM 19388 | DSM 19388 | WFCC |
| *Chryseobacterium formosense* | — | |
| *Chryseobacterium* sp YR005 | — | |
| *Clavibacter* 20772 Branch | — | |
| *Clostridium diolis* DSM 15410 | DSM 15410 | WFCC |
| *Comamonas* sp B 9 | — | |
| *Curtobacterium flaccumfaciens* 20762 Branch | — | |
| *Curtobacterium flaccumfaciens* UCD AKU | — | |
| *Curtobacterium* sp UNCCL17 | — | |
| *Deinococcus aquatilis* DSM 23025 | DSM 23025 | WFCC |
| *Debaromyces hansenii* ATCC 36239 | ATCC 25935 | ATCC |
| *Duganella zoogloeoides* ATCC 25935 | | |
| *Dyadobacter* 575 Branch | — | |
| *Elizabethkingia anophelis* | — | |
| *Empedobacter falsenii* strain 282 | — | |
| *Enterobacter* sp 638 | — | |
| Enterobacteriaceae Family 9 3608 Node 35891 | — | |
| Enterobacteriaceae Family 9 593 Node 36513 | — | |
| *Epilithonimonas lactis* | — | |
| *Epilithonimonas tenax* DSM 16811 | DSM 16811 | WFCC |
| *Erwinia* 35491 Branch | — | |
| *Erwinia amylovora* 35816 Branch | — | |
| *Erwinia pyrifoliae* 35813 Branch | — | |
| *Erwinia tasmaniensis* Et1 99 | DSM 17950 | WFCC |
| *Escherichia coli* ISC11 | — | |
| *Exiguobacterium* 13246 Branch | — | |
| *Exiguobacterium* 13260 Branch | — | |
| *Exiguobacterium sibiricum* 255 15 | DSM 17290 | WFCC |
| *Exiguobacterium* sp 13263 Branch | — | |
| *Exiguobacterium undae* 13250 Branch | — | |
| *Exiguobacterium undae* DSM 14481 | DSM 14481 | WFCC |
| *Flavobacterium* 237 Branch | — | |
| *Flavobacterium aquatile* LMG 4008 | LMG 4008 | WFCC |
| *Flavobacterium chungangense* LMG 26729 | LMG 26729 | WFCC |
| *Flavobacterium daejeonense* DSM 17708 | DSM 17708 | WFCC |
| *Flavobacterium hibernum* strain DSM 12611 | DSM 12611 | WFCC |
| *Flavobacterium hydatis* | — | |
| *Flavobacterium johnsoniae* UW101 | ATCC 17061D-5 | ATCC |
| *Flavobacterium reichenbachii* | — | |
| *Flavobacterium soli* DSM 19725 | DSM 19725 | WFCC |
| *Flavobacterium* sp 238 Branch | — | |
| *Flavobacterium* sp EM1321 | — | |
| *Flavobacterium* sp MEB061 | — | |
| *Hanseniaspora uvarum* ATCC 18859 | — | |
| *Hanseniaspora occidentalis* ATCC 32053 | | |
| *Herminiimonas arsenicoxydans* | | |
| *Hymenobacter swuensis* DY53 | — | |
| *Janthinobacterium* 25694 Branch | — | |
| *Janthinobacterium agaricidamnosum* NBRC 102515 DSM 9628 | DSM 9628 | WFCC |
| *Janthinobacterium lividum* strain RIT308 | — | |
| *Janthinobacterium* sp RA13 | — | |
| *Kocuria* 20614 Branch | — | |
| *Kocuria rhizophila* 20623 Branch | — | |
| *Lactobacillus acetotolerans* | — | |
| *Lactobacillus brevis* | — | |
| *Lactobacillus buchneri* | — | |
| *Lactobacillus futsaii* | — | |
| *Lactobacillus kefiranofaciens* | — | |
| *Lactobacillus panis* | — | |
| *Lactobacillus parafarraginis* | — | |
| *Lactobacillus plantarum* | — | |
| *Lactobacillus rapi* | — | |

TABLE 4-continued

Table 4. Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Lactobacillus crispatus* 5565 Branch | — | |
| *Lactobacillus plantarum* WJL | — | |
| *Lactobacillus reuteri* 5515 Branch | — | |
| *Leuconostoc mesenteroides* ATCC 8293 | — | |
| *Luteibacter* sp 9135 | | |
| *Massilia timonae* CCUG 45783 | — | |
| *Methylobacterium extorquens* 23001 Branch | — | |
| *Methylobacterium* sp 22185 Branch | — | |
| *Methylobacterium* sp 285MFTsu5 1 | — | |
| *Methylobacterium* sp 88A | — | |
| *Methylotenera versatilis* 7 | — | |
| *Microbacterium laevaniformans* OR221 | — | |
| *Microbacterium oleivorans* | — | |
| *Microbacterium* sp MEJ108Y | — | |
| *Microbacterium* sp UCD TDU | — | |
| *Microbacterium testaceum* StLB037 | — | |
| *Micrococcus luteus* strain RIT304 | NCTC 2665 | NCTC |
| *Mycobacterium abscessus* 19573 Branch | — | |
| *Neosartorya fischeri* | — | |
| *Oxalobacteraceae bacterium* AB 14 | — | |
| *Paenibacillus* sp FSL 28088 Branch | — | |
| *Paenibacillus* sp FSL H7 689 | — | |
| *Pantoea* sp. SL1 M5 | — | |
| *Pantoea* 36041 Branch | — | |
| *Pantoea agglomerans* strain 4 | — | |
| *Pantoea agglomerans* strain 4 | — | |
| *Pantoea agglomerans* strain LMAE 2 | — | |
| *Pantoea agglomerans* Tx10 | — | |
| *Pantoea* sp 36061 Branch | — | |
| *Pantoea* sp MBLJ3 | — | |
| *Pantoea* sp SL1 M5 | — | |
| *Paracoccus* sp PAMC 22219 | — | |
| *Patulibacter minatonensis* DSM 18081 | DSM 18081 | WFCC |
| *Pectobacterium carotovorum* subsp *carotovorum* strain 28625 Branch | — | |
| *Pediococcus ethanolidurans* | — | |
| *Pediococcus pentosaceus* ATCC 33314 | — | |
| *Pedobacter* 611 Branch | | |
| *Pedobacter agri* PB92 | — | |
| *Pedobacter borealis* DSM 19626 | DSM 19626 | WFCC |
| *Pedobacter kyungheensis* strain KACC 16221 | — | |
| *Pedobacter* sp R20 19 | — | |
| *Periglandula ipomoeae* | — | |
| *Planomicrobium glaciei* CHR43 | — | |
| *Propionibacterium acnes* | — | |
| *Propionibacterium* 20955 Branch | — | |
| *Propionibacterium acnes* 21065 Branch | — | |
| *Pseudomonas fluorescens* | — | |
| *Pseudomonas* sp. DSM 29167 | — | |
| *Pseudomonas* sp. Leaf15 | — | |
| *Pseudomonas syringae* | — | |
| *Pseudomonas* 39524 Branch | — | |
| *Pseudomonas* 39642 Branch | — | |
| *Pseudomonas* 39733 Branch | — | |
| *Pseudomonas* 39744 Branch | — | |
| *Pseudomonas* 39791 Branch | — | |
| *Pseudomonas* 39821 Branch | — | |
| *Pseudomonas* 39834 Branch | — | |
| *Pseudomonas* 39875 Branch | — | |
| *Pseudomonas* 39880 Branch | — | |
| *Pseudomonas* 39889 Branch | — | |
| *Pseudomonas* 39894 Branch | — | |
| *Pseudomonas* 39913 Branch | — | |
| *Pseudomonas* 39931 Branch | — | |
| *Pseudomonas* 39942 Branch | — | |
| *Pseudomonas* 39979 Branch | — | |
| *Pseudomonas* 39996 Branch | — | |
| *Pseudomonas* 40058 Branch | — | |
| *Pseudomonas* 40185 Branch | — | |
| *Pseudomonas abietaniphila* strain KF717 | — | |
| *Pseudomonas chlororaphis* strain EA105 | — | |

TABLE 4-continued

Table 4. Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Pseudomonas cremoricolorata* DSM 17059 | DSM 17059 | WFCC |
| *Pseudomonas entomophila* L48 | — | |
| *Pseudomonas extremaustralis* 14 3 substr 14 3b | — | |
| *Pseudomonas fluorescens* BBc6R8 | — | |
| *Pseudomonas fluorescens* BS2 | ATCC 12633 | ATCC |
| *Pseudomonas fluorescens* EGD AQ6 | — | |
| *Pseudomonas fluorescens* strain AU 39831 Branch | — | |
| *Pseudomonas fluorescens* strain AU10973 | — | |
| *Pseudomonas fluorescens* strain AU14440 | — | |
| *Pseudomonas fragi* B25 | NCTC 10689 | NCTC |
| *Pseudomonas frederiksbergensis* strain SI8 | — | |
| *Pseudomonas fulva* strain MEJ086 | — | |
| *Pseudomonas fuscovaginae* 39768 Branch | — | |
| *Pseudomonas gingeri* NCPPB 3146 | NCPPB 3146 | NCPPB |
| *Pseudomonas lutea* | — | |
| *Pseudomonas luteola* XLDN4 9 | — | |
| *Pseudomonas mandelii* JR 1 | — | |
| *Pseudomonas moraviensis* R28 S | — | |
| *Pseudomonas mosselii* SJ10 | — | |
| *Pseudomonas plecoglossicida* NB 39639 Branch | — | |
| *Pseudomonas poae* RE*1 1 14 | — | |
| *Pseudomonas pseudoalcaligenes* AD6 | — | |
| *Pseudomonas psychrophila* HA 4 | — | |
| *Pseudomonas putida* DOT T1E | — | |
| *Pseudomonas putida* strain KF703 | — | |
| *Pseudomonas putida* strain MC4 5222 | — | |
| *Pseudomonas rhizosphaerae* | — | |
| *Pseudomonas rhodesiae* strain FF9 | — | |
| *Pseudomonas* sp 39813 Branch | — | |
| *Pseudomonas simiae* strain 2 36 | — | |
| *Pseudomonas simiae* strain MEB105 | — | |
| *Pseudomonas* sp 11 12A | — | |
| *Pseudomonas* sp 2 922010 | — | |
| *Pseudomonas* sp CF149 | — | |
| *Pseudomonas* sp Eur1 9 41 | — | |
| *Pseudomonas* sp LAMO17WK12 I2 | — | |
| *Pseudomonas* sp PAMC 25886 | — | |
| *Pseudomonas* sp PTA1 | — | |
| *Pseudomonas* sp R62 | — | |
| *Pseudomonas* sp WCS374 | — | |
| *Pseudomonas synxantha* BG33R | — | |
| *Pseudomonas synxantha* BG33R | — | |
| *Pseudomonas syringae* 39550 Branch | — | |
| *Pseudomonas syringae* 39596 Branch | — | |
| *Pseudomonas syringae* 40123 Branch | — | |
| *Pseudomonas syringae* CC 39499 Branch | — | |
| *Pseudomonas syringae* pv panici str LMG 2367 | — | |
| *Pseudomonas syringae* strain mixed | — | |
| *Pseudomonas tolaasii* 39796 Branch | — | |
| *Pseudomonas tolaasii* PMS117 | — | |
| *Pseudomonas veronii* 1YdBTEX2 | — | |
| *Pseudomonas viridiflava* CC1582 | — | |
| *Pseudomonas viridiflava* strain LMCA8 | — | |
| *Pseudomonas viridiflava* TA043 | — | |
| *Pseudomonas viridiflava* UASWS0038 | — | |
| *Rahnella* 35969 Branch | — | |
| *Rahnella* 35970 Branch | — | |
| *Rahnella* 35971 Branch | — | |
| *Rahnella aquatilis* HX2 | — | |
| *Rahnella* sp WP5 | — | |
| *Raoultella ornithinolytica* | — | |
| Rhizobiales Order 22324 Branch | — | |
| *Rhizobium* sp YR528 | — | |
| *Rhodococcus fascians* A76 | — | |
| *Rhodococcus* sp BS 15 | — | |
| *Saccharomyces cerevisiae* | DSM 10542 | WFCC |
| *Sanguibacter keddieii* DSM 10542 | | |
| *Serratia fonticola* AU 35657 Branch | — | |
| *Serratia fonticola* AU AP2C | — | |

TABLE 4-continued

Table 4. Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Serratia liquefaciens* ATCC 27592 | ATCC 27592 | ATCC |
| *Serratia* sp H 35589 Branch | — | |
| *Shewanella* 37294 Branch | — | |
| *Shewanella baltica* 37301 Branch | — | |
| *Shewanella baltica* 37315 Branch | — | |
| *Shewanella baltica* OS 37308 Branch | — | |
| *Shewanella baltica* OS 37312 Branch | — | |
| *Shewanella baltica* OS185 | — | |
| *Shewanella baltica* OS223 | — | |
| *Shewanella baltica* OS678 | — | |
| *Shewanella oneidensis* MR 1 | — | |
| *Shewanella putrefaciens* HRCR 6 | — | |
| *Shewanella* sp W3 18 1 | — | |
| *Sphingobacterium* sp ML3W | — | |
| *Sphingobium japonicum* BiD32 | — | |
| *Sphingobium xenophagum* 24443 Branch | — | |
| *Sphingomonas echinoides* ATCC 14820 | ATCC 14820 | ATCC |
| *Sphingomonas parapaucimobilis* NBRC 15100 | ATCC 51231 | ATCC |
| *Sphingomonas paucimobilis* NBRC 13935 | ATCC 29837 | ATCC |
| *Sphingomonas phyllosphaerae* 5 2 | — | |
| *Sphingomonas* sp 23777 Branch | — | |
| *Sphingomonas* sp STIS6 2 | — | |
| *Staphylococcus* 6317 Branch | — | |
| *Staphylococcus equorum* UMC CNS 924 | — | |
| *Staphylococcus* sp 6275 Branch | — | |
| *Staphylococcus* sp 6240 Branch | — | |
| *Staphylococcus* sp OJ82 | — | |
| *Staphylococcus xylosus* strain LSR 02N | — | |
| *Stenotrophomonas* 14028 Branch | — | |
| *Stenotrophomonas* 42816 Branch | — | |
| *Stenotrophomonas maltophilia* 42817 Branch | — | |
| *Stenotrophomonas maltophilia* PML168 | — | |
| *Stenotrophomonas maltophilia* strain ZBG7B | — | |
| *Stenotrophomonas rhizophila* | — | |
| *Stenotrophomonas* sp RIT309 | — | |
| *Streptococcus gallofyticus* subsp *gallofyticus* TX20005 | — | |
| *Streptococcus infantarius* subsp *infantarius* 2242 Branch | — | |
| *Streptococcus infantarius* subsp *infantarius* ATCC BAA 102 | ATCC BAA 102 | ATCC |
| *Streptococcus macedonicus* ACA DC 198 | ATCC BAA-249 | ATCC |
| *Streptomyces olindensis* | — | |
| *Variovorax paradoxus* 110B | — | |
| *Variovorax paradoxus* ZNC0006 | — | |
| *Variovorax* sp CF313 | — | |
| *Vibrio fluvialis* 44473 Branch | — | |
| *Xanthomonas campestris* 37936 Branch | — | |
| *Xanthomonas campestris* pv raphani 756C | — | |

FIG. 1 shows bacterial diversity observed in a set of 12 plant-derived samples as seen by a community reconstruction based on mapping the reads from a shotgun sequencing library into the full genomes of a database containing 36,000 genomes by the k-mer method (CosmosID). The display corresponds to a sunburst plot constructed with the relative abundance for each corresponding genome identified and their taxonomic classification. The genomes identified as unclassified have not been curated in the database with taxonomic identifiers and therefore not assigned to a group. This does not represent novel taxa and it is an artifact of the database updating process.

More specifically, FIG. 1A shows bacterial diversity observed in a green chard. The dominant group is gamma proteobacteria with different *Pseudomonas* species. The members of the group "unclassified" are largely gamma proteobacteria not included in the hierarchical classification as an artifact of the database annotation.

FIG. 1B shows bacterial diversity in red cabbage. There is a large abundance of *Lactobacillus* in the sample followed by a variety of *Pseudomonas* and *Shewanella.*

FIG. 1C shows bacterial diversity in romaine lettuce. *Pseudomonas* and *Duganella* are the dominant groups. A member of the Bacteroidetes was also identified.

FIG. 1D shows bacterial diversity in celery sticks. This sample was dominated by a *Pseudomonas* species that was not annotated yet into the database and therefore appeared as "unclassified" same for *Agrobacterium* and *Acinetobacter.*

FIG. 1E shows bacterial diversity observed in butterhead lettuce grown hydroponically. The sample contains relatively low bacterial complexity dominated by *Pseudomonas fluorescens* and other groups. Also, there is a 9% abundance of *Exiguobacterium.*

FIG. 1F shows bacterial diversity in organic baby spinach. The samples were triple-washed before distribution at the point of sale and therefore it is expected that must of the bacteria detected here are endophytes. Multiple *Pseudomonas* species observed in this sample including *P. fluorescens* and other shown as "unclassified."

FIG. 1G shows bacterial diversity in green crisp gem lettuce. This variety of lettuce showed clear dominance of gamma proteobacteria and with *Pseudomonas, Shewanella, Serratia* as well as other groups such as *Duganella.*

FIG. 1H shows bacterial diversity in red oak leaf lettuce. There is a relative high diversity represented in this sample with members of *Lactobacillus, Microbacterium, Bacteroidetes, Exiguobacterium* and a variety of *Pseudomonas.*

FIG. 1I shows bacterial diversity in green oak leaf lettuce. It is dominated by a single *Pseudomonas* species including *fluorescens* and mostly gamma proteobacteria.

FIG. 1J shows bacterial diversity in cherry tomatoes. It is dominated by 3 species of *Pseudomonas* comprising more than 85% of the total diversity on which *P. fluorescens* comprises 28% of bacterial diversity.

FIG. 1K shows bacterial diversity in crisp red gem lettuce. Dominance by a single *Pseudomonas* species covering 73% of the bacterial diversity, on which *P. fluorescens* comprises 5% of bacterial diversity.

FIG. 1L shows bacterial diversity in broccoli juice. The sample is absolutely dominated by 3 varieties of *Pseudomonas.*

FIG. 2 shows taxonomic composition of blueberries, pickled olives and broccoli head. More specifically, FIG. 2A shows taxonomic composition of broccoli head showing a diversity of fungi and bacteria distinct from the broccoli juice dominated by few *Pseudomonas* species.

FIG. 2B shows taxonomic composition of blueberries including seeds and pericarp (peel) as seen by shotgun sequencing showing dominance of *Pseudomonas* and strains isolated and sequenced.

FIG. 2C shows taxonomic composition of pickled olives showing a variety of lactic acid bacteria present and dominant. Some of the species are recognized as probiotics.

Example 2: In Silico Modeling Outputs for Different Assemblages and DMA Formulation To generate in silico predictions for the effect of different microbial assemblages with a human host a genome-wide metabolic analysis was performed with formulated microbial communities selected from the Agora collection (Magbustoddir et al. (2016) Generation of genome-scale metabolic reconstructions for 773 members of the human gut microbiota. Nat. Biotech. 35, 81-89) and augmented with the genomes of bacterial members detected in the present survey. These simulations predict the "fermentative power" of each assemblage when simulated under different nutritional regimes including relatively high carbon availability (carbon replete) or carbon limited conditions when using plant fibers such as inulin, oligofructose and others as carbon source. The method used for DNA sequencing the sample-associated microbiomes enabled to search for genes detected in the different vegetables related to propionate, butyrate, acetate and bile salt metabolism. This was done by mapping the reads obtained in the samples to reference genes selected for their intermediate role in the synthesis or degradation of these metabolites. There were organisms present in some of the 15 analyzed samples that matched the target pathways indicating their metabolic potential to produce desirable metabolites. Table 5 shows Metabolites in samples.

Table 5. Metabolites in samples.

DMA Formulation

Microbes in nature interact with multiple other groups and form consortia that work in synergy exchanging metabolic products and substrates resulting in thermodynamically favorable reactions as compared to the individual metabolism. For example, in the human colon, the process for plant fiber depolymerization, digestion and fermentation into butyrate is achieved by multiple metabolic groups working in concert. This metabolic synergy is reproduced in the DMA concept where strains are selected to be combined based on their ability to synergize to produce an increased amount of SCFA when grown together and when exposed to substrates such as plant fibers.

TABLE 5

| Name of enzyme | Associated metabolite | Gene symbol | Pathway | E.C. number | Comments |
|---|---|---|---|---|---|
| Acetolactate synthase I | (s)-2-acetolactate | | Butanoate metabolism | 2.2.1.6 | Butyrate production |
| Acetate kinase | Propionate | Acka | Propanoate metabolism | 2.7.2.1 | Propionate |
| Acetyl-coa synthetase | Propionate | Aacs | Propanoate metabolism | 6.2.1.1 | Propionate |
| Acetyl-coa hydrolase | Acetate | | Pyruvate metabolism | 3.1.2.1 | Acetate |
| Bile salt transporter | Bile salts | Acr3 | Bile salt transport | | Bile salt tolerance |

To illustrate this process, a set of 40 bacterial and fungal strains were isolated from food sources and their genomes were sequenced. The assembled and annotated genomes were then used to formulate in silico assemblages considering the human host as one of the metabolic members. Assuming a diet composed of lipids, different carbohydrates and proteins the metabolic fluxes were predicted using an unconstrained model comparing the individual strain production of acetate, propionate and butyrate and compared to the metabolic fluxes with the assemblage.

In the first model, 4 strains were combined into a DMA. Strains 1-4 are predicted to produce acetate as single cultures but the combination into a DMA predicts the flux will increase when modeled on replete media and the flux decreases when modeled on plant fibers. Strain 4 is predicted to utilize the fibers better than the other 3 to produce acetate. Strain 1 is the only member of the assemblage predicted to produce propionate and when modeled with the other 3 strains the predicted flux doubles in replete media and quadruples in the fiber media illustrating the potential metabolic synergy from the assemblage. Strain 3 is the only member of the assemblage predicted to produce butyrate and when modeled with the other 3 strains the predicted flux increase slightly in replete media and doubled in the fiber media illustrating the potential metabolic synergy from the assemblage.

TABLE 6

Table 6. Strains from first DMA model.

| # | Strain |
|---|---|
| Strain 1 | DP6 *Bacillus cereus*-like |
| Strain 2 | DP9 *Pediococcus pentosaceus*-like |
| Strain 3 | *Clostridium butyricum* DSM 10702 |
| Strain 4 | DP1 *Pseudomonas fluorescens*-like |

Figure 5:
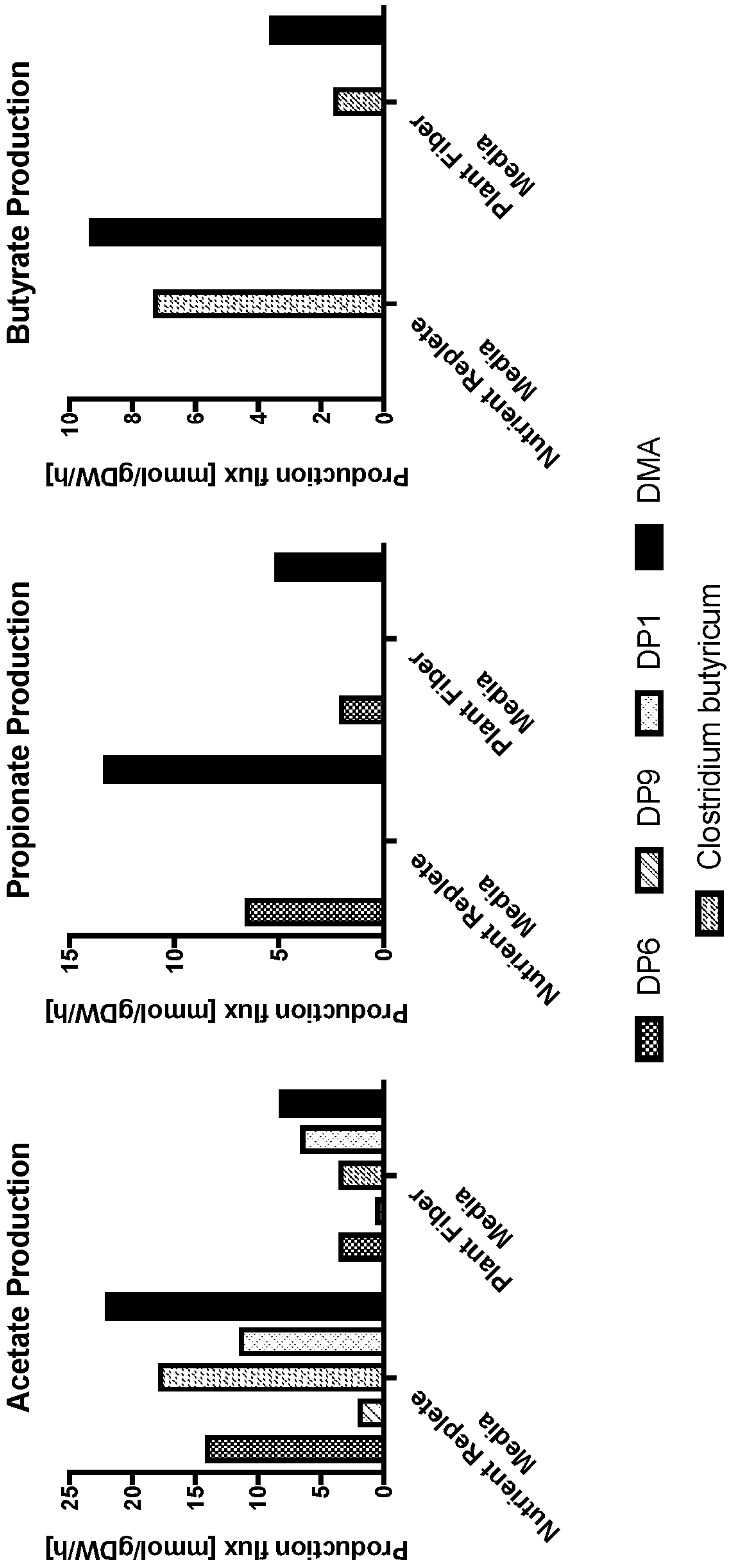
FIG. 5. Genome-wide metabolic model for a DMA formulated in silico with 3 DP strains and one genome from a reference in NCBI. The predicted fluxes for acetate, propionate and butyrate under a nutrient-replete and plant fiber media are indicated.

Substrate availability plays an important role in the establishment of synergistic interactions. Carbon limitation in presence of plant fibers favors fiber depolymerization and fermentation to produce SCFA. Conversely carbon replete conditions will prevent the establishment of synergistic metabolism to degrade fibers as it is not favored thermodynamically when the energy available from simple sugars is available. To illustrate this, we formulated a DMA containing two strains of lactic acid bacteria and run a metabolic prediction assuming a limited media with plant fibers. According to the model, *Leuconostoc* predicted flux is higher than *Pediococcus* and the DMA flux increases five times on the combined strains. When tested in the lab and measured by gas chromatography, the acetate production increases 3 times compared to the single strains (FIG. 5). However, when grown on carbon replete media with available simple sugars, acetate production is correspondingly higher compared to the plant fiber media but there is no benefit of synergistic acetate production when the two strains are grown together into a DMA.

Figure 6:
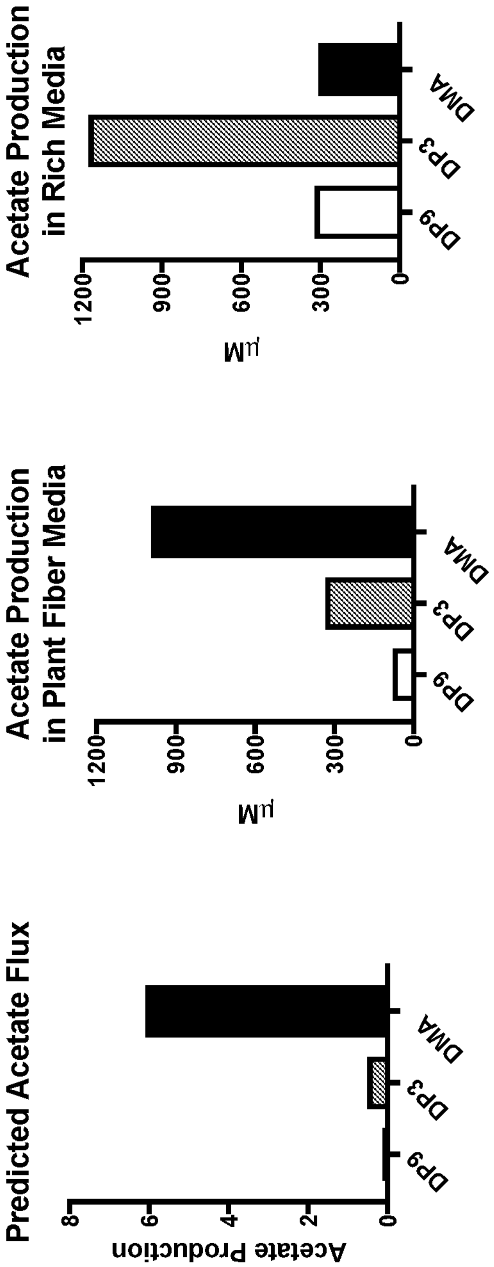
FIG. 6. DMA experimental validation for a combination of strains DP3 and DP9 under nutrient replete and plant fiber media showing that the strains show synergy for increased SCFA production only under plant fiber media but not under rich media.

In addition to acetate, propionate, and butyrate some strains produce other isomers. For example, strains SBI0189 related to *Pseudomonas fluorescens* and SBI0319 related to *Debaromyces hansenii* (yeast) produce isobutyrate when grown in carbon-replete media as single strains, however there is metabolic synergy when tested together as DMA measured as an increase in the isobutyric acid production (FIG. 6).

To describe experimentally the process of DMA validation the following method can be applied to find other candidates applicable to other products:

1. Define a suitable habitat where microbes are with the desirable attributes are abundant based on ecological hypotheses. For example, fresh vegetables are known to have anti-inflammatory effects when consumed in a whole-food plant based diet, and therefore, it is likely they harbor microbes that can colonize the human gut.
2. Apply a selection filter to isolate and characterize only those microbes capable of a relevant gut function. For example, tolerate acid shock, bile salts and low oxygen. In addition, strains need to be compatible with target therapeutic drugs. In type 2 diabetes metformin is a common first line therapy.
3. Selected strains are then cultivated in vitro and their genomes sequenced at 100×coverage to assemble, annotate and use in predictive genome-wide metabolic models.
4. Metabolic fluxes are generated with unconstrained models that consider multiple strains and the human host to determine the synergistic effects from multiple strains when it is assumed they are co-cultured under a simulated substrate conditions.
5. Predicted synergistic combinations are then tested in the laboratory for validation. Single strains are grown to produce a biomass and the spent growth media removed after reaching late log phase. The washed cells are then combined in Defined Microbial Assemblages with 2-10 different strains per DMA and incubated using a culture media with plant fibers as substrates to produce short chain fatty acids to promote gut health.
6. The DMAs are then analyzed by gas chromatography to quantify the short chain fatty acid production where the synergistic effect produces an increased production in the combined assemblage as compared to the individual contributions.

Example 3. Metformin Resistance Experiments

To assess the effect of metformin in the microbiota, metformin is used as a selection agent by applying to a variety of growth media from a filter sterilized metformin stock at 100 mg/ml by adding 20 μL into 4 ml of liquid media for a final concentration of 500 μg/mL. The media tested is potato dextrose broth in liquid, 0.5×R2A liquid media or both formulations in solid media by the addition of 2% agar. Samples containing microbiomes are plated and spread onto solid media and colonies isolated and propagated as pure cultures. DNA is extracted from these strains and sequenced using Illumina's NGS protocols.

A total of 234 strains were isolated using solid 0.5×R2A and their genomes were sequenced. In addition, enrichments in liquid media using the conditions listed above were set up to generate a consortium capable of growing with metformin and to develop its potential therapeutic activity.

The results of the metformin resistance experiments are shown below in Table 7.

Example 4. Gut Simulation Experiments

The experiment comprises an in vitro, system that mimics various sections of the gastrointestinal tract. Isolates of interest are incubated in the presence of conditions that mimic particular stresses in the gastro-intestinal tract (such as low pH or bile salts), heat shock, or metformin. After incubation, surviving populations are recovered. A schematic of the gut simulator experiments is shown in FIG. 3. Utilizing this system, the impact of various oral anti-diabetic therapies alone or in combination with probiotic cocktails of interest on the microbial ecosystem can be tested. Representative isolates are shown in Table 7.

TABLE 7

Table 7: Strains resistant to metformin, listed with heat shock tolerance, acid shock tolerance, and isolation temperature.

| Strain number | Heat shock | Isolation temperature | Acid shock (pH 3) 2 hr | Genus | species |
|---|---|---|---|---|---|
| DP1 | No | 25 | No | *Pseudomonas* | *fluorescens* |
| DP2 | No | 37 | No | *Hanseniaspora* | *occidentalis* |
| DP3 | No | 25 | No | *Leuconostoc* | *mesenteroides* |
| DP4 | No | 25 | No | *Aureobasidium* | *pullanans* |
| DP5 | No | 37 | No | *Debaromyces* | *hansenii* |
| DP6 | Yes | 25 | No | *Bacillus* | *cereus* |
| DP7 | No | 25 | No | *Pichia* | *fermentans* |
| DP8 | No | 25 | No | *Hanseniaspora* | *opuntiae* |
| DP9 | No | 25 | No | *Pediococcus* | *pentosauceus* |
| DP10 | Yes | 25 | No | *Bacillus* | *velezensis* |
| DP11 | No | 25 | No | *Pseudomonas* | *putida* |
| DP12 | No | 25 | Yes | *Microbacterium* | sp. |
| DP13 | No | 25 | Yes | *Bacillus* | *mycoides* |
| DP14 | No | 25 | Yes | *Arthrobacter* | *luteolus* |
| DP15 | No | 25 | No | *Curtobacterium* | sp. |
| DP16 | No | 25 | No | *Cryptococcus* | *laurentii* |
| DP17 | No | 25 | No | *Rahnella* | *aquatilis* |
| DP18 | No | 25 | No | *Pseudomonas* | sp. |
| DP19 | No | 25 | No | *Curtobacterium* | *pusilium* |
| DP20 | No | 25 | No | *Stenotrophomonas* | *rhizophila* |
| DP21 | No | 25 | No | *Candida* | *santamariae* |
| DP22 | No | 25 | No | *Rahnella* | sp. |
| DP23 | No | 25 | No | *Erwinia* | *billingiae* |
| DP24 | No | 25 | No | *Filobasidium* | *globisporum* |
| DP25 | No | 25 | No | *Penicillium* | *solitum* |
| DP26 | No | 25 | No | *Methylobacterium* | sp. |
| DP27 | No | 25 | No | *Sphingomonas* | sp. |
| DP28 | No | 25 | Yes | *Aureobasidium* | *pullulans* |
| DP29 | No | 25 | Yes | *Pseudoclavibacter* | *helvolus* |
| DP30 | No | 25 | Yes | *Microbacterium* | *testaceum* |
| DP31 | No | 25 | Yes | *Sporisorium* | *reilianum* |
| DP32 | No | 25 | No | *Hafnia* | *paralvei* |
| DP33 | No | 25 | No | *Erwinia* | *persicinus* |
| DP34 | No | 25 | Yes | *Plantibacter* | *flavus* |
| DP35 | No | 25 | Yes | *Pantoea* | *ananatis* |
| DP36 | No | 25 | Yes | *Pantoea* | *vagans* |
| DP37 | No | 25 | No | *Pseudomonas* | *rhodesiae* |
| DP38 | No | 25 | No | *Rhodococcus* | sp. |
| DP39 | No | 25 | No | *Agrobacterium* | *tumefaciens* |
| DP40 | No | 37 | No | *Pantoea* | sp. |
| DP41 | Yes | 37 | No | *Corynebacterium* | *mucifaciens* |
| DP42 | No | 37 | No | *Pseudomonas* | *lundensis* |
| DP43 | No | 25 | No | *Janthinobacterium* | sp. |
| DP44 | No | 25 | No | *Herbaspirillum* | sp. |
| DP45 | No | 25 | No | *Sanguibacter* | *keddieii* |
| DP46 | No | 25 | Yes | *Pantoea* | *agglomerans* |
| DP47 | No | 25 | Yes | *Cronobacter* | *dublinensis* |
| DP48 | Yes | 25 | No | *Bacillus* | *paralicheniformis* |
| DP49 | Yes | 25 | No | *Bacillus* | *gibsonii* |
| DP50 | No | 25 | No | *Enterobacter* | sp. |
| DP51 | No | 25 | No | *Klebsiella* | *aerogenes* |
| DP52 | No | 25 | No | *Arthrobacter* | sp. |
| DP53 | No | 25 | No | *Pseudomonas* | *fragi* |
| DP54 | No | 25 | No | *Methylobacterium* | *adhaesivum* |
| DP55 | Yes | 25 | No | *Bacillus* | *megaterium* |
| DP56 | Yes | 25 | No | *Paenibacillus* | *lautus* |
| DP57 | Yes | 25 | No | *Bacillus* | *mycoides* |
| DP58 | No | 25 | No | *Janthinobacterium* | *svalbardensis* |
| DP59 | No | 25 | No | *Kosakonia* | *cowanii* |
| DP60 | Yes | 25 | No | *Bacillus* | simplex |
| DP61 | No | 25 | No | *Lelliottia* | sp. |
| DP62 | No | 25 | No | *Erwinia* | sp. |
| DP63 | No | 25 | Yes | *Pseudomonas* | *azotoformans* |
| DP64 | No | 25 | No | *Saccharomycetaceae* | |
| DP65 | No | 25 | No | *Sporobolomyces* | *carnicolor* |
| DP66 | No | 25 | No | *Pichia* | |

Example 5. Preclinical Experiments

Figure 7:
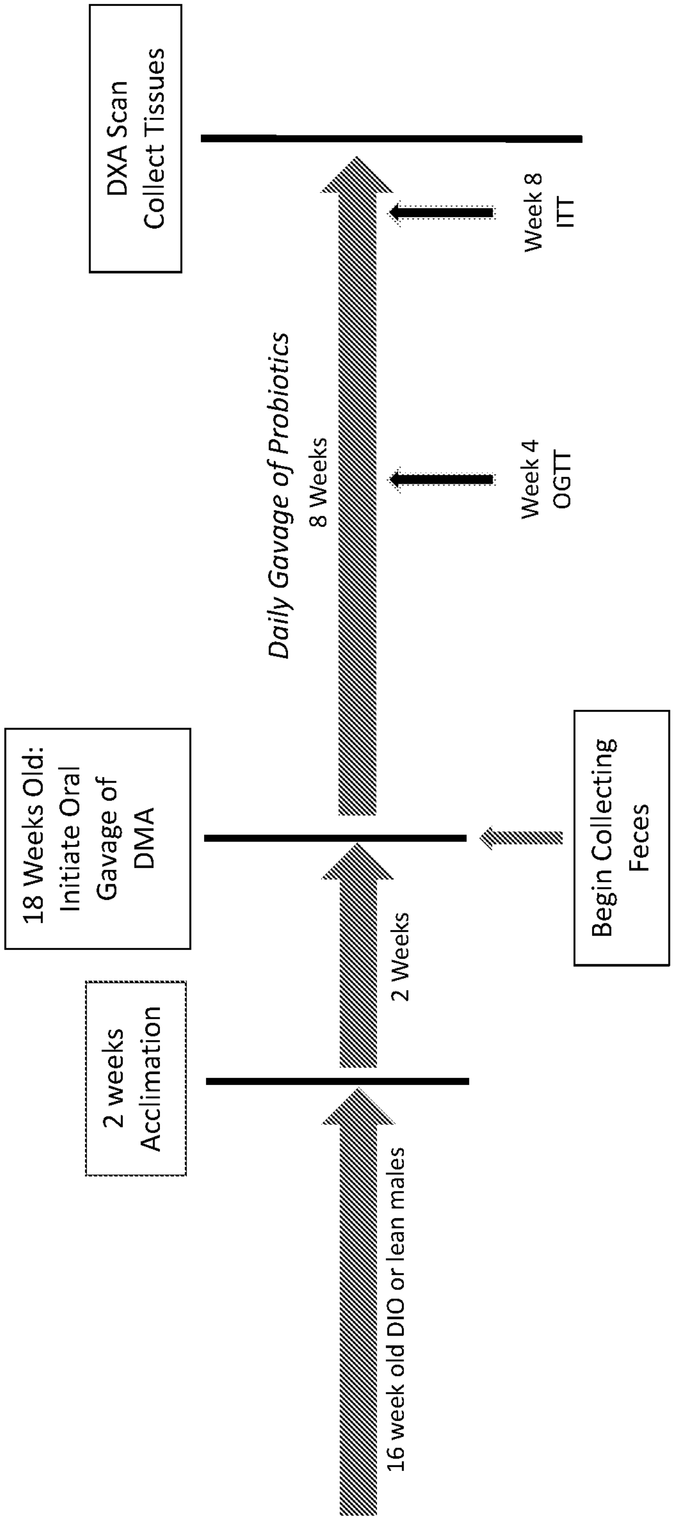
FIG. 7 shows a schematic detailing the experimental procedure for a pre-clinical model testing the disclosed methods. To test the translational viability of enhancing the effects of oral anti-diabetic drugs such as metformin, the diet-induced obesity mouse model, a highly-accepted, clinically relevant animal model of type 2 diabetes (T2D) is used.

To test the effect of the therapeutic compositions disclosed in this application prior to studies in the clinic, experiments are conducted in a mouse model of dietary-induced obesity. FIG. 7 provides a schematic detailing the experimental procedure for this pre-clinical experiment.

DIO Preclinical Study

Male diet induced obese (DIO) and low-fat diet control C57BL/6J mice were purchased from the Jackson Laboratories (Jax) at 16 weeks of age and were singly housed in individually ventilated cages (IVCs) (Allentown Inc) in a room with a 12-hour light/dark schedule at Invivotek (Trenton, N.J.). At Jax, mice were placed on either a low-fat diet (10% kcal, D12450B) or high-fat diet (60% kcal, D12492) (Open Source Diets; Research Diets Inc.) at 5-weeks of age and remained on those respective diets for the duration of the experiment. Mice were allowed to acclimate for 2-weeks at Invivotek prior to the experimental commencement. At 18-weeks of age, test articles were provided to the mice via oral gavage as indicated in Table 1. Control groups were provided sterile water at a dose of 5 mL/kg body weight. Metformin treatment was provided at a dose of 100 mg/kg body weight either independently, or in combination with various Defined Microbial Assemblages (DMAs). DMAs were provided at a dose of $8\times10^{10}$ CFUs/kg body weight. Mice were gavaged with test articles daily for 8-weeks. Here, mice are placed at 5 weeks of age on either a low-fat (10% kcal fat) or high-fat (60% kcal fat) diet. At 16 weeks of age, the mice are delivered to the facility and allowed to acclimate for 2 weeks. After 13 weeks of diet, mice receive a daily oral gavage of saline (control), metformin, probiotic cocktail of interest, or probiotic cocktail in combination with metformin, to quantify the ability of the probiotic cocktail to improve metformin efficacy. Daily gavages continue for 8 weeks, at which point glucose tolerance tests and insulin tolerance tests are performed to evaluate the metabolic health of each mouse. Each week, mice are weighed, and fecal samples are collected to evaluate changes in the microbial composition over time. At sacrifice, adipose tissue depots, blood, liver, small intestine, and colonic tissue from each mouse are collected for downstream mechanistic analysis.

Oral Glucose Tolerance Test (OGTT)

After 4 weeks of dosing mice with test article, an OGTT was performed. Here, mice were fasted for 6 hours after which fasting blood glucose levels were measured via tail vein blood using a glucometer (One-Touch Ultra II). Mice were then dosed with an oral glucose bolus (2 g/kg) via oral gavage, and blood glucose was measured at 20, 40, 60, and 120 minutes post gavage.

Insulin Tolerance Test (ITT)

8 weeks after the first dose of test material, mice were fasted for 4-hours and a baseline blood glucose level measurement was recorded using a glucometer (One-Touch Ultra II). Following baseline measurements, mice received an intraperitoneal (IP) injection of insulin (10 mL/kg at a concentration of 0.1U/mL). After injection, blood glucose was measured at 15, 30, 60, 90, and 120 minutes via tail vein blood.

Body Composition

Body fat percentage was determined using Dual Energy x-ray Absorptiometry (DEXA) scan (PIXImus2 Mouse Densitometer; GE) 8 weeks after initiation of DMA treatment. Prior to DEXA scans, mice were anesthetized via intraperitoneal injection of ketamine (60 mg/kg) and xylazine (4 mg/kg).

TABLE 8

| Group | Diet | Treatment | Gender |
|---|---|---|---|
| 1 | Low Fat | Vehicle (Water) | Male |
| 2 | High Fat | Vehicle (Water) | Male |
| 3 | High Fat | Metformin | Male |
| 4 | High Fat | DMA buffer | Male |
| 5 | High Fat | DMA #2 | Male |
| 6 | High Fat | DMA #3 | Male |
| 7 | High Fat | DMA #4 | Male |
| 8 | High Fat | DMA #5 | Male |
| 9 | High Fat | Metformin + DMA buffer | Male |
| 10 | High Fat | Metformin + DMA #2 | Male |
| 11 | High Fat | Metformin + DMA #3 | Male |
| 12 | High Fat | Metformin + DMA #4 | Male |
| 13 | High Fat | Metformin + DMA #5 | Male |

TABLE 9

Table 9. List of single strains and combinations into DMAs for preclinical experiments. The DMAs were selected based on their ability to produce SCFA synergistically, their growth compatibility, tolerance to metformin, ability to grown on plant fibers and tolerance to cryopreservation.

| Isolate | Genus | Species | Sample origin |
|---|---|---|---|
| DP1 | *Psuedomonas* | *fluorescens* | Cherry tomato |
| DP5 | *Debaryomyces* | *hansenii* | Red cabbage |
| DP2 | *Hanseniaspora* | *uvarum* | Lime |
| DP3 | *Leuconostoc* | *mesenteroides* | Fermented tomatoes |
| DP9 | *Pediococcus* | *pentosaceus* | Fermented cabbage |
| DP22 | *Rahenlla* | Sp. | pomegranate |
| DP53 | *Psuedomonas* | *fragi* | arugula |

DMAs

#2-DP9:DP2:DP53

#3-DP9:DP2:DP3

#4-DP9:DP2:DP22

#5-DP5: DP1

At sacrifice blood is collected from each mouse for downstream mechanistic analysis. This assay, as with the assays described above can be carried out with metformin or any appropriate anti-diabetic therapy. Additionally, adipose tissue depots, blood, liver, small intestine, and colonic tissue are collected from each mouse for subsequent analysis.

Figure 8:
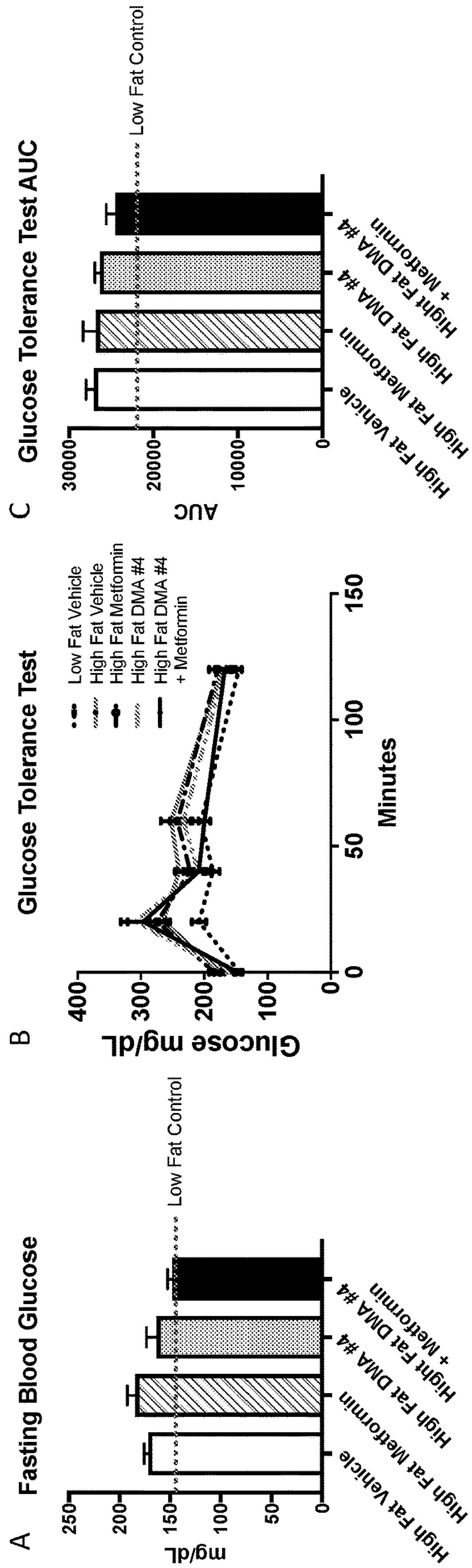
FIG. 8. Glucose tolerance test conducted with mice receiving the formulated DMA4 showing benefit when combined with metformin to reduce fasting glucose, and a rapid glucose clearance after 20 minutes of receiving a glucose dose.

Glucose tolerance test revealed that combination of DMA #4 and metformin led to an improved fasting blood glucose and glucose tolerance compared to either high-fat diet control, metformin monotherapy treated, or DMA #4 monotherapy treated mice. As observed in FIG. 8A, obese mice treated with the combination therapy had a fasting blood glucose identical to low fat control mice, indicative of normal glycemic health despite consuming a high-fat diet. Further, glucose tolerance tests (FIG. 8B) indicate that mice treated with the combination of DMA #4 and Metformin also had improved capacity to respond to a glucose challenge and absorb the glucose from the blood stream compared to either high-fat diet control, metformin monotherapy treated, or DMA #4 monotherapy treated mice. This is observed in (FIG. 8B) where despite a larger increase in blood glucose following challenge compared to lean mice at 15 minutes, the glucose was rapidly absorbed and returned to normal levels by 60 minutes while high-fat diet control, metformin monotherapy treated, or DMA #4 monotherapy treated mice all remained elevated. This effect is also observed by the area under the curve (AUC) in (FIG. 8C).

Figure 9:
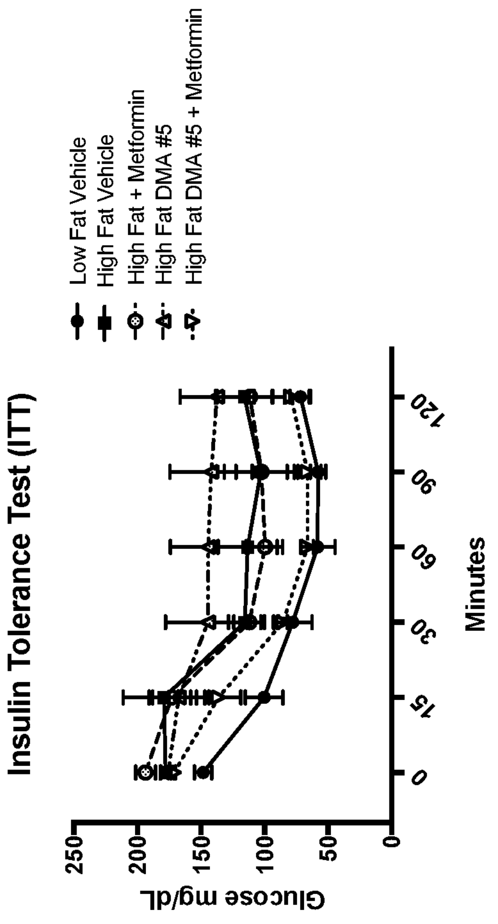
FIG. 9. Insulin tolerance test for mice receiving DMA5 and metformin showing a rapid insulin sensitivity response similar to that of lean mice grown under a low fat diet.

Combination therapy of DMA #5 and metformin improves insulin tolerance in Obese mice (FIG. 9). After 7 weeks of therapeutic intervention, mice received an insulin tolerance test. Here, we found that a combination of DMA #5 and metformin led to a significantly improved response to insulin, as indicated by the rapid clearance of glucose from the blood stream following intraperitoneal injection with insulin. The response to insulin was improved compared to obese controls. In fact, the response was exactly the same as the lean control mice, indicating that these obese mice have the same insulin sensitivity as a healthy mouse even after consuming a high fat diet for 20 weeks. Further, when controlling for the initial elevated fasting blood glucose in obese mice by normalizing to baseline, the significant improvement remained. DMA #5 is comprised of DP5 *Debaromyces hansenii*-like and DP1 *Pseudomonas fluorescens*-like isolates (Table 9).

Example 6. Computation of Microbial Entity Average Nucleotide Identity (ANI)

Microbial whole-genome sequencing has become an important tool for effectively and rapidly analyzing hundreds of bacterial genomes from different environments and with special relevance for human health. The study of bacterial genomes from multiple isolation sources has increased our knowledge of their ecological roles in different ecosystems, led to the identification of novel species, and the tracking of disease outbreaks. However, most of microbes remain uncultured, hampering its characterization and thus the identification of microbial key players and their participation in modulating host homeostasis is still far from complete.

Remarkable advances over the last decade in the human gut microbiome through the Human Microbiome Project (HMP) and the Metagenomics of the Human Intestinal Tract project (MetaHIT) have allowed to describe the baseline diversity found in the gut flora in a healthy and sick host. However, the amount of novel genetic diversity of microbial communities from complex environments such as soil, vegetables, and marine environments, remains essentially unknown.

16S rRNA gene sequencing is a cultured-independent method commonly used to classify bacterial genomes at the species level. However, because of its high sequence conservation, this method offers insufficient genetic resolution to capture intraspecific variation, limiting our knowledge. Alternative methods based on a set of maker genes or universally conserved genes often provide insufficient resolution because these genes show higher sequence conservation than the genome average sequence.

In view of the foregoing limitations, we applied a whole-genome based method, the average nucleotide identity (ANI), to estimate the genetic relatedness among bacterial genomes and profile hundreds of microbial species at a higher resolution taxonomic level (i.e., species- and strain-level classification). ANI is based on the average of the nucleotide identity of all orthologous genes shared between a genome pair. Genomes of the same species present ANI values above 95% and of the same genus values above 80% (Jain et al. 2018).

Taxonomic annotation of the strains combined into DMAs using ANI and the NCBI RefSeq database indicated that these microbes represent species not present in the database and most likely are new bacterial species even when the nucleotide identity based on the 16S rRNA gene is 99%.

TABLE 10

Comparative predictive power of 16S rRNA sequence analysis and Average Nucleotide Identity (ANI) analysis. While 16S rRNA sequence percentage indicates a high degree of homology, ANI analysis demonstrates that the overall genome sequence of the microbial entities isolated from plants and described herein as compared to reference strains is different enough in many cases to qualify as a different species.

| ID | NCBI match | 16S rRNA gene (%) | Closest Reference genome at NCBI | ANI (%) |
|---|---|---|---|---|
| DP3 | *Leuconostoc mesenteroides* (NR_074957.1.) | 99 | *Leuconostoc pseudomesenteroides* (JDVA01000001.1.) | 91.77 |
| DP9 | *Pediococcus pentosauceus* (NR_042058.1.) | 99 | *Pediococcus pentosauceus* (NC_022780.1.) | 99.6 |
| DP53 | *Pseudomonas helleri* (NR_148763.1.) | 99 | *Pseudomonas psychrophile* (NZ_LT629795.1.) | 86.82 |
| DP1 | *Pseudomonas fluorescens* (NR_115715.1.) | 99 | *Pseudomonas antarctica* (NZ_CP015600.1.) | 94.48 |
| DP22 | *Rahnella aquatilis* (NR_025337.1) | 98 | *Rahnella* sp. (NC_015061.1.) | 88.31 |

Example 7. Monitoring the Effect of DMAs on Microbial Flora of a Mammal

Alterations of the gut microbiota have been linked with changes in the host homeostasis such as metabolic diseases. In order to evaluate alterations in the gut microbiota composition in obese individuals, fecal samples were collected from DIO and lean mice and the gut microbiota was characterized. Briefly, DNA was extracted using the Zymo Quick-DNA Fecal/Soil Microbe Kit and quantified using a Qubit 2.0 flurometer with the dsDNA HS assay kit. Metagenomic libraries were prepared using the Illumina Nextera XT DNA library prep kit and an equimolar mixture of the libraries was sequenced on an Illumina NextSeq instrument on a 2×150 bp paired end run. Raw reads from the sequencing run were analyzed using SolexaQA (Cox et al. 2010) for trimming and removing of Illumina adaptors using a Phred score cutoff of 20 and minimum fragment length of 50 bp. Taxonomic classification of the short-read metagenomes was determined using MetaPhlan2, which uses Glade-specific marker genes from approximately 17,000 reference genomes to estimate the relative abundance of microbial members present in the sample (Troung et al. 2015).

Figure 10:
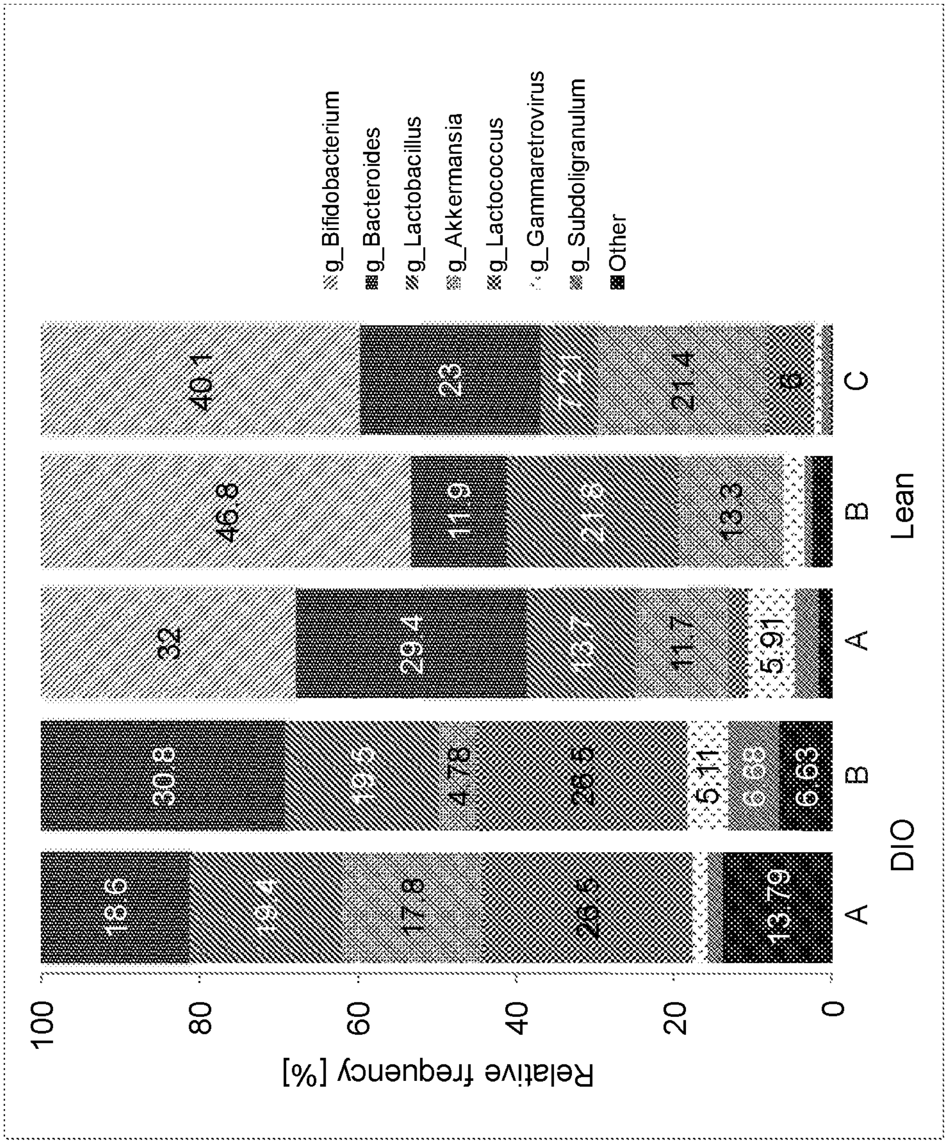
FIG. 10. Stool microbiome baseline for mice grown under high or low fat diet indicating the differences primarily seen as a lack of Bifidobacteria under high fat diet.

FIG. 10 shows the composition of the gut microbial community of DIO and lean mice. Overall, the genus *Bifidobacterium* was the most prevalent taxon detected in lean mice encompassing on average 40% of the total community followed by Bacteorides with 21.4% on average, and Akkermansia with 14.2% on average. In the case of the DIO mice, *Lactococcus* was the most abundant genus with 26.5% on average followed by *Bacteroides* with 24.6% and *Lactobacillus* with 19.4%.

All references, issued patents and patent applications cited within the body of the instant specification are hereby incorporated by reference in their entirety, for all purposes.

```
SEQUENCE LISTING
Seq ID No.
Description
Sequence
1
DP1 16S rRNA
AGTCAGACATGCAAGTCGAGCGGTAGAGAGAAGCTTGCTTCTCTTGAGAGCGGCGGACGGGTGAG

TAAAGCCTAGGAATCTGCCTGGTAGTGGGGGATAACGTTCGGAAACGGACGCTAATACCGCATACGT

CCTACGGGAGAAAGCAGGGGACCTTCGGGCCTTGCGCTATCAGATGAGCCTAGGTCGGATTAGCTAG

TTGGTGAGGTAATGGCTCACCAAGGCGACGATCCGTAACTGGTCTGAGAGGATGATCAGTCACACTG

GAACTGAGACACGGTCCAGACTCCTACGGGAGGCAGCAGTGGGGAATATTGGACAATGGGCGAAAG

CCTGATCCAGCCATGCCGCGTGTGTGAAGAAGGTCTTCGGATTGTAAAGCACTTTAAGTTGGGAGGA

AGGGCATTAACCTAATACGTTAGTGTTTTGACGTTACCGACAGAATAAGCACCGGCTAACTCTGTGCC

AGCAGCCGCGGTAATACAGAGGGTGCAAGCGTTAATCGGAATTACTGGGCGTAAAGCGCGCGTAGGT

GGTTTGTTAAGTTGGATGTGAAATCCCCGGGCTCAACCTGGGAACTGCATTCAAAACTGACTGACTAG

AGTATGGTAGAGGGTGGTGGAATTTCCTGTGTAGCGGTGAAATGCGTAGATATAGGAAGGAACACCA

GTGGCGAAGGCGACCACCTGGACTAATACTGACACTGAGGTGCGAAAGCGTGGGGAGCAAACAGGA

TTAGATACCCTGGTAGTCCACGCCGTAAACGATGTCAACTAGCCGTTGGGAGCCTTGAGCTCTTAGTG

GCGCAGCTAACGCATTAAGTTGACCGCCTGGGGAGTACGGCCGCAAGGTTAAAACTCAAATGAATTG

ACGGGGGCCCGCACAAGCGGTGGAGCATGTGGTTTAATTCGAAGCAACGCGAAGAACCTTACCAGGC

CTTGACATCCAATGAACTTTCTAGAGATAGATTGGTGCCTTCGGGAACATTGAGACAGGTGCTGCATG

GCTGTCGTCAGCTCGTGTCGTGAGATGTTGGGTTAAGTCCCGTAACGAGCGCAACCCTTGTCCTTAGT

TACCAGCACGTAATGGTGGGCACTCTAAGGAGACTGCCGGTGACAAACCGGAGGAAGGTGGGGATG

ACGTCAAGTCATCATGGCCCTTACGGCCTGGGCTACACACGTGCTACAATGGTCGGTACAGAGGGTT

GCCAAGCCGCGAGGTGGAGCTAATCCCATAAAACCGATCGTAGTCCGGATCGCAGTCTGCAACTCGA

CTGCGTGAAGTCGGAATCGCTAGTAATCGCGAATCAGAATGTCGCGGTGAATACGTTCCCGGGCCTT

GTACACACCGCCCGTCACACCATGGGAGTGGGTTGCACCAGAAGTAGCTAGTCTAACCTTCGGGAGG

ACGGTTACCACGGTGTGATTCATGACTGGGGTGAAGTCGTAACAAGGTAGCCGTAGGGGAACCTGCG

GCTGGATCACCTCCTT

2
DP2 ITS sequence
NNNNNNNNNNNNNNNNNNTTGTTGCTCGAGTTCTTGTTTAGATCTTTTACAATAATGTGTATCTTT

AATGAAGATGNGNGCTTAATTGCGCTGCTTTATTAGAGTGTCGCAGTAGAAGTAGTCTTGCTTGAATC

TCAGTCAACGTTTACACACATTGGAGTTTTTTTACTTTAATTTAATTCTTTCTGCTTTGAATCGAAAGG

TTCAAGGCAAAAAACAAACACAAACAATTTTATTTTATTATAATTTTTTAAACTAAACCAAAATTCCT

AACGGAAATTTTAAAATAATTTAAAACTTTCAACAACGGATCTCTTGGTTCTCGCATCGATGAAAAAC

GTACCGAATTGCGATAAGTAATGTGAATTGCAAATACTCGTGAATCATTGAATTTTTGAACGCACATT

GCGCCCTTGAGCATTCTCAAGGGCATGCCTGTTTGAGCGTCATTTCCTTCTCAAAAAATAATTTTTTAT

TTTTTGGTTGTGGGCGATACTCAGGGTTAGCTTGAAATTGGAGACTGTTTCAGTCTTTTTTAATTCAAC
```

-continued

ACTTANCTTCTTTGGAGACGCTGTTCTCGCTGTGATGTATTTATGGATTTATTCGTTTTACTTTACAAG

GGAAATGGTAATGTACCTTAGGCAAAGGGTTGCTTTTAATATTCATCAAGTTTGACCTCAAATCAGGT

AGGATTACCCGCTGAACTTAAGCATATCAATAAGCGGAGGAAAAGAAACCAACTGGGATTACCTTAG

TAACGGCGAGTGAAGCGGTAAAAGCTCAAATTTGAAATCTGGTACTTTCAGTGCCCGAGTTGTAATTT

GTAGAATTTGTCTTTGATTAGGTCCTTGTCTATGTTCCTTGGAACAGGACGTCATAGAGGGTGAGANT

CCCGTTTGNNGAGGATACCTTTTCTCTGTANNACTTTTTCNAAGAGTCGAGTTGNTTGGGAATGCAGC

TCAAANNGGGTNGNAAATTCCATCTAAAGCTAAATATTNGNCNAGAGACCGANAGCGACANTACAG

NGATGGAAAGANGAAANNANTTGAAAAGAANANNGAAAANTACGTGAANNNNNAAANGGNNNGGC

ATTTGATCNNNCATGGNNNTTTTTNCATGNN

3
DP3 16S rRNA
ATTGAGAGTTTGATCCTGGCTCAGGATGAACGCTGGCGGCGTGCCTAATACATGCAAGTCGAACG

CACAGCGAAAGGTGCTTGCACCTTTCAAGTGAGTGGCGAACGGGTGAGTAACACGTGGACAACCTGC

CTCAAGGCTGGGGATAACATTTGGAAACAGATGCTAATACCGAATAAAACTCAGTGTCGCATGACAC

AAAGTTAAAAGGCGCTTTGGCGTCACCTAGAGATGGATCCGCGGTGCATTAGTTAGTTGGTGGGGTA

AAGGCCTACCAAGACAATGATGCATAGCCGAGTTGAGAGACTGATCGGCCACATTGGGACTGAGACA

CGGCCCAAACTCCTACGGGAGGCTGCAGTAGGGAATCTTCCACAATGGGCGAAAGCCTGATGGAGCA

ACGCCGCGTGTGTGATGAAGGCTTTCGGGTCGTAAAGCACTGTTGTACGGGAAGAACAGCTAGAATA

GGGAATGATTTTAGTTTGACGGTACCATACCAGAAAGGGACGGCTAAATACGTGCCAGCAGCCGCGG

TAATACGTATGTCCCGAGCGTTATCCGGATTTATTGGGCGTAAAGCGAGCGCAGACGGTTGATTAAGT

CTGATGTGAAAGCCCGGAGCTCAACTCCGGAATGGCATTGGAAACTGGTTAACTTGAGTGCAGTAGA

GGTAAGTGGAACTCCATGTGTAGCGGTGGAATGCGTAGATATATGGAAGAACACCAGTGGCGAAGGC

GGCTTACTGGACTGTACTGACGTTGAGGCTCGAAAGTGTGGGTAGCAAACAGGATTAGATACCCTGG

TAGTCCACACCGTAAACGATGAACACTAGGTGTTAGGAGGTTTCCGCCTCTTAGTGCCGAAGCTAACG

CATTAAGTGTTCCGCCTGGGGAGTACGACCGCAAGGTTGAAACTCAAAGGAATTGACGGGGACCCGC

ACAAGCGGTGGAGCATGTGGTTTAATTCGAAGCAACGCGAAGAACCTTACCAGGTCTTGACATCCTTT

GAAGCTTTTAGAGATAGAAGTGTTCTCTTCGGAGACAAAGTGACAGGTGGTGCATGGTCGTCGTCAG

CTCGTGTCGTGAGATGTTGGGTTAAGTCCCGCAACGAGCGCAACCCTTATTGTTAGTTGCCAGCATTC

AGATGGGCACTCTAGCGAGACTGCCGGTGACAAACCGGAGGAAGGCGGGGACGACGTCAGATCATC

ATGCCCCTTATGACCTGGGCTACACACGTGCTACAATGGCGTATACAACGAGTTGCCAACCCGCGAG

GGTGAGCTAATCTCTTAAAGTACGTCTCAGTTCGGATTGTAGTCTGCAACTCGACTACATGAAGTCGG

AATCGCTAGTAATCGCGGATCAGCACGCCGCGGTGAATACGTTCCCGGGTCTTGTACACACCGCCCGT

CACACCATGGGAGTTTGTAATGCCCAAAGCCGGTGGCCTAACCTTTTAGGAAGGAGCCGTCTAAGGC

AGGACAGATGACTGGGGTGAAGTCGTAACAAGGTAGCCGTAGGAGAACCTGCGGCTGGATCACCTCC

TTT

4
DP4 16S rRNA
TTGAAGAGTTTGATCATGGCTCAGATTGAACGCTGGCGGCAGGCCTAACACATGCAAGTCGAGCG

GCAGCGGAAAGTAGCTTGCTACTTTGCCGGCGAGCGGCGGACGGGTGAGTAATGTCTGGGAAACTGC

CTGATGGAGGGGGATAACTACTGGAAACGGTAGCTAATACCGCATGACCTCGAAAGAGCAAAGTGG

GGGATCTTCGGACCTCACGCCATCGGATGTGCCCAGATGGGATTAGCTAGTAGGTGAGGTAATGGCT

CACCTAGGCGACGATCCCTAGCTGGTCTGAGAGGATGACCAGCCACACTGGAACTGAGACACGGTCC

AGACTCCTACGGGAGGCAGCAGTGGGGAATATTGCACAATGGGCGCAAGCCTGATGCAGCCATGCCG

-continued

CGTGTGTGAAGAAGGCCTTAGGGTTGTAAAGCACTTTCAGCGAGGAGGAAGGCATCATACTTAATAC

GTGTGGTGATTGACGTTACTCGCAGAAGAAGCACCGGCTAACTCCGTGCCAGCAGCCGCGGTAATAC

GGAGGGTGCAAGCGTTAATCGGAATTACTGGGCGTAAAGCGCACGCAGGCGGTTTGTTAAGTCAGAT

GTGAAATCCCCGCGCTTAACGTGGGAACTGCATTTGAAACTGGCAAGCTAGAGTCTTGTAGAGGGGG

GTAGAATTCCAGGTGTAGCGGTGAAATGCGTAGAGATCTGGAGGAATACCGGTGGCGAAGGCGGCCC

CCTGGACAAAGACTGACGCTCAGGTGCGAAAGCGTGGGGAGCAAACAGGATTAGATACCCTGGTAGT

CCACGCCGTAAACGATGTCGACTTGGAGGTTGTTCCCTTGAGGAGTGGCTTCCGGAGCTAACGCGTTA

AGTCGACCGCCTGGGGAGTACGGCCGCAAGGTTAAAACTCAAATGAATTGACGGGGGCCCGCACAA

GCGGTGGAGCATGTGGTTTAATTCGATGCAACGCGAAGAACCTTACCTACTCTTGACATCCACGGAAT

TTGGCAGAGATGCCTTAGTGCCTTCGGGAACCGTGAGACAGGTGCTGCATGGCTGTCGTCAGCTCGTG

TTGTGAAATGTTGGGTTAAGTCCCGCAACGAGCGCAACCCTTATCCTTTGTTGCCAGCGATTCGGTCG

GGAACTCAAAGGAGACTGCCGGTGATAAACCGGAGGAAGGTGGGGATGACGTCAAGTCATCATGGC

CCTTACGAGTAGGGCTACACACGGCTACAATGGCGCATACAAAGAGAAGCGACCTCGCGAGAGCAA

GCGGACCTCACAAAGTGCGTCGTAGTCCGGATCGGAGTCTGCAACTCGACTCCGTGAAGTCGGAATC

GCTAGTAATCGTGGATCAGAATGCCACGGTGAATACGTTCCCGGGCCTTGTACACACCGCCCGTCACA

CCATGGGAGTGGGTTGCAAAAGAAGTAGGTAGCTTAACCTTCGGGAGGGCGCTTACCACTTTGTGAT

TCATGACTGGGGTGAAGTCGTAACAAGGTAACCGTAGGGGAACCTGCGGTTGGATCACCTCCTT

5
DP5 ITS sequence
NNNNNNNNNNNNNNNNNTGNNGCGCTTATTGCGCGGCGAAAAAACCTTACACACAGTGTTTTTG

TTATTACANNAACTTTTGCTTTGGTCTGGACTAGAAATAGTTTGGGCCAGAGGTTACTAAACTAAACT

TCAATATTTATATTGAATTGTTATTTATTTAATTGTCAATTTGTTGATTAAATTCAAAAAATCTTCAAA

ACTTTCAACAACGGATCTCTTGGTTCTCGCATCGATGAAGAACGCAGCGAAATGCGATAAGTAATAT

GAATTGCAGATTTTCGTGAATCATCGAATCTTTGAACGCACATTGCGCCCTCTGGTATTCCAGAGGGC

ATGCCTGTTTGAGCGTCATTTCTCTCTCAAACCTTCGGGTTTGGTATTGAGTGATACTCTTAGTCGAAC

TAGGCGTTTGCTTGAAATGTATTGGCATGAGTGGTACTGGATAGTGCTATATGACTTTCAATGTATTA

GGTTTATCCAACTCGTTGAATAGTTTAATGGTATATTTCTCGGTATTCTAGGCTCGGCCTTACAATATA

ACAAACAAGTTTGACCTCAAATCAGGTAGGATTACCCGCTGAACTTAAGCATATCAATAAGCGGAGG

AAAAGAAACCAACAGGGATTGCCTTAGTAACGGCGAGTGAAGCGGCAAAAGCTCAAATTTGAAATCT

GGCACCTTCGGTGTCCGAGTTGTAATTTGAAGAAGGTAACTTTGGAGTTGGCTCTTGTCTATGTTCCTT

GGAACAGGACGTCACAGAGGGTGAGAATCCCGTGCGATGAGATGCCCAATTCTATGTAAAGTGCTTT

CGAAGAGTCGAGTTGTTTGGGAATGCAGCTCTAAGTGGGTGGTAAATTCCATCTAAAGCTAAATATTG

GCGAGAGACCGATAGCGAACAAGTACAGTGATGGAAAGATGAAAAGAACTTTGAAAAGAGAGTGAA

AAAGTACGTGAAATTGTTGAAAGGGAAAGGGCTTGAGATCAGACTTGGTATTTTGCGATCCTTTCCTT

CTTGGTTGGGTTCCTCGCAGCTTACTGGGNCAGCATCGGTTTGGATGGNAGGATAANGACTAAGNAA

TGNGGNNCTACTTCGNGGAGTGNNNNAGCNNTGGNNGANNACTNNCNNNCTAAGANCGAGGACTGN

GNNNTTTNN

6
DP6 16S rRNA

7
DP7 16S rRNA

8
DP8 16S rRNA

-continued

9
DP9 16S rRNA
ATGAGAGTTTGATCTTGGCTCAGGATGAACGCTGGCGGCGTGCCTAATACATGCAAGTCGAACGA

ACTTCCGTTAATTGATTATGACGTACTTGTACTGATTGAGATTTTAACACGAAGTGAGTGGCGAACGG

GTGAGTAACACGTGGGTAACCTGCCCAGAAGTAGGGGATAACACCTGGAAACAGATGCTAATACCGT

ATAACAGAGAAAACCGCATGGTTTTCTTTTAAAAGATGGCTCTGCTATCACTTCTGGATGGACCCGCG

GCGTATTAGCTAGTTGGTGAGGCAAAGGCTCACCAAGGCAGTGATACGTAGCCGACCTGAGAGGGTA

ATCGGCCACATTGGGACTGAGACACGGCCCAGACTCCTACGGGAGGCAGCAGTAGGGAATCTTCCAC

AATGGACGCAAGTCTGATGGAGCAACGCCGCGTGAGTGAAGAAGGGTTTCGGCTCGTAAAGCTCTGT

TGTTAAAGAAGAACGTGGGTAAGAGTAACTGTTTACCCAGTGACGGTATTTAACCAGAAAGCCACGG

CTAACTACGTGCCAGCAGCCGCGGTAATACGTAGGTGGCAAGCGTTATCCGGATTTATTGGGCGTAA

AGCGAGCGCAGGCGGTCTTTTAAGTCTAATGTGAAAGCCTTCGGCTCAACCGAAGAAGTGCATTGGA

AACTGGGAGACTTGAGTGCAGAAGAGGACAGTGGAACTCCATGTGTAGCGGTGAAATGCGTAGATAT

ATGGAAGAACACCAGTGGCGAAGGCGGCTGTCTGGTCTGCAACTGACGCTGAGGCTCGAAAGCATGG

GTAGCGAACAGGATTAGATACCCTGGTAGTCCATGCCGTAAACGATGATTACTAAGTGTTGGAGGGT

TTCCGCCCTTCAGTGCTGCAGCTAACGCATTAAGTAATCCGCCTGGGGAGTACGACCGCAAGGTTGAA

ACTCAAAAGAATTGACGGGGGCCCGCACAAGCGGTGGAGCATGTGGTTTAATTCGAAGCTACGCGAA

GAACCTTACCAGGTCTTGACATCTTCTGACAGTCTAAGAGATTAGAGGTTCCCTTCGGGGACAGAATG

ACAGGTGGTGCATGGTTGTCGTCAGCTCGTGTCGTGAGATGTTGGGTTAAGTCCCGCAACGAGCGCA

ACCCTTATTACTAGTTGCCAGCATTAAGTTGGGCACTCTAGTGAGACTGCCGGTGACAAACCGGAGG

AAGGTGGGGACGACGTCAAATCATCATGCCCCTTATGACCTGGGCTACACACGTGCTACAATGGATG

GTACAACGAGTCGCGAGACCGCGAGGTTAAGCTAATCTCTTAAAACCATTCTCAGTTCGGACTGTAG

GCTGCAACTCGCCTACACGAAGTCGGAATCGCTAGTAATCGCGGATCAGCATGCCGCGGTGAATACG

TTCCCGGGCCTTGTACACACCGCCCGTCACACCATGAGAGTTTGTAACACCCAAAGCCGGTGGGGTA

ACCTTTTAGGAGCTAGCCGTCTAAGGTGGGACAGATGATTAGGGTGAAGTCGTAACAAGGTAGCCGT

AGGAGAACCTGCGGCTGGATCACCTCCTT

10
DP10 16S rRNA
CAGATAGTTGGTGAGGTAACGGCTCACCAAGGCAACGATGCGTAGCCGACCTGAGAGGGTGATCG

GCCACACTGGGACTGAGACACGGCCCAGACTCCTACGGGAGGCAGCAGTAGGGAATCTTCCGCAATG

GACGAAAGTCTGACGGAGCAACGCCGCGTGAGTGATGAAGGTTTTCGGATCGTAAAGCTCTGTTGTT

AGGGAAGAACAAGTGCCGTTCAAATAGGGCGGCACCTTGACGGTACCTAACCAGAAAGCCACGGCT

AACTACGTGCCAGCAGCCGCGGTAATACGTAGGTGGCAAGCGTTGTCCGGAATTATTGGGCGTAAAG

GGCTCGCAGGCGGTTTCTTAAGTCTGATGTGAAAGCCCCCGGCTCAACCGGGGAGGGTCATTGGAAA

CTGGGGAACTTGAGTGCAGAAGAGGAGAGTGGAATTCCACGTGTAGCGGTGAAATGCGTAGAGATGT

GGAGGAACACCAGTGGCGAAGGCGACTCTCTGGTCTGTAACTGACGCTGAGGAGCGAAAGCGTGGG

GAGCGAACAGGATTAGATACCCTGGTAGTCCACGCCGTAAACGATGAGTGCTAAGTGTTAGGGGGTT

TCCGCCCCTTAGTGCTGCAGCTAACGCATTAAGCACTCCGCCTGGGGAGTACGGTCGCAAGACTGAA

ACTCAAAGGAATTGACGGGGGCCCGCACAAGCGGTGGAGCATGTGGTTTAATTCGAAGCAACGCGAA

GAACCTTACCAGGTCTTGACATCCTCTGACAATCCTAGAGATAGGACGTCCCCTTCGGGGGCAGAGTG

ACAGGTGGTGCATGGTTGTCGTCAGCTCGTGTCGTGAGATGTTGGGTTAAGTCCCGCAACGAGCGCA

ACCCTTGATCTTAGTTGCCAGCATTCAGTTGGGCACTCTAAGGTGACTGCCGGTGACAAACCGGAGGA

-continued

AGGTGGGGATGACGTCAAATCATCATGCCCCTTATGACCTGGGCTACACACGTGCTACAATGGACAG

AACAAAGGGCAGCGAAACCGCGAGGTTAAGCCAATCCCACAAATCTGTTCTCAGTTCGGATCGCAGT

CTGCAACTCGACTGCGTGAAGCTGGAATCGCTAGTAATCGCGGATCAGCATGCCGCGGTGAATACGT

TCCCGGGCCTTGTACACACCGCCCGTCACACCACGAGAGTTTGTAACACCCGAAGTCGGTGAGGTAA

CCTTTTAGGAGCCAGCCGCCGAAGGTGGGACAGATGATTGGGGTGAAGTCGTAACAAGGTAGCCGTA

TCGGAAGGTGCGGCTGGATCACCTCCTTT

11
DP11 16S rRNA
TGAAGAGTTTGATCATGGCTCAGATTGAACGCTGGCGGCAGGCCTAACACATGCAAGTCGAGCGG

TAGAGAGAAGCTTGCTTCTCTTGAGAGCGGCGGACGGGTGAGTAATGCCTAGGAATCTGCCTGGTAG

TGGGGGATAACGTTCGGAAACGGACGCTAATACCGCATACGTCCTACGGGAGAAAGCAGGGGACCTT

CGGGCCTTGCGCTATCAGATGAGCCTAGGTCGGATTAGCTAGTTGGTGAGGTAATGGCTCACCAAGG

CGACGATCCGTAACTGGTCTGAGAGGATGATCAGTCACACTGGAACTGAGACACGGTCCAGACTCCT

ACGGGAGGCAGCAGTGGGGAATATTGGACAATGGGCGAAAGCCTGATCCAGCCATGCCGCGTGTGTG

AAGAAGGTCTTCGGATTGTAAAGCACTTTAAGTTGGGAGGAAGGGTTGTAGATTAATACTCTGCAATT

TTGACGTTACCGACAGAATAAGCACCGGCTAACTCTGTGCCAGCAGCCGCGGTAATACAGAGGGTGC

AAGCGTTAATCGGAATTACTGGGCGTAAAGCGCGCGTAGGTGGTTCGTTAAGTTGGATGTGAAAGCC

CCGGGCTCAACCTGGGAACTGCATTCAAAACTGACGAGCTAGAGTATGGTAGAGGGTGGTGGAATTT

CCTGTGTAGCGGTGAAATGCGTAGATATAGGAAGGAACACCAGTGGCGAAGGCGACCACCTGGACTG

ATACTGACACTGAGGTGCGAAAGCGTGGGGAGCAAACAGGATTAGATACCCTGGTAGTCCACGCCGT

AAACGATGTCAACTAGCCGTTGGAATCCTTGAGATTTTAGTGGCGCAGCTAACGCATTAAGTTGACCG

CCTGGGGAGTACGGCCGCAAGGTTAAAACTCAAATGAATTGACGGGGGCCCGCACAAGCGGTGGAG

CATGTGGTTTAATTCGAAGCAACGCGAAGAACCTTACCAGGCCTTGACATCCAATGAACTTTCCAGAG

ATGGATGGGTGCCTTCGGGAACATTGAGACAGGTGCTGCATGGCTGTCGTCAGCTCGTGTCGTGAGAT

GTTGGGTTAAGTCCCGTAACGAGCGCAACCCTTGTCCTTAGTTACCAGCACGTTATGGTGGGCACTCT

AAGGAGACTGCCGGTGACAAACCGGAGGAAGGTGGGGATGACGTCAAGTCATCATGGCCCTTACGG

CCTGGGCTACACACGTGCTACAATGGTCGGTACAAAGGGTTGCCAAGCCGCGAGGTGGAGCTAATCC

CATAAAACCGATCGTAGTCCGGATCGCAGTCTGCAACTCGACTGCGTGAAGTCGGAATCGCTAGTAA

TCGCGAATCAGAATGTCGCGGTGAATACGTTCCCGGGCCTTGTACACACCGCCCGTCACATCCCACAC

GAATTGCTTG

12
DP12 16S rRNA
TACGGAGAGTTTGATCCTGGCTCAGGATGAACGCTGGCGGCGTGCTTAACACATGCAAGTCGAAC

GGTGAAGCCAAGCTTGCTTGGTGGATCAGTGGCGAACGGGTGAGTAACACGTGAGCAACCTGCCCTG

GACTCTGGGATAAGCGCTGGAAACGGCGTCTAATACTGGATATGAGCCTTCATCGCATGGTGGGGGT

TGGAAAGATTTTTTGGTCTGGGATGGGCTCGCGGCCTATCAGCTTGTTGGTGAGGTAATGGCTCACCA

AGGCGTCGACGGGTAGCCGGCCTGAGAGGGTGACCGGCCACACTGGGACTGAGACACGGCCCAGAC

TCCTACGGGAGGCAGCAGTGGGGAATATTGCACAATGGGCGAAAGCCTGATGCAGCAACGCCGCGTG

AGGGATGACGGCCTTCGGGTTGTAAACCTCTTTTAGCAGGGAAGAAGCGAAAGTGACGGTACCTGCA

GAAAAAGCGCCGGCTAACTACGTGCCAGCAGCCGCGGTAATACGTAGGGCGCAAGCGTTATCCGGAA

TTATTGGGCGTAAAGAGCTCGTAGGCGGTTTGTCGCGTCTGCTGTGAAATCCCGAGGCTCAACCTCGG

GCCTGCAGTGGGTACGGGCAGACTAGAGTGCGGTAGGGGAGATTGGAATTCCTGGTGTAGCGGTGGA

ATGCGCAGATATCAGGAGGAACACCGATGGCGAAGGCAGATCTCTGGGCCGTAACTGACGCTGAGG

-continued

AGCGAAAGGGTGGGGAGCAAACAGGCTTAGATACCCTGGTAGTCCACCCCGTAAACGTTGGGAACTA

GTTGTGGGGACCATTCCACGGTTTCCGTGACGCAGCTAACGCATTAAGTTCCCCGCCTGGGGAGTACG

GCCGCAAGGCTAAAACTCAAAGGAATTGACGGGGACCCGCACAAGCGGCGGAGCATGCGGATTAAT

TCGATGCAACGCGAAGAACCTTACCAAGGCTTGACATACACCAGAACGGGCCAGAAATGGTCAACTC

TTTGGACACTGGTGAACAGGTGGTGCATGGTTGTCGTCAGCTCGTGTCGTGAGATGTTGGGTTAAGTC

CCGCAACGAGCGCAACCCTCGTTCTATGTTGCCAGCACGTAATGGTGGGAACTCATGGGATACTGCC

GGGGTCAACTCGGAGGAAGGTGGGGATGACGTCAAATCATCATGCCCCTTATGTCTTGGGCTTCACG

CATGCTACAATGGCCGGTACAAAGGGCTGCAATACCGTGAGGTGGAGCGAATCCCAAAAAGCCGGTC

CCAGTTCGGATTGAGGTCTGCAACTCGACCTCATGAAGTCGGAGTCGCTAGTAATCGCAGATCAGCA

ACGCTGCGGTGAATACGTTCCCGGGTCTTGTACACACCGCCCGTCAAGTCATGAAAGTCGGTAACACC

TGAAGCCGGTGGCCCAACCCTTGTGGAGGGAGCCGTCGAAGGTGGGATCGGTAATTAGGACTAAGTC

GTAACAAGGTAGCCGTACCGGAAGGTGCGGCTGGATCACCTCCTTT

13
DP13 16S rRNA
AGTTAGCGGCGGACGGGTGAGTAACACGTGGGTAACCTGCCTATAAGACTGGGATAACTCCGGGA

AACCGGGGCTAATACCGGATAACATTTTGCACCGCATGGTGCGAAATTGAAAGGCGGCTTCGGCTGT

CACTTATAGATGGACCTGCGGCGCATTAGCTAGTTGGTGAGGTAACGGCTCACCAAGGCGACGATGC

GTAGCCGACCTGAGAGGGTGATCGGCCACACTGGGACTGAGACACGGCCCAGACTCCTACGGGAGGC

AGCAGTAGGGAATCTTCCGCAATGGACGAAAGTCTGACGGAGCAACGCCGCGTGAACGATGAAGGC

TTTCGGGTCGTAAAGTTCTGTTGTTAGGGAAGAACAAGTGCTAGTTGAATAAGCTGGCACCTTGACGG

TACCTAACCAGAAAGCCACGGCTAACTACGTGCCAGCAGCCGCGGTAATACGTAGGTGGCAAGCGTT

ATCCGGAATTATTGGGCGTAAAGCGCGCGCAGGTGGTTTCTTAAGTCTGATGTGAAAGCCCACGGCTC

AACCGTGGAGGGTCATTGGAAACTGGGAGACTTGAGTGCAGAAGAGGAAAGTGGAATTCCATGTGTA

GCGGTGAAATGCGTAGAGATATGGAGGAACACCAGTGGCGAAGGCGACTTTCTGGTCTGCAACTGAC

ACTGAGGCGCGAAAGCGTGGGGAGCAAACAGGATTAGATACCCTGGTAGTCCACGCCGTAAACGAT

GAGTGCTAAGTGTTAGAGGGTTTCCGCCCTTTAGTGCTGAAGTTAACGCATTAAGCACTCCGCCTGGG

GAGTACGGCCGCAAGGCTGAAACTCAAAGGAATTGACGGGGGCCCGCACAAGCGGTGGAGCATGTG

GTTTAATTCGAAGCAACGCGAAGAACCTTACCAGGTCTTGACATCCTCTGAAAACCCTAGAGATAGG

GCTTCCCCTTCGGGGGCAGAGTGACAGGTGGTGCATGGTTGTCGTCAGCTCGTGTCGTGAGATGTTGG

GTTAAGTCCCGCAACGAGCGCAACCCTTGATCTTAGTTGCCATCATTAAGTTGGGCACTCTAAGGTGA

CTGCCGGTGACAAACCGGAGGAAGGTGGGGATGACGTCAAATCATCATGCCCCTTATGACCTGGGCT

ACACACGTGCTACAATGGACGGTACAAAGAGTCGCAAGACCGCGAGGTGGAGCTAATCTCATAAAAC

CGTTCTCAGTTCGGATTGTAGGCTGCAACTCGCCTACATGAAGCTGGAATCGCTAGTAATCGCGGATC

AGCATGCCGCGGTGAATACGTTCCCGGGCCTTGTACACACCGCCCGTCACACCACGAGAGTTTGTAAC

ACCCGAAGTCGGTGGGGTAACCTTTTGGAGCCAGCCGCCTAAGGTGGGACAGATGATTGGGGTGAAG

TCGTAACAAGGTAGCCGTATCGGAAGGTGCGGCTGGATCACCTCCTTT

14
DP14 16S rRNA
TACGGAGAGTTTGATCCTGGCTCAGGATGAACGCTGGCGGCGTGCTTAACACATGCAAGTCGAAC

GATGACTTCTGTGCTTGCACAGAATGATTAGTGGCGAACGGGTGAGTAACACGTGAGTAACCTGCCC

TTAACTTCGGGATAAGCCTGGGAAACCGGGTCTAATACCGGATACGACCTCCTGGCGCATGCCATGG

TGGTGGAAAGCTTTAGCGGTTTTGGATGGACTCGCGGCCTATCAGCTTGTTGGTTGGGGTAATGGCCC

-continued

ACCAAGGCGACGACGGGTAGCCGGCCTGAGAGGGTGACCGGCCACACTGGGACTGAGACACGGCCC

AGACTCCTACGGGAGGCAGCAGTGGGGAATATTGCACAATGGGCGAAAGCCTGATGCAGCGACGCC

GCGTGAGGGATGACGGCCTTCGGGTTGTAAACCTCTTTCAGCAGGGAAGAAGCGAAAGTGACGGTAC

CTGCAGAAGAAGCGCCGGCTAACTACGTGCCAGCAGCCGCGGTAATACGTAGGGCGCAAGCGTTATC

CGGAATTATTGGGCGTAAAGAGCTCGTAGGCGGTTTGTCGCGTCTGCTGTGAAAGCCCGGGGCTCAA

CCCCGGGTCTGCAGTGGGTACGGGCAGACTAGAGTGCAGTAGGGGAGACTGGAATTCCTGGTGTAGC

GGTGAAATGCGCAGATATCAGGAGGAACACCGATGGCGAAGGCAGGTCTCTGGGCTGTAACTGACGC

TGAGGAGCGAAAGCATGGGGAGCGAACAGGATTAGATACCCTGGTAGTCCATGCCGTAAACGTTGGG

CACTAGGTGTGGGGGACATTCCACGTTTTCCGCGCCGTAGCTAACGCATTAAGTGCCCCGCCTGGGGA

GTACGGCCGCAAGGCTAAAACTCAAAGGAATTGACGGGGGCCCGCACAAGCGGCGGAGCATGCGGA

TTAATTCGATGCAACGCGAAGAACCTTACCAAGGCTTGACATGAACCGGTAAGACCTGGAAACAGGT

CCCCCACTTGTGGCCGGTTTACAGGTGGTGCATGGTTGTCGTCAGCTCGTGTCGTGAGATGTTGGGTT

AAGTCCCGCAACGAGCGCAACCCTCGTTCTATGTTGCCAGCGGGTTATGCCGGGGACTCATAGGAGA

CTGCCGGGGTCAACTCGGAGGAAGGTGGGGACGACGTCAAATCATCATGCCCCTTATGTCTTGGGCTT

CACGCATGCTACAATGGCCGGTACAAAGGGTTGCGATACTGTGAGGTGGAGCTAATCCCAAAAAGCC

GGTCTCAGTTCGGATTGAGGTCTGCAACTCGACCTCATGAAGTTGGAGTCGCTAGTAATCGCAGATCA

GCAACGCTGCGGTGAATACGTTCCCGGGCCTTGTACACACCGCCCGTCAAGTCACGAAAGTTGGTAA

CACCCGAAGCCGGTGGCCTAACCCCTTGTGGGAGGGAGCCGTCGAAGGTGGGACCGGCGATTGGGAC

AAGTCGTAACAAGGTAGCCGTACCGGAAGGTGCGGCTGGATCACCTCCTTT

15
DP15 16S rRNA
TACGGAGAGTTTGATCCTGGCTCAGGACGAACGCTGGCGGCGTGCTTAACACATGCAAGTCGAAC

GATGATCAGGAGCTTGCTCCTGTGATTAGTGGCGAACGGGTGAGTAACACGTGAGTAACCTGCCCCT

GACTCTGGGATAAGCGTTGGAAACGACGTCTAATACTGGATATGATCACTGGCCGCATGGTCTGGTG

GTGGAAAGATTTTTTGGTTGGGGATGGACTCGCGGCCTATCAGCTTGTTGGTGAGGTAATGGCTCACC

AAGGCGACGACGGGTAGCCGGCCTGAGAGGGTGACCGGCCACACTGGGACTGAGACACGGCCCAGA

CTCCTACGGGAGGCAGCAGTGGGGAATATTGCACAATGGGCGAAAGCCTGATGCAGCAACGCCGCGT

GAGGGATGACGGCCTTCGGGTTGTAAACCTCTTTTAGTAGGGAAGAAGCGAAAGTGACGGTACCTGC

AGAAAAAGCACCGGCTAACTACGTGCCAGCAGCCGCGGTAATACGTAGGGTGCAAGCGTTGTCCGGA

ATTATTGGGCGTAAAGAGCTCGTAGGCGGTTTGTCGCGTCTGCTGTGAAATCCCGAGGCTCAACCTCG

GGCTTGCAGTGGGTACGGGCAGACTAGAGTGCGGTAGGGGAGATTGGAATTCCTGGTGTAGCGGTGG

AATGCGCAGATATCAGGAGGAACACCGATGGCGAAGGCAGATCTCTGGGCCGTAACTGACGCTGAG

GAGCGAAAGCGTGGGGAGCGAACAGGATTAGATACCCTGGTAGTCCACGCCGTAAACGTTGGGCGCT

AGATGTAGGGACCTTTCCACGGTTTCTGTGTCGTAGCTAACGCATTAAGCGCCCCGCCTGGGGAGTAC

GGCCGCAAGGCTAAAACTCAAAGGAATTGACGGGGGCCCGCACAAGCGGCGGAGCATGCGGATTAA

TTCGATGCAACGCGAAGAACCTTACCAAGGCTTGACATACACCGGAAACGGCCAGAGATGGTCGCCC

CCTTGTGGTCGGTGTACAGGTGGTGCATGGTTGTCGTCAGCTCGTGTCGTGAGATGTTGGGTTAAGTC

CCGCAACGAGCGCAACCCTCGTTCTATGTTGCCAGCGCGTTATGGCGGGGACTCATAGGAGACTGCC

GGGGTCAACTCGGAGGAAGGTGGGGATGACGTCAAATCATCATGCCCCTTATGTCTTGGGCTTCACG

CATGCTACAATGGCCGGTACAAAGGGCTGCGATACCGTAAGGTGGAGCGAATCCCAAAAAGCCGGTC

TCAGTTCGGATTGAGGTCTGCAACTCGACCTCATGAAGTCGGAGTCGCTAGTAATCGCAGATCAGCA

ACGCTGCGGTGAATACGTTCCCGGGCCTTGTACACACCGCCCGTCAAGTCATGAAAGTCGGTAACAC

-continued

CCGAAGCCGGTGGCCTAACCCTTGTGGAAGGAGCCGTCGAAGGTGGGATCGGTGATTAGGACTAAGT

CGTAACAAGGTAGCCGTACCGGAAGGTGCGGCTGGATCACCTCCTTT

16
DP16 16S rRNA

17
DP17 16S rRNA
GTGATTGACGTTACTCGCAGAAGAAGCACCGGCTAACTCCGTGCCAGCAGCCGCGGTAATACGGA

GGGTGCAAGCGTTAATCGGAATTACTGGGCGTAAAGCGCACGCAGGCGGTTTGTTAAGTCAGATGTG

AAATCCCCGCGCTTAACGTGGGAACTGCATTTGAAACTGGCAAGCTAGAGTCTTGTAGAGGGGGGTA

GAATTCCAGGTGTAGCGGTGAAATGCGTAGAGATCTGGAGGAATACCGGTGGCGAAGGCGGCCCCCT

GGACAAAGACTGACGCTCAGGTGCGAAAGCGTGGGGAGCAAACAGGATTAGATACCCTGGTAGTCC

ACGCTGTAAACGATGTCGACTTGGAGGTTGTGCCCTTGAGGCGTGGCTTCCGGAGCTAACGCGTTAAG

TCGACCGCCTGGGGAGTACGGCCGCAAGGTTAAAACTCAAATGAATTGACGGGGGCCCGCACAAGCG

GTGGAGCATGTGGTTTAATTCGATGCAACGCGAAGAACCTTACCTACTCTTGACATCCACGGAATTCG

CCAGAGATGGCTTAGTGCCTTCGGGAACCGTGAGACAGGTGCTGCATGGCTGTCGTCAGCTCGTGTTG

TGAAATGTTGGGTTAAGTCCCGCAACGAGCGCAACCCTTATCCTTTGTTGCCAGCACGTAATGGTGGG

AACTCAAAGGAGACTGCCGGTGATAAACCGGAGGAAGGTGGGGATGACGTCAAGTCATCATGGCCCT

TACGAGTAGGGCTACACACGTGCTACAATGGCATATACAAAGAGAAGCGAACTCGCGAGAGCAAGC

GGACCTCATAAAGTATGTCGTAGTCCGGATTGGAGTCTGCAACTCGACTCCATGAAGTCGGAATCGCT

AGTAATCGTAGATCAGAATGCTACGG

18
DP18 16S rRNA
TGAAGAGTTTGATCATGGCTCAGATTGAACGCTGGCGGCAGGCCTAACACATGCAAGTCGAGCGG

ATGAAAGGAGCTTGCTCCTGGATTCAGCGGCGGACGGGTGAGTAATGCCTAGGAATCTGCCTGGTAG

TGGGGGACAACGTTTCGAAAGGAACGCTAATACCGCATACGTCCTACGGGAGAAAGCAGGGGACCTT

CGGGCCTTGCGCTATCAGATGAGCCTAGGTCGGATTAGCTAGTTGGTGAGGTAATGGCTCACCAAGG

CGACGATCCGTAACTGGTCTGAGAGGATGATCAGTCACACTGGAACTGAGACACGGTCCAGACTCCT

ACGGGAGGCAGCAGTGGGGAATATTGGACAATGGGCGAAAGCCTGATCCAGCCATGCCGCGTGTGTG

AAGAAGGTCTTCGGATTGTAAAGCACTTTAAGTTGGGAGGAAGGGCAGTAAATTAATACTTTGCTGTT

TTGACGTTACCGACAGAATAAGCACCGGCTAACTCTGTGCCAGCAGCCGCGGTAATACAGAGGGTGC

AAGCGTTAATCGGAATTACTGGGCGTAAAGCGCGCGTAGGTGGTTTGTTAAGTTGAATGTGAAATCC

CCGGGCTCAACCTGGGAACTGCATCCAAAACTGGCAAGCTAGAGTATGGTAGAGGGTGGTGGAATTT

CCTGTGTAGCGGTGAAATGCGTAGATATAGGAAGGAACACCAGTGGCGAAGGCGACCACCTGGACTG

ATACTGACACTGAGGTGCGAAAGCGTGGGGAGCAAACAGGATTAGATACCCTGGTAGTCCACGCCGT

AAACGATGTCAACTAGCCGTTGGGAGCCTTGAGCTCTTAGTGGCGCAGCTAACGCATTAAGTTGACC

GCCTGGGGAGTACGGCCGCAAGGTTAAAACTCAAATGAATTGACGGGGGCCCGCACAAGCGGTGGA

GCATGTGGTTTAATTCGAAGCAACGCGAAGAACCTTACCAGGCCTTGACATCCAATGAACTTTCCAGA

GATGGATTGGTGCCTTCGGGAACATTGAGACAGGTGCTGCATGGCTGTCGTCAGCTCGTGTCGTGAGA

TGTTGGGTTAAGTCCCGTAACGAGCGCAACCCTTGTCCTTAGTTACCAGCACGTTATGGTGGGCACTC

TAAGGAGACTGCCGGTGACAAACCGGAGGAAGGTGGGGATGACGTCAAGTCATCATGGCCCTTACGG

CCTGGGCTACACACGTGCTACAATGGTCGGTACAAAGGGTTGCCAAGCCGCGAGGTGGAGCTAATCC

CATAAAACCGATCGTAGTCCGGATCGCAGTCTGCAACTCGACTGCGTGAAGTCGGAATCGCTAGTAA

TCGCGAATCAGAATGTCGCGGTGAATACGTTCCCGGGCCTTGTACACACCGCCCGTCACACCATGGG

-continued

AGTGGGTTGCACCAGAAGTAGCTAGTCTAACCTTCGGGAGGACGGTTACCACGGTGTGATTCATGAC

TGGGGTGAAGTCGTAACAAGGTAGCCGTAGGGGAACCTGCGGCTGGATCACCTCCTT

19
DP19 16S rRNA
TACGGAGAGTTTGATCCTGGCTCAGGACGAACGCTGGCGGCGTGCTTAACACATGCAAGTCGAAC

GATGATGCCCAGCTTGCTGGGTGGATTAGTGGCGAACGGGTGAGTAACACGTGAGTAACCTGCCCCT

GACTCTGGGATAAGCGTTGGAAACGACGTCTAATACTGGATACGACTGCCGGCCGCATGGTCTGGTG

GTGGAAAGATTTTTTGGTTGGGGATGGACTCGCGGCCTATCAGCTTGTTGGTGAGGTAATGGCTCACC

AAGGCGACGACGGGTAGCCGGCCTGAGAGGGTGACCGGCCACACTGGGACTGAGACACGGCCCAGA

CTCCTACGGGAGGCAGCAGTGGGGAATATTGCACAATGGGCGAAAGCCTGATGCAGCAACGCCGCGT

GAGGGATGACGGCCTTCGGGTTGTAAACCTCTTTTAGTAGGGAAGAAGCGAAAGTGACGGTACCTGC

AGAAAAAGCACCGGCTAACTACGTGCCAGCAGCCGCGGTAATACGTAGGGTGCAAGCGTTGTCCGGA

ATTATTGGGCGTAAAGAGCTCGTAGGCGGTTTGTCGCGTCTGCTGTGAAATCCCGAGGCTCAACCTCG

GGCTTGCAGTGGGTACGGGCAGACTAGAGTGCGGTAGGGGAGATTGGAATTCCTGGTGTAGCGGTGG

AATGCGCAGATATCAGGAGGAACACCGATGGCGAAGGCAGATCTCTGGGCCGTAACTGACGCTGAG

GAGCGAAAGCGTGGGGAGCGAACAGGATTAGATACCCTGGTAGTCCACGCCGTAAACGTTGGGCGCT

AGATGTAGGGACCTTTCCACGGTTTCTGTGTCGTAGCTAACGCATTAAGCGCCCCGCCTGGGGAGTAC

GGCCGCAAGGCTAAAACTCAAAGGAATTGACGGGGGCCCGCACAAGCGGCGGAGCATGCGGATTAA

TTCGATGCAACGCGAAGAACCTTACCAAGGCTTGACATACACCGGAAACGGCCAGAGATGGTCGCCC

CCTTGTGGTCGGTGTACAGGTGGTGCATGGTTGTCGTCAGCTCGTGTCGTGAGATGTTGGGTTAAGTC

CCGCAACGAGCGCAACCCTCGTTCTATGTTGCCAGCGCGTTATGGCGGGGACTCATAGGAGACTGCC

GGGGTCAACTCGGAGGAAGGTGGGGATGACGTCAAATCATCATGCCCCTTATGTCTTGGGCTTCACG

CATGCTACAATGGCCGGTACAAAGGGCTGCGATACCGTAAGGTGGAGCGAATCCCAAAAAGCCGGTC

TCAGTTCGGATTGAGGTCTGCAACTCGACCTCATGAAGTCGGAGTCGCTAGTAATCGCAGATCAGCA

ACGCTGCGGTGAATACGTTCCCGGGCCTTGTACACACCGCCCGTCAAGTCATGAAAGTCGGTAACAC

CCGAAGCCGGTGGCCTAACCCTTGTGGAAGGAGCCGTCGAAGGTGGGATCGGTGATTAGGACTAAGT

CGTAACAAGGTAGCCGTACCGGAAGGTGCGGCTGGATCACCTCCTTT

20
DP20 16S rRNA
TGAAGAGTTTGATCCTGGCTCAGAGTGAACGCTGGCGGTAGGCCTAACACATGCAAGTCGAACGG

CAGCACAGTAAGAGCTTGCTCTTATGGGTGGCGAGTGGCGGACGGGTGAGGAATACATCGGAATCTA

CCTTTTCGTGGGGGATAACGTAGGGAAACTTACGCTAATACCGCATACGACCTTCGGGTGAAAGCAG

GGGACCTTCGGGCCTTGCGCGGATAGATGAGCCGATGTCGGATTAGCTAGTTGGCGGGGTAAAGGCC

CACCAAGGCGACGATCCGTAGCTGGTCTGAGAGGATGATCAGCCACACTGGAACTGAGACACGGTCC

AGACTCCTACGGGAGGCAGCAGTGGGGAATATTGGACAATGGGCGCAAGCCTGATCCAGCCATACCG

CGTGGGTGAAGAAGGCCTTCGGGTTGTAAAGCCCTTTTGTTGGGAAAGAAAAGCAGTCGGCTAATAC

CCGGTTGTTCTGACGGTACCCAAAGAATAAGCACCGGCTAACTTCGTGCCAGCAGCCGCGGTAATAC

GAAGGGTGCAAGCGTTACTCGGAATTACTGGGCGTAAAGCGTGCGTAGGTGGTTGTTTAAGTCTGTTG

TGAAAGCCCTGGGCTCAACCTGGGAATTGCAGTGGATACTGGGCGACTAGAGTGTGGTAGAGGGTAG

TGGAATTCCCGGTGTAGCAGTGAAATGCGTAGAGATCGGGAGGAACATCCATGGCGAAGGCAGCTAC

CTGGACCAACACTGACACTGAGGCACGAAAGCGTGGGGAGCAAACAGGATTAGATACCCTGGTAGTC

CACGCCCTAAACGATGCGAACTGGATGTTGGGTGCAATTTGGCACGCAGTATCGAAGCTAACGCGTT

-continued

AAGTTCGCCGCCTGGGGAGTACGGTCGCAAGACTGAAACTCAAAGGAATTGACGGGGGCCCGCACA

AGCGGTGGAGTATGTGGTTTAATTCGATGCAACGCGAAGAACCTTACCTGGTCTTGACATGTCGAGA

ACTTTCCAGAGATGGATTGGTGCCTTCGGGAACTCGAACACAGGTGCTGCATGGCTGTCGTCAGCTCG

TGTCGTGAGATGTTGGGTTAAGTCCCGCAACGAGCGCAACCCTTGTCCTTAGTTGCCAGCACGTAATG

GTGGGAACTCTAAGGAGACCGCCGGTGACAAACCGGAGGAAGGTGGGGATGACGTCAAGTCATCAT

GGCCCTTACGACCAGGGCTACACACGTACTACAATGGTAGGGACAGAGGGCTGCAAACCCGCGAGG

GCAAGCCAATCCCAGAAACCCTATCTCAGTCCGGATTGGAGTCTGCAACTCGACTCCATGAAGTCGG

AATCGCTAGTAATCGCAGATCAGCATTGCTGCGGTGAATACGTTCCCGGGCCTTGTACACACCGCCCG

TCACACCATGGGAGTTTGTTGCACCAGAAGCAGGTAGCTTAACCTTCGGGAGGGCGCTTGCCACGGT

GTGGCCGATGACTGGGGTGAAGTCGTAACAAGGTAGCCGTATCGGAAGGTGCGGCTGGATCACCTCC

TTT

21
DP21 16S rRNA

22
DP22 16S rRNA
TTGAAGAGTTTGATCATGGCTCAGATTGAACGCTGGCGGCAGGCCTAACACATGCAAGTCGAGCG

GCAGCGGGAAGTAGCTTGCTACTTTGCCGGCGAGCGGCGGACGGGTGAGTAATGTCTGGGAAACTGC

CTGATGGAGGGGGATAACTACTGGAAACGGTAGCTAATACCGCATGACCTCGCAAGAGCAAAGTGG

GGGACCTTCGGGCCTCACGCCATCGGATGTGCCCAGATGGGATTAGCTAGTAGGTGAGGTAATGGCT

CACCTAGGCGACGATCCCTAGCTGGTCTGAGAGGATGACCAGCCACACTGGAACTGAGACACGGTCC

AGACTCCTACGGGAGGCAGCAGTGGGGAATATTGCACAATGGGCGCAAGCCTGATGCAGCCATGCCG

CGTGTGTGAAGAAGGCCTTAGGGTTGTAAAGCACTTTCAGCGAGGAGGAAGGGTTCAGTGTTAATAG

CACTGAACATTGACGTTACTCGCAGAAGAAGCACCGGCTAACTCCGTGCCAGCAGCCGCGGTAATAC

GGAGGGTGCAAGCGTTAATCGGAATTACTGGGCGTAAAGCGCACGCAGGCGGTTTGTTAAGTCAGAT

GTGAAATCCCCGAGCTTAACTTGGGAACTGCATTTGAAACTGGCAAGCTAGAGTCTTGTAGAGGGGG

GTAGAATTCCAGGTGTAGCGGTGAAATGCGTAGAGATCTGGAGGAATACCGGTGGCGAAGGCGGCCC

CCTGGACAAAGACTGACGCTCAGGTGCGAAAGCGTGGGGAGCAAACAGGATTAGATACCCTGGTAGT

CCACGCTGTAAACGATGTCGACTTGGAGGTTGTGCCCTTGAGGCGTGGCTTCCGGAGCTAACGCGTTA

AGTCGACCGCCTGGGGAGTACGGCCGCAAGGTTAAAACTCAAATGAATTGACGGGGGCCCGCACAA

GCGGTGGAGCATGTGGTTTAATTCGATGCAACGCGAAGAACCTTACCTACTCTTGACATCCAGAGAAT

TCGCTAGAGATAGCTTAGTGCCTTCGGGAACTCTGAGACAGGTGCTGCATGGCTGTCGTCAGCTCGTG

TTGTGAAATGTTGGGTTAAGTCCCGCAACGAGCGCAACCCTTATCCTTTGTTGCCAGCGAGTAATGTC

GGGAACTCAAAGGAGACTGCCGGTGATAAACCGGAGGAAGGTGGGGATGACGTCAAGTCATCATGG

CCCTTACGAGTAGGGCTACACACGTGCTACAATGGCATATACAAAGAGAAGCAAACTCGCGAGAGCA

AGCGGACCTCATAAAGTATGTCGTAGTCCGGATTGGAGTCTGCAACTCGACTCCATGAAGTCGGAAT

CGCTAGTAATCGTAGATCAGAATGCTACGGTGAATACGTTCCCGGGCCTTGTACACACCGCCCGTCAC

ACCATGGGAGTGGGTTGCAAAAGAAGTAGGTAGCTTAACCTTCGGGAGGGCGCTTACCACTTTGTGA

TTCATGACTGGGGTGAAGTCGTAACAAGGTAACCGTAGGGGAACCTGCGGTTGGATCACCTCCTT

23
DP23 16S rRNA
TTGAAGAGTTTGATCATGGCTCAGATTGAACGCTGGCGGCAGGCCTAACACATGCAAGTCGAACG

GTAGCACAGAGAGCTTGCTCTTGGGTGACGAGTGGCGGACGGGTGAGTAATGTCTGGGAAACTGCCC

GATGGAGGGGGATAACTACTGGAAACGGTAGCTAATACCGCATAACGTCTTCGGACCAAAGTGGGGG

-continued

ACCTTCGGGCCTCACACCATCGGATGTGCCCAGATGGGATTAGCTAGTAGGTGGGGTAATGGCTCAC

CTAGGCGACGATCCCTAGCTGGTCTGAGAGGATGACCAGCCACACTGGAACTGAGACACGGTCCAGA

CTCCTACGGGAGGCAGCAGTGGGGAATATTGCACAATGGGCGCAAGCCTGATGCAGCCATGCCGCGT

GTATGAAGAAGGCCTTCGGGTTGTAAAGTACTTTCAGCGGGGAGGAAGGCGATACGGTTAATAACCG

TGTCGATTGACGTTACCCGCAGAAGAAGCACCGGCTAACTCCGTGCCAGCAGCCGCGGTAATACGGA

GGGTGCAAGCGTTAATCGGAATTACTGGGCGTAAAGCGCACGCAGGCGGTCTGTCAAGTCAGATGTG

AAATCCCCGGGCTTAACCTGGGAACTGCATTTGAAACTGGCAGGCTTGAGTCTCGTAGAGGGGGGTA

GAATTCCAGGTGTAGCGGTGAAATGCGTAGAGATCTGGAGGAATACCGGTGGCGAAGGCGGCCCCCT

GGACGAAGACTGACGCTCAGGTGCGAAAGCGTGGGGAGCAAACAGGATTAGATACCCTGGTAGTCC

ACGCTGTAAACGATGTCGACTTGGAGGTTGTGCCCTTGAGGCGTGGCTTCCGGAGCTAACGCGTTAAG

TCGACCGCCTGGGGAGTACGGCCGCAAGGTTAAAACTCAAATGAATTGACGGGGGCCCGCACAAGCG

GTGGAGCATGTGGTTTAATTCGATGCAACGCGAAGAACCTTACCTGGCCTTGACATCCACAGAATTCG

GCAGAGATGCCTTAGTGCCTTCGGGAACTGTGAGACAGGTGCTGCATGGCTGTCGTCAGCTCGTGTTG

TGAAATGTTGGGTTAAGTCCCGCAACGAGCGCAACCCTTATCCTTTGTTGCCAGCGATTCGGTCGGGA

ACTCAAAGGAGACTGCCGGTGATAAACCGGAGGAAGGTGGGGATGACGTCAAGTCATCATGGCCCTT

ACGGCCAGGGCTACACACGTGCTACAATGGCGCATACAAAGAGAAGCGACCTCGCGAGAGCAAGCG

GACCTCATAAAGTGCGTCGTAGTCCGGATCGGAGTCTGCAACTCGACTCCGTGAAGTCGGAATCGCT

AGTAATCGTAGATCAGAATGCTACGGTGAATACGTTCCCGGGCCTTGTACACACCGCCCGTCACACCA

TGGGAGTGGGTTGCAAAAGAAGTAGGTAGCTTAACCTTCGGGAGGGCGCTTACCACTTTGTGATTCAT

GACTGGGGTGAAGTCGTAACAAGGTAACCGTAGGGGAACCTGCGGTTGGATCACCTCCTT

24
DP24 16S rRNA
AGCATTTGATTATGGTGCTTACTGATTGCTATCTAGGGGTTTAACACATGCTAGTCAATGATCTTTT

AGATTATGGCGTACGGGCTAGGAATACTTAGAATGATAACTCTATGATCGCAGTAATAGCGTAAAAG

GTATAATACCGCATAGAGGTTCGCTTCGTATCTAATAGGTAGTTGGTGAGGTAAAGCTCAACAAGCC

GATGATGAGTAATATTGGATGAAAGTCTTAAATATAGCAGTGGAAATGAAAAAGTCCACCGTTATTT

ATTAACGCAGCAGTGGAGAATCGTCGTAATGTGCAGTATTCATTTATGGATAAGCATGAACGCGCTA

CCTAGATTCGGATAGGAGATAGCATCTTCTACCGATAAAAGAACTTAGAATAATGATCTAGTTCTCAT

TAGTGGGTGACAATCGCCGTGCCAGCATCAGCGGTAAAACGGCTTCCGCAAGCAATAGTAATTTAAA

TTGGTGTAAAGGGTACGTAGCCGGCCTTATTAGGCTAGAGTTAGATACGGGTAAGTACAATACTTGG

AGTAGGGCTGATATCTTATGATCCCAAGGGGAGTGCTAAAGGCGAAGGCAACTTACTGGTAATAACT

GACGGTGAGGTACGAAGGTCAGGGCATGGAAAGAGATTAGATACCTCATTACTCCTGACAGTAAACG

ATGTAGATTAAAGATTGGAATAATTCTGTCTTAACGCTAACGCATTAAATCTACCACCTGTAGAGTAT

AGTCGCAAGGCCGAAATACAAATAATTAGACGGCTCTAGAGCAAACGGAGTGAAGCATGTTATTTAA

TACGATAACCCGCGTAAAATCTTACCAGTTCTTGAATCTTAGACAGGTGTTGCATGGTTGTCGTCAGC

TCGTGCTAATGGTGTCTGGTTAATTCCAAATAACGAGCGCAATCCTTACTTCTAGTTTTCTAGGAGTCT

CCATTTGACATACGTGTCAATGGTTTAAGGAATATGACAAACCCTCATGGCCCTTATGGACTGGGCAA

TAGACGTGCCACAAGAATCTAGACAAAATGACGCGAAATGGTAACAATGAGCTAATCATCAAAGAA

GATTAATGTACGAATTATGGGCTGGAACTCGCCCATATGAAGTAGGAATTCCGAGTAATCGCGTATC

AGAACGACGCGGTGAACATCATCTCTGGAGTGTACTAACTGCTCGTCACGGGACGAAAGGGAGTGTA

TTATGAAGTGGGGCTAATTGGTTAACTCCGGTGAGTGTCACGAATAATCCTTCCCGATTGTTCTGAAG

TCGAAACAAGGTAACCGTAAGGGAACTTGCGGTTGA

-continued

25
DP25 16S rRNA
TACGGAGAGTTTGATCCTGGCTCAGGATGAACGCTGGCGGCGTGCTTAACACATGCAAGTCGAAC

GGTGAAGCCAAGCTTGCTTGGTGGATCAGTGGCGAACGGGTGAGTAACACGTGAGCAACCTGCCCTG

GACTCTGGGATAAGCGCTGGAAACGGCGTCTAATACTGGATATGAGCTCCTTCCGCATGGTGGGGGT

TGGAAAGATTTTTCGGTCTGGGATGGGCTCGCGGCCTATCAGCTTGTTGGTGAGGTAATGGCTCACCA

AGGCGTCGACGGGTAGCCGGCCTGAGAGGGTGACCGGCCACACTGGGACTGAGACACGGCCCAGAC

TCCTACGGGAGGCAGCAGTGGGGAATATTGCACAATGGGCGGAAGCCTGATGCAGCAACGCCGCGTG

AGGGATGACGGCCTTCGGGTTGTAAACCTCTTTTAGCAGGGAAGAAGCGAAAGTGACGGTACCTGCA

GAAAAAGCGCCGGCTAACTACGTGCCAGCAGCCGCGGTAATACGTAGGGCGCAAGCGTTATCCGGAA

TTATTGGGCGTAAAGAGCTCGTAGGCGGTTTGTCGCGTCTGCTGTGAAATCCCGAGGCTCAACCTCGG

GCCTGCAGTGGGTACGGGCAGACTAGAGTGCGGTAGGGGAGATTGGAATTCCTGGTGTAGCGGTGGA

ATGCGCAGATATCAGGAGGAACACCGATGGCGAAGGCAGATCTCTGGGCCGTAACTGACGCTGAGG

AGCGAAAGGGTGGGGAGCAAACAGGCTTAGATACCCTGGTAGTCCACCCCGTAAACGTTGGGAACTA

GTTGTGGGGACCATTCCACGGTTTCCGTGACGCAGCTAACGCATTAAGTTCCCCGCCTGGGGAGTACG

GCCGCAAGGCTAAAACTCAAAGGAATTGACGGGGACCCGCACAAGCGGCGGAGCATGCGGATTAAT

TCGATGCAACGCGAAGAACCTTACCAAGGCTTGACATATACGAGAACGGGCCAGAAATGGTCAACTC

TTTGGACACTCGTAAACAGGTGGTGCATGGTTGTCGTCAGCTCGTGTCGTGAGATGTTGGGTTAAGTC

CCGCAACGAGCGCAACCCTCGTTCTATGTTGCCAGCACGTAATGGTGGGAACTCATGGGATACTGCC

GGGGTCAACTCGGAGGAAGGTGGGGATGACGTCAAATCATCATGCCCCTTATGTCTTGGGCTTCACG

CATGCTACAATGGCCGGTACAAAGGGCTGCAATACCGTAAGGTGGAGCGAATCCCAAAAAGCCGGTC

CCAGTTCGGATTGAGGTCTGCAACTCGACCTCATGAAGTCGGAGTCGCTAGTAATCGCAGATCAGCA

ACGCTGCGGTGAATACGTTCCCGGGTCTTGTACACACCGCCCGTCAAGTCATGAAAGTCGGTAACACC

TGAAGCCGGTGGCCCAACCCTTGTGGAGGGAGCCGTCGAAGGTGGGATCGGTAATTAGGACTAAGTC

GTAACAAGGTAGCCGTACCGGAAGGTGCGGCTGGATCACCTCCTTT

26
DP26 16S rRNA
CTTGAGAGTTTGATCCTGGCTCAGAGCGAACGCTGGCGGCAGGCTTAACACATGCAAGTCGAGCG

GGCATCTTCGGATGTCAGCGGCAGACGGGTGAGTAACACGTGGGAACGTACCCTTCGGTTCGGAATA

ACGCTGGGAAACTAGCGCTAATACCGGATACGCCCTTTTGGGGAAAGGTTTACTGCCGAAGGATCGG

CCCGCGTCTGATTAGCTAGTTGGTGGGGTAACGGCCTACCAAGGCGACGATCAGTAGCTGGTCTGAG

AGGATGATCAGCCACACTGGGACTGAGACACGGCCCAGACTCCTACGGGAGGCAGCAGTGGGGAAT

ATTGGACAATGGGCGCAAGCCTGATCCAGCCATGCCGCGTGAGTGATGAAGGCCTTAGGGTTGTAAA

GCTCTTTTGTCCGGGACGATAATGACGGTACCGGAAGAATAAGCCCCGGCTAACTTCGTGCCAGCAG

CCGCGGTAATACGAAGGGGGCTAGCGTTGCTCGGAATCACTGGGCGTAAAGGGCGCGTAGGCGGCCA

TTCAAGTCGGGGGTGAAAGCCTGTGGCTCAACCACAGAATTGCCTTCGATACTGTTTGGCTTGAGTAT

GGTAGAGGTTGGTGGAACTGCGAGTGTAGAGGTGAAATTCGTAGATATTCGCAAGAACACCGGTGGC

GAAGGCGGCCAACTGGACCATTACTGACGCTGAGGCGCGAAAGCGTGGGGAGCAAACAGGATTAGA

TACCCTGGTAGTCCACGCCGTAAACGATGAATGCCAGCTGTTGGGGTGCTTGCACCTCAGTAGCGCAG

CTAACGCTTTAAGCATTCCGCCTGGGGAGTACGGTCGCAAGATTAAAACTCAAAGGAATTGACGGGG

GCCCGCACAAGCGGTGGAGCATGTGGTTTAATTCGAAGCAACGCGCAGAACCTTACCATCCCTTGAC

ATGGCATGTTACCCGGAGAGATTCGGGGTCCACTTCGGTGGCGTGCACACAGGTGCTGCATGGCTGTC

-continued

GTCAGCTCGTGTCGTGAGATGTTGGGTTAAGTCCCGCAACGAGCGCAACCCACGTCCTTAGTTGCCAT

CATTCAGTTGGGCACTCTAGGGAGACTGCCGGTGATAAGCCGCGAGGAAGGTGTGGATGACGTCAAG

TCCTCATGGCCCTTACGGGATGGGCTACACACGTGCTACAATGGCGGTGACAGTGGGACGCGAAGGA

GCGATCTGGAGCAAATCCCCAAAAACCGTCTCAGTTCAGATTGCACTCTGCAACTCGAGTGCATGAA

GGCGGAATCGCTAGTAATCGTGGATCAGCATGCCACGGTGAATACGTTCCCGGGCCTTGTACACACC

GCCCGTCACACCATGGGAGTTGGTCTTACCCGACGGCGCTGCGCCAACCGCAAGGAGGCAGGCGACC

ACGGTAGGGTCAGCGACTGGGGTGAAGTCGTAACAAGGTAGCCGTAGGGGAACCTGCGGCTGGATC

ACCTCCTTT

27
DP27 16S rRNA
CTTGAGAGTTTGATCCTGGCTCAGAACGAACGCTGGCGGCATGCCTAACACATGCAAGTCGAACG

ATGCTTTCGGGCATAGTGGCGCACGGGTGCGTAACGCGTGGGAATCTGCCCTCAGGTTCGGAATAAC

AGCTGGAAACGGCTGCTAATACCGGATGATATCGCAAGATCAAAGATTTATCGCCTGAGGATGAGCC

CGCGTTGGATTAGGTAGTTGGTGGGGTAAAGGCCTACCAAGCCGACGATCCATAGCTGGTCTGAGAG

GATGATCAGCCACACTGGGACTGAGACACGGCCCAGACTCCTACGGGAGGCAGCAGTGGGGAATATT

GGACAATGGGCGCAAGCCTGATCCAGCAATGCCGCGTGAGTGATGAAGGCCCTAGGGTTGTAAAGCT

CTTTTACCCGGGAAGATAATGACTGTACCGGGAGAATAAGCCCCGGCTAACTCCGTGCCAGCAGCCG

CGGTAATACGGAGGGGGCTAGCGTTGTTCGGAATTACTGGGCGTAAAGCGCACGTAGGCGGCTTTGT

AAGTCAGAGGTGAAAGCCTGGAGCTCAACTCCAGAACTGCCTTTGAGACTGCATCGCTTGAATCCAG

GAGAGGTCAGTGGAATTCCGAGTGTAGAGGTGAAATTCGTAGATATTCGGAAGAACACCAGTGGCGA

AGGCGGCTGACTGGACTGGTATTGACGCTGAGGTGCGAAAGCGTGGGGAGCAAACAGGATTAGATA

CCCTGGTAGTCCACGCCGTAAACGATGATAACTAGCTGTCCGGGCACTTGGTGCTTGGGTGGCGCAGC

TAACGCATTAAGTTATCCGCCTGGGGAGTACGGCCGCAAGGTTAAAACTCAAAGGAATTGACGGGGG

CCTGCACAAGCGGTGGAGCATGTGGTTTAATTCGAAGCAACGCGCAGAACCTTACCAGCGTTTGAC

28
DP28 16S rRNA
ATAGTCGGGGGCATCAGTATTCAATTGTCAGAGGTGAAATTCTTGGATTTATTGAAGACTAACTAC

TGCGAAAGCATTTGCCAAGGATGTTTTCATTAATCAGTGAACGAAAGTTAGGGGATCGAAGACGATC

AGATACCGTCGTAGTCTTAACCATAAACTATGCCGACTAGGGATCGGGCGATGTTATCATTTTGACTC

GCTCGGCACCTTACGAGAAATCAAAGTCTTTGGGTTCTGGGGGGAGTATGGTCGCAAGGCTGAAACT

TAAAGAAATTGACGGAAGGGCACCACCAGGCGTGGAGCCTGCGGCTTAATTTGACTCAACACGGGGA

AACTCACCAGGTCCAGACACAATAAGGATTGACAGATTGAGAGCTCTTTCTTGATTTTGTGGGTGGTG

GTGCATGGCCGTTCTTAGTTGGTGGAGTGATTTGTCTGCTTAATTGCGATAACGAACGAGACCTTAAC

CTGCTAAATAGCCCGGCCCGCTTTGGCGGGTCGCCGGCTTCTTAGAGGGACTATCGGCTCAAGCCGAT

GGAAGTTTGAGGCAATAACAGGTCTGTGATGCCCTTAGATGTTCTGGGCCGCACGCGCGCTACACTG

ACAGAGCCAACGAGTTCATTTCCTTGCCCGGAAGGGTTGGGTAATCTTGTTAAACTCTGTCGTGCTGG

GGATAGAGCATTGCAATTATTGCTCTTCAACGAGGAATGCCTAGTAAGCGTACGTCATCAGCGTGCGT

TGATTACGTCCCTGCCCTTTGTACACACCGCCCGTCGCTACTACCGATTGAATGGCTGAGTGAGGCCT

TCGGACTGGCCCAGGGAGGTCGGCAACGACCACCCAGGGCCGGAAAGTTGGTCAAACTCCGTCATTT

AGAGGAAGTAAAAGTCGTAACAAGGTTTCCGTAGGTGAACCTGCGGAAGGATCA

29
DP29 16S rRNA
TACGGAGAGTTTGATCCTGGCTCAGGACGAACGCTGGCGGCGTGCTTAACACATGCAAGTCGAAC

GATGAAGCCCAGCTTGCTGGGTTGATTAGTGGCGAACGGGTGAGTAACACGTGAGCAACGTGCCCAT

-continued

AACTCTGGGATAACCTCCGGAAACGGTGGCTAATACTGGATATCTAACACGATCGCATGGTCTGTGTT

TGGAAAGATTTTTTGGTTATGGATCGGCTCACGGCCTATCAGCTTGTTGGTGAGGTAATGGCTCACCA

AGGCGACGACGGGTAGCCGGCCTGAGAGGGTGACCGGCCACACTGGGACTGAGACACGGCCCAGAC

TCCTACGGGAGGCAGCAGTGGGGAATATTGCACAATGGGCGAAAGCCTGATGCAGCAACGCCGCGTG

AGGGATGACGGCATTCGGGTTGTAAACCTCTTTTAGTAGGGAAGAAGCGAAAGTGACGGTACCTGCA

GAAAAAGCACCGGCTAACTACGTGCCAGCAGCCGCTGTAATACGTAGGGTGCAAGCGTTGTCCGGAA

TTATTGGGCGTAAAGAGCTCGTAGGCGGTTTGTCGCGTCTGCTGTGAAATCCCGAGGCTCAACCTCGG

GTCTGCAGTGGGTACGGGCAGACTAGAGTGTGGTAGGGGAGATTGGAATTCCTGGTGTAGCGGTGGA

ATGCGCAGATATCAGGAGGAACACCGATGGCGAAGGCAGATCTCTGGGCCATTACTGACGCTGAGGA

GCGAAAGCATGGGGAGCGAACAGGATTAGATACCCTGGTAGTCCATGCCGTAAACGTTGGGCGCTAG

ATGTGGGGACCATTCCACGGTTTCCGTGTCGTAGCTAACGCATTAAGCGCCCCGCCTGGGGAGTACGG

CCGCAAGGCTAAAACTCAAAGGAATTGACGGGGGCCCGCACAAGCGGCGGAGCATGCGGATTAATT

CGATGCAACGCGAAGAACCTTACCAAGGCTTGACATATACCGGAAACGTTCAGAAATGTTCGCC

30
DP30 16S rRNA
TACGGAGAGTTTGATCCTGGCTCAGGATGAACGCTGGCGGCGTGCTTAACACATGCAAGTCGAAC

GGTGAAGCCAAGCTTGCTTGGTGGATCAGTGGCGAACGGGTGAGTAACACGTGAGCAACCTGCCCTG

GACTCTGGGATAAGCGCTGGAAACGGCGTCTAATACTGGATATGAGACGTGATCGCATGGTCGTGTT

TGGAAAGATTTTTCGGTCTGGGATGGGCTCGCGGCCTATCAGCTTGTTGGTGAGGTAATGGCTCACCA

AGGCGTCGACGGGTAGCCGGCCTGAGAGGGTGACCGGCCACACTGGGACTGAGACACGGCCCAGAC

TCCTACGGGAGGCAGCAGTGGGGAATATTGCACAATGGGCGAAAGCCTGATGCAGCAACGCCGCGTG

AGGGATGACGGCCTTCGGGTTGTAAACCTCTTTTAGCAGGGAAGAAGCGAAAGTGACGGTACCTGCA

GAAAAAGCGCCGGCTAACTACGTGCCAGCAGCCGCGGTAATACGTAGGGCGCAAGCGTTATCCGGAA

TTATTGGGCGTAAAGAGCTCGTAGGCGGTTTGTCGCGTCTGCTGTGAAATCCCGAGGCTCAACCTCGG

GCCTGCAGTGGGTACGGGCAGACTAGAGTGCGGTAGGGGAGATTGGAATTCCTGGTGTAGCGGTGGA

ATGCGCAGATATCAGGAGGAACACCGATGGCGAAGGCAGATCTCTGGGCCGTAACTGACGCTGAGG

AGCGAAAGGGTGGGGAGCAAACAGGCTTAGATACCCTGGTAGTCCACCCCGTAAACGTTGGGAACTA

GTTGTGGGGACCATTCCACGGTTTCCGTGACGCAGCTAACGCATTAAGTTCCCCGCCTGGGGAGTACG

GCCGCAAGGCTAAAACTCAAAGGAATTGACGGGGACCCGCACAAGCGGCGGAGCATGCGGATTAAT

TCGATGCAACGCGAAGAACCTTACCAAGGCTTGACATATACGAGAACGGGCCAGAAATGGTCAACTC

TTTGGACACTCGTAAACAGGTGGTGCATGGTTGTCGTCAGCTCGTGTCGTGAGATGTTGGGTTAAGTC

CCGCAACGAGCGCAACCCTCGTTCTATGTTGCCAGCACGTAATGGTGGGAACTCATGGGATACTGCC

GGGGTCAACTCGGAGGAAGGTGGGGATGACGTCAAATCATCATGCCCCTTATGTCTTGGGCTTCACG

CATGCTACAATGGCCGGTACAAAGGGCTGCAATACCGTGAGGTGGAGCGAATCCCAAAAAGCCGGTC

CCAGTTCGGATTGAGGTCTGCAACTCGACCTCATGAAGTCGGAGTCGCTAGTAATCGCAGATCAGCA

ACGCTGCGGTGAATACGTTCCCGGGTCTTGTACACACCGCCCGTCAAGTCATGAAAGTCGGTAACACC

TGAAGCCGGTGGCCCAACCCTTGTGGAGGGAGCCGTCGAAGGTGGGATCGGTAATTAGGACTAAGTC

GTAACAAGGTAGCCGTACCGGAAGGTGCGGCTGGATCACCTCCTTT

31
DP31 16S rRNA
CAGCCGGGGGCATTAGTATTTGCACGCTAGAGGTGAAATTCTTGGATTGTGCAAAGACTTCCTACT

GCGAAAGCATTTGCCAAGAATGTTTTCATTAATCAAGAACGAAGGTTAGGGTATCGAAAACGATTAG

-continued
ATACCGTTGTAGTCTTAACAGTAAACTATGCCGACTCCGAATCGGTCGATGCTCATTTCACTGGCTCG

ATCGGCGCGGTACGAGAAATCAAAGTTTTTGGGTTCTGGGGGGAGTATGGTCGCAAGGCTGAAACTT

AAAGAAATTGACGGAAGGGCACCACCAGGAGTGGAGCCTGCGGCTTAATTTGACTCAACACGGGAA

AACTCACCGGGTCCGGACATAGTAAGGATTGACAGATTGATGGCGCTTTCATGATTCTATGGGTGGTG

GTGCATGGCCGTTCTTAGTTGGTGGAGTGATTTGTCTGGTTAATTCCGATAACGAACGAGACCTTGAC

CTGCTAAATAGACGGGTTGACATTTTGTTGGCCCCTTATGTCTTCTTAGAGGGACAATCGACCGTCTA

GGTGATGGAGGCAAAAGGCAATAACAGGTCTGTGATGCCCTTAGATGTTCCGGGCTGCACGCGCGCT

ACACTGACAGAGACAACGAGTGGGGCCCCTTGTCCGAAATGACTGGGTAAACTTGTGAAACTTTGTC

GTGCTGGGGATGGAGCTTTGTAATTTTTGCTCTTCAACGAGGAATTCCTAGTAAGCGCAAGTCATCAG

CTTGCGTTGACTACGTCCCTGCCCTTTGTACACACCGCCCGTCGCTACTACCGATTGAATGGCTTAGTG

AGGACTTGGGAGAGTACATCGGGGAGCCAGCAATGGCACCCTGACGGCTCAAACTCTTACAAACTTG

GTCATTTAGAGGAAGTAAAAGTCGTAACAAGGTATCTGTAGGTGAACCTGCAGATGGATCATTTC

32
DP32 16S rRNA
ACTGAGCATTGACGTTACTCGCAGAAGAAGCACCGGCTAACTCCGTGCCAGCAGCCGCGGTAATA

CGGAGGGTGCAAGCGTTAATCGGAATTACTGGGCGTAAAGCGCACGCAGGCGGTTTGTTAAGTCAGA

TGTGAAATCCCCGAGCTTAACTTGGGAACTGCATTTGAAACTGGCAAGCTAGAGTCTTGTAGAGGGG

GGTAGAATTCCAGGTGTAGCGGTGAAATGCGTAGAGATCTGGAGGAATACCGGTGGCGAAGGCGGC

CCCCTGGACAAAGACTGACGCTCAGGTGCGAAAGCGTGGGGAGCAAACAGGATTAGATACCCTGGTA

GTCCACGCTGTAAACGATGTCGACTTGGAGGTTGTGCCCTTGAGGCGTGGCTTCCGGAGCTAACGCGT

TAAGTCGACCGCCTGGGGAGTACGGCCGCAAGGTTAAAACTCAAATGAATTGACGGGGGCCCGCACA

AGCGGTGGAGCATGTGGTTTAATTCGATGCAACGCGAAGAACCTTACCTACTCTTGACATCCAGAGA

ATTCGCTAGAGATAGCTTAGTGCCTTCGGGAACTCTGAGACAGGTGCTGCATGGCTGTCGTCAGCTCG

TGTTGTGAAATGTTGGGTTAAGTCCCGCAACGAGCGCAACCCTTATCCTTTGTTGCCAGCGAGTAATG

TCGGGAACTCAAAGGAGACTGCCGGTGATAAACCGGAGGAAGGTGGGGATGACGTCAAGTCATCAT

GGCCCTTACGAGTAGGGCTACACACGTGCTACAATGGCATATACAAAGAGAAGCGAACTCGCGAGAG

CAAGCGGACCTCATAAAGTATGTCGTAGTCCGGATTGGAGTCTGCAACTCGACTCCATGAAGTCGGA

ATCGCTAGTAATCGTAGATCAGAATGCTACGGTGAATACGTTCCCGGGCCTTGTACACACCGCCCGTC

ACACCATGGGAGTGGGTTGCAAAAGAAGTAGGTAGCTTAACCTTCGGGAGGGCGCTTACCACTTTGT

GATTCATGACTGGGGTGAAGTCGTAACAAGGTAACCGTAGGGGAACCTGCGGTTGGATCACCTCCTT

33
DP33 16S rRNA
GGAGGAAGGCGTAGAGATCTGGAGGAATACCGGTGGCGAAGGCGGCCCCCTGGACAAAGACTGA

CGCTCAGGTGCGAAAGCGTGGGGAGCAAACAGGATTAGATACCCTGGTAGTCCACGCCGTAAACGAT

GTCGACTTGGAGGTTGTGCCCTTGAGGCGTGGCTTCCGGAGCTAACGCGTTAAGTCGACCGCCTGGGG

AGTACGGCCGCAAGGTTAAAACTCAAATGAATTGACGGGGGCCCGCACAAGCGGTGGAGCATGTGGT

TTAATTCGATGCAACGCGAAGAACCTTACCTGGCCTTGACATCCACGGAATTCGGCAGAGATGCCTTA

GTGCCTTCGGGAACCGTGAGACAGGTGCTGCATGGCTGTCGTCAGCTCGTGTTGTGAAATGTTGGGTT

AAGTCCCGCAACGAGCGCAACCCTTATCCTTTGTTGCCAGCACGTAATGGTGGGAACTCAAAGGAGA

CTGCCGGTGATAAACCGGAGGAAGGTGGGGATGACGTCAAGTCATCATGGCCCTTACGGCCAGGGCT

ACACACGTGCTACAATGGCGCATACAAAGAGAAGCGACCTCGCGAGAGCAAGCGGACCTCATAAAG

TGCGTCGTAGTCCGGATCGGAGTCTGCAACTCGACTCCGTGAAGTCGGAATCGCTAGTAATCGTAGAT

CAGAATGCTACGGTGAATACGTTCCCGGGCCTTGTACACACCGCCCGTCACACCATGGGAGTGGGTT

-continued

GCAAAAGAAGTAGGTAGCTTAACCTTCGGGAGGGCGCTTACCACTTTGTGATTCATGACTGGGGTGA

AGTCGTAACAAGGTAACCGTAGGGGAACCTGCGGTTGGATCACCTCCTT

34
DP34 16S rRNA
TACGGAGAGTTTGATCCTGGCTCAGGACGAACGCTGGCGGCGTGCTTAACACATGCAAGTCGAAC

GATGAAGCCCAGCTTGCTGGGTGGATTAGTGGCGAACGGGTGAGTAACACGTGAGTAACCTGCCCTT

GACTCTGGGATAAGCGTTGGAAACGACGTCTAATACCGGATACGAGCTTCCACCGCATGGTGAGTTG

CTGGAAAGAATTTTGGTCAAGGATGGACTCGCGGCCTATCAGCTTGTTGGTGAGGTAATGGCTCACCA

AGGCGACGACGGGTAGCCGGCCTGAGAGGGTGACCGGCCACACTGGGACTGAGACACGGCCCAGAC

TCCTACGGGAGGCAGCAGTGGGGAATATTGCACAATGGGCGAAAGCCTGATGCAGCAACGCCGCGTG

AGGGACGACGGCCTTCGGGTTGTAAACCTCTTTTAGCAGGGAAGAAGCGAAAGTGACGGTACCTGCA

GAAAAAGCACCGGCTAACTACGTGCCAGCAGCCGCGGTAATACGTAGGGTGCAAGCGTTGTCCGGAA

TTATTGGGCGTAAAGAGCTCGTAGGCGGTTTGTCGCGTCTGCTGTGAAATCCCGAGGCTCAACCTCGG

GTCTGCAGTGGGTACGGGCAGACTAGAGTGCGGTAGGGGAGATTGGAATTCCTGGTGTAGCGGTGGA

ATGCGCAGATATCAGGAGGAACACCGATGGCGAAGGCAGATCTCTGGGCCGCTACTGACGCTGAGGA

GCGAAAGGGTGGGGAGCAAACAGGCTTAGATACCCTGGTAGTCCACCCCGTAAACGTTGGGCGCTAG

ATGTGGGGACCATTCCACGGTTTCCGTGTCGTAGCTAACGCATTAAGCGCCCCGCCTGGGGAGTACGG

CCGCAAGGCTAAAACTCAAAGGAATTGACGGGGGCCCGCACAAGCGGCGGAGCATGCGGATTAATT

CGATGCAACGCGAAGAACCTTACCAAGGCTTGACATATACGAGAACGGGCCAGAAATGGTCAACTCT

TTGGACACTCGTAAACAGGTGGTGCATGGTTGTCGTCAGCTCGTGTCGTGAGATGTTGGGTTAAGTCC

CGCAACGAGCGCAACCCTCGTTCTATGTTGCCAGCACGTAATGGTGGGAACTCATGGGATACTGCCG

GGGTCAACTCGGAGGAAGGTGGGGACGACGTCAAATCATCATGCCCCTTATGTCTTGGGCTTCACGC

ATGCTACAATGGCCAGTACAAAGGGCTGCAATACCGTAAGGTGGAGCGAATCCCAAAAAGCTGGTCC

CAGTTCGGATTGAGGTCTGCAACTCGACCTCATGAAGTCGGAGTCGCTAGTAATCGCAGATCAGCAA

CGCTGCGGTGAATACGTTCCCGGGCCTTGTACACACCGCCCGTCAAGTCATGAAAGTCGGTAACACCC

GAAGCCAGTGGCCTAACCGCAAGGATGGAGCTGTCTAAGGTGGGATCGGTAATTAGGACTAAGTCGT

AACAAGGTAGCCGTACCGGAAGGTGCGGCTGGATCACCTCCTTT

35
DP35 16S rRNA
TTGAAGAGTTTGATCATGGCTCAGATTGAACGCTGGCGGCAGGCCTAACACATGCAAGTCGGACG

GTAGCACAGAGAGCTTGCTCTTGGGTGACGAGTGGCGGACGGGTGAGTAATGTCTGGGGATCTGCCC

GATAGAGGGGGATAACCACTGGAAACGGTGGCTAATACCGCATAACGTCGCAAGACCAAAGAGGGG

GACCTTCGGGCCTCTCACTATCGGATGAACCCAGATGGGATTAGCTAGTAGGCGGGGTAATGGCCCA

CCTAGGCGACGATCCCTAGCTGGTCTGAGAGGATGACCAGCCACACTGGAACTGAGACACGGTCCAG

ACTCCTACGGGAGGCAGCAGTGGGGAATATTGCACAATGGGCGCAAGCCTGATGCAGCCATGCCGCG

TGTATGAAGAAGGCCTTCGGGTTGTAAAGTACTTTCAGCGGGGAGGAAGGCGATGAGGTTAATAACC

GCGTCGATTGACGTTACCCGCAGAAGAAGCACCGGCTAACTCCGTGCCAGCAGCCGCGGTAATACGG

AGGGTGCAAGCGTTAATCGGAATTACTGGGCGTAAAGCGCACGCAGGCGGTCTGTTAAGTCAGATGT

GAAATCCCCGGGCTTAACCTGGGAACTGCATTTGAAACTGGCAGGCTTGAGTCTTGTAGAGGGGGGT

AGAATTCCAGGTGTAGCGGTGAAATGCGTAGAGATCTGGAGGAATACCGGTGGCGAAGGCGGCCCCC

TGGACAAAGACTGACGCTCAGGTGCGAAAGCGTGGGGAGCAAACAGGATTAGATACCCTGGTAGTCC

ACGCCGTAAACGATGTCGACTTGGAGGTTGTTCCCTTGAGGAGTGGCTTCCGGAGCTAACGCGTTAAG

-continued

TCGACCGCCTGGGGAGTACGGCCGCAAGGTTAAAACTCAAATGAATTGACGGGGGCCCGCACAAGCG

GTGGAGCATGTGGTTTAATTCGATGCAACGCGAAGAACCTTACCTACTCTTGACATCCAGCGAACTTA

GCAGAGATGCTTTGGTGCCTTCGGGAACGCTGAGACAGGTGCTGCATGGCTGTCGTCAGCTCGTGTTG

TGAAATGTTGGGTTAAGTCCCGCAACGAGCGCAACCCTTATCCTTTGTTGCCAGCGATTCGGTCGGGA

ACTCAAAGGAGACTGCCGGTGATAAACCGGAGGAAGGTGGGGATGACGTCAAGTCATCATGGCCCTT

ACGAGTAGGGCTACACACGTGCTACAATGGCGCATACAAAGAGAAGCGACCTCGCGAGAGCAAGCG

GACCTCACAAAGTGCGTCGTAGTCCGGATCGGAGTCTGCAACTCGACTCCGTGAAGTCGGAATCGCT

AGTAATCGTGGATCAGAATGCCACGGTGAATACGTTCCCGGGCCTTGTACACACCGCCCGTCACACC

ATGGGAGTGGGTTGCAAAAGAAGTAGGTAGCTTAACCTTCGGGAGGGCGCTTACCACTTTGTGATTC

ATTACTGGGGTGAAGTCGTAACAAGGTAACCGTAGGGGAACCTGCGGTTGGATCACCTCCTT

36
DP36 16S
rRNATTGAAGAGTTTGATCATGGCTCAGATTGAACGCTGGCGGCAGGCCTAACACATGCAAGTCGGAC

GGTAGCACAGAGAGCTTGCTCTTGGGTGACGAGTGGCGGACGGGTGAGTAATGTCTGGGGATCTGCC

CGATAGAGGGGGATAACCACTGGAAACGGTGGCTAATACCGCATAACGTCGCAAGACCAAAGAGGG

GGACCTTCGGGCCTCTCACTATCGGATGAACCCAGATGGGATTAGCTAGTAGGCGGGGTAATGGCCC

ACCTAGGCGACGATCCCTAGCTGGTCTGAGAGGATGACCAGCCACACTGGAACTGAGACACGGTCCA

GACTCCTACGGGAGGCAGCAGTGGGGAATATTGCACAATGGGCGCAAGCCTGATGCAGCCATGCCGC

GTGTATGAAGAAGGCCTTCGGGTTGTAAAGTACTTTCAGCGGGGAGGAAGGCGATGCGGTTAATAAC

CGCGTCGATTGACGTTACCCGCAGAAGAAGCACCGGCTAACTCCGTGCCAGCAGCCGCGGTAATACG

GAGGGTGCAAGCGTTAATCGGAATTACTGGGCGTAAAGCGCACGCAGGCGGTCTGTTAAGTCAGATG

TGAAATCCCCGGGCTTAACCTGGGAACTGCATTTGAAACTGGCAGGCTTGAGTCTTGTAGAGGGGGG

TAGAATTCCAGGTGTAGCGGTGAAATGCGTAGAGATCTGGAGGAATACCGGTGGCGAAGGCGGCCCC

CTGGACAAAGACTGACGCTCAGGTGCGAAAGCGTGGGGAGCAAACAGGATTAGATACCCTGGTAGTC

CACGCCGTAAACGATGTCGACTTGGAGGTTGTTCCCTTGAGGAGTGGCTTCCGGAGCTAACGCGTTAA

GTCGACCGCCTGGGGAGTACGGCCGCAAGGTTAAAACTCAAATGAATTGACGGGGGCCCGCACAAGC

GGTGGAGCATGTGGTTTAATTCGATGCAACGCGAAGAACCTTACCTACTCTTGACATC

37
DP37 16S rRNA
TGAAGAGTTTGATCATGGCTCAGATTGAACGCTGGCGGCAGGCCTAACACATGCAAGTCGAGCGG

TAGAGAGAAGCTTGCTTCTCTTGAGAGCGGCGGACGGGTGAGTAATGCCTAGGAATCTGCCTGGTAG

TGGGGGATAACGTTCGGAAACGAACGCTAATACCGCATACGTCCTACGGGAGAAAGCAGGGGACCTT

CGGGCCTTGCGCTATCAGATGAGCCTAGGTCGGATTAGCTAGTTGGTGGGGTAATGGCTCACCAAGG

CGACGATCCGTAACTGGTCTGAGAGGATGATCAGTCACACTGGAACTGAGACACGGTCCAGACTCCT

ACGGGAGGCAGCAGTGGGGAATATTGGACAATGGGCGAAAGCCTGATCCAGCCATGCCGCGTGTGTG

AAGAAGGTCTTCGGATTGTAAAGCACTTTAAGTTGGGAGGAAGGGCCATTACCTAATACGTGATGGT

TTTGACGTTACCGACAGAATAAGCACCGGCTAACTCTGTGCCAGCAGCCGCGGTAATACAGAGGGTG

CAAGCGTTAATGGAATTACTGGGCGTAAAGCGCGCGTAGGTGGTTTGTTAAGTTGGATGTGAAATCC

CCGGGCTCAACCTGGGAACTGCATTCAAAACTGACTGACTAGAGTATGGTAGAGGGTGGTGGAATTT

CCTGTGTAGCGGTGAAATGCGTAGATATAGGAAGGAACACCAGTGGCGAAGGCGACCACCTGGACTG

ATACTGACACTGAGGTGCGAAAGCGTGGGGAGCAAACAGGATTAGATACCCTGGTAGTCCACGCCGT

AAACGATGTCAACTAGCCGTTGGGAGCCTTGAGCTCTTAGTGGCGCAGCTAACGCATTAAGTTGACC

GCCTGGGGAGTACGGCCGCAAGGTTAAAACTCAAATGAATTGACGGGGGCCCGCACAAGCGGTGGA

-continued

GCATGTGGTTTAATTCGAAGCAACGCGAAGAACCTTACCAGGCCTTGACATCCAATGAACTTTCTAGA

GATAGATTGGTGCCTTCGGGAACATTGAGACAGGTGCTGCATGGCTGTCGTCAGCTCGTGTCGTGAGA

TGTTGGGTTAAGTCCCGTAACGAGCGCAACCCTTGTCCTTAGTTACCAGCACGTAATGGTGGGCACTC

TAAGGAGACTGCCGGTGACAAACCGGAGGAAGGTGGGGATGACGTCAAGTCATCATGGCCCTTACGG

CCTGGGCTACACACGTGCTACAATGGTCGGTACAGAGGGTTGCCAAGCCGCGAGGTGGAGCTAATCC

CATAAAACCGATCGTAGTCCGGATCGCAGTCTGCAACTCGACTGCGTGAAGTCGGAATCGCTAGTAA

TCGCGAATCAGAATGTCGCGGTGAATACGTTCCCGGGCCTTGTACACACCGCCCGTCACACCATGGG

AGTGGGTTGCACCAGAAGTAGCTAGTCTAACCTTCGGGGGGACGGTTACCACGGTGTGATTCATGAC

TGGGGTGAAGTCGTAACAAGGTAGCCGTAGGGGAACCTGCGGCTGGATCACCTCCTT

38
DP38 16S rRNA
TACGGAGAGTTTGATCCTGGCTCAGGACGAACGCTGGCGGCGTGCTTAACACATGCAAGTCGAGC

GGTAAGGCCTTTCGGGGTACACGAGCGGCGAACGGGTGAGTAACACGTGGGTGATCTGCCCTGCACT

CTGGGATAAGCTTGGGAAACTGGGTCTAATACCGGATATGACCACAGCATGCATGTGTTGTGGTGGA

AAGATTTATCGGTGCAGGATGGGCCCGCGGCCTATCAGCTTGTTGGTGGGGTAATGGCCTACCAAGG

CGACGACGGGTAGCCGACCTGAGAGGGTGACCGGCCACACTGGGACTGAGACACGGCCCAGACTCCT

ACGGGAGGCAGCAGTGGGGAATATTGCACAATGGGCGGAAGCCTGATGCAGCGACGCCGCGTGAGG

GATGAAGGCCTTCGGGTTGTAAACCTCTTTCAGCAGGGACGAAGCGTGAGTGACGGTACCTGCAGAA

GAAGCACCGGCTAACTACGTGCCAGCAGCCGCGGTAATACGTAGGGTGCGAGCGTTGTCCGGAATTA

CTGGGCGTAAAGAGTTCGTAGGCGGTTTGTCGCGTCGTTTGTGAAAACCCGGGGCTCAACTTCGGGCT

TGCAGGCGATACGGGCAGACTTGAGTGTTTCAGGGGAGACTGGAATTCCTGGTGTAGCGGTGAAATG

CGCAGATATCAGGAGGAACACCGGTGGCGAAGGCGGGTCTCTGGGAAACAACTGACGCTGAGGAAC

GAAAGCGTGGGTAGCAAACAGGATTAGATACCCTGGTAGTCCACGCCGTAAACGGTGGGCGCTAGGT

GTGGGTTCCTTCCACGGGATCTGTGCCGTAGCTAACGCATTAAGCGCCCCGCCTGGGGAGTACGGCCG

CAAGGCTAAAACTCAAAGGAATTGACGGGGGCCCGCACAAGCGGCGGAGCATGTGGATTAATTCGAT

GCAACGCGAAGAACCTTACCTGGGTTTGACATACACCGGAAAACCGTAGAGATACGGTCCCCCTTGT

GGTCGGTGTACAGGTGGTGCATGGCTGTCGTCAGCTCGTGTCGTGAGATGTTGGGTTAAGTCCCGCAA

CGAGCGCAACCCTTGTCTTATGTTGCCAGCACGTAATGGTGGGGACTCGTAAGAGACTGCCGGGGTC

AACTCGGAGGAAGGTGGGGACGACGTCAAGTCATCATGCCCCTTATGTCCAGGGCTTCACACATGCT

ACAATGGCCAGTACAGAGGGCTGCGAGACCGTGAGGTGGAGCGAATCCCTTAAAGCTGGTCTCAGTT

CGGATCGGGGTCTGCAACTCGACCCCGTGAAGTCGGAGTCGCTAGTAATCGCAGATCAGCAACGCTG

CGGTGAATACGTTCCCGGGCCTTGTACACACCGCCCGTCACGTCATGAAAGTCGGTAACACCCGAAG

CCGGTGGCCTAACCCCTTACGGGGAGGGAGCCGTCGAAGGTGGGATCGGCGATTGGGACGAAGTCGT

AACAAGGTAGCCGTACCGGAAGGTGCGGCTGGATCACCTCCTTT

39
DP39 16S rRNA
CTTGAGAGTTTGATCCTGGCTCAGAACGAACGCTGGCGGCAGGCTTAACACATGCAAGTCGAACG

CCCCGCAAGGGGAGTGGCAGACGGGTGAGTAACGCGTGGGAATCTACCGTGCCCTGCGGAATAGCTC

CGGGAAACTGGAATTAATACCGCATACGCCCTACGGGGGAAAGATTTATCGGGGTATGATGAGCCCG

CGTTGGATTAGCTAGTTGGTGGGGTAAAGGCCTACCAAGGCGACGATCCATAGCTGGTCTGAGAGGA

TGATCAGCCACATTGGGACTGAGACACGGCCCAAACTCCTACGGGAGGCAGCAGTGGGGAATATTGG

ACAATGGGCGCAAGCCTGATCCAGCCATGCCGCGTGAGTGATGAAGGCCTTAGGGTTGTAAAGCTCT

-continued

TTCACCGGAGAAGATAATGACGGTATCCGGAGAAGAAGCCCCGGCTAACTTCGTGCCAGCAGCCGCG

GTAATACGAAGGGGGCTAGCGTTGTTCGGAATTACTGGGCGTAAAGCGCACGTAGGCGGATATTTAA

GTCAGGGGTGAAATCCCAGAGCTCAACTCTGGAACTGCCTTTGATACTGGGTATCTTGAGTATGGAAG

AGGTAAGTGGAATTCCGAGTGTAGAGGTGAAATTCGTAGATATTCGGAGGAACACCAGTGGCGAAGG

CGGCTTACTGGTCCATTACTGACGCTGAGGTGCGAAAGCGTGGGGAGCAAACAGGATTAGATACCCT

GGTAGTCCACGCCGTAAACGATGAATGTTAGCCGTCGGGCAGTATACTGTTCGGTGGCGCAGCTAAC

GCATTAAACATTCCGCCTGGGGAGTACGGTCGCAAGATTAAAACTCAAAGGAATTGACGGGGGCCCG

CACAAGCGGTGGAGCATGTGGTTTAATTCGAAGCAACGCGCAGAACCTTACCAGCTCTTGACATTCG

GGGTTTGGGCAGTGGAGACATTGTCCTTCAGTTAGGCTGGCCCCAGAACAGGTGCTGCATGGCTGTCG

TCAGCTCGTGTCGTGAGATGTTGGGTTAAGTCCCGCAACGAGCGCAACCCTCGCCCTTAGTTGCCAGC

ATTTAGTTGGGCACTCTAAGGGGACTGCCGGTGATAAGCCGAGAGGAAGGTGGGGATGACGTCAAGT

CCTCATGGCCCTTACGGGCTGGGCTACACACGTGCTACAATGGTGGTGACAGTGGGCAGCGAGACAG

CGATGTCGAGCTAATCTCCAAAAGCCATCTCAGTTCGGATTGCACTCTGCAACTCGAGTGCATGAAGT

TGGAATCGCTAGTAATCGCAGATCAGCATGCTGCGGTGAATACGTTCCCGGGCCTTGTACACACCGCC

CGTCACACCATGGGAGTTGGTTTTACCCGAAGGTAGTGCGCTAACCGCAAGGAGGCAGCTAACCACG

GTAGGGTCAGCGACTGGGGTGAAGTCGTAACAAGGTAGCCGTAGGGGAACCTGCGGCTGGATCACCT

CCTTT

40
DP40 16S rRNA
TTGACGTTACCCGCAGAAGAAGCACCGGCTAACTCCGTGCCAGCAGCCGCGGTAATACGGAGGGT

GCAAGCGTTAATCGGAATTACTGGGCGTAAAGCGCACGCAGGCGGTCTGTTAAGTCAGATGTGAAAT

CCCCGGGCTTAACCTGGGAACTGCATTTGAAACTGGCAGGCTTGAGTCTTGTAGAGGGGGGTAGAAT

TCCAGGTGTAGCGGTGAAATGCGTAGAGATCTGGAGGAATACCGGTGGCGAAGGCGGCCCCCTGGAC

AAAGACTGACGCTCAGGTGCGAAAGCGTGGGGAGCAAACAGGATTAGATACCCTGGTAGTCCACGCC

GTAAACGATGTCGACTTGGAGGTTGTTCCCTTGAGGAGTGGCTTCCGGAGCTAACGCGTTAAGTCGAC

CGCCTGGGGAGTACGGCCGCAAGGTTAAAACTCAAATGAATTGACGGGGGCCCGCACAAGCGGTGG

AGCATGTGGTTTAATTCGATGCAACGCGAAGAACCTTACCTACTCTTGACATCCAGAGAACTTTCCAG

AGATGGATTGGTGCCTTCGGGAACTCTGAGACAGGTGCTGCATGGCTGTCGTCAGCTCGTGTTGTGAA

ATGTTGGGTTAAGTCCCGCAACGAGCGCAACCCTTATCCTTTGTTGCCAGCGCGTGATGGCGGGAACT

CAAAGGAGACTGCCGGTGATAAACCGGAGGAAGGTGGGGATGACGTCAAGTCATCATGGCCCTTACG

AGTAGGGCTACACACGTGCTACAATGGCGCATACAAAGAGAAGCGACCTCGCGAGAGCAAGCGGAC

CTCACAAAGTGCGTCGTAGTCCGGATCGGAGTCTGCAACTCGACTCCGTGAAGTCGGAATCGCTAGT

AATCGTGGATCAGAATGCCACGGTGAATACGT

41
DP41 16S rRNA
GTGGAGAGTTTGATCCTGGCTCAGGATGAACGCTGGCGGCGTGCTTAACACATGCAAGTCGAACG

GAAAGGCCCAAGCTTGCTTGGGTACTCGAGTGGCGAACGGGTGAGTAACACGTGGGTGATCTGCCCT

GCACTTCGGGATAAGCCTGGGAAACTGGGTCTAATACCGGATAGGACGATGGTTTGGATGCCATTGT

GGAAAGTTTTTTCGGTGTGGGATGAGCTCGCGGCCTATCAGCTTGTTGGTGGGGTAATGGCCTACCAA

GGCGTCGACGGGTAGCCGGCCTGAGAGGGTGTACGGCCACATTGGGACTGAGATACGGCCCAGACTC

CTACGGGAGGCAGCAGTGGGGAATATTGCACAATGGGCGCAAGCCTGATGCAGCGACGCCGCGTGG

GGGATGACGGCCTTCGGGTTGTAAACTCCTTTCGCTAGGGACGAAGCGTTTTGTGACGGTACCTGGAG

AAGAAGCACCGGCTAACTACGTGCCAGCAGCCGCGGTAATACGTAGGGTGCGAGCGTTGTCCGGAAT

-continued

TACTGGGCGTAAAGAGCTCGTAGGTGGTTTGTCGCGTCGTTTGTGTAAGCCCGCAGCTTAACTGCGGG

ACTGCAGGCGATACGGGCATAACTTGAGTGCTGTAGGGGAGACTGGAATTCCTGGTGTAGCGGTGGA

ATGCGCAGATATCAGGAGGAACACCGATGGCGAAGGCAGGTCTCTGGGCAGTAACTGACGCTGAGG

AGCGAAAGCATGGGTAGCGAACAGGATTAGATACCCTGGTAGTCCATGCCGTAAACGGTGGGCGCTA

GGTGTGAGTCCCTTCCACGGGGTTCGTGCCGTAGCTAACGCATTAAGCGCCCCGCCTGGGGAGTACG

GCCGCAAGGCTAAAACTCAAAGGAATTGACGGGGGCCCGCACAAGCGGCGGAGCATGTGGATTAAT

TCGATGCAACGCGAAGAACCTTACCTGGGCTTGACATACACCAGATCGCCGTAGAGATACGGTTTCC

CTTTGTGGTTGGTGTACAGGTGGTGCATGGTTGTCGTCAGCTCGTGTCGTGAGATGTTGGGTTAAGTC

CCGCAACGAGCGCAACCCTTGTCTTATGTTGCCAGCACGTGATGGTGGGGACTCGTGAGAGACTGCC

GGGGTTAACTCGGAGGAAGGTGGGGATGACGTCAAATCATCATGCCCCTTATGTCCAGGGCTTCACA

CATGCTACAATGGTCGGTACAACGCGCATGCGAGCCTGTGAGGGTGAGCGAATCGCTGTGAAAGCCG

GTCGTAGTTCGGATTGGGGTCTGCAACTCGACCCCATGAAGTCGGAGTCGCTAGTAATCGCAGATCA

GCAACGCTGCGGTGAATACGTTCCCGGGCCTTGTACACACCGCCCGTCACACCATGGGAGTGGGTTG

CAAAAGAAGTAGGTAGCTTAACCTTCGGGAGGGCGCTTACCACTTTGTGAT

42
DP42 16S rRNA
TGAAGAGTTTGATCATGGCTCAGATTGAACGCTGGCGGCAGGCCTAACACATGCAAGTCGAGCGG

TAGAGAGGTGCTTGCACCTCTTGAGAGCGGCGGACGGGTGAGTAATACCTAGGAATCTGCCTGATAG

TGGGGGATAACGTTCGGAAACGGACGCTAATACCGCATACGTCCTACGGGAGAAAGCAGGGGACCTT

CGGGCCTTGCGCTATCAGATGAGCCTAGGTCGGATTAGCTAGTTGGTGAGGTAATGGCTCACCAAGG

CTACGATCCGTAACTGGTCTGAGAGGATGATCAGTCACACTGGAACTGAGACACGGTCCAGACTCCT

ACGGGAGGCAGCAGTGGGGAATATTGGACAATGGGCGAAAGCCTGATCCAGCCATGCCGCGTGTGTG

AAGAAGGTCTTCGGATTGTAAAGCACTTTAAGTTGGGAGGAAGGGCATTAACCTAATACGTTAGTGT

CTTGACGTTACCGACAGAATAAGCACCGGCTAACTCTGTGCCAGCAGCCGCGGTAATACAGAGGGTG

CAAGCGTTAATCGGAATTACTGGGCGTAAAGCGCGCGTAGGTGGTTTGTTAAGTTGAATGTGAAATC

CCCGGGCTCAACCTGGGAACTGCATCCAAAACTGGCAAGCTAGAGTATGGTAGAGGGTAGTGGAATT

TCCTGTGTAGCGGTGAAATGCGTAGATATAGGAAGGAACACCAGTGGCGAAGGCGACTACCTGGACT

GATACTGACACTGAGGTGCGAAAGCGTGGGGAGCAAACAGGATTAGATACCCTGGTAGTCCACGCCG

TAAACGATGTCAACTAGCCGTTGGGAACCTTGAGTTCTTAGTGGCGCAGCTAACGCATTAAGTTGACC

GCCTGGGGAGTACGGCCGCAAGGTTAAAACTCAAATGAATTGACGGGGGCCCGCACAAGCGGTGGA

GCATGTGGTTTAATTCGAAGCAACGCGAAGAACCTTACCAGGCCTTGACATCCAATGAACTTTCCAGA

GATGGATTGGTGCCTTCGGGAACATTGAGACAGGTGCTGCATGGCTGTCGTCAGCTCGTGTCGTGAGA

TGTTGGGTTAAGTCCCGTAACGAGCGCAACCCTTGTCCTTAGTTACCAGCACGTAATGGTGGGCACTC

TAAGGAGACTGCCGGTGACAAACCGGAGGAAGGTGGGGATGACGTCAAGTCATCATGGCCCTTACGG

CCTGGGCTACACACGTGCTACAATGGTCGGTACAAAGGGTTGCCAAGCCGCGAGGTGGAGCTAATCC

CATAAAACCGATCGTAGTCCGGATCGCAGTCTGCAACTCGACTGCGTGAAGTCGGAATCGCTAGTAA

TCGTGAATCAGAATGTCACGGTGAATACGTTCCCGGGCCTTGTACACACCGCCCGTCACACCATGGGA

GTGGGTTGCACCAGAAGTAGCTAGTCTAACCCTCGGGAGGACGGTTACCACGGTGTGATTCATGACT

GGGGTGAAGTCGTAACAAGGTAGCCGTAGGGGAACCTGCGGCTGGATCACCTCCTT

43
DP43 16S rRNA
CTGAGTTTGATCCTGGCTCAGATTGAACGCTGGCGGCATGCCTTACACATGCAAGTCGAACGGCAG

-continued

CACGGAGCTTGCTCTGGTGGCGAGTGGCGAACGGGTGAGTAATATATCGGAACGTACCCTGGAGTGG

GGGATAACGTAGCGAAAGTTACGCTAATACCGCATACGATCTAAGGATGAAAGTGGGGGATCGCAA

GACCTCATGCTCGTGGAGCGGCCGATATCTGATTAGCTAGTTGGTAGGGTAAAAGCCTACCAAGGCA

TCGATCAGTAGCTGGTCTGAGAGGACGACCAGCCACACTGGAACTGAGACACGGTCCAGACTCCTAC

GGGAGGCAGCAGTGGGGAATTTTGGACAATGGGCGAAAGCCTGATCCAGCAATGCCGCGTGAGTGA

AGAAGGCCTTCGGGTTGTAAAGCTCTTTTGTCAGGGAAGAAACGGTGAGAGCTAATATCTCTTGCTAA

TGACGGTACCTGAAGAATAAGCACCGGCTAACTACGTGCCAGCAGCCGCGGTAATACGTAGGGTGCA

AGCGTTAATCGGAATTACTGGGCGTAAAGCGTGCGCAGGCGGTTTTGTAAGTCTGATGTGAAATCCCC

GGGCTCAACCTGGGAATTGCATTGGAGACTGCAAGGCTAGAATCTGGCAGAGGGGGGTAGAATTCCA

CGTGTAGCAGTGAAATGCGTAGATATGTGGAGGAACACCGATGGCGAAGGCAGCCCCCTGGGTCAAG

ATTGACGCTCATGCACGAAAGCGTGGGGAGCAAACAGGATTAGATACCCTGGTAGTCCACGCCCTAA

ACGATGTCTACTAGTTGTCGGGTCTTAATTGACTTGGTAACGCAGCTAACGCGTGAAGTAGACCGCCT

GGGGAGTACGGTCGCAAGATTAAAACTCAAAGGAATTGACGGGGACCCGCACAAGCGGTGGATGAT

GTGGATTAATTCGATGCAACGCGAAAAACCTTACCTACCCTTGACATGGCTGGAATCCTTGAGAGATC

AGGGAGTGCTCGAAAGAGAACCAGTACACAGGTGCTGCATGGCTGTCGTCAGCTCGTGTCGTGAGAT

GTTGGGTTAAGTCCCGCAACGAGCGCAACCCTTGTCATTAGTTGCTACGAAAGGGCACTCTAATGAG

ACTGCCGGTGACAAACCGGAGGAAGGTGGGGATGACGTCAAGTCCTCATGGCCCTTATGGGTAGGGC

TTCACACGTCATACAATGGTACATACAGAGCGCCGCCAACCCGCGAGGGGGAGCTAATCGCAGAAAG

TGTATCGTAGTCCGGATTGTAGTCTGCAACTCGACTGCATGAAGTTGGAATCGCTAGTAATCGCGGAT

CAGCATGTCGCGGTGAATACGTTCCCGGGTCTTGTACACACCGCCCGTCACACCATGGGAGCGGGTTT

TACCAGAAGTAGGTAGCTTAACCGTAAGGAGGGCGCTTACCACGGTAGGATTCGTGACTGGGGTGAA

GTCGTAACAAGGTAGCCGTATCGGAAGGTGCGGCTGGATCACCTCCTTT

44
DP44 16S rRNA
TGGCGGCATGCCTTACACATGCAAGTCGAACGGCAGCATAGGAGCTTGCTCCTGATGGCGAGTGG

CGAACGGGTGAGTAATATATCGGAACGTGCCCTAGAGTGGGGGATAACTAGTCGAAAGACTAGCTAA

TACCGCATACGATCTACGGATGAAAGTGGGGGATCGCAAGACCTCATGCTCCTGGAGCGGCCGATAT

CTGATTAGCTAGTTGGTGGGGTAAAAGCTCACCAAGGCGACGATCAGTAGCTGGTCTGAGAGGACGA

CCAGCCACACTGGGACTGAGACACGGCCCAGACTCCTACGGGAGGCAGCAGTGGGGAATTTTGGACA

ATGGGGGCAACCCTGATCCAGCAATGCCGCGTGAGTGAAGAAGGCCTTCGGGTTGTAAAGCTCTTTT

GTCAGGGAAGAAACGGTTCTGGATAATACCTAGGACTAATGACGGTACCTGAAGAATAAGCACCGGC

TAACTACGTGCCAGCAGCCGCGGTAATACGTAGGGTGCAAGCGTTAATCGGAATTACTGGGCGTAAA

GCGTGCGCAGGCGGTTGTGTAAGTCAGATGTGAAATCCCCGGGCTCAACCTGGGAATTGCATTTGAG

ACTGCACGGCTAGAGTGTGTCAGAGGGGGGTAGAATTCCACGTGTAGCAGTGAAATGCGTAGATATG

TGGAGGAATACCGATGGCGAAGGCAGCCCCCTGGGATAACACTGACGCTCATGCACGAAAGCGTGG

GGAGCAAACAGGATTAGATACCCTGGTAGTCCACGCCCTAAACGATGTCTACTAGTTGTCGGGTCTTA

ATTGACTTGGTAACGCAGCTAACGCGTGAAGTAGACCGCCTGGGGAGTACGGTCGCAAGATTAAAAC

TCAAAGGAATTGACGGGGACCCGCACAAGCGGTGGATGATGTGGATTAATTCGATGCAACGCGAAAA

ACCTTACCTACCCTTGACATGGATGGAATCCCGAAGAGATTTGGGAGTGCTCGAAAGAGAACCATCA

CACAGGTGCTGCATGGCTGTCGTCAGCTCGTGTCGTGAGATGTTGGGTTAAGTCCCGCAACGAGCGCA

ACCCTTGTCATTAGTTGCTACGAAAGGGCACTCTAATGAGACTGCCGGTGACAAACCGGAGGAAGGT

GGGGATGACGTCAAGTCCTCATGGCCCTTATGGGTAGGGCTTCACACGTCATACAATGGTACATACA

-continued

GAGGGCCGCCAACCCGCGAGGGGGAGCTAATCCCAGAAAGTGTATCGTAGTCCGGATTGGAGTCTGC

AACTCGACTCCATGAAGTTGGAATCGCTAGTAATCGCGGATCAGCATGTCGCGGTGAATACGTTCCCG

GGTCTTGTACACACCGCCCGTCACACCATGGGAGCGGGTTTTACCAGAAGTGGGTAGCCTAACCGCA

AGGAGGGCGCTCACCACGGTAGGATTCGTGACTGGGGTGAAGTCGTAACAAGGTAGCCGTATCGGAA

GGTGCGGCTGGATCACCTCCTTT

45
DP45 16S rRNA
TACGGAGAGTTTGATCCTGGCTCAGGACGAACGCTGGCGGCGTGCTTAACACATGCAAGTCGAAC

GGTGACGCTAGAGCTTGCTCTGGTTGATCAGTGGCGAACGGGTGAGTAACACGTGAGTAACCTGCCC

TTGACTCTGGGATAACTCCGGGAAACCGGGGCTAATACCGGATACGAGACGCGACCGCATGGTCGGC

GTCTGGAAAGTTTTTCGGTCAAGGATGGACTCGCGGCCTATCAGCTTGTTGGTGAGGTAATGGCTCAC

CAAGGCGTCGACGGGTAGCCGGCCTGAGAGGGCGACCGGCCACACTGGGACTGAGACACGGCCCAG

ACTCCTACGGGAGGCAGCAGTGGGGAATATTGCACAATGGGCGAAAGCCTGATGCAGCGACGCCGC

GTGAGGGATGAAGGCCTTCGGGTTGTAAACCTCTTTCAGTAGGGAAGAAGCGAAAGTGACGGTACCT

GCAGAAGAAGCGCCGGCTAACTACGTGCCAGCAGCCGCGGTAATACGTAGGGCGCAAGCGTTGTCCG

GAATTATTGGGCGTAAAGAGCTCGTAGGCGGTTTGTCGCGTCTGGTGTGAAAACTCAAGGCTCAACCT

TGAGCTTGCATCGGGTACGGGCAGACTAGAGTGTGGTAGGGGTGACTGGAATTCCTGGTGTAGCGGT

GGAATGCGCAGATATCAGGAGGAACACCGATGGCGAAGGCAGGTCACTGGGCCACTACTGACGCTG

AGGAGCGAAAGCATGGGGAGCGAACAGGATTAGATACCCTGGTAGTCCATGCCGTAAACGTTGGGC

ACTAGGTGTGGGGCTCATTCCACGAGTTCCGCGCCGCAGCTAACGCATTAAGTGCCCCGCCTGGGGA

GTACGGCCGCAAGGCTAAAACTCAAAGGAATTGACGGGGGCCCGCACAAGCGGCGGAGCATGCGGA

TTAATTCGATGCAACGCGAAGAACCTTACCAAGGCTTGACATACACCGGAATCATGCAGAGATGTGT

GCGTCTTCGGACTGGTGTACAGGTGGTGCATGGTTGTCGTCAGCTCGTGTCGTGAGATGTTGGGTTAA

GTCCCGCAACGAGCGCAACCCTCGTCCTATGTTGCCAGCACGTTATGGTGGGGACTCATAGGAGACT

GCCGGGGTCAACTCGGAGGAAGGTGGGGATGACGTCAAATCATCATGCCCCTTATGTCTTGGGCTTC

ACGCATGCTACAATGGCCGGTACAAAGGGCTGCGATACCGCGAGGTGGAGCGAATCCCAAAAAGCC

GGTCTCAGTTCGGATTGGGGTCTGCAACTCGACCCCATGAAGTCGGAGTCGCTAGTAATCGCAGATCA

GCAACGCTGCGGTGAATACGTTCCCGGGCCTTGTACACACCGCCCGTCAAGTCACGAAAGTCGGTAA

CACCCGAAGCCGGTGGCCTAACCCCTTGTGGGATGGAGCCGTCGAAGGTGGGATTGGCGATTGGGAC

TAAGTCGTAACAAGGTAGCCGTACCGGAAGGTGCGGCTGGATCACCTCCTTT

46
DP46 16S rRNA
TTGAAGAGTTTGATCATGGCTCAGATTGAACGCTGGCGGCAGGCCTAACACATGCAAGTCGGACG

GTAGCACAGAGGAGCTGCTCCTTGGGTGACGAGTGGCGGACGGGTGAGTAATGTCTGGGGATCTGCC

CGATAGAGGGGGATAACCACTGGAAACGGTGGCTAATACCGCATAACGTCGCAAGACCAAAGAGGG

GGACCTTCGGGCCTCTCACTATCGGATGAACCCAGATGGGATTAGCTAGTAGGCGGGGTAATGGCCC

ACCTAGGCGACGATCCCTAGCTGGTCTGAGAGGATGACCAGCCACACTGGAACTGAGACACGGTCCA

GACTCCTACGGGAGGCAGCAGTGGGGAATATTGCACAATGGGCGCAAGCCTGATGCAGCCATGCCGC

GTGTATGAAGAAGGCCTTCGGGTTGTAAAGTACTTTCAGCGGGGAGGAAGGCGACAGGGTTAATAAC

CCTGTCGATTGACGTTACCCGCAGAAGAAGCACCGGCTAACTCCGTGCCAGCAGCCGCGGTAATACG

GAGGGTGCAAGCGTTAATCGGAATTACTGGGCGTAAAGCGCACGCAGGCGGTCTGTTAAGTCAGATG

TGAAATCCCCGGGCTTAACCTGGGAACTGCATTTGAAACTGGCAGGCTTTAGTCTTGTAGAGTGGGGT

-continued

AGAATTCCAGGTGTAGCGGTGAAATGCGTAGAGATGTGGAGGAACACCAGTGGCGAAGGCGGCTTTT

TGGTCTGTAACTGACGCTGAGGCGCGAAAGCGTGGGGAGCAAACAGGATTAGATACCCTGGTAGTCC

ACGCCGTAAACGATGAGTGCTAAGTGTT

47
DP47 16S rRNA
AGGGTGCAAGCGTTAATCGGAATTACTGGGCGTAAAGCGCGCGTAGGTGGTTTGTTAAGTTGAAT

GTGAAATCCCCGGGCTCAACCTGGGAACTGCATTTGAAACTGGCAAGCTAGAGTCTCGTAGAGGGGG

GTAGAATTCCAGGTGTAGCGGTGAAATGCGTAGAGATCTGGAGGAATACCGGTGGCGAAGGCGGCCC

CCTGGACGAAGACTGACGCTCAGGTGCGAAAGCGTGGGGAGCAAACAGGATTAGATACCCTGGTAGT

CCACGCCGTAAACGATGTCAACTAGCCGTTGGAAGCCTTGAGCTTTTAGTGGCGCAGCTAACGCATTA

AGTTGACCGCCTGGGGAGTACGGCCGCAAGGTTAAAACTCAAATGAATTGACGGGGGCCCGCACAAG

CGGTGGAGCATGTGGTTTAATTCGAAGCAACGCGAAGAACCTTACCAGGCCTTGACATCCAATGAAC

TTTCTAGAGATAGATTGGTGCCTTCGGGAACATTGAGACAGGTGCTGCATGGCTGTCGTCAGCTCGTG

TCGTGAGATGTTGGGTTAAGTCCCGCAACGAGCGCAACCCTTGTCCTGTGTTGCCAGCGCGTAATGGC

GGGGACTCGCAGGAGACTGCCGGGGTCAACTCGGAGGAAGGTGGGGATGACGTCAAATCATCATGC

CCCTTATGTCTTGGGCTTCACGCATGCTACAATGGCCGGTACAAAGGGCTGCAATACCGTGAGGTGGA

GCGAATCCCAAAAAGCCGGTCCCAGTTCGGATTGAGGTCTGCAACTCGACCTCATGAAGTCGGAGTC

GCTAGTAATCGCAGATCAGCAACGCTGCGGTGAATACGTTCCCGGGTCTTGTACACACCGCCCGTCAA

GTCATGAAAGTCGGTAACACCTGAAGCCGGTGGCCCAACCCTTGTGGAGGGAGCCGTCGAAGGTGGG

ATCGGTAATTAGGACTAAGT

48
DP48 16S rRNA
CATGGAGAGTTTGATCCTGGCTCAGGACGAACGCTGGCGGCGTGCCTAATACATGCAAGTCGAGC

GGACAGATGGGAGCTTGCTCCCTGATGTTAGCGGCGGACGGGTGAGTAACACGTGGGTAACCTGCCT

GTAAGACTGGGATAACTCCGGGAAACCGGGGCTAATACCGGATGCTTGATTGAACCGCATGGTTCAA

TTATAAAAGGTGGCTTTTAGCTACCACTTACAGATGGACCCGCGGCGCATTAGCTAGTTGGTGAGGTA

ACGGCTCACCAAGGCAACGATGCGTAGCCGACCTGAGAGGGTGATCGGCCACACTGGGACTGAGAC

ACGGCCCAGACTCCTACGGGAGGCAGCAGTAGGGAATCTTCCGCAATGGACGAAAGTCTGACGGAGC

AACGCCGCGTGAGTGATGAAGGTTTTCGGATCGTAAAACTCTGTTGTTAGGGAAGAACAAGTACCGT

TCGAATAGGGCGGTACCTTGACGGTACCTAACCAGAAAGCCACGGCTAACTACGTGCCAGCAGCCGC

GGTAATACGTAGGTGGCAAGCGTTGTCCGGAATTATTGGGCGTAAAGCGCGCGCAGGCGGTTTCTTA

AGTCTGATGTGAAAGCCCCCGGCTCAACCGGGGAGGGTCATTGGAAACTGGGGAACTTGAGTGCAGA

AGAGGAGAGTGGAATTCCACGTGTAGCGGTGAAATGCGTAGAGATGTGGAGGAACACCAGTGGCGA

AGGCGACTCTCTGGTCTGTAACTGACGCTGAGGCGCGAAAGCGTGGGGAGCGAACAGGATTAGATAC

CCTGGTAGTCCACGCCGTAAACGATGAGTGCTAAGTGTTAGAGGGTTTCCGCCCTTTAGTGCTGCAGC

AAACGCATTAAGCACTCCGCCTGGGGAGTACGGTCGCAAGACTGAAACTCAAAGGAATTGACGGGG

GCCCGCACAAGCGGTGGAGCATGTGGTTTAATTCGAAGCAACGCGAAGAACCTTACCAGGTCTTGAC

ATCCTCTGACAACCCTAGAGATAGGGCTTCCCCTTCGGGGGCAGAGTGACAGGTGGTGCATGGTTGTC

GTCAGCTCGTGTCGTGAGATGTTGGGTTAAGTCCCGCAACGAGCGCAACCCTTGATCTTAGTTGCCAG

CATTCAGTTGGGCACTCTAAGGTGACTGCCGGTGACAAACCGGAGGAAGGTGGGGATGACGTCAAAT

CATCATGCCCCTTATGACCTGGGCTACACACGTGCTACAATGGGCAGAACAAAGGGCAGCGAAGCCG

CGAGGCTAAGCCAATCCCACAAATCTGTTCTCAGTTCGGATCGCAGTCTGCAACTCGACTGCGTGAAG

CTGGAATCGCTAGTAATCGCGGATCAGCATGCCGCGGTGAATACGTTCCCGGGCCTTGTACACACCGC

-continued

CCGTCACACCACGAGAGTTTGTAACACCCGAAGTCGGTGAGGTAACCTTTTGGAGCCAGCCGCCGAA

GGTGGGACAGATGATTGGGGTGAAGTCGTAACAAGGTAGCCGTATCGGAAGGTGCGGCTGGATCACC

TCCTTT

49
DP49 16S rRNA
TATGGAGAGTTTGATCCTGGCTCAGGACGAACGCTGGCGGCGTGCCTAATACATGCAAGTCGAGC

GGACGTTTTTGAAGCTTGCTTCAAAAACGTTAGCGGCGGACGGGTGAGTAACACGTGGGCAACCTGC

CTTATCGACTGGGATAACTCCGGGAAACCGGGGCTAATACCGGATAATATCTAGCACCTCCTGGTGC

AAGATTAAAAGAGGGCCTTCGGGCTCTCACGGTGAGATGGGCCCGCGGCGCATTAGCTAGTTGGAGA

GGTAATGGCTCCCCAAGGCGACGATGCGTAGCCGACCTGAGAGGGTGATCGGCCACACTGGGACTGA

GACACGGCCCAGACTCCTACGGGAGGCAGCAGTAGGGAATCTTCCGCAATGGACGAAAGTCTGACGG

AGCAACGCCGCGTGAGTGATGAAGGGTTTCGGCTCGTAAAGCTCTGTTATGAGGGAAGAACACGTAC

CGTTCGAATAGGGCGGTACCTTGACGGTACCTCATCAGAAAGCCACGGCTAACTACGTGCCAGCAGC

CGCGGTAATACGTAGGTGGCAAGCGTTGTCCGGAATTATTGGGCGTAAAGCGCGCGCAGGCGGCCTT

TTAAGTCTGATGTGAAATCTTGCGGCTCAACCGCAAGCGGTCATTGGAAACTGGGAGGCTTGAGTAC

AGAAGAGGAGAGTGGAATTCCACGTGTAGCGGTGAAATGCGTAGATATGTGGAGGAACACCAGTGG

CGAAGGCGACTCTCTGGTCTGTAACTGACGCTGAGGCGCGAAAGCGTGGGGAGCAAACAGGATTAGA

TACCCTGGTAGTCCACGCCGTAAACGATGAGTGCTAGGTGTTAGGGGTTTCGATGCCCGTAGTGCCGA

AGTTAACACATTAAGCACTCCGCCTGGGGAGTACGGCCGCAAGGCTGAAACTCAAAGGAATTGACGG

GGGCCCGCACAAGCAGTGGAGCATGTGGTTTAATTCGAAGCAACGCGAAGAACCTTACCAGGTCTTG

ACATCCTTTGACCACTCTGGAGACAGAGCTTCCCCTTCGGGGGCAAAGTGACAGGTGGTGCATGGTTG

TCGTCAGCTCGTGTCGTGAGATGTTGGGTTAAGTCCCGCAACGAGCGCAACCCTTGACCTTAGTTGCC

AGCATTTAGTTGGGCACTCTAAGGTGACTGCCGGTGACAAACCGGAGGAAGGTGGGGATGACGTCAA

ATCATCATGCCCCTTATGACCTGGGCTACACACGTGCTACAATGGATGGTACAAAGGGTTGCGAAGC

CGCGAGGTGAAGCCAATCCCATAAAGCCATTCTCAGTTCGGATTGTAGGCTGCAACTCGCCTGCATGA

AGCTGGAATTGCTAGTAATCGCGGATCAGCATGCCGCGGTGAATACGTTCCCGGGCCTTGTACACACC

GCCCGTCACACCACGAGAGTTTGTAACACCCGAAGTCGGTGAGGTAACCTTTTGGAGCCAGCCGCCG

AAGGTGGGACAGATGATTGGGGTGAAGTCGTAACAAGGTAGCCGTATCGGAAGGTGCGGCTGGATC

ACCTCCTTT

50
DP50 16S rRNA
TTGAAGAGTTTGATCATGGCTCAGATTGAACGCTGGCGGCAGGCCTAACACATGCAAGTCGAACG

GTAGCACAGAGAGCTTGCTCTTGGGTGACGAGTGGCGGACGGGTGAGTAATGTCTGGGAAACTGCCC

GATGGAGGGGGATAACTACTGGAAACGGTAGCTAATACCGCATAACGTCGCAAGACCAAAGTGGGG

GACCTTCGGGCCTCACACCATCGGATGTGCCCAGATGGGATTAGCTAGTAGGTGGGGTAATGGCTCA

CCTAGGCGACGATCCCTAGCTGGTCTGAGAGGATGACCAGCCACACTGGAACTGAGACACGGTCCAG

ACTCCTACGGGAGGCAGCAGTGGGGAATATTGCACAATGGGCGCAAGCCTGATGCAGCCATGCCGCG

TGTATGAAGAAGGCCTTCGGGTTGTAAAGTACTTTCAGCGAGGAGGAAGGCATTGTGGTTAATAACC

GCAGTGATTGACGTTACTCGCAGAAGAAGCACCGGCTAACTCCGTGCCAGCAGCCGCGGTAATACGG

AGGGTGCAAGCGTTAATCGGAATTACTGGGCGTAAAGCGCACGCAGGCGGTCTGTCAAGTCGGATGT

GAAATCCCCGGGCTCAACCTGGGAACTGCATTCGAAACTGGCAGGCTAGAGTCTTGTAGAGGGGGGT

AGAATTCCAGGTGTAGCGGTGAAATGCGTAGAGATCTGGAGGAATACCGGTGGCGAAGGCGGCCCCC

-continued

TGGACAAAGACTGACGCTCAGGTGCGAAAGCGTGGGGAGCAAACAGGATTAGATACCCTGGTAGTCC

ACGCCGTAAACGATGTCGACTTGGAGGTTGTGCCCTTGAGGCGTGGCTTCCGGAGCTAACGCGTTAA

GTCGACCGCCTGGGGAGTACGGCCGCAAGGTTAAAACTCAAATGAATTGACGGGGGCCCGCACAAGC

GGTGGAGCATGTGGTTTAATTCGATGCAACGCGAAGAACCTTACCTACTCTTGACATCCACGGAATTT

AGCAGAGATGCTTTAGTGCCTTCGGGAACCGTGAGACAGGTGCTGCATGGCTGTCGTCAGCTCGTGTT

GTGAAATGTTGGGTTAAGTCCCGCAACGAGCGCAACCCTTATCCTTTGTTGCCAGCGGTTCGGCCGGG

AACTCAAAGGAGACTGCCAGTGATAAACTGGAGGAAGGTGGGGATGACGTCAAGTCATCATGGCCCT

TACGAGTAGGGCTACACACGTGCTACAATGGCATATACAAAGAGAAGCGACCTCGCGAGAGCAAGC

GGACCTCATAAAGTATGTCGTAGTCCGGATCGGAGTCTGCAACTCGACTCCGTGAAGTCGGAATCGCT

AGTAATCGTAGATCAGAATGCTACGGTGAATACGTTCCCGGGCCTTGTACACACCGCCCGTCACACCA

TGGGAGTGGGTTGCAAAAGAAGTAGGTAGCTTAACCTTCGGGAGGGCGCTTACCACTTTGTGATTCAT

GACTGGGGTGAAGTCGTAACAAGGTAACCGTAGGGGAACCTGCGGTTGGATCACCTCCTT

51
DP51 16S rRNA
TTGAAGAGTTTGATCATGGCTCAGATTGAACGCTGGCGGCAGGCCTAACACATGCAAGTCGAGCG

GTAGCACAGGGAGCTTGCTCCTGGGTGACGAGCGGCGGACGGGTGAGTAATGTCTGGGAAACTGCCT

GATGGAGGGGGATAACTACTGGAAACGGTAGCTAATACCGCATAACGTCGCAAGACCAAAGAGGGG

GACCTTCGGGCCTCTTGCCATCAGATGTGCCCAGATGGGATTAGCTAGTAGGTGAGGTAATGGCTCAC

CTAGGCGACGATCCCTAGCTGGTCTGAGAGGATGACCAGCCACACTGGAACTGAGACACGGTCCAGA

CTCCTACGGGAGGCAGCAGTGGGGAATATTGCACAATGGGCGCAAGCCTGATGCAGCCATGCCGCGT

GTATGAAGAAGGCCTTCGGGTTGTAAAGTACTTTCAGCGAGGAGGAAGGCATTAAGGTTAATAACCT

TGGTGATTGACGTTACTCGCAGAAGAAGCACCGGCTAACTCCGTGCCAGCAGCCGCGGTAATACGGG

GGGTGCAAGCGTTAATCGGAATTACTGGGCGTAAAGCGCACGCAGGCGGTTTGTCAAGTCGGATGTG

AAATCCCCGGGCTCAACCTGGGAACTGCATTCGAAACGGGCAAGCTAGAGTCTTGTAGAGGGGGGTA

GAATTCCAGGTGTAGCGGTGAAATGCGTAGAGATCTGGAGGAATACCGGTGGCGAAGGCGGCCCCCT

GGACAAAGACTGACGCTCAGGTGCGAAAGCGTGGGGAGCAAACAGGATTAGATACCCTGGTAGTCC

ACGCCGTAAACGATGTCGACTTGGAGGTTGTGCCCTTGAGGCGTGGCTTCCGGAGCTAACGCGTTAA

GTCGACCGCCTGGGGAGTACGGCCGCAAGGTTAAAACTCAAATGAATTGACGGGGGCCCGCACAAGC

GGTGGAGCATGTGGTTTAATTCGATGCAACGCGAAGAACCTTACCTACTCTTGACATCCAGAGAACTT

TCCAGAGATGGATTGGTGCCTTCGGGAACTCTGAGACAGGTGCTGCATGGCTGTCGTCAGCTCGTGTT

GTGAAATGTTGGGTTAAGTCCCGCAACGAGCGCAACCCTTATCCTTTGTTGCCAGCGAGTAATGTCGG

GAACTCAAAGGAGACTGCCAGTGACAAACTGGAGGAAGGTGGGGATGACGTCAAGTCATCATGGCC

CTTACGAGTAGGGCTACACACGTGCTACAATGGCATATACAAAGAGAAGCGACCTCGCGAGAGCAAG

CGGACCTCACAAAGTATGTCGTAGTCCGGATCGGAGTCTGCAACTCGACTCCGTGAAGTCGGAATCG

CTAGTAATCGTAGATCAGAATGCTACGGTGAATACGTTCCCGGGCCTTGTACACACCGCCCGTCACAC

CATGGGAGTGGGTTGCAAAAGAAGTAGGTAGCTTAACCTTCGGGAGGGCGCTTACCACTTTGTGATT

CATGACTGGGGTGAAGTCGTAACAAGGTAACCGTAGGGGAACCTGCGGTTGGATCACCTCCTT

52
DP52 16S rRNA
ACGGAGAGTTTGATCCTGGCTCAGGATGAACGCTGGCGGCGTGCTTAACACATGCAAGTCGAACG

ATGATCCCAGCTTGCTGGGGGATTAGTGGCGAACGGGTGAGTAACACGTGAGTAACCTGCCCTTGAC

TCTGGGATAAGCCTGGGAAACTGGGTCTAATACCGGATATGACTGTCTGACGCATGTCAGGTGGTGG

AAAGCTTTTGTGGTTTTGGATGGACTCGCGGCCTATCAGCTTGTTGGTGGGGTAATGGCCTACCAAGG

-continued

CGACGACGGGTAGCCGGCCTGAGAGGGTGACCGGCCACACTGGGACTGAGACACGGCCCAGACTCCT

ACGGGAGGCAGCAGTGGGGAATATTGCACAATGGGCGCAAGCCTGATGCAGCGACGCCGCGTGAGG

GATGACGGCCTTCGGGTTGTAAACCTCTTTCAGTAGGGAAGAAGCGAAAGTGACGGTACCTGCAGAA

GAAGCGCCGGCTAACTACGTGCCAGCAGCCGCGGTAATACGTAGGGCGCAAGCGTTATCCGGAATTA

TTGGGCGTAAAGAGCTCGTAGGCGGTTTGTCGCGTCTGCTGTGAAAGACCGGGGCTCAACTCCGGTTC

TGCAGTGGGTACGGGCAGACTAGAGTGCAGTAGGGGAGACTGGAATTCCTGGTGTAGCGGTGAAATG

CGCAGATATCAGGAGGAACACCGATGGCGAAGGCAGGTCTCTGGGCTGTAACTGACGCTGAGGAGC

GAAAGCATGGGGAGCGAACAGGATTAGATACCCTGGTAGTCCATGCCGTAAACGTTGGGCACTAGGT

GTGGGGGACATTCCACGTTTTCCGCGCCGTAGCTAACGCATTAAGTGCCCCGCCTGGGGAGTACGGCC

GCAAGGCTAAAACTCAAAGGAATTGACGGGGGCCCGCACAAGCGGCGGAGCATGCGGATTAATTCG

ATGCAACGCGAAGAACCTTACCAAGGCTTGACATGAACCGGTAATACCTGGAAACAGGTGCCCCGCT

TGCGGTCGGTTTACAGGTGGTGCATGGTTGTCGTCAGCTCGTGTCGTGAGATGTTGGGTTAAGTCCCG

CAACGAGCGCAACCCTCGTTCTATGTTGCCAGCGCGTTATGGCGGGGACTCATAGGAGACTGCCGGG

GTCAACTCGGAGGAAGGTGGGGACGACGTCAAATCATCATGCCCCTTATGTCTTGGGCTTCACGCATG

CTACAATGGCCGGTACAAAGGGTTGCGATACTGTGAGGTGGAGCTAATCCCAAAAAGCCGGTCTCAG

TTCGGATTGGGGTCTGCAACTCGACCCCATGAAGTCGGAGTCGCTAGTAATCGCAGATCAGCAACGC

TGCGGTGAATACGTTCCCGGGCCTTGTACACACCGCCCGTCAAGTCACGAAAGTTGGTAACACCCGA

AGCCGGTGGCCTAACCCTTGTGGGGGGAGCCGTCGAAGGTGGGACCGGCGATTGGGACTAAGTCGTA

ACAAGGTAGCCGTACCGGAAGGTGCGGCTGGATCACCTCCTTT

53
DP53 16S rRNA
TGAAGAGTTTGATCATGGCTCAGATTGAACGCTGGCGGCAGGCCTAACACATGCAAGTCGAGCGG

TAGAGAGAAGCTTGCTTCTCTTGAGAGCGGCGGACGGGTGAGTAATACCTAGGAATCTGCCTGATAG

TGGGGGATAACGTTCGGAAACGGACGCTAATACCGCATACGTCCTACGGGAGAAAGCAGGGGACCTT

CGGGCCTTGCGCTATCAGATGAGCCTAGGTCGGATTAGCTAGTTGGTGAGGTAATGGCTCACCAAGG

CTACGATCCGTAACTGGTCTGAGAGGATGATCAGTCACACTGGAACTGAGACACGGTCCAGACTCCT

ACGGGAGGCAGCAGTGGGGAATATTGGACAATGGGCGAAAGCCTGATCCAGCCATGCCGCGTGTGTG

AAGAAGGTCTTCGGATTGTAAAGCACTTTAAGTTGGGAGGAAGGGCAGTTACCTAATACGTGATTGT

CTGACGTTACCGACAGAATAAGCACCGGCTAACTCTGTGCCAGCAGCCGCGGTAATACAGAGGGTGC

AAGCGTTAATCGGAATTACTGGGCGTAAAGCGCGCGTAGGTGGTTTGTTAAGTTGAATGTGAAATCC

CCGGGCTCAACCTGGGAACTGCATCCAAAACTGGCAAGCTAGAGTATGGTAGAGGGTAGTGGAATTT

CCTGTGTAGCGGTGAAATGCGTAGATATAGGAAGGAACACCAGTGGCGAAGGCGACTACCTGGACTG

ATACTGACACTGAGGTGCGAAAGCGTGGGGAGCAAACAGGATTAGATACCCTGGTAGTCCACGCCGT

AAACGATGTCAACTAGCCGTTGGGAGTCTTGAACTCTTAGTGGCGCAGCTAACGCATTAAGTTGACCG

CCTGGGGAGTACGGCCGCAAGGTTAAAACTCAAATGAATTGACGGGGGCCCGCACAAGCGGTGGAG

CATGTGGTTTAATTCGAAGCAACGCGAAGAACCTTACCAGGCCTTGACATCCAATGAACTTTCTAGAG

ATAGATTGGTGCCTTCGGGAACATTGAGACAGGTGCTGCATGGCTGTCGTCAGCTCGTGTCGTGAGAT

GTTGGGTTAAGTCCCGTAACGAGCGCAACCCTTGTCCTTAGTTACCAGCACGTAATGGTGGGCACTCT

AAGGAGACTGCCGGTGACAAACCGGAGGAAGGTGGGGATGACGTCAAGTCATCATGGCCCTTACGG

CCTGGGCTACACACGTGCTACAATGGTCGGTACAAAGGGTTGCCAAGCCGCGAGGTGGAGCTAATCC

CATAAAACCGATCGTAGTCCGGATCGCAGTCTGCAACTCGACTGCGTGAAGTCGGAATCGCTAGTAA

-continued

TCGTGAATCAGAATGTCACGGTGAATACGTTCCCGGGCCTTGTACACACCGCCCGTCACACCATG

54
DP54 16S rRNA
CTTGAGAGTTTGATCCTGGCTCAGAGCGAACGCTGGCGGCAGGCTTAACACATGCAAGTCGAGCG

GGCACCTTCGGGTGTCAGCGGCAGACGGGTGAGTAACACGTGGGAACGTACCCTTCGGTTCGGAATA

ACGCTGGGAAACTAGCGCTAATACCGGATACGCCCTTTTGGGGAAAGGTTTACTGCCGAAGGATCGG

CCCGCGTCTGATTAGCTAGTTGGTGGGGTAACGGCCTACCAAGGCGACGATCAGTAGCTGGTCTGAG

AGGATGATCAGCCACACTGGGACTGAGACACGGCCCAGACTCCTACGGGAGGCAGCAGTGGGGAAT

ATTGGACAATGGGCGCAAGCCTGATCCAGCCATGCCGCGTGAGTGATGAAGGCCTTAGGGTTGTAAA

GCTCTTTTGTCCGGGACGATAATGACGGTACCGGAAGAATAAGCCCCGGCTAACTTCGTGCCAGCAG

CCGCGGTAATACGAAGGGGGCTAGCGTTGCTCGGAATCACTGGGCGTAAAGGGCGCGTAGGCGGCCA

TTCAAGTCGGGGGTGAAAGCCTGTGGCTCAACCACAGAATTGCCTTCGATACTGTTTGGCTTGAGTTT

GGTAGAGGTTGGTGGAACTGCGAGTGTAGAGGTGAAATTCGTAGATATTCGCAAGAACACCAGTGGC

GAAGGCGGCCAACTGGACCAATACTGACGCTGAGGCGCGAAAGCGTGGGGAGCAAACAGGATTAGA

TACCCTGGTAGTCCACGCCGTAAACGATGAATGCTAGCTGTTGGGGTGCTTGCACCTCAGTAGCGCAG

CTAACGCTTTAAGCATTCCGCCTGGGGAGTACGGTCGCAAGATTAAAACTCAAAGGAATTGACGGGG

GCCCGCACAAGCGGTGGAGCATGTGGTTTAATTCGAAGCAACGCGCAGAACCTTACCATCCCTTGAC

ATGTCGTGCCATCCGGAGAGATCCGGGGTTCCCTTCGGGGACGCGAACACAGGTGCTGCATGGCTGT

CGTCAGCTCGTGTCGTGAGATGTTGGGTTAAGTCCCGCAACGAGCGCAACCCACGTCCTTAGTTGCCA

TCATTTAGTTGGGCACTCTAGGGAGACTGCCGGTGATAAGCCGCGAGGAAGGTGTGGATGACGTC

55
DP55 16S rRNA
TCGGAGAGTTTGATCCTGGCTCAGGATGAACGCTGGCGGCGTGCCTAATACATGCAAGTCGAGCG

AACTGATTAGAAGCTTGCTTCTATGACGTTAGCGGCGGACGGGTGAGTAACACGTGGGCAACCTGCC

TGTAAGACTGGGATAACTTCGGGAAACCGAACTAATACCGGATAGGATCTTCTCCTTCATGGGAGAT

GATTGAAAGATGGTTTCGGCTATCACTTACAGATGGGCCCGCGGTGCATTAGCTAGTTGGTGAGGTAA

CGGCTCACCAAGGCAACGATGCATAGCCGACCTGAGAGGGTGATCGGCCACACTGGGACTGAGACAC

GGCCCAGACTCCTACGGGAGGCAGCAGTAGGGAATCTTCCGCAATGGACGAAAGTCTGACGGAGCA

ACGCCGCGTGAGTGATGAAGGCTTTCGGGTCGTAAAACTCTGTTGTTAGGGAAGAACAAGTACAAGA

GTAACTGCTTGTACCTTGACGGTACCTAACCAGAAAGCCACGGCTAACTACGTGCCAGCAGCCGCGG

TAATACGTAGGTGGCAAGCGTTATCCGGAATTATTGGGCGTAAAGCGCGCGCAGGCGGTTTCTTAAG

TCTGATGTGAAAGCCCACGGCTCAACCGTGGAGGGTCATTGGAAACTGGGGAACTTGAGTGCAGAAG

AGAAAAGCGGAATTCCACGTGTAGCGGTGAAATGCGTAGAGATGTGGAGGAACACCAGTGGCGAAG

GCGGCTTTTTGGTCTGTAACTGACGCTGAGGCGCGAAAGCGTGGGGAGCAAACAGGATTAGATACCC

TGGTAGTCCACGCCGTAAACGATGAGTGCTAAGTGTTAGAGGGTTTCCGCCCTTTAGTGCTGCAGCTA

ACGCATTAAGCACTCCGCCTGGGGAGTACGGTCGCAAGACTGAAACTCAAAGGAATTGACGGGGGCC

CGCACAAGCGGTGGAGCATGTGGTTTAATTCGAAGCAACGCGAAGAACCTTACCAGGTCTTGACATC

CTCTGACAACTCTAGAGATAGAGCGTTCCCCTTCGGGGGACAGAGTGACAGGTGGTGCATGGTTGTC

GTCAGCTCGTGTCGTGAGATGTTGGGTTAAGTCCCGCAACGAGCGCAACCCTTGATCTTAGTTGCCAG

CATTTAGTTGGGCACTCTAAGGTGACTGCCGGTGACAAACCGGAGGAAGGTGGGGATGACGTCAAAT

CATCATGCCCCTTATGACCTGGGCTACACACGTGCTACAATGGATGGTACAAAGGGCTGCAAGACCG

CGAGGTCAAGCCAATCCCATAAAACCATTCTCAGTTCGGATTGTAGGCTGCAACTCGCCTACATGAAG

CTGGAATCGCTAGTAATCGCGGATCAGCATGCT

-continued

56
DP56 16S rRNA
ATTGGAGAGTTTGATCCTGGCTCAGGACGAACGCTGGCGGCGTGCCTAATACATGCAAGTCGAGC

GGACCTGATGGAGTGCTTGCACTCCTGATGGTTAGCGGCGGACGGGTGAGTAACACGTAGGCAACCT

GCCCTCAAGACTGGGATAACTACCGGAAACGGTAGCTAATACCGGATAATTTATTTCACAGCATTGTG

GAATAATGAAAGACGGAGCAATCTGTCACTTGGGGATGGGCCTGCGGCGCATTAGCTAGTTGGTGGG

GTAACGGCTCACCAAGGCGACGATGCGTAGCCGACCTGAGAGGGTGAACGGCCACACTGGGACTGA

GACACGGCCCAGACTCCTACGGGAGGCAGCAGTAGGGAATCTTCCGCAATGGGCGAAAGCCTGACG

GAGCAACGCCGCGTGAGTGATGAAGGTTTTCGGATCGTAAAGCTCTGTTGCCAAGGAAGAACGTCTT

CTAGAGTAACTGCTAGGAGAGTGACGGTACTTGAGAAGAAAGCCCCGGCTAACTACGTGCCAGCAGC

CGCGGTAATACGTAGGGGGCAAGCGTTGTCCGGAATTATTGGGCGTAAAGCGCGCGCAGGCGGTTCT

TTAAGTCTGGTGTTTAAACCCGAGGCTCAACTTCGGGTCGCACTGGAAACTGGGGAACTTGAGTGCA

GAAGAGGAGAGTGGAATTCCACGTGTAGCGGTGAAATGCGTAGATATGTGGAGGAACACCAGTGGC

GAAGGCGACTCTCTGGGCTGTAACTGACGCTGAGGCGCGAAAGCGTGGGGAGCAAACAGGATTAGA

TACCCTGGTAGTCCACGCCGTAAACGATGAATGCTAGGTGTTAGGGGTTTCGATACCCTTGGTGCCGA

AGTTAACACATTAAGCATTCCGCCTGGGGAGTACGGTCGCAAGACTGAAACTCAAAGGAATTGACGG

GGACCCGCACAAGCAGTGGAGTATGTGGTTTAATTCGAAGCAACGCGAAGAACCTTACCAAGTCTTG

ACATCCCTCTGAATCCTCTAGAGATAGAGGCGGCCTTCGGGACAGAGGTGACAGGTGGTGCATGGTT

GTCGTCAGCTCGTGTCGTGAGATGTTGGGTTAAGTCCCGCAACGAGCGCAACCCTTGATTTTAGTTGC

CAGCACATCATGGTGGGCACTCTAGAATGACTGCCGGTGACAAACCGGAGGAAGGCGGGGATGACG

TCAAATCATCATGCCCCTTATGACTTGGGCTACACACGTACTACAATGGCTGGTACAACGGGAAGCG

AAGCCGCGAGGTGGAGCCAATCCTATAAAAGCCAGTCTCAGTTCGGATTGCAGGCTGCAACTCGCCT

GCATGAAGTCGGAATTGCTAGTAATCGCGGATCAGCATGCCGCGGTGAATACGTTCCCGGGTCTTGTA

CACACCGCCCGTCACACCACGAGAGTTTACAACACCCGAAGTCGGTGGGGTAACCCGCAAGGGAGCC

AGCCGCCGAAGGTGGGGTAGATGATTGGGGTGAAGTCGTAACAAGGTAGCCGTATCGGAAGGTGCG

GCTGGATCACCTCCTTT

57
DP57 16S rRNA
ATTGGAGAGTTTGATCCTGGCTCAGGATGAACGCTGGCGGCGTGCCTAATACATGCAAGTCGAGC

GAATGGATTAAGAGCTTGCTCTTATGAAGTTAGCGGCGGACGGGTGAGTAACACGTGGGTAACCTGC

CCATAAGACTGGGATAACTCCGGGAAACCGGGGCTAATACCGGATAACATTTTGCACCGCATGGTGC

GAAATTCAAAGGCGGCTTCGGCTGTCACTTATGGATGGACCCGCGTCGCATTAGCTAGTTGGTGAGGT

AACGGCTCACCAAGGCAACGATGCGTAGCCGACCTGAGAGGGTGATCGGCCACACTGGGACTGAGA

CACGGCCCAGACTCCTACGGGAGGCAGCAGTAGGGAATCTTCCGCAATGGACGAAAGTCTGACGGAG

CAACGCCGCGTGAGTGATGAAGGCTTTCGGGTCGTAAAACTCTGTTGTTAGGGAAGAACAAGTGCTA

GTTGAATAAGCTGGCACCTTGACGGTACCTAACCAGAAAGCCACGGCTAACTACGTGCCAGCAGCCG

CGGTAATACGTAGGTGGCAAGCGTTATCCGGAATTATTGGGCGTAAAGCGCGCGCAGGTGGTTTCTT

AAGTCTGATGTGAAAGCCCACGGCTCAACCGTGGAGGGTCATTGGAAACTGGGAGACTTGAGTGCAG

AAGAGGAAAGTGGAATTCCATGTGTAGCGGTGAAATGCGTAGAGATATGGAGGAACACCAGTGGCG

AAGGCGACTTTCTGGTCTGTAACTGACACTGAGGCGCGAAAGCGTGGGGAGCAAACAGGATTAGATA

CCCTGGTAGTCCACGCCGTAAACGATGAGTGCTAAGTGTTAGAGGGTTTCCGCCCTTTAGTGCTGAAG

TTAACGCATTAAGCACTCCGCCTGGGGAGTACGGCCGCAAGGCTGAAACTCAAAGGAATTGACGGGG

-continued

GCCCGCACAAGCGGTGGAGCATGTGGTTTAATTCGAAGCAACGCGAAGAACCTTACCAGGTCTTGAC

ATCCTCTGACAACCCTAGAGATAGGGCTTCCCCTTCGGGGGCAGAGTGACAGGTGGTGCATGGTTGTC

GTCAGCTCGTGTCGTGAGATGTTGGGTTAAGTCCCGCAACGAGCGCAACCCTTGATCTTAGTTGCCAT

CATTAAGTTGGGCACTCTAAGGTGACTGCCGGTGACAAACCGGAGGAAGGTGGGGATGACGTCAAAT

CATCATGCCCCTTATGACCTGGGCTACACACGTGCTACAATGGACGGTACAAAGAGCTGCAAGACCG

CGAGGTGGAGCTAATCTCATAAAACCGTTCTCAGTTCGGATTGTAGGCTGCAACTCGCCTACATGAAG

CTGGAATCGCTAGTAATCGCGGATCAGCATGCCGCGGTGAATACGTTCCCGGGCCTTGTACACACCGC

CCGTCACACCACGAGAGTTTGTAACACCCGAAGTCGGTGGGGTAACCTTTTTGGAGCCAGCCGCCTA

AGGTGGGACAGATGATTGGGGTGAAGTCGTAACAAGGTAGCCGTATCGGAAGGTGCGGCTGGATCAC

CTCCTTT

58
DP58 16S rRNA
AATGACGGTACCTGAAGAATAAGCACCGGCTAACTACGTGCCAGCAGCCGCGGTAATACGTAGGG

TGCAAGCGTTAATCGGAATTACTGGGCGTAAAGCGTGCGCAGGCGGTTTTGTAAGTCTGATGTGAAA

TCCCCGGGCTCAACCTGGGAATTGCATTGGAGACTGCAAGGCTAGAATCTGGCAGAGGGGGGTAGAA

TTCCACGTGTAGCAGTGAAATGCGTAGATATGTGGAGGAACACCGATGGCGAAGGCAGCCCCCTGGG

TCAAGATTGACGCTCATGCACGAAAGCGTGGGGAGCAAACAGGATTAGATACCCTGGTAGTCCACGC

CCTAAACGATGTCTACTAGTTGTCGGGTCTTAATTGACTTGGTAACGCAGCTAACGCGTGAAGTAGAC

CGCCTGGGGAGTACGGTCGCAAGATTAAAACTCAAAGGAATTGACGGGGACCCGCACAAGCGGTGG

ATGATGTGGATTAATTCGATGCAACGCGAAAAACCTTACCTACCCTTGACATGGCTGGAATCCTCGAG

AGATTGGGGAGTGCTCGAAAGAGAACCAGTACACAGGTGCTGCATGGCTGTCGTCAGCTCGTGTCGT

GAGATGTTGGGTTAAGTCCCGCAACGAGCGCAACCCTTGTCATTAGTTGCTACGAAAGGGCACTCTA

ATGAGACTGCCGGTGACAAACCGGAGGAAGGTGGGGATGACGTCAAGTCCTCATGGCCCTTATGGGT

AGGGCTTCACACGTCATACAATGGTACATACAGAGCGCCGCCAACCCGCGAGGGGGAGCTAATCGCA

GAAAGTGTATCGTAGTCCGGATTGTAGTCTGCAACTCGACTGCATGAAGTTGGAATCGCTAGTAATCG

CGGATCAGCATGTCGCGGTGAATACGTTCCCGGGTCTTGTACACACCGCCCGTCACACCATGGGAGC

GGGTTTTACCAGAAGTAGGTAGCTTAACCGTAAGGAGGGCGCTTACCACGGTAGGATTCGTGACTGG

GGTGAAGTCGTAACAAGGTAGCCGTATCGGAAGGTGCGGCTGGATCACCTCCTTT

59
DP59 16S rRNA
TTGAAGAGTTTGATCATGGCTCAGATTGAACGCTGGCGGCAGGCCTAACACATGCAAGTCGAACG

GTAACAGGAAGCAGCTTGCTGCTTTGCTGACGAGTGGCGGACGGGTGAGTAATGTCTGGGAAACTGC

CTGATGGAGGGGGATAACTACTGGAAACGGTAGCTAATACCGCATAACGTCGCAAGACCAAAGAGG

GGGACCTTCGGGCCTCTTGCCATCAGATGTGCCCAGATGGGATTAGCTAGTAGGTGGGGTAACGGCT

CACCTAGGCGACGATCCCTAGCTGGTCTGAGAGGATGACCAGCCACACTGGAACTGAGACACGGTCC

AGACTCCTACGGGAGGCAGCAGTGGGGAATATTGCACAATGGGCGCAAGCCTGATGCAGCCATGCCG

CGTGTATGAAGAAGGCCTTCGGGTTGTAAAGTACTTTCAGCGGGGAGGAAGGCGATGCGGTTAATAA

CCGCGTCGATTGACGTTACCCGCAGAAGAAGCACCGGCTAACTCCGTGCCAGCAGCCGCGGTAATAC

GGAGGGTGCAAGCGTTAATCGGAATTACTGGGCGTAAAGCGCACGCAGGCGGTCTGTCAAGTCGGAT

GTGAAATCCCCGGGCTCAACCTGGGAACTGCATCCGAAACTGGCAGGCTTGAGTCTCGTAGAGGGGG

GTAGAATTCCAGGTGTAGCGGTGAAATGCGTAGAGATCTGGAGGAATACCGGTGGCGAAGGCGGCCC

CCTGGACGAAGACTGACGCTCAGGTGCGAAAGCGTGGGGAGCAAACAGGATTAGATACCCTGGTAGT

CCACGCCGTAAACGATGTCGACTTGGAGGTTGTGCCCTTGAGGCGTGGCTTCCGGAGCTAACGCGTTA

-continued

AGTCGACCGCCTGGGGAGTACGGCCGCAAGGTTAAAACTCAAATGAATTGACGGGGGCCCGCACAA

GCGGTGGAGCATGTGGTTTAATTCGATGCAACGCGAAGAACCTTACCTGGTCTTGACATCCACAGAA

CTTGGCAGAGATGCCTTGGTGCCTTCGGGAACTGTGAGACAGGTGCTGCATGGCTGTCGTCAGCTCGT

GTTGTGAAATGTTGGGTTAAGTCCCGCAACGAGCGCAACCCTTATCCTTTGTTGCCAGCGGTTAGGCC

GGGAACTCAAAGGAGACTGCCAGTGATAAACTGGAGGAAGGTGGGGATGACGTCAAGTCATCATGG

CCCTTACGACCAGGGCTACACACGTGCTACAATGGCGCATACAAAGAGAAGCGATCTCGCGAGAGCC

AGCGGACCTCATAAAGTGCGTCGTAGTCCGGATTGGAGTCTGCAACTCGACTCCATGAAGTCGGAAT

CGCTAGTAATCGTGAATCAGAATGTCACGGTGAATACGTTCCCGGGCCTTGTACACACCGCCCGTCAC

ACCATGGGAGTGGGTTGCAAAAGAAGTAGGTAGCTTAACCTTCGGGAGGGCGCTTACCACTTTGTGA

TTCATGACTGGGGTGAAGTCGTAACAAGGTAACCGTAGGGGAACCTGCGGTTGGATCACCTCCTT

60
DP60 16S
rRNATCGGAGAGTTTGATCCTGGCTCAGGACGAACGCTGGCGGCGTGCCTAATACATGCAAGTCGAGC

GAATCGATGGGAGCTTGCTCCCTGAGATTAGCGGCGGACGGGTGAGTAACACGTGGGCAACCTGCCT

ATAAGACTGGGATAACTTCGGGAAACCGGAGCTAATACCGGATACGTTCTTTTCTCGCATGAGAGAA

GATGGAAAGACGGTTTTGCTGTCACTTATAGATGGGCCCGCGGCGCATTAGCTAGTTGGTGAGGTAAT

GGCTCACCAAGGCGACGATGCGTAGCCGACCTGAGAGGGTGATCGGCCACACTGGGACTGAGACAC

GGCCCAGACTCCTACGGGAGGCAGCAGTAGGGAATCTTCCGCAATGGACGAAAGTCTGACGGAGCA

ACGCCGCGTGAACGAAGAAGGCCTTCGGGTCGTAAAGTTCTGTTGTTAGGGAAGAACAAGTACCAGA

GTAACTGCTGGTACCTTGACGGTACCTAACCAGAAAGCCACGGCTAACTACGTGCCAGCAGCCGCGG

TAATACGTAGGTGGCAAGCGTTGTCCGGAATTATTGGGCGTAAAGCGCGCGCAGGTGGTTCCTTAAG

TCTGATGTGAAAGCCCACGGCTCAACCGTGGAGGGTCATTGGAAACTGGGGAACTTGAGTGCAGAAG

AGGAAAGTGGAATTCCAAGTGTAGCGGTGAAATGCGTAGAGATTTGGAGGAACACCAGTGGCGAAG

GCGACTTTCTGGTCTGTAACTGACACTGAGGCGCGAAAGCGTGGGGAGCAAACAGGATTAGATACCC

TGGTAGTCCACGCCGTAAACGATGAGTGCTAAGTGTTAGAGGGTTTCCGCCCTTTAGTGCTGCAGCTA

ACGCATTAAGCACTCCGCCTGGGGAGTACGGCCGCAAGGCTGAAACTCAAAGGAATTGACGGGGGCC

CGCACAAGCGGTGGAGCATGTGGTTTAATTCGAAGCAACGCGAAGAACCTTACCAGGTCTTGACATC

CTCTGACAACCCTAGAGATAGGGCGTTCCCCTTCGGGGGACAGAGTGACAGGTGGTGCATGGTTGTC

GTCAGCTCGTGTCGTGAGATGTTGGGTTAAGTCCCGCAACGAGCGCAACCCTTGATCTTAGTTGCCAG

CATTCAGTTGGGCACTCTAAGGTGACTGCCGGTGACAAACCGGAGGAAGGTGGGGATGACGTCAAAT

CATCATGCCCCTTATGACCTGGGCTACACACGTGCTACAATGGATGGTACAAAGGGCTGCAAACCTG

CGAAGGTAAGCGAATCCCATAAAGCCATTCTCAGTTCGGATTGTAGGCTGCAACTCGCCTACATGAA

GCCGGAATCGCTAGTAATCGCGGATCAGCATGCCGCGGTGAATACGTTCCCGGGCCTTGTACACACC

GCCCGTCACACCACGAGAGTTTGTAACACCCGAAGTCGGTGAGGTAACCTTTATGGAGCCAGCCGCC

TAAGGTGGGACAGATGATTGGGGTGAAGTCGTAACAAGGTAGCCGTATCGGAAGGTGCGGCTGGATC

ACCTCCTTT

61
DP61 16S rRNA
GGAAGGCGGTCTGTCAAGTCGGATGTGAAATCCCCGGGCTCAACCTGGGAACTGCATTCGAAACT

GGCAGGCTAGAGTCTTGTAGAGGGGGGTAGAATTCCAGGTGTAGCGGTGAAATGCGTAGAGATCTGG

AGGAATACCGGTGGCGAAGGCGGCCCCCTGGACAAAGACTGACGCTCAGGTGCGAAAGCGTGGGGA

GCAAACAGGATTAGATACCCTGGTAGTCCACGCCGTAAACGATGTCGACTTGGAGGTTGTTCCCTTGA

-continued

GGAGTGGCTTCCGGAGCTAACGCGTTAAGTCGACCGCCTGGGGAGTACGGCCGCAAGGTTAAAACTC

AAATGAATTGACGGGGGCCCGCACAAGCGGTGGAGCATGTGGTTTAATTCGATGCAACGCGAAGAAC

CTTACCTACTCTTGACATCCACGGAATTTAGCAGAGATGCTTTAGTGCCTTCGGGAACCGTGAGACAG

GTGCTGCATGGCTGTCGTCAGCTCGTGTTGTGAAATGTTGGGTTAAGTCCCGCAACGAGCGCAACCCT

TATCCTTTGTTGCCAGCGGTCCGGCCGGGAACTCAAAGGAGACTGCCAGTGATAAACTGGAGGAAGG

TGGGGATGACGTCAAGTCATCATGGCCCTTACGAGTAGGGCTACACACGTGCTACAATGGCGCATAC

AAAGAGAAGCGACCTCGCGAGAGCAAGCGGACCTCATAAAGTGCGTCGTAGTCCGGATCGGAGTCTG

CAACTCGACTCCGTGAAGTCGGAATCGCTAGTAATCGTAGATCAGAATGCTACGGTGAATACGTTCCC

GGGCCTTGTACACACCGCCCGTCACACCATGGGAGTGGGTTGCAAAAGAAGTAGGTAGCTTAACCTT

CGGGAGGGCGCTTACCACTTTGTGATTCATGACTGGGGTGAAGTCGTAACAAGGTAACCGTAGGGGA

ACCTGCGGTTGGATCACCTCCTT

62
DP62 16S rRNA
TGGCTCAGATTGAACGCTGGCGGCAGGCCTAACACATGCAAGTCGAACGGTAGCACAGAGGAGCT

TGCTCCTTGGGTGACGAGTGGCGGACGGGTGAGTAATGTCTGGGAAACTGCCCGATGGAGGGGGATA

ACTACTGGAAACGGTAGCTAATACCGCATAACGTCTTCGGACCAAAGTGGGGGACCTTCGGGCCTCA

CACCATCGGATGTGCCCAGATGGGATTAGCTAGTAGGTGGGGTAATGGCTCACCTAGGCGACGATCC

CTAGCTGGTCTGAGAGGATGACCAGCCACACTGGAACTGAGACACGGTCCAGACTCCTACGGGAGGC

AGCAGTGGGGAATATTGCACAATGGGCGCAAGCCTGATGCAGCCATGCCGCGTGTATGAAGAAGGCC

TTCGGGTTGTAAAGTACTTTCAGTGGGGAGGAAGGCGTTAAGGTTAATAACCTTGGCGATTGACGTTA

CCCGCAGAAGAAGCACCGGCTAACTCCGTGCCAGCAGCCGCGGTAATACGGAGGGTGCAAGCGTTAA

TCGGAATTACTGGGCGTAAAGCGCACGCAGGCGGTCTGTCAAGTCGGATGTGAAATCCCCGGGCTCA

ACCTGGGAACTGCATTCGAAACTGGCAGGCTAGAGTCTTGTAGAGGGGGGTAGAATTCCAGGTGTAG

CGGTGAAATGCGTAGAGATCTGGAGGAATACCGGTGGCGAAGGCGGCCCCCTGGACAAAGACTGAC

GCTCAGGTGCGAAAGCGTGGGGAGCAAACAGGATTAGATACCCTGGTAGTCCACGCCGTAAACGATG

TCGACTTGGAGGTTGTTCCCTTGAGGAGTGGCTTCCGGAGCTAACGCGTTAAGTCGACCGCCTGGGGA

GTACGG

63
DP63 16S rRNA
TGAAGAGTTTGATCATGGCTCAGATTGAACGCTGGCGGCAGGCCTAACACATGCAAGTCGAGCGG

TAGAGAGAAGCTTGCTTCTCTTGAGAGCGGCGGACGGGTGAGTAATGCCTAGGAATCTGCCTGGTAG

TGGGGGATAACGTTCGGAAACGGACGCTAATACCGCATACGTCCTACGGGAGAAAGCAGGGGACCTT

CGGGCCTTGCGCTATCAGATGAGCCTAGGTCGGATTAGCTAGTTGGTGAGGTAATGGCTCACCAAGG

CGACGATCCGTAACTGGTCTGAGAGGATGATCAGTCACACTGGAACTGAGACACGGTCCAGACTCCT

ACGGGAGGCAGCAGTGGGGAATATTGGACAATGGGCGAAAGCCTGATCCAGCCATGCCGCGTGTGTG

AAGAAGGTCTTCGGATTGTAAAGCACTTTAAGTTGGGAGGAAGGGTTGTAGATTAATACTCTGCAATT

TTGACGTTACCGACAGAATAAGCACCGGCTAACTCTGTGCCAGCAGCCGCGGTAATACAGAGGGTGC

AAGCGTTAATCGGAATTACTGGGCGTAAAGCGCGCGTAGGTGGTTTGTTAAGTTGGATGTGAAATCC

CCGGGCTCAACCTGGGAACTGCATTCAAAACTGACTGACTAGAGTATGGTAGAGGGTGGTGGAATTT

CCTGTGTAGCGGTGAAATGCGTAGATATAGGAAGGAACACCAGTGGCGAAGGCGACCACCTGGACTA

ATACTGACACTGAGGTGCGAAAGCGTGGGGAGCAAACAGGATTAGATACCCTGGTAGTCCACGCCGT

AAACGATGTCAACTAGCCGTTGGAAGCCTTGAGCTTTTAGTGGCGCAGCTAACGCATTAAGTTGACCG

CCTGGGGAGTACGGCCGCAAGGTTAAAACTCAAATGAATTGACGGGGGCCCGCACAAGCGGTGGAG

-continued

CATGTGGTTTAATTCGAAGCAACGCGAAGAACCTTACCAGGCCTTGACATCCAATGAACTTTCTAGAG

ATAGATTGGTGCCTTCGGGAACATTGAGACAGGTGCTGCATGGCTGTCGTCAGCTCGTGTCGTGAGAT

GTTGGGTTAAGTCCCGTAACGAGCGCAACCCTTGTTCTTAGTTACCAGCACGTTATGGTGGGCACTCT

AAGGAGACTGCCGGTGACAAACCGGAGGAAGGTGGGGATGACGTCAAGTCATCATGGCCCTTACGG

CCTGGGCTACACACGTGCTACAATGGTCGGTACAGAGGGTTGCCAAGCCGCGAGGTGGAGCTAATCC

CATAAAACCGATCGTAGTCCGGATCGCAGTCTGCAACTCGACTGCGTGAAGTCGGAATCGCTAGTAA

TCGCGAATCAGAATGTCGCGGTGAATACGTTCCCGGGCCTTGTACACACCGCCCGTCACACCATGGG

AGTGGGTTGCACCAGAAGTAGCTAGTCTAACCTTCGGGAGGACGGTTACCACGGTGTGATTCATGAC

TGGGGTGAAGTCGTAACAAGGTAGCCGTAGGGGAACCTGCGGCTGGATCACCTCCTT

64
DP64 ITS sequence
TCCGTAGGTGAACCTGCGGAAGGATCATTAAATAATCAATAATTTTGGCTTGTCCATTATTATCTAT

TTACTGTGAACTGTATTATTACTTGACGCTTGAGGGATGCTCCACTGCTATAAGGATAGGCGGTGGGG

ATGTTAACCGAGTCATAGTCAAGCTTAGGCTTGGTATCCTATTATTATTTACCAAAAGAATTCAGAAT

TAATATTGTAACATAGACCTAAAAAATCTATAAAACAACTTTTAACAACGGATCTCTTGGTTCTCGCA

TCGATGAAGAACGTAGCAAAGTGCGATAACTAGTGTGAATTGCATATTCAGTGAATCATCGAGTCTTT

GAACGCAACTTGCGCTCATTGGTATTCCAATGAGCACGCCTGTTTCAGTATCAAAACAAACCCTCTAT

TCAATATTTTTGTTGAATAGGAATACTGAGAGTCTCTTGATCTTTTCTGATCTCGAACCTCTTGAAATG

TACAAAGGCCTGATCTTGTTTGAATGCCTGAACTTTTTTTTAATATAAAGAGAAGCTCTTGCGGTAAA

CTGTGCTGGGGCCTCCCAAATAATACTCTTTTTAAATTTGATCTGAAATCAGGCGGGATTACCCGCTG

AACTTAAGCATATCAATAAGCGGAGGAAAAGAAAATAACAATGATTTCCCTAGTAACGGCGAGTGAA

GAGGAAAGAGCTCAAAGTTGGAAACTGTTTGGCTTAGCTAAACCGTATTGTAAACTGTAGAAACATT

TTCCTGGCACGCCGGATTAATAAGTCCTTTGGAACAAGGCATCATGGAGGGTGAGAATCCCGTCTTTG

ATCCGAGTAGTTGTCTTTTGTGATATGTTTTCAAAGAGTCAGGTTGTTTGGGAATGCAGCCTAAATTG

GGTGGTAAATCTCACCTAAAGCTAAATATTTGCGAGAGACCGATAGCGAACAAGTACCGTGAGGGAA

AGATGAAAAGAACTTTGAAAAGAGAGTTAAACAGTATGTGAAATTGTTAAAAGGGAACCGTTTGGAG

CCAGACTGGTTTGACTGTAATCAACCTAGAATTCGTTCTGGGTGCACTTGCAGTCTATACCTGCCAAC

AACAGTTTGATTTGGAGGAAAAAATTAGTAGGAATGTAGCCTCTCGAGGTGTTATAGCCTACTATCAT

ACTCTGGATTGGACTGAGGAACGCAGCGAATGCCATTAGGCGAGATTGCTGGGTGCTTTCGCTAATA

AATGTTAGAATTTCTGCTTCGGGTGGTGCTAATGTTTAAAGGAGGAACACATCTAGTATATTTTTTATT

CGCTTAGGTTGTTGGCTTAATGACTCTAAATGACCCGTCTTGAAACACGGACCAAGGAGTCCACCATA

AGTGCAAGTATTTGAGTGACAAACTCATATGCGTAAGGAAACTGATTGATACGAAATCTTTTGATGGC

AGTATCACCCGGCGTTGACGTTTTATACTGAACTGACCGAGGTAAAGCACTTATGATGGGACCCGAA

AGATGGTGAACTATGCCTGAATAGGGTGAAGCCAGAGGAAACTCTGGTGGAGGCTCGTAGCGATTCT

GACGTGCAAATCGATCGTCAAATTTGGGTATAGGGGCGAAAGACTAATCGAACCATCTAGTAGCTGG

TTCCTGCCGAAGTTTCCCTCAGGA

65
DP65 ITS sequence
TCCGTAGGTGAACCTGCGGAAGGATCATTATTGAAAACAAGGGTGTCCAATTTAACTTGGAACCC

GAACTTCTCAATTCTAACTTTGTGCATCTGTATTATGGCGAGCAGTCTTCGGATTGTGAGCCTTCACTT

ATAAACACTAGTCTATGAATGTAAAATTTTTATAACAAATAAAAACTTTCAACAACGGATCTCTTGGC

TCTCGCATCGATGAAGAACGCAGCGAAATGCGATACGTAATGTGAATTGCAGAATTCAGTGAATCAT

-continued

CGAATCTTTGAACGCATCTTGCGCTCTCTGGTATTCCGGAGAGCATGTCTGTTTGAGTGTCATGAATTC

TTCAACCCAATCTTTTCTTGTAATCGATTGGTGTTTGGATTTTGAGCGCTGCTGGCTTCGGCCTAGCTC

GTTCGTAATACATTAGCATCCCTAATACAAGTTTGGATTGACTTGGCGTAATAGACTATTCGCTAAGG

ATTCGGTGGAAACATCGAGCCAACTTCATTAAGGAAGCTCCTAATTTAAAAGTCTACCTTTTGATTAG

ATCTCAAATCAGGCAGGATTACCCGCTGAACTTAAGCATATCAATAAGCGGAGGAAAAGAAACTAAC

AAGGATTCCCCTAGTAGCGGCGAGCGAAGCGGGAAAAGCTCAAATTTGTAATCTGGCGTCTTCGACG

TCCGAGTTGTAATCTCGAGAAGTGTTTTCCGTGATAGACCGCATACAAGTCTCTTGGAACAGAGCGTC

ATAGTGGTGAGAACCCAGTACACGATGCGGATGCCTATTACTTTGTGATACACTTTCGAAGAGTCGAG

TTGTTTGGGAATGCAGCTCAAATTGGGTGGTAAATTCCATCTAAAGCTAAATATTGGCGAGAGACCG

ATAGCGAACAAGTACCGTAAGGGAAAGATGAAAAGCACTTTGGAAAGAGAGTTAACAGTACGTGAA

ATTGTTGGAAGGGAAACACATGCAGTGATACTTGCTATTCGGGGCAACTCGATTGGCAGGCCCGCAT

CAGTTTTTCGGGGCGGAAAAGCGTAGAGAGAAGGTAGCAATTTCGGTTGTGTTATAGCTCTTTACTGG

ATTCGCCCTGGGGGACTGAGGAACGCAGCGTGCTTTTAGCAATTCCTTCGGGAATTCCACGCTTAGGA

TGCGGGTTTATGGCTGTATATGACCCGTCTTGAAACACGGACCAAGGAGTCTAACATGCTTGCGAGTA

TTTGGGTGTCAAACCCGGATGCGCAATGAAAGTGAATGGAGGTGGGAAGCGCAAGCTGCACCATCGA

CCGATCTGGATTTTTTAAGATGGATTTGAGTAAGAGCAAGTATGTTGGGACCCGAAAGATGGTGAAC

TATGCCTGAATAGGGCGAAGCCAGAGGAAACTCTGGTGGAGGCTCGTAGCGGTTCTGACGTGCAAAT

CGATCGTCAAATTTGGGTATAGGGGCGAAAGACTAATCGAACCATCTAGTAGCTGGTTCCTGCCGAA

GTTTCCCTCAGGA

66
DP66 ITS sequence
TCCGTAGGTGAACCTGCGGAAGGATCATTACTGTGATTTATCCACCACACTGCGTGGGCGACACGA

AACACCGAAACCGAACGCACGCCGTCAAGCAAGAAATCCACAAAACTTTCAACAACGGATCTCTTGG

TTCTCGCATCGATGAAGAGCGCAGCGAAATGCGATACCTAGTGTGAATTGCAGCCATCGTGAATCAT

CGAGTTCTTGAACGCACATTGCGCCCGCTGGTATTCCGGCGGGCATGCCTGTCTGAGCGTCGTTTCCT

TCTTGGAGCGGAGCTTCAGACCTGGCGGGCTGTCTTTCGGGACGGCGCGCCCAAAGCGAGGGGCCTT

CTGCGCGAACTAGACTGTGCGCGCGGGGCGGCCGGCGAACTTATACCAAGCTCGACCTCAGATCAGG

CAGGAGTACCCGCTGAACTTAAGCATATCAATAAGCGGAGGAAAAGAAACCAACAGGGATTGCCCC

AGTAGCGGCGAGTGAAGCGGCAAAAGCTCAGATTTGGAATCGCTTCGGCGAGTTGTGAATTGCAGGT

TGGCGCCTCTGCGGCGGCGGCGGTCCAAGTCCCTTGGAACAGGGCGCCATTGAGGGTGAGAGCCCCG

TGGGACCGTTTGCCTATGCTCTGAGGCCCTTCTGACGAGTCGAGTTGTTTGGGAATGCAGCTCTAAGC

GGGTGGTAAATTCCATCTAAGGCTAAATACTGGCGAGAGACCGATAGCGAACAAGTACTGTGAAGGA

AAGATGAAAAGCACTTTGAAAAGAGAGTGAAACAGCACGTGAAATTGTTGAAAGGGAAGGGTATTG

CGCCCGACATGGAGCGTGCGCACCGCTGCCCCTCGTGGGCGGCGCTCTGGGCGTGCTCTGGGCCAGC

ATCGGTTTTTGCCGCGGGAGAAGGGCGGCGGGCATGTAGCTCTTCGGAGTGTTATAGCCTGCCGCCG

GCGCCGCGAGCGGGGACCGAGGACTGCGACTTTTGTCTCGGATGCTGGCACAACGGCGCAACACCGC

CCGTCTTGAAACATGGACCAAGGAGTCTAACGTCTATGCGAGTGTTTGGGTGTGAAACCCCGGGCGC

GTAATGAAAGTGAACGTAGGTCGGACCGCTCCTCTCGGGGGGCGGGCACGATCGACCGATCCTGATG

TCTTCGGATGGATTTGAGTAAGAGCATAGCTGTTGGGACCCGAAAGATGGTGAACTATGCCTGAATA

GGGTGAAGCCAGAGGAAACTCTGGTGGAGGCTCGTAGCGGTTCTGACGTGCAAATCGATCGTCGAAT

TTGGGTATAGGGGCGAAAGACTAATCGAACCATCTAGTAGCTGGTTCCTGCCGAAGTTTCCCTCAGGA

67

-continued

DP53 Glutamine--tRNA ligase
ATGAGCAAGCCCACTGTCGACCCCACTCTGAATCCAAAGGCTGGCCCTGCTGTCCCGGCTAACTTC

CTGCGTCCAATCGTTCAGGCGGACCTAGACTCGGGTAAATACACACAGATCGTGACCCGCTTTCCGCC

GGAGCCAAACGGCTATCTGCACATCGGTCATGCCAAATCCATTTGTGTGAACTTTGGGCTGGCTCAAG

AGTTTGGCGGCGTGACGCATTTGCGTTTTGACGACACCAACCCGGCAAAAGAAGACCAGGAATACAT

CGACGCCATCGAAAGCGACGTCAAGTGGCTGGGCTTCGAGTGGGCCGGTGAAGTGCGTTACGCGTCG

CAATACTTCGATCAACTGCACGAGTGGGCGATTTACCTGATCAAAGAAGGCAAGGCCTACGTCTGCG

ACCTGACGCCCGAGCAAGCCAAGGAATACCGTGGCAGCCTGACCGAGCCCGGCAAGAACAGCCCGTT

CCGCGACCGTAGCGTTGAAGAGAACCTGGATCTGTTCGCCCGCATGACCGCCGGTGAGTTTGAAGAC

GGCAAGCGTGTGCTGCGCGCCAAGATCGACATGACCTCGCCGAACATGAACCTGCGCGACCCGATCA

TGTACCGCATCCGTCATGCCCATCACCACCAGACCGGTGACAAGTGGTGCATCTACCCCAACTATGAC

TTCACCCACGGTCAGTCGGATGCCATTGAAGGCATCACCCATTCGATCTGCACCCTGGAGTTCGAAAG

CCATCGTCCGCTGTACGAATGGTTCCTGGACAGCCTGCCAGTACCGGCGCGCCCGCGTCAGTACGAGT

TCAGCCGTCTGAACCTCAACTACACCATCACCAGCAAGCGCAAGCTCAAGCAGCTGGTCGATGAAAA

GCACGTCAACGGCTGGGATGACCCGCGCATGTCGACGCTGTCGGGTTTCCGCCGTCGCGGTTACACGC

CTAAATCGATTCGTAATTTCTGTGACATGGTCGGCACCAACCGTTCTGACGGTGTTGTTGACTTCGGC

ATGCTGGAATTCAGCATTCGTGACGATTTGGACCACAGCGCGCCGCGCGCCATGTGCGTGCTGCGTCC

ATTGAAGGTGATTATTACCAACTACCCGGAAGGTCAGGTCGAAAACCTCGAGCTGCCTTGCCACCCG

AAAGAAGACATGGGTGTGCGGGTGTTGCCGTTTGCCCGTGAAATCTACATCGACCGTGAAGACTTCA

TGGAAGAGCCGCCAAAAGGCTACAAGCGTCTTGAGCCTGCGGGCGAAGTGCGTTTGCGCGGCAGCTA

TGTGATCCGTGCCGACGAAGCGATCAAGGATGCCGATGGCAACATCGTTGAACTGCATTGCTCGTAC

GATCCGCTGACCCTGGGTAAAAACCCTGAAGGTCGCAAGGTCAAGGGTGTTGTGCACTGGGTGCCGG

CGGCGGCCAGCGTCGAATGCGAAGTGCGTTTGTATGATCGTCTGTTCCGCTCGCCGAACCCTGAAAAG

GCCGAAGACGGCGCGGGCTTCCTGGAAAACATCAACCCTGACTCGCTGCAGGTACTGACCGGTTGTC

GTGCTGAACCCTCGCTGGGCAATGCACAGCCGGAAGACCGTTTCCAGTTCGAGCGCGAAGGCTACTT

CTGCGCAGATATCAAGGACTCGAAACCCGGTCACCCGGTATTCAACCGTACCGTGACCCTGCGTGATT

CGTGGGGCCAGTGA

68
DP53 DNA gyrase subunit B
TTGAGCGAAGAAAACACGTACGACTCAACGAGCATTAAAGTGCTGAAAGGCCTTGATGCCGTACG

CAAACGTCCCGGTATGTACATTGGTGATACTGACGATGGCAGCGGTCTGCACCACATGGTGTTCGAA

GTAGTCGACAACTCCATCGACGAAGCGCTGGCTGGCCATTGCGACGACATCACCATCACGATCCACC

CGGACGAGTCCATCACCGTGCGCGATAACGGCCGCGGTATTCCGGTTGACGTGCATAAAGAAGAAGG

CGTATCTGCAGCCGAGGTCATCATGACCGTGCTGCACGCCGGCGGTAAGTTCGATGACAACTCCTACA

AAGTATCCGGCGGCTTGCACGGTGTAGGTGTTTCGGTGGTAAACGCCCTGTCCGAACTGCTGGTCTTG

ACTGTACGCCGCAGCGGCAAGATCTGGGAACAGACCTACGTCCACGGTGTTCCTCAGGCGCCTATGG

CTATTGTGGGTGAAAGCGAAACCACGGGTACGCAGATCCACTTCAAGCCTTCGGCTGAAACCTTCAA

GAATATCCACTTTAGCTGGGACATCCTGGCCAAGCGGATTCGTGAACTGTCCTTCCTGAACTCCGGTG

TGGGTATCGTCCTCAAGGACGAGCGCAGCGGCAAGGAGGAGCTGTTCAAGTACGAAGGTGGCCTGCG

TGCATTCGTTGATTACCTGAACACCAACAAGAACGCTGTGAACCAGGTGTTCCACTTCAATGTTCAGC

GTGAAGACGGCATCGGCGTAGAAATCGCCCTGCAGTGGAACGACAGCTTCAACGAGAACCTGTTGTG

CTTCACCAACAACATTCCACAGCGCGATGGTGGCACGCACTTGGTGGGCTTCCGCTCTGCCCTGACGC

-continued

GTAACCTCAACACGTACATCGAAGCTGAAGGCCTGGCCAAGAAGCACAAGGTCGCCACCACCGGTGA

TGACGCCCGTGAAGGCTTGACCGCGATCATCTCGGTGAAAGTGCCGGATCCAAAGTTCAGCTCGCAG

ACTAAAGACAAGCTGGTGTCTTCCGAAGTGAAGACCGCTGTTGAACAGGAAATGGGCAAGTTCTTCT

CCGACTTCCTGCTGGAACACCCGAACGAAGCCAAGTTGATTGTCGGCAAGATGATCGACGCAGCCCG

TGCTCGTGAAGCTGCACGTAAAGCCCGTGAGATGACCCGTCGTAAAGGCGCGTTGGACATCGCGGGC

TTGCCGGGCAAGCTGGCTGACTGCCAGGAAAAAGACCCTGCTCTGTCCGAACTGTACCTGGTGGAAG

GTGACTCTGCTGGCGGCTCCGCCAAGCAGGGTCGCAACCGTCGTACCCAAGCCATCCTGCCGTTGAA

AGGTAAAATCCTCAACGTCGAGAAAGCCCGTTTTGACAAGATGATCTCTTCGCAAGAAGTCGGCACC

TTGATCACTGCGCTGGGCTGTGGCATCGGCCGCGAAGAGTACAACATCGACAAACTGCGCTATCACA

ACATCATCATCATGACCGATGCTGACGTTGACGGTTCGCACATCCGTACCCTGCTGCTGACCTTCTTCT

TCCGTCAGTTGCCGGAGCTGATCGAGCGTGGCTACATCTACATCGCCCAGCCACCGTTGTACAAAGTG

AAAAAGGGCAAGCAAGAGCAGTACATCAAAGACGACGAGGCCATGGAAGAGTACATGACCCAGTCG

GCTCTTGAAGATGCCAGCCTGCACTTGAACGAAGATGCCCCTGGCATCTCCGGTGAGGCACTGGAGC

GTCTGGTGTACGACTTCCGCATGGTGATGAAGACCCTCAAGCGTTTGTCGCGCCTGTACCCTCAGGAG

CTGACCGAGCACTTCATCTACCTGCCGGCTGTAAGCCTTGAGCAGTTGGGTGACCACGCTGCCATGCA

GGACTGGATGGCCAAGTTTGAAGAGCGTCTGCGTCTGGTTGAGAAATCGGGCCTGGTCTACAAAGCC

AGCCTGCGTGAAGACCGTGAGCGTAATGTCTGGTTGCCAGAGGTCGAACTGATCTCCCACGGCCACT

CGACGTTCATCACCTTCAACCGCGACTTCTTCGGCAGCAACGATTACAAAACCGTTGTGACCCTGGGC

GCTCAACTGAGCACCCTGCTGGATGAAGGCGCCTATATCCAGCGTGGCGAACGTCGCAAGCAAGTGA

CCGAGTTCAAAGAAGCACTGGACTGGTTGATGGCTGAAAGCACCAAGCGTCACACCATCCAGCGCTA

CAAAGGACTGGGTGAAATGAACCCGGATCAGCTCTGGGAAACCACGATGGACCCAAGCGTGCGTCGC

ATGCTGAAAGTCACCATCGAAGACGCGATCGGCGCCGATCAGATCTTCAACACCTTGATGGGCGATG

CTGTAGAACCACGTCGTGAATTCATCGAGAGCAACGCACTGGCAGTGTCCAACCTGGATTTCTGA

69
DP53 Isoleucine--tRNA ligase
ATGACCGACTACAAAGCCACGCTAAACCTCCCGGACACCGCCTTCCCAATGAAGGCCGGCCTGCC

ACAGCGCGAACCGCAAATTTTGCAGCGCTGGGACAGCATTGGCCTGTACGGGAAGTTGCGCGAGATT

GGCAAGGATCGTCCGAAGTTCGTACTTCACGACGGTCCTCCGTACGCCAACGGCACTATCCATATCGG

TCATGCGCTGAACAAGATTCTGAAAGACATGATCATCCGCTCCAAGACCCTGTCGGGTTTTGACGCGC

CGTATGTGCCGGGCTGGGATTGCCATGGTTTGCCGATTGAACACAAGGTCGAAGTGACCCACGGTAA

AAACCTGAGCGCGGATAAAACCCGCGAGCTGTGCCGTGCCTACGCCACCGAGCAGATCGAGGGGCA

GAAGTCCGAGTTCATCCGTCTGGGTGTGCTGGGTGATTTCGCCAACCCGTACAAGACCATGGACTTCA

AAAACGAAGCCGGTGAAATCCGTGCTTTGGCTGAGATCGTCAAGGGCGGTTTTGTGTTCAAGGGCCT

CAAGCCGGTGAACTGGTGCTTCGATTGCGGTTCGGCCCTGGCTGAAGCTGAAGTTGAATACCAGGAC

AAGAAGTCTGCGGCCATCGACGTTGCCTTCCCGGTTGCCGACGAGGCCAAGCTGGCCGAGGCCTTTG

GTCTGGCGGCACTGAGCAAACCTGCTTCGATCGTGATCTGGACCACCACCCCGTGGACCATTCCGGCC

AACCAGGCGCTTAACGTACACCCGGAATTCACCTACGCGCTGGTCGACGTGGGCGACAAGTTGCTGG

TACTGGCTGAAGAACTGGTCGAATCGAGTCTGGCGCGTTACAACCTGCAGGGTTCGGTCATCGCCACC

ACCACTGGCTCAGCGCTTGAACTAATCAACTTCCGTCACCCGTTCTATGACCGTCTGTCGCCTGTTTAT

CTGGCCGACTACGTTGAGCTGGGTGCTGGCACTGGTGTGGTTCACTCGGCTCCAGCCTACGGCGTAGA

CGACTTCGTGACCTGCAAAGCCTATGGCATGGTCAACGACGACATCATCAACCCGGTGCAAAGCAAT

GGCGTTTACGTGCCGTCGCTGGAGTTCTTCGGTGGCCAGTTCATCTGGAAGGCCAACCAGAACATCAT

-continued

CGACAAGCTGATCGAAGTCGGTTCGCTGATGTTCACCGAGACCATCAGCCACAGCTATATGCACTGCT

GGCGCCACAAGACGCCGCTGATCTACCGTGCCACCGCCCAGTGGTTTATCGGTATGGACAAGCAGCC

GACTGATGGCGATACCTTGCGCACCCGTGCGCTGCAAGCGATCGAAGACACCCAGTTCGTTCCGGCCT

GGGGTCAGGCGCGCCTGCACTCGATGATCGCCAACCGCCCGGACTGGTGCATCTCGCGTCAACGCAA

CTGGGGCGTGCCGATCCCGTTTTTCCTGAACAAGGAAAGCGGCGAGCTGCACCCGCGCACCGTCGAA

ATGATGGAAGAAGTGGCCAAGCGCGTTGAAGTCGAAGGCATCGAGGCGTGGTTCAAGCTGGATGCTG

CCGAGCTGCTGGGCGACGAAGCGCCGCTGTACGACAAGATCAGCGATACCCTCGACGTCTGGTTCGA

TTCGGGCACCACGCACTGGCATGTCCTTCGCGGTTCGCACCCGATGGGTCATGAAACCGGCCCACGCG

CTGATCTCTACCTTGAAGGCTCCGACCAGCACCGTGGCTGGTTCCACTCGTCGTTGCTGACCGGTTGC

GCCATCGACAACCACGCGCCGTACCGCGAGCTGCTGACCCACGGTTTTACCGTGGACGAAGCGGGCC

GCAAGATGTCCAAGTCGCTGGGCAACGTGATTGCACCGCAAAAGGTCAACGACACCCTGGGCGCCGA

CATCATGCGTCTGTGGGTTGCTTCGACCGACTACTCGGGCGAAATCGCGGTTTCCGACCAGATCCTGC

AGCGCAGTGCGGACGCCTACCGACGTATCCGCAATACCGCACGCTTCCTGCTGTCGAACCTGACCGGT

TTCAATCCAGCCACCGACATCCTGCCTGCCGAAGAAATGCTGGCACTGGACCGCTGGGCGGTGGATC

GTGCGTTGCTGCTGCAACGTGAGCTGGAGCTGCATTACGGCGAATACCGTTTCTGGAACGTGTACTCC

AAGGTGCACAACTTCTGCGTTCAGGAGCTGGGCGGTTTCTATCTCGACATCATCAAGGACCGCCAGTA

CACCACCGGCGCCAACAGCAAGGCTCGCCGTTCGTGCCAGACCGCGCTGTTCCACATCTCTGAAGCG

CTGGTGCGCTGGATCGCTCCGATCCTGGCGTTCACCGCTGATGAGTTGTGGCAGTACCTGCCGGGCGA

GCGCAACGAATCGGTCATGCTCAACACCTGGTACGAAGGCCTGACTGAACTGCCGGAAGGCACCGAA

CTGGATCGCGCCTACTGGGAGCGAATCATGGCGGTCAAGGTTGCGGTCAACAAGGAAATGGAAAACT

TGCGCGCAGCCAAGGCCATTGGCGGTAACTTGCAAGCAGAAGTGACCTTGTTCGCCGAAGATCAGCT

GGCTGCTGATTTGTCCAAGTTGAGCAACGAACTGCGTTTCGTGTTGATCACCTCCACTGCCAGCGTTG

CGCCTTTTGCGCAGGCTCCAGCAGATGCCGTGGTTACCGAAGTGGCTGGCCTCAAACTCAAGGTGGTC

AAGTCGGCCCATGCCAAGTGCGCCCGTTGCTGGCACTGCCGTGAAGACGTCGGCGTTAACCCCGAGC

ACCCTGAAATCTGCGGTCGTTGTGTAGACAATATCAGCGGCGCTGGTGAGGTACGTCACTATGCCTAA

70
DP53 NADH-quinone oxidoreductase subunit C/D
ATGACTGCAGGCTCCGCTCTGTACATCCCGCCTTACAAGGCTGACGACCAAGATGTGGTTGTCGAA

CTCAATACCCGTTTTGGCCCTGAGGCGTTCACCGCCCAGGCCACGCGCACCGGCATGCCGGTGCTTTG

GGTTAGCCGCGCAAAACTGGTCGAAGTACTGACCTTCCTGCGCAACCTGCCAAAACCCTACGTCATGC

TCTATGACCTGCACGGTGTGGACGAACGTCTGCGTACCAAGCGTCAGGGCCTGCCATCGGGTGCAGA

CTTCACCGTCTTCTACCACCTGATGTCGCTGGAACGTAACAGCGACGTCATGATCAAGGTGGCCCTGT

CTGAAAAAGACCTGAGTGTCCCTACCGTGACCGGTATCTGGCCGAACGCCAACTGGTACGAGCGTGA

AGTCTGGGACATGTTCGGCATCGATTTCAAAGGCCACCCGCACCTGTCGCGCATCATGATGCCGCCGA

CCTGGGAAGGTCACCCGCTGCGCAAGGACTTCCCGGCCCGTGCCACAGAGTTCGATCCGTACAGCCT

GACCCTGGCCAAGGTGCAGCTGGAAGAGGAAGCCGCGCGCTTCCGCCCGGAAGACTGGGGCATGAA

ACGCTCCGGTGAAAACGAGGACTACATGTTCCTCAACCTGGGCCCTAACCACCCTTCGGCTCACGGTG

CCTTCCGCATCATCCTGCAGCTGGACGGTGAAGAGATCGTCGACTGCGTGCCTGACGTCGGTTACCAC

CACCGTGGCGCCGAGAAAATGGCCGAACGCCAGTCCTGGCACAGTTTCATCCCGTACACCGACCGGA

TCGATTACCTCGGCGGAGTGATGAACAACCTGCCGTACGTGCTCTCGGTCGAGAAGCTGGCCGGTATC

AAAGTGCCGGATCGGGTCGACACCATCCGCATCATGATGGCCGAATTCTTCCGTATCACCAGCCACCT

-continued

GCTGTTCCTGGGTACCTATATCCAGGACGTGGGCGCCATGACCCCGGTGTTCTTCACGTTCACCGACC

GTCAGCGCGCTTACAAGGTGATCGAGGCCATCACCGGTTTCCGTCTGCACCCGGCCTGGTACCGCATC

GGCGGCGTTGCCCACGACCTGCCGAACGGCTGGGATCGCCTGGTCAAGGAATTCATCGACTGGATGC

CCAAGCGTCTGGACGAGTACCAGAAAGCCGCTCTGGACAACAGCATCCTGCGTGGTCGTACCATCGG

CGTTGCCGCCTACAACACCAAAGAGGCCCTGGAATGGGGCGTCACCGGTGCCGGCCTGCGCTCCACC

GGTTGTGACTTCGATATCCGCAAGGCGCGCCCGTATTCCGGCTACGAGAACTTCGAATTCGAAGTCCC

GCTGGCAGCCAACGGCGATGCCTACGATCGTTGCATCGTGCGCGTCGAAGAAATGCGCCAGAGCCTG

AAAATCATCGAGCAGTGCATGCGCAACATGCCGGCCGGCCCGTACAAGGCGGATCACCCGCTGACCA

CGCCGCCGCCTAAAGAACGCACGCTGCAGCATATCGAGACCTTGATCACGCACTTCCTGCAAGTTTCG

TGGGGCCCGGTGATGCCGGCCAACGAATCCTTCCAGATGATCGAAGCGACCAAGGGCATCAACAGTT

ATTACCTGACGAGCGATGGCGGCACCATGAGCTACCGCACCCGGATTCGCACCCCAAGCTTCCCGCA

CCTGCAACAGATCCCTTCGGTGATCAAAGGTGAAATGGTCGCGGACTTGATTGCGTACCTGGGTAGTA

TCGATTTCGTTATGGCCGACGTGGACCGCTAA

71
DP53 Protein RecA
ATGGACGACAACAAGAAGAAAGCCTTGGCTGCGGCCCTGGGTCAGATCGAACGTCAATTCGGCAA

GGGTGCCGTGATGCTGATGGGCGACCAGGAGCGTCAGGCAGTCCCGGCGATCTCCACCGGCTCCCTG

GGTCTGGACATCGCACTGGGCATTGGCGGTCTGCCAAAAGGCCGTATTGTTGAAATCTACGGCCCTGA

GTCGTCGGGTAAAACCACACTGACCCTGTCCGTGATTGCCCAGGCGCAAAAGGCCGGTGCTACCTGC

GCCTTCGTCGATGCCGAGCACGCCCTTGATCCTGAGTACGCTGCCAAACTGGGCGTAAACGTTGATGA

CCTGCTGGTTTCACAGCCTGACACCGGCGAACAGGCACTGGAAATCACCGATATGCTGGTGCGTTCCA

ATGCGGTTGACGTGATCATCATCGACTCCGTTGCTGCACTGACGCCAAAAGCTGAAATCGAAGGCGA

CATGGGCGATACCCACGTTGGCCTGCAAGCCCGTCTGATGTCGCAAGCGCTGCGTAAAATCACCGGT

AACATCAAGAACGCCAACTGCCTGGTTATCTTCATCAACCAGATCCGCATGAAAATCGGCGTGATGTT

CGGCAGCCCTGAAACCACCACCGGTGGTAACGCACTGAAGTTCTACGCTTCGGTACGTCTGGATATCC

GCCGCACCGGCGCCGTAAAAGAAGGCGATGTGGTGGTGGGTAGCGAAACCCGCGTGAAAGTGGTCA

AGAACAAGGTGGCACCACCGTTCCGTCAGGCTGAATTCCAGATCCTGTACGGCAAGGGTATCTACCT

GAACGGTGAAATGATTGACCTGGGCGTACTGCATGGCTTTGTTGAAAAAGCTGGCGCCTGGTACAGC

TACAACGGCAGCAAAATCGGTCAGGGCAAGGCCAACTCCGCCAAGTTCCTGGACGATAACCCGGACA

TCAAGGATGCGCTGGAGAAGCAGCTGCGTGAGAAGTTGCTCGGGCCAAAAACCGATGCCGAACTGGC

AGCGACGGACTGCAATGGACCTGCTCGCGCGACGCGAGCACGGTCGAGTCGAGCTGACGCGCAAGTT

GCGTCAGCGCGGCGCTTGCCCCGACATGATCGACGCTGCCCTTGA

72
DP53 RNA polymerase sigma factor RpoD
ATGTCCGGAAAAGCGCAACAGCAGTCTCGTATCAAAGAGTTGATCACCCTCGGCCGTGAGCAGAA

GTATCTGACTTACGCAGAGGTCAACGACCACCTGCCCGAAGATATTTCAGATCCGGAGCAAGTGGAA

GACATCATCCGCATGATTAATGACATGGGGATCCCCGTACACGAGAGTGCTCCGGATGCGGACGCCC

TTATGTTGGCCGATGCCGACACCGACGAAGCAGCAGCTGAAGAAGCGGCTGCAGCGTTGGCGGCAGT

AGAGACCGACATTGGTCGTACTACCGACCCTGTGCGCATGTATATGCGTGAAATGGGCACGGTAGAA

CTGCTGACACGTGAAGGCGAAATCGAAATCGCCAAGCGTATCGAAGAAGGCATCCGTGAAGTGATGG

GCGCAATCGCGCACTTCCCTGGCACGGTTGACCATATTCTCTCCGAGTACACTCGCGTCACCACCGAA

GGTGGCCGCCTGTCCGACGTTCTGAGCGGTTATATCGACCCGGACGACGGTATTGCGCCGCCCGCAGC

CGAAGTACCTCCTCCTGTCGACACCAAGGTGAAAGCCGAAGGTGATGACGAAGAGGACGACAAGGA

-continued

AGATTCCGGCGAAGACGAGGAAGAGGTCGAAAGCGGCCCTGATCCGATCATCGCGGCCCAGCGCTTT

GGCGCTGTTTTCGATCAGATGGAAATCGCTCGCAAGGCCCTGAAAAAGCACGGTCGCGGCAGCAAGC

AGGCAATTGCCGAGCTGGTTGCACTGGCTGAGCTGTTCATGCCGATCAAACTGGTTCCGAAGCAATTC

GAAGGCCTGGTTGAGCGTGTTCGCAGCGCCCTGGAGCGTCTGCGTGCACAAGAGCGCGCAATCATGC

AGCTGTGTGTACGTGATGCACGCATGCCGCGCACCGATTTCCTGCGTCTGTTCCCGGGCAACGAAGTC

GACGAAAGCTGGAGCGATGCGCTGGCCAAAGGCAAAAGCAAATATGCTGAAGCCATTGGTCGCCTGC

AACCGGACATCATCCGTTGCCAGCAAAAGCTCTCTGCTCTGGAAGCAGAAACCGGCTTGAAGATTGC

CGAGATCAAGGACATCAACCGTCGCATGTCGATCGGCGAGGCCAAGGCCCGCCGCGCGAAGAAAGA

AATGGTTGAAGCCAACTTGCGTCTGGTGATCTCCATCGCCAAGAAGTACACCAACCGTGGCCTGCAGT

TCCTCGATCTGATCCAGGAAGGCAACATCGGCTTGATGAAAGCGGTAGACAAGTTTGAATACCGCCG

CGGCTACAAATTCTCGACTTATGCCACCTGGTGGATCCGTCAGGCGATCACTCGCTCGATCGCCGACC

AGGCCCGCACCATCCGTATTCCGGTGCACATGATCGAGACGATCAACAAGCTCAACCGTATTTCCCGT

CAGATGTTGCAGGAAATGGGCCGTGAACCGACCCCGGAAGAGCTGGGCGAACGCATGGAAATGCCT

GAGGATAAAATCCGCAAGGTATTGAAGATCGCTAAAGAGCCGATCTCCATGGAAACCCCGATCGGTG

ATGACGAAGACTCCCATCTGGGTGACTTCATCGAAGACTCGACCATGCAGTCGCCAATCGATGTTGCT

ACCGTTGAGAGCCTTAAAGAAGCGACACGCGACGTACTCGGCGGCCTCACAGCCCGTGAAGCCAAGG

TACTGCGCATGCGTTTCGGTATCGACATGAATACCGACCACACCCTTGAGGAGGTTGGTAAACAGTTC

GACGTTACCCGTGAGCGGATTCGTCAGATCGAAGCCAAGGCGCTGCGCAAGCTGCGCCACCCGACGA

GAAGCGAGCATTTGCGCTCCTTCCTCGACGAGTGA

73
DP53 DNA-directed RNA polymerase subunit beta
ATGGCTTACTCATATACTGAGAAAAAACGTATCCGCAAGGACTTTAGCAAGTTGCCGGACGTCATG

GATGTGCCGTATCTCTTGGCAATCCAGCTGGATTCGTATCGTGAATTCTTGCAGGCGGGAGCGACTAA

AGATCAGTTCCGCGACGTGGGCCTGCATGCGGCCTTCAAATCCGTTTTCCCGATCATCAGCTACTCCG

GCAATGCTGCGCTGGAGTACGTCGGTTATCGCTTGGGCGAACCGGCATTTGATGTCAAAGAATGCGT

GTTGCGTGGCGTAACGTACGCCGTACCTTTGCGGGTAAAAGTTCGTTTGATCATTTTCGACAAAGAAT

CGTCGAACAAAGCGATCAAGGACATCAAAGAGCAAGAAGTCTACATGGGTGAAATCCCCCTGATGAC

TGAAAACGGTACCTTCGTAATCAACGGTACCGAGCGTGTAATTGTTTCCCAGCTGCACCGTTCCCCGG

GCGTGTTCTTTGCCACGACCGCGGCAAGACGCACAGCTCCGGTAAGCTGCTTTATTCCGCGCGTATCA

TTCCTTACCGTGGTTCGTGGCTCGACTTCGAGTTCGACCCGAAAGACTGCGTGTTCGTGCGTATTGAC

CGTCGTCGCAAGCTGCCTGCATCGGTATTGCTGCGCGCGCTGGGTTATACCACTGAGCAAGTGCTGGA

CGCGTTCTACACCACCAACGTGTTCCACGTTCAGGGTGAGAGCATCAGCCTGGAGCTGGTTCCACAGC

GTCTGCGCGGTGAAATCGCGGCCATCGACATTACCGATGACAAAGGCAAGGTGATTGTTGAGCAGGG

TCGTCGTATCACTGCTCGTCATATCAACCAGCTGGAAAAAGCCGGTGTCAAAGAGCTCGTTATGCCTC

TGGACTATGTCCTGGGTCGCACAACGGCCAAGGCTATCGTGCATCCGGCTACTGGCGAAATCATTGCT

GAGTGCAACACCGAGCTGACCACTGAAATCCTGGCAAAAGTTGCCAAGGGCCAGGTTGTTCGCATCG

AAACGTTGTACACCAACGATATCGACTGCGGTCCGTTCGTCTCCGACACGCTGAAGATCGACTCCACC

AGCAACCAACTGGAAGCGCTGGTCGAAATCTATCGCATGATGCGTCCAGGCGAGCCGCCAACCAAAG

ACGCTGCCGAGACTCTGTTCAACAACCTGTTCTTCAGCCCTGAGCGCTATGACCTGTCTGCGGTCGGC

CGGATGAAGTTCAACCGTCGTATCGGTCGTACCGAGATCGAAGGTTCGGGCGTGTTGTGCAAAGAAG

ACATCGTTGCCGTGCTGAAGACCCTGGTCGACATCCGTAACGGTAAAGGCATCGTCGATGACATCGA

-continued

CCACCTGGGTAACCGTCGTGTTCGCTGTGTAGGCGAAATGGCCGAGAACCAGTTCCGCGTTGGCCTGG

TACGTGTTGAGCGTGCGGTCAAAGAGCGTCTGTCGATGGCTGAAAGCGAAGGCCTGATGCCGCAAGA

CCTGATCAACGCCAAGCCTGTGGCTGCGGCGGTGAAAGAGTTCTTCGGTTCCAGCCAGCTGTCCCAGT

TCATGGACCAGAACAACCCTCTGTCCGAGATCACCCACAAGCGCCGTGTTTCTGCACTGGGCCCGGGC

GGTCTGACGCGTGAGCGTGCGGGCTTTGAAGTTCGTGACGTACACCCGACTCACTACGGCCGTGTTTG

CCCTATTGAGACGCCGGAAGGTCCGAACATCGGTCTGATCAACTCCCTGGCTGCCTATGCGCGCACCA

ACCAGTACGGCTTCCTCGAGAGCCCGTACCGTGTAGTGAAAGACGCACTGGTAACTGACGAGATCGT

TTTCCTGTCCGCCATCGAAGAAGCTGATCACGTGATCGCTCAGGCCTCGGCCACGATGAACGACAAG

AAAGTGCTGATCGACGAGCTGGTTGCTGTTCGTCACTTGAACGAATTCACCGTCAAGGCGCCGGAAG

ACGTCACCTTGATGGACGTTTCGCCGAAGCAGGTTGTTTCGGTTGCAGCGTCGCTGATCCCGTTCCTG

GAACACGATGACGCCAACCGTGCGTTGATGGGTTCCAACATGCAGCGTCAAGCTGTACCAACCCTGC

GCGCTGACAAGCCGCTGGTAGGTACCGGCATGGAGCGTAACGTAGCTCGTGACTCCGGCGTTTGCGT

CGTGGCTCGTCGTGGCGGCGTGATCGACTCTGTTGATGCCAGCCGTATCGTGGTTCGTGTTGCTGATG

ACGAAGTTGAAACTGGCGAAGCCGGTGTCGACATCTACAACCTGACCAAATACACCCGTTCCAACCA

GAACACTTGCATCAACCAGCGTCCGCTGGTGCGCAAGGGTGACCGTGTACAGCGTAGCGACATCATG

GCTGACGGCCCGTCCACCGATATGGGTGAACTGGCGCTGGGTCAAAACATGCGCATCGCGTTCATGG

CCTGGAACGGTTACAACTTCGAAGACTCCATCTGCTTGTCGGAACGAGTTGTTCAAGAAGACCGCTTT

ACCACGATCCACATTCAGGAACTGACCTGTGTGGCACGTGACACCAAGCTTGGGCCTGAAGAGATCA

CTGCAGACATCCCTAACGTGGGTGAAGCTGCACTGAACAAACTGGACGAAGCCGGTATCGTTTACGT

AGGTGCTGAAGTTGGCGCCGGCGACATTCTGGTAGGTAAGGTCACTCCGAAAGGCGAGACCCAGCTG

ACTCCGGAAGAGAAGCTGTTGCGTGCCATCTTCGGTGAAAAAGCCAGCGACGTTAAAGACACCTCCC

TGCGCGTACCTACCGGTACCAAAGGTACTGTTATCGACGTGCAGGTCTTCACCCGTGACGGCGTTGAG

CGTGATGCTCGTGCACTGTCGATCGAGAAGACCCAGCTGGACGAGATCCGCAAGGATCTGAACGAAG

AGTTCCGTATCGTTGAAGGCGCTACCTTCGAACGTCTGCGCTCTGCTCTGGTTGGCCGCATTGCCGAA

GGTGGTGCCGGTCTGAAGAAAGGTCAGGAAATCACCAATGAAATCCTGGACGGTCTTGAGCATGGTC

AGTGGTTCAAACTGCGCATGGCTGAAGATGCTCTGAACGAGCAGCTTGAAAAGGCTCAGGCTTACAT

CATCGATCGCCGTCGTCTGCTGGACGACAAGTTCGAAGACAAGAAGCGCAAACTGCAGCAGGGCGAT

GACCTGGCTCCAGGCGTGCTGAAAATCGTCAAGGTTTACCTGGCAATCCGCCGTCGCATCCAGCCGG

GTGACAAGATGGCCGGTCGTCACGGTAACAAGGGTGTGGTCTCCGTGATCATGCCGGTTGAAGACAT

GCCGTACGATGCCAATGGCACCCCGGTTGATGTGGTCCTCAACCCGTTGGGCGTACCTTCGCGTATGA

ACGTTGGTCAGATTCTCGAAACTCACCTGGGCCTCGCGGCCAAAGGTCTGGGCGAGAAGATCAACCT

CATGATTGAAGAACAACGCAAGGTCGCTGACCTGCGTAAGTTCCTGCATGAGATCTACAACGAAATT

GGCGGTCGTCAAGAAAGCCTGGATGACTTCTCCGATCAGGAAATCCTGGATCTGGCGAAGAACCTTC

GCGGCGGTGTGCCAATGGCTACCCCGGTGTTCGACGGTGCCAAGGAAAGCGAAATCAAGGCAATGCT

TCGTTTGGCAGACCTGCCAGACAGCGGCCAGATGGTGCTGACTGATGGTCGTACCGGCAACAAGTTC

GAGCGTCCGGTTACCGTTGGCTACATGTACATGCTGAAGCTGAACCACTTGGTAGACGACAAGATGC

ACGCTCGTTCTACCGGTTCTTACAGCCTGGTTACCCAGCAGCCGCTGGGTGGTAAGGCGCAGTTCGGT

GGTCAGCGTTTCGGGGAGATGGAGGTCTGGGCGCTGGAAGCCTACGGCGCGGCATACACTCTGCAAG

AAATGCTCACAGTGAAGTCGGACGATGTGAACGGCCGTACCAAGATGTACAAAAACATCGTGGACGG

CGATCACCGTATGGAGCCGGGCATGCCCGAGTCCTTCAACGTGTTGATCAAAGAAATTCGTTCCCTCG

GCATCGATATCGATCTGGAAACCGAATAA

-continued

74
DP9 Glycine--tRNA ligase beta subunit
ATGGCACATAATTATTTACTAGAAATTGGATTGGAAGAAATTCCGGCCCATGTTGTAACTCCAAGT

ATCAAACAGTTAGTACAAAAAGTAACAGCCTTCTTAAAAGAAAATCGCTTAACATACGACTCAATTG

ATCATTTTTCAACTCCTCGTCGTTTGGCAATTCGAATCAATGGGTTAGGCGACCAACAACCTGATATT

GAAGAAGATGCTAAAGGCCCTGCTCGTAAAATTGCTCAAGATGCTGATGGAAATTGGACTAAGGCTG

CAATTGGCTTTACACGTGGACAAGGTCTTACGGTTGACGATATTACTTTTAAAACAATCAAAGGTACG

GACTATGTGTACGTCCATAAGTTAATCAAAGGAAAGATGACTAAGGAAATCCTTACGGGGATAAAAG

AAGTTGTTGAATCAATTAATTTCCCAACAATGATGAAGTGGGCTAACTTTGATTTTAAATATGTACGC

CCAATTCGTTGGCTGGTTTCTATTCTAGATGAAGAAGTCCTTCCTTTTAGTATCTTAGACGTAACTGCG

GGACGCCGAACAGAAGGACATCGTTTCTTAGGTGAAGCTGTCGAACTGGCTAATGCTGAAGAATATG

AAGCAAAATTACACGATCAATTTGTGATTGTTGATGCCGACGAGCGTAAACAATTAATTTCAAACCA

AATTAAAGCAATTGCTGAAAGCAATCGTTGGAACGTTACCCCTAACCCAGGTCTTTTAGAAGAGGTTA

ACAATTTGGTTGAGTGGCCAACCGCTTTTAATGGGGGATTTGATGAAAAGTATTTAGCTATTCCAGAA

GAGGTATTGATAACATCAATGCGTGACCACCAACGCTTCTTCTTTGTCCGCGACCAAGCTGGAAAGCT

ATTGCCAAACTTCATCTCCGTACGAAATGGGAATGAAGAATTTATTGAAAATGTTGTTCGTGGAAATG

AAAAAGTTTTAACTGCACGTTTAGAAGACGCTGCTTTCTTCTACGAAGAAGATCAAAAACATGATATT

AATTATTATGTTGACCGACTTAAAAAGGTTAGTTTCCATGATAAGATTGGTTCAATGTACGAAAAAAT

GCAACGAGTTAATTCTATTGCTAAAGTTATTGGAAACACCTTAAATCTTAATCAAACGGAACTTGATG

ATATCGATCGCGCTACAATGATTTATAAATTTGATTTGGTAACTGGTATGGTTGGTGAGTTCTCAGAA

TTACAAGGAGTAATGGGTGAAAAATATGCTCAACTTAATGGTGAAAACCAAGCAGTAGCCCAAGCCA

TTCGCGAACATTACATGCCAAATAGCGCAGAAGGTGATTTGCCTGAAAGTGTAACGGGCGCGGTAGT

CGCATTAGCTGATAAGTTTGATAACATCTTTAGTTTTTTCTCAGCTGGTATGATTCCAAGTGGTTCAAA

CGATCCATATGCATTACGCCGACATGCATATGGAATTGTTAGAATCTTAAATAGCCGTGATTGGCAAT

TAGATTTAAATCAATTCAAATCACAATTTAAGACTGAATTAGCGGAGAATGGCACAGCGTTTGGTGTG

GATGTCGATCAAAACTTTGACCAAGTACTTAACTTCTTTAATGACCGTATTAAACAATTGCTTGATCA

TCAAAAGATTAGTCATGATATCGTTGAAACGGTGCTTACAGGTAATAATCATGATGTTACGGAAATTA

TCGAAGCTGCCCAAGTACTAGCAGATGCTAAAGCGAGCTCTACATTTAAAGATGATATTGAAGCTTTA

ACACGAGTTCAAAGAATTGCTACAAAGAATGAAGAAAGTGGAGAACTTAATGTAGATCCACAATTAT

TTAATAATGCTTCTGAAGGCGAACTTTTTGATCAAATTATTAAAATTGAAGCTGCAAATAATTTGACA

ATGAGCCAACTATTTGCTAAATTATGCGAGTTGACTCCTGCGATTAGCAAGTACTTTGACGCAACGAT

GGTCATGGACAAAGACGAAAATATTAAGTGTAATCGTTTGAATATGATGAGTCGGTTAGCTAATTTA

ATTCTAAAAATTGGGGATCTAACTAACGTACTTGTAAAATAA

75
DP9 Glutamine synthetase
ATGGCAAAGAAAAATTATTCGCAAGCAGATATTCGTCAGATGGCAAAGGATGAAAATGTACGTTT

TCTCCGATTAATGTTTACAGATCTTTTTGGAATAATTAAGAACGTTGAAGTACCAATTAGTCAATTGG

ACAAACTATTAGATAATAAATTGATGTTTGATGGTTCCTCAATTGACGGGTTTGTTCGGATTGAAGAA

AGTGACATGTATTTATACCCAGATCTTTCTACTTGGATGGTTTTCCCATGGGGAAGCGAACATGGCAA

GGTGGCTCGCATTATTTGTGAAGTATACTCAAATGATCGTAAACCATTCGTGGGTGATCCACGTAACA

ATTTAATTCGAGTACTCCAAGAGATGAAGGATGCAGGATTTACTGATTTTAATATCGGACCTGAACCT

GAGTTTTTCTTGTTGAAATTAGATGAAAATGGTAAACCAACCACTAATTTAAATGATAAAGGTAGTTA

-continued

CTTTGATTTAGCTCCTGTTGATTTAGGTGAAAACTGCCGTCGTGATATTGTTTTGGAACTTGAAAATAT

GGGCTTTGATGTTGAAGCTTCTCATCATGAAGTTGCTCCAGGACAACACGAAATTGACTTTAAATACG

CCGATGCTTTGACCGCTGCCGATAACATTCAAACCTTTAAGTTGGTTGTTAAGACAGTTGCCCGTAAA

TATAACCTGCATGCTACATTTATGCCTAAACCTATGGATGGAATCAATGGTTCAGGGATGCATTTAAA

CATGTCACTTTTCAATAAGGAAGGCAATGCTTTCTATGACGAAAAGGGTGACTTACAACTTTCTCAAA

ATGCTTACTGGTTCCTTGGTGGACTATTGAAGCATGCTCGTAGTTATACGGCCGTATGTAACCCAATT

GTTAACTCGTACAAACGTTTAGTTCCTGGATATGAAGCTCCAGTATACGTTGCTTGGTCAGGTTCAAA

TCGTTCACCACTTATTCGCGTTCCTTCAAGTAAGGGACTCTCAACTCGTTTTGAAGTTCGAAGCGTCGA

TCCAGCTGCTAACCCATACTTAGCAATTGCATCAGTATTGGAAGCAGGCTTAGATGGCATTAGAAACA

AGATTGAACCAGAAGATTCCGTTGATCGTAATATCTATCGAATGAACATTCAAGAACGTAATGAAGA

GCATATTACAGATCTACCTTCAACATTACACAATGCTTTGAAGGAATTCCAAAATGATGATGTAATGC

GTAAGGCATTAGGAGATCACATTTTCCAAAGCTTCCTCGAAGCTAAGAAGTTAGAATGGGCTTCTTAC

CGTCAAGAAGTGACACAATGGGAACGTGATCAATATCTCGAAATGTTCTAG

76
DP9 DNA gyrase subunit B
TTGGCAGACGAAAAAGAAACGAAAGCAGAATTAGCCAGAGAATATGATGCGAGTCAAATTCAGG

TTTTAGAGGGGCTCGAAGCAGTTCGTAAACGCCCAGGAATGTATATTGGGTCGACTAGTTCTCAAGG

ACTACACCATTTGGTTTGGGAAATTATTGATAATGGTATTGATGAAGCTCTTGCAGGATTTGCAGACA

AAATTGATGTGATCGTTGAAAAAGACAATAGTATTACCGTCACTGATAATGGACGTGGGATTCCGGTT

GATATCCAAAAGAAAACTGGAAAACCAGCTTTAGAAACAGTCTTTACGGTCCTACATGCCGGAGGTA

AATTCGGCGGTGGCGGTTATAAAGTTTCTGGAGGATTGCATGGTGTGGGCGCATCCGTTGTAAATGCG

TTATCAACGGAATTAGATGCGCGCGTCATGAAGGACGGTAAAATCTATTACATTGATTTTGCGCTAGG

AAAAGTAAAAACACCGATGAAAACGATTGGTGATACTGAACATCCTGACGATCATGGAACTATTGTT

CATTTCGTTCCAGATCCAGATATTTTCCAAGAAACTACCACATACGACATTAATATCTTAAAAACACG

AATTCGTGAATTAGCCTTTTTGAACAAAGGTCTACGGATTACTTTGAAGGATATGCGTCCTGAAAAGC

CAACTGAAGACGACTTCTTGTATGAAGGTGGGATTCGCCACTACGTTGAATATCTAAACGAAGGCAA

AGAAGTAATTTTCCCTGAACCTATCTATGTTGAAGGGGTTACAAAAGGTATCACTGTTGAAGTAGCTA

TGCAATATATCGAAGGTTATCAAAGTAAATTGTTAACTTTTACTAACAATATTCATACTTACGAAGGC

GGTACCCACGAAGAAGGTTTCAAACGTGCTTTAACACGAGTTATTAACGATTACGCTAAAAACAACA

ATATTTTAAAAGAAAATGATGATAAATTGTCTGGTGATGATGTTCGAGAAGGTTTGACGGCAGTAGTC

AGCGTTAAGCATCCTGATCCTCAATTCGAAGGACAAACGAAAACAAAATTGGGTAACTCAGATGCTC

GGACAGCTGTTAACGAAGTGTTTGCTGAAACTTTCAATAAATTCTTATTGGAAAATCCTAAGGTTGCA

CGTCAAATTGTTGATAAGGGAATCTTGGCAGCAAAAGCAAGAGTCGCCGCTAAACGAGCTCGTGAAG

TTACGCGTAAGAAGAGTGGCCTAGAACTCAATAATCTTCCTGGTAAATTAGCTGATAATACTTCTAAG

GATCCTTCAATTAGTGAATTATTCATTGTCGAGGGTGATTCTGCCGGTGGTAGTGCTAAGTCGGGACG

TTCGCGTCTCACACAAGCTATTTTGCCAATTCGTGGGAAGATTTTGAACGTTGAAAAAGCCACTTTGG

ATCGGGTTTTGGCCAATGAAGAAATTCGTTCACTCTTTACAGCGCTCGGAACTGGATTTGGTGAGGAC

TTTGATGTAAGTAAAGCCAACTATCATAAATTGATTATCATGACCGATGCCGATGTCGATGGTGCTCA

TATTCGGACACTATTATTGACGCTGTTCTATCGTTACATGCGTCCAATGATTGATGCAGGATTTGTTTA

CATTGCTCAACCACCGCTCTACCAAGTACGTCAAGGTAAGATGATTCAATATATCGATTCTGATGAAG

AATTAGAAACAGTACTTGGACAATTGTCACCATCACCAAAACCTGTAATTCAACGTTATAAAGGTCTT

GGTGAAATGGATGCTGAGCAACTTTGGGAAACAACCATGAATCCAGAAAATCGACGCTTGTTACGAG

-continued

TTTCAGCCGAAGATGCTGATGCTGCAAGTGGTGATTTTGAAATGTTGATGGGTGACAAGGTTGAACCA

CGTCGTAAATTCATTGAAGAGAACGCTGTGTTTGTTAAAAACTTGGATATCTAA

77
DP9 Leucine--tRNA ligase
ATGGCTTATAATCATAAAGATATCGAACAGAAGTGGCAGCAATTCTGGAGCGACAATGAGACTTT

TAAGACGGTCGAAGATGCAGACAAACCCAAATATTATGCATTAGACATGTTCCCTTATCCATCAGGTC

AAGGACTCCATGTGGGCCATCCTGAAGGATATACAGCAACAGATATTATGTCACGAATGAAACGGAT

GCAAGGTTACAAAGTACTTCATCCAATGGGATGGGATGCTTTTGGTCTTCCAGCAGAACAATATGCGA

TGAAGACGGGTAACAATCCGCGTGATTTTACAGCTAAGAATATTCAAAACTTTAAGCGTCAAATCCA

ATCACTTGGTTTTTCTTATGACTGGTCGCGAGAAGTTAATACAACTGATCCAGCTTACTACAAGTGGA

CTCAATGGATTTTTGAGCAACTCTACAAGAAGGGCTTAGCTTATGAAAAAGAAACGCTGGTAAACTG

GGCTCCTGATTTAATGGGTGGAACGGTAGTTGCTAACGAAGAAGTTGTGGATGGTAAGACAGAACGT

GGTGGGTTCCCCGTTTATCGTAAACCAATGAAACAATGGATTCTTAAAATTACAGCTTACGCCGACCG

TTTGATTGACGATTTGGACCTGGTAGATTGGCCCGATAGTATTAAAGAAATGCAAAAAAACTGGATT

GGTCGTTCAGTGGGGGCTAGCGTCTTCTTTAATGTTGAAGATAGCGAAAAACAAATTGAAGTATTTAC

AACGCGTCCAGATACATTATTTGGCGCAACATACTTGGTAATTTCACCAGAACATGACCTCGTTGACC

AAATTACAACTCCAGAAAGTAAAGCTGCCGTTGAAGAATACAAGAAAGCTGTTGCAACTAAATCAGA

TCTTGAACGGACGGATTTGAGTAAAGATAAGACGGGAGTCTTTACGGGAGCATACGCGGTTAACCCT

GTTAATGGTAAGAAAATTCCAGTTTGGATTAGTGATTACGTATTGGCTTCATACGGAACTGGAGCAGT

GATGGCTGTTCCTGCTCATGATGGCCGTGACTACGAATTTGCTAAGAAATTCAAGATAGATATGGTGC

CAGTTTATGAAGGTGGCAATCTTGAAGATGGAGTATTGGACAGCGAAGGCGGGCTAATTAACTCTGG

ATTCCTAGATGGGATGGATAAGCAGACGGCTATTGATACCATGATTAGCTGGTTGGAAGAACATGGA

GTTGGTCATAAGAAGGTTAACTATCGTCTTCGTGACTGGGTCTTCTCTCGCCAACGCTACTGGGGTGA

ACCAATCCCTGTAATTCATTGGGAAGATGGAGAAACAACTTTGATTCCTGAAGATGAATTGCCATTGA

GACTCCCGGCTGCAACTGACATTCGTCCTTCCGGTACCGGAGAAAGCCCATTAGCTAACCTAGATGAT

TGGGTAAACGTAGTTGATGAAAATGGTCGTAAGGGTCGCCGGGAAACTAATACAATGCCACAATGGG

CGGGTAGTTCATGGTACTTCCTCCGTTACGTTGATCCTAAGAATGATCAAAAGATTGCTGACGAAGAT

TTACTTAAAGAATGGTTACCAGTCGACTTATATGTTGGTGGAGCTGAACATGCGGTACTTCATTTACT

TTATGCACGTTTCTGGCACAAAGTTTTATATGATCTAGGAGTTGTACCAACTAAGGAACCATTCCAAA

AATTGGTCAACCAAGGGATGATTCTCGGTAGCAATCATGAGAAGATGTCTAAGTCAAAAGGGAACGT

GGTTAATCCAGATGATATTGTTGAGCGCTTTGGAGCGGATACTTTACGATTATACGAAATGTTCATGG

GACCTCTGACAGAATCAGTCGCCTGGAGTGAAGATGGGCTTAACGGAAGTCGTAAGTGGATTGACCG

CGTCTGGCGCTTGATGATTGACGACGAAAACCAATTGCGTGATCATATTGTTACTGAAAATGATGGCA

GTTTGGATATGATTTATAACCAAACTGTTAAGAAGGTAACTGATGATTATGAAAACATGCGCTTTAAC

ACGGCTATTTCACAAATGATGGTCTTTGTTAATGAAGCATACAAGGCTGATAAACTTCCAGCAGTATA

TATGGAAGGATTAGTTAAGATGTTAGCTCCAATTATTCCGCACGTTGCTGAAGAACTTTGGAGTTTGC

TAGGTCACGAAGGTGGTATTTCATACGCTGAATGGCCAACATATGATGAAAGTAAGTTAGTAGAAGC

TACAGTTCAAGTCATTCTACAAGTTAATGGTAAAGTTCGGAGTAAAATTACCGTTGACAAGGATATCG

CCAAAGAAGAACTTGAAAAATTAGCGTTAGCTGATGCTAAGATTCAACAATGGACGGCAGATAAGAC

TGTTCGTAAGGTAATTGTTATTCCTAACAAGATTGTTAATATCGTAGTAGGCTAA

78
DP9 Glucose-6-phosphate isomerase

-continued

ATGGCACATATTTCATTTGACAGTTCTAATGTTGCAGATTTTGTACATGAAAACGAACTTGCAGAA
ATCCAACCACTTGTTACAGCTGCTGATCAGATTTTACGTGATGGCTCTGGCGCTGGTAGTGATTTCCGT
GGATGGATCGATTTACCATCAAATTATGATAAGGACGAATTTGCCCGTATCAAGAAAGCCGCTGATA
AGATCCGCAATGACTCAGAAGTATTCGTTGCTATCGGTATTGGTGGTTCATATTTGGGTGCTCGTGCA
GCCATTGATTTCTTGAACAACACTTTCTACAATCTTCTTACTAAAGAACAACGTAATGGTGCTCCTCA
AGTAATCTTCGCTGGTAACTCAATTAGTTCAACTTACCTTGCTGACGTATTGAACTTAATCGGGGACC
GTGACTTCTCAATTAACGTAATTTCTAAGTCAGGTACAACTACAGAACCAGCTATTGCATTCCGTGTT
CTTAAAGAAAAACTAATCAAGAAGTACGGTGAAGAAGAAGCTAAGAAACGTATCTATGCAACAACT
GACCGTGCTAAAGGCGCCCTAAAGACAGAAGCTGATGCAGAAAACTATGAAGAATTCGTAGTTCCTG
ATGACATTGGTGGTCGTTTCTCTGTTCTTTCAGCTGTTGGTTTATTACCAATCGCGGTTGCCGGTGGCG
ATATTGACCAATTGATGAAGGGTGCTGAAGATGCAAGCAACGAATACAAGGATGCTGATGTTACAAA
GAACGAAGCATACAAGTACGCTGCTTTACGTAACATCCTTTATCGTAAGGGCTACACAACAGAACTTC
TTGAAAACTACGAACCAACACTTCAATACTTCGGCGAATGGTGGAAGCAATTGATGGGTGAATCAGA
AGGTAAAGATCAAAAGGGTATCTACCCATCTTCTGCTAACTTCTCAACTGACTTACATTCACTAGGAC
AATACATCCAAGAAGGTCGTCGCAATTTAATGGAAACAGTTATCAATGTTGAAAAGCCTAACCATGA
CATCGACATTCCTAAGGCTGACCAAGACCTTGATGGATTACGTTATCTCGAAGGTCGCACAATGGACG
AAGTTAACAAGAAAGCTTACCAAGGTGTAACTCTTGCTCATAACGACGGTGGTGTTCCAGTTATGACG
GTTAACATTCCTGATCAAACAGCTTACACATTAGGCTATATGATTTACTTCTTCGAAGCAGCTGTTGCT
GTATCTGGTTACTTGAACGGAATTAATCCATTCAACCAACCAGGTGTTGAAGCATACAAGTCAAATAT
GTTTGCATTACTTGGTAAACCAGGTTATGAAGATAAGACAGCTGAATTAAACGCTCGTCTATAA

79
DP9 Phosphoglucomutase

ATGAGTTGGGAAGATTCTGTCAAAGAATGGCAAGATTATGCAGATTTAGATTTTAATTTAAAAAAA
GAATTAGCAACTTTAGCTGAAGATAAAGATGCTTTAAAAGAAGCCTTTTATGCTCCAATGGAATTTGG
TACAGCAGGAATGCGTGGCGTAATGGGCCCTGGTATCAACCGGATGAATATCTATACGGTTCGTCAA
GCAACAGAAGGTTTAGCTAATTTTATGGATACCTTAGATTTTACTGATAAGAAACGGGGAGTGGCGA
TCAGTTTTGATTCCCGCTATCACTCACAAGAGTTTGCTTTAGCAGCAGCTGGTGTTTTAGGTAAGCATG
GTATTCCAAGTTTTGTTTTTGATAGTATGCGTCCCACTCCAGAATTATCATATACAGTACGTGAGTTAA
ACACTTATGCTGGAATCATGATTACTGCTAGTCATAATCCTAAACAATATAATGGATATAAGATTTAT
GGTCCTGATGGCGGACAAATGCCACCAATGGAATCTGATAAGATTACAGAATATATTCGCCAAGTAA
CTGACATCTTTGGTGTTGAAGCTCTTACTCAAAGTGAATTAAGAGCTAAGGGCTTAATGACCATTATT
GGTGAAGACATTGACCTCAAGTATCTTGAGGAAGTTAAGACGGTATCAATTAATCATGAACTAATCC
AGCGCTTTGGTGCAGACATGAAGTTGATCTACTCACCATTACATGGTACTGGAAAAGTAGTTGGTGGA
CGTGCGTTAGAAAATGCTGGTTTTAAGGATTACACTATGGTCCCTGAACAAGCAATTGCTGACCCAGA
ATTTATTACAACGCCATTCCCTAACCCAGAATTCCCACAAACTTTTGATTTGGCTATTGAATTAGGTAA
AAAGCAAGATGCTGACCTTTTGATTGCCACTGATCCGGATGCCGATCGTTTGGGAGCTGCCGTTCGTT
TACCAAATGGTGACTACAAATTATTGACAGGGAACCAAATTGCAGCCTTGATGTTAGAATACATCTTA
ACTGCGCATGATGCAGCAGGTGACTTGCCAGGTAACGCAGCTGCCGTTAAGTCAATTGTTTCTAGTGA
ACTAGCAACCAGAATTGCCGAAGCCCATCATGTAGAAATGATTAACGTTCTAACTGGGTTTAAGTAC
ATTGCTGACCAAATTAAACATTACGAAGAAAATGGCGACCATACCTTTATGTTTGGTTTCGAAGAAAG
TTATGGCTATCTTGTTCGGCCATTTGTTCGCGATAAAGATGCCATCCAAGGAATTGTCCTATTGGCTGA
AATTGCTGCTTATTATCGTAGTAAGGGGCAAACCTTATATGACGGTCTTCAAAACTTATTTACTACTTA

-continued

CGGATATCATGAAGAAAAGACCATTTCAAAAGATTTCCCTGGAGTTGACGGTAAAGAAAAAATGGCT

GCCATTATGGAAAAGGTTCGTGAAGAACGCCCAAGTCAATTTGATCAGTACAAGGTATTAGAAACTG

AAGACTTCTTAGCTCAAACTAAGTATGAAGCAGATGGATCTACCCAAGCTATCAAATTACCAAAAGC

GGATGTTTTGAAATTTACATTAGATGATGGTACTTGGATTGCAATTCGTCCTTCTGGAACAGAACCAA

AAATTAAATTCTATATTGGTACAGTTGGCGAAGATGAAAAAGATGCTTTGAATAAGATTGATGTTTTT

GAAACAGCTATTAATGAACTTATAAAATAA

80
DP9 2-oxoglutarate carboxylase small subunit
ATGCACCGTATTTTAATTGCCAACCGAGGCGAAATTGCGACCCGAATTATTCGGCAACGCATGAA

CTCGGAAAAACAGCTGTAGCAATTTATGCTAAAGCGGATGAATTTTCTATGCATCGTTTTAAAGCAGA

TGAAGCTTACCAAGTTGGTGAAGATAGTGATCCAATTGGAGCATATTTAAATATTGATGACATTATTC

GTATTGCAAAAGAAAATAATATTGATGCAATTCACCCCGGCTATGGATTTTTGTCGGAAAATGCTGTA

TTTGCGCGAGCAGTTGAAGCAGCTGGGATTAAGTTCATTGGACCTCGACCCGAATTACTAGAAATGTT

TGGTGATAAATTACAAGCTAAAAATGCAGCCATTAAGGCCGGTGTACCAACTATTCCGGGAACGGAA

AAACCAGTTAAAGATGTCGATGACGCGCTAAATTTTGCAGAGCAATTTGGCTATCCTATATTTGTTAA

GTCAGCGGCAGGTGGCGGCGGAAAAGGGATGCGGATTGTACATCATCAACAAGAGATGCGCGAAGC

ATTTAAGATGGCTCAGTCAGAAGCTTCTTCGTCTTTTGGTGACGATGAAATTTACTTAGAACGTTACTT

AGTTGATCCAATCCATATTGAGGTTCAAGTAGTTGCGGATGAACACGGTGAGATGGTTCATTTGTATG

AACGAAATTCATCGATTCAGCGACGCCATCAAAAAATCATTGAATTTGCTCCAGCAGTGGGAATTTCT

GCCACCGTCCGTGATCAAATAAGAAAAGCTGCTTTAAAATTATTGAAGTCGGTCAATTATAGTAACGC

TGCAACCATTGAGTTTTTGGTAGAAGGTAATCAATTTTACTTTATGGAAGTGAATCCACGAATTCAGG

TTGAACATACAGTTACCGAAGAAGTCACGGGAATCGATATTGTGCAAACCCAAATTAAGGTTGCTGA

AGGTCAAAGATTACACGAAGAAATCGGTGTTCCTCAACAAGCCCAAATTGAAGCTGTGGGAGTGGCA

ATTCAAGCCCGAATTACCACTGAAGATCCAATGAATAACTTTATTCCAGATGTCGGTAGAATCCAGAC

GTATCGTTCACCTGGTGGAACAGGTGTGAGATTGGATGCTGGAAATGCCTTTGCTGGAGCCATTGTAA

CTCCGCATTATGATTCACTTCTGACCAAGGCAATTGTCCATGCGCCAACCTTTGACGAAGCCTTGGTA

AAGATGGATCGAGTGCTCAATGAATTTGTAATTGCTGGGGTTAAAACTAATATTCCATTTTTAAAGAA

ATTAATTCATCATCCTATTTTTAGATCGGAATTAGCTCCGACAACCTTTGTGGATGAGACACCAGAAC

TCTTTGATTTAAAAGCTGAAACTCCGGTAGTTACTCAACTTTTGAGTTACATTGCTAATACTACTATCA

ATGGTTATCCAGGCTTAGAAAAGCAGAATCCAGTAGTGTTAACTCGGCCAGTCCGTCCACATTTTGAA

GCACAAGTACCGCATGAAAATGCGAAACAGATCTTGGATAGTAAGGGACCTGATGCCATGATCAATT

GGCTGTTAAAACAAAAGCAGGTCTTGCTAACCGATACGACCATGCGGGATGCCCATCAATCATTATTT

GCTACGCGAATGCGGACCAAAGACATGGTAGAAATTGCCGATCAAGTCCAGAAAGGTCTGCCTAACC

TATTTTCAGCTGAAGTTTGGGGCGGTGCGACCTTTGATGTTGCTTATCGGTTCCTAGGTGAGGATCCAT

GGGAAAGACTCCAACAATTGCGGGCTAAAATGCCAAATACGATGCTCCAAATGCTTTTACGTGGGTC

AAATGCAGTAGGGTATCAAAATTATCCAGACAACGCCATTGACGAATTTATTCGATTGGCTGCCAAA

AATGGAATTGATGTTTTCCGAATCTTTGATTCTCTTAATTGGGTGCCACAGCTTGAAGAATCTATCCAA

CGGGTGCGTGATAATGGAAAAGTGGCTGAAGCAGCCATGGCATATACTGGCGATATTTTAGATACTA

ATCGTACTAAATATAATTTGAAATATTATGTGGATTTGGCTCAAGAACTCCAAGCAGCAGGTGCTCAT

ATTATTGGAATCAAAGATATGTCAGGAATTTTAAAACCACAAGCTGCTTATGCATTAATTTCAGAGTT

AAAAAATCATCTGGATGTGCCAATTCATTTGCATACGCACGATACTACAGGCAACGGCATTTTCTTAT

-continued
ATTCTGAAGCAATACGAGCTGGAGTTGATGTGGTCGACGTTGCCACTTCTGCGCTAGCGGGAACGACT

TCTCAGCCTTCAATGCAGTCTCTTTACTATGCGTTGTCTAATAACCAGCGCCAACCAGATTTAGATATT

CAAAAAGCAGAAAAACTAGATGAATATTGGGGCGGAATTCGACCATATTACGAAGGATTTGGCACCC

AATTAAATGGACCACAAACTGAAATTTATCGAATTGAAATGCCTGGTGGACAGTATACCAACCTTCG

CCAGCAAGCTAACGCAGTCCATTTGGGTAAGCGTTGGGATGAGATTAAGGAAATGTACGCAACCGTC

AATCAAATGTTTGGCGATATTCCAAAGGTTACGCCTTCTTCTAAAGTAGTTGGCGATATGGCACTATT

CATGGTCCAAAATGATTTGACGCCTGAAATGGTAATGAACGATAAGGGACAATTAAGTTTTCCCGAA

TCAGTGGTAAACTTTTTCCGTGGTGATTTAGGACAACCGGCGGGTGGTTTTCCAAAACAGCTCCAAAA

GGTGATTCTAAAAGAGCAAGCCCCATTGACAGTACGACCAGGAGCTTTAGCCGATCCAGTTGATTTTG

ATCAAGTTCGTAAACAGGCAACTAAGGTTTTAGGTCACCAAGCAAGTGATGAAGAAGTTATGTCGTT

TATTATGTATCCAGATGTGATGACCGAATACATTCAACGTCAAAATGAATATGGTCCAGTACCATTAT

TAGATACTCCAATCTTTTTCCAAGGCATGCATATTGGCCAACGCATTGATTTACAATTGGGACGCGGA

AAATCGGTCATTATTGTCCTTCGAGAAATTAGTGAAGCAGATGAGGCGGGCCAAAGGTCACTTTTCTT

TGATATAAATGGACAAAGTGAAGAAGTGATTGTTTATGATGTTAATGCGCAGGTAACGAAAGTAAAG

AAGATTAAAGCTGATCCGACTAAAGCCGAACAGATTGGCGCTACTATGGCGGGCTCGGTCATTGAAG

TCCAAGTAGAAGCGGGCCAAAAGGTCCAGCGAGGTGATAACTTAATTGTCACTGAGGCGATGAAAAT

GGAGACCGCGTTAAGAGCACCTTTCGACGCAACCATTAAGAAGATTTATGCTACCCCTGAAATGCAA

ATCGAGACGGGGGATTTATTGATTGAACTAGAAAAGGAGTAA

81
DP3 Glycine--tRNA ligase beta subunit
ATGTCAACATTTTTATTAGAAATTGGACTTGAAGAAATACCAGCTCATTTGGTAACCAGTTCAGAG

AATCAGTTAATTGAAAGAACTAAAAAGTTCTTATCAGAGCATCGTTTAACAGTAGGTGATATTAAACC

ATATTCAACACCGCGACGTCTGGCTGTCGTTTTGACAGATGTTGCTGAAACATCAGAAAGTTTAAGCG

AAGAAAAGCGTGGACCATCTGTTGACCGTGCACAAGACGAAAACGGTAATTGGACAAAGGCAGCAT

TAGGTTTTGCACGTGGTCAAGGTGCTAATCCTGAAGCATTTGAAATTAAAGATGGATATGTTTGGCTA

ACAAAACGTACTGCTGGTGTAGCCGCGAATGAAATTTTAGCTAAAATTGGTGATGAAGTTGTCGCCC

AAATGAAATTTTCAACTTATATGAAGTGGGCTAATCACAGCTTTTTGTATGTTCGACCTATTCGTTGGC

TCGTAGCACTTCTTGATAGTGAAGTCATTTCTTTCAACGTGTTAGATATTACCACAGATCGTTTCACAC

GTGGTCATCGTTTTTTGTCTTCAGAACATGTTGAAATATCTTCTGCAGATAATTATGTAACGACTTTGC

AGGGTGCTAACGTGGTTGTTGATGCTACAGTGCGCAAAAATGAAATTCGATCGCAGTTGAATGCAAT

TGCTGAAGCTAATGGTTGGGTTCTGCAACTTGAGACCGATGCGGCGCAAGATTTGTTGGAAGAAGTT

AATAACATTGTTGAGTGGCCAACAGCGTTTGCTGGCAGTTTCGATGAGAAATATTTAGAAATACCAG

ATGAAGTTTTGATTACATCAATGCGCGAACATCAGCGTTTCTTCTTTGTGACGAATGAAAAAGGACAA

TTATTGCCACACTTTTTGTCAATAAGAAATGGTAACCGTGAGCATCTAAACAACGTTATTGCTGGAAA

TGAAAAAGTATTGGTAGCAAGGTTAGAAGATGCCGAATTCTTCTATCATGAAGACCAAACCAAATCA

ATTTCTGATTACATGACTAAAGTTAAAAAGTTAGTCTTCCATGAAAAAATTGGTACGGTGTATGAACA

CATGCAACGCACTGGTGCTTTGGCTTCAGCAATGGCGGTGGTTTTGAAGTTTGATGAAGTACAACAGG

CTGATTTGACCCGTGCATCAGAAATTTATAAATTTGATTTGATGACCGGTATGGTTGGTGAATTTGAT

GAACTTCAAGGCATTATGGGTGAGCATTATGCCAAGCTTTTTGGCGAAGATGATGCGGTTGCAACAG

CCATTCGAGAGCATTATATGCCAACTTCAGCTAATGGTGAGGTTGCGCAATCTGAAATTGGTGCTTTG

TTGGCCGTTGCGGATAAACTTGATAGCATTGTGACGTTTTTTGCTGCTGGATTAATACCAAGTGGTTCT

AATGATCCTTATGGCTTACGACGTGCAGCTACTGGCATCGTGCGTACATTGGTGGATAAAAAATGGCA

-continued

TATTGATTTGCGGCCTTTGCTAGCTGATTTTGTGCAACAGCAAGGTAAGGTAACTGACACCGATTTAA

CGACATTTGTTGATTTCATGTTGGATCGTGTTCGTAAATTATCGTTGGATGCTGGAATACGTCAAGAT

ATTGTCATTGCTGGATTAGGCAACGTTGATAGAGCTGATATCGTATATATTAGTCAGCGAGTCGAAGT

TTTGTCCCAACATAGTGGTGATGGCAATTTCCGAGATGTAATTGAGGCACTGACTCGTGTGGATCGCT

TAGCCGTAAAGCAAGTAACTAATGCAACGGTTGATCCTGCTAAGTTTGAAAATCAATCTGAAAAGGA

CCTATATCAAGCAACGTTAACGCTTGATTTAAATACTTTGATGCATGACGGTGCAGAAAATCTCTACA

TGGCCTTAGCAAATTTGCAAAAACCAATTGCGGCTTATTTTGATGAAACCATGGTTAACGCTGAAGAT

GAATCTGTTAAAGATAATCGATATGCGCAGCTGAACGTCATACAACGACTAACCAACGGATTAGGAG

ATTTGACGCAAATCGTCATTAAGTAA

82
DP3 Glutamine synthetase
ATGGCTCGTAAAACATTTACCAAAGAAGAAATTAAACAAATTGTTGTTGATGAAAATGTAGAATT

CATTCGTGTAACATTCACTGATGTCTTAGGTGCGATTAAAAACGTTGAAGTACCAACTTCTCAATTAG

ATAAGGTGCTTGACAACAATTTAATGTTTGACGGTTCATCAATCGAGGGATTTGTTCGTATCAATGAA

TCAGATATGTATCTTTACCCCGATTTATCAACATTTATGATTTTCCCATGGGCAACGGATGGTCATGGT

GGTAAAGTGGCCCGCTTGATTGCCGACATTTATACTGCTGATCGTGAGCCATTTGCTGGAGACCCCCG

TCATGCGTTACGTTCGGTACTCGCTGACGCGCGTGAAGCTGGGTTTACGGCGTTTAATGTCGGGACAG

AACCTGAATTTTTCTTGTTTAAACTTGATGAAAAAGGCAACCCAACCACAGAGTTAAACGACAAAGG

TGGTTATTTTGACCTAGCACCATTGGATATGGGTGAAAATGTTCGTCGTGAAATTGTTTTGACTTTGGA

AAAAATGGGCTTTGAAATTGAAGCTGCTCACCACGAAGTTGCCGAAGGACAGCATGAAGTAGACTTT

AAATACGCTTCAGCTCTTGAAGCCGCTGACAACATTCAGACGTTTAAGTTGGTTGTTAAAACCATCGC

ACGCAAGAATGGTTACTATGCTACCTTTATGCCAAAGCCTGTTGCAGGTATTAACGGATCCGGTATGC

ACACAAACATGTCATTATTTACAAAAGATGGTAACGCATTTGTTGATACATCGGATGAAATGGGCTTG

TCAAAAACAGCATATAACTTCTTGGGTGGTATTTTAGAACATGCGACTGCGTTTACAGCGCTTGCAAA

CCCAACAGTTAACTCATACAAGCGCTTGACACCAGGATTCGAAGCACCTGTTTATGTTGCATGGTCAG

CATCAAATCGTTCACCAATGGTTCGAGTTCCGGCCTCACGTGGTAATTCAACACGTTTGGAACTTCGT

TCAGTTGACCCAACAGCTAATCCTTATACTGCATTGGCAGCCATTTTGGCTTCAGGACTGGATGGGAT

CAAGCGTGAATTAGAGCCTTTGGCCTCAGTTGATAAAAATATTTATTTGATGGATGAGGTCGAACGGG

AAAAGGCAGGCATTACAGACTTACCAGATACTCTGTTGGCTGCAGTTCGTGAGTTGGCGGCTGATGAT

GTTGTTCGTTCAGCTATTGGAGAACATATTGCTGATAAGTTTATTGAAGCAAAGAAGATTGAATACAC

ATCATATCGTCAGTTTGTTTCTGAATGGGAAACAGATTCTTATCTTGAAAATTACTAA

83
DP3 DNA gyrase subunit B
GTGTTCGCAGATTATATCTGTTCACACGCTAATAATATGGCAGAGAATATCGAAAATGAAGCATTG

GAGAACATTGATGGCATCGTAACCGATGATACCGAAATCCGTCAAGCAAGCACCGTTCATGCAGCAG

CAGGCGCTTACAATGCTGATCAGATTCAAGTTTTGGAAGGATTGGAAGCTGTCCGCAAACGCCCTGG

CATGTACATTGGTACGACCACAGCGCAAGGCTTGCACCATTTGGTATGGGAAATTGTTGATAACGGG

ATTGATGAGGCATTAGCAGGGTTTGCGTCACATATTACGGTCACAATCGAAAAGGATAACTCAATCA

CGGTAACCGATGACGGCCGTGGTATTCCTGTCGACATTCAAACTAAAACGGGTAAGCCAGCTCTTGA

AACTGTCTTTACGGTATTACACGCCGGTGGTAAATTTGGCGGTGGCGGTTATAAAGTATCTGGTGGAT

TACACGGTGTTGGAGCTTCTGTTGTCAATGCCTTGTCAACGGATTTGGACGTTAGAGTTGTTCGTGAT

AATACTGTTTATTACATGGACTTCAAAGTGGGACGCGTCAACACACCGATGAAACAATTGACGGAAA

-continued

```
AGCCCACTATTGAGCGTGGTACAATTGTTCATTTTAAGCCCGATGCAGATATTTTCCGTGAAACAACA

GTTTATAACTACAACACATTACTAACACGTGTGCGCGAATTGGCCTTTTTGAATAAAGGTTTGCGCAT

TTCGATTACAGATAATCGACCTGAAGAAGCTGTTTCTGAAAGCTTTCATTTTGAAGGTGGGATTAAAG

AATACGTCAGCTATTTGAATAAGGACAAGACTGCTATTTTCCCTGAACCTGTTTACGTTGAGGGTGAA

GAAAATGGCATTGTAGTGGAAGCTGCCTTACAGTACACTACCGATATTAAAGACAATCTGCGGACGT

TTACTAACAATATCAATACCTATGAAGGTGGGACGCACGAAACTGGCTTTAAAACAGCCTTAACACG

TGTAATCAATGATTACGCTCGTAAAAATGGTCAGCTCAAAGATAATGCAGAAAGTTTGACAGGGGAA

GATGTGCGCGAAGGCATGACTGCTATCGTGTCAATCAAGCACCCAGATCCACAATTTGAAGGACAAA

CCAAAACTAAATTAGGTAACTCCGATGCACGTCAAGCAACGGATCGGATGTTCTCAGAAACGTTCAG

TCGTTTCATGATGGAAAATCCAGCAGTTGCCAAGCAAATTGTTGAAAAAGGTGTCTTAGCCCAAAAA

GCACGATTGGCTGCCAAGCGTGCACGCGAAATGACACGCAAACAATCTGGTTTGGAAATTGGTAATT

TGCCAGGTAAATTAGCTGATAATACCTCAAATGATCCTGAAATTTCAGAATTATTTATTGTTGAGGGT

GATTCAGCCGGTGGTTCAGCTAAGCAAGGACGTAACCGTTTGACGCAAGCTATTTTGCCAATTCGAGG

CAAAATTTTAAATGTTGGGAAAGCCTCATTGGATCGGGTGTTAGCCAACGAAGAAATTCGATCATTGT

TTACAGCAATGGGAACTGGATTTGGTGAGGACTTTAATGTTGAAAAAGCCAATTATCACAAAGTCATT

ATTATGACAGATGCCGATGTCGATGGCGCCCATATTCGAACACTATTGTTAACGCTATTTTATCGTTAT

ATGCGACCACTTGTTGACGCAGGCTATATTTATATTGCGCAGCCACCGCTTTACGGTGTTGCCTTAGG

CAATAATAAATCAATGACGTACATTGATTCTGATGAAGAACTTGAAGACTATTTGTCACAATTGCCAT

CTAATATTAAACCAAAAGTTCAACGTTATAAGGGACTAGGGGAAATGGATTACGATCAACTAGCAGA

TACAACCATGGATCCGCAGAATCGTCGTTTGCTACGTGTTGACCCAACTGATGCTGAAGAAGCCGAA

GCAGTTATTGATATGTTAATGGGTGGGGATGTACCACCACGTCGTAAGTTTATTGAAGACAATGCTGT

CTTTGTTGAGAACTTGGATATTTAA
```

84
DP3 Leucine--tRNA ligase
```
ATGATTTTCGTCAACGAAGCTTACAAAACCGATGCTGTGCCGAAAGCGGCGGCGGAAAACTTCGT

ACAGATGCTGTCCCCACTGGCACCGCATTTGGCAGAAGAACTGTGGGAACGACTTGGTCATACCGAT

ACGATTACGTATGAACCATGGCCAACGTACGATGAGGCTTGGACCATAGAATCCGAAGTGGAAATCG

TCGTGCAAGTGAACGGCAAAATCGTAGAACGCACGAAAATTTCCAAAGACCTGGATCAAGCAGCGAT

GCAAGAACACAGCTTAAGCCTGCCGAATGTTCAGCAGGCTGTGGCTGGGAAGACGATCCGCAAAGTG

ATTGCGGTGCCAGGCAAGCTGGTGAATATCGTCGTTGGATAA
```

85
DP3 Glucose-6-phosphate isomerase
```
ATGGCACACATTACATTTGACACAAAGAACATTGAGAATTTTGTTGCACCATACGAATTGGACGAA

ATGCAACCATTAATTACGATGGCTGACCAACAATTGCGCAATCGTACGGGCGCTGGTGCAGAATATT

CTGATTGGTTGACTCTACCTACTGATTACGACAAGGAAGAATTTGCACGTATTCAAAAGGCGGCGCA

ACAAATTCAATCTGATTCAAAGATTTTGGTTGTCATTGGTATTGGTGGTTCATATTTGGGCGCGAAGA

TGGCGGTTGATTTCTTGAATCCAATGTTTAATAATGAATTGTCGGATGACCAACGTCAAGGTGTTAAA

ATTTATTTTGCTGGTAACTCAACTTCTGCAGCTTACTTAAATGATTTAGTTCGTGTCATTGGTGATCAA

GACTTTTCTGTCAACGTTATCTCAAAGTCTGGCACAACAACGGAACCATCAATCGCTTTCCGTGTGTTT

AAACAATTGTTAGAGAAAAAGTATGGTTCTGATGCTGCTAAGAAGCGTATCTATGCCACAACAGATG

CCAATCGTGGTGCTTTGCACGATGAAGCAGCGGCTTCAGGTTATGAAACATTCACAATTCCTGATGGT

GTCGGTGGTCGCTTCTCTGTTTTGACAGCTGTTGGCTTGTTGCCAATTGCTGCTTCAGGCGCTGATATC

CAAAAATTGATGGACGGCGCTCGTGATGCGCAAAACGAATATACTGATTCTGATTTGAAAAAGAACG
```

-continued

AGGCATATAAATATGCAGCCGTTCGTCGTATTTTGTATGATAAGGGTTATACAACAGAATTGTTGATT

AACTGGGAACCTTCAATGCAATATTTGTCAGAGTGGTGGAAGCAATTGATGGGCGAGTCTGAAGGTA

AAAATCAAAAGGGTATCTATCCATCTTCAGCTAACTTCTCAACCGACTTGCACTCACTTGGACAATAT

ATTCAAGAAGGACGCCGTGATTTGTTTGAGACGGTGGTTAAGTTAGACAATCCTGTATCTAATTTGGA

CCTACCACATGAAGAAGGCAACAATGATGGTTTGCAATATTTGGAAGGTATCACGATCGATGAAGTG

AACACCAAAGCATCTCAAGGGGTTACTTTGGCTCACGTTGATGGTGGTGTGCCTAACTTGGCTGTTCA

CTTGCCAGCACAAGATGCTTATTCACTCGGTTACATGATTTACTTCTTTGAAATGGCTGTTGGGGCGTC

TGGTTATACGTTTGGTATTAACCCATTCAACCAACCGGGTGTCGAAGCCTATAAGACAGCTATGTTTG

CACTATTAGGTAAGCCTGGCTATGAGGAAGCGACAAAAGCATTCCGTGCCCGCTTAGACAAATAA

86
DP3 Beta-phosphoglucomutase
ATGACTAAATTTTCAGATATTAAAGGTTTTGCCTTTGATTTAGATGGGGTTATTGCTGATACGGCGC

GTTTCCATGGTGAAGCTTGGCATCAAACAGCTGATGAGGTTGGCACAACTTGGACACCAGAATTGGC

TGAAGGTTTGAAGGGCATTAGTCGTATGGCTTCCTTGCAAATGATTTTGGATGCTGGGGATCATGCCG

ATGATTTTTCGCAAGCAGATAAAGAAGCATTAGCAGAAAAGAAAAATCATAATTATCAACAACTTAT

TTCAACATTGACGGAAGATGATATTTTGCCTGGCATGAAAGATTTTATTCAATCAGCCAAGGCAGCCG

GCTATACAATGTCGGTGGCATCAGCTTCTAAAAACGCACCAATGATTCTAGATCATTTGGGATTGACC

AAGTATTTTGTCGGCATTGTTGATCCCGCCACTTTGACAAAGGGAAAACCTGATCCTGAAATCTTCGT

TCGTGCTGCGGAAGTCTTACATTTAAATCCAGAAAATGTTATTGGATTGGAAGATTCAGCTGCTGGTA

TTGTGTCAATCAATGGCGCAGGTGAGACATCACTAGCCATTGGTAACGCAGATGTTTTGTCAGGAGCG

GACTTGAATTTTGCGTCTACTTCAGAAGTGACCTTAGCAAATATTGAAGCTAAAATGCAATAG

87
DP3 2-oxoglutarate carboxylase small subunit
ATGTTTAAAAAAGTGCTTGTTGCTAATCGTGGTGAAATTGCGGTTCGCATCATTCGAACGCTCAAA

GAAATGGGGATTGCTTCAGTCGCTATTTACTCGACAGCCGATAAAGATAGTTTACACGTACAAATCGC

TGACGAAGCGATTGCTGTGGGGGGACCGAAACCTAAAGATTCATACTTAAATATGAAAAATATTTTA

AGTGCAGCCCTGCTGTCGGGAGCAGAGGCAATTCATCCAGGATATGGCTTTTTAGCTGAAAATACATT

GTTTGCTGAAATGGTTGGCGAAGTTGGTATTAAATGGATTGGGCCTAGGCCAGAAACAATTGAGTTA

ATGGGTAACAAAGCTAACGCACGTGAAGAAATGCGGCGTGCCGGCGTACCAGTAATTCCAGGTTCAG

AGGGATTTATCCGTGATTTTCATGAAGCAAAAACGGTTGCTGATAAAATTGGCTATCCTTTGTTGCTA

AAAGCTGCCGCTGGTGGTGGTGGTAAAGGCATGCGTTTTGTTTACGGTGAGGATGAGTTATCAGATA

AATTTGATGATGCTCAAAACGAAGCGCGTGCTTCGTTTGGCGATGATCACATGTATATTGAAAAAGTT

ATGTCACGTGTTCGCCACATTGAAATGCAAGTGTTTCGTGATGAGAATGGTCATGTTGTTTACTTGCC

AGAACGAAATTGCTCATTGCAACGCAATAATCAAAAGGTGATTGAAGAATCACCAGCTACGGGTGTA

ACGCCTGAAATGCGTGCGCATCTTGGCGAAATTGTTACTAAAGCCGCAAAAGCATTGGCGTATGAAA

ATACTGGAACCATTGAATTTTTGCAAGATCGCGATGGTCATTTCTACTTTATGGAAATGAACACACGT

ATTCAAGTAGAACATCCAGTTTCTGAAATGGTAACGGGATTAGATTTAATTAAGTTACAAATTCAAGT

TGCTGCAGGCTTAGATTTACCGGTGGTTCAAGATGACGTGATCGTTCAAGGCCACTCTATCGAAGTAC

GTTTGACGGCTGAGCAGCCAGAAAAACACTTTGCACCTAGTGCTGGAACGATTGATTTTGTTTTTTTG

CCAACTGGTGGACCGGGTGTTCGTATTGATTCAGCCTTATTTAATGGCGATAAAATTCAACCATTTTA

CGATTCTATGATTGGCAAATTAATTGTTAAGGCCGATGATCGTGAAACAGCCATGAGAAAGATTCAA

CGTGTGGTTGATGAAACTGTTGTACGTGGTGTAGCAACGAGCCGTAATTTTCAAAAAGCTCTGTTAGC

-continued

TGATCCACAGGTTCAACGTGGCGAATTTGACACACGTTATTGGAAACTGAATTTTTACCGAGATGGA

CACAAACATTGCCAGATAATCAATAA

88
DP1 Glutamine--tRNA ligase
ATGAGCAAGCCCACTGTCGACCCTACCTCGAATTCCAAGGCCGGACCTGCCGTCCCGGTCAATTTC

CTGCGCCCGATCATCCAGGCGGACCTGGATTCGGGCAAGCATACGCAGATCGTCACCCGCTTCCCGCC

AGAGCCCAACGGCTACCTGCACATCGGTCATGCCAAGTCGATTTGTGTGAACTTCGGCCTGGCTCAGG

AGTTCGGTGGCGTTACGCACCTGCGTTTCGACGACACCAACCCGGCCAAGGAAGACCAGGAATACAT

CGACGCCATCGAAAGCGACATCAAGTGGCTGGGCTTCGAATGGTCCGGTGAAGTGCGCTATGCATCC

AAGTATTTCGACCAGCTGTTCGACTGGGCCGTCGAGTTGATCAAGGCCGGCAAGGCCTACGTTGACG

ACCTGACCCCCGAGCAAGCCAAGGAATACCGTGGCAGCCTGACCGAGCCGGGCAAGAACAGCCCGTT

CCGCGACCGTTCGGTCGAAGAGAACCTCGACTGGTTCAACCGCATGCGCGCCGGTGAGTTCCCGGAC

GGCGCCCGCGTGCTGCGCGCCAAGATCGACATGGCCTCGCCGAACATGAACCTGCGCGACCCGATCA

TGTACCGCATTCGCCATGCCCATCACCACCAGACCGGTGACAAGTGGTGCATCTACCCCAACTACGAC

TTCACCCACGGTCAGTCGGACGCCATCGAAGGCATCACCCACTCCATCTGCACCCTGGAGTTCGAAAG

CCATCGCCCTCTGTACGAATGGTTCCTGGACAGCCTGCCGGTGCCGGCGCACCCGCGTCAGTACGAAT

TCAGCCGCCTGAACCTGAACTACACCATCACCAGCAAGCGCAAGCTCAAGCAACTGGTCGATGAAAA

GCACGTGCATGGCTGGGACGACCCGCGCATGTCGACGCTCTCGGGTTTCCGTCGTCGTGGCTACACCC

CGGCGTCGATCCGCAATTTCTGCGACATGGTCGGCACCAACCGTTCTGACGGTGTGGTCGATTACGGC

ATGCTTGAGTTCAGCATCCGTCAGGATCTGGACGCGAACGCGCCGCGCGCCATGTGCGTGCTGCGTCC

GTTGAAAGTCGTGATCACCAACTACCCGGAAGACAAGGTCGACCACCTTGAGCTGCCGCGTCACCCG

CAGAAAGAAGAGCTGGGCGTGCGCAAGCTGCCGTTCGCGCGCGAAATCTACATCGACCGTGACGACT

TCATGGAAGAGCCGCCGAAGGGTTACAAGCGCCTGGAGCCGAACGGCGAAGTGCGCCTGCGTGGCA

GCTACGTGATCCGCGCCGACGAAGCAATCAAGGACGCCGAAGGCAACATCGTCGAACTGCGCTGCTC

GTACGATCCGGAAACACTCGGCAAGAACCCTGAAGGCCGTAAGGTCAAGGGCGTGATCCACTGGGTG

CCGGCCGCTGCCAGCATCGAGTGCGAAGTGCGTCTGTACGATCGTCTGTTCCGATCGCCGAACCCGGA

GAAGGCCGAAGACAGCGCCAGCTTCCTGGACAACATCAACCCTGACTCGCTGCAAGTGCTTACAGGT

TGTCGTGCTGAGCCATCGCTTGGCGACGCACAGCCGGAAGACCGTTTCCAGTTCGAGCGCGAAGGTT

ACTTCTGCGCGGATATCAAGGACTCGAAACCCGGTGCTCCGGTATTCAACCGTACCGTGACCTTGCGT

GATTCGTGGGGCCAGTGA

89
DP1 DNA gyrase subunit B
ATGAGCGAAGAAAACACGTACGACTCGACCAGCATTAAAGTGCTGAAAGGTTTGGATGCCGTACG

CAAACGTCCCGGTATGTACATCGGCGACACCGATGATGGTAGCGGTCTGCACCACATGGTGTTCGAG

GTGGTCGACAACTCCATCGACGAAGCTTTGGCCGGTCACTGCGACGACATCAGCATTATCATCCACCC

GGATGAGTCCATCACGGTGCGCGACAACGGTCGCGGCATTCCGGTCGATGTGCACAAAGAAGAAGGC

GTTTCGGCGGCTGAGGTCATCATGACCGTGCTGCACGCCGGCGGTAAGTTCGATGACAACTCTTATAA

AGTCTCCGGCGGTCTGCACGGTGTAGGTGTGTCGGTAGTGAACGCACTGTCCGAAGAGCTGATCCTG

ACCGTTCGCCGTAGCGGCAAGATTTGGGAGCAGACGTACGTCCATGGTGTGCCACAAGAGCCGATGA

AAATCGTTGGCGACAGTGAATCCACGGGTACGCAGATCCACTTCAAGCCATCGGCTGAAACCTTCAA

GAACATCCACTTTAGCTGGGACATCCTGGCCAAGCGGATTCGCGAACTGTCCTTCCTCAACTCCGGTG

TGGGTATCGTCCTCAAGGACGAGCGCAGCGGCAAGGAAGAACTGTTCAAGTACGAAGGCGGTCTGCG

CGCGTTCGTTGAATACCTGAACACCAATAAGACCGCGGTCAACCAGGTGTTCCACTTCAACATTCAGC

-continued

GTGAAGACGGCATCGGCGTGGAAATCGCCCTGCAGTGGAACGACAGCTTCAACGAGAACTTGTTGTG

CTTCACCAACAACATTCCACAGCGCGATGGCGGTACTCACTTGGTGGGTTTCCGTTCCGCACTGACGC

GTAACCTGAACACTTACATCGAAGCCGAAGGCTTGGCCAAGAAGCACAAAGTCGCCACCACCGGTGA

CGATGCGCGTGAAGGCCTGACCGCGATTATCTCGGTGAAAGTGCCGGATCCCAAGTTCAGCTCCCAG

ACCAAAGACAAGCTGGTTTCTTCCGAGGTGAAGACCGCCGTGGAACAGGAGATGGGCAAGTACTTCT

CCGACTTCCTGCTGGAGAACCCGAACGAAGCCAAGCTGGTCGTCGGCAAGATGATCGACGCTGCACG

TGCTCGCGAAGCGGCGCGTAAAGCCCGTGAGATGACCCGTCGTAAAGGCGCGCTGGATATTGCTGGC

TTGCCTGGCAAGTTGGCTGACTGCCAGGAGAAGGACCCAGCGCTCTCCGAGCTATATCTTGTGGAAG

GTGACTCTGCTGGCGGTTCCGCCAAGCAGGGTCGTAACCGTCGCACCCAGGCGATCCTGCCGTTGAA

AGGCAAGATTCTCAACGTAGAGAAGGCCCGCTTCGACAAGATGATTTCCTCCCAGGAAGTCGGCACC

TTGATTACGGCGTTGGGTTGCGGCATTGGCCGCGATGAGTACAACATCGACAAGCTGCGCTACCACA

ACATCATCATCATGACCGATGCTGACGTCGACGGTTCGCACATCCGTACCTTGCTGCTGACCTTCTTCT

TCCGTCAGTTGCCTGAGCTGATTGAGCGTGGCTACATCTATATCGCGCAGCCGCCGTTGTACAAAGTG

AAAAAGGGCAAGCAAGAGCAGTACATCAAAGACGACGACGCCATGGAAGAGTACATGACGCAGTCG

GCCCTGGAAGATGCAAGCCTGCACTTGAACGACGAAGCACCGGGTATCTCCGGTGAGGCGTTGGAGC

GTCTGGTTAACGACTTCCGTATGGTGATGAAGACCCTCAAGCGTCTATCGCGTCTGTACCCTCAGGAA

CTGACCGAGCACTTCATCTACCTGCCGGCCGTCAGTCTGGAGCAGTTGGGTGATCATGCAGCGATGCA

AGAGTGGCTGGCTCAGTACGAAGTACGCCTGCGCACTGTTGAGAAGTCTGGCCTGGTGTACAAAGCC

AGTCTGCGTGAAGACCGTGAACGTAACGTGTGGCTGCCGGAGGTTGAGTTGATCTCCCACGGCCTGTC

GAATTACGTCACCTTCAACCGCGACTTCTTCGGCAGTAATGACTACAAGACGGTCGTGACCCTCGGCG

CGCAGTTGAGCACCTTGCTGGATGATGGTGCTTACATTCAACGTGGCGAGCGTAAGAAAGCGGTCAA

GGAGTTCAAGGAAGCCTTGGACTGGCTGATGGCGGAAAGCACCAAGCGTCATACCATTCAGCGATAC

AAAGGTCTGGGCGAGATGAACCCTGATCAGTTGTGGGAAACCACCATGGATCCAGCACAGCGTCGCA

TGCTGCGCGTGACCATCGAAGACGCCATTGGCGCAGATCAGATCTTCAACACCCTGATGGGTGATGC

GGTCGAACCTCGCCGTGACTTCATCGAGAGCAATGCCTTGGCGGTGTCCAACCTGGACTTCTGA

90
DP1 Isoleucine--tRNA ligase
ATGACCGACTATAAAGCCACGCTAAACCTTCCGGACACCGCCTTCCCAATGAAGGCCGGCCTGCC

ACAGCGCGAACCGCAGATCCTGCAGCGCTGGGACAGTATTGGCCTGTACGGAAAGTTGCGCGAAATT

GGCAAGGATCGTCCGAAGTTCGTCCTGCACGACGGCCCTCCTTATGCCAACGGCACGATTCACATCGG

TCATGCGCTGAACAAAATTCTCAAGGACATGATCCTGCGCTCGAAAACCCTGTCGGGTTTTGACGCGC

CGTATGTCCCGGGCTGGGACTGCCATGGCCTGCCGATCGAACACAAAGTCGAAGTGACCTACGGCAA

AAACCTGGGCGCGGATAAAACCCGCGAACTGTGCCGTGCCTACGCCACTGAGCAGATCGAAGGGCAG

AAGTCCGAATTCATCCGCCTGGGCGTGCTGGGCGAGTGGGACAACCCGTACAAGACCATGAACTTCA

AGAACGAGGCCGGTGAAATCCGTGCCTTGGCTGAAATCGTCAAAGGCGGTTTTGTGTTCAAGGGCCT

CAAGCCCGTGAACTGGTGCTTCGACTGCGGTTCGGCCCTGGCTGAGGCGGAAGTCGAATACGAAGAC

AAGAAGTCCTCGACCATCGACGTGGCCTTCCCGATCGCCGACGACGCCAAGTTGGCCCAGGCTTTCG

GCCTGGCAAGCCTGAGCAAGCCGGCGGCCATCGTGATCTGGACCACCACCCCGTGGACCATCCCGGC

CAACCAGGCGCTGAACGTGCACCCGGAATTCACCTACGCCCTGGTGGACGTCGGTGATCGCCTGCTG

GTGCTGGCCGAGGAAATGGTCGAGGCCTGTCTGGCGCGCTACGAACTGCAAGGTTCGGTGATCGCCA

CCACCACCGGCTCCGCGCTGGAACTGATCAACTTCCGTCACCCGTTCTATGACCGCCTGTCGCCGGTT

-continued

TACCTGGCTGACTACGTCGAACTGGGTTCGGGTACGGGTGTGGTTCACTCCGCACCGGCCTACGGCGT

TGACGACTTCGTGACCTGCAAAGCCTACGGTATGGTCAACGATGACATCCTCAACCCGGTGCAGAGC

AATGGTGTGTACGCGCCATCGCTGGAGTTCTTCGGCGGCCAGTTCATCTTCAAGGCTAACGAGCCGAT

CATCGACAAACTGCGTGAAGTCGGTGCGCTGCTGCACACCGAAACCATCAAGCACAGCTACATGCAC

TGCTGGCGCCACAAAACCCCGCTGATCTACCGCGCCACCGCGCAGTGGTTTATCGGCATGGACAAAG

AGCCGACCAGCGGCGACACCCTGCGTGTGCGCTCGCTCAAAGCCATCGAAGACACCAAGTTCGTCCC

GGCCTGGGGCCAGGCGCGCCTGCACTCGATGATCGCCAATCGTCCGGACTGGTGCATCTCCCGCCAG

CGTAACTGGGGCGTACCGATCCCGTTCTTCCTGAACAAGGAAAGCGGCGAGCTGCACCCACGCACCG

TCGAGCTGATGGAAGCCGTGGCCTTGCGCGTTGAACAGGAAGGCATCGAAGCCTGGTTCAAGCTGGA

CGCCGCCGAGCTGCTGGGCGACGAAGCGCCGCTGTACGACAAGAAGGCTCGGACCAACACCGTGGCT

GGTTCCACTCGTCGCTGCTGA

91
DP1 NADH-quinone oxidoreductase subunit C/D
ATGACTACAGGCAGTGCTCTGTACATCCCGCCTTATAAGGCAGACGACCAGGATGTGGTTGTCGAA

CTCAATAACCGTTTTGGCCCTGACGCCTTTACCGCCCAGGCCACACGTACCGGCATGCCGGTGCTGTG

GGTGGCGCGCGCCAGGCTCGTCGAAGTCCTGACCTTCCTGCGCAACCTGCCCAAGCCGTACGTCATGC

TCTATGACCTGCATGGCGTGGACGAGCGTCTGCGGACCAAGCGCCAGGGCCTGCCGAGCGGCGCCGA

TTTCACCGTGTTCTATCACCTGCTGTCGATCGAACGTAACAGCGACGTGATGATCAAGGTCGCCCTCT

CCGAAAGCGACCTGAGCGTCCCGACCGTGACCGGCATCTGGCCCAACGCCAGTTGGTACGAGCGTGA

AGTCTGGGACATGTTCGGTATCGACTTCCCTGGCCACCCGCACCTGACGCGCATCATGATGCCGCCGA

CCTGGGAAGGTCACCCGCTGCGCAAGGACTTCCCTGCGCGCGCCACCGAATTCGACCCGTTCAGCCTG

AACCTCGCCAAGCAACAGCTTGAAGAAGAGGCTGCACGCTTCCGGCCGGAAGACTGGGGCATGAAA

CGCTCCGGCACCAACGAGGACTACATGTTCCTCAACCTGGGCCCGAACCACCCTTCGGCGCACGGTG

CCTTCCGTATCATCCTGCAACTGGACGGCGAAGAAATCGTCGACTGCGTGCCGGACATCGGTTACCAC

CACCGTGGTGCCGAGAAGATGGCCGAGCGCCAGTCGTGGCACAGCTTCATCCCGTACACCGACCGTA

TCGACTACCTCGGCGGCGTGATGAACAATCTGCCGTACGTGCTCTCGGTCGAGAAGCTGGCCGGTATC

AAGGTGCCGGACCGCGTCGACACCATCCGCATCATGATGGCCGAGTTCTTCCGGATCACCAGCCACCT

GCTGTTCCTGGGTACCTACATCCAGGACGTCGGCGCCATGACCCCGGTGTTCTTCACCTTCACCGACC

GTCAGCGCGCCTACAAGGTCATCGAAGCCATCACCGGCTTCCGCCTGCACCCGGCCTGGTACCGCATC

GGCGGTGTCGCGCACGACCTGCCAAATGGCTGGGAACGCCTGGTCAAGGAATTCATCGACTGGATGC

CCAAGCGTCTGGACGAGTACCAGAAAGCCGCCCTGGACAACAGCATCCTCAAGGGCCGGACCATTGG

GGTCGCGGCCTACAACACCAAAGAGGCCCTGGAATGGGGCGTCACCGGTGCTGGCCTGCGTTCCACC

GGTTGCGATTTCGACCTGCGTAAAGCGCGCCCGTACTCCGGCTACGAGAACTTCGAATTCGAAGTGCC

GTTGGCGGCCAATGGCGATGCCTACGACCGTTGCATCGTGCGCGTCGAAGAAATGCGCCAGAGCCTG

AAGATCATCGAGCAATGCATGCGCAACATCCGGCAGGCCCGTACAAGGCGGACCACCCGCTGACCAC

GCCGCCGCCGAAAGAGCGCACGCTGCAACACATCGAAACCCTGATCACGCACTTCCTGCAGGTTTCG

TGGGGCCCGGTGATGCCGGCCAACGAATCCTTCCAGATGATCGAAGCGACCAAGGGTATCAACAGTT

ATTACCTGACGAGCGATGGCGGCACCATGAGCTACCGCACCCGGATTCGCACTCCAAGCTTCCCGCA

CCTGCAGCAGATCCCTTCGGTGATCAAAGGTGAAATGGTCGCGGACTTGATTGCGTACCTGGGTAGTA

TCGATTTCGTTATGGCCGACGTGGACCGCTAA

92
DP1 Protein RecA
ATGGACGACAACAAGAAGAAAGCCTTGGCTGCGGCCCTGGGTCAGATCGAACGTCAATTCGGCAA -continued

GGGTGCCGTAATGCGTATGGGCGATCACGACCGTCAGGCGATCCCGGCTATTTCCACTGGCTCTCTGG

GTCTGGACATCGCACTCGGCATTGGCGGCCTGCCAAAAGGCCGTATCGTTGAAATCTACGGCCCTGA

ATCTTCCGGTAAAACCACCCTGACCCTGTCGGTGATTGCCCAGGCGCAAAAAATGGGCGCCACTTGTG

CGTTCGTCGATGCCGAGCACGCTCTTGACCCTGAATACGCCGGCAAGCTGGGCGTCAACGTTGACGA

CCTGCTGGTTTCCCAACCGGACACCGGTGAGCAAGCCTTGGAAATCACCGACATGCTGGTGCGCTCCA

ACGCCATCGACGTGATCGTGGTCGACTCCGTGGCTGCCCTGGTGCCGAAAGCTGAAATCGAAGGCGA

AATGGGCGACATGCACGTGGGCCTGCAAGCCCGTCTGATGTCCCAGGCGCTGCGTAAAATCACCGGT

AACATCAAGAACGCCAACTGCCTGGTGATCTTCATCAACCAGATCCGTATGAAGATTGGCGTGATGTT

CGGCAGCCCGGAAACCACCACCGGTGGTAACGCGTTGAAGTTCTACGCTTCGGTCCGTCTGGATATCC

GCCGTACTGGCGCGGTGAAGGAAGGCGACGAGGTGGTGGGTAGCGAAACCCGCGTTAAAGTTGTGA

AGAACAAGGTGGCCCCGCCATTCCGTCAGGCTGAGTTCCAGATTCTCTACGGCAAGGGTATCTACCTG

AACGGCGAGATGATCGACCTGGGCGTACTGCACGGTTTCGTCGAGAAGTCCGGTGCCTGGTATGCCT

ACAACGGCAGCAAGATCGGTCAGGGCAAGGCCAACTCGGCCAAGTTCCTGGCGGACAACCCGGATAT

CGCTGCCACGCTTGAGAAGCAGATTCGCGACAAGCTGCTGACCCCGGCACCAGACGTGAAAGCTGCT

GCCAACCGCGAGCCGGTTGAAGAAGTAGAAGAAGTCGACACTGACATCTGA

93
DP1 RNA polymerase sigma factor RpoD
ATGGAAATCACCCGCAAGGCTCTGAAAAAGCACGGTCGCGGCAACAAGCTGGCAATTGCCGAGCT

GGTGGCCCTGGCTGAGCTGTTCATGCCAATCAAGCTGGTGCCGAAGCAATTTGAAGGCCTGGTTGAG

CGTGTGCGCAGTGCTCTTGAGCGTCTGCGTGCCCAAGAGCGCGCAATCATGCAGCTCTGCGTACGTGA

TGCACGCATGCCGCGTGCCGACTTCCTGCGCCAGTTCCCGGGCAACGAAGTGGATGAAAGCTGGACC

GACGCACTGGCCAAAGGCAAGGCGAAGTACGCCGAAGCCATTGGTCGCCTGCAGCCGGACATCATCC

GTTGCCAGCAGAAGCTGACCGCGCTTCAAACCGAAACCGGTCTGACGATTGCTGAGATCAAGGACAT

CAACCGTCGCATGTCGATCGGTGAGGCCAAGGCCCGCCGCGCGAAGAAAGAGATGGTTGAAGCGAA

CTTGCGTCTGGTGATCTCCATCGCCAAGAAGTACACCAACCGTGGCCTGCAATTCCTCGATCTGATCC

AGGAAGGCAACATCGGCTTGATGAAGGCTGTGGACAAGTTCGAATACCGTCGCGGCTACAAGTTCTC

GACTTATGCCACCTGGTGGATCCGTCAGGCGATCACTCGCTCGATCGCAGACCAGGCCCGCACCATCC

GTATTCCGGTGCACATGATCGAGACCATCAACAAGCTCAACCGTATTTCCCGGCAGATGTTGCAGGA

AATGGGTCGCGAACCGACGCCGGAAGAGCTGGGCGAACGCATGGAAATGCCTGAGGATAAAATCCG

TAAGGTATTGAAGATCGCTAAAGAGCCGATCTCCATGGAAACGCCGATTGGTGATGACGAAGACTCC

CATCTGGGTGACTTCATCGAAGACTCGACCATGCAGTCGCCCATCGATGTGGCTACCGTTGAGAGCCT

TAAAGAAGCGACTCGCGACGTACTGTCCGGCCTCACTGCCCGTGAAGCCAAGGTACTGCGCATGCGT

TTCGGCATCGACATGAATACCGACCACACCCTTGAGGAAGTCGGTAAGCAGTTTGACGTGACCCGTG

AACGGATCCGTCAGATCGAAGCCAAGGCACTGCGCAAGTTGCGCCACCCGACGCGAAGCGAGCATCT

ACGCTCCTTCCTCGACGAGTGA

94
DP1 DNA-directed RNA polymerase subunit beta
ATGGCTTACTCATATACTGAGAAAAAACGTATCCGCAAGGACTTTAGCAAGTTGCCGGACGTCATG

GATGTCCCGTACCTTCTGGCTATCCAGCTGGATTCGTATCGTGAATTCTTGCAAGCGGGAGCGACTAA

AGATCAGTTCCGCGACGTGGGCCTGCATGCGGCCTTCAAATCCGTTTTCCCGATCATCAGCTACTCCG

GCAATGCTGCGCTGGAGTACGTGGGTTATCGCCTGGGCGAACCGGCATTTGATGTCAAAGAATGCGT

GTTGCGCGGTGTTACGTACGCCGTACCTTTGCGGGTAAAAGTCCGTCTGATCATTTTCGACAAAGAAT

-continued

CGTCGAACAAAGCGATCAAGGACATCAAAGAGCAAGAAGTCTACATGGGCGAAATCCCATTGATGA

CTGAAAACGGTACCTTCGTTATCAACGGTACCGAGCGCGTTATCGTTTCCCAGCTGCACCGTTCCCCG

GGCGTGTTCTTCGACCACGACCGCGGCAAGACGCACAGCTCCGGTAAGCTCCTGTACTCCGCGCGGA

TCATTCCGTACCGCGGCTCGTGGTTGGACTTCGAGTTCGACCCGAAAGACTGCGTGTTCGTGCGTATC

GACCGTCGTCGTAAGCTGCCGGCCTCGGTACTGCTGCGCGCGCTCGGCTATACCACTGAGCAAGTGCT

TGATGCTTTCTACACCACCAACGTATTCAGCCTGAAGGATGAAACCCTCAGCCTGGAACTGATTGCTT

CGCGTCTGCGTGGTGAAATTGCCGTCCTGGATATCCAGGATGAAAACGGCAAGGTCATCGTTGAAGC

TGGCCGCCGTATTACCGCGCGCCACATCAACCAGATCGAAAAAGCCGGTATCAAGTCGCTGGACGTG

CCGCTGGACTACGTCCTGGGTCGCACCACTGCCAAGGTCATCGTTCACCCGGCTACAGGCGAAATCCT

GGCTGAGTGCAACACCGAGCTGAACACCGAGATCCTGGCAAAAATCGCCAAGGCCCAGGTTGTTCGC

ATCGAGACCCTGTACACCAACGACATCGACTGCGGTCCGTTCATCTCCGACACGCTGAAGATCGACTC

CACCAGCAACCAATTGGAAGCGCTGGTCGAGATCTATCGCATGATGCGTCCTGGTGAGCCACCGACC

AAAGACGCTGCCGAGACCCTGTTCAACAACCTGTTCTTCAGCCCTGAGCGCTATGACCTGTCTGCGGT

CGGCCGGATGAAGTTCAACCGTCGTATCGGTCGTACCGAGATCGAAGGTTCGGGCGTGCTGTGCAAG

GAAGACATCGTCGCGGTACTGAAGACCTTGGTCGACATCCGTAACGGTAAAGGCATCGTCGATGACA

TCGACCACTTGGGTAACCGTCGTGTTCGCTGCGTAGGCGAAATGGCCGAGAACCAGTTCCGCGTTGGC

CTGGTACGTGTTGAGCGTGCGGTCAAAGAGCGTCTGTCGATGGCTGAAAGCGAAGGCCTGATGCCGC

AAGATCTGATCAACGCCAAGCCAGTGGCTGCGGCGGTGAAAGAGTTCTTCGGTTCCAGCCAGCTCTC

GCAGTTCATGGACCAGAACAACCCGCTCTCCGAGATCACCCACAAGCGCCGTGTTTCCGCACTGGGC

CCGGGCGGTCTGACCCGTGAGCGTGCAGGCTTTGAAGTTCGTGACGTACACCCAACGCACTACGGTC

GTGTTTGCCCGATCGAAACGCCGGAAGGTCCGAACATCGGTCTGATCAACTCCCTTGCCGCTTATGCA

CGCACTAACCAGTACGGCTTCCTCGAGAGCCCGTACCGTGTAGTGAAAGATGCACTGGTCACCGACG

AGATCGTGTTCCTGTCCGCCATCGAAGAAGCCGATCACGTGATCGCTCAGGCTTCGGCCACGATGAAC

GACAAGAAAGTCCTGATCGACGAGCTGGTAGCTGTTCGTCACTTGAACGAGTTCACCGTTAAGGCGC

CGGAAGACGTCACCTTGATGGACGTTTCGCCGAAGCAGGTAGTTTCGGTTGCAGCGTCGCTGATCCCG

TTCCTGGAGCACGATGACGCCAACCGTGCGTTGATGGGTTCCAACATGCAGCGTCAAGCTGTACCCAC

CCTGCGTGCCGACAAGCCGCTGGTAGGTACCGGCATGGAGCGTAACGTAGCCCGTGACTCCGGCGTT

TGCGTCGTGGCTCGTCGTGGCGGCGTGATCGACTCTGTTGATGCCAGCCGTATCGTGGTTCGTGTTGC

CGATGACGAAGTTGAGACTGGCGAAGCCGGTGTCGACATCTACAACCTGACCAAATACACCCGCTCG

AACCAGAACACCTGCATCAACCAGCGCCCGCTGGTGAGCAAGGGTGATCGCGTTCAGCGTAGCGACA

TCATGGCCGACGGCCCGTCCACCGATATGGGTGAGCTGGCACTGGGTCAGAACATGCGCATCGCGTT

CATGGCATGGAACGGCTTCAACTTCGAAGACTCCATCTGCCTGTCCGAGCGTGTTGTTCAAGAAGACC

GCTTCACCACGATCCACATTCAGGAGCTGACCTGTGTGGCGCGTGACACCAAGCTTGGGCCAGAGGA

AATCACTGCAGACATCCCGAACGTGGGTGAAGCTGCACTGAACAAACTGGACGAAGCCGGTATCGTT

TACGTAGGTGCTGAAGTTGGCGCAGGCGACATCCTGGTTGGTAAGGTCACTCCGAAAGGCGAGACCC

AACTGACTCCGGAAGAGAAGCTGTTGCGTGCCATCTTCGGTGAAAAAGCCAGCGACGTTAAAGACAC

TTCCCTGCGCGTACCTACCGGTACCAAGGGTACTGTCATCGACGTACAGGTCTTCACCCGTGACGGCG

TTGAGCGTGATGCTCGTGCACTGTCCATCGAGAAGACTCAACTCGACGAGATCCGCAAGGACCTGAA

CGAAGAGTTCCGTATCGTTGAAGGCGCGACCTTCGAACGTCTGCGTTCCGCTCTGGTAGGCCACAAGG

CTGAAGGCGGCGCAGGTCTGAAGAAAGGTCAGGACATCACCGACGAAATCCTCGACGGTCTTGAGCA

CGGCCAGTGGTTCAAACTGCGCATGGCTGAAGACGCTCTGAACGAGCAGCTCGAGAAGGCCCAGGCC

```
TATATCGTTGATCGCCGCCGTCTGCTGGACGACAAGTTCGAAGACAAGAAGCGCAAACTGCAGCAGG
GCGATGACCTGGCTCCAGGCGTGCTGAAAATCGTCAAGGTTTACCTGGCAATCCGTCGCCGCATTCAG
CCGGGCGACAAGATGGCCGGTCGTCACGGTAACAAGGGTGTGGTCTCCGTGATCATGCCGGTTGAAG
ACATGCCGCACGATGCCAATGGCACCCCGGTCGACGTCGTCCTCAACCCGTTGGGCGTACCTTCGCGT
ATGAACGTTGGTCAGATCCTTGAAACCCACCTGGGCCTCGCGGCCAAAGGTCTGGGCGAGAAGATCA
ACCGTATGATCGAAGAGCAGCGCAAGGTCGCAGACCTGCGTAAGTTCCTGCACGAGATCTACAACGA
GATCGGCGGTCGCAACGAAGAGCTGGACACCTTCTCCGACCAGGAAATCCTGGATCTGGCGAAGAAC
CTGCGCGGCGGCGTTCCAATGGCTACCCCGGTATTCGACGGTGCCAAGGAAAGCGAAATCAAGGCCA
TGCTGAAACTGGCAGACCTGCCGGAAAGTGGCCAGATGCAGCTGTTCGACGGCCGTACCGGCAACAA
GTTTGAGCGCCCGGTTACTGTTGGCTACATGTACATGCTGAAGCTGAACCACTTGGTAGACGACAAGA
TGCACGCTCGTTCTACCGGTTCGTACAGCCTGGTTACCCAGCAGCCGCTGGGTGGTAAGGCTCAGTTC
GGTGGTCAGCGTTTCGGGGAGATGGAGGTCTGGGCACTGGAAGCATACGGTGCTGCTTACACTCTGC
AAGAAATGCTCACAGTGAAGTCGGACGATGTGAACGGTCGGACCAAGATGTACAAAAACATCGTGG
ACGGCGATCACCGTATGGAGCCGGGCATGCCCGAGTCCTTCAACGTGTTGATCAAAGAAATTCGTTCC
CTCGGCATCGATATCGATCTGGAAACCGAATAA
95
DP22 Glutamine--tRNA ligase
ATGAGTGAGGCTGAAGCCCGCCCAACAAATTTTATCCGTCAGATTATTGATGAAGATCTGGCGACC
GGGAAACACAATACCGTTCATACCCGTTTCCCGCCTGAGCCAAATGGCTATCTGCATATCGGTCATGC
GAAATCTATCTGCCTGAACTTCGGCATTGCGCAAGACTATCAGGGGCAGTGCAACCTGCGTTTTGACG
ATACCAACCCGGCAAAAGAAGACATCGAATTCGTTGAGTCGATCAAACACGACGTCCAGTGGTTAGG
TTTCGACTGGAGCGGTGATATTCACTACTCTTCAGACTATTTTGATCAACTGCACGCTTATGCGCTGGA
ACTGATCAACAAAGGTCTGGCGTACGTTGACGAACTGTCACCGGATCAGATCCGTGAATACCGCGGC
TCGCTGACGTCTCCGGGCAAAAACAGCCCGTACCGTGACCGTTCAGTGGAAGAGAACATCGCGCTGT
TTGAGAAAATGCGTAACGGTGAATTTGCCGAAGGCGCTGCCTGTCTGCGTGCAAAAATCGATATGGC
GTCGCCTTTCTTCGTGATGCGCGATCCGGTTCTGTACCGTATTAAGTTTGCAGAACACCACCAGACCG
GCAAAAAATGGTGCATCTATCCGATGTACGATTTCACCCACTGCATTTCCGATGCGCTGGAAGGGATC
ACCCATTCGCTGTGTACGCTGGAATTCCAGGACAACCGCCGTCTGTACGACTGGGTTCTGGATAACAT
CTCCATTCCATGCCACCCGCGTCAGTACGAGTTCTCCCGTCTGAATCTCGAGTACTCCATCATGTCTAA
GCGTAAGCTGAACCAGCTGGTGACCGAGAAGATTGTGGAAGGCTGGGACGACCCGCGTATGCCGACT
GTTTCAGGTCTGCGTCGTCGTGGTTACACCGCCGCGTCTATCCGTGAATTCTGCCGTCGTATCGGCGTC
ACCAAGCAAGACAACAACGTCGAAATGATGGCGCTGGAATCCTGTATCCGTGACGATCTGAACGAAA
ATGCACCGCGCGCCATGGCGGTGATCAACCCGGTTAAAGTGATCATTGAAAACTTTACCGGTGATGA
CGTGCAGAGGGTGAAAATGCCGAACCACCCGAGCAAACCGGAAATGGGCACCCGCGAAGTGCCATT
TACCCGTGAGATTTATATCGATCAGGCAGATTTCCGCGAAGAAGCGAACAAGCAATACAAGCGTCTG
GTGCTCGGCAAAGAAGTGCGTCTGCGCAATGCGTATGTGATCAAAGCAGAACGTATCGAGAAAGATG
CAGAAGGCAATATCACCACGATCTTCTGTTCTTACGATATCGATACACTGAGCAAAGATCCTGCCGAT
GGCCGCAAGGTGAAAGGCGTGATCCACTGGGTTTCGGCGTCAGAAGGCAAACCGGCGGAGTTCCGCC
TGTATGACCGTCTGTTCAGCGTCGCCAACCCGGGTCAGGCAGAAGATTTCCTGACCACCATCAACCCG
GAATCTCTGGTGATTTCCCACGGTTTCGTGGAGCCATCACTGGTGGCTGCACAGGCTGAAATCAGCCT
GCAGTTCGAGCGTGAAGGTTACTTCTGCGCCGACAGCCGCTACTCAAGCGCTGAACATCTGGTGTTTA
```

-continued
ACCGTACCGTTGGCCTGCGCGATACCTGGGAAAGCAAACCCGTCGTGTAA

96
DP22 DNA gyrase subunit B
ATGTCGAATTCTTATGACTCCTCAAGTATCAAGGTATTAAAAGGGCTGGACGCGGTGCGTAAGCGC

CCCGGCATGTATATCGGCGATACCGATGACGGCACTGGTCTGCACCACATGGTATTCGAGGTTGTGGA

CAACGCTATCGACGAAGCCCTCGCGGGCCACTGTAAAGAGATTCAGGTCACGATCCATGCGGATAAC

TCTGTGTCCGTACAGGATGATGGTCGTGGCATTCCGACCGGTATTCATGAAGAAGAGGGCGTTTCTGC

TGCTCAGGTCATCATGACCGTTCTTCACGCCGGCGGTAAATTTGACGATAACTCGTATAAAGTCTCCG

GCGGTCTGCATGGCGTGGGTGTTTCCGTCGTTAACGCCCTGTCAGAAAAACTGGAACTGGTTATCCGC

CGCGAAGGCAAAGTGCACACCCAGACTTACGTGCATGGCGAACCTCAGGATCCGCTGAAAGTGATTG

GCGATACTGACGTGACCGGTACCACGGTACGTTTCTGGCCAAGCTTCAACACCTTCACCAATCACACT

GAATTCGAGTATGACATTCTGGCGAAACGCCTGCGTGAACTGTCATTCCTGAACTCCGGCGTGGCGAT

CCGCCTGCTGGATAAACGTGATGGTAAAAACGATCACTTCCATTATGAAGGCGGTATCAAAGCTTTCG

TGGAATATCTGAACAAAAACAAAACCCCAATCCATCCGACCGTATTCTATTTCTCCACGGTCAAAGAT

GACATTGGCGTTGAAGTGGCGTTGCAGTGGAACGACGGTTTCCAGGAAAACATTTACTGCTTCACCA

ACAACATTCCACAGCGCGATGGCGGGACTCACTTAGCCGGTTTCCGTTCGGCAATGACCCGTACCCTG

AACGCGTACATGGATAAAGAAGGCTACAGCAAGAAATCCAAAATCAGCGCCACCGGTGATGATGCC

CGTGAAGGCCTGATTGCTGTGGTGTCGGTGAAGGTGCCGGATCCTAAGTTCTCTTCTCAGACCAAAGA

CAAACTGGTGTCTTCTGAAGTGAAAACAGCGGTTGAAACGCTGATGAACGAGAAGCTGGTGGATTAC

CTGATGGAAAACCCGTCAGACGCCAAAATCGTTGTCGGTAAAATCATCGACGCAGCGCGTGCCCGTG

AAGCAGCACGTAAAGCGCGTGAAATGACCCGCCGTAAAGGCGCGCTGGATCTGGCTGGCTTGCCAGG

CAAACTGGCGGACTGTCAGGAACGCGATCCGGCACATTCCGAACTGTACTTAGTGGAAGGGGACTCA

GCGGGCGGCTCTGCAAAACAAGGCCGTAACCGTAAGAACCAGGCGATTCTGCCGTTGAAAGGTAAAA

TCCTCAACGTGGAGAAAGCGCGCTTCGACAAAATGCTCTCTTCTCAGGAAGTGGCAACGCTGATTAC

AGCACTCGGTTGCGGCATTGGCCGTGACGAATACAACCCGGACAAACTGCGCTATCACAGCATCATC

ATCATGACCGATGCCGACGTCGATGGTTCGCACATCCGTACCCTGTTGCTGACATTCTTCTACCGTCA

GATGCCTGAAATTGTAGAACGTGGCCACGTGTTTATCGCCCAGCCGCCGTTGTACAAAGTGAAAAAA

GGCAAGCAGGAACAGTACATTAAAGATGACGAAGCGATGGATCAGTATCAGATTTCCATTGCGATGG

ACGGGGCAACGTTACACGCCAACGCTCATGCGCCAGCCCTGGCGGGTGAACCGCTGGAGAAACTGGT

CGCTGAACATCACAGCGTGCAGAAAATGATTGGCCGCATGGAACGTCGTTATCCGCGTGCGCTGCTG

AATAACCTGATCTATCAGCCGACCCTGCCGGGTGCAGATCTGGCCGATCAGGCGAAAGTGCAGGCCT

GGATGGAATCGCTGGTGGCGCGTCTCAACGAGAAAGAGCAGCACGGCAGTTCTTACAGCGCGATCGT

GCGTGAAAACCGCGAACATCAGCTGTTCGAACCGGTTCTGCGTATCCGCACCCACGGTGTTGATACCG

ATTACGATCTGGATGCCGACTTCATCAAAGGCGGCGAATACCGCAAAATCTGTGCGCTGGGTGAACA

GCTGCGCGGCCTGATCGAAGAAGATGCCTTCATCGAACGTGGCGAACGCCGTCAGCCCGTCACCAGC

TTCGAACAGGCGCTGGAATGGCTGGTGAAAGAGTCCCGTCGTGGTCTGTCGATTCAGCGATACAAAG

GTCTGGGTGAAATGAACCCTGAACAGCTGTGGGAAACCACCATGGATCCTGAGCAACGTCGCATGTT

ACGTGTGACCGTGAAGGATGCCATCGCCGCTGACCAGTTGTTCACGACGCTGATGGGCGATGCGGTT

GAACCGCGCCGCGCCTTTATCGAAGAGAACGCCCTGAAAGCCGCCAATATCGATATCTGA

97
DP22 Isoleucine--tRNA ligase
ATGAGTGACTACAAGAACACCCTGAATTTGCCGGAAACAGGGTTCCCGATGCGTGGCGATCTGGC

CAAGCGTGAACCTGACATGCTGAAAAATTGGTATGACCAGGATCTGTACGGGATTATTCGTGCTGCC

-continued

AAGAAAGGCAAAAAAACCTTTATTTTGCATGACGGCCCTCCGTATGCGAACGGCAGCATTCATATTG

GTCACTCAGTAAACAAAATTCTTAAAGACATGATTATCAAGTCCAAAGGACTTGCGGGCTTTGATGCG

CCGTATGTGCCGGGCTGGGATTGTCATGGTCTGCCGATCGAGCTGAAAGTCGAACAACTGATCGGTA

AGCCGGGCGAGAAAGTTACGGCGGCGGAATTCCGTGAAGCCTGCCGTAAATATGCCGCAGAACAGGT

TGAAGGCCAGAAGAAAGACTTCATCCGTCTGGGCGTGCTGGGCGACTGGGATCATCCGTACCTGACG

ATGGATTTCAAAACCGAAGCCAACATCATCCGTGCGCTGGGCAAAATCATCGGTAACGGCCACCTGC

ATAAAGGCGCCAAGCCGGTGCACTGGTGTACAGATTGCGGTTCGTCGCTGGCCGAAGCCGAAGTCGA

ATATTACGACAAAGCCTCGCCTTCTATTGATGTGGCGTTCAACGCGACGGATGCCGCAGCCGTGGCAG

CGAAATTTGGCGTTACTGCCTTTAATGGCCCGATCTCGCTGGTTATCTGGACCACAACACCGTGGACT

ATGCCCGCTAACCGCGCCATTTCACTGAATCCTGAGTTTGCTTATCAGCTGGTTCAGGTCGAAGGTCA

GTGTCTGATCCTGGCAACCGATCTGGTTGAAAGCGTCATGAAACGTGCCGGTATTGCCGGATGGACC

GTTCTGGGCGAGTGCAAAGGCGCAGACCTCGAACTGCTGCGCTTCAAACACCCGTTCCTCGGTTTCGA

CGTTCCGGCGATCCTGGGCGATCACGTGACGCTCGATGCGGGTACCGGTGCCGTGCATACCGCACCA

GGCCACGGCCCTGACGACTTTGTTATCGGCCAGAAATACGGTCTGGAAGTGGCGAATCCGGTAGGGC

CGAACGGTTGCTACCTGCCGGGCACTTACCCGACGCTGGACGGTAAATTTGTCTTTAAAGCCAACGAC

CTGATCGTTGAGTTGCTGCGTGAAAAAGGCGCATTGCTGCACGTTGAGAAAATCACGCACAGCTATC

CTTGCTGCTGGCGCCACAAAACGCCAATCATCTTCCGCGCGACGCCGCAATGGTTCATCAGCATGGAT

CAGAAGGGCCTGCGTCAGCAGTCGCTGGAAGAGATCAAAGGCGTGCAGTGGATCCCGGACTGGGGTC

AGGCACGTATCGAAAACATGGTCGCTAACCGTCCTGACTGGTGTATCTCCCGTCAGCGTACCTGGGGC

GTGCCGATGTCTCTGTTCGTTCACAAAGACACTGAGCAGCTGCATCCGCGCAGCCTTGAGCTGATGGA

AGAAGTGGCGAAACGTGTTGAGGTGGATGGCATTCAGGCGTGGTGGGATCTGAATCCGGAAGACATT

CTGGGTGCAGACGCCGCAGATTACGTCAAAGTACCGGACACGCTGGACGTCTGGTTTGACTCCGGTTC

AACGCATTCTTCCGTTGTGGATGTGCGTCCTGAGTTCAACGGGCATTCTCCTGATCTGTATCTGGAAG

GTTCTGACCAGCATCGCGGCTGGTTCATGTCTTCCCTGATGATTTCGACGGCAATGAAAGGCAAAGCG

CCTTACAAACAAGTGCTGACTCACGGTTTCACCGTGGATGGTCAGGGCCGCAAAATGTCTAAATCCAT

CGGCAATACCATCGCGCCGCAAGACGTGATGAACAAGCTGGGTGGCGACATTCTGCGTCTGTGGGTC

GCGTCGACGGATTACACCGGCGAAATCGCCGTGTCCGACGAAATCCTCAAACGTGCTGCTGATTCTTA

CCGCCGTATCCGTAACACCGCGCGCTTCCTGCTGGCGAACCTTAACGGTTTCGATCCGGCGCTGCACA

GCGTGGCTCCGGAAGACATGGTGGTGCTGGACCGCTGGGCGGTTGGCCGTGCGAAAGCCGCTCAGGA

AGAAATCATTGCTGCGTATGAAGCCTATGATTTCCATGGCGTTGTTCAGCGTCTGATGCAGTTCTGCT

CGATCGAAATGGGTTCCTTCTATCTGGATATCATTAAAGATCGTCAGTACACCGCGAAAAGCGACAG

CGTTGCACGTCGCAGCTGTCAGACCGCGCTGTATCACATCAGTGAAGCGCTGGTTCGCTGGATGGCAC

CGATCATGTCGTTCACAGCCGATGAAATCTGGGCGGAACTGCCGGGAAGCCGTGAGAAATTCGTCTT

CACCGAAGAGTGGTACGACGGTCTGTTCGGTCTCGCAGGCAACGAATCCATGAACGATGCGTTCTGG

GATGAACTGCTGAAAGTGCGTGGCGAAGTGAACAAAGTGATCGAACAGGCGCGTGCGGATAAACGT

CTGGGCGGTTCTCTGGAAGCAGCGGTTACGCTGTTTGCTGATGATGCGCTGGCAACAGACCTGCGTTC

TCTGGGCAATGAACTGCGCTTTGTGCTGCTGACGTCAGGGGCGAAAGTTGCCGCACTGAGTGATGCA

GATGACGCGGCTCAGTCGAGTGAATTGCTGAAAGGCCTGAAGATTGGTCTGGCGAAAGCAGAAGGCG

ACAAGTGCCCGCGCTGCTGGCATTACACTACCGATTAA

98
DP22 NADH-quinone oxidoreductase subunit C/D

-continued

ATGACAGATTTGACGACGCAAGATTCCGCCCTGCCAGCATGGCATACCCGTGATCATCTCGATGAT

CCGGTTATCGGCGAATTGCGTAACCGTTTTGGGCCAGAGGCCTTTACTGTCCAGGCAACCCGCACCGG

AATTCCCGTGGTGTGGTTCAAGCGTGAACAGTTACTGGAAGCGATTACCTTTTTACGAAAACAGCCAA

AACCTTACGTCATGCTTTTCGATTTGCATGGCTTTGATGAGCGTTTACGTACACACCGCGACGGTTTAC

CGGCTGCGGATTTTTCCGTTTTCTACCACCTGATCTCCGTCGAGCGTAACCGCGACATCATGATCAAA

GTGGCGTTGTCAGAAAACGATCTTCATGTTCCGACGATCACCAAAGTGTTCCCGAACGCTAACTGGTA

CGAACGCGAAACATGGGAAATGTTCGGTATTACCTTCGACGGCCATCCGCACCTGACGCGCATCATG

ATGCCGCAGACCTGGGAAGGGCATCCGCTGCGTAAAGACTATCCGGCGCGCGCCACCGAGTTCGATC

CTTATGAGCTGACTAAGCAAAAAGAAGAACTCGAGATGGAATCGCTGACCTTCAAGCCGGAAGACTG

GGGCATGAAGCGCGGTACCGATAACGAGGACTTTATGTTCCTCAACCTCGGTCCTAACCACCCGTCAG

CGCATGGTGCATTCCGTATTATCCTGCAGCTGGATGGCGAAGAGATTGTCGACTGCGTGCCTGACGTC

GGTTACCACCACCGTGGTGCGGAGAAAATGGGCGAACGCCAGTCATGGCACAGCTACATTCCGTATA

CTGACCGTATCGAATATCTCGGCGGTTGTGTTAACGAAATGCCTTACGTGCTGGCTGTTGAAAAACTC

GCCGGTATCGTGACGCCGGATCGCGTTAACACCATCCGTGTGATGCTGTCTGAACTGTTCCGTATCAA

CAGCCATCTGCTGTACATCTCTACGTTTATTCAGGACGTGGGTGCGATGACGCCGGTATTCTTCGCCTT

TACCGATCGTCAGAAAATTTACGATCTGGTGGAAGCGATCACCGGTTTCCGTATGCACCCGGCCTGGT

TCCGTATCGGTGGCGTAGCGCATGACCTGCCGAAAGGCTGGGACCGCCTGCTGCGTGAATTCCTTGAC

TGGATGCCAGCCCGTTTGGATTCCTACGTCAAAGCGGCGCTGAGAAACACCATTCTGATTGGCCGTTC

CAAAGGCGTGGCCGCGTATAACGCCGACGACGCACTGGCCTGGGGCACCACCGGTGCTGGCCTGCGC

GCAACGGGTATCCCGTTCGATGTGCGTAAATGGCGTCCGTATTCAGGTTATGAAAACTTTGACTTTGA

AGTGCCGACCGGTGATGGCGTCAGTGACTGCTATTCCCGCGTGATGCTGAAAGTGGAAGAACTTCGT

CAGAGCCTGCGCATTCTGGAACAGTGCTACAAAAACATGCCGGAAGGCCCGTTCAAGGCGGATCACC

CGCTGACCACGCCGCCACCGAAAGAGCGCACGCTGCAACACATCGAGACCCTGATCACGCACTTCCT

GCAAGTGTCGTGGGGGCCGGTCATGCCTGCACAAGAATCTTTCCAGATGGTTGAAGCAACCAAAGGG

ATCAACAGCTACTACCTGACCAGTGACGGCAGCACCATGAGCTACCGCACCCGTGTCCGTACGCCGA

GCTTCCCGCATTTGCAGCAGATCCCGTCCGTAATCCGTGGCAGCCTGGTATCCGACCTGATCGTGTAT

CTGGGCAGTATCGATTTTGTAATGTCAGATGTGGACCGCTAA

99
DP22 Protein RecA
ATGGCTATTGATGAGAACAAGCAAAAAGCGTTAGCTGCAGCACTGGGCCAGATTGAAAAGCAATT

CGGTAAAGGCTCCATCATGCGTCTGGGTGAAGATCGCTCCATGGACGTTGAAACGATCTCTACCGGCT

CTTTGTCTCTGGATATCGCGTTAGGTGCCGGCGGTTTGCCAATGGGCCGTATCGTTGAGATCTATGGC

CCGGAATCTTCCGGTAAAACAACGCTGACCTTGCAAGTTATCGCGGCTGCACAGCGTGAAGGCAAAA

CCTGTGCGTTCATCGATGCAGAACACGCCCTGGACCCGATCTACGCTAAAAAACTGGGCGTGGATAT

CGATAACCTGCTGTGTTCTCAGCCAGATACCGGCGAACAGGCTCTGGAAATCTGTGACGCGCTGACCC

GTTCAGGCGCTGTTGACGTGATCATCGTTGACTCCGTTGCCGCACTGACACCGAAAGCGGAAATCGA

AGGCGAAATTGGTGACTCTCACATGGGCCTCGCGGCACGTATGATGAGCCAGGCGATGCGTAAGCTG

GCCGGTAACCTGAAAAACGCCAACACCTTGCTGATCTTCATCAACCAGATCCGTATGAAAATTGGTGT

GATGTTCGGTAACCCGGAAACCACCACCGGCGGTAACGCCCTGAAATTCTACGCTTCTGTGCGTCTGG

ATATCCGCCGTATCGGCGCGATCAAAGAAGGCGATGTGGTTGTCGGTAGCGAAACGCGTGTGAAAGT

GGTGAAGAACAAAATCGCTGCGCCATTTAAACAAGCTGAATTCCAGATCATGTACGGCGAAGGCATC

AATATCAACGGCGAGCTGATTGATCTCGGCGTGAAGCACAAGCTGATCGAAAAAGCCGGTGCATGGT

-continued

ATAGCTACAACGGTGAGAAGATTGGTCAGGGTAAAGCGAACTCCTGCAACTTCCTGAAAGAAAACCC

GAAAGTGGCTGCCGAGCTGGATAAAAAACTGCGTGATATGCTGTTGAGCGGTACCGGTGAACTGAGT

GCTGCGACCACGGCTGAAGATGCTGACGACAACATGGAAACCAGCGAAGAGTTTTAA

100
DP22 RNA polymerase sigma factor RpoD
ATGGAGCAAAACCCGCAGTCACAGCTTAAGCTACTTGTCACCCGTGGTAAGGAGCAAGGCTATCT

GACCTATGCTGAGGTCAATGACCATCTGCCGGAAGATATCGTCGATTCCGACCAGATCGAAGACATC

ATCCAGATGATTAACGACATGGGCATCCAGGTACTTGAAGAAGCACCGGACGCCGATGATTTGATGC

TGGCCGAAAACCGCCCTGATACCGATGAAGACGCTGCAGAAGCCGCGGCGCAGGTGCTTTCCAGCGT

TGAATCCGAAATTGGCCGTACCACCGACCCTGTGCGTATGTATATGCGCGAGATGGGTACCGTTGAGT

TGCTGACCCGTGAAGGCGAAATCGACATCGCCAAACGTATCGAAGACGGTATCAATCAGGTCCAGTG

CTCCGTTGCTGAATATCCTGAAGCTATCACTTATTTGTTAGAGCAATATGACCGTGTGGAAGCAGGCG

AAGTACGTCTGTCTGACCTGATCACCGGTTTTGTTGACCCGAACGCCGAAGAAGAAATCGCACCAACT

GCGACTCACGTGGGTTCTGAACTGACCACTGAAGAGCAGAATGATGACGACGAAGACGAAGATGAA

GACGACGACGCTGAAGACGACAACAGCATCGATCCGGAACTGGCTCGCCAGAAGTTCACCGAACTGC

GTGAACAGCATGAAGCGACGCGTCTGGTCATCAAGAAAAACGGCCGTAGTCACAAGAGCGCAGCAG

AAGAAATCCTGAAGCTGTCCGATGTGTTCAAACAGTTCCGTCTGGTGCCAAAACAGTTCGATTTCCTG

GTTAACAGCATGCGTTCCATGATGGATCGCGTTCGTGCTCAGGAACGTCTGATCATGAAAGTGTGCGT

TGAACAGTGCAAAATGCCGAAGAAAAACTTCGTCAATCTGTTCGCCGGTAACGAAACCAGCGATACC

TGGTTTGATGCCGCTCTGGCAATGGGTAAACCATGGTCCGAGAAGCTGAAAGAAGTCACCGAAGACG

TGCAACGCGGCCTGATGAAACTGCGTCAGATCGAAGAAGAAACCGGCCTGACTATCGAACAGGTTAA

AGACATCAACCGTCGCATGTCGATCGGCGAAGCGAAAGCCCGTCGCGCGAAGAAAGAGATGGTTGA

AGCAAACTTACGTCTGGTTATTTCTATCGCCAAGAAATACACCAACCGTGGTCTGCAGTTCCTTGACC

TGATCCAGGAAGGTAACATCGGCCTGATGAAAGCCGTTGATAAGTTTGAATATCGCCGTGGTTATAA

GTTCTCAACTTATGCGACCTGGTGGATCCGTCAGGCTATCACCCGCTCCATCGCCGACCAGGCGCGTA

CCATCCGTATCCCGGTACATATGATTGAGACGATCAACAAACTCAACCGTATCTCCCGTCAGATGCTG

CAAGAGATGGGCCGCGAACCGACACCGGAAGAGCTGGCTGAGCGTATGTTGATGCCGGAAGACAAA

ATCCGCAAAGTGCTGAAAATTGCCAAAGAGCCAATCTCCATGGAAACGCCAATCGGCGACGATGAAG

ATTCGCATCTGGGCGATTTCATCGAGGATACCACCCTCGAGCTGCCACTGGATTCTGCGACGTCTGAA

AGCCTGCGTTCTGCAACGCATGACGTTCTGGCTGGCCTGACTGCACGTGAAGCGAAAGTTCTGCGTAT

GCGTTTCGGTATCGATATGAACACTGACCACACGCTGGAAGAAGTGGGCAAACAGTTCGACGTGACC

CGTGAGCGTATCCGTCAGATCGAAGCGAAAGCGTTGCGTAAACTGCGCCACCCGAGCCGCTCCGAAG

TACTGCGCAGCTTCCTGGACGATTAA

101
DP22 DNA-directed RNA polymerase subunit beta'
GTGAAAGACTTACTAAAGTTTCTGAAAGCGCAAACTAAGACCGAAGAGTTTGATGCGATCAAAAT

TGCTCTGGCATCGCCAGACATGATCCGTTCTTGGTCTTTTGGTGAAGTTAAGAAGCCAGAAACCATTA

ACTACCGTACGTTCAAACCAGAACGTGACGGCCTTTTCTGTGCCCGTATTTTCGGACCAGTAAAAGAC

TACGAATGCCTGTGCGGTAAGTACAAGCGTTTAAAACATCGCGGCGTGATCTGCGAGAAGTGCGGCG

TTGAAGTGACCCAGACTAAAGTACGCCGTGAGCGTATGGGCCACATCGAACTGGCTTCCCCGACTGC

ACACATCTGGTTCCTGAAATCGCTGCCATCGCGCATCGGTTTGCTGCTGGATATGCCACTGCGTGACA

TCGAACGTGTTCTGTACTTCGAATCCTATGTGGTTATCGAAGGCGGCATGACTAACCTCGAAAAACGC

-continued

CAGATCCTGACTGAAGAGCAGTATCTGGATGCGTTGGAAGAGTTTGGTGATGAGTTCGACGCGAAGA

TGGGTGCGGAAGCTATTCAGGCCCTGTTGAAAAACATGGATCTGGAAGCAGAGTGCGAGCAACTGCG

TGAAGAGTTGAACGAAACCAACTCCGAAACCAAACGTAAGAAGCTGACCAAGCGTATCAAGCTGCTG

GAAGCGTTCGTTCAGTCTGGTAACAAACCAGAGTGGATGATCCTGACTGTGCTGCCGGTACTGCCACC

AGACTTGCGTCCATTGGTTCCGTTGGACGGCGGCCGTTTCGCAACGTCGGATCTGAACGATCTGTATC

GTCGCGTGATCAACCGTAACAACCGTCTGAAACGCCTGCTGGATCTGGCTGCGCCAGACATCATCGTA

CGTAACGAAAAACGTATGCTGCAAGAAGCGGTAGATGCTTTGCTGGATAACGGCCGTCGCGGTCGTG

CTATCACCGGCTCTAACAAGCGTCCGCTGAAATCTCTGGCAGACATGATTAAAGGTAAACAGGGTCG

TTTCCGTCAGAACTTGCTGGGTAAACGTGTCGACTACTCTGGTCGTTCCGTTATCACCGTAGGTCCATA

CCTGCGTCTGCACCAGTGTGGTCTGCCGAAGAAAATGGCACTGGAACTGTTCAAACCGTTCATCTACG

GCAAGCTGGAACTGCGTGGCCTGGCCACCACCATCAAAGCCGCGAAGAAAATGGTTGAGCGCGAAG

AAGCTGTCGTTTGGGACATCCTGGACGAAGTTATCCGCGAACACCCGGTACTGCTGAACCGTGCACC

AACCCTGCACCGTTTGGGTATCCAGGCGTTTGAACCGGTTCTGATCGAAGGTAAAGCAATCCAGCTGC

ACCCGCTGGTTTGTGCGGCATATAACGCCGACTTCGATGGTGACCAGATGGCTGTTCACGTACCGTTG

ACGCTGGAAGCCCAGCTGGAAGCGCGTGCGTTGATGATGTCTACCAACAACATCCTGTCACCTGCGA

ACGGCGAGCCAATCATCGTTCCTTCTCAGGACGTTGTATTGGGTCTGTACTACATGACCCGTGACTGT

GTTAACGCCAAAGGCGAAGGCATGGTTCTGACCGGTCCTAAAGAAGCTGAGCGTATTTACCGCGCCG

GTTTGGCCTCTCTGCATGCGCGTGTCAAAGTGCGTATTACAGAAGAGATCAAAAATACCGAAGGCGA

AGTTACGCACAAGACGTCGATTATCGACACGACAGTTGGTCGCGCCATCCTTTGGATGATCGTACCTA

AAGGTCTGCCGTTCTCTATCGTCAACCAGCCTCTGGGCAAAAAAGCTATCTCCAAAATGCTGAACACC

TGTTACCGCATTTTGGGCCTGAAGCCGACCGTTATTTTTGCTGACCAGATCATGTACACCGGTTTTGCT

TACGCTGCCCGTTCAGGCGCGTCAGTAGGTATCGATGACATGGTAATCCCTGCGAAGAAAGCAGAGA

TCATCGAAGAAGCAGAAACCGAAGTTGCTGAAATCCAGGAACAGTTCCAGTCTGGTCTGGTCACTGC

TGGCGAACGCTATAACAAAGTGATCGACATCTGGGCTGCGGCCAACGAACGTGTTGCTAAGGCAATG

ATGGAAAACTTGTCTGTTGAAGACGTCGTCAACCGTGACGGTGTTGTTGAACAGCAGGTTTCCTTCAA

CAGTATCTTTATGATGGCCGACTCCGGTGCGCGTGGTTCTGCTGCACAGATTCGTCAGCTGGCCGGTA

TGCGTGGCCTGATGGCGAAACCAGATGGTTCCATCATTGAAACGCCAATCACCGCGAACTTCCGTGA

AGGTCTGAACGTACTCCAGTACTTCATCTCTACTCACGGTGCTCGTAAAGGTTTGGCGGATACCGCAC

TTAAAACGGCTAACTCCGGTTATCTGACCCGTCGTCTGGTTGACGTCGCGCAGGATCTGGTTGTGACC

GAAGACGACTGTGGGACTCACGAAGGCATCATGATGACTCCGGTCATCGAAGGTGGCGACGTTAAAG

AACCACTGCGTGAGCGTGTACTGGGTCGTGTGACTGCAGAAGATATCCTCAAGCCGGGTACGGCGGA

TATCCTGGTTCCACGTAACACCCTGCTTCACGAGAAGACGTGTGATCTGTTAGAAGAGAACTCAGTCG

ACAGCGTGAAAGTACGTTCAGTCGTAAGTTGCGAAACCGACTTTGGTGTGTGTGCAAACTGCTACGGT

CGCGACCTGGCACGTGGTCACATCATCAACAAAGGTGAAGCGATCGGTGTTATTGCAGCACAGTCCA

TCGGTGAGCCGGGTACCCAGCTGACGATGCGTACGTTCCACATCGGTGGTGCGGCATCTCGTGCGGC

AGCGGAATCCAGCATCCAGGTTAAGAACACTGGTACCATTAAACTGAGCAACCACAAGCACGTTAGC

AACTCTAACGGCAAACTGGTGATCACTTCCCGTAACACTGAGCTGAAATTGATCGACGAATTCGGTCG

TACCAAAGAAAGCTATAAAGTGCCTTACGGTTCCGTGATGGGCAAAGGCGATGGCGCATCAGTTAAC

GGCGGCGAAACCGTTGCTAACTGGGATCCGCACACCATGCCAGTTATCAGTGAAGTGAGTGGTTTCA

TTCGCTTTGCCGATATGGTGGATACTCAGACCATCACACGCCAGACCGACGACCTGACCGGTTTGTCT

TCTCTGGTTGTTCTGGACTCTGCAGAGCGTACCGGTAGCGGTAAAGACCTGCGTCCGGCACTGAAAAT

-continued

CGTTGACGCTAAAGGCGACGACGTATTGATTCCAGGTACTGATATGCCTGCTCAATACTTCCTGCCAG

GTAAAGCGATTGTTCAGCTGGAAGATGGTACTCAGATCCACTCTGGTGACACCCTGGCGCGTATTCCT

CAGGAATCCGGCGGTACCAAGGACATCACCGGTGGTCTGCCACGCGTTGCTGACCTGTTCGAAGCAC

GTCGTCCGAAAGAGCCTGCAATCCTTGCTGAAATCAGCGGGATCATCTCCTTCGGTAAAGAAACCAA

AGGCAAACGTCGTCTGGTAATTTCTCCGTTAGATGGCAGCGATGCTTACGAAGAAATGATCCCTAAAT

GGCGTCAGCTGAACGTGTTCGAAGGCGAAGTTGTGGAACGTGGTGACGTCGTATCCGACGGCCCTGA

GTCTCCGCACGACATCTTGCGTTTACGTGGTGTTCACGCGGTTACCCGCTACATCACCAACGAAGTGC

AGGAAGTTTACCGTCTGCAAGGCGTTAAGATTAACGATAAGCACATCGAAGTTATCGTTCGTCAGAT

GTTGCGTAAAGGCACCATCGTTAGCGCTGGTGGCACTGACTTCCTGGAAGGCGAGCAGGCAGAAATG

TCTCGCGTTAAAATCGCTAACCGTAAGCTGGAAGCTGAAGGCAAAATCACGGCAACATTCAGCCGTG

ACCTGCTCGGTATCACCAAGGCATCCCTGGCGACCGAATCCTTCATCTCTGCAGCGTCGTTCCAGGAA

ACCACGCGTGTTCTTACCGAAGCGGCTGTTGCCGGTAAACGTGATGAACTGCGTGGCCTGAAAGAGA

ACGTTATCGTTGGCCGTCTGATCCCAGCCGGTACCGGTTACGCTTATCATCAGGATCGTGCACGCCGT

AAAGCACAAGGCGAAGTGCCAGTTGTACCGCAAGTCAGCGCGGATGAAGCAACGGCTAACCTGGCT

GAACTGCTGAACGCAGGTTTCGGTAACAGCGACGATTAA

102
DP67 Glutamine--tRNA ligase
ATGAGTGAGGCTGAAGCCCGCCCAACTAACTTTATTCGTCAGATTATCGACGAAGATCTGGCGAAC

GGTAAGCACAGTTCAGTGCACACCCGCTTCCCGCCTGAGCCGAATGGCTATCTGCATATTGGCCATGC

GAAATCAATCTGCCTGAACTTTGGTATCGCTCAGGATTATCAGGGGCAGTGTAACCTGCGCTTTGATG

ACACTAACCCGGTGAAAGAAGATCTGGAGTTTGTTGAATCAATCAAGCGTGATGTGCAGTGGCTGGG

CTTTAAGTGGAGTGGTGACGTACGCTACTCATCTGACTATTTCGAGCAACTGCACAATTATGCCGTTG

AGCTGATTAGTAAAGGGCTGGCGTACGTTGATGAACTGTCACCGGAGCAGATCCGTGAATACCGTGG

CAGCCTGACCTCAGCGGGTAAAAACAGCCCCTTCCGCGATCGCAGCGTGGACGAAAACCTTGCGCTC

TTTGCAAAAATGCGCGCGGGCGGCTTTGCCGAGGGCACCGCGTGTTTACGAGCCAAAATTGATATGG

CTTCCAACTTTATCGTTCTGCGCGATCCGGTGATCTACCGCATCAAATTTGCCGAACATCATCAGACC

GGCAATAAGTGGTGCATCTATCCGATGTATGACTTTACCCACTGCATCTCTGATGCGCTGGAAGGCAT

TACTCACTCACTGTGTACGCTGGAATTCCAGGATAACCGTCGCCTGTACGACTGGGTGCTGGATAACA

TCACCATTCCGGTTCATCCGCGTCAGTATGAATTCTCTCGCCTGAATCTTGAATATGCCATCATGTCCA

AGCGTAAGTTGAGTCAGTTGGTGACCGAGAACGTGGTGGAAGGTTGGGATGATCCCCGTATGCTGAC

TGTTTCGGGTTTGCGCCGCCGTGGCTACACTGCGGAATCCATCCGTGAATTCTGCCGCCGCATTGGGG

TGACCAAGCAGGACAATATTGTTGAAATGGCCGCTCTGGAATCCTGTATCCGTGACGACCTCAATGA

GAATGCCCCGCGTGCCATGGCAGTGATGGATCCGGTAAAAGTGGTGATAGAAAATCTGCCTGCGCAT

CACGATGAGGTGATCACCATGCCGAATCATCCGAGCAAGCCGGAAATGGGTACCCGCGAAGTCCCGT

TCAGTCGTGAGATCTACATCGATCGTGCTGACTTCCGTGAGGAAGCAAACAAGCAGTACAAGCGGCT

GGTGCTGGGCAAAGAAGTGCGTCTGCGTAACGCTTATGTGATCAAAGCCGAGCGCGTGGCAAAGGAC

GATGAAGGCAACATTACCTGCCTGTTCTGTACCTGTGATGTGGATACTCTGAGCAAGGATCCGGCCGA

CGGGCGTAAAGTGAAGGGCGTTATCCACTGGGTGTCAGCTGTTCATGCCCTTCCGGCAGAGTTCCGTC

TGTACGATCGGCTGTTCAGCGTACCGAATCCGGGGGCGGCAGAAGACTTCCTGGCCAGCATCAACCC

GGAATCTCTGGTGATCCGTCAGGGCTTCGTGGAGCCCGGGATGCAGCAGGCGGAGGCGTCAGCCCCG

TATCAGTTTGAGCGTGAAGGCTACTTCTGCGCTGACAGTGTCTACTCCAGTGCCAGCAATCTGGTGTT

-continued

CAACCGCACCGTTGGCCTGCGTGACACCTGGGCGAAAGTCGGCGAGTAA

103
DP67 DNA gyrase subunit B
ATGTCGAATTCTTATGACTCCTCCAGTATCAAAGTTCTGAAAGGGCTCGATGCTGTACGCAAACGC

CCGGGTATGTATATCGGCGATACGGATGACGGTACCGGTCTGCATCACATGGTATTTGAGGTCGTGGA

TAACGCCATTGACGAAGCGCTCGCCGGTCACTGTTCCGATATTCTTGTCACTATTCATGCCGATAACT

CTGTTTCCGTTGTGGATGATGGCCGTGGTATTCCGACCGGTATTCACGAAGAAGAAGGCATCTCAGCC

GCTGAAGTGATCATGACCGTGCTGCACGCCGGCGGTAAGTTCGACGATAACTCTTATAAAGTCTCCGG

CGGCCTGCACGGCGTGGGCGTGTCAGTGGTGAACGCCCTGTCGGAAAAACTGGAGCTGACCATTCGT

CGCGAAGGGAAAGTTCACCAGCAGACTTACGTCCACGGCGTGCCACAGGCCCCGTTGAGTGTGAGCG

GTGAAACTGACCTGACGGGAACGCGCGTGCGTTTCTGGCCCAGCCATCAGACGTTCACTAACGTCGT

GGAGTTCGAGTACGAAATTTTGGCAAAGCGCCTGCGTGAGCTGTCGTTCCTGAACTCCGGTGTATCAA

TCAAGCTGGAAGATAAGCGCGACGGTAAAAGCGACCATTACCACTATGAAGGTGGTATCAAGGCGTT

TGTTGAGTACCTCAACAAGAACAAAACCCCGATCCACCCGAATGTGTTCTATTTCTCAACCGAGAAAG

ACGGCATTGGTGTGGAAGTGGCGCTGCAGTGGAACGATGGTTTCCAGGAAAATATCTACTGCTTTACC

AACAACATCCCACAGCGGGATGGGGGCACGCACCTCGTTGGTTTCCGTACCGCGATGACCCGTACCC

TGAATGCCTACATGGATAAAGAAGGCTACAGCAAGAAAGCCAAAGTCAGCGCCACCGGTGACGACG

CGCGTGAAGGCCTGATTGCTGTGGTGTCGGTGAAAGTGCCGGATCCGAAATTCTCTTCACAGACCAA

AGATAAACTGGTCTCTTCTGAAGTGAAAACCGCCGTTGAGCAGCAGATGAACGAGCTGCTGGCAGAA

TACCTGCTGGAAAACCCGACCGATGCCAAAATCGTCGTCGGTAAAATCATTGATGCGGCCCGCGCCC

GTGAAGCGGCCCGTCGTGCACGTGAAATGACCCGCCGTAAAGGCGCGCTGGATCTGGCAGGCCTGCC

GGGCAAACTGGCGGACTGCCAGGAGCGTGATCCGGCTCTGTCCGAAATTTACCTGGTGGAAGGGGAC

TCTGCGGGCGGCTCTGCCAAGCAGGGACGTAACCGTAAAAACCAGGCCATCCTGCCGCTGAAGGGTA

AAATCCTCAACGTCGAGAAGGCGCGCTTTGACAAGATGCTCGCGTCGCAGGAAGTCGCTACGCTGAT

CACCGCGCTGGGCTGTGGTATCGGTCGTGATGAGTACAACCCCGACAAACTGCGCTATCACAGCATC

ATTATCATGACCGATGCCGACGTGGATGGCTCGCATATCCGTACCCTGCTGCTGACCTTCTTCTACCGT

CAGATGCCAGAAATCATTGAGCGTGGTCATGTCTATATTGCCCAGCCACCGCTGTACAAGGTGAAAA

AAGGCAAGCAGGAGCAGTATATTAAAGACGACGATGCGATGGATCAGTACCAGATCGCCATCGCGCT

GGACGGTGCCACGCTGCATGCGAACGCCAGCGCCCCGGCCCTTGGCGGTAAGCCACTGGAAGATCTG

GTGTCTGAGTTCAACAGCACGCGCAAGATGATCAAGCGCATGGAGCGCCGTTACCCGGTGGCCTTGC

TGAATGCGCTGGTCTACAACCCGACCCTGAGCGATTTGACCGCCGAAGCGCCGGTACAGAGCTGGAT

GGATGTGCTGGTGAAGTATCTGAACGACAACGACCAGCACGGCAGCACCTACAGCGGTCTGGTACGC

GAAAATCTGGAGCTGCATATCTTTGAGCCGGTACTGCGTATCAAAACCCACGGCGTGGATACCGATT

ATCCGCTCGACAGCGAGTTTATGCTCGGCGGCGAATACCGTAAGCTCTGCGCGCTGGGTGAGAAGCT

GCGTGGCCTGATCGAAGAAGACGCGTTCATCGAACGTGGTGAGCGGCGTCAGCCGATTGCCAGCTTT

GAGCAGGCGATGGAGTGGCTGGTTAAAGAGTCACGCCGTGGCCTGACGGTTCAGCGTTATAAAGGTC

TGGGCGAGATGAACCCGGATCAGCTGTGGGAAACCACCATGGATCCGGACAGCCGCCGTATGCTGCG

CGTGACCATCAAAGATGCCGTGGCCGCCGACCAGCTGTTCACCACCCTGATGGGGGATGCGGTAGAG

CCCCGTCGTGCCTTTATTGAAGAGAACGCCCTGCGCGCGGCAAACATCGATATCTGA

104
DP67 Isoleucine--tRNA ligase
ATGAGTGACTATAAATCTACCCTGAATTTGCCGGAAACGGGGTTCCCGATGCGTGGCGATCTGGCC

AAACGCGAACCGGGTATGCTGCAACGTTGGTATGATGACAAGCTGTACGGCATCATTCGCGAAGCCA

-continued

AGAAAGGGAAAAAAACCTTTATCCTGCACGATGGCCCTCCTTACGCCAACGGCAGCATTCATATTGG

TCACTCCGTTAACAAGATTCTGAAAGACATTATCGTTAAGTCGAAAGGCATGGCGGGCTATGACTCGC

CTTATGTACCGGGTTGGGACTGCCACGGTCTGCCTATCGAGCATAAAGTTGAGCAGATGATCGGTAA

GCCGGGAGAGAAAGTCAGCGCCGCTGAGTTCCGTGCTGCCTGCCGCAAATACGCTGCCGAGCAGGTG

GAAGGGCAGAAAGCCGACTTTATCCGTCTGGGTGTGTTGGGTGACTGGGATCGTCCGTATCTGACAAT

GAACTTCCAGACCGAAGCCAATATTATCCGTGCGCTGGGTAAAATCATCGGTAACGGGCACCTGCAC

AAAGGGGCCAAGCCGGTACACTGGTGCCTGGACTGCCGTTCTGCCCTGGCTGAGGCGGAAGTGGAGT

ACTACGATAAAACCTCTCCGTCTATCGATGTCATGTTCAATGCGACTGATAAAGAGGGGGTACAGGC

CAAATTTGCGGCAACGAATGTTGACGGCCCGATCTCGCTGGTGATCTGGACTACCACGCCGTGGACC

ATGCCGGCTAACCGCGCTATCTCACTGCATCCTGAATTCGACTACCAGCTGGTACAGATTGAAGGCCG

TGCTCTGATCCTCGCCAAAGAGATGGTTGAGAGCGTGATGCAGCGCGTTGGTGTTGCCGCCTGGACCG

TGCTGGGCGAAGCGAAAGGGGCAGACCTGGAGCTGATGGGCTTCCAGCATCCGTTCCTCGACCATAC

CTCTCCGGTTGTGCTGGGTGAGCATGTCACGCTGGAAGCCGGTACCGGTGCGGTCCATACCGCACCAG

GCCATGGCCCGGACGACTATGTTATCGGTCAGAAATACGGTATCGAAGTGGCTAACCCGGTCGGCCC

GGATGGCTGCTACCTGCCGGGAACCTACCCGACGCTGGATGGTGTGAACGTCTTTAAAGCCAACGAT

ATGATCGTTGAACTGCTGCGTGAAAAGGGTGCTCTGCTGCACGTTGAGAAACTGTTCCACAGCTATCC

ACACTGCTGGCGTCATAAAACGCCCATCATCTTCCGCGCTACGCCACAGTGGTTTATCAGCATGGATC

AGAAGGGCCTGCGTGCGCAGTCGCTGAAAGAGATCAAGGGCGTGCAGTGGATCCCGGACTGGGGTC

AGGCACGTATTGAATCGATGGTCGCGAACCGTCCTGACTGGTGTATTTCCCGTCAGCGTACCTGGGGC

GTGCCGATGGCGCTGTTCGTCCATAAAGACACCGAACAGCTGCACCCGGATTCGCTGGAGCTGATGG

AGAAAGTGGCGAAGCGGGTTGAGCAGGACGGCATTCAGGCATGGTGGGATCTTGATGCCCGCGACCT

GATGGGCGCCGATGCTGACAACTACGTTAAAGTCCCGGATACCCTGGACGTCTGGTTTGACTCCGGTT

CAACCAGCTACTCGGTCGTCGATGCCCGCCCTGAATTTGACGGCAATGCCCCTGACCTGTATCTGGAA

GGATCGGATCAGCACCGCGGCTGGTTTATGTCCTCACTGATGATCTCGACCGCGATGAAAGGCAAAG

CGCCTTACCGTCAGGTACTGACGCACGGCTTCACCGTCGATGGTCAGGGCCGTAAGATGTCCAAGTCA

CTGGGCAATACTGTCAGCCCGCAGGATGTGATGAACAAACTGGGCGCCGATATTCTGCGCCTGTGGG

TCGCCTCTACGGACTACTCCGGTGAGATCGCCGTATCCGACGAGATCCTTAAACGCTCTGCCGACAGC

TATCGCCGCATCCGTAACACCGCACGTTTCCTGCTGGCAAACCTTGCCGGTTTTAATCCGGAAACCGA

TAGGGTGAAACCGGAAGAGATGGTGGTGGTGGATCGCTGGGCCGTTGGCCGTGCGCTGGCGGCACAG

AATGATATCGTAGCCTCGTATGAAGCTTATGACTTCCATGAAGTCGTGCAGCGTCTGATGCAGTTCTG

TTCGGTTGAGATGGGCTCCTTCTACCTGGATATCATCAAGGATCGTCAGTACACCGCGAAGGCCGATG

GCCTGGCGCGTCGCAGCTGTCAGACGGCGCTGTGGTATATCGTGGAAGCGCTGGTGCGCTGGATGGC

ACCGATTATGTCCTTCACTGCCGATGAAATCTGGGGTTACCTGCCGGGTAAACGCAGCCAGTATGTCT

TTACCGAAGAGTGGTTTGACGGGCTGTTCAGCCTGGAGGACAATCAGCCGATGAACGACAGTTACTG

GGCAGAACTGCTGAAAGTACGCGGTGAAGTCAACAAGGTGATCGAGCAGGCCCGCGCTGATAAGCG

GATTGGCGGGTCTCTGGAAGCCAGCGTGACGCTGTATGCTGACGCAGACCTGGCCGCGAAGCTGACC

AGCCTGGGTGAGGAGCTGCGCTTTGTGTTGCTGACTTCCGGGGCGCAGGTTGCGGATTATGCGCAGGC

CACCGCTGATGCACAGCAAAGCGAAGGGGTAAAAGGTCTGAAAATTGCCCTGAGCAAAGCGGAAGG

CGAGAAGTGCCCGCGCTGCTGGCATTACACTAACGATATCGGCCAGAATGCTGAACACGCTGACGTG

TGCGGCCGTTGTGTCACTAACGTCGCGGGCAGCGGCGAACAGCGTAAGTTTGCATGA

-continued

105
DP67 NADH-quinone oxidoreductase subunit C/D
GTGATCGGCGAGCTGCGTAATCGTTTTGGGCCTGATGCCTTTACAGTACAAGCGACCCGTACCGGC

GTGCCGGTGGTCTGGGTAAAACGTGAGCAGTTGCTTGAGATTATTGAGTTCCTGCGCAAGCTGCCTAA

ACCCTATGTGATGCTGTATGACCTGCATGGCATGGATGAGCGCCTGCGTACTCACCGTGCCGGTTTAC

CGGCGGCGGATTTTTCCGTTTTCTATCACTTCATCTCCATTGAACGTAACCGCGACATCATGCTCAAGG

TGGCGTTGTCTGAAAACGATTTGAATGTGCCCACCATCACCAAAATTTTCCCGAATGCCAACTGGTAT

GAGCGTGAAACCTGGGAGATGTTTGGTATCAATGTTGAAGGCCACCCGCACCTGACGCGCATTATGA

TGCCGCAGAGCTGGGAAGGGCATCCGCTGCGCAAAGATTACCCTGCGCGTGCGACCGAGTTCGATCC

GTTTGAACTGACCAAGCAGAAAGAAGATCTGGAGATGGAATCTCTGACCTTCAAGCCTGAAGACTGG

GGCATGAAGCGTTCGACCAACAATGAGGACTTCATGTTCCTCAACCTGGGCCCGAACCACCCTTCTGC

GCACGGCGCGTTCCGTATCATCCTGCAACTGGACGGTGAAGAGATCGTCGACTGCGTGCCGGATATC

GGATACCACCATCGTGGTGCCGAAAAAATGGGTGAACGCCAGTCCTGGCACAGCTACATTCCGTATA

CCGACCGTATTGAGTATCTCGGCGGCTGCGTAAACGAAATGCCGTACGTGCTGGCGGTAGAAAAGCT

GGCTGGTATCAAAGTCCCTGAGCGCGTGGAAGTCATTCGCGTGATGCTATCAGAGCTGTTCCGTATAA

ACAGCCACCTGCTGTACATCTCTACGTTTATCCAGGACGTCGGTGCTATGTCCCCGGTGTTCTTTGCCT

TTACTGACCGCCAGAAAATTTACGACGTGGTAGAAGCCATTACCGGCTTCCGTATGCATCCGGCCTGG

TTCCGCATTGGTGGCGTGGCGCATGATCTGCCTAAAGGCTGGGAGCGCCTGCTGCGTGAGTTCCTGGA

TTGGATGCCTAAGCGTCTGAAAGCCTATGAGCAGACCGCACTGAAAAACTCCGTGCTTATTGCCCGTT

CCAAAGGGGTTTCTGCCTATAACATGGAAGAAGCACTGGCCTGGGGCACGACGGGGGCTGGCCTGCG

TGGTACCGGTCTGGACTTTGATGTGCGTAAATGGCGTCCATATTCCGGTTATGAAAACTTCGATTTCG

AAGTGCCAATCGGAGATGGCGTAAGCTGTGCTTACACCCGTGTCATGCTGAAGATGGAAGAGATGCG

CCAGAGTATGCGCATCCTGGAACAGTGCCTGAAGAACATGCCAGCAGGCCCGTTCAAGGCTGACCAT

CCGCTGACCACGCCGCCGCCGAAAGAGCGCACGCTGCAGCATATCGAAACCCTGATCACTCACTTCC

TGCAGGTTTCGTGGGGCCCGGTAATGCCGGCAAACGAATCCTTCCAGATGATTGAAGCGACCAAAGG

GATCAACAGTTACTACCTGACCAGTGATGGCAGCACGATGAGCTACCGCACCCGCGTGCGTACGCCG

AGCTTCCCGCATTTGCAACAGATCCCATCGGTGATCAACGGCAGCCTGGTATCCGATCTGATCGTATA

CCTCGGTAGTATCGATTTTGTTATGTCAGACGTGGACCGCTAA

106
DP67 Protein RecA
ATGGCTATCGACGAAAACAAGCAAAAAGCACTGGCAGCAGCGCTGGGCCAGATTGAAAAGCAGT

TTGGTAAAGGCTCCATCATGCGCCTGGGTGAAGACCGCACCATGGATGTGGAAACCATCTCAACCGG

TTCTTTATCACTGGATATCGCGCTGGGTGCCGGTGGTTTACCAATGGGCCGTATCGTTGAAATCTATG

GCCCGGAGTCTTCCGGTAAAACCACCCTGACGCTGCAGGTTATCGCTTCTGCACAGCGTAAAGGGAA

AACCTGTGCATTTATCGATGCCGAGCATGCTCTGGACCCGGTCTACGCTAAAAAACTGGGCGTGGATA

TCGATAACTTGCTGTGTTCTCAGCCGGATACCGGTGAGCAGGCGCTGGAAATCTGTGATGCGCTGGCC

CGTTCCGGTGCGGTTGACGTCATCATCGTCGACTCCGTAGCGGCGTTGACACCAAAAGCAGAAATCG

AAGGTGAAATCGGTGACTCTCATATGGGCCTTGCGGCACGTATGATGAGCCAGGCGATGCGTAAGCT

GGCCGGTAACCTGAAGAACTCCGGTACGCTGCTGATCTTTATCAACCAGATCCGTATGAAAATTGGCG

TGATGTTCGGTAACCCGGAAACCACTACCGGTGGTAACGCTCTGAAATTCTACGCTTCTGTCCGTCTG

GATATTCGCCGCATCGGCGCGATCAAAGAGGGTGATGAAGTGGTGGGTAGCGAAACCCGCGTTAAAG

TGGTGAAAAACAAAATCGCAGCACCGTTTAAACAGGCTGAGTTCCAGATCATGTACGGCGAAGGTAT

CAACGTTTACGGTGAGCTGGTCGACCTGGGCGTGAAGCACAAGCTGATCGAAAAAGCCGGTGCCTGG

-continued

TACAGCTATAACGGTGACAAGATTGGTCAGGGTAAAGCCAACTCAGGTAACTTCCTGAAAGAGAACC

CGGCTATCGCTAACGAAATCGAAGCAAAACTGCGTGAAATGCTGTTGAACAGCCCGGACGATAAGCC

TGATTTTGTTCCGGCTCCGCATGAAGCCGATAGTGAAGTTAACGAAGATATCTAA

107
RNA polymerase sigma factor RpoD
ATGGAGCAAAACCCGCAGTCACAGCTTAAGCTACTTGTCACCCGTGGTAAGGAGCAAGGCTATCT

GACCTATGCCGAGGTCAATGACCATCTGCCGGAAGATATCGTCGACTCCGATCAGATTGAAGACATC

ATTCAGATGATCAACGACATGGGCATTCAGGTTGTAGAAGAAGCGCCTGATGCCGATGATTTGATGC

TGAATGAGAACAACAACGACACGGACGAAGACGCTGCCGAAGCGGCTGCTCAGGTATTATCCAGCGT

AGAATCTGAAATCGGACGTACCACCGACCCGGTGCGCATGTACATGCGCGAAATGGGGACGGTTGAA

CTGCTGACGCGTGAAGGCGAGATCGATATCGCCAAACGCATCGAAGAGGGTATCAACCAGGTACAGT

GTTCCGTTGCTGAATATCCTGAAGCGATTACTTACCTGCTTGAGCAATATGACCGTGTTGAAGCGGGC

GAAGCGCGCCTGTCGGATCTGATCACCGGTTTTGTCGACCCGAATGCCGAAGCAGAGATCGCCCCTA

CTGCGACTCACGTGGGTTCAGAACTTTCCGCTGAAGAGCGTGATGACGAAGAAGAAGACGAAGAGTC

TGACGACGACAGCTCGGATGATGACAACAGCATCGATCCGGAACTGGCGCGGGAAAAAATTCAACGA

CCTGCGCGTTCAGTACGAAACCACCCGTACCGTTATCAAAGCGAAAAGCCGCAGCCACGCTGATGCC

ATCGCTGAGATCCAGAATCTGTCCGACGTGTTCAAGCAGTTCCGCCTGGTGCCGAAGCAGTTCGACTT

CCTGGTGAACAGCATGCGCACCATGATGGATCGCGTCCGTACTCAGGAACGCCTGATCCTCAAGCTGT

GCGTAGAAATCTGTAAGATGCCGAAGAAGAACTTCATTACCCTGTTCACCGGTAATGAAACCAGCGA

AACCTGGTTCAAAGCGGCACTGGCAATGAATAAGCCGTGGTCAGAGAAGCTGAACGATGTGTCAGAT

GACGTACACCGTAGCCTGATGAAGCTGCAGCAGATCGAAACGGAAACTGGCCTGACGATTGAACAGG

TAAAAGACATCAACCGTCGTATGTCGATCGGCGAAGCGAAAGCGCGCCGTGCGAAGAAAGAGATGG

TTGAGGCTAACCTGCGTCTGGTTATCTCTATCGCCAAGAAGTACACCAACCGTGGCCTGCAGTTCCTG

GATCTGATTCAGGAAGGTAACATCGGTCTGATGAAAGCGGTGGATAAGTTTGAATATCGCCGTGGTT

ATAAGTTCTCGACTTATGCCACCTGGTGGATCCGTCAGGCGATCACCCGTTCAATCGCTGACCAGGCG

CGTACCATCCGTATTCCGGTGCACATGATTGAGACGATTAACAAGCTCAACCGTATTTCCCGCCAGAT

GCTGCAAGAGATGGGCCGTGAGCCGACGCCGGAAGAGCTGGCCGAGCGTATGCTGATGCCGGAAGA

TAAGATCCGTAAGGTGCTGAAAATTGCCAAAGAGCCGATCTCTATGGAGACGCCGATTGGTGATGAT

GAAGATTCACATCTGGGTGATTTTATCGAAGACACCACGCTGGAGCTGCCGCTGGACTCCGCGACGTC

AGAGAGCCTGCGTTCTGCCACGCACGACGTGCTGGCCGGTCTGACCGCGCGTGAAGCCAAAGTACTG

CGTATGCGTTTCGGTATCGATATGAATACCGACCACACGCTGGAAGAAGTGGGCAAACAGTTCGACG

TAACGCGTGAGCGTATTCGTCAGATTGAGGCGAAAGCGCTGCGTAAGCTGCGTCACCCAAGCCGCTC

TGAAGTGCTGCGCAGCTTCCTCGACGATTAA

108
DNA-directed RNA polymerase subunit beta
ATGGTTTACTCCTATACCGAGAAAAAACGTATTCGTAAGGATTTTGGAAAGCGTCCACAAGTTCTG

GACATTCCATATCTCCTTTCTATCCAGCTTGACTCGTTCCAGAAGTTCATCGAGCAAGATCCGGAAGG

TCAATATGGTCTGGAAGCAGCATTCCGCTCCGTATTTCCAATCCAAAGCTATAGCGGTAATTCTGAGC

TGCAGTACGTCAGCTACCGTTTAGGCGAACCCGTCTTTGATGTGAAAGAGTGTCAGATTCGTGGCGTC

ACGTATTCTGCTCCTCTGCGCGTAAAACTGCGCCTGGTGATCTACGAGCGCGAAGCGCCGGAAGGCA

CCGTTAAAGACATCAAAGAACAAGAAGTTTACATGGGCGAAATTCCGCTCATGACGGATAACGGTAC

CTTTGTTATCAACGGTACTGAGCGCGTTATCGTTTCTCAGCTCCACCGTAGTCCTGGTGTCTTCTTCGA

-continued

CAGCGATAAGGGTAAAACCCACTCGTCCGGTAAAGTGCTGTATAACGCACGTATCATCCCTTACCGTG

GTTCATGGCTGGACTTCGAGTTCGACCCGAAAGACAACCTGTTCGTCCGTATTGACCGTCGCCGTAAA

CTGCCAGCGACCATCATTCTGCGCGCGTTGAATTACACCACTGAACAGATCCTCGACCTGTTCTTCGA

TAAAGTGGTTTACCAAATTCGCGACAACAAGCTGCAGATGGAGCTTATTCCTGAGCGCCTGCGTGGTG

AGACCGCTTCATTTGATATTGAAGCGAACGGCACCGTTTACGTCGAAAAAGGCCGCCGTATTACTGCG

CGCCATATTCGCCAGCTTGAGAAAGATGCTGTTGCCCACATCGAAGTGCCGGTTGAGTATATTGCCGG

TAAAGTGGTCGCTAAAGACTACGTTGATGAGAGCACCGGTGAACTGCTGATCGCAGCGAACATGGAA

CTGTCACTGGATCTGCTGGCTAAACTCAGCCAGTCCGGTCACAAGCGCATTGAAACCCTGTTCACCAA

CGATCTGGATCACGGTGCGTACATGTCTGAGACGGTACGTGTCGACCCAACCAGCGATCGCCTGAGC

GCTCTGGTTGAGATCTACCGCATGATGCGTCCTGGTGAGCCACCAACGCGTGAAGCGGCTGAAAACC

TGTTTGAGAACCTGTTCTTCTCTGAAGACCGCTATGATCTGTCTGCGGTTGGTCGTATGAAGTTCAACC

GTTCTCTGCTGCGCGACGAGATCGAAGGTTCCGGTATCCTGAGCAAAGACGACATCATTCAGGTGAT

GAAGAAGCTCATCGGTATCCGTAACGGTATTGGCGAAGTGGATGATATCGACCACCTCGGCAACCGT

CGTATCCGTTCCGTTGGCGAAATGGCTGAAAACCAGTTCCGTGTTGGCCTTGTGCGCGTAGAGCGTGC

GGTGAAAGAGCGTCTGTCCCTGGGCGATCTGGATACCCTGATGCCACAGGACATGATCAACGCCAAG

CCAATTTCTGCGGCAGTGAAAGAGTTCTTCGGCTCCAGCCAGCTGTCACAGTTTATGGACCAGAACAA

CCCGTTGTCTGAGATCACGCATAAGCGTCGTATCTCTGCACTGGGTCCGGGCGGTCTGACGCGTGAGC

GTGCAGGCTTCGAAGTTCGAGACGTACACCCGACGCACTACGGTCGCGTATGTCCAATCGAAACGCC

GGAAGGTCCAAACATCGGTCTGATCAACTCCTTGTCTGTGTATGCACAGACCAATGAGTACGGTTTCC

TGGAAACCCCATACCGTCGCGTTCGCGAAGGCGTGGTGACCGACGAAATTCATTACCTCTCTGCTATT

GAAGAGGGTAACTACGTTATCGCTCAGGCAAACACCAATCTCGACGACGAAGGTCACTTCGTAGACG

ACCTGGTCACCTGCCGTAGCAAAGGCGAATCGAGTCTCTTCAACCGCGATCAAGTTGACTACATGGA

CGTTTCCACCCAGCAGGTGGTTTCCGTCGGTGCGTCACTGATCCCGTTCCTGGAGCACGATGACGCCA

ACCGCGCATTGATGGGTGCAAACATGCAACGTCAGGCGGTTCCTACTCTGCGTGCTGATAAGCCGCTG

GTAGGTACCGGTATGGAGCGTGCGGTTGCGGTTGACTCCGGTGTTACTGCCGTAGCGAAACGTGGTG

GTACCGTGCAGTACGTGGATGCATCCCGTATCGTTATTAAAGTTAACGAAGACGAAATGTATCCGGG

CGAAGCCGGTATCGACATTTACAACCTGACCAAATATACCCGTTCTAACCAGAACACCTGCATCAACC

AGATGCCTTGCGTGAACCTGGGTGAGCCAATCGAACGTGGTGATGTGCTGGCTGATGGCCCTTCAACC

GATCTCGGCGAACTGGCACTCGGTCAGAACATGCGCGTCGCGTTCATGCCGTGGAACGGCTACAACT

TCGAAGACTCCATTCTGGTCTCGGAGCGCGTTGTTCAGGAAGATCGCTTCACCACTATCCACATTCAG

GAACTGGCGTGTGTGTCTCGTGACACCAAGCTGGGGCCAGAAGAGATCACCGCTGACATCCCTAACG

TGGGTGAAGCTGCGCTCTCTAAACTGGATGAGTCCGGTATCGTGTATATCGGTGCGGAAGTGACCGGT

GGGGACATTCTGGTTGGTAAGGTAACACCTAAAGGTGAAACCCAGCTGACGCCAGAAGAGAAACTGC

TGCGTGCGATCTTCGGTGAAAAAGCGTCTGACGTTAAAGACTCTTCTCTGCGCGTACCAAACGGTGTG

TCAGGGACAATCATCGACGTTCAGGTCTTTACCCGCGATGGCGTGGAAAAAGACAAGCGTGCGCTGG

AAATCGAAGAGATGCAGCTGAAGCAGGCGAAGAAAGACCTGTCTGAAGAATTGCAGATCCTCGAAG

CCGGCTTGTTCAGCCGTATTAACTACCTGCTGGTTGCCGGCGGTGTTGAAGCGGAAAAACTGGAGAA

GCTGCCACGTGAGCGCTGGCTCGAACTGGGCCTGACCGACGAAGAGAAGCAAAATCAGCTGGAACA

GCTGGCCGAGCAGTACGACGAGCTGAAGCACGAGTTTGAGAAAAAACTTGAAGCCAAGCGCCGTAA

AATCACTCAGGGCGATGACCTGGCACCTGGCGTGCTGAAAATCGTGAAAGTGTATCTGGCCGTTAAA

CGTCAGATCCAGCCTGGTGACAAAATGGCAGGTCGTCACGGGAACAAAGGTGTTATCTCCAAGATCA

-continued

ACCCGATCGAAGATATGCCATACGATGAGTTCGGTACGCCGGTCGACATCGTACTGAACCCGCTGGG

CGTTCCATCACGTATGAACATTGGTCAGATTCTTGAAACCCACCTGGGTATGGCTGCGAAAGGCATTG

GCGAGAAAATTAACGCTATGCTTAAGAAGCAGGAAGAAGTGTCCAAGCTGCGTGAATTCATTCAGCG

TGCTTACGATCTGGGCAGCGATCTGCGTCAGAAAGTTGACCTGAACACCTTCACCGATGACGAAGTG

CTGCGCCTGGCAGAGAATCTGAAAAAAGGTATGCCAATTGCAACACCAGTGTTTGACGGCGCGAAAG

AGAGCGAAATCAAAGAGCTGTTACAGCTCGGCGGCCTGCCTTCTTCTGGCCAGATCACGCTGTTTGAT

GGTCGTACCGGTGAGCAGTTCGAACGTCAGGTTACCGTTGGCTACATGTACATGCTGAAGCTGAACC

ACCTGGTTGATGACAAAATGCATGCGCGTTCTACCGGTTCTTACAGCCTCGTTACTCAGCAGCCGCTG

GGTGGTAAGGCGCAGTTCGGTGGTCAGCGCTTCGGTGAGATGGAAGTGTGGGCACTGGAAGCATACG

GTGCCGCGTATACCCTGCAGGAAATGCTGACCGTGAAGTCTGATGACGTTAACGGCCGTACCAAGAT

GTATAAAAACATCGTTGACGGCAACCATCAGATGGAACCGGGCATGCCGGAATCTTTCAACGTACTG

TTGAAAGAGATCCGCTCGCTGGGTATCAACATCGAGCTGGAAGACGAGTAA

109
DP68 Glutamine--tRNA ligase
ATGAGCAAGCCCACTGTCGACCCTACCTCGAATTCCAAGGCCGGACCTGCCGTCCCGGTCAATTTC

CTGCGCCCGATCATCCAGGCGGACCTGGATTCGGGCAAGCACACGCAGATCGTCACCCGCTTCCCGC

CAGAGCCCAACGGCTACCTGCACATCGGTCACGCCAAGTCGATCTGTGTGAACTTCGGCCTGGCCCA

GGAGTTCGGTGGCGTCACGCACCTGCGTTTCGACGACACCAACCCGGCCAAGGAAGACCAGGAATAC

ATCGACGCCATCGAAAGCGACATCAAGTGGCTGGGCTTCGAATGGTCCGGTGAAGTGCGCTATGCGT

CCAAGTATTTCGACCAGTTGTTCGACTGGGCCGTCGAGCTGATCAAGGCCGGCAAGGCCTACGTCGA

CGACCTGACCCCGGAGCAGGCCAAGGAATACCGTGGCACGCTGACCGAGCCGGGCAAGAACAGCCC

GTTCCGTGACCGTTCGGTAGAAGAGAACCTCGACTGGTTCAACCGCATGCGCGCCGGTGAGTTCCCG

GACGGCGCCCGCGTGCTGCGCGCCAAGATCGACATGGCCTCGCCGAACATGAACCTGCGCGACCCGA

TCATGTACCGCATCCGCCACGCCCATCACCACCAGACCGGTGACAAGTGGTGCATCTACCCGAACTAT

GACTTCACCCACGGTCAGTCGGACGCCATCGAAGGCATCACCCACTCCATCTGCACCCTGGAGTTCGA

AAGCCATCGCCCGCTGTATGAGTGGTTCCTCGACAGCCTGCCGGTTCCGGCGCACCCGCGTCAGTACG

AGTTCAGCCGCCTGAACCTGAACTACACCATCACCAGCAAGCGCAAGCTCAAGCAGTTGGTGGACGA

AAAGCACGTGCATGGCTGGGATGACCCGCGCATGTCCACCCTGTCGGGTTTCCGCCGTCGCGGCTACA

CCCCGGCGTCGATCCGCAGCTTCTGCGACATGGTCGGCACCAACCGCTCCGACGGCGTGGTCGATTAC

GGCATGCTCGAGTTCAGCATCCGTCAGGACCTGGACGCCAACGCGCCGCGTGCCATGTGCGTATTGC

GCCCGTTGAAAGTCGTGATCACCAACTATCCGGAAGACAAGGTCGACCACCTCGAACTGCCGCGTCA

CCCGCAGAAAGAAGAACTTGGCGTGCGCAAGCTGCCGTTCGCGCGTGAAATCTACATCGACCGTGAT

GACTTCATGGAAGAGCCGCCGAAAGGCTACAAGCGCCTGGAGCCTAACGGCGAAGTGCGCCTGCGCG

GCAGCTACGTGATCCGTGCCGATGAAGCGATCAAGGACGCCGATGGCAACATCGTCGAACTGCGATG

CTCCTACGACCCGGAAACCCTGGGCAAGAACCCTGAAGGCCGCAAGGTCAAAGGCGTCGTTCACTGG

GTGCCGGCTGCTGCCAGCATCGAGTGCGAAGTGCGCCTGTACGATCGTCTGTTCCGTTCGCCGAACCC

TGAGAAGGCTGAAGACAGCGCCAGCTTCCTGGACAACATCAACCCTGACTCCCTGCAAGTTCTCACG

GGTTGTCGTGCCGAGCCATCGCTTGGCGACGCACAGCCGGAAGACCGTTTCCAGTTCGAGCGCGAAG

GTTACTTCTGCGCGGATATCAAGGACTCCAAACCTGGTCATCCGGTCTTCAACCGTACCGTGACCTTG

CGTGATTCGTGGGGCCAGTG

110
DP68 DNA gyrase subunit B

-continued

ATGAGCGAAGAAAACACGTACGACTCGACCAGCATTAAAGTGCTGAAAGGTTTGGATGCCGTACG

CAAACGTCCCGGTATGTACATCGGCGACACCGATGATGGTAGCGGTCTGCACCACATGGTGTTCGAG

GTGGTCGACAACTCCATCGACGAAGCTTTGGCCGGTCACTGCGACGACATCAGCATTATCATCCACCC

GGATGAGTCCATCACCGTGCGCGACAACGGTCGCGGTATTCCGGTCGATGTGCACAAAGAAGAAGGC

GTATCGGCGGCAGAGGTCATCATGACCGTGCTTCACGCCGGCGGTAAGTTCGACGACAACTCCTATA

AAGTTTCCGGCGGTTTGCACGGTGTAGGTGTGTCGGTGGTGAACGCTCTGTCCGAAGAGCTTATCCTG

ACTGTTCGCCGTAGCGGCAAGATCTGGGAACAGACCTACGTGCATGGTGTTCCACAAGAACCGATGA

AAATCGTTGGCGACAGTGAATCCACCGGTACGCAGATCCACTTCAAGCCTTCGGCAGAAACCTTCAA

GAATATCCACTTCAGTTGGGACATCCTGGCCAAGCGTATTCGTGAACTGTCGTTCCTTAACTCCGGTG

TGGGTATCGTCCTCAAGGACGAGCGCAGCGGCAAGGAAGAGTTGTTCAAGTACGAAGGCGGCTTGCG

TGCGTTCGTTGAGTACCTGAACACCAACAAGACTGCGGTCAACCAGGTGTTCCACTTCAACATCCAGC

GTGAAGACGGTATCGGCGTTGAAATCGCCCTGCAGTGGAACGACAGCTTCAACGAGAACCTGTTGTG

CTTCACCAACAACATTCCACAGCGCGACGGCGGTACTCACTTGGTGGGTTTCCGTTCCGCACTGACGC

GTAACCTGAACACCTACATCGAAGCGGAAGGCTTGGCCAAGAAGCACAAAGTGGCCACTACCGGTGA

CGATGCGCGTGAAGGCCTGACGGCGATTATCTCGGTGAAAGTGCCGGATCCAAAGTTCAGCTCCCAG

ACCAAAGACAAGCTGGTGTCTTCCGAAGTGAAGACCGCAGTGGAACAGGAGATGGGCAAGTACTTCT

CCGACTTCCTGCTGGAAAACCCGAACGAAGCCAAGTTGGTTGTCGGCAAGATGATCGACGCGGCGCG

TGCCCGTGAAGCGGCGCGTAAAGCCCGTGAGATGACCCGCCGTAAAGGCGCGTTGGATATCGCCGGC

CTGCCGGGCAAACTGGCTGACTGCCAGGAGAAGGACCCTGCCCTCTCCGAACTGTACCTGGTGGAAG

GTGACTCTGCTGGCGGTTCCGCCAAGCAGGGTCGTAACCGTCGCACCCAGGCTATCCTGCCGTTGAAG

GGTAAGATCCTCAACGTCGAGAAGGCCCGCTTCGACAAGATGATTTCCTCTCAGGAAGTCGGCACCTT

GATCACGGCGTTGGGCTGCGGTATTGGCCGCGATGAGTACAACATCGACAAACTGCGTTACCACAAC

ATCATCATCATGACCGATGCTGACGTCGACGGTTCGCACATCCGTACCCTGCTGCTGACCTTCTTCTTC

CGTCAGTTGCCGGAGCTGATCGAGCGTGGCTACATCTACATCGCTCAGCCGCCGTTGTACAAAGTGAA

AAAGGGCAAGCAAGAGCAGTACATCAAAGACGACGACGCCATGGAAGAGTACATGACGCAGTCGGC

CCTGGAAGATGCCAGCCTGCACTTGAACGACGAAGCCCCGGGCATTTCCGGTGAGGCGCTGGAGCGT

TTGGTTAACGACTTCCGCATGGTAATGAAGACCCTCAAGCGTCTGTCGCGCCTGTACCCTCAGGAGCT

GACCGAGCACTTCATCTACCTGCCTTCCGTGAGCCTGGAGCAGTTGGGCGATCACGCCCACATGCAGA

ATTGGCTGGCTCAGTACGAAGTACGTCTGCGCACCGTCGAGAAGTCTGGCCTGGTTTACAAAGCCAG

CTTGCGTGAAGACCGTGAACGTAACGTGTGGCTGCCGGAGGTTGAACTGATCTCCCACGGCCTGTCG

AACTACGTCACCTTCAACCGCGACTTCTTCGGCAGCAACGACTACAAGACCGTGGTTACCCTCGGCGC

GCAATTGAGCACCCTGTTGGACGACGGTGCTTACATCCAGCGTGGCGAGCGTAAGAAAGCGGTCAAG

GAGTTCAAGGAAGCCCTGGACTGGTTGATGGCTGAAAGCACCAAGCGCCACACCATCCAGCGATACA

AAGGTCTGGGCGAGATGAACCCGGATCAACTGTGGGAAACCACCATGGATCCTGCTCAGCGTCGCAT

GCTACGCGTGACCATCGAAGACGCCATTGGCGCAGACCAGATCTTCAACACCCTGATGGGTGATGCG

GTCGAGCCTCGCCGTGACTTCATCGAGAGCAACGCCTTGGCGGTGTCTAACCTGGATTTCTGA

111
DP68 Isoleucine--tRNA ligase
ATGACCGACTATAAAGCCACGCTAAACCTTCCGGACACCGCCTTCCCAATGAAGGCCGGCCTGCC

ACAGCGCGAACCGCAGATCCTGCAGCGCTGGGACAGTATTGGCCTGTACGGAAAGTTGCGCGAAATT

GGCAAGGATCGTCCGAAGTTCGTCCTGCACGACGGCCCTCCTTATGCCAACGGCACGATTCACATCGG

TCATGCGCTGAACAAAATTCTCAAGGACATGATCCTGCGTTCGAAAACCCTGTCGGGCTTCGACGCGC

-continued

CTTATGTTCCGGGCTGGGACTGCCACGGCCTGCCGATCGAACACAAAGTCGAAGTGACCTACGGCAA

GAACCTGGGCGCGGATAAAACCCGCGAACTGTGCCGTGCCTACGCCACCGAGCAGATCGAAGGGCA

GAAGTCCGAATTCATCCGCCTGGGCGTGCTGGGCGAGTGGGACAACCCGTACAAGACCATGAACTTC

AAGAACGAGGCCGGTGAAATCCGTGCCTTGGCTGAAATCGTCAAAGGCGGTTTCGTGTTCAAGGGCC

TCAAGCCCGTGAACTGGTGCTTCGACTGCGGTTCGGCCCTGGCTGAAGCGGAAGTCGAGTACGAAGA

CAAGAAGTCCTCGACCATCGACGTGGCCTTCCCGATCGCCGACGACGACAAGCTGGCTCAAGCCTTT

GGCCTGTCCAGCCTGCCAAAGCCTGCAGCCATCGTGATCTGGACCACCACCCCGTGGACCATCCCGGC

CAACCAGGCGCTGAACGTGCACCCGGAATTCACCTACGCCCTGGTGGACGTCGGTGATCGCCTGCTG

GTGCTGGCTGAAGAAATGGTCGAGGCCTGCCTGGCGCGCTACGAGCTGCAAGGTTCGGTCATCGCCA

CCACCACCGGCACTGCGCTGGAGCTGATCAATTTCCGTCACCCGTTCTATGACCGTCTGTCGCCGGTG

TACCTGGCTGACTACGTAGAGCTGGGTTCGGGTACTGGTGTGGTTCACTCCGCGCCGGCCTACGGCGT

TGATGACTTTGTGACCTGCAAAGCCTACGGCATGGTCAACGATGACATCCTCAACCCGGTGCAGAGC

AATGGCGTGTACGCGCCGTCGCTGGAGTTCTTTGGCGGCCAGTTCATCTTCAAGGCCAACGAGCCGAT

CATCGACAAACTGCGTGAAGTCGGTTCGCTGCTGCACACCGAAACCATCAAGCACAGCTACATGCAC

TGCTGGCGTCACAAGACCCCGCTGATCTACCGCGCTACCGCGCAGTGGTTTATCGGCATGGACAAAG

AGCCGACCAGCGGCGACACCCTGCGTGTGCGCTCGCTCAAAGCGATCGAAGAGACCAAGTTTGTCCC

GGCCTGGGGCCAGGCGCGCCTGCACTCGATGATCGCCAACCGCCCGGACTGGTGCATCTCCCGCCAG

CGCAACTGGGGCGTGCCGATTCCGTTCTTCCTGAACAAGGAAAGCGGCGAGCTGCACCCACGTACCG

TTGAACTGATGGAAGCAGTGGCGCTGCGCGTTGAGCAGGAAGGCATCGAAGCCTGGTTCAAGCTGGA

CGCCGCCGAACTGCTGGGCGACGAAGCGCCGCTGTACGACAAGATCAGCGACACCCTCGACGTGTGG

TTCGACTCGGGTACCACCCACTGGCACGTGCTGCGCGGTTCGCACCCGATGGGTCACGCCACCGGCCC

GCGTGCCGACCTGTACCTGGAAGGCTCGGACCAACACCGTGGCTGGTTCCACTCGTCGTTGCTGACCG

GCTGCGCCATCGACAACCACGCGCCGTACCGCGAACTGCTGACCCACGGCTTCACCGTCGACGAGAC

GGGCCGCAAGATGTCCAAGTCGCTGAAAAACGTGATCGAGCCGAAAAAGATCAACGACACCCTGGG

CGCCGATATCATGCGTCTGTGGGTCGCCTCGACCGATTACTCGGGCGAAATCGCCGTGTCGGACCAGA

TCCTGGCCCGTAGCGCCGATGCCTACCGCCGTATCCGTAATACCGCACGCTTCCTGCTGTCGAACCTG

ACCGGTTTCAACCCGGCCACCGACATCCTGCCGGCCGAGGACATGCTCGCCCTGGACCGTTGGGCCGT

GGACCGTACGCTGTTGCTGCAGCGCGAGTTGCAGGAACACTACGGCGAATACCGTTTCTGGAACGTG

TACTCCAAGATCCACAACTTCTGCGTGCAGGAGCTGGGTGGTTTCTACCTCGATATCATCAAGGACCG

CCAGTACACCACCGGCGCCAACAGCAAGGCGCGCCGCTCGGCGCAGACCGCGCTGTACCACATCTCT

GAAGCGCTGGTGCGCTGGATCGCACCGATCCTGGCCTTCACCGCTGACGAACTGTGGGAATACCTGC

CGGGCGAGCGTAACGAATCGGTGATGCTCAACACCTGGTACGAAGGCCTGACCGAATTGCCGGCCAA

CTTCGAACTGGGCCGCGAGTACTGGGAAGGCGTGATGGCCGTCAAGGTTGCGGTGAACAAGGAGCTG

GAAGTTCAGCGCGCGGCCAAGGCCGTCGGTGGCAACCTGCAAGCCGAAGTCACCCTGTTTGCCGAGG

AAGGCCTGACCGCCGACCTGGCCAAGCTGAGCAACGAACTGCGCTTCGTACTGATCACCTCGACCGC

GAGCCTGGCACCGTTTGCCCAGGCACCTGCGGACGCAGTGGCCACCGAAGTGCCGGGCCTCAAGCTC

AAAGTGGTCAAGTCGGCCTTTCCTAAGTGCGCCCGTTGCTGGCACTGCCGTGAAGACGTCGGCGTGA

ACCCAGAGCATCCGGAAATCTGCGGTCGTTGCGTCGACAACATCAGCGGTGCTGGCGAGGTTCGCCA

CTATGCCTAA

112
DP68 NADH-quinone oxidoreductase subunit C/D

-continued

ATGACTACAGGCAGTGCTCTGTACATCCCGCCTTACAAGGCAGACGACCAGGATGTGGTTGTCGA

ACTCAATAACCGTTTTGGCCCTGACGCCTTCACCGCCCAGGCCACACGCACCGGTATGCCGGTGCTGT

GGGTGGCGCGCGCCAAGCTCGTCGAAGTCCTGAGCTTCCTGCGCAACCTGCCCAAGCCGTACGTCAT

GCTTTATGACCTGCATGGCGTGGACGAGCGTCTGCGCACCAAGCGTCAAGGTTTGCCGAGCGGTGCC

GATTTCACCGTGTTCTACCACTTGATGTCGCTGGAACGTAACAGCGACGTGATGATCAAGGTCGCGCT

GTCCGAAAGCGACTTGAGCATCCCGACCGTCACCGGTATCTGGCCGAATGCCAGCTGGTACGAGCGC

GAAGTTTGGGACATGTTCGGTATCGACTTCCCGGGCCACCCGCACCTGACGCGCATCATGATGCCGCC

GACCTGGGAAGGTCACCCGCTGCGCAAGGACTTTCCTGCCCGCGCAACCGAATTCGACCCGTTCAGC

CTCAACCTCGCCAAGCAGCAGCTTGAAGAAGAAGCTGCACGCTTCCGTCCGGAAGACTGGGGCATGA

AACGCTCCGGCACCAACGAGGACTACATGTTCCTCAACCTGGGCCCGAACCACCCTTCGGCTCACGGT

GCCTTCCGTATCATCCTGCAACTGGACGGCGAAGAAATCGTCGACTGTGTGCCGGACATCGGTTACCA

CCACCGTGGTGCCGAGAAGATGGCCGAGCGCCAGTCCTGGCACAGCTTCATCCCGTACACCGACCGT

ATCGACTACCTCGGCGGCGTGATGAACAACCTGCCGTACGTGCTGTCGGTCGAGAAGCTGGCCGGTA

TCAAGGTGCCGGACCGCGTCGACACCATCCGCATCATGATGGCCGAGTTCTTCCGCATCACCAGCCAC

CTGCTGTTCCTGGGTACCTATATCCAGGACGTTGGCGCCATGACCCCGGTGTTCTTCACCTTCACCGAC

CGTCAACGCGCCTACAAGGTGATCGAAGCCATCACCGGTTTCCGCCTGCACCCGGCCTGGTATCGCAT

CGGCGGCGTGGCGCACGACCTGCCGAACGGCTGGGAGCGCCTGGTCAAGGAATTCATCGACTGGATG

CCCAAGCGTCTGGACGAGTACCAAAAGGCTGCGCTGGACAACAGCATCCTCAAGGGTCGTACCATCG

GCGTCGCGCAGTACAACACCAAAGAAGCCCTGGAATGGGGCGTCACTGGTGCCGGCCTGCGTTCGAC

CGGCTGCGACTTCGACCTGCGTAAAGCACGGCCGTACTCGGGCTACGAGAACTTCGAGTTCGAAGTG

CCGCTGGCCGCCAATGGCGATGCCTACGACCGGTGCATCGTGCGCGTTGAAGAAATGCGCCAGAGCC

TGAAGATCATCGAGCAGTGCATGCGCAACATGCCGGCTGGCCCGTACAAGGCGGATCATCCGCTGAC

CACACCGCCGCCGAAAGAGCGCACGCTGCAGCACATCGAAACCCTGATCACGCACTTCCTGCAAGTT

TCGTGGGGCCCGGTGATGCCGGCCAACGAATCCTTCCAGATGATCGAAGCGACCAAGGGTATCAACA

GTTATTACCTGACGAGCGATGGCGGCACCATGAGCTACCGCACCCGGATTCGTACCCCAAGCTTTGCC

CACTTGCAGCAGATCCCTTCGGTGATCAAAGGCGAGATGGTCGCGGACTTGATTGCGTACCTGGGTA

GTATCGATTTCGTTATGGCCGACGTGGACCGCTAA

113
DP68 Protein RecA
ATGGACGACAACAAGAAGAAAGCCTTGGCTGCGGCCCTGGGTCAGATCGAACGTCAATTCGGCAA

GGGTGCCGTAATGCGTATGGGCGATCACGACCGTCAGGCGATCCCGGCTATTTCCACTGGCTCTCTGG

GTCTGGACATCGCACTCGGCATTGGCGGCCTGCCAAAAGGCCGTATCGTTGAAATCTACGGTCCTGAA

TCTTCCGGTAAAACCACCCTGACCCTGTCGGTGATTGCCCAGGCGCAAAAAATGGGCGCCACCTGTGC

GTTCGTCGACGCCGAGCACGCCCTGGACCCGGAATACGCCGGTAAGCTGGGCGTCAACGTTGACGAC

CTGCTGGTTTCCCAGCCGGACACCGGTGAGCAAGCCCTGGAAATCACCGACATGCTGGTGCGCTCCA

ACGCCATCGACGTGATCGTGGTCGACTCCGTGGCTGCCCTGGTACCGAAAGCTGAAATCGAAGGCGA

AATGGGCGACATGCACGTGGGCCTGCAAGCCCGCCTGATGTCCCAGGCGCTGCGTAAAATTACCGGT

AACATCAAGAACGCCAACTGCCTGGTGATCTTCATCAACCAGATCCGTATGAAGATCGGCGTAATGTT

CGGCAGCCCGGAAACCACTACCGGTGGTAACGCGCTGAAGTTCTACGCTTCGGTCCGTCTGGACATCC

GCCGTACCGGCGCGGTGAAGGAAGGTGACGAAGTTGTTGGTAGCGAAACTCGCGTTAAAGTCGTGAA

GAACAAGGTCGCTCCGCCTTTCCGTCAGGCAGAGTTCCAGATTCTCTACGGCAAGGGTATCTACCTGA

ACGGCGAGATGATTGACCTGGGCGTACTGCACGGTTTCGTCGAGAAGTCCGGTGCCTGGTATGCCTAC

-continued

AACGGCAGCAAGATCGGTCAGGGCAAGGCCAACTCGGCCAAGTTCCTGGCAGACAACCCGGATATCG

CTGCCACGCTTGAGAAGCAGATTCGCGACAAGCTGCTGACCCCAGCGCCAGACGTGAAAGCTGCCGC

CAACCGCGAGCCGGTTGAAGAAGTGGAAGAAGCTGACACTGATATCTGA

114
DP68 RNA polymerase sigma factor RpoD
ATGTCCGGAAAAGCGCAACAACAGTCTCGTATTAAAGAGTTGATCACCCTTGGTCGTGAGCAGAA

ATATCTGACTTACGCAGAGGTCAACGATCACCTGCCTGAGGATATTTCAGATCCTGAGCAGGTGGAA

GACATCATCCGCATGATTAATGACATGGGGATCCCCGTACACGAGAGTGCTCCGGATGCGGACGCCC

TTATGTTGGCCGACTCCGATACCGACGAGGCAGCTGCTGAAGAAGCGGCTGCTGCGCTGGCAGCGGT

GGAGACCGACATCGGTCGTACGACTGACCCTGTGCGCATGTATATGCGTGAAATGGGTACCGTCGAG

CTGCTGACACGTGAAGGCGAAATCGAAATCGCCAAACGTATTGAAGAGGGTATCCGTGAAGTGATGG

GCGCAATCGCGCACTTCCCTGGCACGGTTGACCACATTCTCTCCGAGTACACTCGCGTCACCACCGAA

GGTGGCCGCCTGTCTGACGTTCTGAGCGGCTACATCGACCCGGACGACGGCATTGCGCCGCCTGCCGC

CGAAGTACCGCCGCCCGTCGATGCGAAAGCCGCGAAGGCTGACGACGACACCGAAGACGACGATGC

TGAAGCCAGCAGCGACGACGAAGATGAAGTTGAAAGCGGCCCGGACCCGATCATCGCAGCCCAGCG

TTTCGGTGCGGTTTCCGATCAAATGGAAATCACCCGCAAGGCCCTGAAAAAGCACGGTCGCTCCAAC

AAGCTGGCGATTGCCGAGCTGGTGGCCCTGGCTGAGCTGTTCATGCCGATCAAGCTGGTACCGAAGC

AATTCGAAGGCTTGGTTGAGCGTGTTCGCAGTGCCCTTGAACGTCTGCGTGCGCAAGAACGCGCAATC

ATGCAGCTGTGTGTACGTGATGCACGTATGCCGCGGGCTGACTTCCTGCGCCAGTTCCCGGGCAACGA

AGTAGACGAAAGCTGGACCGACGCACTGGCCAAAGGCAAGGCGAAATACGCCGAAGCCATTGGTCG

CCTGCAGCCGGACATCATCCGTTGCCAGCAGAAGCTGACCGCGCTTGAGACCGAAACCGGTCTGACG

ATTGCTGAAATCAAAGACATCAACCGTCGCATGTCGATCGGTGAGGCCAAGGCCCGCCGCGCGAAGA

AAGAGATGGTTGAAGCGAACTTGCGTCTGGTGATCTCGATCGCCAAGAAGTACACCAACCGTGGTCT

GCAATTCCTCGATCTGATCCAGGAAGGCAACATCGGCTTGATGAAGGCGGTGGACAAGTTCGAATAC

CGTCGCGGCTACAAGTTCTCGACTTATGCCACCTGGTGGATCCGTCAGGCGATCACTCGCTCGATCGC

CGACCAGGCTCGCACCATCCGTATTCCGGTGCACATGATCGAGACGATCAACAAGCTCAACCGTATTT

CCCGGCAGATGTTGCAGGAAATGGGTCGCGAACCGACCCCGGAAGAGCTGGGCGAACGCATGGAAA

TGCCTGAGGATAAAATCCGCAAGGTATTGAAGATCGCTAAAGAGCCGATCTCCATGGAAACGCCGAT

TGGTGATGACGAAGACTCCCACCTGGGTGACTTCATCGAAGACTCGACCATGCAGTCGCCAATCGAT

GTCGCCACTGTTGAGAGCCTTAAAGAAGCGACTCGCGACGTACTGTCCGGCCTCACTGCCCGTGAAG

CCAAGGTACTGCGCATGCGTTTCGGCATCGACATGAATACCGACCACACCCTTGAGGAAGTCGGTAA

GCAGTTTGACGTGACCCGCGAGCGGATCCGTCAGATCGAAGCCAAGGCGCTGCGCAAGTTGCGCCAC

CCGACGCGAAGCGAGCATCTGCGCTCCTTCCTCGACGAGTGA

115
DP68 DNA-directed RNA polymerase subunit beta
ATGGCTTACTCATATACTGAGAAAAAACGTATCCGCAAGGACTTTAGCAAGTTGCCGGACGTCATG

GATGTCCCGTACCTTCTGGCTATCCAGCTGGATTCGTATCGTGAATTCTTGCAGGCGGGAGCGACCAA

AGATCAGTTCCGCGACGTGGGCCTGCATGCGGCCTTCAAATCCGTTTTCCCGATCATCAGCTACTCCG

GCAATGCTGCGCTGGAGTACGTGGGTTATCGCCTGGGCGAACCGGCATTTGATGTCAAAGAATGCGT

GTTGCGCGGTGTTACGTACGCCGTACCTTTGCGGGTAAAAGTCCGCCTGATCATTTTCGACAAAGAAT

CGTCGAACAAAGCGATCAAGGACATCAAAGAGCAAGAAGTCTACATGGGCGAAATCCCACTGATGA

CTGAAAACGGTACCTTCGTAATCAACGGTACCGAGCGTGTTATTGTTTCCCAGCTGCACCGTTCCCCG

-continued

GGCGTGTTCTTCGACCACGACCGCGGCAAGACGCACAGCTCCGGTAAACTCCTGTACTCCGCGCGGA

TCATTCCGTACCGCGGTTCGTGGTTGGACTTCGAGTTCGACCCGAAAGACTGCGTGTTCGTGCGTATC

GACCGTCGTCGCAAGCTGCCGGCCTCGGTACTGCTGCGCGCGCTCGGTTACACCACTGAGCAGGTGCT

GGACGCTTTCTACACCACCAACGTATTCAGCCTGAAGGATGAAACCCTCAGCCTGGAGCTGATTGCTT

CGCGTCTGCGTGGTGAAATTGCCGTTCTGGACATTCAGGACGAAAACGGCAAAGTGATCGTTGAAGC

GGGTCGTCGTATTACTGCGCGCCACATCAACCAGATCGAAAAAGCCGGCATCAAGTCGCTGGAAGTG

CCTCTGGACTACGTCCTGGGTCGCACCACCGCCAAGGTTATCGTTCACCCGGCTACAGGCGAAATCCT

GGCTGAGTGCAACACCGAGCTGAACACCGAAATCCTGGCAAAAATCGCCAAGGCCCAGGTTGTTCGC

ATCGAGACCCTGTACACCAACGACATCGACTGCGGTCCGTTCATCTCCGACACACTGAAGATCGACTC

CACCAGCAACCAATTGGAAGCGCTGGTCGAGATCTATCGCATGATGCGTCCTGGTGAGCCACCGACC

AAAGACGCTGCCGAGACCCTGTTCAACAACCTGTTCTTCAGCCCTGAGCGTTATGACCTGTCTGCGGT

CGGCCGGATGAAGTTCAACCGTCGTATCGGTCGTACCGAGATCGAAGGTTCGGGCGTGCTGTGCAAG

GAAGATATCGTCGCGGTACTGAAGACTCTGGTCGACATCCGTAACGGTAAAGGCATCGTCGATGACA

TCGACCACCTGGGTAACCGTCGTGTTCGCTGCGTAGGCGAAATGGCCGAAAACCAGTTCCGCGTTGG

CCTTGTGCGTGTTGAACGTGCGGTCAAAGAGCGTCTGTCGATGGCTGAAAGCGAAGGCCTGATGCCG

CAAGACCTGATCAACGCCAAGCCAGTGGCTGCGGCAGTGAAAGAGTTCTTCGGTTCCAGCCAGCTTT

CCCAGTTCATGGACCAGAACAACCCGCTCTCCGAGATCACCCACAAGCGCCGTGTTTCTGCACTGGGC

CCGGGCGGTCTGACCCGTGAGCGTGCTGGCTTTGAAGTTCGTGACGTACACCCGACGCACTACGGTCG

TGTTTGCCCGATCGAAACGCCGGAAGGTCCGAACATCGGTCTGATCAACTCCCTGGCCGCTTATGCGC

GCACCAACCAGTACGGCTTCCTCGAGAGCCCGTACCGCGTGGTGAAAGACGCTCTGGTCACCGACGA

GATCGTATTCCTGTCCGCCATCGAAGAAGCTGATCACGTGATCGCTCAGGCTTCGGCCACGATGAACG

ACAAGAAAGTCCTGATCGACGAGCTGGTAGCTGTTCGTCACTTGAACGAGTTCACCGTCAAGGCGCC

GGAAGACGTCACCTTGATGGACGTTTCGCCGAAGCAGGTAGTTTCGGTTGCAGCGTCGCTGATCCCGT

TCCTGGAACACGATGACGCCAACCGTGCGTTGATGGGTTCCAACATGCAGCGTCAAGCTGTACCAAC

CCTGCGCGCTGACAAGCCGCTGGTAGGTACCGGCATGGAGCGTAACGTAGCCCGTGACTCCGGCGTT

TGCGTCGTAGCCCGTCGTGGCGGCGTGATCGACTCCGTTGATGCCAGCCGTATCGTGGTTCGTGTTGC

CGATGATGAAGTTGAAACTGGCGAAGCCGGTGTCGACATCTACAACCTGACCAAATACACCCGCTCG

AACCAGAACACCTGCATCAACCAGCGTCCGCTGGTGAGCAAGGGTGACCGCGTTCAGCGTAGCGACA

TCATGGCCGACGGCCCGTCCACTGACATGGGTGAACTGGCTCTGGGTCAGAACATGCGCATCGCGTTC

ATGGCATGGAACGGCTTCAACTTCGAAGACTCCATCTGCCTGTCCGAGCGTGTTGTTCAAGAAGACCG

TTTCACCACGATCCACATTCAGGAACTGACCTGTGTGGCACGTGATACCAAGCTTGGGCCAGAGGAA

ATCACTGCAGACATCCCGAACGTGGGTGAAGCTGCACTGAACAAGCTGGACGAAGCCGGTATCGTTT

ACGTAGGTGCTGAAGTTGGCGCAGGCGACATCCTGGTAGGTAAGGTCACTCCGAAAGGCGAGACCCA

ACTGACTCCGGAAGAGAAGCTGCTGCGTGCCATCTTCGGTGAAAAAGCCAGCGACGTTAAAGACACC

TCCCTGCGTGTACCTACCGGTACCAAGGGTACTGTTATCGACGTACAGGTCTTCACCCGTGACGGCGT

TGAGCGTGATGCTCGTGCACTGTCCATCGAGAAGACTCAACTCGACGAGATCCGCAAGGACCTGAAC

GAAGAGTTCCGTATCGTTGAAGGCGCGACCTTCGAACGTCTGCGTTCCGCTCTGGTAGGCCACAAGGC

TGAAGGCGGCGCAGGTCTGAAGAAAGGTCAGGACATCACCGACGAAGTACTCGACGGTCTTGAGCAC

GGCCAGTGGTTCAAACTGCGCATGGCTGAAGATGCTCTGAACGAGCAGCTCGAGAAGGCCCAGGCCT

ACATCGTTGATCGCCGTCGTCTGCTGGACGACAAGTTCGAAGACAAGAAGCGCAAACTGCAGCAGGG

CGATGACCTGGCTCCAGGCGTGCTGAAAATCGTCAAGGTTTACCTGGCAATCCGTCGCCGCATCCAGC

-continued

CGGGCGACAAGATGGCCGGTCGTCACGGTAACAAAGGTGTGGTCTCCGTGATCATGCCGGTTGAAGA

CATGCCGCACGATGCCAATGGCACCCCGGTCGACGTCGTCCTCAACCCGTTGGGCGTACCTTCGCGTA

TGAACGTTGGTCAGATCCTCGAAACCCACCTGGGCCTCGCGGCCAAAGGTCTGGGCGAGAAGATCAA

CCGTATGATCGAAGAGCAGCGCAAGGTTGCTGACCTGCGTAAGTTCCTGCACGAGATCTACAACGAG

ATCGGCGGTCGCAACGAAGAGCTGGACACCTTCTCCGACCAGGAAATCCTGGACTTGGCGAAGAACC

TGCGCGGCGGCGTTCCAATGGCTACCCCGGTGTTCGACGGTGCCAAGGAAAGCGAAATCAAGGCCAT

GCTGAAACTGGCAGACCTGCCGGAAAGCGGCCAGATGCAGCTGTTCGACGGCCGTACCGGCAACAAG

TTTGAGCGCCCGGTTACTGTTGGCTACATGTACATGCTGAAGCTGAACCACTTGGTAGACGACAAGAT

GCACGCTCGTTCTACCGGTTCGTACAGCCTGGTTACCCAGCAGCCGCTGGGTGGTAAGGCTCAGTTCG

GTGGTCAGCGTTTCGGGGAGATGGAGGTCTGGGCACTGGAAGCATACGGTGCTGCATACACTCTGCA

AGAAATGCTCACAGTGAAGTCGGACGATGTGAACGGTCGGACCAAGATGTACAAAAACATCGTGGA

CGGCGATCACCGTATGGAGCCGGGCATGCCCGAGTCCTTCAACGTGTTGATCAAAGAAATTCGTTCCC

TCGGCATCGATATCGATCTGGAAACCGAATAA

116
DP69 Glutamine--tRNA ligase
GTGCGCGAGGACCTGGCCAGCGGAAAGCACCAGGCGATCAAGACCCGCTTCCCGCCGGAGCCGAA

CGGCTACCTGCACATCGGCCACGCCAAGTCGATCTGCCTGAACTTCGGCATCGCCGGTGAGTTCAGCG

GCGTCTGCAACCTGCGTTTCGACGACACCAATCCGGCCAAGGAAGACCCGGAGTACGTGGCCGCGAT

CCAGGACGACGTGCGCTGGCTGGGCTTTGAATGGAACGAGCTGCGCCACGCCTCGGACTACTTCCAG

ACCTATTACCTGGCCGCCGAGAAGCTGATCGAACAGGGCAAGGCCTACGTCTGCGACCTGTCGGCCG

AGGAAGTGCGCGCCTACCGCGGCACCCTGACCGAGCCGGGCCGCCCGTCGCCGTGGCGTGACCGCAG

CGTCGAGGAGAACCTCGACCTGTTCCGCCGCATGCGTGCCGGTGAATTCCCCGATGGCGCGCGCACC

GTGCGCGCCAAGATCGACATGGCCAGCGGCAACATCAACCTGCGTGATCCGGCGCTGTACCGCATCA

AGCACGTCGAGCACCAGAACACCGGCAACGCGTGGCCGATCTACCCGATGTACGACTTCGCCCATGC

GCTGGGCGATTCGATCGAGGGCATCACCCACTCGCTGTGCACGCTGGAATTCGAAGACCACCGCCCG

CTGTACGACTGGTGCGTGGACAACGTCGACTTCGCCCACGATGACGCGCTGACCCAGCCGCTGGTCG

ACGCCGGCCTGCCGCGCGAAGCGGCCAAACCGCGCCAGATCGAGTTCTCGCGCCTGAACATCAACTA

CACGGTGATGAGCAAGCGCAAGCTGATGGCGCTGGTCACCGAACAGCTGGTGGACGGCTGGGAAGA

CCCGCGCATGCCGACCCTGCAGGGCCTGCGTCGCCGTGGCTACACCCCGGCAGCGATGCGCCTGTTCG

CCGAGCGCGTGGGCATCAGCAAGCAGAATTCGCTGATCGATTTCAGCGTGCTGGAAGGCGCGCTGCG

CGAAGACCTGGACAGCGCCGCACCGCGCCGCATGGCCGTGGTCGACCCGGTCAAGCTGGTGCTGACC

AACCTGGCCGAAGGCCACGAAGAGCAGCTGACCTTCAGCAACCACCCGAAGGACGAGAGCTTCGGT

ACCCGCGAAGTGCCGTTCGCACGTGAAGTGTGGATCGACCGCGAGGACTTCGCCGAAGTGCCGCCGA

AGGGCTGGAAGCGCCTGGTTCCCGGTGGTGAAGTGCGCCTGCGCGGCGCCGGCATCATCCGCTGCGA

CGACGTGATCAAGGATGCCGACGGCACCATCACCGAGCTGCGCGGCTGGCTGGATCCGGAATCGCGC

CCGGGCATGGAAGGCGCCAACCGCAAGGTCAAGGGCACCATCCACTGGGTCAGCGCGGTGCACGGT

GTGCCGGCCGAGATCCGCCTGTATGACCGCCTGTTCTCGGTGCCGAACCCGGACGATGAATCGGAAG

GCAAGACCTACCGCGACTACCTCAATCCGGACTCGCGCCGCACCGTCACCGGCTATGTCGAGCCGGC

GGCTGCCAGCGCTGCGCCGGAACAGTCGTTCCAGTTCGAGCGCACCGGCTACTTCGTTGCCGACCGCC

GCGACCACACCGAAGCCAAGCCGGTGTTCAACCGCAGCGTGACCCTGCGCGACACCTGGTCGGCCTG

A

-continued

117
DP69 DNA gyrase subunit B
ATGACCGACGAACAGAACACCCCGGCAAACAACGGCAACTACGACGCCAACAGCATTACGGCCCT

GGAAGGCCTGGAGGCTGTCCGCAAGCGCCCAGGCATGTACATCGGCGACGTCCATGACGGCACCGGC

CTGCATCACATGGTGTTCGAGGTCGTCGACAACTCAATCGACGAAGCCCTCGCCGGCCATGCCGACC

ACGTCTCGGTGACGATCCATGCCGATGGCTCGGTAGGCGTGTCCGACAACGGTCGCGGCATCCCGAC

GGGCAAGCACGAGCAGATGAGCAAGAAGCTCGACCGCGATGTGTCTGCAGCCGAAGTGGTGATGAC

GGTCCTGCACGCAGGCGGCAAGTTCGACGACAACAGCTACAAGGTTTCCGGCGGCCTGCACGGCGTG

GGCGTCAGCGTGGTCAACGCGCTGTCGCAGAAGCTGGTCCTGGATATCTACCAGGGTGGCTTCCACTA

CCAGCAGGAGTACGCCGACGGCGCAGCACTGCATCCGCTGAAGCAGATCGGCCCCAGCACCAAGCGC

GGGACCACCCTGCGCTTCTGGCCCTCGGTAAAGGCTTTCCACGACAACGTGGAATTCCACTACGACAT

CCTGGCCCGGCGCCTGCGCGAACTGTCCTTCCTCAATTCCGGCGTCAAGATCGTGCTGGTGGACGAGC

GTGGTGATGGCCGCCGCGACGACTTCCATTACGAGGGCGGCATCCGCAGCTTCGTGGAGCATCTGGC

GCAGTTGAAGACGCCGTTGCACCCGAACGTGATCTCGGTGACCGGCGAATCCAATGGCATCACCGTG

GAAGTGGCGCTGCAGTGGACCGACTCCTACCAGGAGACGATGTACTGCTTCACCAACAACATTCCGC

AGAAGGACGGCGGTACCCACCTGGCCGGCTTCCGTGGCGCATTGACCCGCGTGCTCAACAACTACAT

CGAGCAGAACGGCATCGCCAAGCAGGCCAAGATCAACCTGACCGGCGATGACATGCGCGAAGGCAT

GATCGCGGTGCTGTCGGTGAAGGTGCCGGATCCCAGCTTCTCCAGCCAGACCAAGGAAAAGCTGGTC

AGCTCGGATGTGCGCCCGGCCGTGGAAAGCGCGTTCGGCCAGCGCCTGGAAGAGTTCCTGCAGGAAA

ACCCGAACGAAGCCAAGGCCATCGCCGGCAAGATCGTCGACGCTGCCCGTGCCCGCGAAGCGGCGCG

CAAGGCCCGCGACCTGACCCGCCGCAAGGGTGCGCTGGATATCGCCGGCCTGCCGGGCAAGCTGGCC

GACTGCCAGGAAAAGGATCCGGCGCTGTCCGAACTGTTCATCGTCGAGGGTGACTCGGCAGGTGGTT

CGGCCAAGCAGGGTCGCAACCGCAAGAACCAGGCGGTGCTGCCGCTGCGCGGCAAGATCCTCAACGT

GGAACGTGCGCGCTTCGACCGCATGCTGGCGTCCGACCAGGTGGGTACGCTGATCACCGCGCTGGGT

ACCGGCATCGGTCGTGACGAGTACAACCCGGACAAGCTGCGGTACCACAAGATCATCATCATGACCG

ACGCCGACGTCGACGGCGCGCACATCCGCACCCTGCTGCTGACGTTCTTCTACCGTCAGATGCCGGAG

CTGATCGAGCGCGGTTATGTCTATATCGGCCTGCCGCCGTTGTACAAGATCAAGCAGGGCAAGCAGG

AGCTGTACCTGAAGGACGACCCGGCGCTGGACAGCTATCTGGCCAGCAGCGCGGTGGAGAACGCTGG

GCTGGTGCCGGCCAGCGGCGAGCCGCCGATCGACGGCGTGGCACTGGAAAAGCTGCTGCTCGCCTAC

GCTGCCGCGCAGGACACGATCAACCGCAATACCCACCGCTACGACCGCAACCTGCTCGAAGCGCTGG

TCGACTTCATGCCGCTGGAGCTGGAAAACCTGCGCACTGCAGGTCCTGGCGAAGGTCTGGACGCGTT

GGCCAAGCACCTCAACCAGGGCAACCTCGGCAGCGCCCGCTTCACCCTGGAACTGCAGGAACCCAAC

GAGCAGCGTCCGGCGGCCGTACTGGTGACCCGCAGCCACATGGGCGAACAGCACATCCAGGTGCTGC

CGCTGTCCGCGCTGGAAAGCGGCGAACTGCGCGGCATCCATCAGGCAGCGCAGCTGCTGCACGGTCT

GGTCCGCGAAGGCGCGGTCATCACCCGTGGCGCCAAGTCGATCGAGATCGACTCGTTCGCACAGGCC

CGCAACTGGCTGTTGGACGAAGCCAAGCGCGGCCGGCAGATCCAGCGATTCAAGGGTCTGGGCGAAA

TGAATCCGGAACAGCTGTGGGATACCACCGTCAATCCCGATACCCGTCGCCTGCTGCAGGTGCGCATC

GAAGACGCGGTGGCCGCTGACCAGATCTTCAGCACCCTGATGGGTGATGTGGTCGAACCGCGTCGTG

ACTTCATCGAAGACAACGCGTTGAAGGTCGCCAACCTGGATATCTGA

118
DP69 Isoleucine--tRNA ligase
GTGAGCCAGGACTACAAGACCACCCTCAACCTGCCGGCCACCGAATTCCCGATGCGCGGCGACCT

GCCCAAGCGCGAGCCGGGCATTCTGGCGCGCTGGGAAGAGCAGGGGCTCTACCAGCAGCTGCGCGAC

-continued

AACGCCGCCGGCCGCCCGCTGTTCGTGCTGCATGACGGCCCGCCGTACGCCAATGCGCGCATCCACCT

GGGCCATGCGGTCAACAAGATCCTCAAGGACATCATCGTCAAGTCGCGCTACCTGGCCGGCTTCGAT

GCGCCCTACGTGCCGGGCTGGGACTGCCATGGCCTGCCGATCGAAATCGCGGTGGAAAAGAAGTGGG

GCAAGGTCGGGGTGAAGCTCGATGCGGTCGAGTTCCGGCAGAAGTGCCGCGAGTTCGCCGAAGAACA

GATCGACATCCAGCGTGCCGACTTCAAGCGCCTGGGCGTCACCGGCGACTGGGACAACCCGTACAAG

ACCCTAAGCTTCGATTTCGAGGCCAACGAGATCCGTGCGCTGTCCAAGATCGTGGCCAACGGCCATCT

GCTGCGTGGCGCCAAGCCGGTCTACTGGTGCTTCGACTGCGGCTCGGCACTGGCCGAGGCCGAGATC

GAGTACCACGAGAAGACCTCGCCGGCGATCGACGTGGCCTACACCGCGCGTGATCCGCAGGCGGTGG

CGCAGGCGTTCGGCGTCAGCCTGCCGGCCGATGTCGAAGTGGCGGTGCCGATCTGGACCACCACTCC

GTGGACGCTGCCGGCTTCGCTGGCGGTGTCGCTGGGCGCGGACATCCGCTACGTGCTGGCCGAAGGC

CCGGCGCACAACGGCAAGCGCCGTTGGCTGGTGCTGGCTGCTGCGCTGGCCGAACGGTCGCTGCAGC

GCTACGGCGTGGACGCGGTGGTGCTGCACGGTGAAGCCGAAGGTTCGGCGCTGGAAAACCAGCTGCT

GGCGCACCCGTTCTACCCGGAGCGCGAGATCCCCGTGCTCAACGGCGAACACGTGTCCGACGAGGAC

GGTACCGGTGCGGTGCACACTGCCCCCGGCCACGGCCAGGAAGACTACGTGGTCAGCCAGAAGTACG

GCCTGCTGGAGAAGTACAACGCCGGCCAGATCAATCCGGTCGACGGTGCGGGCGTGTACCTGGCGTC

CACCCCGCCCGCCGGTGACCTGGTGCTGGCCGGTACCCACATCTGGAAGGCGCAGCAGCCGATCATC

GAAGTGCTGGCCGCCAGCGGCGCGCTGCTCAAGGCCGTGGAGATCGTGCACAGTTATCCGCATTGTT

GGCGCCACAAGAAGACCCCGCTGGTGTTCCGCGCCACCCCGCAGTGGTTCATTTCGATGGACAAGGC

CAACCTGCGCAACGATGCGCTGGCCGCGATCGATACCGTCGGCTGGTTCCCGAGCTGGGGCAAGGCG

CGCATCCAAAGCATGATCGACGGCCGCCCGGACTGGACCATCTCGCGCCAGCGCACCTGGGGCGTGC

CGATCGCGCTGTTCACCCACCGCCAGACCGGCGAGATCCACCCGCGTTCGGTGGAGCTGATGCAGCA

GGTGGCCGACCGCGTTGAAGCCGAAGGCATCGACGTGTGGTACTCGCTGGATGCGGCTGAACTGCTG

GGCGCTGAAGCGGCCGACTACGAGAAGGTCACCGACATCCTCGATGTCTGGTTCGATTCCGGCGTGA

CCCACGAAGCCGTGCTGGCTGCCCGTGGCTTCGGCAAGCCGGCCGATCTGTACCTGGAAGGTTCGGA

CCAGCATCGCGGCTGGTTCCAGTCCTCGCTGCTGACCGGCGTGGCCATCGACAAGCGCGCGCCGTAC

AAGCAGTGCCTCACCCACGGTTTCACCGTGGACGAGCACGGCCGCAAGATGTCCAAGTCGCTGGGCA

ACGGCATCGAACCGCAGGAAATCATGAACAAGCTGGGCGCGGACATCCTGCGCCTGTGGATCGCCTC

GGCCGACTACAGCAACGAGATGTCGCTGTCGCAGGAAATCCTCAAGCGCACCGCCGACGCCTACCGC

CGCCTGCGCAACACCGCCCGCTTCCTGCTGGGCAACCTGGACGGTTTCGATCCGGCCCAGCACCTGCG

CCCGCTCAACGAGATGGTCGCGCTGGACCGCTGGATCGTGCATCGCGCCTGGGAGCTGCAGGAGAAG

ATCAAGGCGGCGTATGACAACTACGACATGGCCGAGATCGTGCAGTTGCTGCTGAACTTCTGCAGCG

TGGACCTGGGCTCGCTGTACCTGGACGTGACCAAGGATCGCCTGTATACGATGCCGACCGATTCGGAT

GGTCGTCGTTCGGCGCAGAGCGCGATGTACCACATCGCCGAAGCGTTCACCCGCTGGGTGGCGCCGA

TCCTGACCTTCACCGCCGACGAGCTGTGGGGCTACCTGCCGGGCGATCGTGCCGGCCACGTGCTGTTC

ACTACCTGGTACGAGGGCCTGGCACCGCTGCCGACCGATGCACAGCTCAACGCTGCCGACTTCGATC

AGCTGCTGGCCGTGCGCGAGCAGGTGGCCAAGGTGCTGGAGCCGATGCGCGCCAATGGTGCGATCGG

TGCCGCGCTGGAAGCGGAGATCACCATCGCCGCCAGCGAAGAGCAGGCCGCGCGCTGGCAGCCGCTG

GCCGATGAACTGCGTTTCCTGTTCATCAGTGGTGACGTGCAGGTGCGTCCGGCGACCACCGACGAGGT

GTTCGTCAGCGCGCAGCCGACGCAGAAGTCCAAGTGCGTGCGCTGCTGGCACCACCGTGCCGACGTT

GGCAGCAATGCCGACCACCCGGAACTGTGCGGCCGCTGCGTGACCAACATCGCCGGTGCCGGCGAAG

-continued

CGCGGAGCTGGTTCTGA

119
DP69 Glycine--tRNA ligase beta subunit
ATGAGCCACTTGTCTCCCCTGCTGATTGAACTGGGCACCGAAGAGTTGCCGGTCAAGGCGCTGCCG

GGCCTGGCCCAGGCCTTCTTCGACGGTGTTGTCGATGGCCTGCGCAAGCGCGGCGTCGAACTGGAGCT

GGGCGATGCCCGCCCGCTGTCGACCCCGCGCCGCCTGGCCGTGCTGCTGCCGGGCGTTGGCCTGGAA

CAGCCGGAACAACACAGCGAAGTGCTGGGCCCGTACCTGAACATCGCGCTGGACGCCGAAGGCCAG

CCGACCAAGGCGCTGCAGGGTTTCGCGGCCAAGGCCGGGATCGACTGGACCGCGCTGGAGAAGACC

ACCGACAACAAGGGTGAGCGCTTCGTGCACCGTGCGGTGACTCCGGGCGCGCGCACCGCTGCGCTGC

TGCCGGAGATCCTGCGCGAGGCCATCGCCGGCATGCCGATTCCCAAGCCGATGCGCTGGGGCGACCA

CAGCTGGGGCTTCGCCCGCCCGGTGCACTGGCTGGTGCTGCTGCATGGCGGCGACGTGGTCGAGGCC

GAACTGTTTGGCCTGAAGGCCGACCGCATGAGCCGCGGCCACCGCTTCCTGCACGACAAGACCGTGT

GGCTGACCCAGCCGCAGGACTATGTCGAATCGCTGCGCGCCGCCTTCGTGCTGGTCGATCCGGCCGA

GCGCCGCCGGCGCATCGTTGCCGAAGTGGAAGCCGCTGCCGCCACCGCCGGTGGCAGCGCACGCATC

ACCGAGGACAACCTGGAGCAGGTGGTGAACCTGGTCGAGTGGCCGGCGGCAGTGTTGTGCAGCTTCG

AGCGCGCGTTCCTGGCGGTACCGCAGGAAGCGCTGATCGAGACGATGGAGATCAACCAGAAGTTCTT

CCCGGTGCTGGATGACGGCGGCAAGCTGACCGAGAAGTTCATCGGCATCGCCAACATCGAGTCCAAG

GACGTGGCCGAAGTGGCCAAGGGCTACGAGCGCGTGATCCGCCCGCGCTTCGCCGATGCCAAGTTCT

TCTTCGACGAAGACCTGAAGCAGGGCCTGCAGGCGATGGGCGAGGGCCTGAAGACGGTGACCTACCA

GGCCAAGCTGGGCAGCGTGGCCGACAAGGTCGCGCGCGTGGCGGCGCTGGCCGAGGTGATCGCTGCG

CAGGTGGGGGCCGACCCGGTGCTGGCCAAGCGTGCCGCGCAGCTGGCCAAGAACGACCTGCAGTCGC

GCATGGTCAATGAGTTCCCGGAACTGCAGGGCATCGCTGGCCGCCACTACGCGGTGGCCGGTGGCGA

GTCGCCGGAGGTGGCGCTGGCCATCGACGAGGCCTACCAGCCGCGCTTCGGTGGCGATGACATCGCG

CTGTCGCCGCTGGGCAAGGTGCTGGCGATCGCCGAGCGTGTGGACACGCTGGCCGGCGGTTTCGCCG

CGGGCCTGAAGCCGACCGGCAACAAGGACCCGTTCGCCCTGCGCCGCAACGCGCTGGGCCTGGCCCG

CACGATTATCGAAAGTGGCTTCGAGCTGGACCTGCGCGCGCTGCTGGCCAGCGCCAATGCCGGGCTG

ACCGTGCGCAACGTGCAGGCCGACGTGGCTGAGCTGTACGACTTCATCCTCGACCGCCTGAAGGGCT

ACTACAGCGACAAGGGCGTGCCGGCCAGCCACTTCAATGCGGTGGCTGAGCTGAAGCCGGTCTCGCT

GTACGATTTCGACCGTCGCCTGGACGCCATCGGTATCTTCGCGGCGCTGCCGGAGGCCGAGGCGCTG

GCAGCGGCCAACAAGCGCATCCGCAACATCCTGCGCAAGGCCGAAGGCGATATTCCGGGCCAGATCG

ATGCGGCCCTGTTGCAGGAAGATGCCGAGCGCGCGCTGGCGGAAGCCGTGACTGCAGCCATCGACGA

CACCGGCGCCAGCCTGCACCAGAAGGACTACGTGGCCGTGCTGGCGCGCCTGGCCCGCCTGCGTCCG

CAGGTCGATGCGTTCTTCGATGGGGTGATGGTCAATGCCGAGGATCCGGCACTGCGCGGCAACCGCC

TGGCGCTGCTGACGATGCTGGGCGAGCGCTTGGGCAAGGTCGCGGCGATCGAGCATCTGTCGAGCTG

A

120
DP69 Glutamine synthetase
ATGTCCGTGGAAACCGTAGAGAAGCTGATCAAGGACAACCAGATCGAGTTCGTCGATCTGCGCTT

CGTCGACATGCGTGGTGTCGAACAGCATGTGACCTTCCCGGTCAGCATCGTCGAGCCGTCGCTGTTTG

AAGAAGGCAAGATGTTCGATGGCAGCTCGATCGCCGGCTGGAAGGGCATCAACGAGTCGGACATGGT

GCTGCTGCCGGACACCGCCAGCGCCTACGTCGACCCGTTCTACGCCGATCCGACCATCGTGATCAGCT

GCGACATCCTCGACCCGGCCACCATGCAGCCGTATGGCCGTTGCCCGCGCGGCATCGCCAAGCGCGC

CGAGTCCTACCTGAAGTCCTCGGGCATCGCCGAAACCGCGTTCTTCGGCCCGGAGCCGGAGTTCTTCA

-continued

TCTTCGACTCGGTGCGTTTCGCCAATGAAATGGGCAACACCTTCTTCAAGGTCGACTCGGAAGAAGCG

GCGTGGAACAGCGGCGCCAAGTACGACGGCGCCAACAGCGGCTACCGTCCGGGCGTGAAGGGCGGT

TATTTCCCCGTTCCGCCGACCGACACCCTGCACGACCTGCGTGCGGAGATGTGCAAGACCCTGGAACA

GGTCGGCATCGAAGTGGAAGTGCAGCACCACGAAGTGGCCACCGCCGGCCAGTGCGAGATCGGCAC

CAAGTTCAGCACCCTGGTGCAGAAGGCCGACGAACTGCTGCGGATGAAGTACGTCATCAAGAACGTC

GCCCACCGCAACGGCAAGACCGTCACCTTCATGCCCAAGCCGATCGTCGGCGACAACGGCAGCGGCA

TGCACGTGCACCAGTCGCTGTCCAAGGGCGGCACCAACCTGTTCTCCGGTGACGGCTACGGTGGCCTG

AGCCAGATGGCGCTGTGGTACATCGGCGGCATCTTCAAGCATGCCAAGGCGATCAACGCCTTTGCCA

ACTCGGGTACCAACAGCTACAAGCGCCTGGTGCCGGGCTTCGAAGCCCCGGTGATGCTGGCCTACTC

GGCGCGCAACCGTTCGGCCTCGTGCCGCATTCCGTGGGTGTCCAACCCGAAGGCGCGTCGCATTGAA

ATGCGCTTCCCCGATCCGATCCAGTCGGGCTACCTGACCTTCACCGCGCTGATGATGGCCGGCCTGGA

CGGCATCAAGAACCAGATCGACCCGGGCGCACCGAGCGACAAGGATCTGTACGACCTGCCGCCGGA

AGAAGAGAAGCTGATTCCGCAGGTCTGCTCCTCGCTGGACCAGGCCCTGGAAGCGCTGGACAAGGAC

CGTGAGTTCCTCAAGGCCGGTGGCGTGATGAGCGATGACTTCATCGACGGCTACATCGCGCTGAAGA

TGCAGGAAGTGACCAAGTTCCGCGCGGCGACCCACCCGCTGGAATACCAGTTGTACTACGCCAGCTG

A

121
DP69 Glucose-6-phosphate isomerase
ATGACAACGAACAACGGATTCGACTCGCTGCATTCCCACGCCCAGCGCCTGAAGGGCGCAAGCAT

CCCCAGCCTGCTCGCCGCCGAACCCGGCCGCGTACAGGACCTGGCGCTGCGGGTCGGTCCGTTGTATG

TCAACTTCGCCCGGCAGAAATACGATGCCGCGGCGTTGCAGGCGCTGTTGGCGCTGGCTGCCGAACG

TGATGTCGGCGGCGCCATCACGCGCCTGTTCCGTGGCGAGCAGGTCAATCTGACCGAAGGCCGCGCC

GCACTGCACACCGCACTGCGCGGCGACGTGGTCGATGCGCCGGTTGCCGCCGAGGCCTATGCCACGG

CCCGCGAAATCCGCCAGCGCATGGGCGTGCTGGTGCGCGCACTGGAAGACAGTGGCGTGACCGATGT

GGTCAGTGTCGGCATCGGCGGTTCCGATCTCGGTCCGCGTCTGGTCGCCGACGCACTGCGTCCAGTCA

CTGGCGCTCGCCTGCGCGTGCATTTCGTGTCTAACGTGGACGGCGCTGCCATGCAGCGCACGCTGGCC

ACGCTGGATCCGGCGAAGACCGCCGGCATCCTCATTTCCAAGACCTTCGGTACCCAGGAAACCCTGCT

CAACGGCCAGATCCTGCACGATTGGCTGGGTGGCAGCGAGCGCCTGTACGCGGTCAGCGCCAATCCG

GAACGCGCCGCCAAGGCCTTCGCCATCGCCGCCGAGCGCGTGCTGCCGATGTGGGACTGGGTAGGGG

GGCGCTATTCGCTGTGGTCGGCCGTCGGTTTCCCGATCGCACTGGCCATCGGCTTCGAGCGTTTCGAG

CAGTTGCTGGAAGGCGCCGCGCAGATGGATGCGCATGCGCTGGACGCGCCGCTGGAGCGCAACCTGC

CGGTGCTGCACGGCCTGACCGACATCTGGAACCGCAATCTGCTGGGCTCTGCCACGCATGCGGTGAT

GACCTACGACCAGCGCTTGGCGCTGCTGCCGGCCTACCTGCAGCAGCTGGTGATGGAAAGCCTGGGC

AAGCGCGTGCAGCGCGATGGCCAGCCGGTCACCACCGACACCGTGCCGGTGTGGTGGGGCGGTGCCG

GCACCGATGTGCAGCACAGCTTCTTCCAGGCCCTGCACCAGGGCACCAGCATCATTCCGGCCGATTTC

ATCGGCTGCGTGCACAACGACGATCCGTATACGGTCAACCACCAGGCGTTGATGGCCAACCTGCTGG

CGCAGACCGAAGCGCTGGCCAACGGCCAGGGCAGTGACGATCCGCACCGCGATTATCCGGGTGGCCG

CCCGAGCACGATGATCCTGCTCGACGCGCTCACCCCGCAGGCGCTGGGCGCCTTGATCGCGATGTAC

GAACACGCCGTGTACGTGCAGTCGGTGATCTGGAACATCAACGCCTTCGACCAGTTCGGTGTCGAGCT

GGGCAAGCAGCTGGCCAGTGGCCTGCTGCCCGCTCTGCAGGGTGAGGATGTCGAGGTCAACGACCCG

CTGACCCGTGAGCTGCTGGCCCAGCTGAAGGGCTGA

-continued
122
DP69 Leucine--tRNA ligase
ATGACCAGCGTCGAACCCAACGTTTACGATCCGCAGCAGGTTGAATCCGCCGCCCAGAAGTACTG
GGACGCTACCCGTGCCTTCGAGGTCGATGAAGCCTCGGACAAGCCGAAGTACTACTGCCTGTCGATG
CTTCCGTATCCGTCCGGTGCGCTGCACATGGGCCACGTGCGCAATTACACGATCGGCGACGTGATCAG
CCGCTACAAGCGCATGACCGGCCACAACGTGCTGCAGCCGATGGGCTGGGACGCGTTTGGCCTGCCG
GCGGAAAACGCTGCGATCAAGAACAAGACCGCGCCGGCCGCCTGGACCTACAAGAACATCGACCAC
ATGCGCAGCCAGCTGCAGTCGCTGGGCTATGCCATCGACTGGTCGCGCGAGTTCGCCACCTGCCGCCC
GGACTATTACGTCCACGAGCAGCGCATGTTCACCCGCCTGATGCGCAAGGGCCTGGCCTACCGCCGC
AACGCGGTGGTGAACTGGGACCCGGTCGACCAGACCGTGCTGGCCAACGAGCAGGTCATCGACGGCC
GTGGCTGGCGCTCCGGCGCGCTTGTGGAAAAGCGCGAGATCCCGCAGTGGTTCCTGCGCATCACCGA
CTACGCCCAGGAACTGCTGGACGGCCTGGATGAGCTGGACGGCTGGCCGGAGTCGGTCAAGACCATG
CAGCGCAACTGGATCGGCCGCTCCGAAGGGCTGGAAATCCAGTTCGACGTGCGCGACGTCGATGGTG
CCGCACTGGATCCGCTGCGCGTGTTCACCACCCGCCCGGACACCGTGATGGGCGTGACTTTCGTGTCG
ATCGCGGCCGAACATCCGCTGGCGCTGCATGCCGCGAAGAACAACCCGGAACTGGCTGCGCTGCTGT
CGGAAATGAAGCAGGGCGGCGTGTCCGAGGCCGAGCTGGAGACCCAGGAAAAGCGCGGCATGGATA
CCGGCCTGCGCGCCGTGCATCCGGTTACCGGTGCCCAGGTGCCGGTGTGGGTCGCCAACTTCGTGCTG
ATGGGCTACGGCACTGGCGCGGTGATGGCCGTACCGGGCCACGACCAGCGCGACAATGAATTCGCCA
ACAAGTACAACCTGCCGATCCGCCAGGTCATCGCGCTGAAGTCGCTGCGCAAGGACGAAGGCGCCTA
CGACGCGACGCGCTGGCAGGACTGGTACGGCGACAAGACCCGCGAGACCGAACTGGTCAACTCCGA
AGAGTTCGACGGCCTGGACTTCCAGGGCGCTTTCGAGGCGCTGGCCGAACGGTTCGAGCGCAAGGCC
CAGGGACAGCGCCGGGTGAACTACCGCCTGCGCGACTGGGGCGTGAGCCGCCAGCGCTACTGGGGCT
GCCCGATTCCGGTGATCTACTGCGACAAGTGTGGCGCGGTACCGGTGCCGGAAGACCAGCTGCCGGT
GGTGCTGCCGGAAGACGTGGCGTTCGCCGGTACCGGTTCGCCGATCAAGACCGATCCGGAATGGCGC
AAGACCACCTGCCCGGACTGCGGCGGTGCGGCCGAGCGTGAGACCGACACCTTCGACACCTTCATGG
AGTCGAGCTGGTACTACGCCCGCTACACCTCGCCGGGCGCCCGCGATGCGGTCGACAAGCGCGGCAA
CTACTGGCTGCCGGTGGACCAGTACATCGGTGGCATCGAACACGCGATCCTGCACCTGATGTATTTCC
GCTTCTACCACAAGCTGCTGCGCGACGCGCGGATGGTGGACAGCAACGAACCCGCGCGGAACCTGCT
GTGCCAGGGCATGGTGATCGCTGAGACCTACTACCGCCCGAACCCGGACGGCTCGAAGGACTGGATC
AACCCGGCCGATGTGGAAGTGCAGCGCGACGAGCGCGGCCGCATCACCGGCGCCACCCTGATCGCCG
ACGGTCAGCCGGTGGTGGTCGGTGGTACCGAGAAGATGTCCAAGTCGAAGAACAACGGCGTGGACCC
GCAGGCGATGGTCGGCAAGTACGGCGCCGATACCGTGCGCCTGTTCTCGATGTTCGCTGCACCGCCG
GAACAGTCGCTGGAATGGAACGAAGCCGGCGTGGACGGCATGGCCCGCTTCCTGCGCCGCCTGTGGG
CACAGGTGCAGAAGCACGCTGCCGAGGGTGCCGCACCGGCGCTCGACGCGGCCGCGCTGGATGCCGG
CCAGAAGGCCCTGCGCCGCAAGACCCACGAGACCATCGGCAAGGTCGGCGACGACTACGGCCGCCG
CCACAGCTTCAACACCGCCATTGCCGCGGTGATGGAGCTGATGAACGCGCTGGCCAAGTTCGAGGAC
GGCAGTGAACAGGGGCGCGCCGTGCGCCAGGAAGCACTGCAGGCCATCGTGCTGCTGCTCAACCCGA
TCACCCCGCATGCCAGCCACGCCCTGTGGCAGGTACTGGGCCATGGCGAAACGCTGCTGGAAGATCA
GCCGTTCCCGCAGGCCGACAGCAGTGCGCTGGTGCGCGATGCGCTGACTTTGGCCGTGCAGGTCAAT
GGCAAGCTGCGTGGCACCATCGAGGTCGCCGCCGATGCCGCGCGCGAGCAGATCGAAGCGCTGGCCC
TGGCCGAGCCGAACGCGGCCAAGTTCCTGGAAGGCCTGACGGTGCGCAAGATCATCATCGTTCCCGG
CAAGATCGTGAACATCGTCGCTGCCTGA -continued 123
DP70 Glycine--tRNA ligase beta subunit
ATGTCTAAACATACAGTATTGTTCGAATTGGGCTGTGAAGAACTTCCACCTAAAAGCCTCAAAAAA

TTACGTGATGCACTGCATGCTGAAACGGTAAAAGGCTTAAAAGATGCAGGCTTAGCATTCGACTCAA

TCGAAGCTTATGCAGCACCGCGTCGTTTGGCACTTAAAATTGTGAATATCGATGGCGCTCAGCCTGAT

ACACAAAAACGCTTTGACGGCCCTGCAAAAGAAGCGGCTTATGATGCTGAAGGCAAACCAAGCAAA

GCATTAGAAGGCTTTATGCGTGGTCAAGGCATCACTGCGGATCAAGTCACCACGTTCCAAGCGGGTA

AAGTTGAAAAGGTTTGCTATTTAAAAGATGTTAAAGGTCAAAGCCTTGAGGTTTTACTGCCACAAATT

CTACAAGCAGCTTTGGACAATCTTCCAATTGCAAAACGTATGCGTTCAGCGGCAAGCCGTACTGAATT

CGTGCGTCCTGTAAAATGGGTGGTGTTGCTCAAAGACAATGATGTGATTGCAGCCACTATTCAAGATC

ACAAAGCAGGCAATGTGACTTATGGTCATCGTTTCCATGCCCCTGAAGCGATTACTTTGGCTCATGCA

GATGAATATCTTGCCAAGTTAAAAGCGGCTTATGTGGTTGCTGACTTTGCAGAACGCCAAGCCATCAT

TGACCAACAAGTCAAAGCGTTGGCTGATGAAGTTAATGCGATTGCGATTGTACCAAGCGACCTGCGT

GATGAAGTGACCGCATTGGTGGAATGGCCTGTTGCGCTACGTGCCAGCTTTGAGGAGCGTTTCCTTGC

TGTACCGCAAGAAGCTTTGATTACCACGATGCAAGACAACCAAAAATACTTCTGTTTGGTGAATAGTG

ATAACAAGCTACAGCCTTATTTCATTACTGTTTCAAATATTGAGTCTAAAGATCCGATTCAAATTATTG

AAGGCAATGAAAAAGTGGTTCGTCCACGTTTGTCGGATGCTGAATTCTTCTTCTTGCAAGATCAAAAG

CAACCACTAGCTTCTCGTAAAGAAAAACTGGCTAACATGGTGTTCCAAGCACAATTGGGTACGCTGT

GGGATAAGTCACAACGTATTGCAAAATTGGCTGTGGCTTTATCGAACATCACGGGTGCAACTGCGGC

TGATGCTGAAAAAGCAGCATTGCTGGCAAAATGTGACTTAACCTCTGAATTGGTGGGTGAATTCCCTG

AACTTCAAGGCATTGCGGGAACCTATTACGCACGCATTGAAGGTGAAAACCATGAAGTGGCTGAAGC

TTTAGGCGAACAGTATTTACCTAAATTTGCAGGCGATGTTTTACCGCAAACAAAAACAGGCACAACC

ATTGCCCTTGCCGACCGTTTAGACACGCTCACGGGTATTTTTGGTATTGGTCAAGCACCTACAGGTTCT

AAAGATCCGTTTGCATTACGTCGTTCTGCAATCGGTATTTTACGTTTGGTGACTGAAAACAATCTTGAT

GTGTCGATTGAAGATTTAATCCAGCTGGCATTAAACGCTTATGGCGATGTTGTAGCGGATCATGCGAA

GACTTTAGCGGATGCTGTTGCATTCCTTGAAGGTCGTTACCGTGCCAAGTATGAAGACCAAGGCGTTG

CAGTTGATGTGATTCAAGCGGTTCAAGCATTATCACCAAAATCACCTTTAGATTTTGATAAGCGTGTG

ACTGCGGTAAATCATTTCCGTGCATTGCCTGAAGCTGCTGCACTGGCTGCTGCAAATAAGCGTGTTGC

CAACATTCTTGCCAAAGAAGCAGAACTAACAGGCGCAGTGGTTGAAGCAAACTTGGTTGAAGAGGCT

GAAAAAGCATTATTCGCTGTACTTGCTAAAATTACGCCTGAAGTTGAACCATTATTTGCTGCCAAAGA

TTACACCACTGCATTGTCTAAGCTTGCTGCTTTACGTGCGCCTGTGGATGCATTCTTTGAAGGCGTCAT

GGTCATGGCAGATGATGCAGAATTGAAAGCCAACCGTTTACGTTTATTGGCTCAATTACGTGGTTTGT

TTACAAGTGTTGCGGATATTTCGGTGTTGCAGCACTAA

124
DP70 DNA gyrase subunit B
ATGAGTTCAGAAGATCAAGCTGCTTCTCAAACAGAACAAACCAATGAAAAGGCTTATGATTCCTCT

AGTATCAAAGTATTACGTGGCCTAGATGCTGTTCGTAAGCGTCCGGGTATGTATATTGGTGATACGGA

CGATGGTTCAGGTTTACATCACATGGTGTTTGAGGTGGTCGATAATGCGATTGATGAAGCCTTAGCGG

GTCACTGTGATGAAATCTTAGTCACCATCCATGAAGATGAGTCTGTAAGTGTTGCAGATAACGGTCGT

GGGATTCCAACGGATATTCACCCTGAAGAAGGGGTATCTGCCGCTGAAGTGATTTTAACCATTTTGCA

TGCTGGCGGTAAGTTTGATGATAATAGCTATAAAGTTTCCGGTGGTTTACACGGGGTAGGTGTTTCTG

TTGTAAATGCCTTGTCGAGTAAATTATTACTAAATATTCGTCGTGCAGGAAAAGTATATGAACAGGAA

-continued

TATCACCATGGTGATCCTGTCTATCCATTACGCGCGATTGGTGATACTGAAGAAACCGGTACCACCGT

TCGTTTCTATCCGAGTGAATTAACCTTCTCTCAAACGATTTTTAATGTTGATATTTTAGCGCGTCGTTT

GCGCGAACTTTCATTCTTAAATGCAGGGGTTCGTATTGTATTACGTGATGAACGTATCAATGCTGAAC

ATGTATTTGATTATGAAGGTGGTTTGTCTGAATTTGTAAAATATATCAATCAAGGTAAAACCCACTTG

AATGAGATTTTTCATTTTACCAGTGAAGTTGTGGAAACAGGAATTACTGTTGAAGTAGCATTACAGTG

GAATGATACTTATCAAGAAAATGTCCGTTGCTTTACCAATAACATCCCACAAAAAGATGGTGGTACG

CATTTAGCCGGTTTCCGTGCCGCGTTAACACGGGGTTTAAACCAGTATCTTGATAGTGAAAATATTCT

TAAGAAAGAAAAAGTTGCTGTCACAGGTGATGATGCCCGTGAAGGTTTAACGGCGATTGTTTCAGTG

AAAGTGCCTGATCCAAAATTCTCATCACAAACCAAAGAAAAATTGGTTTCCAGTGAAGTGAAAACTG

CTGTAGAGCAGGCGATGAACAAGTCTTTTTCTGAATATCTTTTAGAAAATCCACAAGCGGCTAAATCG

ATTGCCGGCAAAATTATTGATGCTGCACGTGCACGTGATGCTGCGCGTAAAGCACGTGAAATGACAC

GTCGTAAGAGTGCATTAGATATTGCTGGTCTGCCTGGTAAACTGGCGGATTGCCAAGAAAAAGATCC

AGCATTGTCTGAACTTTACTTGGTCGAAGGTGACTCGGCGGGCGGTTCTGCAAAACAGGGTCGTAACC

GTAAGATGCAAGCTATTCTGCCGCTTAAAGGTAAAATCTTAAACGTAGAACGTGCACGTTTTGACAA

AATGATTTCATCGCAAGAAGTGGGCACGCTGATTACTGCACTGGGCTGTGGTATTGGTCGTGAGGAAT

ACAATCCTGATAAATTGCGTTATCACAAAATCATTATCATGACCGATGCCGACGTCGATGGTTCGCAC

ATTCGTACGCTCCTGTTGACCTTCTTCTTCCGTCAAATGCCAGAACTTGTGGAACGTGGTTATATTTAT

ATTGCACAGCCACCGTTGTATAAGTTGAAAAAAGGTAAGCAAGAGCAATATCTTAAAGATAATGATG

CTTTAGAAACCTATCTTATTTCGAATGCCATTGATGAGCTTGAACTGCATATTAGTGCTGAGGCACCT

GCGATTCGTGGTGAATCTTTGGCTAAAGTGATTGCTGATTATCAAACCTCACAAAAAAGTTTAAATCG

TTTAACGCTACGTTATCCTGCAAGCTTGCTGGATGGTTTACTTGGTTTGGATGCATTTAAACTTGATCA

AAATCATGATGAAGATTATGTAAAACAATGGTCTGAACAATTGCGTGCAGCAATTGAACAACACCAA

CCAAGTTTGCGTCCTGAAATCACCTTAGAAGCTTTTGAAAAAGAGCATGCAGATGGTGAGAAAGTGA

CGCATTATTGGCCACGTGTAACGGTCTATGTACATAACTTGCCGCATCATTATTTACTTGATTCTGGAT

TATTGGCTTCAAGTGAATACAAGCGTTTACTGCAAAATTCGAAGAGTTGGTTCACATTGCTTGAAGAT

GGCGCTTATTTGCAAAAAGGTGAGCGTAAAATTCATGTCGCCACTTTCCATCAAGTTTGGCAACATAT

TTTATCCGACTCGCGTCGTGGCATGATGATCCAGCGCTATAAAGGTTTGGGTGAGATGAACGCGGAA

CAGCTTTGGGAAACCACCATGGATCCTGAAAACCGTAACATGTTGCAAGTCACCATTAATGATGCGA

TTGAAGCGGATCGTATGTTCTCTTGTTTGATGGGAGATGATGTGGAACCACGTCGTGCCTTCATTGAA

GAAAATGCTTTAAATGCGGATATTGACGCTTAA

125
DP70 Leucine--tRNA ligase
ATGACTACTTCTCACATTGACCCTGAATATCAAGCGAGCGCGATTGAATCCACTGTCCAACAAGAC

TGGGAAACTCGCAAAGCCTTTAAAGTTGCCGACACTGTAGAAGGTAAACATCGTTATATCCTCTCGAT

GTTCCCTTATCCAAGTGGCAAGCTGCATATGGGTCATGTGCGTAACTACACCATTGGCGACGTGATTA

GCCGTTTCCACCGTCTCAAAGGTGAAACTGTCCTACAACCGATGGGTTGGGATGCTTTTGGTCTGCCT

GCGGAAAATGCAGCGATTGCACACCAAGTTGCCCCTGCAAAATGGACCTTTGAAAACATCGCGTACA

TGCGTGACCAGTTAAAAAAATTGGGTCTGTCAGTCGATTGGGATCGTGAATTTGCGACCTGTACGCCA

GAGTATTATCACTGGGAACAATGGTTATTTGTACAGCTGTATAAAAAAGGGCTGATTTATCGCAAACT

TTCAACGGTAAACTGGGATCCTGTCGATCAGACTGTACTTGCTAATGAACAAGTTGAAAATGGTCGTG

GTTGGCGTTCGGGTGCATTGGTTGAAAAACGTGATATTCCAATGTATTACTTCCGTATTACCGATTAT

GCACAAGAATTATTAGACGATTTAGATTCGCTTAAAGATGGTTGGCCGCAACAAGTCTTGACCATGCA

-continued

ACGCAACTGGATTGGTCGTTCACAAGGCATGGAAATCACCTTTCCATCTGCGAACCCTGAAATCTATG

CAGATGATTTAACGGTTTATACCACACGTGGTGACACCTTGATGGGCGTGACGTATGTTGCGGTTGCC

GCTGAACATCCAATGGCGCTTAAAGCGGCTGAAACAAATCCCGAATTGGCTGCATTTATTGAAGAAT

GCCGTATGGGTTCAGTGGCTGAAGCAGATCTTGCCACTGCCGAGAAAAAAGGCATGGCCACTGGTTT

GTCTGTGAAGCATCCTGTAACGGGTGAAGTGGTTCCAGTGTGGATTGCGAACTATGTATTGATGTCAT

ACGGTTCAGGTGCGGTGATGGCAGTTCCAGCACACGACGAACGTGATTTCGAATTTGCCAACAAATA

TGGTTTAACCCTCCAGCAAGTGATTGATGCCAAAGGTGCAGACGATGCTGAATTTTCTGCAACTGAAT

GGCAGGAATGGTATGGCTCGAAAGAAGGCAAACTGGTTAATTCTGGCGAATTTGACGGTTTAGACTT

CCAAGCTGCATTTGATGCATTCATTGCAAAATTAGAACCACAAAAACTGGCAAATACGAAAGTTCAG

TTCCGTCTACGTGACTGGGGTGTTTCGCGTCAGCGTTATTGGGGTTGTCCAATTCCAATGATCAACTGT

GAAACTTGTGGTCAAGTACCTGTACCTGAAGAACAACTTCCAGTAATTTTACCAACTGACGTGGTGCC

AGATGGTTCAGGCAATCCGTTAAATAAAATGCCTGAATTTTATGAAACCCAATGTCCATGTTGTGGTG

CAGGTGCACGCCGTGAAACCGATACTTTGGATACGTTCGTAGAGTCATCTTGGTACTATGCACGTTAT

GCATCTCCAGATTTCACTGGCGGTTTAGTTAAACCTGAAGCTGCAAAATCATGGCTACCAGTCAACCA

ATATATTGGCGGTGTGGAACATGCAATTTTGCATTTATTGTATGCCCGTTTCTTCCATAAATTGATGCG

TGATGAAGGCGTCGTTGAAGGCAATGAACCTTTCGCTAACTTACTGACTCAAGGTATGGTTTTAGCTG

ATACCTTCTACCGTGAAGCCGAATCAGGTAAGAAAACATGGTTTAATCCTGCGGATATTGAATTAGA

AAAAGACGAAAAAGGTCGTGTTCTTTCTGCTAAATACACAGGTGATGGCCAAGAAGTTGTGGTTGGC

GGTCAAGAAAAAATGTCGAAATCGAAAAATAATGGCATCGACCCGCAATCGATTATTGATCAATACG

GCGCAGATACTGCACGTGTATTTATGATGTTTGCGGCCCCACCCGATCAATCGCTTGAATGGTCTGAT

GCCGGTGTGGAAGGTGCAAACCGTTTCTTGAAACGTGTATGGCGTTTAACCACAGGTTTCTTAGAAAA

AGGCAACCATGCTGCTGTAATTGATGTTGCGAATTTGTCATCAGCGGCACAAGACTTACGTCGTAAAA

CCCACGAAACCATTCAAAAAGTCGGTGATGACATTGAACGTCGTCATGCCTTCAATACTGCCATTGCA

GCGCAAATGGAATTATTGAATGCTTGCAATAAATTTGAAGCCAAAGATGATAATGACGTTGCGGTTG

AACGCGATGCTATTGTTAGCTTACTCACTTTACTTGCACCATTTGCACCACATTTAAGTCAGACCCTAT

TGGCTCAATTCGGTATTGAGTTAACTGAAACCTTGTTCCCTACTGTGGATGAGTCTGCGCTAACCCGC

AACACACAAACTATTGTGGTACAGGTCAATGGTAAACTTCGTGGCAAGTTGGAAGTGTCTGTTGATCT

CTCTAAAGAAGATATTTTGGATCAAGCCAAAGCATTGCCTGAAGTACAACAATTCTTAACCGGTCCAA

CCAAGAAAGAAATTGTGGTGCCGAATAAATTGGTCAATTTGGTGGTTTAA

126
DP70 Glucose-6-phosphate isomerase
ATGAATAGTATTGAAAAATTTCCCTTGCATGATACGGATCTGATTCAGGAAAAACTAAAAAGTTTT

GCCCAACAAGAGCAAGAGATTAATTTAAATTATTTATTTAAAAAAAATAAAAAACGTTTTGATGAAT

ATTCCGTTCATGCGGGTCAGTTATGTTTTGATTATAGTAAGCACCGTGTTGATGAGCGTATTATTAACG

AGCTTATTTGTTATGCGGAATCACAACATTTGGGTAACTGGATTCAGCGCTTATTTTCTTTAGAAAAA

ATTAATTACACTGAAAATCGCGCAGCGATGCATTGGGCTTTGCGTTTGCCGAAGCAAGATAGTACAC

ATGCAGATTTGGCAGCGCAGGTACATAGTCAGCTTGATCGTATGTATCAATTGGTCGAGAAAATTCAT

CAGGGGCAGTATCGAGGAGCTACAGGTGAGGTCATCCATGATGTGGTCAATATTGGTGTCGGTGGAT

CAGATCTTGGTCCTTTAATGGTGTCTCAAGCGCTGACTGATTTTAAAGTTCAAACGGCTCAAAAATTA

AAAGTCCATTTTGTTTCGACGATGGATGGCAGCCAACTTTCAGATCTTTTACATCAGTTTCGCCCAGA

AACCACCTTGTTTATTATTTCATCCAAGTCTTTTGGCACCATTGATACGCTTTCCAATGCACAAACGGC

-continued

AAAATGCTGGCTTGAGCAATCTTTAGGAACGTCGAAATCAGTTCTAAGATGTCACTTTGTTGGTGTTT

CAACCAAGCCCGATAAGATGACCGAGTGGGGAATCAGCACTGAAAATCAATTCTTATTGTGGGATTG

GGTCGGTGGGCGCTATTCACTATGGTCGTGTATTGGTTTGCCTATTGCATTAAGTATTGGGGTCGAGG

GCTTTAAACAGTTGCTTGCTGGTGCTTATGAAATGGATCAGCATTTTCAGAACACACCACTTGAACAA

AATATTCCTGTGTTGATGGGTTTACTGGGAATATGGAATAACAACTTCCTGAATATTCAAACTCATGC

GGTACTTCCTTATGATGGTCGGCTGAAATATTTTGCGGCTTATTTACAGCAATTGGAAATGGAGTCGA

ATGGTAAGTCGATTCAGCGTTCTGGTGAAAAAGTCGTATTAGATACCTGCCCAATTTTATGGGGTGAA

GTTGGACCAAATGCACAACATGCTTTTTATCAGCTGCTGCATCAAGGTACACATGCTGTGAGTTGTGA

CTTTATTGCACCTGTGAAACGCTATAATGCCAATCAATTTACCTATGTTGAAAATGCAGAGGCTTTAG

TTGAACAACACCATTTAGCCTTATCGAATTGTTTGGCACAATCACGTCTATTGGCCTTTGGTAATCATG

TTCTAGATCCGAAAGAAGTAGAAAGTTCACCGAAATATAAACAATATGCAGGCAACCAACCGACCAC

AACAATTTTGTTAAAAGAGTTGAATCCGCGCAGTTTAGGTATGCTCATTGCGATGTATGAGCACAAGG

TATTTGTGCAATCCGTGATGTGGAATATTAATCCATTTGACCAATGGGGCGTAGAAAAAGGTAAAGA

AATTGCCAATCAACTGTTACCGATTCTCAATCAAGAGCAAGCTGATGTTTCTGATCTTGATTCTTCAAC

GCAAGGTCTATTAAGAATTTTACTGGGAAAAGCTGATGGCTAA

127
DP70 NADH-quinone oxidoreductase subunit C/D
ATGGCTGAAACTGACATTGCTATGCCAGAATCAACGCCTGTTGATTCACGCCCAGCATTTGCAATT

GTAGAAGAGCTCAAAGCCAAATTTGGTGAGAACTTCTATGTGCAAGCGACTTTTGAAGATTTTCCAAC

GGTCTGGGTTGAGCGCGCGCGCGTACAAGATGTTTTAATGTTCTTGCGTAAAGTATCACGTCCATACG

TGATGCTGTTCGACTTGTCTGCGGTAGATGAGCGTTTACGTACCCACCGTGACGGTTTACCTGCATCA

GACTTCACTGTGTTTTATCATTTGTTGTCGCTAGAGCGCAACAGTGATATTCGTATTAAAGTTGCGTTG

AGTGAGAGTGATCTCAATCTTCCAACCGCAACCAACATTTGGCCAAATGCCAACTGGTACGAACGTG

AAGCTTACGATATGTTCGGGATCAATTTCGAAGGGCATCCAATGCTCCGTCGTATTTTGTTGCCAACC

TATTGGGAAGGTCACCCACTGCGTAAAGAATATTCTGCACGTGCGACTGAATATACACCGTATATGCA

GAACCAAGCGAAGCAGGATTTCGAGCAAGAACATTTACGTTTTGTTCCTGAAGATTGGGGTCTATCAC

GCGGTAATGCCGATGAAGATTTCATGTTCTTGAACTTAGGTCCAAACCATCCATCTGCGCACGGTGCA

TTCCGTATCATTTTGCAGTTGGACGGTGAAGAAGTGAAAGACTGTGTGCCTGATATTGGCTATCACCA

CCGTGGTGTGGAAAAGATGGCTGAACGTCAAACTTGGCATTCATTCATTCCATATACCGACCGTGTTG

ACTACTTGGGTGGTTGTGCGCAAAACATGCCTTATGTGATGGGTGTGGAGCAAATGGCAGGAATTAC

TGTTCCTGACCGTGCACAATGTATCCGTGTCATGATGTCTGAATTATTCCGTATCAATAACCATTTATT

GTTTATTGGTACTGCAATTCAAGATGCCGGCGGTATGACGCCAGTCTTCTATATGTTTGCCGATCGTC

AAAAGATCTATGATGCGATTGAAGCGATTACAGGCTACCGTATGCATCCAGCATGGTTCCGTATTGGC

GGGACTGCGCACGACCTTCCAAACAATTGGCAACATCTGATTCGTGAAATTCTCGAATGGATGCCGA

AGCGTATGAATGAATACTATACAGCTGCACTACGCAACTCAGTATTTATTGGTCGTACCCGTAATGTT

GCACAATACGATGCAAAATCTGCATTGGCTTGGGGTGTAACAGGTACAGGTCTACGCGCGACAGGGA

TTGATTTCGACGTGCGTAAATACCGTCCGTATAGCGGTTATGAAAACTACGACTTCGACGTGCCTTTA

GAATACGAAGGCGATGCTTACGCTCGTGTGATGGTTCACTTCCGTGAAATTGAAGAATCACTGAAAA

TTGTGAAGCAGTGCTTGGATAACATGCCATCTGGTCCATATAAAGCGGATCATCCTTTGGCTGTTCCA

CCACCAAAAGACAAGACATTACAAGATATTGAAACTTTGATTACGCACTTCTTGAGCGTGTCATGGG

GTCCTGTGATGCCTGCGGGTGAAGCGTCTGTAATGGCTGAAGTGGTAAAAGGTGCATCGAACTACTA

CTTGACTTCAGACAAGTCAACCATGAGTTATCGTACCCGTATTCGTACACCAACTTTCACGCACTTAC

-continued

AGCAAATGCCTTCTGTGATTAATGGCAGTCTTGTATCTGACTTGATCATTTATTTAGCGACCATTGACG

TCGTAATGGCTGACGTGGATCGCTAG

128
DP70 Protein RecA
ATGGATGATAATAAAAGTAAGGCGCTTAATGCTGCCCTAAGCCAGATTGAAAAACAATTTGGTAA

AAATACCGTAATGCGTCTTGGTGATAATACCGTATTGGCCGTTGAAGCGGTCTCTACAGGTTCTTTAA

CACTAGACATTGCACTTGGTATTGGTGGCTTACCAAAAGGTCGTATCGTTGAAATTTACGGTCCTGAA

TCTTCTGGTAAAACCACAATGACATTGCAAGCGATTGCACAATGTCAAAAAGCCGGTGGTACTTGTGC

TTTTATCGATGCAGAACATGCACTCGATCCTCAGTATGCACGTAAGCTTGGTGTCGACCTTGACAACC

TGTTGGTTTCTCAACCAGACCACGGTGAACAAGCCCTTGAAATTGCAGACATGTTAGTCCGCTCTGGT

GCTATTGACATGATCGTTGTCGATTCCGTGGCTGCACTGACACCTCGCGCTGAAATTGAAGGTGAAAT

GGGCGACTCACATATGGGCTTACAAGCACGTTTGATGAGTCAGGCATTACGTAAAATTACTGGTAAT

GCAAAACGCTCAAACTGTATGGTGATCTTCATTAACCAAATCCGTATGAAGATTGGTGTAATGTTTGG

TAGCCCTGAAACCACAACAGGTGGTAATGCACTCAAATTCTACGCTTCTGTACGTTTGGATATCCGTC

GTATTGGTCAAGTGAAAGAAGGCGATGAAATTGTCGGTTCAGAAACCCGCGTTAAAGTCGTAAAAAA

TAAAATGGCACCTCCTTTTAAGGAAGCGTTATTCCAAATTTTATATGGCAAAGGTGTCAATCAACTGG

GTGAACTGGTTGATCTTGCTGTTGCGCAAGAACTGGTACAAAAAGCAGGTGCTTGGTATTCATATCAA

GGCAATAAAATTGGTCAAGGTAAAAACAACGTGATCCGCCATTTAGAGGAAAATCCTCAAATTGCAC

AAGAACTTGATCGCCTGATTCGTGAAAAATTGTTGACACCAACGACCACGCCTATTGAAGAAAAAGA

TGAAGTAGAACCAGACTTTCTAGATGCTTAA

129
DP70 RNA polymerase sigma factor RpoD
ATGAGCGATATGACTTCCCCTACTTCGCAAGTAGCGGCTCTGATTAGCCGAGGCAAAGAGCAAGG

TTACTTAACTTACGCTGAGGTTAACGATCATCTCCCAGACTCGATCACGGAAAGCGAACAGATTGAA

GACATTATTCAAATGCTTCAAGATGTCGGCATTCCAGTGCATGAACGTGCGCCTGAATCTGATGACAC

CATGTTCGACGGTAACAATGCAGAAGCAACCGATGAAGTCGCTGAAGAAGAAGCGGCAGCTGTTCTT

GCTTCAGTTGAAAGCGAACCTGGTCGTACCACCGATCCAGTACGTATGTACATGCGTGAAATGGGAA

CGGTTGAACTATTAACGCGTGAAGGCGAAATTAGCATTGCAAAACGCATTGAAGAAGGTATTCGTGA

CGTTCTTCATTCGATTGCGTACTGGCCAAATGCAGTTGAAGTTGTATTAAAAGAATATAGCGATGTTG

CTGAAGGCGAACGTCGTCTTGCTGATATTTTATCTGGTTATTTAGACCCAGAATCTGACGAAGAAATT

CCAGAAGTTTTAGAAGAAGAAGCTGAAATTGTTGAAGATGATGAAGCGACGACTAAAACCACTAAA

GATGTAAAATTGGACGATGACGAAGAAGAAGAATCTGAAAGTGATGATGATTCTGAAGGTGAGTCTG

GTCCAGATCCAGAAATTGCACGTGTTCGTTTCACTGAATTAGAAGATGCGTGGAAAGTAACCAAAGC

CACCATTGAAAAGCATGGCCGTAACAGCAAACAAGCAGATGAAGCGCTTGAAGCTCTTGCAACTGTG

TTTATGATGTTCAAATTTACACCACGTTTATTTGAAATCATTTCAGAAATGATTCGTGGCACGCATGA

ACAAATTCGTACAGCAGAACGTGAAGTGATGCGTTACGCAGTTCGTCGTGGTCGTATGGACCGTACC

CAATTCCGTACATCGTTCCCAGGCCAAGAGTCAAATCCAGCTTGGTTAGATGAACAAATTGCTAAAGC

ACCTGCGGATCAAAAAGGTTATTTAGAAAAAGTACGTCCAGATGTTGTTGCATTCCAGCAAAAGATT

GCCGATATCGAAAAAGAATTGGGCTTAGATGTTAAAGACATCAAAGACATTTCTAAACGTATGGCTG

TGGGTGAAGCGAAAGCACGTCGCGCGAAAAAAGAAATGGTTGAAGCAAACTTACGTTTGGTGATTTC

GATTGCGAAAAAATATACCAACCGTGGTTTACAATTCCTTGACTTGATTCAAGAAGGTAACATCGGTT

TGATGAAAGCCGTAGACAAGTTTGAATACCGTCGTGGTTATAAATTCTCGACTTATGCAACTTGGTGG

-continued

ATTCGTCAGGCGATTACCCGTTCGATTGCCGATCAAGCACGTACCATCCGTATTCCAGTACACATGAT

CGAAACCATTAACAAGATCAACCGTGTATCTCGTCAACTTCTTCAAGAAATGGGCCGTGAGCCTACCC

CTGAAGAATTAGGCGAACGTCTGGAAATGGACGAAGTTAAAGTACGTAAAGTGCTGAAAATTGCCAA

AGAACCGATTTCGATGGAAACACCGATTGGTGATGACGAAGATTCGCATCTTGGTGACTTCATTGAA

GATGGTAACATTACCTCTCCAATTGATGCCGCGACTTCTGAAGGCTTAAAAGAAGCAACACGTGAAG

TGCTGGAAAACTTGACCGAACGTGAAGCGAAAGTCTTAAAAATGCGTTTTGGTATTGATATGCCAAC

CGACCATACTTTAGAAGAAGTGGGTAAACAATTTGATGTAACACGTGAACGTATTCGTCAGATTGAA

GCCAAAGCTTTACGTAAATTACGTCACCCTTCTCGTTCTGAACACTTACGTTCATTCCTAGAAAATGA

CTAA

130
DP71 Glutamine--tRNA ligase
ATGAGTGAGGCTGAAGCCCGCCCAACAAATTTTATCCGTCAGATTATTGATGAAGATCTGGCGACC

GGGAAACACAATACCGTTCACACCCGTTTCCCGCCTGAGCCTAATGGCTATTTGCATATCGGCCATGC

GAAGTCTATCTGCCTGAATTTCGGCATTGCGCAAGACTACCAGGGTCAGTGCAATCTGCGTTTTGACG

ATACTAACCCGGCAAAAGAAGACATCGAATTCGTTGAGTCGATCAAATACGACGTCCAGTGGCTGGG

CTTCGACTGGAGCGGTGATATTCACTACTCCTCAGACTATTTCGATCAACTGCACGCATACGCGCTGG

AGCTAATCAACAAAGGTCTGGCGTACGTTGACGAACTGTCTCCCGATCAAATTCGCGAATACCGTGGT

TCGCTGACCGCACCGGGCAAAAACAGCCCGTATCGCGATCGCAGCGTGGAAGAAAATATCGCGCTGT

TTGAAAAAATGCGTAACGGTGAATTCGCCGAAGGTGCCGCTTGCCTGCGTGCCAAAATCGATATGGC

GTCGCCATTCTTCGTGATGCGCGATCCGGTCATCTACCGTATTAAGTTTGCCGAACATCATCAGACTG

GCACAAAATGGTGCATCTACCCGATGTACGATTTCACTCACTGCATTTCCGATGCGCTGGAAGGGATC

ACCCATTCACTGTGTACGCTGGAATTCCAGGACAACCGCCGTCTGTACGACTGGGTACTGGATAACAT

CACTATTCCATGCCATCCGCGTCAGTATGAGTTCTCCCGTCTGAATCTTGAATACTCCATCATGTCCAA

GCGTAAGCTGAACCTGCTGGTGACGGATAAGATTGTAGAAGGTTGGGACGATCCGCGTATGCCGACG

GTTTCCGGTCTGCGTCGCCGTGGTTATACCGCCGCGTCTATCCGCGAATTCTGCCGTCGTATCGGCGTG

ACCAAGCAGGACAACAACGTTGAAATGATGGCGCTGGAATCCTGTATTCGTGACGATCTGAACGAAA

ACGCACCGCGCGCCATGGCCGTTATTAACCCGGTTAAAGTTGTCATTGAGAACTTCACCGGTGATGAC

GTGCAAATGGTGAAAATGCCGAATCATCCGAGCAAACCGGAAATGGGCACCCGCGAAGTGCCGTTCA

CCCGTGAGATTTACATCGATCAGGCTGATTTCCGCGAAGAAGCGAACAAACAGTACAAACGTCTGGT

GCTGGGCAAAGAAGTTCGCCTGCGCAATGCGTATGTGATCAAAGCGGAACACATCGAGAAAGACGC

GGAAGGGAATATCACCACCATCTTCTGTTCTTACGATATCGATACGCTGAGCAAAGATCCCGCTGATG

GCCGTAAGGTGAAAGGCGTGATTCACTGGGTTTCTGCTTCTGAAGGTAAACCGGCAGAATTTCGCCTG

TATGACCGTCTGTTCAGTGTTGCGAACCCTGGCCAGGCTGAAGATTTCCTGACCACCATCAACCCGGA

ATCTCTGGTGATTGCTCAGGGCTTCGTTGAGCCGTCTCTGGTCGCTGCTCAGGCAGAAGTCAGTGTGC

AGTTCGAACGTGAAGGTTACTTCTGTGCCGACAGCCGCTATTCAAGTGCTGAGCATCTGGTGTTCAAC

CGCACCGTCGGCCTTCGCGACACCTGGGAAAGCAAACCCGTCGCCTGA

131
DP71 DNA gyrase subunit B
ATGTCGAATTCTTATGACTCCTCAAGTATCAAGGTATTAAAAGGGCTGGACGCGGTGCGTAAGCGC

CCCGGCATGTATATCGGCGATACCGATGACGGCACTGGTCTGCACCACATGGTATTCGAGGTTGTGGA

CAACGCTATCGACGAAGCCCTCGCGGGCCACTGTAAAGAGATTCAGGTCACGATCCATGCGGATAAC

TCTGTTTCCGTACAGGATGATGGTCGTGGTATTCCTACCGGCATTCACGAAGAAGAGGGCGTTTCTGC

TGCTCAGGTCATCATGACCGTACTTCATGCCGGCGGTAAATTTGACGATAACTCGTACAAAGTCTCCG

-continued

GCGGTCTGCATGGCGTGGGTGTTTCCGTCGTTAACGCCCTGTCGGAAAAACTGGAGCTGGTTATCCGC

CGTGAAGGCAAAGTGCACACCCAGACTTACGTCCACGGTGAGCCGCAGGATCCGCTGAAAGTGGTTG

GCGATACCGAGGCGACCGGTACGACCGTGCGCTTCTGGCCAAGCTACGCCACCTTCACCAATCAAAC

AGAATTCGAGTATGACATTCTGGCGAAACGCCTCCGTGAGCTGTCATTCCTGAACTCTGGTGTGGCGA

TCCGCCTGCTCGACAAACGCGATGGCAAGAACGATCACTTCCATTATGAAGGCGGTATCAAAGCTTTC

GTGGAATACCTGAACAAAAACAAAACCCCAATCCACCCAACCGTGTTCTATTTCTCCACCGTGAAAG

ACGATATCGGTGTGGAAGTGGCGTTGCAGTGGAATGATGGTTTCCAGGAAAATATTTACTGCTTTACC

AACAATATCCCTCAGCGCGACGGCGGCACCCATCTGGTAGGCTTCCGTTCTGCGATGACCCGTACGCT

TAACGCGTATATGGATAAAGAAGGCTACAGCAAGAAATCCAAAATCAGCGCCACCGGTGATGATGCC

CGTGAAGGCCTGATCGCCGTGGTTTCGGTAAAAGTGCCGGATCCTAAGTTCTCCTCTCAGACCAAAGA

CAAACTGGTTTCTTCCGAAGTGAAGACCGCCGTTGAGTCTCTGATGAACGAGAAGCTGGTTGATTATC

TGATGGAAAACCCGGCCGACGCGAAAATCGTTGTCGGTAAAATCATCGATGCAGCCCGTGCGCGTGA

AGCCGCGCGTAAAGCACGTGAAATGACCCGTCGTAAAGGCGCGCTCGATCTGGCCGGTCTGCCAGGC

AAACTGGCTGACTGTCAGGAACGCGACCCGGCACATTCCGAACTGTACTTAGTGGAAGGGGACTCAG

CGGGCGGCTCTGCAAAACAAGGCCGTAACCGTAAGAACCAGGCGATTCTGCCGTTGAAAGGGAAAAT

CCTCAACGTTGAGAAAGCGCGCTTCGACAAAATGCTCTCTTCTCAGGAAGTGGCGACGCTGATTACCG

CGCTCGGTTGCGGTATCGGCCGTGACGAATACAACCCGGATAAACTGCGTTATCACAGCATCATCATC

ATGACCGATGCCGACGTCGATGGTTCGCACATCCGTACCCTGTTACTGACATTCTTCTACCGTCAGAT

GCCTGAAATTGTAGAGCGTGGCCACGTGTTTATCGCGCAGCCTCCGCTGTACAAAGTGAAAAAAGGC

AAACAGGAACAGTACATTAAAGATGATGAAGCGATGGATCAGTATCAAATCTCTATCGCGATGGACG

GGGCAACGTTACACGCCAACGCCCATGCACCAGCACTGGCGGGCGAACCGCTGGAGAAACTGGTGGC

TGAACATCACAGCGTGCAGAAAATGATTGGCCGTATGGAACGTCGTTATCCGCGTGCGCTGCTGAAT

AATCTGGTCTATCAGCCAACGCTGGCGGGTGCTGAACTTGCCGACGAAGCGAAAGTGAAGGAATGGA

TTGAAACGCTGGTGTCTCGTCTGAACGAGAAAGAGCAGCACGGCAGCAGCTACAGTGCGATCGTGCG

CGAAAATCTTGAACACCAGCTGTTCGAGCCAATCCTGCGCATTCGTACTCACGGTGTGGATACCGACT

ACGATCTCGATGCAGACTTCATTCAGGGCGGCGAATACCGCAAAATCTGTACCCTGGGTGAAAAACT

GCGCGGCCTGATCGAAGAAGATGCTTACATCGAACGTGGCGAACGCCGTCAGCCAGTGACCAGCTTC

GAGCAGGCGCTGGAATGGCTGGTGAAAGAGTCGCGTCGCGGTCTGTCGATTCAGCGTTATAAAGGTC

TGGGTGAAATGAACCCTGAGCAATTGTGGGAAACCACGATGGATCCGACACAACGCCGCATGCTGCG

CGTGACGGTGAAAGATGCTATCGCGGCGGACCAGCTGTTCACCACGCTGATGGGCGATGCGGTTGAA

CCGCGCCGCGCCTTCATCGAAGAGAACGCCCTTAAAGCTGCCAATATCGATATCTGA

132
DP71 Isoleucine--tRNA ligase
ATGAGTGACTACAAGAACACCCTGAATTTGCCGGAAACAGGGTTCCCGATGCGTGGCGATCTGGC

CAAGCGTGAACCTGACATGCTGAAGAATTGGTATGACCAGGATCTGTACGGGATTATTCGTGCTGCC

AAGAAAGGCAAGAAAACCTTTATCTTGCATGACGGCCCTCCGTATGCGAACGGCAGCATTCATATTG

GTCACTCAGTAAACAAAATTCTTAAAGACATGATCGTTAAGTCCAAAGGACTGGCGGGCTTTGATGC

GCCGTATGTTCCGGGCTGGGATTGTCATGGTCTGCCGATTGAACTGAAAGTTGAACAGCTGATCGGTA

AGCCGGGCGAAAAAGTCACGGCGGCGGAATTCCGTGAAGCCTGCCGCAAGTACGCTGCTGAACAGGT

TGAAGGTCAGAAGAAAGACTTCATCCGTCTGGGCGTGCTCGGTGACTGGGATCATCCGTACCTGACC

ATGGACTTCAAAACAGAAGCCAACATCATTCGTGCCCTGGGTAAAATCATCGGCAACGGTCACCTGC

-continued

ATAAAGGTGCGAAACCTGTTCACTGGTGTACCGATTGCGGATCTTCACTGGCTGAAGCCGAAGTCGA

ATATTACGACAAAGTGTCTCCGTCTATCGACGTGACGTTTAATGCGACGGATGCCGCCGCTGTTGCTG

CGAAATTCGGTGCCACTGCTTTCAATGGCCCGGTTTCTCTGGTCATCTGGACCACCACCCCGTGGACC

ATGCCAGCTAACCGCGCGATTTCACTCAACGCTGAGTTCTCTTATCAGCTGGTGCAGATTGAAGGTCA

GTGCCTGATCCTGGCTACCGATCTGGTAGAAAGCGTGATGAATCGCGCCGGTATCGCTGAGTGGACT

GTGCTGGGCGAATGTAAAGGTGCGGATCTTGAATTGCTTCGATTCCAGCATCCGTTCCTCGGTTTCGA

TGTTCCGGCGATCCTCGGCGATCACGTTACTCTCGATGCCGGTACCGGTGCTGTACATACCGCACCTG

GCCACGGTCCTGATGACTTTGTCATTGGCCAGAAATACGGTCTGGAAGTCGCAAACCCGGTTGGACC

GAACGGCTGCTACCTGCCGGGCACTTATCCGACGCTGGATGGCAAATTCGTCTTTAAAGCGAATGATC

TGATCGTTGAATTGCTGCGTGAGAAGGGCGCACTGCTGCACGTTGAGAAAATGAACCACAGCTATCC

GTGCTGCTGGCGTCACAAAACGCCGATCATCTTCCGCGCTACGCCACAATGGTTCATCAGCATGGATC

AGAAAGGTTTGCGTCAGAAGTCTCTGGAAGAGATCAAAGGCGTGCAGTGGATCCCTGACTGGGGTCA

GGCGCGTATCGAAAACATGGTCGCTAACCGTCCTGACTGGTGTATCTCCCGCCAGCGTACGTGGGGC

GTACCGATGTCTCTGTTCGTGCATAAAGATACCGAACAGCTTCATCCGCGCAGCCTTGAGCTGATGGA

AGAAGTGGCAAAACGCGTGGAAGCCGATGGCATTCAGGCATGGTGGGATCTGAACCCTGAAGAGATT

TTGGGTGCAGACGCTGCCGATTACGTCAAAGTGCCGGATACGCTGGACGTCTGGTTTGACTCCGGTTC

CACGCACTCCTCCGTTGTGGATGTGCGCCCTGAGTTCAACGGTCATTCACCGGATCTGTATCTGGAAG

GTTCTGACCAGCATCGCGGCTGGTTCATGTCTTCTCTGATGATTTCTACGGCGATGAAAGGCAAAGCG

CCTTACAAACAAGTACTGACTCACGGTTTCACCGTCGATGGTCAGGGCCGTAAAATGTCTAAATCCAT

CGGTAACACCATCGCGCCTCAGGATGTGATGAATAAGCTGGGTGGCGACATCCTGCGTTTGTGGGTG

GCATCTACGGATTACACCGGCGAAATCGCCGTGTCCGACGAAATCCTCAAACGTGCTGCCGATTCTTA

TCGCCGTATCCGTAACACCGCGCGCTTCCTGCTGGCGAACCTTAACGGTTTCGATCCGGCGCTGCACA

GCGTGGCACCGGAAGAGATGGTTGTGCTGGATCGCTGGGCGGTTGGCCGCGCGAAAGCTGCACAAGA

CGAGATCATTGCTGCGTACGAAGCCTATGATTTCCACGGCGTTGTTCAGCGTCTGATGCAGTTCTGCT

CGATCGAAATGGGTTCGTTCTATCTGGATATCATTAAAGATCGCCAGTACACCGCGAAGAGCGACAG

CGTTGCGCGCCGCAGCTGCCAGACCGCGCTGTATCACATCTGCGAAGCACTGGTTCGCTGGATGGCGC

CAATCATGTCCTTCACTGCCGATGAAATCTGGGCTGAACTGCCAGGTCATCGCGAGAAGTTCGTCTTT

ACTGAAGAATGGTACGACGGTCTGTTTGGCCTGATCGGTAACGAATCCATGAACGATGCGTTCTGGG

ATGAGCTGCTGAAAGTGCGTGGTGAAGTGAACAAAGTGATCGAACAGGCGCGTGCTGATAAACGTCT

GGGCGGTTCTCTGGAAGCAGCCGTGACCTTATATGCAGACGACGCGCTGGCAACAGACCTGCGTTCT

CTGGGTAACGAACTGCGCTTTGTGCTCCTGACTTCCGGTGCGAAAGTCGCCGCGCTGTCTGAAGCTGA

TGACTCAGCGCAGGCCAGCGAATTGTTGAAAGGACTGAAAATTGGTCTGGCGAAAGCAGAAGGCGA

GAAGTGCCCGCGCTGCTGGCATTTCACCACTGATATCGGCCAGAATGCGGAACACAGTGACATCTGT

GGCCGTTGTGTGACTAACATTGCCGGTGACGGCGAAGAGCGTAAGTTTGCATAA

133
DP71 NADH-quinone oxidoreductase subunit C/D
ATGTCAGAACTTACTCATATTAATGCTTCCGGCGACGCCCACATGGTGGATGTCTCCGGTAAAGAC

GACACCGTTCGTGAAGCCCGTGCCGAAGCCTTTGTTGAAATGGCCGAAAGCACGCTGGCGATGATCA

TCGGCGGTAATCACCATAAGGGTGACGTGTTCGCGACCGCGCGGATTGCCGGTATTCAGGCAGCGAA

GAAAACCTGGGATCTGATCCCGCTGTGTCATCCGCTGTTGCTGACCAAGGTGGAAGTGAATCTTGAAG

CGCAGCCAGAATTTAATCGTGTACGTATTGAATCCCGCTGCCGCCTGAGCGGTAAAACCGGCGTCGA

GATGGAAGCGCTGACCTTCAAGCCTGAAGACTGGGGAATGAAGCGCGGCACCGAAAACGAGGACTT

-continued

CATGTTCCTCAACCTCGGACCTAACCATCCGTCTGCGCACGGTGCGTTCCGCATCATCCTGCAGCTTG

ATGGCGAAGAAATTGTCGACTGTGTACCGGACGTCGGTTACCACCACCGTGGTGCTGAGAAGATGGG

CGAGCGCCAGTCATGGCACAGCTACATTCCATACACGGACCGTATCGAATACCTCGGCGGTTGCGTTA

ACGAGATGCCATACGTACTGGCTGTTGAAAAACTGGCGGGTATCGTCGTGCCGGATCGCGTTAACAC

CATCCGCGTGATGCTGTCTGAACTGTTCCGTATCAACAGCCACCTGCTGTACATCTCTACGTTTATTCA

GGACGTGGGCGCGATGACGCCAGTGTTCTTCGCCTTTACCGATCGTCAGAAAATTTACGATCTGGTGG

AAGCGATCACCGGTTTCCGTATGCACCCGGCCTGGTTCCGTATTGGTGGCGTTGCACACGACCTGCCG

AAAGGCTGGGAGCGTCTGCTGCGTGAATTCCTTGACTGGATGCCAGCCCGTCTGGATTCCTACGTCAA

GGCAGCGCTGAAAAACACCATTCTGATTGGACGTTCCAAAGGCGTAGCAGCATACAACGCCGATGAT

GCGCTGGCGTGGGGCACCACCGGTGCTGGCCTGCGTGCGACCGGGATCGACTTCGATGTCCGCAAAT

GGCGTCCATATTCAGGTTACGAAAACTTCGATTTTGAAGTGCCGGTCGGCGATGGCGTCAGTGATTGC

TATTCCCGCGTGATGCTAAAAGTGGAAGAGCTTCGTCAGAGCCTGCGCATTCTGGAACAGTGCTACA

AAAACATGCCGGAAGGCCCGTTCAAGGCGGATCACCCGCTGACCACGCCGCCACCGAAAGAGCGTAC

GCTGCAACACATCGAAACCCTGATCACTCACTTCCTGCAAGTGTCGTGGGGTCCGATCATGCCTGCGC

AAGAATCTTTCCAGATGGTTGAAGCCACCAAAGGGATCAACAGCTACTACCTGACCAGTGACGGCAG

CACCATGAGCTACCGCACGCGCGTCCGTACGCCAAGCTTCCCGCATTTGCAGCAGATCCCGTCCGTAA

TCCGTGGCAGCCTGGTATCCGACCTGATCGTGTATCTGGGCAGTATCGATTTTGTAATGTCAGATGTG

GACCGCTAA

134
DP71 Protein RecA
ATGGCTATTGATGAGAACAAGCAAAAAGCGTTAGCTGCAGCACTGGGCCAGATTGAAAAGCAATT

CGGTAAAGGCTCCATCATGCGTCTGGGTGAAGATCGCTCTATGGACGTGGAAACGATCTCTACCGGCT

CTTTGTCTCTGGATATCGCGTTAGGCGCCGGTGGTTTGCCGATGGGCCGTATCGTTGAGATTTATGGC

CCGGAATCCTCCGGTAAAACTACGCTGACCCTTCAGGTTATTGCTGCCGCACAGCGCGAAGGCAAAA

CCTGTGCGTTCATCGATGCGGAACATGCACTTGACCCTATCTACGCGAAGAAATTGGGCGTAGATATC

GACAACCTGTTGTGTTCTCAGCCGGATACCGGCGAACAGGCTCTGGAAATCTGTGACGCGCTGACCC

GTTCAGGCGCGGTCGACGTTATCATCGTCGACTCCGTTGCTGCACTGACGCCAAAAGCAGAAATCGA

AGGCGAAATCGGTGACTCTCACATGGGCCTTGCGGCACGTATGATGAGCCAGGCAATGCGTAAGCTT

GCCGGTAACCTGAAAAACGCCAACACCTTGCTGATCTTCATCAACCAGATCCGTATGAAAATCGGTGT

GATGTTCGGTAACCCGGAAACCACCACCGGTGGTAACGCCCTGAAATTCTACGCCTCTGTGCGTCTGG

ATATCCGCCGCATCGGCGCTATCAAAGAAGGCGACGTGGTGATCGGCAGTGAAACGCGCGTGAAAGT

TGTGAAGAACAAAATCGCTGCGCCTTTCAAACAGGCTGAATTCCAGATCCTATACGGCGAAGGCATC

AACATTAACGGCGAGCTGATCGATTTGGGCGTTAAGCACAAACTGGTCGAAAAAGCCGGTGCATGGT

ACAGCTACAACGGCGAGAAGATTGGTCAGGGTAAATCTAACTCCTGCAACTATCTGAAAGAAAACCC

GAAAATCGCTGCTGAACTGGATAAAAAACTGCGTGATATGTTGTTGAGTGGCACTGGTGAACTGGCC

GCTGCAACCACAGCAGAACTTGCAGACGACGATATGGAAACCAGCGAAGAGTTTTAA

135
DP71 RNA polymerase sigma factor RpoD
GGTAAGGAGCAAGGCTATCTGACCTTTGCTGAGGTCAATGACCATCTGCCGGAAGATATCGTCGA

CTCCGACCAGATCGAAGACATCATCCAGATGATTAACGACATGGGCATCCAGGTTCTTGAAGAAGCG

CCGGACGCCGATGATTTGATGCTGGCCGAAAACCGCCCTGATACCGATGAAGATGCTGCAGAAGCAG

CGGCTCAGGTGCTTTCCAGCGTTGAATCTGAAATTGGCCGTACCACCGACCCTGTGCGTATGTATATG

-continued

CGCGAAATGGGTACCGTTGAGCTCCTGACCCGTGAAGGCGAAATCGACATCGCCAAACGTATCGAAG

ACGGTATCAATCAGGTCCAGTGCTCCGTTGCTGAATATCCTGAAGCTATCACCTATTTGTTAGAGCAA

TATGACCGTGTTGAAGCAGGCGAAGCACGTCTGTCTGATTTGATCACCGGTTTTGTTGATCCGAACGC

CGAAGAAGAAATCGCGCCGACTGCGACTCACGTGGGTTCTGAACTGACCACTGAAGAGCAAAATGAT

ACCGACGACGATGAAGAAGACGACGACGATGCTGAAGACGACAACAGCATCGACCCGGAACTGGCG

CGTCAGAAGTTCACCGATCTGCGTGAGCAACATGAAGCGACCCGTGCCGTCATCAAGAAAAATGGCC

GTAGCCACAAAAGCGCCGCAGAAGAAATTCTGAAGCTGTCCGATGTGTTTAAACAGTTCCGTCTGGT

ACCAAAACAGTTCGATTTCCTGGTGAACAGCATGCGCTCCATGATGGATCGCGTCCGTACTCAGGAAC

GTCTGATCATGAAAGTGTGCGTTGAACAGTGCAAAATGCCGAAGAAAAACTTCGTCAATCTGTTCGC

CGGTAACGAAACCAGCAGTACCTGGTTTGATGCTGCTCTGGCAATGGGTAAACCATGGTCTGAGAAG

CTGAAAGAAGTGACCGAAGACGTGCAGCGCGGCCTGATGAAACTGCGCCAAATCGAAGAAGAAACT

GGCCTGACTATCGAACAGGTAAAAGACATTAACCGTCGCATGTCGATCGGCGAAGCGAAAGCACGCC

GCGCGAAGAAAGAGATGGTTGAAGCGAACTTACGTCTGGTTATCTCTATCGCGAAGAAATACACCAA

CCGTGGCTTGCAGTTCCTTGACCTGATTCAGGAAGGTAACATCGGCCTGATGAAAGCCGTTGATAAGT

TTGAATATCGCCGTGGTTATAAGTTCTCTACTTATGCGACCTGGTGGATCCGTCAGGCTATCACCCGCT

CCATCGCCGACCAGGCACGTACCATCCGTATTCCGGTGCATATGATTGAGACCATCAACAAACTCAAC

CGTATTTCGCGCCAGATGTTGCAGGAGATGGGCCGTGAGCCGACGCCGGAAGAGCTGGCTGAACGCA

TGCTGATGCCGGAAGACAAGATCCGTAAAGTGCTGAAAATTGCTAAAGAGCCAATCTCCATGGAAAC

GCCAATCGGCGACGATGAAGATTCGCATCTGGGTGATTTCATCGAGGATACTACCCTCGAGCTGCCGC

TGGATTCTGCGACCTCTGAAAGCCTGCGTTCTGCAACGCACGACGTTCTGGCTGGCCTGACCGCACGT

GAAGCGAAAGTTCTGCGTATGCGTTTCGGTATCGATATGAACACTGACCACACTCTGGAAGAAGTGG

GCAAACAGTTCGACGTAACCCGTGAACGTATCCGTCAGATCGAAGCCAAAGCGTTGCGTAAACTACG

CCACCCAAGCCGCTCCGAAGTGCTGCGCAGCTTCCTCGACGACTAG

136
DP71 DNA-directed RNA polymerase subunit beta
ATGGACCAGAACAACCCGTTGTCTGAGATCACGCACAAACGTCGTATCTCTGCACTGGGCCCGGG

CGGTTTGACCCGTGAACGTGCTGGCTTTGAAGTTCGAGACGTACACCCGACGCACTACGGTCGCGTAT

GTCCAATCGAAACGCCAGAAGGTCCAAACATCGGTCTGATCAACTCATTATCTGTCTATGCACAGACA

AATGAGTATGGTTTCCTGGAAACCCCTTACCGCCGTGTGCGTGAAGGTATGGTTACCGATGAAATTAA

CTACCTGTCTGCCATCGAAGAAGGCAACTTTGTTATCGCTCAGGCGAACTCCAACCTGGATGACGAAG

GCCACTTCCTGGAAGATTTAGTCACTTGTCGTAGCAAAGGCGAATCAAGCCTGTTCAGCCGCGACCAG

GTTGACTACATGGACGTTTCTACCCAGCAGATCGTATCCGTTGGTGCTTCACTGATTCCATTCCTGGAA

CACGATGACGCCAACCGTGCATTGATGGGTGCGAACATGCAACGTCAGGCAGTTCCTACTCTGCGTG

CTGATAAGCCGCTGGTAGGTACTGGTATGGAACGTGCTGTTGCGGTTGACTCCGGTGTTACTGCCGTT

GCCAAACGTGGTGGTACTGTTCAGTACGTAGATGCATCCCGTATCGTTATTCGTGTTAACGAAGAAGA

GATGAATCCAGGCGAAGCAGGTATCGACATTTATAACCTGACTAAGTACACCCGTTCTAACCAGAAC

ACCTGCATCAACCAGATGCCGTGTGTGAATCTGGGCGAGCCAATCGAGCGCGGCGACGTGCTGGCAG

ATGGTCCGTCAACAGATCTGGGCGAACTGGCACTGGGTCAGAACATGCGTGTCGCGTTCATGCCTTGG

AACGGTTACAACTTCGAAGACTCCATCTTGGTCTCCGAACGTGTTGTGCAGGAAGATCGCTTCACGAC

CATCCATATCCAGGAACTGGCATGTGTGTCCCGTGACACAAAGTTAGGGCCTGAAGAGATCACTGCT

GATATCCCTAACGTGGGTGAAGCTGCGCTCTCCAAACTGGATGAGTCCGGTATTGTGTATATCGGTGC

TGAAGTGACCGGTGGTGACATTCTGGTCGGTAAAGTTACGCCTAAAGGCGAAACCCAGCTGACTCCA

-continued

GAAGAGAAACTGCTGCGTGCGATCTTCGGTGAGAAAGCGTCTGACGTTAAAGATTCTTCTCTGCGTGT

ACCAAACGGCGTTTCCGGTACGATTATTGACGTGCAAGTCTTTACCCGCGATGGCGTGGAAAAAGAT

AAGCGTGCGTTAGAAATCGAAGAAATGCAGCTGAAACAGGCTAAGAAAGACCTGACTGAAGAGCTG

CAAATTCTGGAAGCTGGTCTGTTTGCACGTATCCAGTCCGCGCTGGTTGCTGGCGGTGTTGAAGCCGA

TAAGCTGGGCAAATTGCCACGCGATCGTTGGCTTGAACTGTCACTGACTGACGAAGACAAACAGAAT

CAGTTGGAACAGCTTGCTGAACAGTACGACGAACTGAAATCCGAGTTTGAGAAAAAACTCGAAGCTA

AACGTCGTAAAATCACTCAGGGCGATGACCTAGCACCAGGTGTGCTGAAAATCGTTAAAGTGTACCT

GGCCGTTAAACGTCAGATCCAACCTGGTGACAAAATGGCAGGCCGCCACGGTAACAAAGGTGTTATC

TCCAAGATCAACCCGATCGAAGATATGCCTTACGATGAAAACGGGACTCCTGTTGACATCGTACTGA

ACCCGCTGGGCGTTCCATCACGTATGAACATTGGTCAGATTTTAGAAACCCACCTGGGTATGGCCGCG

AAAGGTATTGGTGAAAAAATCAATGCCATGCTTAAGAAACATGAAGAAGTTTCTAAGCTGCGCGAGT

TCATCCAGCGTGCCTATGATCTGGGCGACGACGTACGTCAGAAAGTTGATCTGACCACCTTCACCGAT

GATGAAGTATTGCGTTTGGCTGAAAACCTGAAAAAGGGTATGCCAATTGCAACACCAGTCTTCGACG

GTGCGAAAGAGACAGAGATCAAGCAACTGCTTGAAATGGGCGGCGTCCCAACCTCTGGCCAGATCAC

ACTGTTTGACGGCCGTACCGGCGAGCAATTCGAGCGCCAGGTTACCGTCGGCTACATGTACATGCTGA

AACTGAACCACCTGGTTGACGATAAGATGCATGCGCGTTCTACCGGTTCTTACAGCCTTGTTACTCAG

CAGCCGCTGGGTGGTAAAGCTCAGTTCGGTGGTCAGCGCTTCGGTGAGATGGAAGTGTGGGCACTGG

AAGCATACGGTGCCGCTTATACCCTGCAGGAAATGCTGACTGTTAAGTCCGATGACGTGAACGGCCG

TACTAAGATGTATAAAAACATCGTAGATGGCGATCACCGGATGGAACCAGGCATGCCGGAATCATTC

AACGTACTGTTGAAAGAAATCCGCTCTCTGGGTATCAACATCGAGCTGGAAGACGAGTAA

The invention claimed is:

1. A composition comprising a mixture of a plurality of purified, viable microbes and a prebiotic polysaccharide, wherein at least two microbes have at least 99 percent identity to any of SEQ ID NOs. 1, 2, 3, 5, and 22, or 100 percent identity to SEQ ID NOs. 9 and 10 at the 16S rRNA or fungal ITS locus, and wherein the composition is formulated in an oral dosage form selected from the group consisting of powder, tablet, capsule, caplet, granules, pellets, emulsion, and syrup.

2. The composition of claim 1, wherein the at least two microbes have 100 percent identity to any of SEQ ID NOs. 1, 2, 3, 5, 9, 10, or 22 at the 16S rRNA or fungal ITS locus.

3. The composition of claim 1, further comprising an anti-diabetic drug.

4. The composition of claim 3, wherein the anti-diabetic drug is selected from the group consisting of metformin, repaglinide, and glipizide.

5. A composition comprising a defined microbial mixture comprising a first purified viable microbial population isolated from a first plant-based sample, a second purified viable microbial population isolated from a second plant-based sample, and a prebiotic polysaccharide, which in combination with an anti-diabetic therapy, improves at least one selected from the group consisting of fasting blood glucose, glucose tolerance, insulin sensitivity, glycated hemoglobin (HbA1c), and/or homeostatic model assessment for insulin resistance (HOMA-IR) compared to levels found in a subject treated with the anti-diabetic therapy alone, and wherein at least two of the microbes has at least 99 percent identity at the 16S rRNA or the fungal ITS locus to any of SEQ ID NOs. 1, 2, 3, 5, and 22, or 100 percent identity to SEQ ID NOs. 9 and 10, and wherein the composition is formulated in an oral dosage form selected from the group consisting of powder, tablet, capsule, caplet, granules, pellets, emulsion, and syrup.

6. The composition of claim 5, wherein at least three of the microbes have at least 99 percent identity at the 16S rRNA or the fungal ITS locus to any of SEQ ID NOs. 1, 2, 3, 5, 9, 10, or 22.

7. The composition of claim 5, wherein at least two of the microbes have 100 percent identity at the 16S rRNA locus or the fungal ITS locus to any of SEQ ID NOs. 1, 2, 3, 5, 9, 10 or 22.

8. The composition of claim 5, wherein the anti-diabetic therapy comprises an anti-diabetic drug selected from the group consisting of metformin, repaglinide, and glipizide.

9. The composition of claim 5, wherein the first plant-based sample and/or the second plant-based sample are selected from the group consisting of cherry tomato, red cabbage, lime, fermented tomatoes, fermented cabbage, pomegranate, and arugula.

10. The composition of claim 1, wherein administration of the composition in combination with metformin to mice results in improved glucose tolerance and/or increased response to insulin compared to control mice treated with metformin alone.

* * * * *

SEQUENCE LISTING

<160> NUMBER OF SEQ ID NOS: 136

<210> SEQ ID NO 1
<211> LENGTH: 1490
<212> TYPE: DNA
<213> ORGANISM: Unknown
<220> FEATURE:
<223> OTHER INFORMATION: Description of Unknown:
      DP1 16S rRNA microbial sequence

<400> SEQUENCE: 1
agtcagacat gcaagtcgag cggtagagag aagcttgctt ctcttgagag cggcggacgg 60
gtgagtaaag cctaggaatc tgcctggtag tgggggataa cgttcggaaa cggacgctaa 120
taccgcatac gtcctacggg agaaagcagg ggaccttcgg gccttgcgct atcagatgag 180
cctaggtcgg attagctagt tggtgaggta atggctcacc aaggcgacga tccgtaactg 240
gtctgagagg atgatcagtc acactggaac tgagacacgg tccagactcc tacgggaggc 300
agcagtgggg aatattggac aatgggcgaa agcctgatcc agccatgccg cgtgtgtgaa 360
gaaggtcttc ggattgtaaa gcactttaag ttgggaggaa gggcattaac ctaatacgtt 420
agtgttttga cgttaccgac agaataagca ccggctaact ctgtgccagc agccgcggta 480
atacagaggg tgcaagcgtt aatcggaatt actgggcgta aagcgcgcgt aggtggtttg 540
ttaagttgga tgtgaaatcc ccgggctcaa cctgggaact gcattcaaaa ctgactgact 600
agagtatggt agagggtggt ggaatttcct gtgtagcggt gaaatgcgta gatataggaa 660

```
ggaacaccag tggcgaaggc gaccacctgg actaatactg acactgaggt gcgaaagcgt    720

ggggagcaaa caggattaga taccctggta gtccacgccg taaacgatgt caactagccg    780

ttgggagcct tgagctctta gtggcgcagc taacgcatta agttgaccgc ctggggagta    840

cggccgcaag gttaaaactc aaatgaattg acgggggccc gcacaagcgg tggagcatgt    900

ggtttaattc gaagcaacgc gaagaacctt accaggcctt gacatccaat gaactttcta    960

gagatagatt ggtgccttcg ggaacattga gacaggtgct gcatggctgt cgtcagctcg   1020

tgtcgtgaga tgttgggtta agtcccgtaa cgagcgcaac ccttgtcctt agttaccagc   1080

acgtaatggt gggcactcta aggagactgc cggtgacaaa ccggaggaag gtggggatga   1140

cgtcaagtca tcatggccct tacggcctgg gctacacacg tgctacaatg gtcggtacag   1200

agggttgcca agccgcgagg tggagctaat cccataaaac cgatcgtagt ccggatcgca   1260

gtctgcaact cgactgcgtg aagtcggaat cgctagtaat cgcgaatcag aatgtcgcgg   1320

tgaatacgtt cccgggcctt gtacacaccg cccgtcacac catgggagtg ggttgcacca   1380

gaagtagcta gtctaacctt cgggaggacg gttaccacgg tgtgattcat gactggggtg   1440

aagtcgtaac aaggtagccg taggggaacc tgcggctgga tcacctcctt              1490


<210> SEQ ID NO 2
<211> LENGTH: 1115
<212> TYPE: DNA
<213> ORGANISM: Unknown
<220> FEATURE:
<223> OTHER INFORMATION: Description of Unknown:
      DP2 ITS microbial sequence
<220> FEATURE:
<221> NAME/KEY: modified_base
<222> LOCATION: (1)..(18)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (79)..(79)
<223> OTHER INFORMATION: a, c, t, g, unknown or other
<220> FEATURE:
<221> NAME/KEY: modified_base
<222> LOCATION: (551)..(551)
<223> OTHER INFORMATION: a, c, t, g, unknown or other
<220> FEATURE:
<221> NAME/KEY: modified_base
<222> LOCATION: (884)..(884)
<223> OTHER INFORMATION: a, c, t, g, unknown or other
<220> FEATURE:
<221> NAME/KEY: modified_base
<222> LOCATION: (894)..(895)
<223> OTHER INFORMATION: a, c, t, g, unknown or other
<220> FEATURE:
<221> NAME/KEY: modified_base
<222> LOCATION: (916)..(917)
<223> OTHER INFORMATION: a, c, t, g, unknown or other
<220> FEATURE:
<221> NAME/KEY: modified_base
<222> LOCATION: (926)..(926)
<223> OTHER INFORMATION: a, c, t, g, unknown or other
<220> FEATURE:
<221> NAME/KEY: modified_base
<222> LOCATION: (940)..(940)
<223> OTHER INFORMATION: a, c, t, g, unknown or other
<220> FEATURE:
<221> NAME/KEY: modified_base
<222> LOCATION: (959)..(960)
<223> OTHER INFORMATION: a, c, t, g, unknown or other
<220> FEATURE:
<221> NAME/KEY: modified_base
<222> LOCATION: (965)..(965)
```

<223> OTHER INFORMATION: a, c, t, g, unknown or other
<220> FEATURE:
<221> NAME/KEY: modified_base
<222> LOCATION: (967)..(967)
<223> OTHER INFORMATION: a, c, t, g, unknown or other
<220> FEATURE:
<221> NAME/KEY: modified_base
<222> LOCATION: (992)..(992)
<223> OTHER INFORMATION: a, c, t, g, unknown or other
<220> FEATURE:
<221> NAME/KEY: modified_base
<222> LOCATION: (994)..(994)
<223> OTHER INFORMATION: a, c, t, g, unknown or other
<220> FEATURE:
<221> NAME/KEY: modified_base
<222> LOCATION: (996)..(996)
<223> OTHER INFORMATION: a, c, t, g, unknown or other
<220> FEATURE:
<221> NAME/KEY: modified_base
<222> LOCATION: (1006)..(1006)
<223> OTHER INFORMATION: a, c, t, g, unknown or other
<220> FEATURE:
<221> NAME/KEY: modified_base
<222> LOCATION: (1014)..(1014)
<223> OTHER INFORMATION: a, c, t, g, unknown or other
<220> FEATURE:
<221> NAME/KEY: modified_base
<222> LOCATION: (1020)..(1020)
<223> OTHER INFORMATION: a, c, t, g, unknown or other
<220> FEATURE:
<221> NAME/KEY: modified_base
<222> LOCATION: (1031)..(1031)
<223> OTHER INFORMATION: a, c, t, g, unknown or other
<220> FEATURE:
<221> NAME/KEY: modified_base
<222> LOCATION: (1036)..(1037)
<223> OTHER INFORMATION: a, c, t, g, unknown or other
<220> FEATURE:
<221> NAME/KEY: modified_base
<222> LOCATION: (1039)..(1039)
<223> OTHER INFORMATION: a, c, t, g, unknown or other
<220> FEATURE:
<221> NAME/KEY: modified_base
<222> LOCATION: (1050)..(1050)
<223> OTHER INFORMATION: a, c, t, g, unknown or other
<220> FEATURE:
<221> NAME/KEY: modified_base
<222> LOCATION: (1052)..(1053)
<223> OTHER INFORMATION: a, c, t, g, unknown or other
<220> FEATURE:
<221> NAME/KEY: modified_base
<222> LOCATION: (1059)..(1059)
<223> OTHER INFORMATION: a, c, t, g, unknown or other
<220> FEATURE:
<221> NAME/KEY: modified_base
<222> LOCATION: (1068)..(1072)
<223> OTHER INFORMATION: a, c, t, g, unknown or other
<220> FEATURE:
<221> NAME/KEY: modified_base
<222> LOCATION: (1076)..(1076)
<223> OTHER INFORMATION: a, c, t, g, unknown or other
<220> FEATURE:
<221> NAME/KEY: modified_base
<222> LOCATION: (1079)..(1081)
<223> OTHER INFORMATION: a, c, t, g, unknown or other
<220> FEATURE:
<221> NAME/KEY: modified_base
<222> LOCATION: (1093)..(1095)
<223> OTHER INFORMATION: a, c, t, g, unknown or other
<220> FEATURE:
<221> NAME/KEY: modified_base
<222> LOCATION: (1101)..(1103)
<223> OTHER INFORMATION: a, c, t, g, unknown or other
<220> FEATURE:
<221> NAME/KEY: modified_base
<222> LOCATION: (1109)..(1109)
<223> OTHER INFORMATION: a, c, t, g, unknown or other
<220> FEATURE:
<221> NAME/KEY: modified_base
<222> LOCATION: (1114)..(1115)
<223> OTHER INFORMATION: a, c, t, g, unknown or other

<400> SEQUENCE: 2

```
nnnnnnnnnn nnnnnnnntt gttgctcgag ttcttgttta gatcttttac aataatgtgt     60
atctttaatg aagatgngng cttaattgcg ctgctttatt agagtgtcgc agtagaagta    120
gtcttgcttg aatctcagtc aacgtttaca cacattggag ttttttact ttaatttaat     180
tctttctgct ttgaatcgaa aggttcaagg caaaaaacaa acacaaacaa ttttatttta    240
ttataatttt ttaaactaaa ccaaaattcc taacggaaat tttaaaataa tttaaaactt    300
tcaacaacgg atctcttggt tctcgcatcg atgaaaaacg taccgaattg cgataagtaa    360
tgtgaattgc aaatactcgt gaatcattga atttttgaac gcacattgcg cccttgagca    420
ttctcaaggg catgcctgtt tgagcgtcat ttccttctca aaaaataatt ttttattttt    480
tggttgtggg cgatactcag ggttagcttg aaattggaga ctgtttcagt ctttttaat     540
tcaacactta ncttctttgg agacgctgtt ctcgctgtga tgtatttatg gatttattcg    600
ttttacttta caagggaaat ggtaatgtac cttaggcaaa gggttgcttt taatattcat    660
caagtttgac ctcaaatcag gtaggattac ccgctgaact taagcatatc aataagcgga    720
ggaaaagaaa ccaactggga ttaccttagt aacggcgagt gaagcggtaa aagctcaaat    780
ttgaaatctg gtactttcag tgcccgagtt gtaatttgta gaatttgtct ttgattaggt    840
ccttgtctat gttccttgga acaggacgtc atagagggtg agantcccgt ttgnngagga    900
taccttttct ctgtannact ttttcnaaga gtcgagttgn ttgggaatgc agctcaaann    960
gggtngnaaa ttccatctaa agctaaatat tngncnagag accganagcg acantacagn   1020
gatggaaaga ngaaannant tgaaaagaan anngaaaant acgtgaannn nnaaanggnn   1080
nggcatttga tcnnncatgg nnntttttnc atgnn                              1115
```

<210> SEQ ID NO 3
<211> LENGTH: 1547
<212> TYPE: DNA
<213> ORGANISM: Unknown
<220> FEATURE:
<223> OTHER INFORMATION: Description of Unknown:
DP3 16S rRNA microbial sequence

<400> SEQUENCE: 3

```
attgagagtt tgatcctggc tcaggatgaa cgctggcggc gtgcctaata catgcaagtc     60
gaacgcacag cgaaaggtgc ttgcaccttt caagtgagtg gcgaacgggt gagtaacacg    120
tggacaacct gcctcaaggc tggggataac atttggaaac agatgctaat accgaataaa    180
actcagtgtc gcatgacaca aagttaaaag gcgctttggc gtcacctaga gatggatccg    240
cggtgcatta gttagttggt ggggtaaagg cctaccaaga caatgatgca tagccgagtt    300
gagagactga tcggccacat tgggactgag acacggccca aactcctacg ggaggctgca    360
gtagggaatc ttccacaatg ggcgaaagcc tgatggagca acgccgcgtg tgtgatgaag    420
gctttcgggt cgtaaagcac tgttgtacgg gaagaacagc tagaataggg aatgatttta    480
gtttgacggt accataccag aaagggacgg ctaaatacgt gccagcagcc gcggtaatac    540
gtatgtcccg agcgttatcc ggatttattg ggcgtaaagc gagcgcagac ggttgattaa    600
gtctgatgtg aaagcccgga gctcaactcc ggaatggcat tggaaactgg ttaacttgag    660
tgcagtagag gtaagtggaa ctccatgtgt agcggtggaa tgcgtagata tatggaagaa    720
caccagtggc gaaggcggct tactggactg tactgacgtt gaggctcgaa agtgtgggta    780
```

-continued

```
gcaaacagga ttagataccc tggtagtcca caccgtaaac gatgaacact aggtgttagg    840
aggtttccgc ctcttagtgc cgaagctaac gcattaagtg ttccgcctgg ggagtacgac    900
cgcaaggttg aaactcaaag gaattgacgg ggacccgcac aagcggtgga gcatgtggtt    960
taattcgaag caacgcgaag aaccttacca ggtcttgaca tcctttgaag cttttagaga   1020
tagaagtgtt ctcttcggag acaaagtgac aggtggtgca tggtcgtcgt cagctcgtgt   1080
cgtgagatgt tgggttaagt cccgcaacga gcgcaaccct tattgttagt tgccagcatt   1140
cagatgggca ctctagcgag actgccggtg acaaaccgga ggaaggcggg gacgacgtca   1200
gatcatcatg ccccttatga cctgggctac acacgtgcta caatggcgta tacaacgagt   1260
tgccaacccg cgagggtgag ctaatctctt aaagtacgtc tcagttcgga ttgtagtctg   1320
caactcgact acatgaagtc ggaatcgcta gtaatcgcgg atcagcacgc cgcggtgaat   1380
acgttcccgg gtcttgtaca caccgcccgt cacaccatgg gagtttgtaa tgcccaaagc   1440
cggtggccta accttttagg aaggagccgt ctaaggcagg acagatgact ggggtgaagt   1500
cgtaacaagg tagccgtagg agaacctgcg gctggatcac ctccttt                 1547
```

```
<210> SEQ ID NO 4
<211> LENGTH: 1537
<212> TYPE: DNA
<213> ORGANISM: Unknown
<220> FEATURE:
<223> OTHER INFORMATION: Description of Unknown:
      DP4 16S rRNA microbial sequence

<400> SEQUENCE: 4
```

```
ttgaagagtt tgatcatggc tcagattgaa cgctggcggc aggcctaaca catgcaagtc     60
gagcggcagc ggaaagtagc ttgctacttt gccggcgagc ggcggacggg tgagtaatgt    120
ctgggaaact gcctgatgga gggggataac tactggaaac ggtagctaat accgcatgac    180
ctcgaaagag caaagtgggg gatcttcgga cctcacgcca tcggatgtgc ccagatggga    240
ttagctagta ggtgaggtaa tggctcacct aggcgacgat ccctagctgg tctgagagga    300
tgaccagcca cactggaact gagacacggt ccagactcct acgggaggca gcagtgggga    360
atattgcaca atgggcgcaa gcctgatgca gccatgccgc gtgtgtgaag aaggccttag    420
ggttgtaaag cactttcagc gaggaggaag gcatcatact taatacgtgt ggtgattgac    480
gttactcgca gaagaagcac cggctaactc cgtgccagca gccgcggtaa tacggagggt    540
gcaagcgtta atcggaatta ctgggcgtaa agcgcacgca ggcggtttgt taagtcagat    600
gtgaaatccc cgcgcttaac gtgggaactg catttgaaac tggcaagcta gagtcttgta    660
gaggggggta gaattccagg tgtagcggtg aaatgcgtag agatctggag gaataccggt    720
ggcgaaggcg gccccctgga caaagactga cgctcaggtg cgaaagcgtg gggagcaaac    780
aggattagat accctggtag tccacgccgt aaacgatgtc gacttggagg ttgttccctt    840
gaggagtggc ttccggagct aacgcgttaa gtcgaccgcc tggggagtac ggccgcaagg    900
ttaaaactca aatgaattga cgggggcccg cacaagcggt ggagcatgtg gtttaattcg    960
atgcaacgcg aagaacctta cctactcttg acatccacgg aatttggcag agatgcctta   1020
gtgccttcgg gaaccgtgag acaggtgctg catggctgtc gtcagctcgt gttgtgaaat   1080
gttgggttaa gtcccgcaac gagcgcaacc cttatccttt gttgccagcg attcggtcgg   1140
gaactcaaag gagactgccg gtgataaacc ggaggaaggt ggggatgacg tcaagtcatc   1200
atggccctta cgagtagggc tacacacggc tacaatggcg catacaaaga gaagcgacct   1260
```

```
cgcgagagca agcggacctc acaaagtgcg tcgtagtccg gatcggagtc tgcaactcga    1320

ctccgtgaag tcggaatcgc tagtaatcgt ggatcagaat gccacggtga atacgttccc    1380

gggccttgta cacaccgccc gtcacaccat gggagtgggt tgcaaaagaa gtaggtagct    1440

taaccttcgg gagggcgctt accactttgt gattcatgac tggggtgaag tcgtaacaag    1500

gtaaccgtag gggaacctgc ggttggatca cctcctt                              1537
```

<210> SEQ ID NO 5
<211> LENGTH: 1157
<212> TYPE: DNA
<213> ORGANISM: Unknown
<220> FEATURE:
<223> OTHER INFORMATION: Description of Unknown:
      DP5 ITS microbial sequence
<220> FEATURE:
<221> NAME/KEY: modified_base
<222> LOCATION: (1)..(17)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (74)..(75)
<223> OTHER INFORMATION: a, c, t, g, unknown or other
<220> FEATURE:
<221> NAME/KEY: modified_base
<222> LOCATION: (1045)..(1045)
<223> OTHER INFORMATION: a, c, t, g, unknown or other
<220> FEATURE:
<221> NAME/KEY: modified_base
<222> LOCATION: (1064)..(1064)
<223> OTHER INFORMATION: a, c, t, g, unknown or other
<220> FEATURE:
<221> NAME/KEY: modified_base
<222> LOCATION: (1072)..(1072)
<223> OTHER INFORMATION: a, c, t, g, unknown or other
<220> FEATURE:
<221> NAME/KEY: modified_base
<222> LOCATION: (1080)..(1080)
<223> OTHER INFORMATION: a, c, t, g, unknown or other
<220> FEATURE:
<221> NAME/KEY: modified_base
<222> LOCATION: (1085)..(1085)
<223> OTHER INFORMATION: a, c, t, g, unknown or other
<220> FEATURE:
<221> NAME/KEY: modified_base
<222> LOCATION: (1088)..(1089)
<223> OTHER INFORMATION: a, c, t, g, unknown or other
<220> FEATURE:
<221> NAME/KEY: modified_base
<222> LOCATION: (1098)..(1098)
<223> OTHER INFORMATION: a, c, t, g, unknown or other
<220> FEATURE:
<221> NAME/KEY: modified_base
<222> LOCATION: (1105)..(1108)
<223> OTHER INFORMATION: a, c, t, g, unknown or other
<220> FEATURE:
<221> NAME/KEY: modified_base
<222> LOCATION: (1112)..(1113)
<223> OTHER INFORMATION: a, c, t, g, unknown or other
<220> FEATURE:
<221> NAME/KEY: modified_base
<222> LOCATION: (1117)..(1118)
<223> OTHER INFORMATION: a, c, t, g, unknown or other
<220> FEATURE:
<221> NAME/KEY: modified_base
<222> LOCATION: (1121)..(1122)
<223> OTHER INFORMATION: a, c, t, g, unknown or other
<220> FEATURE:
<221> NAME/KEY: modified_base
<222> LOCATION: (1126)..(1127)
<223> OTHER INFORMATION: a, c, t, g, unknown or other
<220> FEATURE:
<221> NAME/KEY: modified_base
<222> LOCATION: (1129)..(1131)
<223> OTHER INFORMATION: a, c, t, g, unknown or other
<220> FEATURE:
<221> NAME/KEY: modified_base
<222> LOCATION: (1138)..(1138)
<223> OTHER INFORMATION: a, c, t, g, unknown or other
<220> FEATURE:
<221> NAME/KEY: modified_base
<222> LOCATION: (1148)..(1148)
<223> OTHER INFORMATION: a, c, t, g, unknown or other
<220> FEATURE:
<221> NAME/KEY: modified_base
<222> LOCATION: (1150)..(1152)
<223> OTHER INFORMATION: a, c, t, g, unknown or other
<220> FEATURE:
<221> NAME/KEY: modified_base
<222> LOCATION: (1156)..(1157)
<223> OTHER INFORMATION: a, c, t, g, unknown or other

<400> SEQUENCE: 5
nnnnnnnnnn nnnnnnntgn ngcgcttatt gcgcggcgaa aaaaccttac acacagtgtt 60
ttttgttatt acannaactt ttgctttggt ctggactaga aatagtttgg gccagaggtt 120
actaaactaa acttcaatat ttatattgaa ttgttattta tttaattgtc aatttgttga 180
ttaaattcaa aaaatcttca aaactttcaa caacggatct cttggttctc gcatcgatga 240
agaacgcagc gaaatgcgat aagtaatatg aattgcagat tttcgtgaat catcgaatct 300
ttgaacgcac attgcgccct ctggtattcc agagggcatg cctgtttgag cgtcatttct 360
ctctcaaacc ttcgggtttg gtattgagtg atactcttag tcgaactagg cgtttgcttg 420
aaatgtattg gcatgagtgg tactggatag tgctatatga ctttcaatgt attaggttta 480
tccaactcgt tgaatagttt aatggtatat ttctcggtat tctaggctcg gccttacaat 540
ataacaaaca agtttgacct caaatcaggt aggattaccc gctgaactta agcatatcaa 600
taagcggagg aaaagaaacc aacagggatt gccttagtaa cggcgagtga agcggcaaaa 660
gctcaaattt gaaatctggc accttcggtg tccgagttgt aatttgaaga aggtaacttt 720
ggagttggct cttgtctatg ttccttggaa caggacgtca cagagggtga gaatcccgtg 780
cgatgagatg cccaattcta tgtaaagtgc tttcgaagag tcgagttgtt tgggaatgca 840
gctctaagtg ggtggtaaat tccatctaaa gctaaatatt ggcgagagac cgatagcgaa 900
caagtacagt gatggaaaga tgaaaagaac tttgaaaaga gagtgaaaaa gtacgtgaaa 960
ttgttgaaag ggaaagggct tgagatcaga cttggtattt tgcgatcctt tccttcttgg 1020
ttgggttcct cgcagcttac tgggncagca tcggtttgga tggnaggata angactaagn 1080
aatgnggnnc tacttcgngg agtgnnnnag cnntggnnga nnactnncnn nctaagancg 1140
aggactgngn nntttnn 1157

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9
<211> LENGTH: 1572
<212> TYPE: DNA
<213> ORGANISM: Unknown
<220> FEATURE:
<223> OTHER INFORMATION: Description of Unknown:
DP9 16S rRNA microbial sequence

<400> SEQUENCE: 9

```
atgagagttt gatcttggct caggatgaac gctggcggcg tgcctaatac atgcaagtcg     60

aacgaacttc cgttaattga ttatgacgta cttgtactga ttgagatttt aacacgaagt    120

gagtggcgaa cgggtgagta acacgtgggt aacctgccca gaagtagggg ataacacctg    180

gaaacagatg ctaataccgt ataacagaga aaaccgcatg gttttctttt aaaagatggc    240

tctgctatca cttctggatg gacccgcggc gtattagcta gttggtgagg caaaggctca    300

ccaaggcagt gatacgtagc cgacctgaga gggtaatcgg ccacattggg actgagacac    360

ggcccagact cctacgggag gcagcagtag ggaatcttcc acaatggacg caagtctgat    420

ggagcaacgc cgcgtgagtg aagaagggtt tcggctcgta aagctctgtt gttaaagaag    480

aacgtgggta agagtaactg tttacccagt gacggtattt aaccagaaag ccacggctaa    540

ctacgtgcca gcagccgcgg taatacgtag gtggcaagcg ttatccggat ttattgggcg    600

taaagcgagc gcaggcggtc ttttaagtct aatgtgaaag ccttcggctc aaccgaagaa    660

gtgcattgga aactgggaga cttgagtgca gaagaggaca gtggaactcc atgtgtagcg    720

gtgaaatgcg tagatatatg gaagaacacc agtggcgaag gcggctgtct ggtctgcaac    780

tgacgctgag gctcgaaagc atgggtagcg aacaggatta gataccctgg tagtccatgc    840

cgtaaacgat gattactaag tgttggaggg tttccgccct tcagtgctgc agctaacgca    900

ttaagtaatc cgcctgggga gtacgaccgc aaggttgaaa ctcaaaagaa ttgacggggg    960

cccgcacaag cggtggagca tgtggtttaa ttcgaagcta cgcgaagaac cttaccaggt   1020

cttgacatct tctgacagtc taagagatta gaggttccct tcggggacag aatgacaggt   1080

ggtgcatggt tgtcgtcagc tcgtgtcgtg agatgttggg ttaagtcccg caacgagcgc   1140

aacccttatt actagttgcc agcattaagt tgggcactct agtgagactg ccggtgacaa   1200

accggaggaa ggtggggacg acgtcaaatc atcatgcccc ttatgacctg ggctacacac   1260

gtgctacaat ggatggtaca acgagtcgcg agaccgcgag gttaagctaa tctcttaaaa   1320

ccattctcag ttcggactgt aggctgcaac tcgcctacac gaagtcggaa tcgctagtaa   1380

tcgcggatca gcatgccgcg gtgaatacgt tcccgggcct tgtacacacc gcccgtcaca   1440

ccatgagagt ttgtaacacc caaagccggt ggggtaacct tttaggagct agccgtctaa   1500

ggtgggacag atgattaggg tgaagtcgta acaaggtagc cgtaggagaa cctgcggctg   1560

gatcacctcc tt                                                       1572
```

<210> SEQ ID NO 10
<211> LENGTH: 1300
<212> TYPE: DNA
<213> ORGANISM: Unknown
<220> FEATURE:
<223> OTHER INFORMATION: Description of Unknown:
DP10 16S rRNA microbial sequence

<400> SEQUENCE: 10
cagatagttg gtgaggtaac ggctcaccaa ggcaacgatg cgtagccgac ctgagagggt 60
gatcggccac actgggactg agacacggcc cagactccta cgggaggcag cagtagggaa 120
tcttccgcaa tggacgaaag tctgacggag caacgccgcg tgagtgatga aggttttcgg 180
atcgtaaagc tctgttgtta gggaagaaca agtgccgttc aaatagggcg gcaccttgac 240
ggtacctaac cagaaagcca cggctaacta cgtgccagca gccgcggtaa tacgtaggtg 300
gcaagcgttg tccggaatta ttgggcgtaa agggctcgca ggcggtttct taagtctgat 360
gtgaaagccc ccggctcaac cggggagggt cattggaaac tggggaactt gagtgcagaa 420
gaggagagtg gaattccacg tgtagcggtg aaatgcgtag agatgtggag gaacaccagt 480
ggcgaaggcg actctctggt ctgtaactga cgctgaggag cgaaagcgtg gggagcgaac 540
aggattagat accctggtag tccacgccgt aaacgatgag tgctaagtgt tagggggttt 600
ccgcccctta gtgctgcagc taacgcatta agcactccgc ctggggagta cggtcgcaag 660
actgaaactc aaaggaattg acgggggccc gcacaagcgg tggagcatgt ggtttaattc 720
gaagcaacgc gaagaacctt accaggtctt gacatcctct gacaatccta gagataggac 780
gtccccttcg gggggcagagt gacaggtggt gcatggttgt cgtcagctcg tgtcgtgaga 840
tgttgggtta agtcccgcaa cgagcgcaac ccttgatctt agttgccagc attcagttgg 900
gcactctaag gtgactgccg gtgacaaacc ggaggaaggt ggggatgacg tcaaatcatc 960
atgcccctta tgacctgggc tacacacgtg ctacaatgga cagaacaaag ggcagcgaaa 1020
ccgcgaggtt aagccaatcc cacaaatctg ttctcagttc ggatcgcagt ctgcaactcg 1080
actgcgtgaa gctggaatcg ctagtaatcg cggatcagca tgccgcggtg aatacgttcc 1140
cgggccttgt acacaccgcc cgtcacacca cgagagtttg taacacccga agtcggtgag 1200
gtaacctttt aggagccagc cgccgaaggt gggacagatg attggggtga agtcgtaaca 1260
aggtagccgt atcggaaggt gcggctggat cacctccttt 1300

<210> SEQ ID NO 11
<211> LENGTH: 1419
<212> TYPE: DNA
<213> ORGANISM: Unknown
<220> FEATURE:
<223> OTHER INFORMATION: Description of Unknown:
DP11 16S rRNA microbial sequence

<400> SEQUENCE: 11
tgaagagttt gatcatggct cagattgaac gctggcggca ggcctaacac atgcaagtcg 60
agcggtagag agaagcttgc ttctcttgag agcggcggac gggtgagtaa tgcctaggaa 120
tctgcctggt agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggcgac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggttgta gattaatact ctgcaatttt gacgttaccg 480
acagaataag caccggctaa ctctgtgcca gcagccgcgg taatacagag ggtgcaagcg 540
ttaatcggaa ttactgggcg taaagcgcgc gtaggtggtt cgttaagttg gatgtgaaag 600
ccccgggctc aacctgggaa ctgcattcaa aactgacgag ctagagtatg gtagagggtg 660

-continued

```
gtggaatttc ctgtgtagcg gtgaaatgcg tagatatagg aaggaacacc agtggcgaag    720

gcgaccacct ggactgatac tgacactgag gtgcgaaagc gtggggagca aacaggatta    780

gataccctgg tagtccacgc cgtaaacgat gtcaactagc cgttggaatc cttgagattt    840

tagtggcgca gctaacgcat taagttgacc gcctggggag tacggccgca aggttaaaac    900

tcaaatgaat tgacgggggc ccgcacaagc ggtggagcat gtggtttaat tcgaagcaac    960

gcgaagaacc ttaccaggcc ttgacatcca atgaactttc cagagatgga tgggtgcctt   1020

cgggaacatt gagacaggtg ctgcatggct gtcgtcagct cgtgtcgtga gatgttgggt   1080

taagtcccgt aacgagcgca acccttgtcc ttagttacca gcacgttatg gtgggcactc   1140

taaggagact gccggtgaca aaccggagga aggtggggat gacgtcaagt catcatggcc   1200

cttacggcct gggctacaca cgtgctacaa tggtcggtac aaagggttgc caagccgcga   1260

ggtggagcta atcccataaa accgatcgta gtccggatcg cagtctgcaa ctcgactgcg   1320

tgaagtcgga atcgctagta atcgcgaatc agaatgtcgc ggtgaatacg ttcccgggcc   1380

ttgtacacac cgcccgtcac atcccacacg aattgcttg                          1419
```

<210> SEQ ID NO 12
<211> LENGTH: 1520
<212> TYPE: DNA
<213> ORGANISM: Unknown
<220> FEATURE:
<223> OTHER INFORMATION: Description of Unknown:
DP12 16S rRNA microbial sequence

<400> SEQUENCE: 12

```
tacggagagt ttgatcctgg ctcaggatga acgctggcgg cgtgcttaac acatgcaagt     60

cgaacggtga agccaagctt gcttggtgga tcagtggcga acgggtgagt aacacgtgag    120

caacctgccc tggactctgg gataagcgct ggaaacggcg tctaatactg gatatgagcc    180

ttcatcgcat ggtgggggtt ggaaagattt tttggtctgg gatgggctcg cggcctatca    240

gcttgttggt gaggtaatgg ctcaccaagg cgtcgacggg tagccggcct gagagggtga    300

ccggccacac tgggactgag acacggccca gactcctacg ggaggcagca gtggggaata    360

ttgcacaatg ggcgaaagcc tgatgcagca acgccgcgtg agggatgacg gccttcgggt    420

tgtaaacctc ttttagcagg gaagaagcga aagtgacggt acctgcagaa aaagcgccgg    480

ctaactacgt gccagcagcc gcggtaatac gtagggcgca agcgttatcc ggaattattg    540

ggcgtaaaga gctcgtaggc ggtttgtcgc gtctgctgtg aaatcccgag gctcaacctc    600

gggcctgcag tgggtacggg cagactagag tgcggtaggg gagattggaa ttcctggtgt    660

agcggtggaa tgcgcagata tcaggaggaa caccgatggc gaaggcagat ctctgggccg    720

taactgacgc tgaggagcga aagggtgggg agcaaacagg cttagatacc ctggtagtcc    780

accccgtaaa cgttgggaac tagttgtggg gaccattcca cggtttccgt gacgcagcta    840

acgcattaag ttccccgcct ggggagtacg gccgcaaggc taaaactcaa aggaattgac    900

ggggacccgc acaagcggcg gagcatgcgg attaattcga tgcaacgcga agaaccttac    960

caaggcttga catacaccag aacgggccag aaatggtcaa ctctttggac actggtgaac   1020

aggtggtgca tggttgtcgt cagctcgtgt cgtgagatgt tgggttaagt cccgcaacga   1080

gcgcaaccct cgttctatgt tgccagcacg taatggtggg aactcatggg atactgccgg   1140

ggtcaactcg gaggaaggtg gggatgacgt caaatcatca tgccccttat gtcttgggct   1200

tcacgcatgc tacaatggcc ggtacaaagg gctgcaatac cgtgaggtgg agcgaatccc   1260
```

-continued

```
aaaaagccgg tcccagttcg gattgaggtc tgcaactcga cctcatgaag tcggagtcgc   1320

tagtaatcgc agatcagcaa cgctgcggtg aatacgttcc cgggtcttgt acacaccgcc   1380

cgtcaagtca tgaaagtcgg taacacctga agccggtggc ccaacccttg tggagggagc   1440

cgtcgaaggt gggatcggta attaggacta agtcgtaaca aggtagccgt accggaaggt   1500

gcggctggat cacctccttt                                               1520
```

<210> SEQ ID NO 13
<211> LENGTH: 1457
<212> TYPE: DNA
<213> ORGANISM: Unknown
<220> FEATURE:
<223> OTHER INFORMATION: Description of Unknown:
DP13 16S rRNA microbial sequence

<400> SEQUENCE: 13

```
agttagcggc ggacgggtga gtaacacgtg ggtaacctgc ctataagact gggataactc     60

cgggaaaccg gggctaatac cggataacat tttgcaccgc atggtgcgaa attgaaaggc    120

ggcttcggct gtcacttata gatggacctg cggcgcatta gctagttggt gaggtaacgg    180

ctcaccaagg cgacgatgcg tagccgacct gagagggtga tcggccacac tgggactgag    240

acacggccca gactcctacg ggaggcagca gtagggaatc ttccgcaatg gacgaaagtc    300

tgacggagca acgccgcgtg aacgatgaag gctttcgggt cgtaaagttc tgttgttagg    360

gaagaacaag tgctagttga ataagctggc accttgacgg tacctaacca gaaagccacg    420

gctaactacg tgccagcagc cgcggtaata cgtaggtggc aagcgttatc cggaattatt    480

gggcgtaaag cgcgcgcagg tggtttctta agtctgatgt gaaagcccac ggctcaaccg    540

tggagggtca ttggaaactg ggagacttga gtgcagaaga ggaaagtgga attccatgtg    600

tagcggtgaa atgcgtagag atatggagga acaccagtgg cgaaggcgac tttctggtct    660

gcaactgaca ctgaggcgcg aaagcgtggg gagcaaacag gattagatac cctggtagtc    720

cacgccgtaa acgatgagtg ctaagtgtta gagggtttcc gccctttagt gctgaagtta    780

acgcattaag cactccgcct ggggagtacg gccgcaaggc tgaaactcaa aggaattgac    840

gggggcccgc acaagcggtg gagcatgtgg tttaattcga agcaacgcga agaaccttac    900

caggtcttga catcctctga aaaccctaga gatagggctt ccccttcggg ggcagagtga    960

caggtggtgc atggttgtcg tcagctcgtg tcgtgagatg ttgggttaag tcccgcaacg   1020

agcgcaaccc ttgatcttag ttgccatcat taagttgggc actctaaggt gactgccggt   1080

gacaaaccgg aggaaggtgg ggatgacgtc aaatcatcat gccccttatg acctgggcta   1140

cacacgtgct acaatggacg gtacaaagag tcgcaagacc gcgaggtgga gctaatctca   1200

taaaaccgtt ctcagttcgg attgtaggct gcaactcgcc tacatgaagc tggaatcgct   1260

agtaatcgcg gatcagcatg ccgcggtgaa tacgttcccg ggccttgtac acaccgcccg   1320

tcacaccacg agagtttgta acacccgaag tcggtggggt aacctttttgg agccagccgc   1380

ctaaggtggg acagatgatt ggggtgaagt cgtaacaagg tagccgtatc ggaaggtgcg   1440

gctggatcac ctccttt                                                   1457
```

<210> SEQ ID NO 14
<211> LENGTH: 1525
<212> TYPE: DNA
<213> ORGANISM: Unknown
<220> FEATURE:
<223> OTHER INFORMATION: Description of Unknown:
DP14 16S rRNA microbial sequence

<400> SEQUENCE: 14
tacggagagt ttgatcctgg ctcaggatga acgctggcgg cgtgcttaac acatgcaagt 60
cgaacgatga cttctgtgct tgcacagaat gattagtggc gaacgggtga gtaacacgtg 120
agtaacctgc ccttaacttc gggataagcc tgggaaaccg ggtctaatac cggatacgac 180
ctcctggcgc atgccatggt ggtggaaagc tttagcggtt ttggatggac tcgcggccta 240
tcagcttgtt ggttggggta atggcccacc aaggcgacga cgggtagccg gcctgagagg 300
gtgaccggcc acactgggac tgagacacgg cccagactcc tacgggaggc agcagtgggg 360
aatattgcac aatgggcgaa agcctgatgc agcgacgccg cgtgagggat gacggccttc 420
gggttgtaaa cctctttcag cagggaagaa gcgaaagtga cggtacctgc agaagaagcg 480
ccggctaact acgtgccagc agccgcggta atacgtaggg cgcaagcgtt atccggaatt 540
attgggcgta aagagctcgt aggcggtttg tcgcgtctgc tgtgaaagcc cggggctcaa 600
ccccgggtct gcagtgggta cgggcagact agagtgcagt aggggagact ggaattcctg 660
gtgtagcggt gaaatgcgca gatatcagga ggaacaccga tggcgaaggc aggtctctgg 720
gctgtaactg acgctgagga gcgaaagcat ggggagcgaa caggattaga taccctggta 780
gtccatgccg taaacgttgg gcactaggtg tgggggacat tccacgtttt ccgcgccgta 840
gctaacgcat taagtgcccc gcctggggag tacggccgca aggctaaaac tcaaaggaat 900
tgacgggggc ccgcacaagc ggcggagcat gcggattaat tcgatgcaac gcgaagaacc 960
ttaccaaggc ttgacatgaa ccggtaagac ctggaaacag gtcccccact tgtggccggt 1020
ttacaggtgg tgcatggttg tcgtcagctc gtgtcgtgag atgttgggtt aagtcccgca 1080
acgagcgcaa ccctcgttct atgttgccag cgggttatgc cggggactca taggagactg 1140
ccggggtcaa ctcggaggaa ggtggggacg acgtcaaatc atcatgcccc ttatgtcttg 1200
ggcttcacgc atgctacaat ggccggtaca aagggttgcg atactgtgag gtggagctaa 1260
tcccaaaaag ccggtctcag ttcggattga ggtctgcaac tcgacctcat gaagttggag 1320
tcgctagtaa tcgcagatca gcaacgctgc ggtgaatacg ttcccgggcc ttgtacacac 1380
cgcccgtcaa gtcacgaaag ttggtaacac ccgaagccgg tggcctaacc ccttgtggga 1440
gggagccgtc gaaggtggga ccggcgattg ggacaagtcg taacaaggta gccgtaccgg 1500
aaggtgcggc tggatcacct ccttt 1525

<210> SEQ ID NO 15
<211> LENGTH: 1520
<212> TYPE: DNA
<213> ORGANISM: Unknown
<220> FEATURE:
<223> OTHER INFORMATION: Description of Unknown:
DP15 16S rRNA microbial sequence

<400> SEQUENCE: 15
tacggagagt ttgatcctgg ctcaggacga acgctggcgg cgtgcttaac acatgcaagt 60
cgaacgatga tcaggagctt gctcctgtga ttagtggcga acgggtgagt aacacgtgag 120
taacctgccc ctgactctgg gataagcgtt ggaaacgacg tctaatactg gatatgatca 180
ctggccgcat ggtctggtgg tggaaagatt ttttggttgg ggatggactc gcggcctatc 240
agcttgttgg tgaggtaatg gctcaccaag gcgacgacgg gtagccggcc tgagagggtg 300
accggccaca ctgggactga gacacggccc agactcctac gggaggcagc agtggggaat 360
attgcacaat gggcgaaagc ctgatgcagc aacgccgcgt gagggatgac ggccttcggg 420

```
ttgtaaacct cttttagtag ggaagaagcg aaagtgacgg tacctgcaga aaaagcaccg    480

gctaactacg tgccagcagc cgcggtaata cgtagggtgc aagcgttgtc cggaattatt    540

gggcgtaaag agctcgtagg cggtttgtcg cgtctgctgt gaaatcccga ggctcaacct    600

cgggcttgca gtgggtacgg gcagactaga gtgcggtagg ggagattgga attcctggtg    660

tagcggtgga atgcgcagat atcaggagga acaccgatgg cgaaggcaga tctctgggcc    720

gtaactgacg ctgaggagcg aaagcgtggg gagcgaacag gattagatac cctggtagtc    780

cacgccgtaa acgttgggcg ctagatgtag ggacctttcc acggtttctg tgtcgtagct    840

aacgcattaa gcgccccgcc tggggagtac ggccgcaagg ctaaaactca aaggaattga    900

cgggggcccg cacaagcggc ggagcatgcg gattaattcg atgcaacgcg aagaacctta    960

ccaaggcttg acatacaccg gaaacggcca gagatggtcg ccccccttgtg gtcggtgtac   1020

aggtggtgca tggttgtcgt cagctcgtgt cgtgagatgt tgggttaagt cccgcaacga   1080

gcgcaaccct cgttctatgt tgccagcgcg ttatggcggg gactcatagg agactgccgg   1140

ggtcaactcg gaggaaggtg gggatgacgt caaatcatca tgccccttat gtcttgggct   1200

tcacgcatgc tacaatggcc ggtacaaagg gctgcgatac cgtaaggtgg agcgaatccc   1260

aaaaagccgg tctcagttcg gattgaggtc tgcaactcga cctcatgaag tcggagtcgc   1320

tagtaatcgc agatcagcaa cgctgcggtg aatacgttcc cgggccttgt acacaccgcc   1380

cgtcaagtca tgaaagtcgg taacacccga agccggtggc ctaacccttg tggaaggagc   1440

cgtcgaaggt gggatcggtg attaggacta agtcgtaaca aggtagccgt accggaaggt   1500

gcggctggat cacctccttt                                                1520
```

<210> SEQ ID NO 16

<400> SEQUENCE: 16

000

<210> SEQ ID NO 17
<211> LENGTH: 898
<212> TYPE: DNA
<213> ORGANISM: Unknown
<220> FEATURE:
<223> OTHER INFORMATION: Description of Unknown:
DP17 16S rRNA microbial sequence

<400> SEQUENCE: 17

```
gtgattgacg ttactcgcag aagaagcacc ggctaactcc gtgccagcag ccgcggtaat     60

acggagggtg caagcgttaa tcggaattac tgggcgtaaa gcgcacgcag gcggtttgtt    120

aagtcagatg tgaaatcccc gcgcttaacg tgggaactgc atttgaaact ggcaagctag    180

agtcttgtag agggggggtag aattccaggt gtagcggtga aatgcgtaga gatctggagg    240

aataccggtg gcgaaggcgg ccccctggac aaagactgac gctcaggtgc gaaagcgtgg    300

ggagcaaaca ggattagata ccctggtagt ccacgctgta aacgatgtcg acttggaggt    360

tgtgcccttg aggcgtggct tccggagcta acgcgttaag tcgaccgcct ggggagtacg    420

gccgcaaggt taaaactcaa atgaattgac gggggcccgc acaagcggtg gagcatgtgg    480

tttaattcga tgcaacgcga agaaccttac ctactcttga catccacgga attcgccaga    540

gatggcttag tgccttcggg aaccgtgaga caggtgctgc atggctgtcg tcagctcgtg    600

ttgtgaaatg ttgggttaag tcccgcaacg agcgcaaccc ttatcctttg ttgccagcac    660
```

```
gtaatggtgg gaactcaaag gagactgccg gtgataaacc ggaggaaggt ggggatgacg    720

tcaagtcatc atggccctta cgagtagggc tacacacgtg ctacaatggc atatacaaag    780

agaagcgaac tcgcgagagc aagcggacct cataaagtat gtcgtagtcc ggattggagt    840

ctgcaactcg actccatgaa gtcggaatcg ctagtaatcg tagatcagaa tgctacgg      898
```

<210> SEQ ID NO 18
<211> LENGTH: 1532
<212> TYPE: DNA
<213> ORGANISM: Unknown
<220> FEATURE:
<223> OTHER INFORMATION: Description of Unknown:
DP18 16S rRNA microbial sequence

<400> SEQUENCE: 18

```
tgaagagttt gatcatggct cagattgaac gctggcggca ggcctaacac atgcaagtcg     60

agcggatgaa aggagcttgc tcctggattc agcggcggac gggtgagtaa tgcctaggaa    120

tctgcctggt agtgggggac aacgtttcga aaggaacgct aataccgcat acgtcctacg    180

ggagaaagca ggggaccttc gggccttgcg ctatcagatg agcctaggtc ggattagcta    240

gttggtgagg taatggctca ccaaggcgac gatccgtaac tggtctgaga ggatgatcag    300

tcacactgga actgagacac ggtccagact cctacgggag gcagcagtgg ggaatattgg    360

acaatgggcg aaagcctgat ccagccatgc cgcgtgtgtg aagaaggtct tcggattgta    420

aagcacttta agttgggagg aagggcagta aattaatact ttgctgtttt gacgttaccg    480

acagaataag caccggctaa ctctgtgcca gcagccgcgg taatacagag ggtgcaagcg    540

ttaatcggaa ttactgggcg taaagcgcgc gtaggtggtt tgttaagttg aatgtgaaat    600

ccccgggctc aacctgggaa ctgcatccaa aactggcaag ctagagtatg gtagagggtg    660

gtggaatttc ctgtgtagcg gtgaaatgcg tagatatagg aaggaacacc agtggcgaag    720

gcgaccacct ggactgatac tgacactgag gtgcgaaagc gtggggagca aacaggatta    780

gataccctgg tagtccacgc cgtaaacgat gtcaactagc cgttgggagc cttgagctct    840

tagtggcgca gctaacgcat taagttgacc gcctggggag tacggccgca aggttaaaac    900

tcaaatgaat tgacgggggc ccgcacaagc ggtggagcat gtggtttaat tcgaagcaac    960

gcgaagaacc ttaccaggcc ttgacatcca atgaactttc cagagatgga ttggtgcctt   1020

cgggaacatt gagacaggtg ctgcatggct gtcgtcagct cgtgtcgtga gatgttgggt   1080

taagtcccgt aacgagcgca acccttgtcc ttagttacca gcacgttatg gtgggcactc   1140

taaggagact gccggtgaca aaccggagga aggtggggat gacgtcaagt catcatggcc   1200

cttacggcct gggctacaca cgtgctacaa tggtcggtac aaagggttgc caagccgcga   1260

ggtggagcta atcccataaa accgatcgta gtccggatcg cagtctgcaa ctcgactgcg   1320

tgaagtcgga atcgctagta atcgcgaatc agaatgtcgc ggtgaatacg ttcccgggcc   1380

ttgtacacac cgcccgtcac accatgggag tgggttgcac cagaagtagc tagtctaacc   1440

ttcgggagga cggttaccac ggtgtgattc atgactgggg tgaagtcgta acaaggtagc   1500

cgtaggggaa cctgcggctg gatcacctcc tt                                 1532
```

<210> SEQ ID NO 19
<211> LENGTH: 1520
<212> TYPE: DNA
<213> ORGANISM: Unknown
<220> FEATURE:
<223> OTHER INFORMATION: Description of Unknown:
DP19 16S rRNA microbial sequence

<400> SEQUENCE: 19

```
tacggagagt ttgatcctgg ctcaggacga acgctggcgg cgtgcttaac acatgcaagt     60
cgaacgatga tgcccagctt gctgggtgga ttagtggcga acgggtgagt aacacgtgag    120
taacctgccc ctgactctgg gataagcgtt ggaaacgacg tctaatactg gatacgactg    180
ccggccgcat ggtctggtgg tggaaagatt ttttggttgg ggatggactc gcggcctatc    240
agcttgttgg tgaggtaatg gctcaccaag gcgacgacgg gtagccggcc tgagagggtg    300
accggccaca ctgggactga gacacggccc agactcctac gggaggcagc agtggggaat    360
attgcacaat gggcgaaagc ctgatgcagc aacgccgcgt gagggatgac ggccttcggg    420
ttgtaaacct cttttagtag ggaagaagcg aaagtgacgg tacctgcaga aaaagcaccg    480
gctaactacg tgccagcagc cgcggtaata cgtagggtgc aagcgttgtc cggaattatt    540
gggcgtaaag agctcgtagg cggtttgtcg cgtctgctgt gaaatcccga ggctcaacct    600
cgggcttgca gtgggtacgg gcagactaga gtgcggtagg ggagattgga attcctggtg    660
tagcggtgga atgcgcagat atcaggagga acaccgatgg cgaaggcaga tctctgggcc    720
gtaactgacg ctgaggagcg aaagcgtggg gagcgaacag gattagatac cctggtagtc    780
cacgccgtaa acgttgggcg ctagatgtag ggacctttcc acggtttctg tgtcgtagct    840
aacgcattaa gcgccccgcc tggggagtac ggccgcaagg ctaaaactca aaggaattga    900
cgggggcccg cacaagcggc ggagcatgcg gattaattcg atgcaacgcg aagaacctta    960
ccaaggcttg acatacaccg gaaacggcca gagatggtcg ccccttgtg gtcggtgtac    1020
aggtggtgca tggttgtcgt cagctcgtgt cgtgagatgt tgggttaagt cccgcaacga   1080
gcgcaaccct cgttctatgt tgccagcgcg ttatggcggg gactcatagg agactgccgg   1140
ggtcaactcg gaggaaggtg gggatgacgt caaatcatca tgccccttat gtcttgggct   1200
tcacgcatgc tacaatggcc ggtacaaagg gctgcgatac cgtaaggtgg agcgaatccc   1260
aaaaagccgg tctcagttcg gattgaggtc tgcaactcga cctcatgaag tcggagtcgc   1320
tagtaatcgc agatcagcaa cgctgcggtg aatacgttcc cgggccttgt acacaccgcc   1380
cgtcaagtca tgaaagtcgg taacacccga agccggtggc ctaacccttg tggaaggagc   1440
cgtcgaaggt gggatcggtg attaggacta agtcgtaaca aggtagccgt accggaaggt   1500
gcggctggat cacctccttt                                               1520
```

<210> SEQ ID NO 20
<211> LENGTH: 1543
<212> TYPE: DNA
<213> ORGANISM: Unknown
<220> FEATURE:
<223> OTHER INFORMATION: Description of Unknown:
DP20 16S rRNA microbial sequence

<400> SEQUENCE: 20

```
tgaagagttt gatcctggct cagagtgaac gctggcggta ggcctaacac atgcaagtcg     60
aacggcagca cagtaagagc ttgctcttat gggtggcgag tggcggacgg gtgaggaata    120
catcggaatc taccttttcg tgggggataa cgtagggaaa cttacgctaa taccgcatac    180
gaccttcggg tgaaagcagg ggaccttcgg gccttgcgcg gatagatgag ccgatgtcgg    240
attagctagt tggcggggta aaggcccacc aaggcgacga tccgtagctg gtctgagagg    300
atgatcagcc acactggaac tgagacacgg tccagactcc tacgggaggc agcagtgggg    360
aatattggac aatgggcgca agcctgatcc agccataccg cgtgggtgaa gaaggccttc    420
```

gggttgtaaa gcccttttgt tgggaaagaa aagcagtcgg ctaatacccg gttgttctga 480
cggtacccaa agaataagca ccggctaact tcgtgccagc agccgcggta atacgaaggg 540
tgcaagcgtt actcggaatt actgggcgta aagcgtgcgt aggtggttgt ttaagtctgt 600
tgtgaaagcc ctgggctcaa cctgggaatt gcagtggata ctgggcgact agagtgtggt 660
agagggtagt ggaattcccg gtgtagcagt gaaatgcgta gagatcggga ggaacatcca 720
tggcgaaggc agctacctgg accaacactg acactgaggc acgaaagcgt ggggagcaaa 780
caggattaga taccctggta gtccacgccc taaacgatgc gaactggatg ttgggtgcaa 840
tttggcacgc agtatcgaag ctaacgcgtt aagttcgccg cctggggagt acggtcgcaa 900
gactgaaact caaaggaatt gacgggggcc cgcacaagcg gtggagtatg tggtttaatt 960
cgatgcaacg cgaagaacct tacctggtct tgacatgtcg agaactttcc agagatggat 1020
tggtgccttc gggaactcga acacaggtgc tgcatggctg tcgtcagctc gtgtcgtgag 1080
atgttgggtt aagtcccgca acgagcgcaa cccttgtcct tagttgccag cacgtaatgg 1140
tgggaactct aaggagaccg ccggtgacaa accggaggaa ggtggggatg acgtcaagtc 1200
atcatggccc ttacgaccag ggctacacac gtactacaat ggtagggaca gagggctgca 1260
aacccgcgag ggcaagccaa tcccagaaac cctatctcag tccggattgg agtctgcaac 1320
tcgactccat gaagtcggaa tcgctagtaa tcgcagatca gcattgctgc ggtgaatacg 1380
ttcccgggcc ttgtacacac cgcccgtcac accatgggag tttgttgcac cagaagcagg 1440
tagcttaacc ttcgggaggg cgcttgccac ggtgtggccg atgactgggg tgaagtcgta 1500
acaaggtagc cgtatcggaa ggtgcggctg gatcacctcc ttt 1543

<210> SEQ ID NO 21

<400> SEQUENCE: 21

000

<210> SEQ ID NO 22
<211> LENGTH: 1539
<212> TYPE: DNA
<213> ORGANISM: Unknown
<220> FEATURE:
<223> OTHER INFORMATION: Description of Unknown:
DP22 16S rRNA microbial sequence

<400> SEQUENCE: 22
ttgaagagtt tgatcatggc tcagattgaa cgctggcggc aggcctaaca catgcaagtc 60
gagcggcagc gggaagtagc ttgctacttt gccggcgagc ggcggacggg tgagtaatgt 120
ctgggaaact gcctgatgga gggggataac tactggaaac ggtagctaat accgcatgac 180
ctcgcaagag caaagtgggg gaccttcggg cctcacgcca tcggatgtgc ccagatggga 240
ttagctagta ggtgaggtaa tggctcacct aggcgacgat ccctagctgg tctgagagga 300
tgaccagcca cactggaact gagacacggt ccagactcct acgggaggca gcagtgggga 360
atattgcaca atgggcgcaa gcctgatgca gccatgccgc gtgtgtgaag aaggccttag 420
ggttgtaaag cactttcagc gaggaggaag ggttcagtgt taatagcact gaacattgac 480
gttactcgca gaagaagcac cggctaactc cgtgccagca gccgcggtaa tacggagggt 540
gcaagcgtta atcggaatta ctgggcgtaa agcgcacgca ggcggtttgt taagtcagat 600
gtgaaatccc cgagcttaac ttgggaactg catttgaaac tggcaagcta gagtcttgta 660 gagggggggta gaattccagg tgtagcggtg aaatgcgtag agatctggag gaataccggt 720
ggcgaaggcg gccccctgga caaagactga cgctcaggtg cgaaagcgtg gggagcaaac 780
aggattagat accctggtag tccacgctgt aaacgatgtc gacttggagg ttgtgccctt 840
gaggcgtggc ttccggagct aacgcgttaa gtcgaccgcc tggggagtac ggccgcaagg 900
ttaaaactca aatgaattga cgggggcccg cacaagcggt ggagcatgtg gtttaattcg 960
atgcaacgcg aagaacctta cctactcttg acatccagag aattcgctag agatagctta 1020
gtgccttcgg gaactctgag acaggtgctg catggctgtc gtcagctcgt gttgtgaaat 1080
gttgggttaa gtcccgcaac gagcgcaacc cttatccttt gttgccagcg agtaatgtcg 1140
ggaactcaaa ggagactgcc ggtgataaac cggaggaagg tggggatgac gtcaagtcat 1200
catggccctt acgagtaggg ctacacacgt gctacaatgg catatacaaa gagaagcaaa 1260
ctcgcgagag caagcggacc tcataaagta tgtcgtagtc cggattggag tctgcaactc 1320
gactccatga agtcggaatc gctagtaatc gtagatcaga atgctacggt gaatacgttc 1380
ccgggccttg tacacaccgc ccgtcacacc atgggagtgg gttgcaaaag aagtaggtag 1440
cttaaccttc gggagggcgc ttaccacttt gtgattcatg actggggtga agtcgtaaca 1500
aggtaaccgt aggggaacct gcggttggat cacctcctt 1539

<210> SEQ ID NO 23
<211> LENGTH: 1536
<212> TYPE: DNA
<213> ORGANISM: Unknown
<220> FEATURE:
<223> OTHER INFORMATION: Description of Unknown:
DP23 16S rRNA microbial sequence

<400> SEQUENCE: 23
ttgaagagtt tgatcatggc tcagattgaa cgctggcggc aggcctaaca catgcaagtc 60
gaacggtagc acagagagct tgctcttggg tgacgagtgg cggacgggtg agtaatgtct 120
gggaaactgc ccgatggagg gggataacta ctggaaacgg tagctaatac cgcataacgt 180
cttcggacca aagtggggga ccttcgggcc tcacaccatc ggatgtgccc agatgggatt 240
agctagtagg tggggtaatg gctcacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcgg ggaggaaggc gatacggtta ataaccgtgt cgattgacgt 480
tacccgcaga agaagcaccg gctaactccg tgccagcagc cgcggtaata cggagggtgc 540
aagcgttaat cggaattact gggcgtaaag cgcacgcagg cggtctgtca agtcagatgt 600
gaaatccccg ggcttaacct gggaactgca tttgaaactg gcaggcttga gtctcgtaga 660
ggggggtaga attccaggtg tagcggtgaa atgcgtagag atctggagga ataccggtgg 720
cgaaggcggc cccctggacg aagactgacg ctcaggtgcg aaagcgtggg gagcaaacag 780
gattagatac cctggtagtc cacgctgtaa acgatgtcga cttggaggtt gtgcccttga 840
ggcgtggctt ccggagctaa cgcgttaagt cgaccgcctg gggagtacgg ccgcaaggtt 900
aaaactcaaa tgaattgacg ggggcccgca caagcggtgg agcatgtggt ttaattcgat 960
gcaacgcgaa gaaccttacc tggccttgac atccacagaa ttcggcagag atgccttagt 1020
gccttcggga actgtgagac aggtgctgca tggctgtcgt cagctcgtgt tgtgaaatgt 1080
tgggttaagt cccgcaacga gcgcaaccct tatcctttgt tgccagcgat tcggtcggga 1140

-continued actcaaagga gactgccggt gataaaccgg aggaaggtgg ggatgacgtc aagtcatcat 1200
ggcccttacg gccagggcta cacacgtgct acaatggcgc atacaaagag aagcgacctc 1260
gcgagagcaa gcggacctca taaagtgcgt cgtagtccgg atcggagtct gcaactcgac 1320
tccgtgaagt cggaatcgct agtaatcgta gatcagaatg ctacggtgaa tacgttcccg 1380
ggccttgtac acaccgcccg tcacaccatg ggagtgggtt gcaaaagaag taggtagctt 1440
aaccttcggg agggcgctta ccactttgtg attcatgact ggggtgaagt cgtaacaagg 1500
taaccgtagg ggaacctgcg gttggatcac ctcctt 1536

<210> SEQ ID NO 24
<211> LENGTH: 1315
<212> TYPE: DNA
<213> ORGANISM: Unknown
<220> FEATURE:
<223> OTHER INFORMATION: Description of Unknown:
DP24 16S rRNA microbial sequence

<400> SEQUENCE: 24
agcatttgat tatggtgctt actgattgct atctaggggt ttaacacatg ctagtcaatg 60
atcttttaga ttatggcgta cggqctagga atacttagaa tgataactct atgatcgcag 120
taatagcgta aaaggtataa taccgcatag aggttcgctt cgtatctaat aggtagttgg 180
tgaggtaaag ctcaacaagc cgatgatgag taatattgga tgaaagtctt aaatatagca 240
gtggaaatga aaaagtccac cgttatttat taacgcagca gtggagaatc gtcgtaatgt 300
gcagtattca tttatggata agcatgaacg cgctacctag attcggatag gagatagcat 360
cttctaccga taaaagaact tagaataatg atctagttct cattagtggg tgacaatcgc 420
cgtgccagca tcagcggtaa aacggcttcc gcaagcaata gtaatttaaa ttggtgtaaa 480
gggtacgtag ccggccttat taggctagag ttagatacgg gtaagtacaa tacttggagt 540
agggctgata tcttatgatc ccaaggggag tgctaaaggc gaaggcaact tactggtaat 600
aactgacggt gaggtacgaa ggtcagggca tggaaagaga ttagatacct cattactcct 660
gacagtaaac gatgtagatt aaagattgga ataattctgt cttaacgcta acgcattaaa 720
tctaccacct gtagagtata gtcgcaaggc cgaaatacaa ataattagac ggctctagag 780
caaacggagt gaagcatgtt atttaatacg ataacccgcg taaaatctta ccagttcttg 840
aatcttagac aggtgttgca tggttgtcgt cagctcgtgc taatggtgtc tggttaattc 900
caaataacga gcgcaatcct tacttctagt tttctaggag tctccatttg acatacgtgt 960
caatggttta aggaatatga caaaccctca tggcccttat ggactgggca atagacgtgc 1020
cacaagaatc tagacaaaat gacgcgaaat ggtaacaatg agctaatcat caaagaagat 1080
taatgtacga attatgggct ggaactcgcc catatgaagt aggaattccg agtaatcgcg 1140
tatcagaacg acgcggtgaa catcatctct ggagtgtact aactgctcgt cacgggacga 1200
aagggagtgt attatgaagt ggggctaatt ggttaactcc ggtgagtgtc acgaataatc 1260
cttcccgatt gttctgaagt cgaaacaagg taaccgtaag ggaacttgcg gttga 1315

<210> SEQ ID NO 25
<211> LENGTH: 1520
<212> TYPE: DNA
<213> ORGANISM: Unknown
<220> FEATURE:
<223> OTHER INFORMATION: Description of Unknown:
DP25 16S rRNA microbial sequence

<400> SEQUENCE: 25

```
tacggagagt ttgatcctgg ctcaggatga acgctggcgg cgtgcttaac acatgcaagt     60

cgaacggtga agccaagctt gcttggtgga tcagtggcga acgggtgagt aacacgtgag    120

caacctgccc tggactctgg gataagcgct ggaaacggcg tctaatactg gatatgagct    180

ccttccgcat ggtgggggtt ggaaagattt ttcggtctgg gatgggctcg cggcctatca    240

gcttgttggt gaggtaatgg ctcaccaagg cgtcgacggg tagccggcct gagagggtga    300

ccggccacac tgggactgag acacggccca gactcctacg ggaggcagca gtggggaata    360

ttgcacaatg ggcggaagcc tgatgcagca acgccgcgtg agggatgacg gccttcgggt    420

tgtaaacctc ttttagcagg gaagaagcga aagtgacggt acctgcagaa aaagcgccgg    480

ctaactacgt gccagcagcc gcggtaatac gtagggcgca agcgttatcc ggaattattg    540

ggcgtaaaga gctcgtaggc ggtttgtcgc gtctgctgtg aaatcccgag gctcaacctc    600

gggcctgcag tgggtacggg cagactagag tgcggtaggg gagattggaa ttcctggtgt    660

agcggtggaa tgcgcagata tcaggaggaa caccgatggc gaaggcagat ctctgggccg    720

taactgacgc tgaggagcga aagggtgggg agcaaacagg cttagatacc ctggtagtcc    780

accccgtaaa cgttgggaac tagttgtggg gaccattcca cggtttccgt gacgcagcta    840

acgcattaag ttccccgcct ggggagtacg gccgcaaggc taaaactcaa aggaattgac    900

ggggacccgc acaagcggcg gagcatgcgg attaattcga tgcaacgcga agaaccttac    960

caaggcttga catatacgag aacgggccag aaatggtcaa ctctttggac actcgtaaac   1020

aggtggtgca tggttgtcgt cagctcgtgt cgtgagatgt tgggttaagt cccgcaacga   1080

gcgcaaccct cgttctatgt tgccagcacg taatggtggg aactcatggg atactgccgg   1140

ggtcaactcg gaggaaggtg gggatgacgt caaatcatca tgccccttat gtcttgggct   1200

tcacgcatgc tacaatggcc ggtacaaagg gctgcaatac cgtaaggtgg agcgaatccc   1260

aaaaagccgg tcccagttcg gattgaggtc tgcaactcga cctcatgaag tcggagtcgc   1320

tagtaatcgc agatcagcaa cgctgcggtg aatacgttcc cgggtcttgt acacaccgcc   1380

cgtcaagtca tgaaagtcgg taacacctga agccggtggc ccaacccttg tggagggagc   1440

cgtcgaaggt gggatcggta attaggacta agtcgtaaca aggtagccgt accggaaggt   1500

gcggctggat cacctccttt                                                1520
```

```
<210> SEQ ID NO 26
<211> LENGTH: 1482
<212> TYPE: DNA
<213> ORGANISM: Unknown
<220> FEATURE:
<223> OTHER INFORMATION: Description of Unknown:
      DP26 16S rRNA microbial sequence

<400> SEQUENCE: 26
```

```
cttgagagtt tgatcctggc tcagagcgaa cgctggcggc aggcttaaca catgcaagtc     60

gagcgggcat cttcggatgt cagcggcaga cgggtgagta acacgtggga acgtaccctt    120

cggttcggaa taacgctggg aaactagcgc taataccgga tacgcccttt tggggaaagg    180

tttactgccg aaggatcggc ccgcgtctga ttagctagtt ggtggggtaa cggcctacca    240

aggcgacgat cagtagctgg tctgagagga tgatcagcca cactgggact gagacacggc    300

ccagactcct acgggaggca gcagtgggga atattggaca atgggcgcaa gcctgatcca    360

gccatgccgc gtgagtgatg aaggccttag ggttgtaaag ctcttttgtc cgggacgata    420

atgacggtac cggaagaata agccccggct aacttcgtgc cagcagccgc ggtaatacga    480
```

-continued

```
agggggctag cgttgctcgg aatcactggg cgtaaagggc gcgtaggcgg ccattcaagt    540

cgggggtgaa agcctgtggc tcaaccacag aattgccttc gatactgttt ggcttgagta    600

tggtagaggt tggtggaact gcgagtgtag aggtgaaatt cgtagatatt cgcaagaaca    660

ccggtggcga aggcggccaa ctggaccatt actgacgctg aggcgcgaaa gcgtggggag    720

caaacaggat tagataccct ggtagtccac gccgtaaacg atgaatgcca gctgttgggg    780

tgcttgcacc tcagtagcgc agctaacgct ttaagcattc cgcctgggga gtacggtcgc    840

aagattaaaa ctcaaaggaa ttgacggggg cccgcacaag cggtggagca tgtggtttaa    900

ttcgaagcaa cgcgcagaac cttaccatcc cttgacatgg catgttaccc ggagagattc    960

ggggtccact tcggtggcgt gcacacaggt gctgcatggc tgtcgtcagc tcgtgtcgtg   1020

agatgttggg ttaagtcccg caacgagcgc aacccacgtc cttagttgcc atcattcagt   1080

tgggcactct agggagactg ccggtgataa gccgcgagga aggtgtggat gacgtcaagt   1140

cctcatggcc cttacgggat gggctacaca cgtgctacaa tggcggtgac agtgggacgc   1200

gaaggagcga tctggagcaa atccccaaaa accgtctcag ttcagattgc actctgcaac   1260

tcgagtgcat gaaggcggaa tcgctagtaa tcgtggatca gcatgccacg gtgaatacgt   1320

tcccgggcct tgtacacacc gcccgtcaca ccatgggagt tggtcttacc cgacggcgct   1380

gcgccaaccg caaggaggca ggcgaccacg gtagggtcag cgactggggt gaagtcgtaa   1440

caaggtagcc gtaggggaac ctgcggctgg atcacctcct tt                      1482
```

<210> SEQ ID NO 27
<211> LENGTH: 935
<212> TYPE: DNA
<213> ORGANISM: Unknown
<220> FEATURE:
<223> OTHER INFORMATION: Description of Unknown:
      DP27 16S rRNA microbial sequence

<400> SEQUENCE: 27

```
cttgagagtt tgatcctggc tcagaacgaa cgctggcggc atgcctaaca catgcaagtc     60

gaacgatgct ttcgggcata gtggcgcacg ggtgcgtaac gcgtgggaat ctgccctcag    120

gttcggaata acagctggaa acggctgcta ataccggatg atatcgcaag atcaaagatt    180

tatcgcctga ggatgagccc gcgttggatt aggtagttgg tggggtaaag gcctaccaag    240

ccgacgatcc atagctggtc tgagaggatg atcagccaca ctgggactga gacacggccc    300

agactcctac gggaggcagc agtggggaat attggacaat gggcgcaagc ctgatccagc    360

aatgccgcgt gagtgatgaa ggccctaggg ttgtaaagct cttttacccg ggaagataat    420

gactgtaccg ggagaataag ccccggctaa ctccgtgcca gcagccgcgg taatacggag    480

ggggctagcg ttgttcggaa ttactgggcg taaagcgcac gtaggcggct ttgtaagtca    540

gaggtgaaag cctggagctc aactccagaa ctgcctttga gactgcatcg cttgaatcca    600

ggagaggtca gtggaattcc gagtgtagag gtgaaattcg tagatattcg gaagaacacc    660

agtggcgaag gcggctgact ggactggtat tgacgctgag gtgcgaaagc gtggggagca    720

aacaggatta gataccctgg tagtccacgc cgtaaacgat gataactagc tgtccgggca    780

cttggtgctt gggtggcgca gctaacgcat taagttatcc gcctggggag tacggccgca    840

aggttaaaac tcaaaggaat tgacgggggc ctgcacaagc ggtggagcat gtggtttaat    900

tcgaagcaac gcgcagaacc ttaccagcgt ttgac                               935
```

<210> SEQ ID NO 28
<211> LENGTH: 931
<212> TYPE: DNA
<213> ORGANISM: Unknown
<220> FEATURE:
<223> OTHER INFORMATION: Description of Unknown:
DP28 16S rRNA microbial sequence

<400> SEQUENCE: 28
atagtcgggg gcatcagtat tcaattgtca gaggtgaaat tcttggattt attgaagact 60
aactactgcg aaagcatttg ccaaggatgt tttcattaat cagtgaacga aagttagggg 120
atcgaagacg atcagatacc gtcgtagtct taaccataaa ctatgccgac tagggatcgg 180
gcgatgttat cattttgact cgctcggcac cttacgagaa atcaaagtct ttgggttctg 240
gggggagtat ggtcgcaagg ctgaaactta aagaaattga cggaagggca ccaccaggcg 300
tggagcctgc ggcttaattt gactcaacac ggggaaactc accaggtcca gacacaataa 360
ggattgacag attgagagct ctttcttgat tttgtgggtg gtggtgcatg gccgttctta 420
gttggtggag tgatttgtct gcttaattgc gataacgaac gagaccttaa cctgctaaat 480
agcccggccc gctttggcgg gtcgccggct tcttagaggg actatcggct caagccgatg 540
gaagtttgag gcaataacag gtctgtgatg cccttagatg ttctgggccg cacgcgcgct 600
acactgacag agccaacgag ttcatttcct tgcccggaag ggttgggtaa tcttgttaaa 660
ctctgtcgtg ctggggatag agcattgcaa ttattgctct tcaacgagga atgcctagta 720
agcgtacgtc atcagcgtgc gttgattacg tccctgccct ttgtacacac cgcccgtcgc 780
tactaccgat tgaatggctg agtgaggcct tcggactggc ccagggaggt cggcaacgac 840
cacccagggc cggaaagttg gtcaaactcc gtcatttaga ggaagtaaaa gtcgtaacaa 900
ggtttccgta ggtgaacctg cggaaggatc a 931

<210> SEQ ID NO 29
<211> LENGTH: 1002
<212> TYPE: DNA
<213> ORGANISM: Unknown
<220> FEATURE:
<223> OTHER INFORMATION: Description of Unknown:
DP29 16S rRNA microbial sequence

<400> SEQUENCE: 29
tacggagagt ttgatcctgg ctcaggacga acgctggcgg cgtgcttaac acatgcaagt 60
cgaacgatga agcccagctt gctgggttga ttagtggcga acgggtgagt aacacgtgag 120
caacgtgccc ataactctgg gataacctcc ggaaacggtg gctaatactg gatatctaac 180
acgatcgcat ggtctgtgtt tggaaagatt ttttggttat ggatcggctc acggcctatc 240
agcttgttgg tgaggtaatg gctcaccaag gcgacgacgg gtagccggcc tgagagggtg 300
accggccaca ctgggactga gacacggccc agactcctac gggaggcagc agtggggaat 360
attgcacaat gggcgaaagc ctgatgcagc aacgccgcgt gagggatgac ggcattcggg 420
ttgtaaacct cttttagtag ggaagaagcg aaagtgacgg tacctgcaga aaaagcaccg 480
gctaactacg tgccagcagc cgctgtaata cgtagggtgc aagcgttgtc cggaattatt 540
gggcgtaaag agctcgtagg cggtttgtcg cgtctgctgt gaaatcccga ggctcaacct 600
cgggtctgca gtgggtacgg gcagactaga gtgtggtagg ggagattgga attcctggtg 660
tagcggtgga atgcgcagat atcaggagga acaccgatgg cgaaggcaga tctctgggcc 720
attactgacg ctgaggagcg aaagcatggg gagcgaacag gattagatac cctggtagtc 780
catgccgtaa acgttgggcg ctagatgtgg ggaccattcc acggtttccg tgtcgtagct 840
aacgcattaa gcgccccgcc tggggagtac ggccgcaagg ctaaaactca aaggaattga 900
cgggggcccg cacaagcggc ggagcatgcg gattaattcg atgcaacgcg aagaacctta 960
ccaaggcttg acatataccg gaaacgttca gaaatgttcg cc 1002

<210> SEQ ID NO 30
<211> LENGTH: 1520
<212> TYPE: DNA
<213> ORGANISM: Unknown
<220> FEATURE:
<223> OTHER INFORMATION: Description of Unknown:
DP30 16S rRNA microbial sequence

<400> SEQUENCE: 30
tacggagagt ttgatcctgg ctcaggatga acgctggcgg cgtgcttaac acatgcaagt 60
cgaacggtga agccaagctt gcttggtgga tcagtggcga acgggtgagt aacacgtgag 120
caacctgccc tggactctgg gataagcgct ggaaacggcg tctaatactg gatatgagac 180
gtgatcgcat ggtcgtgttt ggaaagattt ttcggtctgg gatgggctcg cggcctatca 240
gcttgttggt gaggtaatgg ctcaccaagg cgtcgacggg tagccggcct gagagggtga 300
ccggccacac tgggactgag acacggccca gactcctacg ggaggcagca gtggggaata 360
ttgcacaatg ggcgaaagcc tgatgcagca acgccgcgtg agggatgacg gccttcgggt 420
tgtaaacctc ttttagcagg gaagaagcga aagtgacggt acctgcagaa aaagcgccgg 480
ctaactacgt gccagcagcc gcggtaatac gtagggcgca agcgttatcc ggaattattg 540
ggcgtaaaga gctcgtaggc ggtttgtcgc gtctgctgtg aaatcccgag gctcaacctc 600
gggcctgcag tgggtacggg cagactagag tgcggtaggg gagattggaa ttcctggtgt 660
agcggtggaa tgcgcagata tcaggaggaa caccgatggc gaaggcagat ctctgggccg 720
taactgacgc tgaggagcga aagggtgggg agcaaacagg cttagatacc ctggtagtcc 780
accccgtaaa cgttgggaac tagttgtggg gaccattcca cggtttccgt gacgcagcta 840
acgcattaag ttccccgcct ggggagtacg gccgcaaggc taaaactcaa aggaattgac 900
ggggacccgc acaagcggcg gagcatgcgg attaattcga tgcaacgcga agaaccttac 960
caaggcttga catatacgag aacgggccag aaatggtcaa ctctttggac actcgtaaac 1020
aggtggtgca tggttgtcgt cagctcgtgt cgtgagatgt tgggttaagt cccgcaacga 1080
gcgcaaccct cgttctatgt tgccagcacg taatggtggg aactcatggg atactgccgg 1140
ggtcaactcg gaggaaggtg gggatgacgt caaatcatca tgccccttat gtcttgggct 1200
tcacgcatgc tacaatggcc ggtacaaagg gctgcaatac cgtgaggtgg agcgaatccc 1260
aaaaagccgg tcccagttcg gattgaggtc tgcaactcga cctcatgaag tcggagtcgc 1320
tagtaatcgc agatcagcaa cgctgcggtg aatacgttcc cgggtcttgt acacaccgcc 1380
cgtcaagtca tgaaagtcgg taacacctga agccggtggc ccaacccttg tggagggagc 1440
cgtcgaaggt gggatcggta attaggacta agtcgtaaca aggtagccgt accggaaggt 1500
gcggctggat cacctccttt 1520

<210> SEQ ID NO 31
<211> LENGTH: 941
<212> TYPE: DNA
<213> ORGANISM: Unknown
<220> FEATURE:
<223> OTHER INFORMATION: Description of Unknown:
DP31 16S rRNA microbial sequence

<400> SEQUENCE: 31
cagccggggg cattagtatt tgcacgctag aggtgaaatt cttggattgt gcaaagactt 60
cctactgcga aagcatttgc caagaatgtt ttcattaatc aagaacgaag gttagggtat 120
cgaaaacgat tagataccgt tgtagtctta acagtaaact atgccgactc cgaatcggtc 180
gatgctcatt tcactggctc gatcggcgcg gtacgagaaa tcaaagtttt tgggttctgg 240
ggggagtatg gtcgcaaggc tgaaacttaa agaaattgac ggaagggcac caccaggagt 300
ggagcctgcg gcttaatttg actcaacacg ggaaaactca ccgggtccgg acatagtaag 360
gattgacaga ttgatggcgc tttcatgatt ctatgggtgg tggtgcatgg ccgttcttag 420
ttggtggagt gatttgtctg gttaattccg ataacgaacg agaccttgac ctgctaaata 480
gacgggttga cattttgttg gcccttatg tcttcttaga gggacaatcg accgtctagg 540
tgatggaggc aaaaggcaat aacaggtctg tgatgccctt agatgttccg ggctgcacgc 600
gcgctacact gacagagaca acgagtgggg ccccttgtcc gaaatgactg ggtaaacttg 660
tgaaactttg tcgtgctggg gatggagctt tgtaattttt gctcttcaac gaggaattcc 720
tagtaagcgc aagtcatcag cttgcgttga ctacgtccct gccctttgta cacaccgccc 780
gtcgctacta ccgattgaat ggcttagtga ggacttggga gagtacatcg gggagccagc 840
aatggcaccc tgacggctca aactcttaca aacttggtca tttagaggaa gtaaaagtcg 900
taacaaggta tctgtaggtg aacctgcaga tggatcattt c 941

<210> SEQ ID NO 32
<211> LENGTH: 1072
<212> TYPE: DNA
<213> ORGANISM: Unknown
<220> FEATURE:
<223> OTHER INFORMATION: Description of Unknown:
DP32 16S rRNA microbial sequence

<400> SEQUENCE: 32
actgagcatt gacgttactc gcagaagaag caccggctaa ctccgtgcca gcagccgcgg 60
taatacggag ggtgcaagcg ttaatcggaa ttactgggcg taaagcgcac gcaggcggtt 120
tgttaagtca gatgtgaaat ccccgagctt aacttgggaa ctgcatttga aactggcaag 180
ctagagtctt gtagaggggg gtagaattcc aggtgtagcg gtgaaatgcg tagagatctg 240
gaggaatacc ggtggcgaag gcggcccct ggacaaagac tgacgctcag gtgcgaaagc 300
gtggggagca aacaggatta gataccctgg tagtccacgc tgtaaacgat gtcgacttgg 360
aggttgtgcc cttgaggcgt ggcttccgga gctaacgcgt taagtcgacc gcctggggag 420
tacggccgca aggttaaaac tcaaatgaat tgacgggggc ccgcacaagc ggtggagcat 480
gtggtttaat tcgatgcaac gcgaagaacc ttacctactc ttgacatcca gagaattcgc 540
tagagatagc ttagtgcctt cgggaactct gagacaggtg ctgcatggct gtcgtcagct 600
cgtgttgtga aatgttgggt taagtcccgc aacgagcgca acccttatcc tttgttgcca 660
gcgagtaatg tcgggaactc aaaggagact gccggtgata aaccggagga aggtggggat 720
gacgtcaagt catcatggcc cttacgagta gggctacaca cgtgctacaa tggcatatac 780
aaagagaagc gaactcgcga gagcaagcgg acctcataaa gtatgtcgta gtccggattg 840
gagtctgcaa ctcgactcca tgaagtcgga atcgctagta atcgtagatc agaatgctac 900
ggtgaatacg ttcccgggcc ttgtacacac cgcccgtcac accatgggag tgggttgcaa 960
aagaagtagg tagcttaacc ttcgggaggg cgcttaccac tttgtgattc atgactgggg 1020
tgaagtcgta acaaggtaac cgtaggggaa cctgcggttg gatcacctcc tt 1072

<210> SEQ ID NO 33
<211> LENGTH: 853
<212> TYPE: DNA
<213> ORGANISM: Unknown
<220> FEATURE:
<223> OTHER INFORMATION: Description of Unknown:
DP33 16S rRNA microbial sequence

<400> SEQUENCE: 33
ggaggaaggc gtagagatct ggaggaatac cggtggcgaa ggcggccccc tggacaaaga 60
ctgacgctca ggtgcgaaag cgtggggagc aaacaggatt agataccctg gtagtccacg 120
ccgtaaacga tgtcgacttg gaggttgtgc ccttgaggcg tggcttccgg agctaacgcg 180
ttaagtcgac cgcctgggga gtacggccgc aaggttaaaa ctcaaatgaa ttgacggggg 240
cccgcacaag cggtggagca tgtggtttaa ttcgatgcaa cgcgaagaac cttacctggc 300
cttgacatcc acggaattcg gcagagatgc cttagtgcct tcgggaaccg tgagacaggt 360
gctgcatggc tgtcgtcagc tcgtgttgtg aaatgttggg ttaagtcccg caacgagcgc 420
aacccttatc ctttgttgcc agcacgtaat ggtgggaact caaaggagac tgccggtgat 480
aaaccggagg aaggtgggga tgacgtcaag tcatcatggc ccttacggcc agggctacac 540
acgtgctaca atggcgcata caaagagaag cgacctcgcg agagcaagcg gacctcataa 600
agtgcgtcgt agtccggatc ggagtctgca actcgactcc gtgaagtcgg aatcgctagt 660
aatcgtagat cagaatgcta cggtgaatac gttcccgggc cttgtacaca ccgcccgtca 720
caccatggga gtgggttgca aaagaagtag gtagcttaac cttcgggagg gcgcttacca 780
ctttgtgatt catgactggg gtgaagtcgt aacaaggtaa ccgtagggga acctgcggtt 840
ggatcacctc ctt 853

<210> SEQ ID NO 34
<211> LENGTH: 1519
<212> TYPE: DNA
<213> ORGANISM: Unknown
<220> FEATURE:
<223> OTHER INFORMATION: Description of Unknown:
DP34 16S rRNA microbial sequence

<400> SEQUENCE: 34
tacggagagt ttgatcctgg ctcaggacga acgctggcgg cgtgcttaac acatgcaagt 60
cgaacgatga agcccagctt gctgggtgga ttagtggcga acgggtgagt aacacgtgag 120
taacctgccc ttgactctgg gataagcgtt ggaaacgacg tctaataccg gatacgagct 180
tccaccgcat ggtgagttgc tggaaagaat tttggtcaag gatggactcg cggcctatca 240
gcttgttggt gaggtaatgg ctcaccaagg cgacgacggg tagccggcct gagagggtga 300
ccggccacac tgggactgag acacggccca gactcctacg ggaggcagca gtggggaata 360
ttgcacaatg ggcgaaagcc tgatgcagca acgccgcgtg agggacgacg gccttcgggt 420
tgtaaacctc ttttagcagg gaagaagcga aagtgacggt acctgcagaa aaagcaccgg 480
ctaactacgt gccagcagcc gcggtaatac gtagggtgca agcgttgtcc ggaattattg 540
ggcgtaaaga gctcgtaggc ggtttgtcgc gtctgctgtg aaatcccgag gctcaacctc 600
gggtctgcag tgggtacggg cagactagag tgcggtaggg gagattggaa ttcctggtgt 660
agcggtggaa tgcgcagata tcaggaggaa caccgatggc gaaggcagat ctctgggccg 720
ctactgacgc tgaggagcga aagggtgggg agcaaacagg cttagatacc ctggtagtcc 780
accccgtaaa cgttgggcgc tagatgtggg gaccattcca cggtttccgt gtcgtagcta 840
acgcattaag cgccccgcct ggggagtacg gccgcaaggc taaaactcaa aggaattgac 900
gggggcccgc acaagcggcg gagcatgcgg attaattcga tgcaacgcga agaaccttac 960
caaggcttga catatacgag aacgggccag aaatggtcaa ctctttggac actcgtaaac 1020
aggtggtgca tggttgtcgt cagctcgtgt cgtgagatgt tgggttaagt cccgcaacga 1080
gcgcaaccct cgttctatgt tgccagcacg taatggtggg aactcatggg atactgccgg 1140
ggtcaactcg gaggaaggtg gggacgacgt caaatcatca tgccccttat gtcttgggct 1200
tcacgcatgc tacaatggcc agtacaaagg gctgcaatac cgtaaggtgg agcgaatccc 1260
aaaaagctgg tcccagttcg gattgaggtc tgcaactcga cctcatgaag tcggagtcgc 1320
tagtaatcgc agatcagcaa cgctgcggtg aatacgttcc cgggccttgt acacaccgcc 1380
cgtcaagtca tgaaagtcgg taacacccga agccagtggc ctaaccgcaa ggatggagct 1440
gtctaaggtg ggatcggtaa ttaggactaa gtcgtaacaa ggtagccgta ccggaaggtg 1500
cggctggatc acctccttt 1519

<210> SEQ ID NO 35
<211> LENGTH: 1536
<212> TYPE: DNA
<213> ORGANISM: Unknown
<220> FEATURE:
<223> OTHER INFORMATION: Description of Unknown:
DP35 16S rRNA microbial sequence

<400> SEQUENCE: 35
ttgaagagtt tgatcatggc tcagattgaa cgctggcggc aggcctaaca catgcaagtc 60
ggacggtagc acagagagct tgctcttggg tgacgagtgg cggacgggtg agtaatgtct 120
ggggatctgc ccgatagagg gggataacca ctggaaacgg tggctaatac cgcataacgt 180
cgcaagacca aagaggggga ccttcgggcc tctcactatc ggatgaaccc agatgggatt 240
agctagtagg cggggtaatg gcccacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcgg ggaggaaggc gatgaggtta ataaccgcgt cgattgacgt 480
tacccgcaga agaagcaccg gctaactccg tgccagcagc cgcggtaata cggagggtgc 540
aagcgttaat cggaattact gggcgtaaag cgcacgcagg cggtctgtta agtcagatgt 600
gaaatccccg ggcttaacct gggaactgca tttgaaactg gcaggcttga gtcttgtaga 660
ggggggtaga attccaggtg tagcggtgaa atgcgtagag atctggagga ataccggtgg 720
cgaaggcggc cccctggaca aagactgacg ctcaggtgcg aaagcgtggg gagcaaacag 780
gattagatac cctggtagtc cacgccgtaa acgatgtcga cttggaggtt gttcccttga 840
ggagtggctt ccggagctaa cgcgttaagt cgaccgcctg gggagtacgg ccgcaaggtt 900
aaaactcaaa tgaattgacg ggggcccgca caagcggtgg agcatgtggt ttaattcgat 960
gcaacgcgaa gaaccttacc tactcttgac atccagcgaa cttagcagag atgctttggt 1020
gccttcggga acgctgagac aggtgctgca tggctgtcgt cagctcgtgt tgtgaaatgt 1080
tgggttaagt cccgcaacga gcgcaaccct tatcctttgt tgccagcgat tcggtcggga 1140
actcaaagga gactgccggt gataaaccgg aggaaggtgg ggatgacgtc aagtcatcat 1200 ggccccttacg agtagggcta cacacgtgct acaatggcgc atacaaagag aagcgacctc 1260
gcgagagcaa gcggacctca caaagtgcgt cgtagtccgg atcggagtct gcaactcgac 1320
tccgtgaagt cggaatcgct agtaatcgtg gatcagaatg ccacggtgaa tacgttcccg 1380
ggccttgtac acaccgcccg tcacaccatg ggagtgggtt gcaaaagaag taggtagctt 1440
aaccttcggg agggcgctta ccactttgtg attcattact ggggtgaagt cgtaacaagg 1500
taaccgtagg ggaacctgcg gttggatcac ctcctt 1536

<210> SEQ ID NO 36
<211> LENGTH: 993
<212> TYPE: DNA
<213> ORGANISM: Unknown
<220> FEATURE:
<223> OTHER INFORMATION: Description of Unknown:
DP36 16S rRNA microbial sequence

<400> SEQUENCE: 36
ttgaagagtt tgatcatggc tcagattgaa cgctggcggc aggcctaaca catgcaagtc 60
ggacggtagc acagagagct tgctcttggg tgacgagtgg cggacgggtg agtaatgtct 120
ggggatctgc ccgatagagg gggataacca ctggaaacgg tggctaatac cgcataacgt 180
cgcaagacca aagaggggga ccttcgggcc tctcactatc ggatgaaccc agatgggatt 240
agctagtagg cggggtaatg gcccacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcgg ggaggaaggc gatgcggtta ataaccgcgt cgattgacgt 480
tacccgcaga agaagcaccg gctaactccg tgccagcagc cgcggtaata cggagggtgc 540
aagcgttaat cggaattact gggcgtaaag cgcacgcagg cggtctgtta agtcagatgt 600
gaaatccccg ggcttaacct gggaactgca tttgaaactg gcaggcttga gtcttgtaga 660
ggggggtaga attccaggtg tagcggtgaa atgcgtagag atctggagga ataccggtgg 720
cgaaggcggc cccctggaca aagactgacg ctcaggtgcg aaagcgtggg gagcaaacag 780
gattagatac cctggtagtc cacgccgtaa acgatgtcga cttggaggtt gttcccttga 840
ggagtggctt ccggagctaa cgcgttaagt cgaccgcctg gggagtacgg ccgcaaggtt 900
aaaactcaaa tgaattgacg gggcccgca caagcggtgg agcatgtggt ttaattcgat 960
gcaacgcgaa gaaccttacc tactcttgac atc 993

<210> SEQ ID NO 37
<211> LENGTH: 1531
<212> TYPE: DNA
<213> ORGANISM: Unknown
<220> FEATURE:
<223> OTHER INFORMATION: Description of Unknown:
DP37 16S rRNA microbial sequence

<400> SEQUENCE: 37
tgaagagttt gatcatggct cagattgaac gctggcggca ggcctaacac atgcaagtcg 60
agcggtagag agaagcttgc ttctcttgag agcggcggac gggtgagtaa tgcctaggaa 120
tctgcctggt agtgggggat aacgttcgga aacgaacgct aataccgcat acgtcctacg 180
ggagaaagca ggggaccttc gggccttgcg ctatcagatg agcctaggtc ggattagcta 240
gttggtgggg taatggctca ccaaggcgac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggccatt acctaatacg tgatggtttt gacgttaccg 480
acagaataag caccggctaa ctctgtgcca gcagccgcgg taatacagag ggtgcaagcg 540
ttaatggaat tactgggcgt aaagcgcgcg taggtggttt gttaagttgg atgtgaaatc 600
cccgggctca acctgggaac tgcattcaaa actgactgac tagagtatgg tagagggtgg 660
tggaatttcc tgtgtagcgg tgaaatgcgt agatatagga aggaacacca gtggcgaagg 720
cgaccacctg gactgatact gacactgagg tgcgaaagcg tggggagcaa acaggattag 780
ataccctggt agtccacgcc gtaaacgatg tcaactagcc gttgggagcc ttgagctctt 840
agtggcgcag ctaacgcatt aagttgaccg cctggggagt acggccgcaa ggttaaaact 900
caaatgaatt gacgggggcc cgcacaagcg gtggagcatg tggtttaatt cgaagcaacg 960
cgaagaacct taccaggcct tgacatccaa tgaactttct agagatagat tggtgccttc 1020
gggaacattg agacaggtgc tgcatggctg tcgtcagctc gtgtcgtgag atgttgggtt 1080
aagtcccgta acgagcgcaa cccttgtcct tagttaccag cacgtaatgg tgggcactct 1140
aaggagactg ccggtgacaa accggaggaa ggtggggatg acgtcaagtc atcatggccc 1200
ttacggcctg ggctacacac gtgctacaat ggtcggtaca gagggttgcc aagccgcgag 1260
gtggagctaa tcccataaaa ccgatcgtag tccggatcgc agtctgcaac tcgactgcgt 1320
gaagtcggaa tcgctagtaa tcgcgaatca gaatgtcgcg gtgaatacgt tcccgggcct 1380
tgtacacacc gcccgtcaca ccatgggagt gggttgcacc agaagtagct agtctaacct 1440
tcggggggac ggttaccacg gtgtgattca tgactggggt gaagtcgtaa caaggtagcc 1500
gtaggggaac ctgcggctgg atcacctcct t 1531

<210> SEQ ID NO 38
<211> LENGTH: 1517
<212> TYPE: DNA
<213> ORGANISM: Unknown
<220> FEATURE:
<223> OTHER INFORMATION: Description of Unknown:
DP38 16S rRNA microbial sequence

<400> SEQUENCE: 38
tacggagagt ttgatcctgg ctcaggacga acgctggcgg cgtgcttaac acatgcaagt 60
cgagcggtaa ggcctttcgg ggtacacgag cggcgaacgg gtgagtaaca cgtgggtgat 120
ctgccctgca ctctgggata agcttgggaa actgggtcta ataccggata tgaccacagc 180
atgcatgtgt tgtggtggaa agatttatcg gtgcaggatg ggcccgcggc ctatcagctt 240
gttggtgggg taatggccta ccaaggcgac gacgggtagc cgacctgaga gggtgaccgg 300
ccacactggg actgagacac ggcccagact cctacgggag gcagcagtgg ggaatattgc 360
acaatgggcg gaagcctgat gcagcgacgc cgcgtgaggg atgaaggcct tcgggttgta 420
aacctctttc agcagggacg aagcgtgagt gacggtacct gcagaagaag caccggctaa 480
ctacgtgcca gcagccgcgg taatacgtag ggtgcgagcg ttgtccggaa ttactgggcg 540
taaagagttc gtaggcggtt tgtcgcgtcg tttgtgaaaa cccggggctc aacttcgggc 600
ttgcaggcga tacgggcaga cttgagtgtt tcaggggaga ctggaattcc tggtgtagcg 660
gtgaaatgcg cagatatcag gaggaacacc ggtggcgaag gcgggtctct gggaaacaac 720
tgacgctgag gaacgaaagc gtgggtagca aacaggatta gataccctgg tagtccacgc 780
cgtaaacggt gggcgctagg tgtgggttcc ttccacggga tctgtgccgt agctaacgca 840
ttaagcgccc cgcctgggga gtacggccgc aaggctaaaa ctcaaaggaa ttgacggggg 900
cccgcacaag cggcggagca tgtggattaa ttcgatgcaa cgcgaagaac cttacctggg 960
tttgacatac accggaaaac cgtagagata cggtccccct tgtggtcggt gtacaggtgg 1020
tgcatggctg tcgtcagctc gtgtcgtgag atgttgggtt aagtcccgca acgagcgcaa 1080
cccttgtctt atgttgccag cacgtaatgg tggggactcg taagagactg ccggggtcaa 1140
ctcggaggaa ggtggggacg acgtcaagtc atcatgcccc ttatgtccag ggcttcacac 1200
atgctacaat ggccagtaca gagggctgcg agaccgtgag gtggagcgaa tcccttaaag 1260
ctggtctcag ttcggatcgg ggtctgcaac tcgaccccgt gaagtcggag tcgctagtaa 1320
tcgcagatca gcaacgctgc ggtgaatacg ttcccgggcc ttgtacacac cgcccgtcac 1380
gtcatgaaag tcggtaacac ccgaagccgg tggcctaacc ccttacgggg agggagccgt 1440
cgaaggtggg atcggcgatt gggacgaagt cgtaacaagg tagccgtacc ggaaggtgcg 1500
gctggatcac ctccttt 1517

<210> SEQ ID NO 39
<211> LENGTH: 1482
<212> TYPE: DNA
<213> ORGANISM: Unknown
<220> FEATURE:
<223> OTHER INFORMATION: Description of Unknown:
DP39 16S rRNA microbial sequence

<400> SEQUENCE: 39
cttgagagtt tgatcctggc tcagaacgaa cgctggcggc aggcttaaca catgcaagtc 60
gaacgccccg caaggggagt ggcagacggg tgagtaacgc gtgggaatct accgtgccct 120
gcggaatagc tccgggaaac tggaattaat accgcatacg ccctacgggg gaaagattta 180
tcggggtatg atgagcccgc gttggattag ctagttggtg gggtaaaggc ctaccaaggc 240
gacgatccat agctggtctg agaggatgat cagccacatt gggactgaga cacggcccaa 300
actcctacgg gaggcagcag tggggaatat tggacaatgg gcgcaagcct gatccagcca 360
tgccgcgtga gtgatgaagg ccttagggtt gtaaagctct ttcaccggag aagataatga 420
cggtatccgg agaagaagcc ccggctaact tcgtgccagc agccgcggta atacgaaggg 480
ggctagcgtt gttcggaatt actgggcgta aagcgcacgt aggcggatat ttaagtcagg 540
ggtgaaatcc cagagctcaa ctctggaact gcctttgata ctgggtatct tgagtatgga 600
agaggtaagt ggaattccga gtgtagaggt gaaattcgta gatattcgga ggaacaccag 660
tggcgaaggc ggcttactgg tccattactg acgctgaggt gcgaaagcgt ggggagcaaa 720
caggattaga taccctggta gtccacgccg taaacgatga atgttagccg tcgggcagta 780
tactgttcgg tggcgcagct aacgcattaa acattccgcc tggggagtac ggtcgcaaga 840
ttaaaactca aaggaattga cgggggcccg cacaagcggt ggagcatgtg gtttaattcg 900
aagcaacgcg cagaacctta ccagctcttg acattcgggg tttgggcagt ggagacattg 960
tccttcagtt aggctggccc cagaacaggt gctgcatggc tgtcgtcagc tcgtgtcgtg 1020
agatgttggg ttaagtcccg caacgagcgc aaccctcgcc cttagttgcc agcatttagt 1080
tgggcactct aaggggactg ccggtgataa gccgagagga aggtggggat gacgtcaagt 1140
cctcatggcc cttacgggct gggctacaca cgtgctacaa tggtggtgac agtgggcagc 1200
gagacagcga tgtcgagcta atctccaaaa gccatctcag ttcggattgc actctgcaac 1260
tcgagtgcat gaagttggaa tcgctagtaa tcgcagatca gcatgctgcg gtgaatacgt 1320
tcccgggcct tgtacacacc gcccgtcaca ccatgggagt tggttttacc cgaaggtagt 1380
gcgctaaccg caaggaggca gctaaccacg gtagggtcag cgactggggt gaagtcgtaa 1440
caaggtagcc gtaggggaac ctgcggctgg atcacctcct tt 1482

<210> SEQ ID NO 40
<211> LENGTH: 903
<212> TYPE: DNA
<213> ORGANISM: Unknown
<220> FEATURE:
<223> OTHER INFORMATION: Description of Unknown:
DP40 16S rRNA microbial sequence

<400> SEQUENCE: 40
ttgacgttac ccgcagaaga agcaccggct aactccgtgc cagcagccgc ggtaatacgg 60
agggtgcaag cgttaatcgg aattactggg cgtaaagcgc acgcaggcgg tctgttaagt 120
cagatgtgaa atccccgggc ttaacctggg aactgcattt gaaactggca ggcttgagtc 180
ttgtagaggg gggtagaatt ccaggtgtag cggtgaaatg cgtagagatc tggaggaata 240
ccggtggcga aggcggcccc ctggacaaag actgacgctc aggtgcgaaa gcgtggggag 300
caaacaggat tagataccct ggtagtccac gccgtaaacg atgtcgactt ggaggttgtt 360
cccttgagga gtggcttccg gagctaacgc gttaagtcga ccgcctgggg agtacggccg 420
caaggttaaa actcaaatga attgacgggg gcccgcacaa gcggtggagc atgtggttta 480
attcgatgca acgcgaagaa ccttacctac tcttgacatc cagagaactt tccagagatg 540
gattggtgcc ttcgggaact ctgagacagg tgctgcatgg ctgtcgtcag ctcgtgttgt 600
gaaatgttgg gttaagtccc gcaacgagcg caacccttat cctttgttgc cagcgcgtga 660
tggcgggaac tcaaaggaga ctgccggtga taaaccggag gaaggtgggg atgacgtcaa 720
gtcatcatgg cccttacgag tagggctaca cacgtgctac aatggcgcat acaaagagaa 780
gcgacctcgc gagagcaagc ggacctcaca aagtgcgtcg tagtccggat cggagtctgc 840
aactcgactc cgtgaagtcg gaatcgctag taatcgtgga tcagaatgcc acggtgaata 900
cgt 903

<210> SEQ ID NO 41
<211> LENGTH: 1457
<212> TYPE: DNA
<213> ORGANISM: Unknown
<220> FEATURE:
<223> OTHER INFORMATION: Description of Unknown:
DP41 16S rRNA microbial sequence

<400> SEQUENCE: 41
gtggagagtt tgatcctggc tcaggatgaa cgctggcggc gtgcttaaca catgcaagtc 60
gaacggaaag gcccaagctt gcttgggtac tcgagtggcg aacgggtgag taacacgtgg 120
gtgatctgcc ctgcacttcg ggataagcct gggaaactgg gtctaatacc ggataggacg 180
atggtttgga tgccattgtg gaaagttttt tcggtgtggg atgagctcgc ggcctatcag 240
cttgttggtg gggtaatggc ctaccaaggc gtcgacgggt agccggcctg agagggtgta 300
cggccacatt gggactgaga tacggcccag actcctacgg gaggcagcag tggggaatat 360
tgcacaatgg gcgcaagcct gatgcagcga cgccgcgtgg gggatgacgg ccttcgggtt 420
gtaaactcct ttcgctaggg acgaagcgtt ttgtgacggt acctggagaa gaagcaccgg 480
ctaactacgt gccagcagcc gcggtaatac gtagggtgcg agcgttgtcc ggaattactg 540

-continued

```
ggcgtaaaga gctcgtaggt ggtttgtcgc gtcgtttgtg taagcccgca gcttaactgc    600
gggactgcag gcgatacggg cataacttga gtgctgtagg ggagactgga attcctggtg    660
tagcggtgga atgcgcagat atcaggagga acaccgatgg cgaaggcagg tctctgggca    720
gtaactgacg ctgaggagcg aaagcatggg tagcgaacag gattagatac cctggtagtc    780
catgccgtaa acggtgggcg ctaggtgtga gtcccttcca cggggttcgt gccgtagcta    840
acgcattaag cgccccgcct ggggagtacg gccgcaaggc taaaactcaa aggaattgac    900
gggggcccgc acaagcggcg gagcatgtgg attaattcga tgcaacgcga agaaccttac    960
ctgggcttga catacaccag atcgccgtag agatacggtt tccctttgtg gttggtgtac   1020
aggtggtgca tggttgtcgt cagctcgtgt cgtgagatgt tgggttaagt cccgcaacga   1080
gcgcaaccct tgtcttatgt tgccagcacg tgatggtggg gactcgtgag agactgccgg   1140
ggttaactcg gaggaaggtg gggatgacgt caaatcatca tgccccttat gtccagggct   1200
tcacacatgc tacaatggtc ggtacaacgc gcatgcgagc ctgtgagggt gagcgaatcg   1260
ctgtgaaagc cggtcgtagt tcggattggg gtctgcaact cgaccccatg aagtcggagt   1320
cgctagtaat cgcagatcag caacgctgcg gtgaatacgt tcccgggcct tgtacacacc   1380
gcccgtcaca ccatgggagt gggttgcaaa agaagtaggt agcttaacct tcgggagggc   1440
gcttaccact ttgtgat                                                  1457
```

```
<210> SEQ ID NO 42
<211> LENGTH: 1532
<212> TYPE: DNA
<213> ORGANISM: Unknown
<220> FEATURE:
<223> OTHER INFORMATION: Description of Unknown:
      DP42 16S rRNA microbial sequence

<400> SEQUENCE: 42
```

```
tgaagagttt gatcatggct cagattgaac gctggcggca ggcctaacac atgcaagtcg     60
agcggtagag aggtgcttgc acctcttgag agcggcggac gggtgagtaa tacctaggaa    120
tctgcctgat agtgggggat aacgttcgga aacggacgct aataccgcat acgtcctacg    180
ggagaaagca ggggaccttc gggccttgcg ctatcagatg agcctaggtc ggattagcta    240
gttggtgagg taatggctca ccaaggctac gatccgtaac tggtctgaga ggatgatcag    300
tcacactgga actgagacac ggtccagact cctacgggag gcagcagtgg ggaatattgg    360
acaatgggcg aaagcctgat ccagccatgc cgcgtgtgtg aagaaggtct tcggattgta    420
aagcacttta agttgggagg aagggcatta acctaatacg ttagtgtctt gacgttaccg    480
acagaataag caccggctaa ctctgtgcca gcagccgcgg taatacagag ggtgcaagcg    540
ttaatcggaa ttactgggcg taaagcgcgc gtaggtggtt tgttaagttg aatgtgaaat    600
ccccgggctc aacctgggaa ctgcatccaa aactggcaag ctagagtatg gtagagggta    660
gtggaatttc ctgtgtagcg gtgaaatgcg tagatatagg aaggaacacc agtggcgaag    720
gcgactacct ggactgatac tgacactgag gtgcgaaagc gtggggagca aacaggatta    780
gataccctgg tagtccacgc cgtaaacgat gtcaactagc cgttgggaac cttgagttct    840
tagtggcgca gctaacgcat taagttgacc gcctggggag tacggccgca aggttaaaac    900
tcaaatgaat tgacgggggc ccgcacaagc ggtggagcat gtggtttaat tcgaagcaac    960
gcgaagaacc ttaccaggcc ttgacatcca atgaactttc cagagatgga ttggtgcctt   1020
cgggaacatt gagacaggtg ctgcatggct gtcgtcagct cgtgtcgtga gatgttgggt   1080
```

-continued

```
taagtcccgt aacgagcgca acccttgtcc ttagttacca gcacgtaatg gtgggcactc   1140

taaggagact gccggtgaca aaccggagga aggtggggat gacgtcaagt catcatggcc   1200

cttacggcct gggctacaca cgtgctacaa tggtcggtac aaagggttgc caagccgcga   1260

ggtggagcta atcccataaa accgatcgta gtccggatcg cagtctgcaa ctcgactgcg   1320

tgaagtcgga atcgctagta atcgtgaatc agaatgtcac ggtgaatacg ttcccgggcc   1380

ttgtacacac cgcccgtcac accatgggag tgggttgcac cagaagtagc tagtctaacc   1440

ctcgggagga cggttaccac ggtgtgattc atgactgggg tgaagtcgta acaaggtagc   1500

cgtaggggaa cctgcggctg gatcacctcc tt                                 1532
```

```
<210> SEQ ID NO 43
<211> LENGTH: 1525
<212> TYPE: DNA
<213> ORGANISM: Unknown
<220> FEATURE:
<223> OTHER INFORMATION: Description of Unknown:
      DP43 16S rRNA microbial sequence

<400> SEQUENCE: 43
```

```
ctgagtttga tcctggctca gattgaacgc tggcggcatg ccttacacat gcaagtcgaa     60

cggcagcacg gagcttgctc tggtggcgag tggcgaacgg gtgagtaata tatcggaacg    120

taccctggag tgggggataa cgtagcgaaa gttacgctaa taccgcatac gatctaagga    180

tgaaagtggg ggatcgcaag acctcatgct cgtggagcgg ccgatatctg attagctagt    240

tggtagggta aaagcctacc aaggcatcga tcagtagctg gtctgagagg acgaccagcc    300

acactggaac tgagacacgg tccagactcc tacgggaggc agcagtgggg aattttggac    360

aatgggcgaa agcctgatcc agcaatgccg cgtgagtgaa gaaggccttc gggttgtaaa    420

gctcttttgt cagggaagaa acggtgagag ctaatatctc ttgctaatga cggtacctga    480

agaataagca ccggctaact acgtgccagc agccgcggta atacgtaggg tgcaagcgtt    540

aatcggaatt actgggcgta aagcgtgcgc aggcggtttt gtaagtctga tgtgaaatcc    600

ccgggctcaa cctgggaatt gcattggaga ctgcaaggct agaatctggc agaggggggt    660

agaattccac gtgtagcagt gaaatgcgta gatatgtgga ggaacaccga tggcgaaggc    720

agccccctgg gtcaagattg acgctcatgc acgaaagcgt ggggagcaaa caggattaga    780

taccctggta gtccacgccc taaacgatgt ctactagttg tcgggtctta attgacttgg    840

taacgcagct aacgcgtgaa gtagaccgcc tggggagtac ggtcgcaaga ttaaaactca    900

aaggaattga cggggacccg cacaagcggt ggatgatgtg gattaattcg atgcaacgcg    960

aaaaacctta cctacccttg acatggctgg aatccttgag agatcaggga gtgctcgaaa   1020

gagaaccagt acacaggtgc tgcatggctg tcgtcagctc gtgtcgtgag atgttgggtt   1080

aagtcccgca acgagcgcaa cccttgtcat tagttgctac gaaagggcac tctaatgaga   1140

ctgccggtga caaaccggag gaaggtgggg atgacgtcaa gtcctcatgg cccttatggg   1200

tagggcttca cacgtcatac aatggtacat acagagcgcc gccaacccgc gaggggggagc  1260

taatcgcaga aagtgtatcg tagtccggat tgtagtctgc aactcgactg catgaagttg   1320

gaatcgctag taatcgcgga tcagcatgtc gcggtgaata cgttcccggg tcttgtacac   1380

accgcccgtc acaccatggg agcgggtttt accagaagta ggtagcttaa ccgtaaggag   1440

ggcgcttacc acggtaggat tcgtgactgg ggtgaagtcg taacaaggta gccgtatcgg   1500

aaggtgcggc tggatcacct ccttt                                         1525
```

<210> SEQ ID NO 44
<211> LENGTH: 1497
<212> TYPE: DNA
<213> ORGANISM: Unknown
<220> FEATURE:
<223> OTHER INFORMATION: Description of Unknown:
DP44 16S rRNA microbial sequence

<400> SEQUENCE: 44
tggcggcatg ccttacacat gcaagtcgaa cggcagcata ggagcttgct cctgatggcg 60
agtggcgaac gggtgagtaa tatatcggaa cgtgccctag agtgggggat aactagtcga 120
aagactagct aataccgcat acgatctacg gatgaaagtg gggggatcgca agacctcatg 180 ctcctggagc ggccgatatc tgattagcta gttggtgggg taaaagctca ccaaggcgac 240
gatcagtagc tggtctgaga ggacgaccag ccacactggg actgagacac ggcccagact 300
cctacgggag gcagcagtgg ggaattttgg acaatggggg caaccctgat ccagcaatgc 360
cgcgtgagtg aagaaggcct tcgggttgta aagctctttt gtcagggaag aaacggttct 420
ggataatacc taggactaat gacggtacct gaagaataag caccggctaa ctacgtgcca 480
gcagccgcgg taatacgtag ggtgcaagcg ttaatcggaa ttactgggcg taaagcgtgc 540
gcaggcggtt gtgtaagtca gatgtgaaat ccccgggctc aacctgggaa ttgcatttga 600
gactgcacgg ctagagtgtg tcagaggggg gtagaattcc acgtgtagca gtgaaatgcg 660
tagatatgtg gaggaatacc gatggcgaag gcagcccccct gggataacac tgacgctcat 720
gcacgaaagc gtggggagca aacaggatta gataccctgg tagtccacgc cctaaacgat 780
gtctactagt tgtcgggtct taattgactt ggtaacgcag ctaacgcgtg aagtagaccg 840
cctggggagt acggtcgcaa gattaaaact caaaggaatt gacggggacc cgcacaagcg 900
gtggatgatg tggattaatt cgatgcaacg cgaaaaacct tacctaccct tgacatggat 960
ggaatcccga agagatttgg gagtgctcga aagagaacca tcacacaggt gctgcatggc 1020
tgtcgtcagc tcgtgtcgtg agatgttggg ttaagtcccg caacgagcgc aacccttgtc 1080
attagttgct acgaaagggc actctaatga gactgccggt gacaaaccgg aggaaggtgg 1140
ggatgacgtc aagtcctcat ggcccttatg ggtagggctt cacacgtcat acaatggtac 1200
atacagaggg ccgccaaccc gcgaggggga gctaatccca gaaagtgtat cgtagtccgg 1260
attggagtct gcaactcgac tccatgaagt tggaatcgct agtaatcgcg gatcagcatg 1320
tcgcggtgaa tacgttcccg ggtcttgtac acaccgcccg tcacaccatg ggagcgggtt 1380
ttaccagaag tgggtagcct aaccgcaagg agggcgctca ccacggtagg attcgtgact 1440
ggggtgaagt cgtaacaagg tagccgtatc ggaaggtgcg gctggatcac ctccttt 1497

<210> SEQ ID NO 45
<211> LENGTH: 1522
<212> TYPE: DNA
<213> ORGANISM: Unknown
<220> FEATURE:
<223> OTHER INFORMATION: Description of Unknown:
DP45 16S rRNA microbial sequence

<400> SEQUENCE: 45
tacggagagt ttgatcctgg ctcaggacga acgctggcgg cgtgcttaac acatgcaagt 60
cgaacggtga cgctagagct tgctctggtt gatcagtggc gaacgggtga gtaacacgtg 120
agtaacctgc ccttgactct gggataactc cgggaaaccg gggctaatac cggatacgag 180
acgcgaccgc atggtcggcg tctggaaagt ttttcggtca aggatggact cgcggcctat 240
cagcttgttg gtgaggtaat ggctcaccaa ggcgtcgacg ggtagccggc ctgagagggc 300
gaccggccac actgggactg agacacggcc cagactccta cgggaggcag cagtggggaa 360
tattgcacaa tgggcgaaag cctgatgcag cgacgccgcg tgagggatga aggccttcgg 420
gttgtaaacc tctttcagta gggaagaagc gaaagtgacg gtacctgcag aagaagcgcc 480
ggctaactac gtgccagcag ccgcggtaat acgtagggcg caagcgttgt ccggaattat 540
tgggcgtaaa gagctcgtag gcggtttgtc gcgtctggtg tgaaaactca aggctcaacc 600
ttgagcttgc atcgggtacg ggcagactag agtgtggtag gggtgactgg aattcctggt 660
gtagcggtgg aatgcgcaga tatcaggagg aacaccgatg gcgaaggcag gtcactgggc 720
cactactgac gctgaggagc gaaagcatgg ggagcgaaca ggattagata ccctggtagt 780
ccatgccgta aacgttgggc actaggtgtg ggctcattc cacgagttcc gcgccgcagc 840
taacgcatta agtgccccgc ctggggagta cggccgcaag gctaaaactc aaaggaattg 900
acgggggccc gcacaagcgg cggagcatgc ggattaattc gatgcaacgc gaagaacctt 960
accaaggctt gacatacacc ggaatcatgc agagatgtgt gcgtcttcgg actggtgtac 1020
aggtggtgca tggttgtcgt cagctcgtgt cgtgagatgt tgggttaagt cccgcaacga 1080
gcgcaaccct cgtcctatgt tgccagcacg ttatggtggg gactcatagg agactgccgg 1140
ggtcaactcg gaggaaggtg gggatgacgt caaatcatca tgccccttat gtcttgggct 1200
tcacgcatgc tacaatggcc ggtacaaagg gctgcgatac cgcgaggtgg agcgaatccc 1260
aaaaagccgg tctcagttcg gattggggtc tgcaactcga ccccatgaag tcggagtcgc 1320
tagtaatcgc agatcagcaa cgctgcggtg aatacgttcc cgggccttgt acacaccgcc 1380
cgtcaagtca cgaaagtcgg taacacccga agccggtggc ctaacccctt gtgggatgga 1440
gccgtcgaag gtgggattgg cgattgggac taagtcgtaa caaggtagcc gtaccggaag 1500
gtgcggctgg atcacctcct tt 1522

<210> SEQ ID NO 46
<211> LENGTH: 830
<212> TYPE: DNA
<213> ORGANISM: Unknown
<220> FEATURE:
<223> OTHER INFORMATION: Description of Unknown:
DP46 16S rRNA microbial sequence

<400> SEQUENCE: 46
ttgaagagtt tgatcatggc tcagattgaa cgctggcggc aggcctaaca catgcaagtc 60
ggacggtagc acagaggagc tgctccttgg gtgacgagtg gcggacgggt gagtaatgtc 120
tggggatctg cccgatagag gggataacc actggaaacg gtggctaata ccgcataacg 180
tcgcaagacc aaagaggggg accttcgggc ctctcactat cggatgaacc cagatgggat 240
tagctagtag gcggggtaat ggcccaccta ggcgacgatc cctagctggt ctgagaggat 300
gaccagccac actggaactg agacacggtc cagactccta cgggaggcag cagtggggaa 360
tattgcacaa tgggcgcaag cctgatgcag ccatgccgcg tgtatgaaga aggccttcgg 420
gttgtaaagt actttcagcg gggaggaagg cgacagggtt aataaccctg tcgattgacg 480
ttacccgcag aagaagcacc ggctaactcc gtgccagcag ccgcggtaat acggagggtg 540
caagcgttaa tcggaattac tgggcgtaaa gcgcacgcag gcggtctgtt aagtcagatg 600
tgaaatcccc gggcttaacc tgggaactgc atttgaaact ggcaggcttt agtcttgtag 660
agtggggtag aattccaggt gtagcggtga aatgcgtaga gatgtggagg aacaccagtg 720
gcgaaggcgg ctttttggtc tgtaactgac gctgaggcgc gaaagcgtgg ggagcaaaca 780
ggattagata ccctggtagt ccacgccgta aacgatgagt gctaagtgtt 830

<210> SEQ ID NO 47
<211> LENGTH: 960
<212> TYPE: DNA
<213> ORGANISM: Unknown
<220> FEATURE:
<223> OTHER INFORMATION: Description of Unknown:
DP47 16S rRNA microbial sequence

<400> SEQUENCE: 47
agggtgcaag cgttaatcgg aattactggg cgtaaagcgc gcgtaggtgg tttgttaagt 60
tgaatgtgaa atccccgggc tcaacctggg aactgcattt gaaactggca agctagagtc 120
tcgtagaggg gggtagaatt ccaggtgtag cggtgaaatg cgtagagatc tggaggaata 180
ccggtggcga aggcggcccc ctggacgaag actgacgctc aggtgcgaaa gcgtggggag 240
caaacaggat tagataccct ggtagtccac gccgtaaacg atgtcaacta gccgttggaa 300
gccttgagct tttagtggcg cagctaacgc attaagttga ccgcctgggg agtacggccg 360
caaggttaaa actcaaatga attgacgggg gcccgcacaa gcggtggagc atgtggttta 420
attcgaagca acgcgaagaa ccttaccagg ccttgacatc caatgaactt tctagagata 480
gattggtgcc ttcgggaaca ttgagacagg tgctgcatgg ctgtcgtcag ctcgtgtcgt 540
gagatgttgg gttaagtccc gcaacgagcg caacccttgt cctgtgttgc cagcgcgtaa 600
tggcggggac tcgcaggaga ctgccggggt caactcggag gaaggtgggg atgacgtcaa 660
atcatcatgc cccttatgtc ttgggcttca cgcatgctac aatggccggt acaaagggct 720
gcaataccgt gaggtggagc gaatcccaaa aagccggtcc cagttcggat tgaggtctgc 780
aactcgacct catgaagtcg gagtcgctag taatcgcaga tcagcaacgc tgcggtgaat 840
acgttcccgg gtcttgtaca caccgcccgt caagtcatga aagtcggtaa cacctgaagc 900
cggtggccca acccttgtgg agggagccgt cgaaggtggg atcggtaatt aggactaagt 960

<210> SEQ ID NO 48
<211> LENGTH: 1548
<212> TYPE: DNA
<213> ORGANISM: Unknown
<220> FEATURE:
<223> OTHER INFORMATION: Description of Unknown:
DP48 16S rRNA microbial sequence

<400> SEQUENCE: 48
catggagagt ttgatcctgg ctcaggacga acgctggcgg cgtgcctaat acatgcaagt 60
cgagcggaca gatgggagct tgctccctga tgttagcggc ggacgggtga gtaacacgtg 120
ggtaacctgc ctgtaagact gggataactc cgggaaaccg gggctaatac cggatgcttg 180
attgaaccgc atggttcaat tataaaaggt ggcttttagc taccacttac agatggaccc 240
gcggcgcatt agctagttgg tgaggtaacg gctcaccaag gcaacgatgc gtagccgacc 300
tgagagggtg atcggccaca ctgggactga gacacggccc agactcctac gggaggcagc 360
agtagggaat cttccgcaat ggacgaaagt ctgacggagc aacgccgcgt gagtgatgaa 420
ggttttcgga tcgtaaaact ctgttgttag ggaagaacaa gtaccgttcg aatagggcgg 480
taccttgacg gtacctaacc agaaagccac ggctaactac gtgccagcag ccgcggtaat 540
acgtaggtgg caagcgttgt ccggaattat tgggcgtaaa gcgcgcgcag gcggtttctt 600

-continued

```
aagtctgatg tgaaagcccc cggctcaacc ggggagggtc attggaaact ggggaacttg    660

agtgcagaag aggagagtgg aattccacgt gtagcggtga aatgcgtaga gatgtggagg    720

aacaccagtg gcgaaggcga ctctctggtc tgtaactgac gctgaggcgc gaaagcgtgg    780

ggagcgaaca ggattagata ccctggtagt ccacgccgta aacgatgagt gctaagtgtt    840

agagggtttc cgccctttag tgctgcagca aacgcattaa gcactccgcc tggggagtac    900

ggtcgcaaga ctgaaactca aaggaattga cgggggcccg cacaagcggt ggagcatgtg    960

gtttaattcg aagcaacgcg aagaacctta ccaggtcttg acatcctctg acaaccctag   1020

agatagggct tccccttcgg gggcagagtg acaggtggtg catggttgtc gtcagctcgt   1080

gtcgtgagat gttgggttaa gtcccgcaac gagcgcaacc cttgatctta gttgccagca   1140

ttcagttggg cactctaagg tgactgccgg tgacaaaccg gaggaaggtg gggatgacgt   1200

caaatcatca tgccccttat gacctgggct acacacgtgc tacaatgggc agaacaaagg   1260

gcagcgaagc cgcgaggcta agccaatccc acaaatctgt tctcagttcg gatcgcagtc   1320

tgcaactcga ctgcgtgaag ctggaatcgc tagtaatcgc ggatcagcat gccgcggtga   1380

atacgttccc gggccttgta cacaccgccc gtcacaccac gagagtttgt aacacccgaa   1440

gtcggtgagg taacctttg gagccagccg ccgaaggtgg gacagatgat tggggtgaag    1500

tcgtaacaag gtagccgtat cggaaggtgc ggctggatca cctccttt                1548
```

```
<210> SEQ ID NO 49
<211> LENGTH: 1551
<212> TYPE: DNA
<213> ORGANISM: Unknown
<220> FEATURE:
<223> OTHER INFORMATION: Description of Unknown:
      DP49 16S rRNA microbial sequence

<400> SEQUENCE: 49
```

```
tatggagagt ttgatcctgg ctcaggacga acgctggcgg cgtgcctaat acatgcaagt     60

cgagcggacg tttttgaagc ttgcttcaaa aacgttagcg gcggacgggt gagtaacacg    120

tgggcaacct gccttatcga ctgggataac tccgggaaac cggggctaat accggataat    180

atctagcacc tcctggtgca agattaaaag agggccttcg ggctctcacg gtgagatggg    240

cccgcggcgc attagctagt tggagaggta atggctcccc aaggcgacga tgcgtagccg    300

acctgagagg gtgatcggcc acactgggac tgagacacgg cccagactcc tacgggaggc    360

agcagtaggg aatcttccgc aatggacgaa agtctgacgg agcaacgccg cgtgagtgat    420

gaagggtttc ggctcgtaaa gctctgttat gagggaagaa cacgtaccgt tcgaataggg    480

cggtaccttg acggtacctc atcagaaagc cacggctaac tacgtgccag cagccgcggt    540

aatacgtagg tggcaagcgt tgtccggaat tattgggcgt aaagcgcgcg caggcggcct    600

tttaagtctg atgtgaaatc ttgcggctca accgcaagcg gtcattggaa actgggaggc    660

ttgagtacag aagaggagag tggaattcca cgtgtagcgg tgaaatgcgt agatatgtgg    720

aggaacacca gtggcgaagg cgactctctg gtctgtaact gacgctgagg cgcgaaagcg    780

tggggagcaa acaggattag ataccctggt agtccacgcc gtaaacgatg agtgctaggt    840

gttaggggtt tcgatgcccg tagtgccgaa gttaacacat taagcactcc gcctggggag    900

tacggccgca aggctgaaac tcaaaggaat tgacgggggc ccgcacaagc agtggagcat    960

gtggtttaat tcgaagcaac gcgaagaacc ttaccaggtc ttgacatcct ttgaccactc   1020

tggagacaga gcttcccctt cgggggcaaa gtgacaggtg gtgcatggtt gtcgtcagct   1080
```

```
cgtgtcgtga gatgttgggt taagtcccgc aacgagcgca acccttgacc ttagttgcca   1140

gcatttagtt gggcactcta aggtgactgc cggtgacaaa ccggaggaag gtggggatga   1200

cgtcaaatca tcatgcccct tatgacctgg gctacacacg tgctacaatg gatggtacaa   1260

agggttgcga agccgcgagg tgaagccaat cccataaagc cattctcagt tcggattgta   1320

ggctgcaact cgcctgcatg aagctggaat tgctagtaat cgcggatcag catgccgcgg   1380

tgaatacgtt cccgggcctt gtacacaccg cccgtcacac cacgagagtt tgtaacaccc   1440

gaagtcggtg aggtaacctt ttggagccag ccgccgaagg tgggacagat gattggggtg   1500

aagtcgtaac aaggtagccg tatcggaagg tgcggctgga tcacctcctt t            1551
```

<210> SEQ ID NO 50
<211> LENGTH: 1536
<212> TYPE: DNA
<213> ORGANISM: Unknown
<220> FEATURE:
<223> OTHER INFORMATION: Description of Unknown:
DP50 16S rRNA microbial sequence

<400> SEQUENCE: 50

```
ttgaagagtt tgatcatggc tcagattgaa cgctggcggc aggcctaaca catgcaagtc     60

gaacggtagc acagagagct tgctcttggg tgacgagtgg cggacgggtg agtaatgtct    120

gggaaactgc ccgatggagg gggataacta ctggaaacgg tagctaatac cgcataacgt    180

cgcaagacca aagtggggga ccttcgggcc tcacaccatc ggatgtgccc agatgggatt    240

agctagtagg tggggtaatg gctcacctag gcgacgatcc ctagctggtc tgagaggatg    300

accagccaca ctggaactga gacacggtcc agactcctac gggaggcagc agtggggaat    360

attgcacaat gggcgcaagc ctgatgcagc catgccgcgt gtatgaagaa ggccttcggg    420

ttgtaaagta ctttcagcga ggaggaaggc attgtggtta ataaccgcag tgattgacgt    480

tactcgcaga agaagcaccg gctaactccg tgccagcagc cgcggtaata cggagggtgc    540

aagcgttaat cggaattact gggcgtaaag cgcacgcagg cggtctgtca agtcggatgt    600

gaaatccccg ggctcaacct gggaactgca ttcgaaactg gcaggctaga gtcttgtaga    660

ggggggtaga attccaggtg tagcggtgaa atgcgtagag atctggagga ataccggtgg    720

cgaaggcggc cccctggaca aagactgacg ctcaggtgcg aaagcgtggg gagcaaacag    780

gattagatac cctggtagtc cacgccgtaa acgatgtcga cttggaggtt gtgcccttga    840

ggcgtggctt ccggagctaa cgcgttaagt cgaccgcctg gggagtacgg ccgcaaggtt    900

aaaactcaaa tgaattgacg ggggcccgca caagcggtgg agcatgtggt ttaattcgat    960

gcaacgcgaa gaaccttacc tactcttgac atccacggaa tttagcagag atgctttagt   1020

gccttcggga accgtgagac aggtgctgca tggctgtcgt cagctcgtgt tgtgaaatgt   1080

tgggttaagt cccgcaacga gcgcaaccct tatcctttgt tgccagcggt tcggccggga   1140

actcaaagga gactgccagt gataaactgg aggaaggtgg ggatgacgtc aagtcatcat   1200

ggcccttacg agtagggcta cacacgtgct acaatggcat atacaaagag aagcgacctc   1260

gcgagagcaa gcggacctca taaagtatgt cgtagtccgg atcggagtct gcaactcgac   1320

tccgtgaagt cggaatcgct agtaatcgta gatcagaatg ctacggtgaa tacgttcccg   1380

ggccttgtac acaccgcccg tcacaccatg ggagtgggtt gcaaaagaag taggtagctt   1440

aaccttcggg agggcgctta ccactttgtg attcatgact ggggtgaagt cgtaacaagg   1500

taaccgtagg ggaacctgcg gttggatcac ctcctt                             1536
```

<210> SEQ ID NO 51
<211> LENGTH: 1537
<212> TYPE: DNA
<213> ORGANISM: Unknown
<220> FEATURE:
<223> OTHER INFORMATION: Description of Unknown:
DP51 16S rRNA microbial sequence

<400> SEQUENCE: 51
ttgaagagtt tgatcatggc tcagattgaa cgctggcggc aggcctaaca catgcaagtc 60
gagcggtagc acagggagct tgctcctggg tgacgagcgg cggacgggtg agtaatgtct 120
gggaaactgc ctgatggagg gggataacta ctggaaacgg tagctaatac cgcataacgt 180
cgcaagacca aagaggggga ccttcgggcc tcttgccatc agatgtgccc agatgggatt 240
agctagtagg tgaggtaatg gctcacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcga ggaggaaggc attaaggtta ataaccttgg tgattgacgt 480
tactcgcaga agaagcaccg gctaactccg tgccagcagc cgcggtaata cgggggggtgc 540 aagcgttaat cggaattact gggcgtaaag cgcacgcagg cggtttgtca agtcggatgt 600
gaaatccccg ggctcaacct gggaactgca ttcgaaacgg gcaagctaga gtcttgtaga 660
ggggggtaga attccaggtg tagcggtgaa atgcgtagag atctggagga ataccggtgg 720
cgaaggcggc cccctggaca aagactgacg ctcaggtgcg aaagcgtggg gagcaaacag 780
gattagatac cctggtagtc cacgccgtaa acgatgtcga cttggaggtt gtgcccttga 840
ggcgtggctt ccggagctaa cgcgttaagt cgaccgcctg gggagtacgg ccgcaaggtt 900
aaaactcaaa tgaattgacg ggggcccgca caagcggtgg agcatgtggt ttaattcgat 960
gcaacgcgaa gaaccttacc tactcttgac atccagagaa ctttccagag atggattggt 1020
gccttcggga actctgagac aggtgctgca tggctgtcgt cagctcgtgt tgtgaaatgt 1080
tgggttaagt cccgcaacga gcgcaaccct tatcctttgt tgccagcgag taatgtcggg 1140
aactcaaagg agactgccag tgacaaactg gaggaaggtg gggatgacgt caagtcatca 1200
tggcccttac gagtagggct acacacgtgc tacaatggca tatacaaaga gaagcgacct 1260
cgcgagagca agcggacctc acaaagtatg tcgtagtccg gatcggagtc tgcaactcga 1320
ctccgtgaag tcggaatcgc tagtaatcgt agatcagaat gctacggtga atacgttccc 1380
gggccttgta cacaccgccc gtcacaccat gggagtgggt tgcaaaagaa gtaggtagct 1440
taaccttcgg gagggcgctt accactttgt gattcatgac tggggtgaag tcgtaacaag 1500
gtaaccgtag gggaacctgc ggttggatca cctcctt 1537

<210> SEQ ID NO 52
<211> LENGTH: 1517
<212> TYPE: DNA
<213> ORGANISM: Unknown
<220> FEATURE:
<223> OTHER INFORMATION: Description of Unknown:
DP52 16S rRNA microbial sequence

<400> SEQUENCE: 52
acggagagtt tgatcctggc tcaggatgaa cgctggcggc gtgcttaaca catgcaagtc 60
gaacgatgat cccagcttgc tgggggatta gtggcgaacg ggtgagtaac acgtgagtaa 120
cctgcccttg actctgggat aagcctggga aactgggtct aataccggat atgactgtct 180
gacgcatgtc aggtggtgga aagcttttgt ggttttggat ggactcgcgg cctatcagct 240
tgttggtggg gtaatggcct accaaggcga cgacgggtag ccggcctgag agggtgaccg 300
gccacactgg gactgagaca cggcccagac tcctacggga ggcagcagtg gggaatattg 360
cacaatgggc gcaagcctga tgcagcgacg ccgcgtgagg gatgacggcc ttcgggttgt 420
aaacctcttt cagtagggaa gaagcgaaag tgacggtacc tgcagaagaa gcgccggcta 480
actacgtgcc agcagccgcg gtaatacgta gggcgcaagc gttatccgga attattgggc 540
gtaaagagct cgtaggcggt ttgtcgcgtc tgctgtgaaa gaccggggct caactccggt 600
tctgcagtgg gtacgggcag actagagtgc agtaggggag actggaattc ctggtgtagc 660
ggtgaaatgc gcagatatca ggaggaacac cgatggcgaa ggcaggtctc tgggctgtaa 720
ctgacgctga ggagcgaaag catggggagc gaacaggatt agataccctg gtagtccatg 780
ccgtaaacgt tgggcactag gtgtggggga cattccacgt tttccgcgcc gtagctaacg 840
cattaagtgc cccgcctggg gagtacggcc gcaaggctaa aactcaaagg aattgacggg 900
ggcccgcaca agcggcggag catgcggatt aattcgatgc aacgcgaaga accttaccaa 960
ggcttgacat gaaccggtaa tacctggaaa caggtgcccc gcttgcggtc ggtttacagg 1020
tggtgcatgg ttgtcgtcag ctcgtgtcgt gagatgttgg gttaagtccc gcaacgagcg 1080
caaccctcgt tctatgttgc cagcgcgtta tggcggggac tcataggaga ctgccggggt 1140
caactcggag gaaggtgggg acgacgtcaa atcatcatgc cccttatgtc ttgggcttca 1200
cgcatgctac aatggccggt acaaagggtt gcgatactgt gaggtggagc taatcccaaa 1260
aagccggtct cagttcggat tggggtctgc aactcgaccc catgaagtcg gagtcgctag 1320
taatcgcaga tcagcaacgc tgcggtgaat acgttcccgg gccttgtaca caccgcccgt 1380
caagtcacga aagttggtaa cacccgaagc cggtggccta acccttgtgg ggggagccgt 1440
cgaaggtggg accggcgatt gggactaagt cgtaacaagg tagccgtacc ggaaggtgcg 1500
gctggatcac ctccttt 1517

<210> SEQ ID NO 53
<211> LENGTH: 1405
<212> TYPE: DNA
<213> ORGANISM: Unknown
<220> FEATURE:
<223> OTHER INFORMATION: Description of Unknown:
DP53 16S rRNA microbial sequence

<400> SEQUENCE: 53
tgaagagttt gatcatggct cagattgaac gctggcggca ggcctaacac atgcaagtcg 60
agcggtagag agaagcttgc ttctcttgag agcggcggac gggtgagtaa tacctaggaa 120
tctgcctgat agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggctac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggcagtt acctaatacg tgattgtctg acgttaccga 480
cagaataagc accggctaac tctgtgccag cagccgcggt aatacagagg gtgcaagcgt 540
taatcggaat tactgggcgt aaagcgcgcg taggtggttt gttaagttga atgtgaaatc 600
cccgggctca acctgggaac tgcatccaaa actggcaagc tagagtatgg tagagggtag 660
tggaatttcc tgtgtagcgg tgaaatgcgt agatatagga aggaacacca gtggcgaagg 720
cgactacctg gactgatact gacactgagg tgcgaaagcg tggggagcaa acaggattag 780
ataccctggt agtccacgcc gtaaacgatg tcaactagcc gttgggagtc ttgaactctt 840
agtggcgcag ctaacgcatt aagttgaccg cctggggagt acggccgcaa ggttaaaact 900
caaatgaatt gacgggggcc cgcacaagcg gtggagcatg tggtttaatt cgaagcaacg 960
cgaagaacct taccaggcct tgacatccaa tgaactttct agagatagat tggtgccttc 1020
gggaacattg agacaggtgc tgcatggctg tcgtcagctc gtgtcgtgag atgttgggtt 1080
aagtcccgta acgagcgcaa cccttgtcct tagttaccag cacgtaatgg tgggcactct 1140
aaggagactg ccggtgacaa accggaggaa ggtggggatg acgtcaagtc atcatggccc 1200
ttacggcctg ggctacacac gtgctacaat ggtcggtaca aagggttgcc aagccgcgag 1260
gtggagctaa tcccataaaa ccgatcgtag tccggatcgc agtctgcaac tcgactgcgt 1320
gaagtcggaa tcgctagtaa tcgtgaatca gaatgtcacg gtgaatacgt tcccgggcct 1380
tgtacacacc gcccgtcaca ccatg 1405

<210> SEQ ID NO 54
<211> LENGTH: 1136
<212> TYPE: DNA
<213> ORGANISM: Unknown
<220> FEATURE:
<223> OTHER INFORMATION: Description of Unknown:
DP54 16S rRNA microbial sequence

<400> SEQUENCE: 54
cttgagagtt tgatcctggc tcagagcgaa cgctggcggc aggcttaaca catgcaagtc 60
gagcgggcac cttcgggtgt cagcggcaga cgggtgagta acacgtggga acgtaccctt 120
cggttcggaa taacgctggg aaactagcgc taataccgga tacgcccttt tggggaaagg 180
tttactgccg aaggatcggc ccgcgtctga ttagctagtt ggtggggtaa cggcctacca 240
aggcgacgat cagtagctgg tctgagagga tgatcagcca cactgggact gagacacggc 300
ccagactcct acgggaggca gcagtgggga atattggaca atgggcgcaa gcctgatcca 360
gccatgccgc gtgagtgatg aaggccttag ggttgtaaag ctcttttgtc cgggacgata 420
atgacggtac cggaagaata agccccggct aacttcgtgc cagcagccgc ggtaatacga 480
agggggctag cgttgctcgg aatcactggg cgtaaagggc gcgtaggcgg ccattcaagt 540
cgggggtgaa agcctgtggc tcaaccacag aattgccttc gatactgttt ggcttgagtt 600
tggtagaggt tggtggaact gcgagtgtag aggtgaaatt cgtagatatt cgcaagaaca 660
ccagtggcga aggcggccaa ctggaccaat actgacgctg aggcgcgaaa gcgtggggag 720
caaacaggat tagataccct ggtagtccac gccgtaaacg atgaatgcta gctgttgggg 780
tgcttgcacc tcagtagcgc agctaacgct ttaagcattc cgcctgggga gtacggtcgc 840
aagattaaaa ctcaaaggaa ttgacggggg cccgcacaag cggtggagca tgtggtttaa 900
ttcgaagcaa cgcgcagaac cttaccatcc cttgacatgt cgtgccatcc ggagagatcc 960
ggggttccct tcggggacgc gaacacaggt gctgcatggc tgtcgtcagc tcgtgtcgtg 1020
agatgttggg ttaagtcccg caacgagcgc aacccacgtc cttagttgcc atcatttagt 1080
tgggcactct agggagactg ccggtgataa gccgcgagga aggtgtggat gacgtc 1136

<210> SEQ ID NO 55
<211> LENGTH: 1373

<212> TYPE: DNA
<213> ORGANISM: Unknown
<220> FEATURE:
<223> OTHER INFORMATION: Description of Unknown:
DP55 16S rRNA microbial sequence

<400> SEQUENCE: 55
tcggagagtt tgatcctggc tcaggatgaa cgctggcggc gtgcctaata catgcaagtc 60
gagcgaactg attagaagct tgcttctatg acgttagcgg cggacgggtg agtaacacgt 120
gggcaacctg cctgtaagac tgggataact tcgggaaacc gaactaatac cggataggat 180
cttctccttc atgggagatg attgaaagat ggtttcggct atcacttaca gatgggcccg 240
cggtgcatta gctagttggt gaggtaacgg ctcaccaagg caacgatgca tagccgacct 300
gagagggtga tcggccacac tgggactgag acacggccca gactcctacg ggaggcagca 360
gtagggaatc ttccgcaatg gacgaaagtc tgacggagca acgccgcgtg agtgatgaag 420
gctttcgggt cgtaaaactc tgttgttagg gaagaacaag tacaagagta actgcttgta 480
ccttgacggt acctaaccag aaagccacgg ctaactacgt gccagcagcc gcggtaatac 540
gtaggtggca agcgttatcc ggaattattg ggcgtaaagc gcgcgcaggc ggtttcttaa 600
gtctgatgtg aaagcccacg gctcaaccgt ggagggtcat tggaaactgg ggaacttgag 660
tgcagaagag aaaagcggaa ttccacgtgt agcggtgaaa tgcgtagaga tgtggaggaa 720
caccagtggc gaaggcggct ttttggtctg taactgacgc tgaggcgcga aagcgtgggg 780
agcaaacagg attagatacc ctggtagtcc acgccgtaaa cgatgagtgc taagtgttag 840
agggtttccg ccctttagtg ctgcagctaa cgcattaagc actccgcctg gggagtacgg 900
tcgcaagact gaaactcaaa ggaattgacg ggggcccgca caagcggtgg agcatgtggt 960
ttaattcgaa gcaacgcgaa gaaccttacc aggtcttgac atcctctgac aactctagag 1020
atagagcgtt ccccttcggg ggacagagtg acaggtggtg catggttgtc gtcagctcgt 1080
gtcgtgagat gttgggttaa gtcccgcaac gagcgcaacc cttgatctta gttgccagca 1140
tttagttggg cactctaagg tgactgccgg tgacaaaccg gaggaaggtg gggatgacgt 1200
caaatcatca tgccccttat gacctgggct acacacgtgc tacaatggat ggtacaaagg 1260
gctgcaagac cgcgaggtca agccaatccc ataaaaccat tctcagttcg gattgtaggc 1320
tgcaactcgc ctacatgaag ctggaatcgc tagtaatcgc ggatcagcat gct 1373

<210> SEQ ID NO 56
<211> LENGTH: 1554
<212> TYPE: DNA
<213> ORGANISM: Unknown
<220> FEATURE:
<223> OTHER INFORMATION: Description of Unknown:
DP56 16S rRNA microbial sequence

<400> SEQUENCE: 56
attggagagt ttgatcctgg ctcaggacga acgctggcgg cgtgcctaat acatgcaagt 60
cgagcggacc tgatggagtg cttgcactcc tgatggttag cggcggacgg gtgagtaaca 120
cgtaggcaac ctgccctcaa gactgggata actaccggaa acggtagcta ataccggata 180
atttatttca cagcattgtg gaataatgaa agacggagca atctgtcact tggggatggg 240
cctgcggcgc attagctagt tggtggggta acggctcacc aaggcgacga tgcgtagccg 300
acctgagagg gtgaacggcc acactgggac tgagacacgg cccagactcc tacgggaggc 360
agcagtaggg aatcttccgc aatgggcgaa agcctgacgg agcaacgccg cgtgagtgat 420
gaaggttttc ggatcgtaaa gctctgttgc caaggaagaa cgtcttctag agtaactgct 480
aggagagtga cggtacttga gaagaaagcc ccggctaact acgtgccagc agccgcggta 540
atacgtaggg ggcaagcgtt gtccggaatt attgggcgta aagcgcgcgc aggcggttct 600
ttaagtctgg tgtttaaacc cgaggctcaa cttcgggtcg cactggaaac tggggaactt 660
gagtgcagaa gaggagagtg gaattccacg tgtagcggtg aaatgcgtag atatgtggag 720
gaacaccagt ggcgaaggcg actctctggg ctgtaactga cgctgaggcg cgaaagcgtg 780
gggagcaaac aggattagat accctggtag tccacgccgt aaacgatgaa tgctaggtgt 840
taggggtttc gatacccttg gtgccgaagt taacacatta agcattccgc ctggggagta 900
cggtcgcaag actgaaactc aaaggaattg acggggaccc gcacaagcag tggagtatgt 960
ggtttaattc gaagcaacgc gaagaacctt accaagtctt gacatccctc tgaatcctct 1020
agagatagag gcggccttcg ggacagaggt gacaggtggt gcatggttgt cgtcagctcg 1080
tgtcgtgaga tgttgggtta agtcccgcaa cgagcgcaac ccttgatttt agttgccagc 1140
acatcatggt gggcactcta gaatgactgc cggtgacaaa ccggaggaag gcggggatga 1200
cgtcaaatca tcatgcccct tatgacttgg gctacacacg tactacaatg gctggtacaa 1260
cgggaagcga agccgcgagg tggagccaat cctataaaag ccagtctcag ttcggattgc 1320
aggctgcaac tcgcctgcat gaagtcggaa ttgctagtaa tcgcggatca gcatgccgcg 1380
gtgaatacgt tcccgggtct tgtacacacc gcccgtcaca ccacgagagt ttacaacacc 1440
cgaagtcggt ggggtaaccc gcaagggagc cagccgccga aggtggggta gatgattggg 1500
gtgaagtcgt aacaaggtag ccgtatcgga aggtgcggct ggatcacctc cttt 1554

<210> SEQ ID NO 57
<211> LENGTH: 1550
<212> TYPE: DNA
<213> ORGANISM: Unknown
<220> FEATURE:
<223> OTHER INFORMATION: Description of Unknown:
DP57 16S rRNA microbial sequence

<400> SEQUENCE: 57
attggagagt ttgatcctgg ctcaggatga acgctggcgg cgtgcctaat acatgcaagt 60
cgagcgaatg gattaagagc ttgctcttat gaagttagcg gcggacgggt gagtaacacg 120
tgggtaacct gcccataaga ctgggataac tccgggaaac cggggctaat accggataac 180
attttgcacc gcatggtgcg aaattcaaag gcggcttcgg ctgtcactta tggatggacc 240
cgcgtcgcat tagctagttg gtgaggtaac ggctcaccaa ggcaacgatg cgtagccgac 300
ctgagagggt gatcggccac actgggactg agacacggcc cagactccta cgggaggcag 360
cagtagggaa tcttccgcaa tggacgaaag tctgacggag caacgccgcg tgagtgatga 420
aggctttcgg gtcgtaaaac tctgttgtta gggaagaaca agtgctagtt gaataagctg 480
gcaccttgac ggtacctaac cagaaagcca cggctaacta cgtgccagca gccgcggtaa 540
tacgtaggtg gcaagcgtta tccggaatta ttgggcgtaa agcgcgcgca ggtggtttct 600
taagtctgat gtgaaagccc acggctcaac cgtggagggt cattggaaac tgggagactt 660
gagtgcagaa gaggaaagtg gaattccatg tgtagcggtg aaatgcgtag agatatggag 720
gaacaccagt ggcgaaggcg actttctggt ctgtaactga cactgaggcg cgaaagcgtg 780
gggagcaaac aggattagat accctggtag tccacgccgt aaacgatgag tgctaagtgt 840
tagagggttt ccgcccttta gtgctgaagt taacgcatta agcactccgc ctggggagta 900

```
cggccgcaag gctgaaactc aaaggaattg acgggggccc gcacaagcgg tggagcatgt     960

ggtttaattc gaagcaacgc gaagaacctt accaggtctt gacatcctct gacaacccta    1020

gagatagggc ttccccttcg gggggcagagt gacaggtggt gcatggttgt cgtcagctcg    1080

tgtcgtgaga tgttgggtta agtcccgcaa cgagcgcaac ccttgatctt agttgccatc    1140

attaagttgg gcactctaag gtgactgccg gtgacaaacc ggaggaaggt ggggatgacg    1200

tcaaatcatc atgcccctta tgacctgggc tacacacgtg ctacaatgga cggtacaaag    1260

agctgcaaga ccgcgaggtg gagctaatct cataaaaccg ttctcagttc ggattgtagg    1320

ctgcaactcg cctacatgaa gctggaatcg ctagtaatcg cggatcagca tgccgcggtg    1380

aatacgttcc cgggccttgt acacaccgcc cgtcacacca cgagagtttg taacacccga    1440

agtcggtggg gtaacctttt tggagccagc cgcctaaggt gggacagatg attggggtga    1500

agtcgtaaca aggtagccgt atcggaaggt gcggctggat cacctccttt               1550
```

```
<210> SEQ ID NO 58
<211> LENGTH: 1060
<212> TYPE: DNA
<213> ORGANISM: Unknown
<220> FEATURE:
<223> OTHER INFORMATION: Description of Unknown:
      DP58 16S rRNA microbial sequence

<400> SEQUENCE: 58

aatgacggta cctgaagaat aagcaccggc taactacgtg ccagcagccg cggtaatacg      60

tagggtgcaa gcgttaatcg gaattactgg gcgtaaagcg tgcgcaggcg gttttgtaag     120

tctgatgtga aatccccggg ctcaacctgg gaattgcatt ggagactgca aggctagaat     180

ctggcagagg ggggtagaat tccacgtgta gcagtgaaat gcgtagatat gtggaggaac     240

accgatggcg aaggcagccc cctgggtcaa gattgacgct catgcacgaa agcgtgggga     300

gcaaacagga ttagataccc tggtagtcca cgccctaaac gatgtctact agttgtcggg     360

tcttaattga cttggtaacg cagctaacgc gtgaagtaga ccgcctgggg agtacggtcg     420

caagattaaa actcaaagga attgacgggg acccgcacaa gcggtggatg atgtggatta     480

attcgatgca acgcgaaaaa ccttacctac ccttgacatg gctggaatcc tcgagagatt     540

ggggagtgct cgaaagagaa ccagtacaca ggtgctgcat ggctgtcgtc agctcgtgtc     600

gtgagatgtt gggttaagtc ccgcaacgag cgcaaccctt gtcattagtt gctacgaaag     660

ggcactctaa tgagactgcc ggtgacaaac cggaggaagg tggggatgac gtcaagtcct     720

catggccctt atgggtaggg cttcacacgt catacaatgg tacatacaga gcgccgccaa     780

cccgcgaggg ggagctaatc gcagaaagtg tatcgtagtc cggattgtag tctgcaactc     840

gactgcatga agttggaatc gctagtaatc gcggatcagc atgtcgcggt gaatacgttc     900

ccgggtcttg tacacaccgc ccgtcacacc atgggagcgg gttttaccag aagtaggtag     960

cttaaccgta aggagggcgc ttaccacggt aggattcgtg actggggtga agtcgtaaca    1020

aggtagccgt atcggaaggt gcggctggat cacctccttt                          1060
```

```
<210> SEQ ID NO 59
<211> LENGTH: 1538
<212> TYPE: DNA
<213> ORGANISM: Unknown
<220> FEATURE:
<223> OTHER INFORMATION: Description of Unknown:
      DP59 16S rRNA microbial sequence

<400> SEQUENCE: 59
```

```
ttgaagagtt tgatcatggc tcagattgaa cgctggcggc aggcctaaca catgcaagtc     60

gaacggtaac aggaagcagc ttgctgcttt gctgacgagt ggcggacggg tgagtaatgt    120

ctgggaaact gcctgatgga gggggataac tactggaaac ggtagctaat accgcataac    180

gtcgcaagac caaagagggg gaccttcggg cctcttgcca tcagatgtgc ccagatggga    240

ttagctagta ggtggggtaa cggctcacct aggcgacgat ccctagctgg tctgagagga    300

tgaccagcca cactggaact gagacacggt ccagactcct acgggaggca gcagtgggga    360

atattgcaca atgggcgcaa gcctgatgca gccatgccgc gtgtatgaag aaggccttcg    420

ggttgtaaag tactttcagc ggggaggaag gcgatgcggt taataaccgc gtcgattgac    480

gttacccgca gaagaagcac cggctaactc cgtgccagca gccgcggtaa tacggagggt    540

gcaagcgtta atcggaatta ctgggcgtaa agcgcacgca ggcggtctgt caagtcggat    600

gtgaaatccc cgggctcaac ctgggaactg catccgaaac tggcaggctt gagtctcgta    660

gagggggta gaattccagg tgtagcggtg aaatgcgtag agatctggag gaataccggt    720

ggcgaaggcg gccccctgga cgaagactga cgctcaggtg cgaaagcgtg gggagcaaac    780

aggattagat accctggtag tccacgccgt aaacgatgtc gacttggagg ttgtgccctt    840

gaggcgtggc ttccggagct aacgcgttaa gtcgaccgcc tggggagtac ggccgcaagg    900

ttaaaactca aatgaattga cgggggcccg cacaagcggt ggagcatgtg gtttaattcg    960

atgcaacgcg aagaacctta cctggtcttg acatccacag aacttggcag agatgccttg   1020

gtgccttcgg gaactgtgag acaggtgctg catggctgtc gtcagctcgt gttgtgaaat   1080

gttgggttaa gtcccgcaac gagcgcaacc cttatccttt gttgccagcg gttaggccgg   1140

gaactcaaag gagactgcca gtgataaact ggaggaaggt ggggatgacg tcaagtcatc   1200

atggccctta cgaccagggc tacacacgtg ctacaatggc gcatacaaag agaagcgatc   1260

tcgcgagagc cagcggacct cataaagtgc gtcgtagtcc ggattggagt ctgcaactcg   1320

actccatgaa gtcggaatcg ctagtaatcg tgaatcagaa tgtcacggtg aatacgttcc   1380

cgggccttgt acacaccgcc cgtcacacca tgggagtggg ttgcaaaaga agtaggtagc   1440

ttaaccttcg ggagggcgct taccactttg tgattcatga ctggggtgaa gtcgtaacaa   1500

ggtaaccgta ggggaacctg cggttggatc acctcctt                           1538
```

<210> SEQ ID NO 60
<211> LENGTH: 1547
<212> TYPE: DNA
<213> ORGANISM: Unknown
<220> FEATURE:
<223> OTHER INFORMATION: Description of Unknown:
DP60 16S rRNA microbial sequence

<400> SEQUENCE: 60

```
tcggagagtt tgatcctggc tcaggacgaa cgctggcggc gtgcctaata catgcaagtc     60

gagcgaatcg atgggagctt gctccctgag attagcggcg gacgggtgag taacacgtgg    120

gcaacctgcc tataagactg ggataacttc gggaaaccgg agctaatacc ggatacgttc    180

ttttctcgca tgagagaaga tggaaagacg gttttgctgt cacttataga tgggcccgcg    240

gcgcattagc tagttggtga ggtaatggct caccaaggcg acgatgcgta gccgacctga    300

gagggtgatc ggccacactg ggactgagac acggcccaga ctcctacggg aggcagcagt    360

agggaatctt ccgcaatgga cgaaagtctg acggagcaac gccgcgtgaa cgaagaaggc    420

cttcgggtcg taaagttctg ttgttaggga agaacaagta ccagagtaac tgctggtacc    480
```

-continued

```
ttgacggtac ctaaccagaa agccacggct aactacgtgc cagcagccgc ggtaatacgt    540

aggtggcaag cgttgtccgg aattattggg cgtaaagcgc gcgcaggtgg ttccttaagt    600

ctgatgtgaa agcccacggc tcaaccgtgg agggtcattg gaaactgggg aacttgagtg    660

cagaagagga aagtggaatt ccaagtgtag cggtgaaatg cgtagagatt tggaggaaca    720

ccagtggcga aggcgacttt ctggtctgta actgacactg aggcgcgaaa gcgtggggag    780

caaacaggat tagataccct ggtagtccac gccgtaaacg atgagtgcta agtgttagag    840

ggtttccgcc ctttagtgct gcagctaacg cattaagcac tccgcctggg gagtacggcc    900

gcaaggctga aactcaaagg aattgacggg ggcccgcaca agcggtggag catgtggttt    960

aattcgaagc aacgcgaaga accttaccag gtcttgacat cctctgacaa ccctagagat   1020

agggcgttcc ccttcggggg acagagtgac aggtggtgca tggttgtcgt cagctcgtgt   1080

cgtgagatgt tgggttaagt cccgcaacga gcgcaaccct tgatcttagt tgccagcatt   1140

cagttgggca ctctaaggtg actgccggtg acaaaccgga ggaaggtggg gatgacgtca   1200

aatcatcatg ccccttatga cctgggctac acacgtgcta caatggatgg tacaaagggc   1260

tgcaaacctg cgaaggtaag cgaatcccat aaagccattc tcagttcgga ttgtaggctg   1320

caactcgcct acatgaagcc ggaatcgcta gtaatcgcgg atcagcatgc cgcggtgaat   1380

acgttcccgg gccttgtaca caccgcccgt cacaccacga gagtttgtaa cacccgaagt   1440

cggtgaggta acctttatgg agccagccgc ctaaggtggg acagatgatt ggggtgaagt   1500

cgtaacaagg tagccgtatc ggaaggtgcg gctggatcac ctccttt                 1547


<210> SEQ ID NO 61
<211> LENGTH: 962
<212> TYPE: DNA
<213> ORGANISM: Unknown
<220> FEATURE:
<223> OTHER INFORMATION: Description of Unknown:
      DP61 16S rRNA microbial sequence

<400> SEQUENCE: 61

ggaaggcggt ctgtcaagtc ggatgtgaaa tccccgggct caacctggga actgcattcg     60

aaactggcag gctagagtct tgtagagggg ggtagaattc caggtgtagc ggtgaaatgc    120

gtagagatct ggaggaatac cggtggcgaa ggcggccccc tggacaaaga ctgacgctca    180

ggtgcgaaag cgtggggagc aaacaggatt agataccctg gtagtccacg ccgtaaacga    240

tgtcgacttg gaggttgttc ccttgaggag tggcttccgg agctaacgcg ttaagtcgac    300

cgcctgggga gtacggccgc aaggttaaaa ctcaaatgaa ttgacggggg cccgcacaag    360

cggtggagca tgtggtttaa ttcgatgcaa cgcgaagaac cttacctact cttgacatcc    420

acggaattta gcagagatgc tttagtgcct tcgggaaccg tgagacaggt gctgcatggc    480

tgtcgtcagc tcgtgttgtg aaatgttggg ttaagtcccg caacgagcgc aacccttatc    540

ctttgttgcc agcggtccgg ccgggaactc aaaggagact gccagtgata aactggagga    600

aggtggggat gacgtcaagt catcatggcc cttacgagta gggctacaca cgtgctacaa    660

tggcgcatac aaagagaagc gacctcgcga gagcaagcgg acctcataaa gtgcgtcgta    720

gtccggatcg gagtctgcaa ctcgactccg tgaagtcgga atcgctagta atcgtagatc    780

agaatgctac ggtgaatacg ttcccgggcc ttgtacacac cgcccgtcac accatgggag    840

tgggttgcaa aagaagtagg tagcttaacc ttcgggaggg cgcttaccac tttgtgattc    900

atgactgggg tgaagtcgta acaaggtaac cgtaggggaa cctgcggttg gatcacctcc    960
```

tt 962

<210> SEQ ID NO 62
<211> LENGTH: 876
<212> TYPE: DNA
<213> ORGANISM: Unknown
<220> FEATURE:
<223> OTHER INFORMATION: Description of Unknown:
DP62 16S rRNA microbial sequence

<400> SEQUENCE: 62
tggctcagat tgaacgctgg cggcaggcct aacacatgca agtcgaacgg tagcacagag 60
gagcttgctc cttgggtgac gagtggcgga cgggtgagta atgtctggga aactgcccga 120
tggaggggga taactactgg aaacggtagc taataccgca taacgtcttc ggaccaaagt 180
gggggacctt cgggcctcac accatcggat gtgcccagat gggattagct agtaggtggg 240
gtaatggctc acctaggcga cgatccctag ctggtctgag aggatgacca gccacactgg 300
aactgagaca cggtccagac tcctacggga ggcagcagtg gggaatattg cacaatgggc 360
gcaagcctga tgcagccatg ccgcgtgtat gaagaaggcc ttcgggttgt aaagtacttt 420
cagtggggag gaaggcgtta aggttaataa ccttggcgat tgacgttacc cgcagaagaa 480
gcaccggcta actccgtgcc agcagccgcg gtaatacgga gggtgcaagc gttaatcgga 540
attactgggc gtaaagcgca cgcaggcggt ctgtcaagtc ggatgtgaaa tccccgggct 600
caacctggga actgcattcg aaactggcag gctagagtct tgtagagggg ggtagaattc 660
caggtgtagc ggtgaaatgc gtagagatct ggaggaatac cggtggcgaa ggcggccccc 720
tggacaaaga ctgacgctca ggtgcgaaag cgtggggagc aaacaggatt agataccctg 780
gtagtccacg ccgtaaacga tgtcgacttg gaggttgttc ccttgaggag tggcttccgg 840
agctaacgcg ttaagtcgac cgcctgggga gtacgg 876

<210> SEQ ID NO 63
<211> LENGTH: 1532
<212> TYPE: DNA
<213> ORGANISM: Unknown
<220> FEATURE:
<223> OTHER INFORMATION: Description of Unknown:
DP63 16S rRNA microbial sequence

<400> SEQUENCE: 63
tgaagagttt gatcatggct cagattgaac gctggcggca ggcctaacac atgcaagtcg 60
agcggtagag agaagcttgc ttctcttgag agcggcggac gggtgagtaa tgcctaggaa 120
tctgcctggt agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggcgac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggttgta gattaatact ctgcaatttt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg gatgtgaaat 600
ccccgggctc aacctgggaa ctgcattcaa aactgactga ctagagtatg gtagagggtg 660
gtggaatttc ctgtgtagcg gtgaaatgcg tagatatagg aaggaacacc agtggcgaag 720

```
gcgaccacct ggactaatac tgacactgag gtgcgaaagc gtggggagca aacaggatta    780

gataccctgg tagtccacgc cgtaaacgat gtcaactagc cgttggaagc cttgagcttt    840

tagtggcgca gctaacgcat taagttgacc gcctggggag tacggccgca aggttaaaac    900

tcaaatgaat tgacgggggc ccgcacaagc ggtggagcat gtggtttaat tcgaagcaac    960

gcgaagaacc ttaccaggcc ttgacatcca atgaactttc tagagataga ttggtgcctt   1020

cgggaacatt gagacaggtg ctgcatggct gtcgtcagct cgtgtcgtga gatgttgggt   1080

taagtcccgt aacgagcgca acccttgttc ttagttacca gcacgttatg gtgggcactc   1140

taaggagact gccggtgaca aaccggagga aggtggggat gacgtcaagt catcatggcc   1200

cttacggcct gggctacaca cgtgctacaa tggtcggtac agagggttgc caagccgcga   1260

ggtggagcta atcccataaa accgatcgta gtccggatcg cagtctgcaa ctcgactgcg   1320

tgaagtcgga atcgctagta atcgcgaatc agaatgtcgc ggtgaatacg ttcccgggcc   1380

ttgtacacac cgcccgtcac accatgggag tgggttgcac cagaagtagc tagtctaacc   1440

ttcgggagga cggttaccac ggtgtgattc atgactgggg tgaagtcgta acaaggtagc   1500

cgtaggggaa cctgcggctg gatcacctcc tt                                 1532
```

```
<210> SEQ ID NO 64
<211> LENGTH: 1649
<212> TYPE: DNA
<213> ORGANISM: Unknown
<220> FEATURE:
<223> OTHER INFORMATION: Description of Unknown:
      DP64 ITS microbial sequence

<400> SEQUENCE: 64

tccgtaggtg aacctgcgga aggatcatta aataatcaat aattttggct tgtccattat     60

tatctattta ctgtgaactg tattattact tgacgcttga gggatgctcc actgctataa    120

ggataggcgg tggggatgtt aaccgagtca tagtcaagct taggcttggt atcctattat    180

tatttaccaa aagaattcag aattaatatt gtaacataga cctaaaaaat ctataaaaca    240

acttttaaca acggatctct tggttctcgc atcgatgaag aacgtagcaa agtgcgataa    300

ctagtgtgaa ttgcatattc agtgaatcat cgagtctttg aacgcaactt gcgctcattg    360

gtattccaat gagcacgcct gtttcagtat caaaacaaac cctctattca atatttttgt    420

tgaataggaa tactgagagt ctcttgatct tttctgatct cgaacctctt gaaatgtaca    480

aaggcctgat cttgtttgaa tgcctgaact ttttttaat ataaagagaa gctcttgcgg     540

taaactgtgc tggggcctcc caaataatac tctttttaaa tttgatctga aatcaggcgg    600

gattacccgc tgaacttaag catatcaata agcggaggaa aagaaaataa caatgatttc    660

cctagtaacg gcgagtgaag aggaaagagc tcaaagttgg aaactgtttg gcttagctaa    720

accgtattgt aaactgtaga aacattttcc tggcacgccg gattaataag tcctttggaa    780

caaggcatca tggagggtga gaatcccgtc tttgatccga gtagttgtct tttgtgatat    840

gttttcaaag agtcaggttg tttgggaatg cagcctaaat tgggtggtaa atctcaccta    900

aagctaaata tttgcgagag accgatagcg aacaagtacc gtgagggaaa gatgaaaaga    960

actttgaaaa gagagttaaa cagtatgtga aattgttaaa agggaaccgt ttggagccag   1020

actggtttga ctgtaatcaa cctagaattc gttctgggtg cacttgcagt ctatacctgc   1080

caacaacagt ttgatttgga ggaaaaaatt agtaggaatg tagcctctcg aggtgttata   1140

gcctactatc atactctgga ttggactgag gaacgcagcg aatgccatta ggcgagattg   1200
```

-continued ctgggtgctt tcgctaataa atgttagaat ttctgcttcg ggtggtgcta atgtttaaag 1260
gaggaacaca tctagtatat tttttattcg cttaggttgt tggcttaatg actctaaatg 1320
acccgtcttg aaacacggac caaggagtcc accataagtg caagtatttg agtgacaaac 1380
tcatatgcgt aaggaaactg attgatacga aatcttttga tggcagtatc acccggcgtt 1440
gacgttttat actgaactga ccgaggtaaa gcacttatga tgggacccga aagatggtga 1500
actatgcctg aatagggtga agccagagga aactctggtg gaggctcgta gcgattctga 1560
cgtgcaaatc gatcgtcaaa tttgggtata ggggcgaaag actaatcgaa ccatctagta 1620
gctggttcct gccgaagttt ccctcagga 1649

<210> SEQ ID NO 65
<211> LENGTH: 1498
<212> TYPE: DNA
<213> ORGANISM: Unknown
<220> FEATURE:
<223> OTHER INFORMATION: Description of Unknown:
DP65 ITS microbial sequence

<400> SEQUENCE: 65
tccgtaggtg aacctgcgga aggatcatta ttgaaaacaa gggtgtccaa tttaacttgg 60
aacccgaact tctcaattct aactttgtgc atctgtatta tggcgagcag tcttcggatt 120
gtgagccttc acttataaac actagtctat gaatgtaaaa tttttataac aaataaaaac 180
tttcaacaac ggatctcttg gctctcgcat cgatgaagaa cgcagcgaaa tgcgatacgt 240
aatgtgaatt gcagaattca gtgaatcatc gaatctttga acgcatcttg cgctctctgg 300
tattccggag agcatgtctg tttgagtgtc atgaattctt caacccaatc ttttcttgta 360
atcgattggt gtttggattt tgagcgctgc tggcttcggc ctagctcgtt cgtaatacat 420
tagcatccct aatacaagtt tggattgact tggcgtaata gactattcgc taaggattcg 480
gtggaaacat cgagccaact tcattaagga agctcctaat ttaaaagtct accttttgat 540
tagatctcaa atcaggcagg attacccgct gaacttaagc atatcaataa gcggaggaaa 600
agaaactaac aaggattccc ctagtagcgg cgagcgaagc gggaaaagct caaatttgta 660
atctggcgtc ttcgacgtcc gagttgtaat ctcgagaagt gttttccgtg atagaccgca 720
tacaagtctc ttggaacaga gcgtcatagt ggtgagaacc cagtacacga tgcggatgcc 780
tattactttg tgatacactt tcgaagagtc gagttgtttg ggaatgcagc tcaaattggg 840
tggtaaattc catctaaagc taaatattgg cgagagaccg atagcgaaca agtaccgtaa 900
gggaaagatg aaaagcactt tggaaagaga gttaacagta cgtgaaattg ttggaaggga 960
aacacatgca gtgatacttg ctattcgggg caactcgatt ggcaggcccg catcagtttt 1020
tcggggcgga aaagcgtaga gagaaggtag caatttcggt tgtgttatag ctctttactg 1080
gattcgccct gggggactga ggaacgcagc gtgcttttag caattccttc gggaattcca 1140
cgcttaggat gcgggtttat ggctgtatat gacccgtctt gaaacacgga ccaaggagtc 1200
taacatgctt gcgagtattt gggtgtcaaa cccggatgcg caatgaaagt gaatggaggt 1260
gggaagcgca agctgcacca tcgaccgatc tggatttttt aagatggatt tgagtaagag 1320
caagtatgtt gggacccgaa agatggtgaa ctatgcctga atagggcgaa gccagaggaa 1380
actctggtgg aggctcgtag cggttctgac gtgcaaatcg atcgtcaaat ttgggtatag 1440
gggcgaaaga ctaatcgaac catctagtag ctggttcctg ccgaagtttc cctcagga 1498

<210> SEQ ID NO 66

<211> LENGTH: 1340
<212> TYPE: DNA
<213> ORGANISM: Unknown
<220> FEATURE:
<223> OTHER INFORMATION: Description of Unknown:
DP66 ITS microbial sequence

<400> SEQUENCE: 66

```
tccgtaggtg aacctgcgga aggatcatta ctgtgattta tccaccacac tgcgtgggcg     60
acacgaaaca ccgaaaccga acgcacgccg tcaagcaaga aatccacaaa actttcaaca    120
acggatctct tggttctcgc atcgatgaag agcgcagcga aatgcgatac ctagtgtgaa    180
ttgcagccat cgtgaatcat cgagttcttg aacgcacatt gcgcccgctg gtattccggc    240
gggcatgcct gtctgagcgt cgtttccttc ttggagcgga gcttcagacc tggcgggctg    300
tctttcggga cggcgcgccc aaagcgaggg gccttctgcg cgaactagac tgtgcgcgcg    360
gggcggccgg cgaacttata ccaagctcga cctcagatca ggcaggagta cccgctgaac    420
ttaagcatat caataagcgg aggaaaagaa accaacaggg attgccccag tagcggcgag    480
tgaagcggca aaagctcaga tttggaatcg cttcggcgag ttgtgaattg caggttggcg    540
cctctgcggc ggcggcggtc caagtccctt ggaacagggc gccattgagg gtgagagccc    600
cgtgggaccg tttgcctatg ctctgaggcc cttctgacga gtcgagttgt ttgggaatgc    660
agctctaagc gggtggtaaa ttccatctaa ggctaaatac tggcgagaga ccgatagcga    720
acaagtactg tgaaggaaag atgaaaagca ctttgaaaag agagtgaaac agcacgtgaa    780
attgttgaaa gggaagggta ttgcgcccga catggagcgt gcgcaccgct gcccctcgtg    840
ggcggcgctc tgggcgtgct ctgggccagc atcggttttt gccgcgggag aagggcggcg    900
ggcatgtagc tcttcggagt gttatagcct gccgccggcg ccgcgagcgg ggaccgagga    960
ctgcgacttt tgtctcggat gctggcacaa cggcgcaaca ccgccccgtct tgaaacatgg   1020
accaaggagt ctaacgtcta tgcgagtgtt tgggtgtgaa accccgggcg cgtaatgaaa   1080
gtgaacgtag gtcggaccgc tcctctcggg gggcgggcac gatcgaccga tcctgatgtc   1140
ttcggatgga tttgagtaag agcatagctg ttgggacccg aaagatggtg aactatgcct   1200
gaatagggtg aagccagagg aaactctggt ggaggctcgt agcggttctg acgtgcaaat   1260
cgatcgtcga atttgggtat aggggcgaaa gactaatcga accatctagt agctggttcc   1320
tgccgaagtt tccctcagga                                                1340
```

<210> SEQ ID NO 67
<211> LENGTH: 1698
<212> TYPE: DNA
<213> ORGANISM: Unknown
<220> FEATURE:
<223> OTHER INFORMATION: Description of Unknown:
DP53 Glutamine--tRNA ligase microbial sequence

<400> SEQUENCE: 67

```
atgagcaagc ccactgtcga ccccactctg aatccaaagg ctggccctgc tgtcccggct     60
aacttcctgc gtccaatcgt tcaggcggac ctagactcgg gtaaatacac acagatcgtg    120
acccgctttc cgccggagcc aaacggctat ctgcacatcg gtcatgccaa atccatttgt    180
gtgaactttg ggctggctca agagtttggc ggcgtgacgc atttgcgttt tgacgacacc    240
aacccggcaa aagaagacca ggaatacatc gacgccatcg aaagcgacgt caagtggctg    300
ggcttcgagt gggccggtga agtgcgttac gcgtcgcaat acttcgatca actgcacgag    360
tgggcgattt acctgatcaa agaaggcaag gcctacgtct gcgacctgac gcccgagcaa    420
```

gccaaggaat accgtggcag cctgaccgag cccggcaaga acagcccgtt ccgcgaccgt 480
agcgttgaag agaacctgga tctgttcgcc cgcatgaccg ccggtgagtt tgaagacggc 540
aagcgtgtgc tgcgcgccaa gatcgacatg acctcgccga acatgaacct gcgcgacccg 600
atcatgtacc gcatccgtca tgcccatcac caccagaccg gtgacaagtg gtgcatctac 660
cccaactatg acttcaccca cggtcagtcg gatgccattg aaggcatcac ccattcgatc 720
tgcaccctgg agttcgaaag ccatcgtccg ctgtacgaat ggttcctgga cagcctgcca 780
gtaccggcgc gcccgcgtca gtacgagttc agccgtctga acctcaacta caccatcacc 840
agcaagcgca agctcaagca gctggtcgat gaaaagcacg tcaacggctg ggatgacccg 900
cgcatgtcga cgctgtcggg tttccgccgt cgcggttaca cgcctaaatc gattcgtaat 960
ttctgtgaca tggtcggcac caaccgttct gacggtgttg ttgacttcgg catgctggaa 1020
ttcagcattc gtgacgattt ggaccacagc gcgccgcgcg ccatgtgcgt gctgcgtcca 1080
ttgaaggtga ttattaccaa ctacccggaa ggtcaggtcg aaaacctcga gctgccttgc 1140
cacccgaaag aagacatggg tgtgcgggtg ttgccgtttg cccgtgaaat ctacatcgac 1200
cgtgaagact tcatggaaga gccgccaaaa ggctacaagc gtcttgagcc tgcgggcgaa 1260
gtgcgtttgc gcggcagcta tgtgatccgt gccgacgaag cgatcaagga tgccgatggc 1320
aacatcgttg aactgcattg ctcgtacgat ccgctgaccc tgggtaaaaa ccctgaaggt 1380
cgcaaggtca agggtgttgt gcactgggtg ccggcggcgg ccagcgtcga atgcgaagtg 1440
cgtttgtatg atcgtctgtt ccgctcgccg aaccctgaaa aggccgaaga cggcgcgggc 1500
ttcctggaaa acatcaaccc tgactcgctg caggtactga ccggttgtcg tgctgaaccc 1560
tcgctgggca atgcacagcc ggaagaccgt ttccagttcg agcgcgaagg ctacttctgc 1620
gcagatatca aggactcgaa acccggtcac ccggtattca accgtaccgt gaccctgcgt 1680
gattcgtggg gccagtga 1698

<210> SEQ ID NO 68
<211> LENGTH: 2418
<212> TYPE: DNA
<213> ORGANISM: Unknown
<220> FEATURE:
<223> OTHER INFORMATION: Description of Unknown:
DP53 DNA gyrase subunit B microbial sequence

<400> SEQUENCE: 68
ttgagcgaag aaaacacgta cgactcaacg agcattaaag tgctgaaagg ccttgatgcc 60
gtacgcaaac gtcccggtat gtacattggt gatactgacg atggcagcgg tctgcaccac 120
atggtgttcg aagtagtcga caactccatc gacgaagcgc tggctggcca ttgcgacgac 180
atcaccatca cgatccaccc ggacgagtcc atcaccgtgc gcgataacgg ccgcggtatt 240
ccggttgacg tgcataaaga agaaggcgta tctgcagccg aggtcatcat gaccgtgctg 300
cacgccggcg gtaagttcga tgacaactcc tacaaagtat ccggcggctt gcacggtgta 360
ggtgtttcgg tggtaaacgc cctgtccgaa ctgctggtct tgactgtacg ccgcagcggc 420
aagatctggg aacagaccta cgtccacggt gttcctcagg cgcctatggc tattgtgggt 480
gaaagcgaaa ccacgggtac gcagatccac ttcaagcctt cggctgaaac cttcaagaat 540
atccacttta gctgggacat cctggccaag cggattcgtg aactgtcctt cctgaactcc 600
ggtgtgggta tcgtcctcaa ggacgagcgc agcggcaagg aggagctgtt caagtacgaa 660
ggtggcctgc gtgcattcgt tgattacctg aacaccaaca agaacgctgt gaaccaggtg 720

```
ttccacttca atgttcagcg tgaagacggc atcggcgtag aaatcgccct gcagtggaac    780

gacagcttca acgagaacct gttgtgcttc accaacaaca ttccacagcg cgatggtggc    840

acgcacttgg tgggcttccg ctctgccctg acgcgtaacc tcaacacgta catcgaagct    900

gaaggcctgg ccaagaagca caaggtcgcc accaccggtg atgacgcccg tgaaggcttg    960

accgcgatca tctcggtgaa agtgccggat ccaaagttca gctcgcagac taaagacaag   1020

ctggtgtctt ccgaagtgaa gaccgctgtt gaacaggaaa tgggcaagtt cttctccgac   1080

ttcctgctgg aacacccgaa cgaagccaag ttgattgtcg gcaagatgat cgacgcagcc   1140

cgtgctcgtg aagctgcacg taaagcccgt gagatgaccc gtcgtaaagg cgcgttggac   1200

atcgcgggct tgccgggcaa gctggctgac tgccaggaaa aagaccctgc tctgtccgaa   1260

ctgtacctgg tggaaggtga ctctgctggc ggctccgcca agcagggtcg caaccgtcgt   1320

acccaagcca tcctgccgtt gaaaggtaaa atcctcaacg tcgagaaagc ccgttttgac   1380

aagatgatct cttcgcaaga agtcggcacc ttgatcactg cgctgggctg tggcatcggc   1440

cgcgaagagt acaacatcga caaactgcgc tatcacaaca tcatcatcat gaccgatgct   1500

gacgttgacg gttcgcacat ccgtaccctg ctgctgacct tcttcttccg tcagttgccg   1560

gagctgatcg agcgtggcta catctacatc gcccagccac cgttgtacaa agtgaaaaag   1620

ggcaagcaag agcagtacat caaagacgac gaggccatgg aagagtacat gacccagtcg   1680

gctcttgaag atgccagcct gcacttgaac gaagatgccc ctggcatctc cggtgaggca   1740

ctggagcgtc tggtgtacga cttccgcatg gtgatgaaga ccctcaagcg tttgtcgcgc   1800

ctgtaccctc aggagctgac cgagcacttc atctacctgc cggctgtaag ccttgagcag   1860

ttgggtgacc acgctgccat gcaggactgg atggccaagt ttgaagagcg tctgcgtctg   1920

gttgagaaat cgggcctggt ctacaaagcc agcctgcgtg aagaccgtga gcgtaatgtc   1980

tggttgccag aggtcgaact gatctcccac ggccactcga cgttcatcac cttcaaccgc   2040

gacttcttcg gcagcaacga ttacaaaacc gttgtgaccc tgggcgctca actgagcacc   2100

ctgctggatg aaggcgccta tatccagcgt ggcgaacgtc gcaagcaagt gaccgagttc   2160

aaagaagcac tggactggtt gatggctgaa agcaccaagc gtcacaccat ccagcgctac   2220

aaaggactgg gtgaaatgaa cccggatcag ctctgggaaa ccacgatgga cccaagcgtg   2280

cgtcgcatgc tgaaagtcac catcgaagac gcgatcggcg ccgatcagat cttcaacacc   2340

ttgatgggcg atgctgtaga accacgtcgt gaattcatcg agagcaacgc actggcagtg   2400

tccaacctgg atttctga                                                 2418
```

```
<210> SEQ ID NO 69
<211> LENGTH: 2832
<212> TYPE: DNA
<213> ORGANISM: Unknown
<220> FEATURE:
<223> OTHER INFORMATION: Description of Unknown:
      DP53 Isoleucine--tRNA ligase microbial sequence

<400> SEQUENCE: 69

atgaccgact acaaagccac gctaaacctc ccggacaccg ccttcccaat gaaggccggc     60

ctgccacagc gcgaaccgca aattttgcag cgctgggaca gcattggcct gtacgggaag    120

ttgcgcgaga ttggcaagga tcgtccgaag ttcgtacttc acgacggtcc tccgtacgcc    180

aacggcacta tccatatcgg tcatgcgctg aacaagattc tgaaagacat gatcatccgc    240

tccaagaccc tgtcgggttt tgacgcgccg tatgtgccgg gctgggattg ccatggtttg    300
```

```
ccgattgaac acaaggtcga agtgacccac ggtaaaaacc tgagcgcgga taaaacccgc    360
gagctgtgcc gtgcctacgc caccgagcag atcgaggggc agaagtccga gttcatccgt    420
ctgggtgtgc tgggtgattt cgccaacccg tacaagacca tggacttcaa aaacgaagcc    480
ggtgaaatcc gtgctttggc tgagatcgtc aagggcggtt ttgtgttcaa gggcctcaag    540
ccggtgaact ggtgcttcga ttgcggttcg gccctggctg aagctgaagt tgaataccag    600
gacaagaagt ctgcggccat cgacgttgcc ttcccggttg ccgacgaggc caagctggcc    660
gaggcctttg gtctggcggc actgagcaaa cctgcttcga tcgtgatctg gaccaccacc    720
ccgtggacca ttccggccaa ccaggcgctt aacgtacacc cggaattcac ctacgcgctg    780
gtcgacgtgg gcgacaagtt gctggtactg gctgaagaac tggtcgaatc gagtctggcg    840
cgttacaacc tgcagggttc ggtcatcgcc accaccactg gctcagcgct tgaactaatc    900
aacttccgtc acccgttcta tgaccgtctg tcgcctgttt atctggccga ctacgttgag    960
ctgggtgctg gcactggtgt ggttcactcg gctccagcct acggcgtaga cgacttcgtg   1020
acctgcaaag cctatggcat ggtcaacgac gacatcatca acccggtgca aagcaatggc   1080
gtttacgtgc cgtcgctgga gttcttcggt ggccagttca tctggaaggc caaccagaac   1140
atcatcgaca agctgatcga agtcggttcg ctgatgttca ccgagaccat cagccacagc   1200
tatatgcact gctggcgcca caagacgccg ctgatctacc gtgccaccgc ccagtggttt   1260
atcggtatgg acaagcagcc gactgatggc gataccttgc gcacccgtgc gctgcaagcg   1320
atcgaagaca cccagttcgt tccggcctgg ggtcaggcgc gcctgcactc gatgatcgcc   1380
aaccgcccgg actggtgcat ctcgcgtcaa cgcaactggg gcgtgccgat cccgtttttc   1440
ctgaacaagg aaagcggcga gctgcacccg cgcaccgtcg aaatgatgga agaagtggcc   1500
aagcgcgttg aagtcgaagg catcgaggcg tggttcaagc tggatgctgc cgagctgctg   1560
ggcgacgaag cgccgctgta cgacaagatc agcgataccc tcgacgtctg gttcgattcg   1620
ggcaccacgc actggcatgt ccttcgcggt tcgcacccga tgggtcatga aaccggccca   1680
cgcgctgatc tctaccttga aggctccgac cagcaccgtg gctggttcca ctcgtcgttg   1740
ctgaccggtt gcgccatcga caaccacgcg ccgtaccgcg agctgctgac ccacggtttt   1800
accgtggacg aagcgggccg caagatgtcc aagtcgctgg gcaacgtgat tgcaccgcaa   1860
aaggtcaacg acaccctggg cgccgacatc atgcgtctgt gggttgcttc gaccgactac   1920
tcgggcgaaa tcgcggtttc cgaccagatc ctgcagcgca gtgcggacgc ctaccgacgt   1980
atccgcaata ccgcacgctt cctgctgtcg aacctgaccg gtttcaatcc agccaccgac   2040
atcctgcctg ccgaagaaat gctggcactg gaccgctggg cggtggatcg tgcgttgctg   2100
ctgcaacgtg agctggagct gcattacggc gaataccgtt tctggaacgt gtactccaag   2160
gtgcacaact tctgcgttca ggagctgggc ggtttctatc tcgacatcat caaggaccgc   2220
cagtacacca ccggcgccaa cagcaaggct cgccgttcgt gccagaccgc gctgttccac   2280
atctctgaag cgctggtgcg ctggatcgct ccgatcctgg cgttcaccgc tgatgagttg   2340
tggcagtacc tgccgggcga gcgcaacgaa tcggtcatgc tcaacacctg gtacgaaggc   2400
ctgactgaac tgccggaagg caccgaactg gatcgcgcct actgggagcg aatcatggcg   2460
gtcaaggttg cggtcaacaa ggaaatggaa aacttgcgcg cagccaaggc cattggcggt   2520
aacttgcaag cagaagtgac cttgttcgcc gaagatcagc tggctgctga tttgtccaag   2580
ttgagcaacg aactgcgttt cgtgttgatc acctccactg ccagcgttgc gccttttgcg   2640
```

caggctccag cagatgccgt ggttaccgaa gtggctggcc tcaaactcaa ggtggtcaag 2700
tcggcccatg ccaagtgcgc ccgttgctgg cactgccgtg aagacgtcgg cgttaacccc 2760
gagcaccctg aaatctgcgg tcgttgtgta gacaatatca gcggcgctgg tgaggtacgt 2820
cactatgcct aa 2832

<210> SEQ ID NO 70
<211> LENGTH: 1785
<212> TYPE: DNA
<213> ORGANISM: Unknown
<220> FEATURE:
<223> OTHER INFORMATION: Description of Unknown:
DP53 NADH-quinone oxidoreductase subunit C/D
microbial sequence

<400> SEQUENCE: 70
atgactgcag gctccgctct gtacatcccg ccttacaagg ctgacgacca agatgtggtt 60
gtcgaactca atacccgttt tggccctgag gcgttcaccg cccaggccac gcgcaccggc 120
atgccggtgc tttgggttag ccgcgcaaaa ctggtcgaag tactgacctt cctgcgcaac 180
ctgccaaaac cctacgtcat gctctatgac ctgcacggtg tggacgaacg tctgcgtacc 240
aagcgtcagg gcctgccatc gggtgcagac ttcaccgtct tctaccacct gatgtcgctg 300
gaacgtaaca gcgacgtcat gatcaaggtg gccctgtctg aaaaagacct gagtgtccct 360
accgtgaccg gtatctggcc gaacgccaac tggtacgagc gtgaagtctg ggacatgttc 420
ggcatcgatt tcaaaggcca cccgcacctg tcgcgcatca tgatgccgcc gacctgggaa 480
ggtcacccgc tgcgcaagga cttcccggcc cgtgccacag agttcgatcc gtacagcctg 540
accctggcca aggtgcagct ggaagaggaa gccgcgcgct tccgcccgga agactggggc 600
atgaaacgct ccggtgaaaa cgaggactac atgttcctca acctgggccc taaccaccct 660
tcggctcacg gtgccttccg catcatcctg cagctggacg gtgaagagat cgtcgactgc 720
gtgcctgacg tcggttacca ccaccgtggc gccgagaaaa tggccgaacg ccagtcctgg 780
cacagtttca tcccgtacac cgaccggatc gattacctcg gcggagtgat gaacaacctg 840
ccgtacgtgc tctcggtcga gaagctggcc ggtatcaaag tgccggatcg ggtcgacacc 900
atccgcatca tgatggccga attcttccgt atcaccagcc acctgctgtt cctgggtacc 960
tatatccagg acgtgggcgc catgaccccg gtgttcttca cgttcaccga ccgtcagcgc 1020
gcttacaagg tgatcgaggc catcaccggt ttccgtctgc acccggcctg gtaccgcatc 1080
ggcggcgttg cccacgacct gccgaacggc tgggatcgcc tggtcaagga attcatcgac 1140
tggatgccca agcgtctgga cgagtaccag aaagccgctc tggacaacag catcctgcgt 1200
ggtcgtacca tcggcgttgc cgcctacaac accaaagagg ccctggaatg gggcgtcacc 1260
ggtgccggcc tgcgctccac cggttgtgac ttcgatatcc gcaaggcgcg cccgtattcc 1320
ggctacgaga acttcgaatt cgaagtcccg ctggcagcca acggcgatgc ctacgatcgt 1380
tgcatcgtgc gcgtcgaaga aatgcgccag agcctgaaaa tcatcgagca gtgcatgcgc 1440
aacatgccgg ccggcccgta caaggcggat cacccgctga ccacgccgcc gcctaaagaa 1500
cgcacgctgc agcatatcga gaccttgatc acgcacttcc tgcaagtttc gtggggcccg 1560
gtgatgccgg ccaacgaatc cttccagatg atcgaagcga ccaagggcat caacagttat 1620
tacctgacga gcgatggcgg caccatgagc taccgcaccc ggattcgcac cccaagcttc 1680
ccgcacctgc aacagatccc ttcggtgatc aaaggtgaaa tggtcgcgga cttgattgcg 1740
tacctgggta gtatcgattt cgttatggcc gacgtggacc gctaa 1785

<210> SEQ ID NO 71
<211> LENGTH: 1119
<212> TYPE: DNA
<213> ORGANISM: Unknown
<220> FEATURE:
<223> OTHER INFORMATION: Description of Unknown:
DP53 Protein RecA microbial sequence

<400> SEQUENCE: 71
atggacgaca acaagaagaa agccttggct gcggccctgg gtcagatcga acgtcaattc 60
ggcaagggtg ccgtgatgct gatgggcgac caggagcgtc aggcagtccc ggcgatctcc 120
accggctccc tgggtctgga catcgcactg ggcattggcg gtctgccaaa aggccgtatt 180
gttgaaatct acggccctga gtcgtcgggt aaaaccacac tgaccctgtc cgtgattgcc 240
caggcgcaaa aggccggtgc tacctgcgcc ttcgtcgatg ccgagcacgc ccttgatcct 300
gagtacgctg ccaaactggg cgtaaacgtt gatgacctgc tggtttcaca gcctgacacc 360
ggcgaacagg cactggaaat caccgatatg ctggtgcgtt ccaatgcggt tgacgtgatc 420
atcatcgact ccgttgctgc actgacgcca aaagctgaaa tcgaaggcga catgggcgat 480
acccacgttg gcctgcaagc ccgtctgatg tcgcaagcgc tgcgtaaaat caccggtaac 540
atcaagaacg ccaactgcct ggttatcttc atcaaccaga tccgcatgaa aatcggcgtg 600
atgttcggca gccctgaaac caccaccggt ggtaacgcac tgaagttcta cgcttcggta 660
cgtctggata tccgccgcac cggcgccgta aaagaaggcg atgtggtggt gggtagcgaa 720
acccgcgtga aagtggtcaa gaacaaggtg gcaccaccgt tccgtcaggc tgaattccag 780
atcctgtacg gcaagggtat ctacctgaac ggtgaaatga ttgacctggg cgtactgcat 840
ggctttgttg aaaaagctgg cgcctggtac agctacaacg gcagcaaaat cggtcagggc 900
aaggccaact ccgccaagtt cctggacgat aacccggaca tcaaggatgc gctggagaag 960
cagctgcgtg agaagttgct cgggccaaaa accgatgccg aactggcagc gacggactgc 1020
aatggacctg ctcgcgcgac gcgagcacgg tcgagtcgag ctgacgcgca agttgcgtca 1080
gcgcggcgct tgccccgaca tgatcgacgc tgcccttga 1119

<210> SEQ ID NO 72
<211> LENGTH: 1848
<212> TYPE: DNA
<213> ORGANISM: Unknown
<220> FEATURE:
<223> OTHER INFORMATION: Description of Unknown:
DP53 RNA polymerase sigma factor RpoD microbial sequence

<400> SEQUENCE: 72
atgtccggaa aagcgcaaca gcagtctcgt atcaaagagt tgatcaccct cggccgtgag 60
cagaagtatc tgacttacgc agaggtcaac gaccacctgc ccgaagatat ttcagatccg 120
gagcaagtgg aagacatcat ccgcatgatt aatgacatgg ggatccccgt acacgagagt 180
gctccggatg cggacgccct tatgttggcc gatgccgaca ccgacgaagc agcagctgaa 240
gaagcggctg cagcgttggc ggcagtagag accgacattg gtcgtactac cgaccctgtg 300
cgcatgtata tgcgtgaaat gggcacggta gaactgctga cacgtgaagg cgaaatcgaa 360
atcgccaagc gtatcgaaga aggcatccgt gaagtgatgg gcgcaatcgc gcacttccct 420
ggcacggttg accatattct ctccgagtac actcgcgtca ccaccgaagg tggccgcctg 480
tccgacgttc tgagcggtta tatcgacccg gacgacggta ttgcgccgcc cgcagccgaa 540

```
gtacctcctc ctgtcgacac caaggtgaaa gccgaaggtg atgacgaaga ggacgacaag    600

gaagattccg gcgaagacga ggaagaggtc gaaagcggcc ctgatccgat catcgcggcc    660

cagcgctttg gcgctgtttt cgatcagatg gaaatcgctc gcaaggccct gaaaaagcac    720

ggtcgcggca gcaagcaggc aattgccgag ctggttgcac tggctgagct gttcatgccg    780

atcaaactgg ttccgaagca attcgaaggc ctggttgagc gtgttcgcag cgccctggag    840

cgtctgcgtg cacaagagcg cgcaatcatg cagctgtgtg tacgtgatgc acgcatgccg    900

cgcaccgatt tcctgcgtct gttcccgggc aacgaagtcg acgaaagctg gagcgatgcg    960

ctggccaaag gcaaaagcaa atatgctgaa gccattggtc gcctgcaacc ggacatcatc   1020

cgttgccagc aaaagctctc tgctctggaa gcagaaaccg gcttgaagat tgccgagatc   1080

aaggacatca accgtcgcat gtcgatcggc gaggccaagg cccgccgcgc gaagaaagaa   1140

atggttgaag ccaacttgcg tctggtgatc tccatcgcca agaagtacac caaccgtggc   1200

ctgcagttcc tcgatctgat ccaggaaggc aacatcggct tgatgaaagc ggtagacaag   1260

tttgaatacc gccgcggcta caaattctcg acttatgcca cctggtggat ccgtcaggcg   1320

atcactcgct cgatcgccga ccaggcccgc accatccgta ttccggtgca catgatcgag   1380

acgatcaaca agctcaaccg tatttcccgt cagatgttgc aggaaatggg ccgtgaaccg   1440

accccggaag agctgggcga acgcatggaa atgcctgagg ataaaatccg caaggtattg   1500

aagatcgcta aagagccgat ctccatggaa accccgatcg gtgatgacga agactcccat   1560

ctgggtgact tcatcgaaga ctcgaccatg cagtcgccaa tcgatgttgc taccgttgag   1620

agccttaaag aagcgacacg cgacgtactc ggcggcctca cagcccgtga agccaaggta   1680

ctgcgcatgc gtttcggtat cgacatgaat accgaccaca cccttgagga ggttggtaaa   1740

cagttcgacg ttacccgtga gcggattcgt cagatcgaag ccaaggcgct gcgcaagctg   1800

cgccacccga cgagaagcga gcatttgcgc tccttcctcg acgagtga                1848
```

<210> SEQ ID NO 73
<211> LENGTH: 4073
<212> TYPE: DNA
<213> ORGANISM: Unknown
<220> FEATURE:
<223> OTHER INFORMATION: Description of Unknown:
DP53 DNA-directed RNA polymerase subunit beta
microbial sequence

<400> SEQUENCE: 73

```
atggcttact catatactga gaaaaaacgt atccgcaagg actttagcaa gttgccggac     60

gtcatggatg tgccgtatct cttggcaatc cagctggatt cgtatcgtga attcttgcag    120

gcgggagcga ctaaagatca gttccgcgac gtgggcctgc atgcggcctt caaatccgtt    180

ttcccgatca tcagctactc cggcaatgct gcgctggagt acgtcggtta tcgcttgggc    240

gaaccggcat ttgatgtcaa agaatgcgtg ttgcgtggcg taacgtacgc cgtacctttg    300

cgggtaaaag ttcgtttgat cattttcgac aaagaatcgt cgaacaaagc gatcaaggac    360

atcaaagagc aagaagtcta catgggtgaa atccccctga tgactgaaaa cggtaccttc    420

gtaatcaacg gtaccgagcg tgtaattgtt tcccagctgc accgttcccc gggcgtgttc    480

tttgccacga ccgcggcaag acgcacagct ccggtaagct gctttattcc gcgcgtatca    540

ttccttaccg tggttcgtgg ctcgacttcg agttcgaccc gaaagactgc gtgttcgtgc    600

gtattgaccg tcgtcgcaag ctgcctgcat cggtattgct gcgcgcgctg ggttatacca    660

ctgagcaagt gctggacgcg ttctacacca ccaacgtgtt ccacgttcag ggtgagagca    720
```

-continued

```
tcagcctgga gctggttcca cagcgtctgc gcggtgaaat cgcggccatc gacattaccg    780
atgacaaagg caaggtgatt gttgagcagg gtcgtcgtat cactgctcgt catatcaacc    840
agctggaaaa agccggtgtc aaagagctcg ttatgcctct ggactatgtc ctgggtcgca    900
caacggccaa ggctatcgtg catccggcta ctggcgaaat cattgctgag tgcaacaccg    960
agctgaccac tgaaatcctg gcaaaagttg ccaagggcca ggttgttcgc atcgaaacgt   1020
tgtacaccaa cgatatcgac tgcggtccgt tcgtctccga cacgctgaag atcgactcca   1080
ccagcaacca actggaagcg ctggtcgaaa tctatcgcat gatgcgtcca ggcgagccgc   1140
caaccaaaga cgctgccgag actctgttca acaacctgtt cttcagccct gagcgctatg   1200
acctgtctgc ggtcggccgg atgaagttca accgtcgtat cggtcgtacc gagatcgaag   1260
gttcgggcgt gttgtgcaaa gaagacatcg ttgccgtgct gaagaccctg gtcgacatcc   1320
gtaacggtaa aggcatcgtc gatgacatcg accacctggg taaccgtcgt gttcgctgtg   1380
taggcgaaat ggccgagaac cagttccgcg ttggcctggt acgtgttgag cgtgcggtca   1440
aagagcgtct gtcgatggct gaaagcgaag gcctgatgcc gcaagacctg atcaacgcca   1500
agcctgtggc tgcggcggtg aaagagttct tcggttccag ccagctgtcc cagttcatgg   1560
accagaacaa ccctctgtcc gagatcaccc acaagcgccg tgtttctgca ctgggcccgg   1620
gcggtctgac gcgtgagcgt gcgggctttg aagttcgtga cgtacacccg actcactacg   1680
gccgtgtttg ccctattgag acgccggaag gtccgaacat cggtctgatc aactccctgg   1740
ctgcctatgc gcgcaccaac cagtacggct tcctcgagag cccgtaccgt gtagtgaaag   1800
acgcactggt aactgacgag atcgttttcc tgtccgccat cgaagaagct gatcacgtga   1860
tcgctcaggc ctcggccacg atgaacgaca agaaagtgct gatcgacgag ctggttgctg   1920
ttcgtcactt gaacgaattc accgtcaagg cgccggaaga cgtcaccttg atggacgttt   1980
cgccgaagca ggttgtttcg gttgcagcgt cgctgatccc gttcctggaa cacgatgacg   2040
ccaaccgtgc gttgatgggt tccaacatgc agcgtcaagc tgtaccaacc ctgcgcgctg   2100
acaagccgct ggtaggtacc ggcatggagc gtaacgtagc tcgtgactcc ggcgtttgcg   2160
tcgtggctcg tcgtggcggc gtgatcgact ctgttgatgc cagccgtatc gtggttcgtg   2220
ttgctgatga cgaagttgaa actggcgaag ccggtgtcga catctacaac ctgaccaaat   2280
acacccgttc caaccagaac acttgcatca accagcgtcc gctggtgcgc aagggtgacc   2340
gtgtacagcg tagcgacatc atggctgacg gcccgtccac cgatatgggt gaactggcgc   2400
tgggtcaaaa catgcgcatc gcgttcatgg cctggaacgg ttacaacttc gaagactcca   2460
tctgcttgtc ggaacgagtt gttcaagaag accgctttac cacgatccac attcaggaac   2520
tgacctgtgt ggcacgtgac accaagcttg ggcctgaaga gatcactgca gacatcccta   2580
acgtgggtga agctgcactg aacaaactgg acgaagccgg tatcgtttac gtaggtgctg   2640
aagttggcgc cggcgacatt ctggtaggta aggtcactcc gaaaggcgag acccagctga   2700
ctccggaaga gaagctgttg cgtgccatct tcggtgaaaa agccagcgac gttaaagaca   2760
cctccctgcg cgtacctacc ggtaccaaag gtactgttat cgacgtgcag gtcttcaccc   2820
gtgacggcgt tgagcgtgat gctcgtgcac tgtcgatcga gaagacccag ctggacgaga   2880
tccgcaagga tctgaacgaa gagttccgta tcgttgaagg cgctaccttc gaacgtctgc   2940
gctctgctct ggttggccgc attgccgaag gtggtgccgg tctgaagaaa ggtcaggaaa   3000
tcaccaatga aatcctggac ggtcttgagc atggtcagtg gttcaaactg cgcatggctg   3060
```

-continued aagatgctct gaacgagcag cttgaaaagg ctcaggctta catcatcgat cgccgtcgtc 3120
tgctggacga caagttcgaa gacaagaagc gcaaactgca gcagggcgat gacctggctc 3180
caggcgtgct gaaaatcgtc aaggtttacc tggcaatccg ccgtcgcatc cagccgggtg 3240
acaagatggc cggtcgtcac ggtaacaagg gtgtggtctc cgtgatcatg ccggttgaag 3300
acatgccgta cgatgccaat ggcaccccgg ttgatgtggt cctcaacccg ttgggcgtac 3360
cttcgcgtat gaacgttggt cagattctcg aaactcacct gggcctcgcg gccaaaggtc 3420
tgggcgagaa gatcaacctc atgattgaag aacaacgcaa ggtcgctgac ctgcgtaagt 3480
tcctgcatga gatctacaac gaaattggcg gtcgtcaaga aagcctggat gacttctccg 3540
atcaggaaat cctggatctg gcgaagaacc ttcgcggcgg tgtgccaatg gctaccccgg 3600
tgttcgacgg tgccaaggaa agcgaaatca aggcaatgct tcgtttggca gacctgccag 3660
acagcggcca gatggtgctg actgatggtc gtaccggcaa caagttcgag cgtccggtta 3720
ccgttggcta catgtacatg ctgaagctga accacttggt agacgacaag atgcacgctc 3780
gttctaccgg ttcttacagc ctggttaccc agcagccgct gggtggtaag gcgcagttcg 3840
gtggtcagcg tttcggggag atggaggtct gggcgctgga agcctacggc gcggcataca 3900
ctctgcaaga aatgctcaca gtgaagtcgg acgatgtgaa cggccgtacc aagatgtaca 3960
aaaacatcgt ggacggcgat caccgtatgg agccgggcat gcccgagtcc ttcaacgtgt 4020
tgatcaaaga aattcgttcc ctcggcatcg atatcgatct ggaaaccgaa taa 4073

<210> SEQ ID NO 74
<211> LENGTH: 2073
<212> TYPE: DNA
<213> ORGANISM: Unknown
<220> FEATURE:
<223> OTHER INFORMATION: Description of Unknown:
DP9 Glycine--tRNA ligase beta subunit microbial sequence

<400> SEQUENCE: 74
atggcacata attatttact agaaattgga ttggaagaaa ttccggccca tgttgtaact 60
ccaagtatca aacagttagt acaaaaagta acagccttct taaaagaaaa tcgcttaaca 120
tacgactcaa ttgatcattt ttcaactcct cgtcgtttgg caattcgaat caatgggtta 180
ggcgaccaac aacctgatat tgaagaagat gctaaaggcc ctgctcgtaa aattgctcaa 240
gatgctgatg gaaattggac taaggctgca attggcttta cacgtggaca aggtcttacg 300
gttgacgata ttacttttaa aacaatcaaa ggtacggact atgtgtacgt ccataagtta 360
atcaaaggaa agatgactaa ggaaatcctt acggggataa aagaagttgt tgaatcaatt 420
aatttcccaa caatgatgaa gtgggctaac tttgatttta aatatgtacg cccaattcgt 480
tggctggttt ctattctaga tgaagaagtc cttcctttta gtatcttaga cgtaactgcg 540
ggacgccgaa cagaaggaca tcgtttctta ggtgaagctg tcgaactggc taatgctgaa 600
gaatatgaag caaaattaca cgatcaattt gtgattgttg atgccgacga gcgtaaacaa 660
ttaatttcaa accaaattaa agcaattgct gaaagcaatc gttggaacgt taccccctaac 720 ccaggtcttt tagaagaggt taacaatttg gttgagtggc caaccgcttt taatggggga 780
tttgatgaaa agtatttagc tattccagaa gaggtattga taacatcaat gcgtgaccac 840
caacgcttct tctttgtccg cgaccaagct ggaaagctat tgccaaactt catctccgta 900
cgaaatggga atgaagaatt tattgaaaat gttgttcgtg gaaatgaaaa agttttaact 960
gcacgtttag aagacgctgc tttcttctac gaagaagatc aaaaacatga tattaattat 1020

-continued

```
tatgttgacc gacttaaaaa ggttagtttc catgataaga ttggttcaat gtacgaaaaa   1080
atgcaacgag ttaattctat tgctaaagtt attggaaaca ccttaaatct taatcaaacg   1140
gaacttgatg atatcgatcg cgctacaatg atttataaat ttgatttggt aactggtatg   1200
gttggtgagt tctcagaatt acaaggagta atgggtgaaa aatatgctca acttaatggt   1260
gaaaaccaag cagtagccca agccattcgc gaacattaca tgccaaatag cgcagaaggt   1320
gatttgcctg aaagtgtaac gggcgcggta gtcgcattag ctgataagtt tgataacatc   1380
tttagttttt tctcagctgg tatgattcca agtggttcaa acgatccata tgcattacgc   1440
cgacatgcat atggaattgt tagaatctta aatagccgtg attggcaatt agatttaaat   1500
caattcaaat cacaatttaa gactgaatta gcggagaatg gcacagcgtt tggtgtggat   1560
gtcgatcaaa actttgacca agtacttaac ttctttaatg accgtattaa acaattgctt   1620
gatcatcaaa agattagtca tgatatcgtt gaaacggtgc ttacaggtaa taatcatgat   1680
gttacggaaa ttatcgaagc tgcccaagta ctagcagatg ctaaagcgag ctctacattt   1740
aaagatgata ttgaagcttt aacacgagtt caaagaattg ctacaaagaa tgaagaaagt   1800
ggagaactta atgtagatcc acaattattt aataatgctt ctgaaggcga actttttgat   1860
caaattatta aaattgaagc tgcaaataat ttgacaatga gccaactatt tgctaaatta   1920
tgcgagttga ctcctgcgat tagcaagtac tttgacgcaa cgatggtcat ggacaaagac   1980
gaaaatatta agtgtaatcg tttgaatatg atgagtcggt tagctaattt aattctaaaa   2040
attggggatc taactaacgt acttgtaaaa taa                                2073
```

<210> SEQ ID NO 75
<211> LENGTH: 1341
<212> TYPE: DNA
<213> ORGANISM: Unknown
<220> FEATURE:
<223> OTHER INFORMATION: Description of Unknown:
      DP9 Glutamine synthetase microbial sequence

<400> SEQUENCE: 75

```
atggcaaaga aaaattattc gcaagcagat attcgtcaga tggcaaagga tgaaaatgta     60
cgttttctcc gattaatgtt tacagatctt tttggaataa ttaagaacgt tgaagtacca    120
attagtcaat tggacaaact attagataat aaattgatgt ttgatggttc ctcaattgac    180
gggtttgttc ggattgaaga aagtgacatg tatttatacc cagatctttc tacttggatg    240
gttttcccat ggggaagcga acatggcaag gtggctcgca ttatttgtga agtatactca    300
aatgatcgta aaccattcgt gggtgatcca cgtaacaatt taattcgagt actccaagag    360
atgaaggatg caggatttac tgattttaat atcggacctg aacctgagtt tttcttgttg    420
aaattagatg aaaatggtaa accaaccact aatttaaatg ataaaggtag ttactttgat    480
ttagctcctg ttgatttagg tgaaaactgc cgtcgtgata ttgttttgga acttgaaaat    540
atgggctttg atgttgaagc ttctcatcat gaagttgctc caggacaaca cgaaattgac    600
tttaaatacg ccgatgcttt gaccgctgcc gataacattc aaacctttaa gttggttgtt    660
aagacagttg cccgtaaata taacctgcat gctacattta tgcctaaacc tatggatgga    720
atcaatggtt cagggatgca tttaaacatg tcacttttca ataaggaagg caatgctttc    780
tatgacgaaa agggtgactt acaactttct caaaatgctt actggttcct tggtggacta    840
ttgaagcatg ctcgtagtta tacggccgta tgtaacccaa ttgttaactc gtacaaacgt    900
ttagttcctg gatatgaagc tccagtatac gttgcttggt caggttcaaa tcgttcacca    960
```

-continued cttattcgcg ttccttcaag taagggactc tcaactcgtt ttgaagttcg aagcgtcgat 1020
ccagctgcta acccatactt agcaattgca tcagtattgg aagcaggctt agatggcatt 1080
agaaacaaga ttgaaccaga agattccgtt gatcgtaata tctatcgaat gaacattcaa 1140
gaacgtaatg aagagcatat tacagatcta ccttcaacat tacacaatgc tttgaaggaa 1200
ttccaaaatg atgatgtaat gcgtaaggca ttaggagatc acattttcca aagcttcctc 1260
gaagctaaga agttagaatg ggcttcttac cgtcaagaag tgacacaatg ggaacgtgat 1320
caatatctcg aaatgttcta g 1341

<210> SEQ ID NO 76
<211> LENGTH: 1947
<212> TYPE: DNA
<213> ORGANISM: Unknown
<220> FEATURE:
<223> OTHER INFORMATION: Description of Unknown:
DP9 DNA gyrase subunit B microbial sequence

<400> SEQUENCE: 76
ttggcagacg aaaaagaaac gaaagcagaa ttagccagag aatatgatgc gagtcaaatt 60
caggttttag aggggctcga agcagttcgt aaacgcccag gaatgtatat tgggtcgact 120
agttctcaag gactacacca tttggtttgg gaaattattg ataatggtat tgatgaagct 180
cttgcaggat ttgcagacaa aattgatgtg atcgttgaaa aagacaatag tattaccgtc 240
actgataatg gacgtgggat tccggttgat atccaaaaga aaactggaaa accagcttta 300
gaaacagtct ttacggtcct acatgccgga ggtaaattcg gcggtggcgg ttataaagtt 360
tctggaggat tgcatggtgt gggcgcatcc gttgtaaatg cgttatcaac ggaattagat 420
gcgcgcgtca tgaaggacgg taaaatctat tacattgatt ttgcgctagg aaaagtaaaa 480
acaccgatga aaacgattgg tgatactgaa catcctgacg atcatggaac tattgttcat 540
ttcgttccag atccagatat tttccaagaa actaccacat acgacattaa tatcttaaaa 600
acacgaattc gtgaattagc ctttttgaac aaaggtctac ggattacttt gaaggatatg 660
cgtcctgaaa agccaactga agacgacttc ttgtatgaag gtgggattcg ccactacgtt 720
gaatatctaa acgaaggcaa agaagtaatt ttccctgaac ctatctatgt tgaaggggtt 780
acaaaaggta tcactgttga agtagctatg caatatatcg aaggttatca aagtaaattg 840
ttaactttta ctaacaatat tcatacttac gaaggcggta cccacgaaga aggtttcaaa 900
cgtgctttaa cacgagttat taacgattac gctaaaaaca acaatatttt aaaagaaaat 960
gatgataaat tgtctggtga tgatgttcga gaaggtttga cggcagtagt cagcgttaag 1020
catcctgatc ctcaattcga aggacaaacg aaaacaaaat tgggtaactc agatgctcgg 1080
acagctgtta acgaagtgtt tgctgaaact ttcaataaat tcttattgga aaatcctaag 1140
gttgcacgtc aaattgttga taagggaatc ttggcagcaa aagcaagagt cgccgctaaa 1200
cgagctcgtg aagttacgcg taagaagagt ggcctagaac tcaataatct tcctggtaaa 1260
ttagctgata atacttctaa ggatccttca attagtgaat tattcattgt cgagggtgat 1320
tctgccggtg gtagtgctaa gtcgggacgt tcgcgtctca cacaagctat tttgccaatt 1380
cgtgggaaga ttttgaacgt tgaaaaagcc actttggatc gggttttggc caatgaagaa 1440
attcgttcac tctttacagc gctcggaact ggatttggtg aggactttga tgtaagtaaa 1500
gccaactatc ataaattgat tatcatgacc gatgccgatg tcgatggtgc tcatattcgg 1560
acactattat tgacgctgtt ctatcgttac atgcgtccaa tgattgatgc aggatttgtt 1620
tacattgctc aaccaccgct ctaccaagta cgtcaaggta agatgattca atatatcgat 1680
tctgatgaag aattagaaac agtacttgga caattgtcac catcaccaaa acctgtaatt 1740
caacgttata aaggtcttgg tgaaatggat gctgagcaac tttgggaaac aaccatgaat 1800
ccagaaaatc gacgcttgtt acgagtttca gccgaagatg ctgatgctgc aagtggtgat 1860
tttgaaatgt tgatgggtga caaggttgaa ccacgtcgta aattcattga agagaacgct 1920
gtgtttgtta aaaacttgga tatctaa 1947

<210> SEQ ID NO 77
<211> LENGTH: 2418
<212> TYPE: DNA
<213> ORGANISM: Unknown
<220> FEATURE:
<223> OTHER INFORMATION: Description of Unknown:
DP9 Leucine--tRNA ligase microbial sequence

<400> SEQUENCE: 77
atggcttata atcataaaga tatcgaacag aagtggcagc aattctggag cgacaatgag 60
acttttaaga cggtcgaaga tgcagacaaa cccaaatatt atgcattaga catgttccct 120
tatccatcag gtcaaggact ccatgtgggc catcctgaag gatatacagc aacagatatt 180
atgtcacgaa tgaaacggat gcaaggttac aaagtacttc atccaatggg atgggatgct 240
tttggtcttc cagcagaaca atatgcgatg aagacgggta acaatccgcg tgattttaca 300
gctaagaata ttcaaaactt taagcgtcaa atccaatcac ttggtttttc ttatgactgg 360
tcgcgagaag ttaatacaac tgatccagct tactacaagt ggactcaatg gatttttgag 420
caactctaca agaagggctt agcttatgaa aaagaaacgc tggtaaactg ggctcctgat 480
ttaatgggtg gaacggtagt tgctaacgaa gaagttgtgg atggtaagac agaacgtggt 540
gggttccccg tttatcgtaa accaatgaaa caatggattc ttaaaattac agcttacgcc 600
gaccgtttga ttgacgattt ggacctggta gattggcccg atagtattaa agaaatgcaa 660
aaaaactgga ttggtcgttc agtgggggct agcgtcttct ttaatgttga agatagcgaa 720
aaacaaattg aagtatttac aacgcgtcca gatacattat ttggcgcaac atacttggta 780
atttcaccag aacatgacct cgttgaccaa attacaactc cagaaagtaa agctgccgtt 840
gaagaataca agaaagctgt tgcaactaaa tcagatcttg aacggacgga tttgagtaaa 900
gataagacgg gagtctttac gggagcatac gcggttaacc ctgttaatgg taagaaaatt 960
ccagtttgga ttagtgatta cgtattggct tcatacggaa ctggagcagt gatggctgtt 1020
cctgctcatg atggccgtga ctacgaattt gctaagaaat tcaagataga tatggtgcca 1080
gtttatgaag gtggcaatct tgaagatgga gtattggaca gcgaaggcgg gctaattaac 1140
tctggattcc tagatgggat ggataagcag acggctattg ataccatgat tagctggttg 1200
gaagaacatg gagttggtca taagaaggtt aactatcgtc ttcgtgactg ggtcttctct 1260
cgccaacgct actggggtga accaatccct gtaattcatt gggaagatgg agaaacaact 1320
ttgattcctg aagatgaatt gccattgaga ctcccggctg caactgacat tcgtccttcc 1380
ggtaccggag aaagcccatt agctaaccta gatgattggg taaacgtagt tgatgaaaat 1440
ggtcgtaagg gtcgccggga aactaataca atgccacaat gggcgggtag ttcatggtac 1500
ttcctccgtt acgttgatcc taagaatgat caaaagattg ctgacgaaga tttacttaaa 1560
gaatggttac cagtcgactt atatgttggt ggagctgaac atgcggtact tcatttactt 1620
tatgcacgtt tctggcacaa agttttatat gatctaggag ttgtaccaac taaggaacca 1680
ttccaaaaat tggtcaacca agggatgatt ctcggtagca atcatgagaa gatgtctaag 1740
tcaaaaggga acgtggttaa tccagatgat attgttgagc gctttggagc ggatacttta 1800
cgattatacg aaatgttcat gggacctctg acagaatcag tcgcctggag tgaagatggg 1860
cttaacggaa gtcgtaagtg gattgaccgc gtctggcgct tgatgattga cgacgaaaac 1920
caattgcgtg atcatattgt tactgaaaat gatggcagtt tggatatgat ttataaccaa 1980
actgttaaga aggtaactga tgattatgaa aacatgcgct ttaacacggc tatttcacaa 2040
atgatggtct ttgttaatga agcatacaag gctgataaac ttccagcagt atatatggaa 2100
ggattagtta agatgttagc tccaattatt ccgcacgttg ctgaagaact ttggagtttg 2160
ctaggtcacg aaggtggtat ttcatacgct gaatggccaa catatgatga aagtaagtta 2220
gtagaagcta cagttcaagt cattctacaa gttaatggta aagttcggag taaaattacc 2280
gttgacaagg atatcgccaa agaagaactt gaaaaattag cgttagctga tgctaagatt 2340
caacaatgga cggcagataa gactgttcgt aaggtaattg ttattcctaa caagattgtt 2400
aatatcgtag taggctaa 2418

<210> SEQ ID NO 78
<211> LENGTH: 1350
<212> TYPE: DNA
<213> ORGANISM: Unknown
<220> FEATURE:
<223> OTHER INFORMATION: Description of Unknown:
DP9 Glucose-6-phosphate isomerase microbial sequence

<400> SEQUENCE: 78
atggcacata tttcatttga cagttctaat gttgcagatt ttgtacatga aaacgaactt 60
gcagaaatcc aaccacttgt tacagctgct gatcagattt tacgtgatgg ctctggcgct 120
ggtagtgatt tccgtggatg gatcgattta ccatcaaatt atgataagga cgaatttgcc 180
cgtatcaaga aagccgctga taagatccgc aatgactcag aagtattcgt tgctatcggt 240
attggtggtt catatttggg tgctcgtgca gccattgatt tcttgaacaa cactttctac 300
aatcttctta ctaaagaaca acgtaatggt gctcctcaag taatcttcgc tggtaactca 360
attagttcaa cttaccttgc tgacgtattg aacttaatcg gggaccgtga cttctcaatt 420
aacgtaattt ctaagtcagg tacaactaca gaaccagcta ttgcattccg tgttcttaaa 480
gaaaaactaa tcaagaagta cggtgaagaa gaagctaaga aacgtatcta tgcaacaact 540
gaccgtgcta aaggcgccct aaagacagaa gctgatgcag aaaactatga agaattcgta 600
gttcctgatg acattggtgg tcgtttctct gttctttcag ctgttggttt attaccaatc 660
gcggttgccg gtggcgatat tgaccaattg atgaagggtg ctgaagatgc aagcaacgaa 720
tacaaggatg ctgatgttac aaagaacgaa gcatacaagt acgctgcttt acgtaacatc 780
ctttatcgta agggctacac aacagaactt cttgaaaact acgaaccaac acttcaatac 840
ttcggcgaat ggtggaagca attgatgggt gaatcagaag gtaaagatca aaagggtatc 900
tacccatctt ctgctaactt ctcaactgac ttacattcac taggacaata catccaagaa 960
ggtcgtcgca atttaatgga aacagttatc aatgttgaaa agcctaacca tgacatcgac 1020
attcctaagg ctgaccaaga ccttgatgga ttacgttatc tcgaaggtcg cacaatggac 1080
gaagttaaca agaaagctta ccaaggtgta actcttgctc ataacgacgg tggtgttcca 1140
gttatgacgg ttaacattcc tgatcaaaca gcttacacat taggctatat gatttacttc 1200
ttcgaagcag ctgttgctgt atctggttac ttgaacggaa ttaatccatt caaccaacca 1260
ggtgttgaag catacaagtc aaatatgttt gcattacttg gtaaaccagg ttatgaagat 1320
aagacagctg aattaaacgc tcgtctataa 1350

<210> SEQ ID NO 79
<211> LENGTH: 1725
<212> TYPE: DNA
<213> ORGANISM: Unknown
<220> FEATURE:
<223> OTHER INFORMATION: Description of Unknown:
DP9 Phosphoglucomutase microbial sequence

<400> SEQUENCE: 79
atgagttggg aagattctgt caaagaatgg caagattatg cagatttaga ttttaattta 60
aaaaaagaat tagcaacttt agctgaagat aaagatgctt taaaagaagc cttttatgct 120
ccaatggaat ttggtacagc aggaatgcgt ggcgtaatgg gccctggtat caaccggatg 180
aatatctata cggttcgtca agcaacagaa ggtttagcta attttatgga taccttagat 240
tttactgata agaaacgggg agtggcgatc agttttgatt cccgctatca ctcacaagag 300
tttgctttag cagcagctgg tgttttaggt aagcatggta ttccaagttt tgtttttgat 360
agtatgcgtc ccactccaga attatcatat acagtacgtg agttaaacac ttatgctgga 420
atcatgatta ctgctagtca taatcctaaa caatataatg gatataagat ttatggtcct 480
gatggcggac aaatgccacc aatggaatct gataagatta cagaatatat tcgccaagta 540
actgacatct ttggtgttga agctcttact caaagtgaat taagagctaa gggcttaatg 600
accattattg gtgaagacat tgacctcaag tatcttgagg aagttaagac ggtatcaatt 660
aatcatgaac taatccagcg ctttggtgca gacatgaagt tgatctactc accattacat 720
ggtactggaa aagtagttgg tggacgtgcg ttagaaaatg ctggttttaa ggattacact 780
atggtccctg aacaagcaat tgctgaccca gaatttatta caacgccatt ccctaaccca 840
gaattcccac aaacttttga tttggctatt gaattaggta aaaagcaaga tgctgacctt 900
ttgattgcca ctgatccgga tgccgatcgt ttgggagctg ccgttcgttt accaaatggt 960
gactacaaat tattgacagg gaaccaaatt gcagccttga tgttagaata catcttaact 1020
gcgcatgatg cagcaggtga cttgccaggt aacgcagctg ccgttaagtc aattgtttct 1080
agtgaactag caaccagaat tgccgaagcc catcatgtag aaatgattaa cgttctaact 1140
gggtttaagt acattgctga ccaaattaaa cattacgaag aaaatggcga ccatacettt 1200 atgtttggtt tcgaagaaag ttatggctat cttgttcggc catttgttcg cgataaagat 1260
gccatccaag gaattgtcct attggctgaa attgctgctt attatcgtag taaggggcaa 1320
accttatatg acggtcttca aaacttattt actacttacg gatatcatga agaaaagacc 1380
atttcaaaag atttccctgg agttgacggt aaagaaaaaa tggctgccat tatggaaaag 1440
gttcgtgaag aacgcccaag tcaatttgat cagtacaagg tattagaaac tgaagacttc 1500
ttagctcaaa ctaagtatga agcagatgga tctacccaag ctatcaaatt accaaaagcg 1560
gatgttttga aatttacatt agatgatggt acttggattg caattcgtcc ttctggaaca 1620
gaaccaaaaa ttaaattcta tattggtaca gttggcgaag atgaaaaaga tgctttgaat 1680
aagattgatg tttttgaaac agctattaat gaacttataa aataa 1725

<210> SEQ ID NO 80
<211> LENGTH: 3426
<212> TYPE: DNA
<213> ORGANISM: Unknown
<220> FEATURE:

-continued

<223> OTHER INFORMATION: Description of Unknown:
DP9 2-oxoglutarate carboxylase small subunit
microbial sequence

<400> SEQUENCE: 80

```
atgcaccgta ttttaattgc caaccgaggc gaaattgcga cccgaattat tcgggcaacg     60
catgaactcg gaaaaacagc tgtagcaatt tatgctaaag cggatgaatt ttctatgcat    120
cgttttaaag cagatgaagc ttaccaagtt ggtgaagata gtgatccaat tggagcatat    180
ttaaatattg atgacattat tcgtattgca aaagaaaata atattgatgc aattcacccc    240
ggctatggat tttgtcgga aaatgctgta tttgcgcgag cagttgaagc agctgggatt    300
aagttcattg gacctcgacc cgaattacta gaaatgtttg gtgataaatt acaagctaaa    360
aatgcagcca ttaaggccgg tgtaccaact attccgggaa cggaaaaacc agttaaagat    420
gtcgatgacg cgctaaattt tgcagagcaa tttggctatc ctatatttgt taagtcagcg    480
gcaggtggcg gcggaaaagg gatgcggatt gtacatcatc aacaagagat gcgcgaagca    540
tttaagatgg ctcagtcaga agcttcttcg tcttttggtg acgatgaaat ttacttagaa    600
cgttacttag ttgatccaat ccatattgag gttcaagtag ttgcggatga acacggtgag    660
atggttcatt tgtatgaacg aaattcatcg attcagcgac gccatcaaaa aatcattgaa    720
tttgctccag cagtgggaat ttctgccacc gtccgtgatc aaataagaaa agctgcttta    780
aaattattga agtcggtcaa ttatagtaac gctgcaacca ttgagttttt ggtagaaggt    840
aatcaatttt actttatgga agtgaatcca cgaattcagg ttgaacatac agttaccgaa    900
gaagtcacgg gaatcgatat tgtgcaaacc caaattaagg ttgctgaagg tcaaagatta    960
cacgaagaaa tcggtgttcc tcaacaagcc caaattgaag ctgtgggagt ggcaattcaa   1020
gcccgaatta ccactgaaga tccaatgaat aactttattc cagatgtcgg tagaatccag   1080
acgtatcgtt cacctggtgg aacaggtgtg agattggatg ctggaaatgc ctttgctgga   1140
gccattgtaa ctccgcatta tgattcactt ctgaccaagg caattgtcca tgcgccaacc   1200
tttgacgaag ccttggtaaa gatggatcga gtgctcaatg aatttgtaat tgctggggtt   1260
aaaactaata ttccattttt aaagaaatta attcatcatc ctatttttag atcggaatta   1320
gctccgacaa cctttgtgga tgagacacca gaactctttg atttaaaagc tgaaactccg   1380
gtagttactc aacttttgag ttacattgct aatactacta tcaatggtta tccaggctta   1440
gaaaagcaga atccagtagt gttaactcgg ccagtccgtc cacattttga agcacaagta   1500
ccgcatgaaa atgcgaaaca gatcttggat agtaagggac ctgatgccat gatcaattgg   1560
ctgttaaaac aaaagcaggt cttgctaacc gatacgacca tgcgggatgc ccatcaatca   1620
ttatttgcta cgcgaatgcg gaccaaagac atggtagaaa ttgccgatca agtccagaaa   1680
ggtctgccta acctatttc agctgaagtt tggggcggtg cgacctttga tgttgcttat    1740
cggttcctag gtgaggatcc atgggaaaga ctccaacaat tgcgggctaa aatgccaaat   1800
acgatgctcc aaatgctttt acgtgggtca aatgcagtag ggtatcaaaa ttatccagac   1860
aacgccattg acgaatttat tcgattggct gccaaaaatg gaattgatgt tttccgaatc   1920
tttgattctc ttaattgggt gccacagctt gaagaatcta tccaacgggt gcgtgataat   1980
ggaaaagtgg ctgaagcagc catggcatat actggcgata ttttagatac taatcgtact   2040
aaatataatt tgaaatatta tgtggatttg gctcaagaac tccaagcagc aggtgctcat   2100
attattggaa tcaaagatat gtcaggaatt ttaaaaccac aagctgctta tgcattaatt   2160
tcagagttaa aaaatcatct ggatgtgcca attcatttgc atacgcacga tactacaggc   2220
```

```
aacggcattt tcttatattc tgaagcaata cgagctggag ttgatgtggt cgacgttgcc   2280
acttctgcgc tagcgggaac gacttctcag ccttcaatgc agtctcttta ctatgcgttg   2340
tctaataacc agcgccaacc agatttagat attcaaaaag cagaaaaact agatgaatat   2400
tggggcggaa ttcgaccata ttacgaagga tttggcaccc aattaaatgg accacaaact   2460
gaaatttatc gaattgaaat gcctggtgga cagtatacca accttcgcca gcaagctaac   2520
gcagtccatt tgggtaagcg ttgggatgag attaaggaaa tgtacgcaac cgtcaatcaa   2580
atgtttggcg atattccaaa ggttacgcct tcttctaaag tagttggcga tatggcacta   2640
ttcatggtcc aaaatgattt gacgcctgaa atggtaatga acgataaggg acaattaagt   2700
tttcccgaat cagtggtaaa ctttttccgt ggtgatttag gacaaccggc gggtggtttt   2760
ccaaaacagc tccaaaaggt gattctaaaa gagcaagccc cattgacagt acgaccagga   2820
gctttagccg atccagttga ttttgatcaa gttcgtaaac aggcaactaa ggttttaggt   2880
caccaagcaa gtgatgaaga agttatgtcg tttattatgt atccagatgt gatgaccgaa   2940
tacattcaac gtcaaaatga atatggtcca gtaccattat tagatactcc aatctttttc   3000
caaggcatgc atattggcca acgcattgat ttacaattgg gacgcggaaa atcggtcatt   3060
attgtccttc gagaaattag tgaagcagat gaggcgggcc aaaggtcact tttctttgat   3120
ataaatggac aaagtgaaga agtgattgtt tatgatgtta atgcgcaggt aacgaaagta   3180
aagaagatta aagctgatcc gactaaagcc gaacagattg gcgctactat ggcgggctcg   3240
gtcattgaag tccaagtaga agcgggccaa aaggtccagc gaggtgataa cttaattgtc   3300
actgaggcga tgaaaatgga gaccgcgtta agagcacctt tcgacgcaac cattaagaag   3360
atttatgcta cccctgaaat gcaaatcgag acgggggatt tattgattga actagaaaag   3420
gagtaa                                                              3426
```

```
<210> SEQ ID NO 81
<211> LENGTH: 2058
<212> TYPE: DNA
<213> ORGANISM: Unknown
<220> FEATURE:
<223> OTHER INFORMATION: Description of Unknown:
      DP3 Glycine--tRNA ligase beta subunit microbial sequence

<400> SEQUENCE: 81
```

```
atgtcaacat ttttattaga aattggactt gaagaaatac cagctcattt ggtaaccagt     60
tcagagaatc agttaattga aagaactaaa aagttcttat cagagcatcg tttaacagta    120
ggtgatatta aaccatattc aacaccgcga cgtctggctg tcgttttgac agatgttgct    180
gaaacatcag aaagtttaag cgaagaaaag cgtggaccat ctgttgaccg tgcacaagac    240
gaaaacggta attggacaaa ggcagcatta ggttttgcac gtggtcaagg tgctaatcct    300
gaagcatttg aaattaaaga tggatatgtt tggctaacaa aacgtactgc tggtgtagcc    360
gcgaatgaaa ttttagctaa aattggtgat gaagttgtcg cccaaatgaa attttcaact    420
tatatgaagt gggctaatca cagctttttg tatgttcgac ctattcgttg gctcgtagca    480
cttcttgata gtgaagtcat ttctttcaac gtgttagata ttaccacaga tcgtttcaca    540
cgtggtcatc gtttttttgtc ttcagaacat gttgaaatat cttctgcaga taattatgta    600
acgactttgc agggtgctaa cgtggttgtt gatgctacag tgcgcaaaaa tgaaattcga    660
tcgcagttga atgcaattgc tgaagctaat ggttgggttc tgcaacttga gaccgatgcg    720
gcgcaagatt tgttggaaga agttaataac attgttgagt ggccaacagc gtttgctggc    780
```

```
agtttcgatg agaaatattt agaaatacca gatgaagttt tgattacatc aatgcgcgaa    840

catcagcgtt tcttctttgt gacgaatgaa aaaggacaat tattgccaca ctttttgtca    900

ataagaaatg gtaaccgtga gcatctaaac aacgttattg ctggaaatga aaaagtattg    960

gtagcaaggt tagaagatgc cgaattcttc tatcatgaag accaaaccaa atcaatttct   1020

gattacatga ctaaagttaa aaagttagtc ttccatgaaa aaattggtac ggtgtatgaa   1080

cacatgcaac gcactggtgc tttggcttca gcaatggcgg tggttttgaa gtttgatgaa   1140

gtacaacagg ctgatttgac ccgtgcatca gaaatttata aatttgattt gatgaccggt   1200

atggttggtg aatttgatga acttcaaggc attatgggtg agcattatgc caagcttttt   1260

ggcgaagatg atgcggttgc aacagccatt cgagagcatt atatgccaac ttcagctaat   1320

ggtgaggttg cgcaatctga aattggtgct ttgttggccg ttgcggataa acttgatagc   1380

attgtgacgt tttttgctgc tggattaata ccaagtggtt ctaatgatcc ttatggctta   1440

cgacgtgcag ctactggcat cgtgcgtaca ttggtggata aaaaatggca tattgatttg   1500

cggcctttgc tagctgattt tgtgcaacag caaggtaagg taactgacac cgatttaacg   1560

acatttgttg atttcatgtt ggatcgtgtt cgtaaattat cgttggatgc tggaatacgt   1620

caagatattg tcattgctgg attaggcaac gttgatagag ctgatatcgt atatattagt   1680

cagcgagtcg aagttttgtc ccaacatagt ggtgatggca atttccgaga tgtaattgag   1740

gcactgactc gtgtggatcg cttagccgta aagcaagtaa ctaatgcaac ggttgatcct   1800

gctaagtttg aaaatcaatc tgaaaaggac ctatatcaag caacgttaac gcttgattta   1860

aatactttga tgcatgacgg tgcagaaaat ctctacatgg ccttagcaaa tttgcaaaaa   1920

ccaattgcgg cttattttga tgaaaccatg gttaacgctg aagatgaatc tgttaaagat   1980

aatcgatatg cgcagctgaa cgtcatacaa cgactaacca acggattagg agatttgacg   2040

caaatcgtca ttaagtaa                                                 2058
```

<210> SEQ ID NO 82
<211> LENGTH: 1347
<212> TYPE: DNA
<213> ORGANISM: Unknown
<220> FEATURE:
<223> OTHER INFORMATION: Description of Unknown:
DP3 Glutamine synthetase microbial sequence

<400> SEQUENCE: 82

```
atggctcgta aaacatttac caaagaagaa attaaacaaa ttgttgttga tgaaaatgta     60

gaattcattc gtgtaacatt cactgatgtc ttaggtgcga ttaaaaacgt tgaagtacca    120

acttctcaat tagataaggt gcttgacaac aatttaatgt ttgacggttc atcaatcgag    180

ggatttgttc gtatcaatga atcagatatg tatctttacc ccgatttatc aacatttatg    240

attttcccat gggcaacgga tggtcatggt ggtaaagtgg cccgcttgat tgccgacatt    300

tatactgctg atcgtgagcc atttgctgga gaccccccgtc atgcgttacg ttcggtactc    360

gctgacgcgc gtgaagctgg gtttacggcg tttaatgtcg ggacagaacc tgaatttttc    420

ttgtttaaac ttgatgaaaa aggcaaccca accacagagt taaacgacaa aggtggttat    480

tttgacctag caccattgga tatgggtgaa aatgttcgtc gtgaaattgt tttgactttg    540

gaaaaaatgg gctttgaaat tgaagctgct caccacgaag ttgccgaagg acagcatgaa    600

gtagacttta aatacgcttc agctcttgaa gccgctgaca acattcagac gtttaagttg    660

gttgttaaaa ccatcgcacg caagaatggt tactatgcta cctttatgcc aaagcctgtt    720
```

gcaggtatta acggatccgg tatgcacaca aacatgtcat tatttacaaa agatggtaac 780
gcatttgttg atacatcgga tgaaatgggc ttgtcaaaaa cagcatataa cttcttgggt 840
ggtattttag aacatgcgac tgcgtttaca gcgcttgcaa acccaacagt taactcatac 900
aagcgcttga caccaggatt cgaagcacct gtttatgttg catggtcagc atcaaatcgt 960
tcaccaatgg ttcgagttcc ggcctcacgt ggtaattcaa cacgtttgga acttcgttca 1020
gttgacccaa cagctaatcc ttatactgca ttggcagcca ttttggcttc aggactggat 1080
gggatcaagc gtgaattaga gcctttggcc tcagttgata aaaatattta tttgatggat 1140
gaggtcgaac gggaaaaggc aggcattaca gacttaccag atactctgtt ggctgcagtt 1200
cgtgagttgg cggctgatga tgttgttcgt tcagctattg gagaacatat tgctgataag 1260
tttattgaag caaagaagat tgaatacaca tcatatcgtc agtttgtttc tgaatgggaa 1320
acagattctt atcttgaaaa ttactaa 1347

<210> SEQ ID NO 83
<211> LENGTH: 2049
<212> TYPE: DNA
<213> ORGANISM: Unknown
<220> FEATURE:
<223> OTHER INFORMATION: Description of Unknown:
DP3 DNA gyrase subunit B microbial sequence

<400> SEQUENCE: 83
gtgttcgcag attatatctg ttcacacgct aataatatgg cagagaatat cgaaaatgaa 60
gcattggaga acattgatgg catcgtaacc gatgataccg aaatccgtca agcaagcacc 120
gttcatgcag cagcaggcgc ttacaatgct gatcagattc aagttttgga aggattggaa 180
gctgtccgca aacgccctgg catgtacatt ggtacgacca cagcgcaagg cttgcaccat 240
ttggtatggg aaattgttga taacgggatt gatgaggcat tagcagggtt tgcgtcacat 300
attacggtca caatcgaaaa ggataactca atcacggtaa ccgatgacgg ccgtggtatt 360
cctgtcgaca ttcaaactaa aacgggtaag ccagctcttg aaactgtctt tacggtatta 420
cacgccggtg gtaaatttgg cggtggcggt tataaagtat ctggtggatt acacggtgtt 480
ggagcttctg ttgtcaatgc cttgtcaacg gatttggacg ttagagttgt tcgtgataat 540
actgtttatt acatggactt caaagtggga cgcgtcaaca caccgatgaa acaattgacg 600
gaaaagccca ctattgagcg tggtacaatt gttcatttta agcccgatgc agatattttc 660
cgtgaaacaa cagtttataa ctacaacaca ttactaacac gtgtgcgcga attggccttt 720
ttgaataaag gtttgcgcat ttcgattaca gataatcgac ctgaagaagc tgtttctgaa 780
agctttcatt ttgaaggtgg gattaaagaa tacgtcagct atttgaataa ggacaagact 840
gctattttcc ctgaacctgt ttacgttgag ggtgaagaaa atggcattgt agtggaagct 900
gccttacagt acactaccga tattaaagac aatctgcgga cgtttactaa caatatcaat 960
acctatgaag gtgggacgca cgaaactggc tttaaaacag ccttaacacg tgtaatcaat 1020
gattacgctc gtaaaaatgg tcagctcaaa gataatgcag aaagtttgac aggggaagat 1080
gtgcgcgaag gcatgactgc tatcgtgtca atcaagcacc cagatccaca atttgaagga 1140
caaaccaaaa ctaaattagg taactccgat gcacgtcaag caacggatcg gatgttctca 1200
gaaacgttca gtcgtttcat gatggaaaat ccagcagttg ccaagcaaat tgttgaaaaa 1260
ggtgtcttag cccaaaaagc acgattggct gccaagcgtg cacgcgaaat gacacgcaaa 1320
caatctggtt tggaaattgg taatttgcca ggtaaattag ctgataatac ctcaaatgat 1380
cctgaaattt cagaattatt tattgttgag ggtgattcag ccggtggttc agctaagcaa 1440
ggacgtaacc gtttgacgca agctattttg ccaattcgag gcaaaatttt aaatgttggg 1500
aaagcctcat tggatcgggt gttagccaac gaagaaattc gatcattgtt tacagcaatg 1560
ggaactggat ttggtgagga ctttaatgtt gaaaaagcca attatcacaa agtcattatt 1620
atgacagatg ccgatgtcga tggcgcccat attcgaacac tattgttaac gctattttat 1680
cgttatatgc gaccacttgt tgacgcaggc tatatttata ttgcgcagcc accgctttac 1740
ggtgttgcct taggcaataa taaatcaatg acgtacattg attctgatga agaacttgaa 1800
gactatttgt cacaattgcc atctaatatt aaaccaaaag ttcaacgtta taagggacta 1860
ggggaaatgg attacgatca actagcagat acaaccatgg atccgcagaa tcgtcgtttg 1920
ctacgtgttg acccaactga tgctgaagaa gccgaagcag ttattgatat gttaatgggt 1980
ggggatgtac caccacgtcg taagtttatt gaagacaatg ctgtctttgt tgagaacttg 2040
gatatttaa 2049

<210> SEQ ID NO 84
<211> LENGTH: 375
<212> TYPE: DNA
<213> ORGANISM: Unknown
<220> FEATURE:
<223> OTHER INFORMATION: Description of Unknown:
DP3 Leucine--tRNA ligase microbial sequence

<400> SEQUENCE: 84
atgattttcg tcaacgaagc ttacaaaacc gatgctgtgc cgaaagcggc ggcggaaaac 60
ttcgtacaga tgctgtcccc actggcaccg catttggcag aagaactgtg ggaacgactt 120
ggtcataccg atacgattac gtatgaacca tggccaacgt acgatgaggc ttggaccata 180
gaatccgaag tggaaatcgt cgtgcaagtg aacggcaaaa tcgtagaacg cacgaaaatt 240
tccaaagacc tggatcaagc agcgatgcaa gaacacagct taagcctgcc gaatgttcag 300
caggctgtgg ctgggaagac gatccgcaaa gtgattgcgg tgccaggcaa gctggtgaat 360
atcgtcgttg gataa 375

<210> SEQ ID NO 85
<211> LENGTH: 1353
<212> TYPE: DNA
<213> ORGANISM: Unknown
<220> FEATURE:
<223> OTHER INFORMATION: Description of Unknown:
DP3 Glucose-6-phosphate isomerase microbial sequence

<400> SEQUENCE: 85
atggcacaca ttacatttga cacaaagaac attgagaatt ttgttgcacc atacgaattg 60
gacgaaatgc aaccattaat tacgatggct gaccaacaat tgcgcaatcg tacgggcgct 120
ggtgcagaat attctgattg gttgactcta cctactgatt acgacaagga agaatttgca 180
cgtattcaaa aggcggcgca acaaattcaa tctgattcaa agattttggt tgtcattggt 240
attggtggtt catatttggg cgcgaagatg gcggttgatt tcttgaatcc aatgtttaat 300
aatgaattgt cggatgacca acgtcaaggt gttaaaattt attttgctgg taactcaact 360
tctgcagctt acttaaatga tttagttcgt gtcattggtg atcaagactt ttctgtcaac 420
gttatctcaa agtctggcac aacaacggaa ccatcaatcg ctttccgtgt gtttaaacaa 480
ttgttagaga aaaagtatgg ttctgatgct gctaagaagc gtatctatgc cacaacagat 540
gccaatcgtg gtgctttgca cgatgaagca gcggcttcag gttatgaaac attcacaatt 600
cctgatggtg tcggtggtcg cttctctgtt ttgacagctg ttggcttgtt gccaattgct 660
gcttcaggcg ctgatatcca aaaattgatg gacggcgctc gtgatgcgca aaacgaatat 720
actgattctg atttgaaaaa gaacgaggca tataaatatg cagccgttcg tcgtattttg 780
tatgataagg gttatacaac agaattgttg attaactggg aaccttcaat gcaatatttg 840
tcagagtggt ggaagcaatt gatgggcgag tctgaaggta aaaatcaaaa gggtatctat 900
ccatcttcag ctaacttctc aaccgacttg cactcacttg gacaatatat tcaagaagga 960
cgccgtgatt tgtttgagac ggtggttaag ttagacaatc ctgtatctaa tttggaccta 1020
ccacatgaag aaggcaacaa tgatggtttg caatatttgg aaggtatcac gatcgatgaa 1080
gtgaacacca aagcatctca aggggttact ttggctcacg ttgatggtgg tgtgcctaac 1140
ttggctgttc acttgccagc acaagatgct tattcactcg gttacatgat ttacttcttt 1200
gaaatggctg ttggggcgtc tggttatacg tttggtatta acccattcaa ccaaccgggt 1260
gtcgaagcct ataagacagc tatgtttgca ctattaggta agcctggcta tgaggaagcg 1320
acaaaagcat tccgtgcccg cttagacaaa taa 1353

<210> SEQ ID NO 86
<211> LENGTH: 672
<212> TYPE: DNA
<213> ORGANISM: Unknown
<220> FEATURE:
<223> OTHER INFORMATION: Description of Unknown:
DP3 Beta-phosphoglucomutase microbial sequence

<400> SEQUENCE: 86
atgactaaat tttcagatat taaaggtttt gcctttgatt tagatggggt tattgctgat 60
acggcgcgtt tccatggtga agcttggcat caaacagctg atgaggttgg cacaacttgg 120
acaccagaat tggctgaagg tttgaagggc attagtcgta tggcttcctt gcaaatgatt 180
ttggatgctg gggatcatgc cgatgatttt tcgcaagcag ataaagaagc attagcagaa 240
aagaaaaatc ataattatca acaacttatt tcaacattga cggaagatga tattttgcct 300
ggcatgaaag attttattca atcagccaag gcagccggct atacaatgtc ggtggcatca 360
gcttctaaaa acgcaccaat gattctagat catttgggat tgaccaagta ttttgtcggc 420
attgttgatc ccgccacttt gacaaaggga aaacctgatc ctgaaatctt cgttcgtgct 480
gcggaagtct tacatttaaa tccagaaaat gttattggat tggaagattc agctgctggt 540
attgtgtcaa tcaatggcgc aggtgagaca tcactagcca ttggtaacgc agatgttttg 600
tcaggagcgg acttgaattt tgcgtctact tcagaagtga ccttagcaaa tattgaagct 660
aaaatgcaat ag 672

<210> SEQ ID NO 87
<211> LENGTH: 1377
<212> TYPE: DNA
<213> ORGANISM: Unknown
<220> FEATURE:
<223> OTHER INFORMATION: Description of Unknown:
DP3 2-oxoglutarate carboxylase small subunit
microbial sequence

<400> SEQUENCE: 87
atgtttaaaa aagtgcttgt tgctaatcgt ggtgaaattg cggttcgcat cattcgaacg 60
ctcaaagaaa tggggattgc ttcagtcgct atttactcga cagccgataa agatagttta 120

-continued

```
cacgtacaaa tcgctgacga agcgattgct gtggggggac cgaaacctaa agattcatac    180
ttaaatatga aaaatatttt aagtgcagcc ctgctgtcgg gagcagaggc aattcatcca    240
ggatatggct ttttagctga aaatacattg tttgctgaaa tggttggcga agttggtatt    300
aaatggattg ggcctaggcc agaaacaatt gagttaatgg gtaacaaagc taacgcacgt    360
gaagaaatgc ggcgtgccgg cgtaccagta attccaggtt cagagggatt tatccgtgat    420
tttcatgaag caaaaacggt tgctgataaa attggctatc ctttgttgct aaaagctgcc    480
gctggtggtg gtggtaaagg catgcgtttt gtttacggtg aggatgagtt atcagataaa    540
tttgatgatg ctcaaaacga agcgcgtgct tcgtttggcg atgatcacat gtatattgaa    600
aaagttatgt cacgtgttcg ccacattgaa atgcaagtgt ttcgtgatga gaatggtcat    660
gttgtttact tgccagaacg aaattgctca ttgcaacgca ataatcaaaa ggtgattgaa    720
gaatcaccag ctacgggtgt aacgcctgaa atgcgtgcgc atcttggcga aattgttact    780
aaagccgcaa aagcattggc gtatgaaaat actggaacca ttgaattttt gcaagatcgc    840
gatggtcatt tctactttat ggaaatgaac acacgtattc aagtagaaca tccagtttct    900
gaaatggtaa cgggattaga tttaattaag ttacaaattc aagttgctgc aggcttagat    960
ttaccggtgg ttcaagatga cgtgatcgtt caaggccact ctatcgaagt acgtttgacg   1020
gctgagcagc cagaaaaaca ctttgcacct agtgctggaa cgattgattt tgttttttttg   1080
ccaactggtg gaccgggtgt tcgtattgat tcagccttat ttaatggcga taaaattcaa   1140
ccattttacg attctatgat tggcaaatta attgttaagg ccgatgatcg tgaaacagcc   1200
atgagaaaga ttcaacgtgt ggttgatgaa actgttgtac gtggtgtagc aacgagccgt   1260
aattttcaaa aagctctgtt agctgatcca caggttcaac gtggcgaatt tgacacacgt   1320
tatttggaaa ctgaattttt accgagatgg acacaaacat tgccagataa tcaataa      1377
```

<210> SEQ ID NO 88
<211> LENGTH: 1701
<212> TYPE: DNA
<213> ORGANISM: Unknown
<220> FEATURE:
<223> OTHER INFORMATION: Description of Unknown:
      DP1 Glutamine--tRNA ligase microbial sequence

<400> SEQUENCE: 88

```
atgagcaagc ccactgtcga ccctacctcg aattccaagg ccggacctgc cgtcccggtc     60
aatttcctgc gcccgatcat ccaggcggac ctggattcgg gcaagcatac gcagatcgtc    120
acccgcttcc cgccagagcc caacggctac ctgcacatcg gtcatgccaa gtcgatttgt    180
gtgaacttcg gcctggctca ggagttcggt ggcgttacgc acctgcgttt cgacgacacc    240
aacccggcca aggaagacca ggaatacatc gacgccatcg aaagcgacat caagtggctg    300
ggcttcgaat ggtccggtga agtgcgctat gcatccaagt atttcgacca gctgttcgac    360
tgggccgtcg agttgatcaa ggccggcaag gcctacgttg acgacctgac cccgagcaa     420
gccaaggaat accgtggcag cctgaccgag ccgggcaaga acagcccgtt ccgcgaccgt    480
tcggtcgaag agaacctcga ctggttcaac cgcatgcgcg ccggtgagtt cccggacggc    540
gcccgcgtgc tgcgcgccaa gatcgacatg gcctcgccga acatgaacct gcgcgacccg    600
atcatgtacc gcattcgcca tgcccatcac caccagaccg gtgacaagtg gtgcatctac    660
cccaactacg acttcaccca cggtcagtcg gacgccatcg aaggcatcac ccactccatc    720
tgcaccctgg agttcgaaag ccatcgccct ctgtacgaat ggttcctgga cagcctgccg    780
```

-continued

```
gtgccggcgc acccgcgtca gtacgaattc agccgcctga acctgaacta caccatcacc    840

agcaagcgca agctcaagca actggtcgat gaaaagcacg tgcatggctg ggacgacccg    900

cgcatgtcga cgctctcggg tttccgtcgt cgtggctaca ccccggcgtc gatccgcaat    960

ttctgcgaca tggtcggcac caaccgttct gacggtgtgg tcgattacgg catgcttgag   1020

ttcagcatcc gtcaggatct ggacgcgaac gcgccgcgcg ccatgtgcgt gctgcgtccg   1080

ttgaaagtcg tgatcaccaa ctacccggaa gacaaggtcg accaccttga gctgccgcgt   1140

cacccgcaga aagaagagct gggcgtgcgc aagctgccgt tcgcgcgcga aatctacatc   1200

gaccgtgacg acttcatgga agagccgccg aagggttaca agcgcctgga gccgaacggc   1260

gaagtgcgcc tgcgtggcag ctacgtgatc cgcgccgacg aagcaatcaa ggacgccgaa   1320

ggcaacatcg tcgaactgcg ctgctcgtac gatccggaaa cactcggcaa gaaccctgaa   1380

ggccgtaagg tcaagggcgt gatccactgg gtgccggccg ctgccagcat cgagtgcgaa   1440

gtgcgtctgt acgatcgtct gttccgatcg ccgaacccgg agaaggccga agacagcgcc   1500

agcttcctgg acaacatcaa ccctgactcg ctgcaagtgc ttacaggttg tcgtgctgag   1560

ccatcgcttg gcgacgcaca gccggaagac cgtttccagt tcgagcgcga aggttacttc   1620

tgcgcggata tcaaggactc gaaacccggt gctccggtat tcaaccgtac cgtgaccttg   1680

cgtgattcgt ggggccagtg a                                             1701
```

```
<210> SEQ ID NO 89
<211> LENGTH: 2418
<212> TYPE: DNA
<213> ORGANISM: Unknown
<220> FEATURE:
<223> OTHER INFORMATION: Description of Unknown:
      DP1 DNA gyrase subunit B microbial sequence

<400> SEQUENCE: 89

atgagcgaag aaaacacgta cgactcgacc agcattaaag tgctgaaagg tttggatgcc     60

gtacgcaaac gtcccggtat gtacatcggc gacaccgatg atggtagcgg tctgcaccac    120

atggtgttcg aggtggtcga caactccatc gacgaagctt tggccggtca ctgcgacgac    180

atcagcatta tcatccaccc ggatgagtcc atcacggtgc gcgacaacgg tcgcggcatt    240

ccggtcgatg tgcacaaaga agaaggcgtt tcggcggctg aggtcatcat gaccgtgctg    300

cacgccggcg gtaagttcga tgacaactct tataaagtct ccggcggtct gcacggtgta    360

ggtgtgtcgg tagtgaacgc actgtccgaa gagctgatcc tgaccgttcg ccgtagcggc    420

aagatttggg agcagacgta cgtccatggt gtgccacaag agccgatgaa aatcgttggc    480

gacagtgaat ccacgggtac gcagatccac ttcaagccat cggctgaaac cttcaagaac    540

atccacttta gctgggacat cctggccaag cggattcgcg aactgtcctt cctcaactcc    600

ggtgtgggta tcgtcctcaa ggacgagcgc agcggcaagg aagaactgtt caagtacgaa    660

ggcggtctgc gcgcgttcgt tgaatacctg aacaccaata agaccgcggt caaccaggtg    720

ttccacttca acattcagcg tgaagacggc atcggcgtgg aaatcgccct gcagtggaac    780

gacagcttca acgagaactt gttgtgcttc accaacaaca ttccacagcg cgatggcggt    840

actcacttgg tgggtttccg ttccgcactg acgcgtaacc tgaacactta catcgaagcc    900

gaaggcttgg ccaagaagca caaagtcgcc accaccggtg acgatgcgcg tgaaggcctg    960

accgcgatta tctcggtgaa agtgccggat cccaagttca gctcccagac caaagacaag   1020

ctggtttctt ccgaggtgaa gaccgccgtg gaacaggaga tgggcaagta cttctccgac   1080
```

-continued ttcctgctgg agaacccgaa cgaagccaag ctggtcgtcg gcaagatgat cgacgctgca 1140
cgtgctcgcg aagcggcgcg taaagcccgt gagatgaccc gtcgtaaagg cgcgctggat 1200
attgctggct tgcctggcaa gttggctgac tgccaggaga aggacccagc gctctccgag 1260
ctatatcttg tggaaggtga ctctgctggc ggttccgcca agcagggtcg taaccgtcgc 1320
acccaggcga tcctgccgtt gaaaggcaag attctcaacg tagagaaggc ccgcttcgac 1380
aagatgattt cctcccagga agtcggcacc ttgattacgg cgttgggttg cggcattggc 1440
cgcgatgagt acaacatcga caagctgcgc taccacaaca tcatcatcat gaccgatgct 1500
gacgtcgacg gttcgcacat ccgtaccttg ctgctgacct tcttcttccg tcagttgcct 1560
gagctgattg agcgtggcta catctatatc gcgcagccgc cgttgtacaa agtgaaaaag 1620
ggcaagcaag agcagtacat caaagacgac gacgccatgg aagagtacat gacgcagtcg 1680
gccctggaag atgcaagcct gcacttgaac gacgaagcac cgggtatctc cggtgaggcg 1740
ttggagcgtc tggttaacga cttccgtatg gtgatgaaga ccctcaagcg tctatcgcgt 1800
ctgtaccctc aggaactgac cgagcacttc atctacctgc cggccgtcag tctggagcag 1860
ttgggtgatc atgcagcgat gcaagagtgg ctggctcagt acgaagtacg cctgcgcact 1920
gttgagaagt ctggcctggt gtacaaagcc agtctgcgtg aagaccgtga acgtaacgtg 1980
tggctgccgg aggttgagtt gatctcccac ggcctgtcga attacgtcac cttcaaccgc 2040
gacttcttcg gcagtaatga ctacaagacg gtcgtgaccc tcggcgcgca gttgagcacc 2100
ttgctggatg atggtgctta cattcaacgt ggcgagcgta agaaagcggt caaggagttc 2160
aaggaagcct tggactggct gatggcggaa agcaccaagc gtcataccat tcagcgatac 2220
aaaggtctgg gcgagatgaa ccctgatcag ttgtgggaaa ccaccatgga tccagcacag 2280
cgtcgcatgc tgcgcgtgac catcgaagac gccattggcg cagatcagat cttcaacacc 2340
ctgatgggtg atgcggtcga acctcgccgt gacttcatcg agagcaatgc cttggcggtg 2400
tccaacctgg acttctga 2418

<210> SEQ ID NO 90
<211> LENGTH: 1632
<212> TYPE: DNA
<213> ORGANISM: Unknown
<220> FEATURE:
<223> OTHER INFORMATION: Description of Unknown:
DP1 Isoleucine--tRNA ligase microbial sequence

<400> SEQUENCE: 90
atgaccgact ataaagccac gctaaacctt ccggacaccg ccttcccaat gaaggccggc 60
ctgccacagc gcgaaccgca gatcctgcag cgctgggaca gtattggcct gtacggaaag 120
ttgcgcgaaa ttggcaagga tcgtccgaag ttcgtcctgc acgacggccc tccttatgcc 180
aacggcacga ttcacatcgg tcatgcgctg aacaaaattc tcaaggacat gatcctgcgc 240
tcgaaaaccc tgtcgggttt tgacgcgccg tatgtcccgg gctgggactg ccatggcctg 300
ccgatcgaac acaaagtcga agtgacctac ggcaaaaacc tgggcgcgga taaaacccgc 360
gaactgtgcc gtgcctacgc cactgagcag atcgaagggc agaagtccga attcatccgc 420
ctgggcgtgc tgggcgagtg ggacaacccg tacaagacca tgaacttcaa gaacgaggcc 480
ggtgaaatcc gtgccttggc tgaaatcgtc aaaggcggtt ttgtgttcaa gggcctcaag 540
cccgtgaact ggtgcttcga ctgcggttcg gccctggctg aggcggaagt cgaatacgaa 600
gacaagaagt cctcgaccat cgacgtggcc ttcccgatcg ccgacgacgc caagttggcc 660

-continued caggctttcg gcctggcaag cctgagcaag ccggcggcca tcgtgatctg gaccaccacc 720
ccgtggacca tcccggccaa ccaggcgctg aacgtgcacc cggaattcac ctacgccctg 780
gtggacgtcg gtgatcgcct gctggtgctg gccgaggaaa tggtcgaggc ctgtctggcg 840
cgctacgaac tgcaaggttc ggtgatcgcc accaccaccg gctccgcgct ggaactgatc 900
aacttccgtc acccgttcta tgaccgcctg tcgccggttt acctggctga ctacgtcgaa 960
ctgggttcgg gtacgggtgt ggttcactcc gcaccggcct acggcgttga cgacttcgtg 1020
acctgcaaag cctacggtat ggtcaacgat gacatcctca acccggtgca gagcaatggt 1080
gtgtacgcgc catcgctgga gttcttcggc ggccagttca tcttcaaggc taacgagccg 1140
atcatcgaca aactgcgtga agtcggtgcg ctgctgcaca ccgaaaccat caagcacagc 1200
tacatgcact gctggcgcca caaaaccccg ctgatctacc gcgccaccgc gcagtggttt 1260
atcggcatgg acaaagagcc gaccagcggc gacaccctgc gtgtgcgctc gctcaaagcc 1320
atcgaagaca ccaagttcgt cccggcctgg ggccaggcgc gcctgcactc gatgatcgcc 1380
aatcgtccgg actggtgcat ctcccgccag cgtaactggg gcgtaccgat cccgttcttc 1440
ctgaacaagg aaagcggcga gctgcaccca cgcaccgtcg agctgatgga agccgtggcc 1500
ttgcgcgttg aacaggaagg catcgaagcc tggttcaagc tggacgccgc cgagctgctg 1560
ggcgacgaag cgccgctgta cgacaagaag gctcggacca acaccgtggc tggttccact 1620
cgtcgctgct ga 1632

<210> SEQ ID NO 91
<211> LENGTH: 1784
<212> TYPE: DNA
<213> ORGANISM: Unknown
<220> FEATURE:
<223> OTHER INFORMATION: Description of Unknown:
DP1 NADH-quinone oxidoreductase subunit C/D microbial sequence

<400> SEQUENCE: 91
atgactacag gcagtgctct gtacatcccg ccttataagg cagacgacca ggatgtggtt 60
gtcgaactca ataaccgttt tggccctgac gcctttaccg cccaggccac acgtaccggc 120
atgccggtgc tgtgggtggc gcgcgccagg ctcgtcgaag tcctgacctt cctgcgcaac 180
ctgcccaagc cgtacgtcat gctctatgac ctgcatggcg tggacgagcg tctgcggacc 240
aagcgccagg gcctgccgag cggcgccgat ttcaccgtgt tctatcacct gctgtcgatc 300
gaacgtaaca gcgacgtgat gatcaaggtc gccctctccg aaagcgacct gagcgtcccg 360
accgtgaccg gcatctggcc caacgccagt tggtacgagc gtgaagtctg ggacatgttc 420
ggtatcgact tccctggcca cccgcacctg acgcgcatca tgatgccgcc gacctgggaa 480
ggtcacccgc tgcgcaagga cttccctgcg cgcgccaccg aattcgaccc gttcagcctg 540
aacctcgcca agcaacagct tgaagaagag gctgcacgct tccggccgga agactggggc 600
atgaaacgct ccggcaccaa cgaggactac atgttcctca acctgggccc gaaccaccct 660
tcggcgcacg gtgccttccg tatcatcctg caactggacg gcgaagaaat cgtcgactgc 720
gtgccggaca tcggttacca ccaccgtggt gccgagaaga tggccgagcg ccagtcgtgg 780
cacagcttca tcccgtacac cgaccgtatc gactacctcg gcggcgtgat gaacaatctg 840
ccgtacgtgc tctcggtcga gaagctggcc ggtatcaagg tgccggaccg cgtcgacacc 900
atccgcatca tgatggccga gttcttccgg atcaccagcc acctgctgtt cctgggtacc 960
tacatccagg acgtcggcgc catgaccccg gtgttcttca ccttcaccga ccgtcagcgc 1020
gcctacaagg tcatcgaagc catcaccggc ttccgcctgc acccggcctg gtaccgcatc 1080
ggcggtgtcg cgcacgacct gccaaatggc tgggaacgcc tggtcaagga attcatcgac 1140
tggatgccca agcgtctgga cgagtaccag aaagccgccc tggacaacag catcctcaag 1200
ggccggacca ttggggtcgc ggcctacaac accaaagagg ccctggaatg ggcgtcacc 1260 ggtgctggcc tgcgttccac cggttgcgat ttcgacctgc gtaaagcgcg cccgtactcc 1320
ggctacgaga acttcgaatt cgaagtgccg ttggcggcca atggcgatgc ctacgaccgt 1380
tgcatcgtgc gcgtcgaaga aatgcgccag agcctgaaga tcatcgagca atgcatgcgc 1440
aacatccggc aggcccgtac aaggcggacc acccgctgac cacgccgccg ccgaaagagc 1500
gcacgctgca acacatcgaa accctgatca cgcacttcct gcaggtttcg tggggcccgg 1560
tgatgccggc caacgaatcc ttccagatga tcgaagcgac caagggtatc aacagttatt 1620
acctgacgag cgatggcggc accatgagct accgcacccg gattcgcact ccaagcttcc 1680
cgcacctgca gcagatccct tcggtgatca aaggtgaaat ggtcgcggac ttgattgcgt 1740
acctgggtag tatcgatttc gttatggccg acgtggaccg ctaa 1784

<210> SEQ ID NO 92
<211> LENGTH: 1059
<212> TYPE: DNA
<213> ORGANISM: Unknown
<220> FEATURE:
<223> OTHER INFORMATION: Description of Unknown:
DP1 Protein RecA microbial sequence

<400> SEQUENCE: 92
atggacgaca acaagaagaa agccttggct gcggccctgg gtcagatcga acgtcaattc 60
ggcaagggtg ccgtaatgcg tatgggcgat cacgaccgtc aggcgatccc ggctatttcc 120
actggctctc tgggtctgga catcgcactc ggcattggcg gcctgccaaa aggccgtatc 180
gttgaaatct acggccctga atcttccggt aaaaccaccc tgaccctgtc ggtgattgcc 240
caggcgcaaa aaatgggcgc cacttgtgcg ttcgtcgatg ccgagcacgc tcttgaccct 300
gaatacgccg gcaagctggg cgtcaacgtt gacgacctgc tggtttccca accggacacc 360
ggtgagcaag ccttggaaat caccgacatg ctggtgcgct ccaacgccat cgacgtgatc 420
gtggtcgact ccgtggctgc cctggtgccg aaagctgaaa tcgaaggcga aatgggcgac 480
atgcacgtgg gcctgcaagc ccgtctgatg tcccaggcgc tgcgtaaaat caccggtaac 540
atcaagaacg ccaactgcct ggtgatcttc atcaaccaga tccgtatgaa gattggcgtg 600
atgttcggca gcccggaaac caccaccggt ggtaacgcgt tgaagttcta cgcttcggtc 660
cgtctggata tccgccgtac tggcgcggtg aaggaaggcg acgaggtggt gggtagcgaa 720
acccgcgtta aagttgtgaa gaacaaggtg gccccgccat tccgtcaggc tgagttccag 780
attctctacg gcaagggtat ctacctgaac ggcgagatga tcgacctggg cgtactgcac 840
ggtttcgtcg agaagtccgg tgcctggtat gcctacaacg gcagcaagat cggtcagggc 900
aaggccaact cggccaagtt cctggcggac aacccggata tcgctgccac gcttgagaag 960
cagattcgcg acaagctgct gaccccggca ccagacgtga aagctgctgc caaccgcgag 1020
ccggttgaag aagtagaaga agtcgacact gacatctga 1059

<210> SEQ ID NO 93
<211> LENGTH: 1161
<212> TYPE: DNA
<213> ORGANISM: Unknown
<220> FEATURE:

<223> OTHER INFORMATION: Description of Unknown:
DP1 RNA polymerase sigma factor RpoD microbial sequence

<400> SEQUENCE: 93

```
atggaaatca cccgcaaggc tctgaaaaag cacggtcgcg gcaacaagct ggcaattgcc     60
gagctggtgg ccctggctga gctgttcatg ccaatcaagc tggtgccgaa gcaatttgaa    120
ggcctggttg agcgtgtgcg cagtgctctt gagcgtctgc gtgcccaaga gcgcgcaatc    180
atgcagctct gcgtacgtga tgcacgcatg ccgcgtgccg acttcctgcg ccagttcccg    240
ggcaacgaag tggatgaaag ctggaccgac gcactggcca aaggcaaggc gaagtacgcc    300
gaagccattg gtcgcctgca gccggacatc atccgttgcc agcagaagct gaccgcgctt    360
caaaccgaaa ccggtctgac gattgctgag atcaaggaca tcaaccgtcg catgtcgatc    420
ggtgaggcca aggcccgccg cgcgaagaaa gagatggttg aagcgaactt gcgtctggtg    480
atctccatcg ccaagaagta caccaaccgt ggcctgcaat tcctcgatct gatccaggaa    540
ggcaacatcg gcttgatgaa ggctgtggac aagttcgaat accgtcgcgg ctacaagttc    600
tcgacttatg ccacctggtg gatccgtcag gcgatcactc gctcgatcgc agaccaggcc    660
cgcaccatcc gtattccggt gcacatgatc gagaccatca acaagctcaa ccgtatttcc    720
cggcagatgt tgcaggaaat gggtcgcgaa ccgacgccgg aagagctggg cgaacgcatg    780
gaaatgcctg aggataaaat ccgtaaggta ttgaagatcg ctaaagagcc gatctccatg    840
gaaacgccga ttggtgatga cgaagactcc catctgggtg acttcatcga agactcgacc    900
atgcagtcgc ccatcgatgt ggctaccgtt gagagcctta aagaagcgac tcgcgacgta    960
ctgtccggcc tcactgcccg tgaagccaag gtactgcgca tgcgtttcgg catcgacatg   1020
aataccgacc acacccttga ggaagtcggt aagcagtttg acgtgacccg tgaacggatc   1080
cgtcagatcg aagccaaggc actgcgcaag ttgcgccacc cgacgcgaag cgagcatcta   1140
cgctccttcc tcgacgagtg a                                             1161
```

<210> SEQ ID NO 94
<211> LENGTH: 4074
<212> TYPE: DNA
<213> ORGANISM: Unknown
<220> FEATURE:
<223> OTHER INFORMATION: Description of Unknown:
DP1 DNA-directed RNA polymerase subunit beta
microbial sequence

<400> SEQUENCE: 94

```
atggcttact catatactga gaaaaaacgt atccgcaagg actttagcaa gttgccggac     60
gtcatggatg tcccgtacct tctggctatc cagctggatt cgtatcgtga attcttgcaa    120
gcgggagcga ctaaagatca gttccgcgac gtgggcctgc atgcggcctt caaatccgtt    180
ttcccgatca tcagctactc cggcaatgct gcgctggagt acgtgggtta tcgcctgggc    240
gaaccggcat ttgatgtcaa agaatgcgtg ttgcgcggtg ttacgtacgc cgtacctttg    300
cgggtaaaag tccgtctgat cattttcgac aaagaatcgt cgaacaaagc gatcaaggac    360
atcaaagagc aagaagtcta catgggcgaa atcccattga tgactgaaaa cggtaccttc    420
gttatcaacg gtaccgagcg cgttatcgtt tcccagctgc accgttcccc gggcgtgttc    480
ttcgaccacg accgcggcaa gacgcacagc tccggtaagc tcctgtactc cgcgcggatc    540
attccgtacc gcggctcgtg gttggacttc gagttcgacc cgaaagactg cgtgttcgtg    600
cgtatcgacc gtcgtcgtaa gctgccggcc tcggtactgc tgcgcgcgct cggctatacc    660
```

-continued

```
actgagcaag tgcttgatgc tttctacacc accaacgtat tcagcctgaa ggatgaaacc    720
ctcagcctgg aactgattgc ttcgcgtctg cgtggtgaaa ttgccgtcct ggatatccag    780
gatgaaaacg gcaaggtcat cgttgaagct ggccgccgta ttaccgcgcg ccacatcaac    840
cagatcgaaa aagccggtat caagtcgctg gacgtgccgc tggactacgt cctgggtcgc    900
accactgcca aggtcatcgt tcacccggct acaggcgaaa tcctggctga gtgcaacacc    960
gagctgaaca ccgagatcct ggcaaaaatc gccaaggccc aggttgttcg catcgagacc   1020
ctgtacacca acgacatcga ctgcggtccg ttcatctccg acacgctgaa gatcgactcc   1080
accagcaacc aattggaagc gctggtcgag atctatcgca tgatgcgtcc tggtgagcca   1140
ccgaccaaag acgctgccga gaccctgttc aacaacctgt tcttcagccc tgagcgctat   1200
gacctgtctg cggtcggccg gatgaagttc aaccgtcgta tcggtcgtac cgagatcgaa   1260
ggttcgggcg tgctgtgcaa ggaagacatc gtcgcggtac tgaagacctt ggtcgacatc   1320
cgtaacggta aaggcatcgt cgatgacatc gaccacttgg gtaaccgtcg tgttcgctgc   1380
gtaggcgaaa tggccgagaa ccagttccgc gttggcctgg tacgtgttga gcgtgcggtc   1440
aaagagcgtc tgtcgatggc tgaaagcgaa ggcctgatgc cgcaagatct gatcaacgcc   1500
aagccagtgg ctgcggcggt gaaagagttc ttcggttcca gccagctctc gcagttcatg   1560
gaccagaaca acccgctctc cgagatcacc cacaagcgcc gtgtttccgc actgggcccg   1620
ggcggtctga cccgtgagcg tgcaggcttt gaagttcgtg acgtacaccc aacgcactac   1680
ggtcgtgttt gcccgatcga aacgccggaa ggtccgaaca tcggtctgat caactccctt   1740
gccgcttatg cacgcactaa ccagtacggc ttcctcgaga gcccgtaccg tgtagtgaaa   1800
gatgcactgg tcaccgacga gatcgtgttc ctgtccgcca tcgaagaagc cgatcacgtg   1860
atcgctcagg cttcggccac gatgaacgac aagaaagtcc tgatcgacga gctggtagct   1920
gttcgtcact tgaacgagtt caccgttaag gcgccggaag acgtcacctt gatggacgtt   1980
tcgccgaagc aggtagtttc ggttgcagcg tcgctgatcc cgttcctgga gcacgatgac   2040
gccaaccgtg cgttgatggg ttccaacatg cagcgtcaag ctgtacccac cctgcgtgcc   2100
gacaagccgc tggtaggtac cggcatggag cgtaacgtag cccgtgactc cggcgtttgc   2160
gtcgtggctc gtcgtggcgg cgtgatcgac tctgttgatg ccagccgtat cgtggttcgt   2220
gttgccgatg acgaagttga gactggcgaa gccggtgtcg acatctacaa cctgaccaaa   2280
tacacccgct cgaaccagaa cacctgcatc aaccagcgcc cgctggtgag caagggtgat   2340
cgcgttcagc gtagcgacat catggccgac ggcccgtcca ccgatatggg tgagctggca   2400
ctgggtcaga acatgcgcat cgcgttcatg gcatggaacg gcttcaactt cgaagactcc   2460
atctgcctgt ccgagcgtgt tgttcaagaa gaccgcttca ccacgatcca cattcaggag   2520
ctgacctgtg tggcgcgtga caccaagctt gggccagagg aaatcactgc agacatcccg   2580
aacgtgggtg aagctgcact gaacaaactg gacgaagccg gtatcgttta cgtaggtgct   2640
gaagttggcg caggcgacat cctggttggt aaggtcactc cgaaaggcga gacccaactg   2700
actccggaag agaagctgtt gcgtgccatc ttcggtgaaa aagccagcga cgttaaagac   2760
acttccctgc gcgtacctac cggtaccaag ggtactgtca tcgacgtaca ggtcttcacc   2820
cgtgacggcg ttgagcgtga tgctcgtgca ctgtccatcg agaagactca actcgacgag   2880
atccgcaagg acctgaacga agagttccgt atcgttgaag gcgcgacctt cgaacgtctg   2940
cgttccgctc tggtaggcca caaggctgaa ggcggcgcag gtctgaagaa aggtcaggac   3000
atcaccgacg aaatcctcga cggtcttgag cacggccagt ggttcaaact gcgcatggct   3060
```

gaagacgctc tgaacgagca gctcgagaag gcccaggcct atatcgttga tcgccgccgt 3120
ctgctggacg acaagttcga agacaagaag cgcaaactgc agcagggcga tgacctggct 3180
ccaggcgtgc tgaaaatcgt caaggtttac ctggcaatcc gtcgccgcat tcagccgggc 3240
gacaagatgg ccggtcgtca cggtaacaag ggtgtggtct ccgtgatcat gccggttgaa 3300
gacatgcccg acgatgccaa tggcaccccg gtcgacgtcg tcctcaaccc gttgggcgta 3360
ccttcgcgta tgaacgttgg tcagatcctt gaaacccacc tgggcctcgc ggccaaaggt 3420
ctgggcgaga agatcaaccg tatgatcgaa gagcagcgca aggtcgcaga cctgcgtaag 3480
ttcctgcacg agatctacaa cgagatcggc ggtcgcaacg aagagctgga caccttctcc 3540
gaccaggaaa tcctggatct ggcgaagaac ctgcgcggcg gcgttccaat ggctaccccg 3600
gtattcgacg gtgccaagga aagcgaaatc aaggccatgc tgaaactggc agacctgccg 3660
gaaagtggcc agatgcagct gttcgacggc cgtaccggca acaagtttga gcgcccggtt 3720
actgttggct acatgtacat gctgaagctg aaccacttgg tagacgacaa gatgcacgct 3780
cgttctaccg gttcgtacag cctggttacc cagcagccgc tgggtggtaa ggctcagttc 3840
ggtggtcagc gtttcgggga gatggaggtc tgggcactgg aagcatacgg tgctgcttac 3900
actctgcaag aaatgctcac agtgaagtcg gacgatgtga acggtcggac caagatgtac 3960
aaaaacatcg tggacggcga tcaccgtatg gagccgggca tgcccgagtc cttcaacgtg 4020
ttgatcaaag aaattcgttc cctcggcatc gatatcgatc tggaaaccga ataa 4074

<210> SEQ ID NO 95
<211> LENGTH: 1671
<212> TYPE: DNA
<213> ORGANISM: Unknown
<220> FEATURE:
<223> OTHER INFORMATION: Description of Unknown:
DP22 Glutamine--tRNA ligase microbial sequence

<400> SEQUENCE: 95
atgagtgagg ctgaagcccg cccaacaaat tttatccgtc agattattga tgaagatctg 60
gcgaccggga aacacaatac cgttcatacc cgtttcccgc ctgagccaaa tggctatctg 120
catatcggtc atgcgaaatc tatctgcctg aacttcggca ttgcgcaaga ctatcagggg 180
cagtgcaacc tgcgttttga cgataccaac ccggcaaaag aagacatcga attcgttgag 240
tcgatcaaac acgacgtcca gtggttaggt ttcgactgga gcggtgatat tcactactct 300
tcagactatt ttgatcaact gcacgcttat gcgctggaac tgatcaacaa aggtctggcg 360
tacgttgacg aactgtcacc ggatcagatc cgtgaatacc gcggctcgct gacgtctccg 420
ggcaaaaaca gcccgtaccg tgaccgttca gtggaagaga acatcgcgct gtttgagaaa 480
atgcgtaacg gtgaatttgc cgaaggcgct gcctgtctgc gtgcaaaaat cgatatggcg 540
tcgcctttct tcgtgatgcg cgatccggtt ctgtaccgta ttaagtttgc agaacaccac 600
cagaccggca aaaaatggtg catctatccg atgtacgatt tcacccactg catttccgat 660
gcgctggaag ggatcaccca ttcgctgtgt acgctggaat tccaggacaa ccgccgtctg 720
tacgactggg ttctggataa catctccatt ccatgccacc cgcgtcagta cgagttctcc 780
cgtctgaatc tcgagtactc catcatgtct aagcgtaagc tgaaccagct ggtgaccgag 840
aagattgtgg aaggctggga cgacccgcgt atgccgactg tttcaggtct gcgtcgtcgt 900
ggttacaccg ccgcgtctat ccgtgaattc tgccgtcgta tcggcgtcac caagcaagac 960
aacaacgtcg aaatgatggc gctggaatcc tgtatccgtg acgatctgaa cgaaaatgca 1020
ccgcgcgcca tggcggtgat caaccccggtt aaagtgatca ttgaaaactt taccggtgat 1080
gacgtgcaga gggtgaaaat gccgaaccac ccgagcaaac cggaaatggg cacccgcgaa 1140
gtgccattta cccgtgagat ttatatcgat caggcagatt tccgcgaaga agcgaacaag 1200
caatacaagc gtctggtgct cggcaaagaa gtgcgtctgc gcaatgcgta tgtgatcaaa 1260
gcagaacgta tcgagaaaga tgcagaaggc aatatcacca cgatcttctg ttcttacgat 1320
atcgatacac tgagcaaaga tcctgccgat ggccgcaagg tgaaaggcgt gatccactgg 1380
gtttcggcgt cagaaggcaa accggcggag ttccgcctgt atgaccgtct gttcagcgtc 1440
gccaacccgg gtcaggcaga agatttcctg accaccatca acccggaatc tctggtgatt 1500
tcccacggtt tcgtggagcc atcactggtg gctgcacagg ctgaaatcag cctgcagttc 1560
gagcgtgaag gttacttctg cgccgacagc cgctactcaa gcgctgaaca tctggtgttt 1620
aaccgtaccg ttggcctgcg cgatacctgg gaaagcaaac ccgtcgtgta a 1671

<210> SEQ ID NO 96
<211> LENGTH: 2415
<212> TYPE: DNA
<213> ORGANISM: Unknown
<220> FEATURE:
<223> OTHER INFORMATION: Description of Unknown:
DP22 DNA gyrase subunit B microbial sequence

<400> SEQUENCE: 96
atgtcgaatt cttatgactc ctcaagtatc aaggtattaa aagggctgga cgcggtgcgt 60
aagcgccccg gcatgtatat cggcgatacc gatgacggca ctggtctgca ccacatggta 120
ttcgaggttg tggacaacgc tatcgacgaa gccctcgcgg gccactgtaa agagattcag 180
gtcacgatcc atgcggataa ctctgtgtcc gtacaggatg atggtcgtgg cattccgacc 240
ggtattcatg aagaagaggg cgtttctgct gctcaggtca tcatgaccgt tcttcacgcc 300
ggcggtaaat ttgacgataa ctcgtataaa gtctccggcg gtctgcatgg cgtgggtgtt 360
tccgtcgtta acgccctgtc agaaaaactg gaactggtta tccgccgcga aggcaaagtg 420
cacacccaga cttacgtgca tggcgaacct caggatccgc tgaaagtgat tggcgatact 480
gacgtgaccg gtaccacggt acgtttctgg ccaagcttca acaccttcac caatcacact 540
gaattcgagt atgacattct ggcgaaacgc ctgcgtgaac tgtcattcct gaactccggc 600
gtggcgatcc gcctgctgga taaacgtgat ggtaaaaacg atcacttcca ttatgaaggc 660
ggtatcaaag ctttcgtgga atatctgaac aaaaacaaaa ccccaatcca tccgaccgta 720
ttctatttct ccacggtcaa agatgacatt ggcgttgaag tggcgttgca gtggaacgac 780
ggtttccagg aaaacattta ctgcttcacc aacaacattc cacagcgcga tggcgggact 840
cacttagccg gtttccgttc ggcaatgacc cgtaccctga acgcgtacat ggataaagaa 900
ggctacagca agaaatccaa aatcagcgcc accggtgatg atgcccgtga aggcctgatt 960
gctgtggtgt cggtgaaggt gccggatcct aagttctctt ctcagaccaa agacaaactg 1020
gtgtcttctg aagtgaaaac agcggttgaa acgctgatga acgagaagct ggtggattac 1080
ctgatggaaa acccgtcaga cgccaaaatc gttgtcggta aaatcatcga cgcagcgcgt 1140
gcccgtgaag cagcacgtaa agcgcgtgaa atgacccgcc gtaaaggcgc gctggatctg 1200
gctggcttgc caggcaaact ggcggactgt caggaacgcg atccggcaca ttccgaactg 1260
tacttagtgg aaggggactc agcgggcggc tctgcaaaac aaggccgtaa ccgtaagaac 1320
caggcgattc tgccgttgaa aggtaaaatc ctcaacgtgg agaaagcgcg cttcgacaaa 1380

```
atgctctctt ctcaggaagt ggcaacgctg attacagcac tcggttgcgg cattggccgt   1440

gacgaataca acccggacaa actgcgctat cacagcatca tcatcatgac cgatgccgac   1500

gtcgatggtt cgcacatccg taccctgttg ctgacattct tctaccgtca gatgcctgaa   1560

attgtagaac gtggccacgt gtttatcgcc cagccgccgt tgtacaaagt gaaaaaaggc   1620

aagcaggaac agtacattaa agatgacgaa gcgatggatc agtatcagat ttccattgcg   1680

atggacgggg caacgttaca cgccaacgct catgcgccag ccctggcggg tgaaccgctg   1740

gagaaactgg tcgctgaaca tcacagcgtg cagaaaatga ttggccgcat ggaacgtcgt   1800

tatccgcgtg cgctgctgaa taacctgatc tatcagccga ccctgccggg tgcagatctg   1860

gccgatcagg cgaaagtgca ggcctggatg gaatcgctgg tggcgcgtct caacgagaaa   1920

gagcagcacg gcagttctta cagcgcgatc gtgcgtgaaa accgcgaaca tcagctgttc   1980

gaaccggttc tgcgtatccg cacccacggt gttgataccg attacgatct ggatgccgac   2040

ttcatcaaag gcggcgaata ccgcaaaatc tgtgcgctgg gtgaacagct gcgcggcctg   2100

atcgaagaag atgccttcat cgaacgtggc gaacgccgtc agcccgtcac cagcttcgaa   2160

caggcgctgg aatggctggt gaaagagtcc cgtcgtggtc tgtcgattca gcgatacaaa   2220

ggtctgggtg aaatgaaccc tgaacagctg tgggaaacca ccatggatcc tgagcaacgt   2280

cgcatgttac gtgtgaccgt gaaggatgcc atcgccgctg accagttgtt cacgacgctg   2340

atgggcgatg cggttgaacc gcgccgcgcc tttatcgaag agaacgccct gaaagccgcc   2400

aatatcgata tctga                                                    2415
```

<210> SEQ ID NO 97
<211> LENGTH: 2733
<212> TYPE: DNA
<213> ORGANISM: Unknown
<220> FEATURE:
<223> OTHER INFORMATION: Description of Unknown:
      DP22 Isoleucine--tRNA ligase microbial sequence

<400> SEQUENCE: 97

```
atgagtgact acaagaacac cctgaatttg ccggaaacag ggttcccgat gcgtggcgat     60

ctggccaagc gtgaacctga catgctgaaa aattggtatg accaggatct gtacgggatt    120

attcgtgctg ccaagaaagg caaaaaaacc tttattttgc atgacggccc tccgtatgcg    180

aacggcagca ttcatattgg tcactcagta aacaaaattc ttaaagacat gattatcaag    240

tccaaaggac ttgcgggctt tgatgcgccg tatgtgccgg gctgggattg tcatggtctg    300

ccgatcgagc tgaaagtcga acaactgatc ggtaagccgg gcgagaaagt tacggcggcg    360

gaattccgtg aagcctgccg taaatatgcc gcagaacagg ttgaaggcca gaagaaagac    420

ttcatccgtc tgggcgtgct gggcgactgg gatcatccgt acctgacgat ggatttcaaa    480

accgaagcca acatcatccg tgcgctgggc aaaatcatcg gtaacggcca cctgcataaa    540

ggcgccaagc cggtgcactg gtgtacagat tgcggttcgt cgctggccga agccgaagtc    600

gaatattacg acaaagcctc gccttctatt gatgtggcgt tcaacgcgac ggatgccgca    660

gccgtggcag cgaaatttgg cgttactgcc tttaatggcc cgatctcgct ggttatctgg    720

accacaacac cgtggactat gcccgctaac cgcgccattt cactgaatcc tgagtttgct    780

tatcagctgg ttcaggtcga aggtcagtgt ctgatcctgg caaccgatct ggttgaaagc    840

gtcatgaaac gtgccggtat tgccggatgg accgttctgg gcgagtgcaa aggcgcagac    900

ctcgaactgc tgcgcttcaa acacccgttc ctcggtttcg acgttccggc gatcctgggc    960
```

gatcacgtga cgctcgatgc gggtaccggt gccgtgcata ccgcaccagg ccacggccct 1020
gacgactttg ttatcggcca gaaatacggt ctggaagtgg cgaatccggt agggccgaac 1080
ggttgctacc tgccgggcac ttacccgacg ctggacggta aatttgtctt taaagccaac 1140
gacctgatcg ttgagttgct gcgtgaaaaa ggcgcattgc tgcacgttga gaaaatcacg 1200
cacagctatc cttgctgctg gcgccacaaa acgccaatca tcttccgcgc gacgccgcaa 1260
tggttcatca gcatggatca gaagggcctg cgtcagcagt cgctggaaga gatcaaaggc 1320
gtgcagtgga tcccggactg ggtcaggca cgtatcgaaa acatggtcgc taaccgtcct 1380
gactggtgta tctcccgtca gcgtacctgg ggcgtgccga tgtctctgtt cgttcacaaa 1440
gacactgagc agctgcatcc gcgcagcctt gagctgatgg aagaagtggc gaaacgtgtt 1500
gaggtggatg gcattcaggc gtggtgggat ctgaatccgg aagacattct gggtgcagac 1560
gccgcagatt acgtcaaagt accggacacg ctggacgtct ggtttgactc cggttcaacg 1620
cattcttccg ttgtggatgt gcgtcctgag ttcaacgggc attctcctga tctgtatctg 1680
gaaggttctg accagcatcg cggctggttc atgtcttccc tgatgatttc gacggcaatg 1740
aaaggcaaag cgccttacaa acaagtgctg actcacggtt tcaccgtgga tggtcagggc 1800
cgcaaaatgt ctaaatccat cggcaatacc atcgcgccgc aagacgtgat gaacaagctg 1860
ggtggcgaca ttctgcgtct gtgggtcgcg tcgacggatt acaccggcga aatcgccgtg 1920
tccgacgaaa tcctcaaacg tgctgctgat tcttaccgcc gtatccgtaa caccgcgcgc 1980
ttcctgctgg cgaaccttaa cggtttcgat ccggcgctgc acagcgtggc tccggaagac 2040
atggtggtgc tggaccgctg ggcggttggc cgtgcgaaag ccgctcagga agaaatcatt 2100
gctgcgtatg aagcctatga tttccatggc gttgttcagc gtctgatgca gttctgctcg 2160
atcgaaatgg gttccttcta tctggatatc attaaagatc gtcagtacac cgcgaaaagc 2220
gacagcgttg cacgtcgcag ctgtcagacc gcgctgtatc acatcagtga agcgctggtt 2280
cgctggatgg caccgatcat gtcgttcaca gccgatgaaa tctgggcgga actgccggga 2340
agccgtgaga aattcgtctt caccgaagag tggtacgacg gtctgttcgg tctcgcaggc 2400
aacgaatcca tgaacgatgc gttctgggat gaactgctga aagtgcgtgg cgaagtgaac 2460
aaagtgatcg aacaggcgcg tgcggataaa cgtctgggcg gttctctgga agcagcggtt 2520
acgctgtttg ctgatgatgc gctggcaaca gacctgcgtt ctctgggcaa tgaactgcgc 2580
tttgtgctgc tgacgtcagg ggcgaaagtt gccgcactga gtgatgcaga tgacgcggct 2640
cagtcgagtg aattgctgaa aggcctgaag attggtctgg cgaaagcaga aggcgacaag 2700
tgcccgcgct gctggcatta cactaccgat taa 2733

<210> SEQ ID NO 98
<211> LENGTH: 1800
<212> TYPE: DNA
<213> ORGANISM: Unknown
<220> FEATURE:
<223> OTHER INFORMATION: Description of Unknown:
DP22 NADH-quinone oxidoreductase subunit C/D
microbial sequence

<400> SEQUENCE: 98
atgacagatt tgacgacgca agattccgcc ctgccagcat ggcatacccg tgatcatctc 60
gatgatccgg ttatcggcga attgcgtaac cgttttgggc cagaggcctt tactgtccag 120
gcaacccgca ccggaattcc cgtggtgtgg ttcaagcgtg aacagttact ggaagcgatt 180
acctttttac gaaaacagcc aaaaccttac gtcatgcttt tcgatttgca tggctttgat 240
gagcgtttac gtacacaccg cgacggttta ccggctgcgg atttttccgt tttctaccac 300
ctgatctccg tcgagcgtaa ccgcgacatc atgatcaaag tggcgttgtc agaaaacgat 360
cttcatgttc cgacgatcac caaagtgttc ccgaacgcta actggtacga acgcgaaaca 420
tgggaaatgt tcggtattac cttcgacggc catccgcacc tgacgcgcat catgatgccg 480
cagacctggg aagggcatcc gctgcgtaaa gactatccgg cgcgcgccac cgagttcgat 540
ccttatgagc tgactaagca aaaagaagaa ctcgagatgg aatcgctgac cttcaagccg 600
gaagactggg gcatgaagcg cggtaccgat aacgaggact ttatgttcct caacctcggt 660
cctaaccacc cgtcagcgca tggtgcattc cgtattatcc tgcagctgga tggcgaagag 720
attgtcgact gcgtgcctga cgtcggttac caccaccgtg gtgcggagaa aatgggcgaa 780
cgccagtcat ggcacagcta cattccgtat actgaccgta tcgaatatct cggcggttgt 840
gttaacgaaa tgccttacgt gctggctgtt gaaaaactcg ccggtatcgt gacgccggat 900
cgcgttaaca ccatccgtgt gatgctgtct gaactgttcc gtatcaacag ccatctgctg 960
tacatctcta cgtttattca ggacgtgggt gcgatgacgc cggtattctt cgcctttacc 1020
gatcgtcaga aaatttacga tctggtggaa gcgatcaccg gtttccgtat gcacccggcc 1080
tggttccgta tcggtggcgt agcgcatgac ctgccgaaag gctgggaccg cctgctgcgt 1140
gaattccttg actggatgcc agcccgtttg gattcctacg tcaaagcggc gctgagaaac 1200
accattctga ttggccgttc caaaggcgtg gccgcgtata acgccgacga cgcactggcc 1260
tggggcacca ccggtgctgg cctgcgcgca acgggtatcc cgttcgatgt gcgtaaatgg 1320
cgtccgtatt caggttatga aaactttgac tttgaagtgc cgaccggtga tggcgtcagt 1380
gactgctatt cccgcgtgat gctgaaagtg gaagaacttc gtcagagcct gcgcattctg 1440
gaacagtgct acaaaaacat gccggaaggc ccgttcaagg cggatcaccc gctgaccacg 1500
ccgccaccga aagagcgcac gctgcaacac atcgagaccc tgatcacgca cttcctgcaa 1560
gtgtcgtggg ggccggtcat gcctgcacaa gaatctttcc agatggttga agcaaccaaa 1620
gggatcaaca gctactacct gaccagtgac ggcagcacca tgagctaccg cacccgtgtc 1680
cgtacgccga gcttcccgca tttgcagcag atcccgtccg taatccgtgg cagcctggta 1740
tccgacctga tcgtgtatct gggcagtatc gattttgtaa tgtcagatgt ggaccgctaa 1800

<210> SEQ ID NO 99
<211> LENGTH: 1065
<212> TYPE: DNA
<213> ORGANISM: Unknown
<220> FEATURE:
<223> OTHER INFORMATION: Description of Unknown:
DP22 Protein RecA microbial sequence

<400> SEQUENCE: 99
atggctattg atgagaacaa gcaaaaagcg ttagctgcag cactgggcca gattgaaaag 60
caattcggta aaggctccat catgcgtctg ggtgaagatc gctccatgga cgttgaaacg 120
atctctaccg gctctttgtc tctggatatc gcgttaggtg ccggcggttt gccaatgggc 180
cgtatcgttg agatctatgg cccggaatct tccggtaaaa caacgctgac cttgcaagtt 240
atcgcggctg cacagcgtga aggcaaaacc tgtgcgttca tcgatgcaga acacgccctg 300
gacccgatct acgctaaaaa actgggcgtg gatatcgata acctgctgtg ttctcagcca 360
gataccggcg aacaggctct ggaaatctgt gacgcgctga cccgttcagg cgctgttgac 420

-continued

```
gtgatcatcg ttgactccgt tgccgcactg acaccgaaag cggaaatcga aggcgaaatt    480

ggtgactctc acatgggcct cgcggcacgt atgatgagcc aggcgatgcg taagctggcc    540

ggtaacctga aaaacgccaa caccttgctg atcttcatca accagatccg tatgaaaatt    600

ggtgtgatgt tcggtaaccc ggaaaccacc accggcggta acgccctgaa attctacgct    660

tctgtgcgtc tggatatccg ccgtatcggc gcgatcaaag aaggcgatgt ggttgtcggt    720

agcgaaacgc gtgtgaaagt ggtgaagaac aaaatcgctg cgccatttaa acaagctgaa    780

ttccagatca tgtacggcga aggcatcaat atcaacggcg agctgattga tctcggcgtg    840

aagcacaagc tgatcgaaaa agccggtgca tggtatagct acaacggtga gaagattggt    900

cagggtaaag cgaactcctg caacttcctg aaagaaaacc cgaaagtggc tgccgagctg    960

gataaaaaac tgcgtgatat gctgttgagc ggtaccggtg aactgagtgc tgcgaccacg   1020

gctgaagatg ctgacgacaa catggaaacc agcgaagagt tttaa                   1065
```

```
<210> SEQ ID NO 100
<211> LENGTH: 1839
<212> TYPE: DNA
<213> ORGANISM: Unknown
<220> FEATURE:
<223> OTHER INFORMATION: Description of Unknown:
      DP22 RNA polymerase sigma factor RpoD microbial sequence

<400> SEQUENCE: 100

atggagcaaa acccgcagtc acagcttaag ctacttgtca cccgtggtaa ggagcaaggc     60

tatctgacct atgctgaggt caatgaccat ctgccggaag atatcgtcga ttccgaccag    120

atcgaagaca tcatccagat gattaacgac atgggcatcc aggtacttga agaagcaccg    180

gacgccgatg atttgatgct ggccgaaaac cgccctgata ccgatgaaga cgctgcagaa    240

gccgcggcgc aggtgctttc cagcgttgaa tccgaaattg gccgtaccac cgaccctgtg    300

cgtatgtata tgcgcgagat gggtaccgtt gagttgctga cccgtgaagg cgaaatcgac    360

atcgccaaac gtatcgaaga cggtatcaat caggtccagt gctccgttgc tgaatatcct    420

gaagctatca cttatttgtt agagcaatat gaccgtgtgg aagcaggcga agtacgtctg    480

tctgacctga tcaccggttt tgttgacccg aacgccgaag aagaaatcgc accaactgcg    540

actcacgtgg gttctgaact gaccactgaa gagcagaatg atgacgacga agacgaagat    600

gaagacgacg acgctgaaga cgacaacagc atcgatccgg aactggctcg ccagaagttc    660

accgaactgc gtgaacagca tgaagcgacg cgtctggtca tcaagaaaaa cggccgtagt    720

cacaagagcg cagcagaaga aatcctgaag ctgtccgatg tgttcaaaca gttccgtctg    780

gtgccaaaac agttcgattt cctggttaac agcatgcgtt ccatgatgga tcgcgttcgt    840

gctcaggaac gtctgatcat gaaagtgtgc gttgaacagt gcaaaatgcc gaagaaaaac    900

ttcgtcaatc tgttcgccgg taacgaaacc agcgatacct ggtttgatgc cgctctggca    960

atgggtaaac catggtccga gaagctgaaa gaagtcaccg aagacgtgca acgcggcctg   1020

atgaaactgc gtcagatcga agaagaaacc ggcctgacta tcgaacaggt taaagacatc   1080

aaccgtcgca tgtcgatcgg cgaagcgaaa gcccgtcgcg cgaagaaaga gatggttgaa   1140

gcaaacttac gtctggttat ttctatcgcc aagaaataca ccaaccgtgg tctgcagttc   1200

cttgacctga tccaggaagg taacatcggc ctgatgaaag ccgttgataa gtttgaatat   1260

cgccgtggtt ataagttctc aacttatgcg acctggtgga tccgtcaggc tatcacccgc   1320

tccatcgccg accaggcgcg taccatccgt atcccggtac atatgattga gacgatcaac   1380
```

-continued

```
aaactcaacc gtatctcccg tcagatgctg caagagatgg gccgcgaacc gacaccggaa   1440

gagctggctg agcgtatgtt gatgccggaa gacaaaatcc gcaaagtgct gaaaattgcc   1500

aaagagccaa tctccatgga aacgccaatc ggcgacgatg aagattcgca tctgggcgat   1560

ttcatcgagg ataccaccct cgagctgcca ctggattctg cgacgtctga aagcctgcgt   1620

tctgcaacgc atgacgttct ggctggcctg actgcacgtg aagcgaaagt tctgcgtatg   1680

cgtttcggta tcgatatgaa cactgaccac acgctggaag aagtgggcaa acagttcgac   1740

gtgacccgtg agcgtatccg tcagatcgaa gcgaaagcgt tgcgtaaact gcgccacccg   1800

agccgctccg aagtactgcg cagcttcctg gacgattaa                          1839
```

```
<210> SEQ ID NO 101
<211> LENGTH: 4221
<212> TYPE: DNA
<213> ORGANISM: Unknown
<220> FEATURE:
<223> OTHER INFORMATION: Description of Unknown:
      DP22 DNA-directed RNA polymerase subunit beta'
      microbial sequence

<400> SEQUENCE: 101

gtgaaagact tactaaagtt tctgaaagcg caaactaaga ccgaagagtt tgatgcgatc     60

aaaattgctc tggcatcgcc agacatgatc cgttcttggt cttttggtga agttaagaag    120

ccagaaacca ttaactaccg tacgttcaaa ccagaacgtg acggcctttt ctgtgcccgt    180

attttcggac cagtaaaaga ctacgaatgc ctgtgcggta agtacaagcg tttaaaacat    240

cgcggcgtga tctgcgagaa gtgcggcgtt gaagtgaccc agactaaagt acgccgtgag    300

cgtatgggcc acatcgaact ggcttccccg actgcacaca tctggttcct gaaatcgctg    360

ccatcgcgca tcggtttgct gctggatatg ccactgcgtg acatcgaacg tgttctgtac    420

ttcgaatcct atgtggttat cgaaggcggc atgactaacc tcgaaaaacg ccagatcctg    480

actgaagagc agtatctgga tgcgttggaa gagtttggtg atgagttcga cgcgaagatg    540

ggtgcggaag ctattcaggc cctgttgaaa aacatggatc tggaagcaga gtgcgagcaa    600

ctgcgtgaag agttgaacga aaccaactcc gaaaccaaac gtaagaagct gaccaagcgt    660

atcaagctgc tggaagcgtt cgttcagtct ggtaacaaac cagagtggat gatcctgact    720

gtgctgccgg tactgccacc agacttgcgt ccattggttc cgttggacgg cggccgtttc    780

gcaacgtcgg atctgaacga tctgtatcgt cgcgtgatca accgtaacaa ccgtctgaaa    840

cgcctgctgg atctggctgc gccagacatc atcgtacgta acgaaaaacg tatgctgcaa    900

gaagcggtag atgctttgct ggataacggc cgtcgcggtc gtgctatcac cggctctaac    960

aagcgtccgc tgaaatctct ggcagacatg attaaaggta aacagggtcg tttccgtcag   1020

aacttgctgg gtaaacgtgt cgactactct ggtcgttccg ttatcaccgt aggtccatac   1080

ctgcgtctgc accagtgtgg tctgccgaag aaaatggcac tggaactgtt caaaccgttc   1140

atctacggca agctggaact gcgtggcctg gccaccacca tcaaagccgc gaagaaaatg   1200

gttgagcgcg aagaagctgt cgtttgggac atcctggacg aagttatccg cgaacacccg   1260

gtactgctga accgtgcacc aaccctgcac cgtttgggta tccaggcgtt tgaaccggtt   1320

ctgatcgaag gtaaagcaat ccagctgcac ccgctggttt gtgcggcata taacgccgac   1380

ttcgatggtg accagatggc tgttcacgta ccgttgacgc tggaagccca gctggaagcg   1440

cgtgcgttga tgatgtctac caacaacatc ctgtcacctg cgaacggcga gccaatcatc   1500

gttccttctc aggacgttgt attgggtctg tactacatga cccgtgactg tgttaacgcc   1560
```

```
aaaggcgaag gcatggttct gaccggtcct aaagaagctg agcgtattta ccgcgccggt   1620
ttggcctctc tgcatgcgcg tgtcaaagtg cgtattacag aagagatcaa aaataccgaa   1680
ggcgaagtta cgcacaagac gtcgattatc gacacgacag ttggtcgcgc catcctttgg   1740
atgatcgtac ctaaaggtct gccgttctct atcgtcaacc agcctctggg caaaaaagct   1800
atctccaaaa tgctgaacac ctgttaccgc attttgggcc tgaagccgac cgttattttt   1860
gctgaccaga tcatgtacac cggttttgct tacgctgccc gttcaggcgc gtcagtaggt   1920
atcgatgaca tggtaatccc tgcgaagaaa gcagagatca tcgaagaagc agaaaccgaa   1980
gttgctgaaa tccaggaaca gttccagtct ggtctggtca ctgctggcga acgctataac   2040
aaagtgatcg acatctgggc tgcggccaac gaacgtgttg ctaaggcaat gatggaaaac   2100
ttgtctgttg aagacgtcgt caaccgtgac ggtgttgttg aacagcaggt ttccttcaac   2160
agtatcttta tgatggccga ctccggtgcg cgtggttctg ctgcacagat tcgtcagctg   2220
gccggtatgc gtggcctgat ggcgaaacca gatggttcca tcattgaaac gccaatcacc   2280
gcgaacttcc gtgaaggtct gaacgtactc cagtacttca tctctactca cggtgctcgt   2340
aaaggtttgg cggataccgc acttaaaacg gctaactccg gttatctgac ccgtcgtctg   2400
gttgacgtcg cgcaggatct ggttgtgacc gaagacgact gtgggactca cgaaggcatc   2460
atgatgactc cggtcatcga aggtggcgac gttaaagaac cactgcgtga gcgtgtactg   2520
ggtcgtgtga ctgcagaaga tatcctcaag ccgggtacgg cggatatcct ggttccacgt   2580
aacaccctgc ttcacgagaa gacgtgtgat ctgttagaag agaactcagt cgacagcgtg   2640
aaagtacgtt cagtcgtaag ttgcgaaacc gactttggtg tgtgtgcaaa ctgctacggt   2700
cgcgacctgg cacgtggtca catcatcaac aaaggtgaag cgatcggtgt tattgcagca   2760
cagtccatcg gtgagccggg tacccagctg acgatgcgta cgttccacat cggtggtgcg   2820
gcatctcgtg cggcagcgga atccagcatc caggttaaga acactggtac cattaaactg   2880
agcaaccaca agcacgttag caactctaac ggcaaactgg tgatcacttc ccgtaacact   2940
gagctgaaat tgatcgacga attcggtcgt accaaagaaa gctataaagt gccttacggt   3000
tccgtgatgg gcaaaggcga tggcgcatca gttaacggcg gcgaaaccgt tgctaactgg   3060
gatccgcaca ccatgccagt tatcagtgaa gtgagtggtt tcattcgctt tgccgatatg   3120
gtggatactc agaccatcac acgccagacc gacgacctga ccggtttgtc ttctctggtt   3180
gttctggact ctgcagagcg taccggtagc ggtaaagacc tgcgtccggc actgaaaatc   3240
gttgacgcta aaggcgacga cgtattgatt ccaggtactg atatgcctgc tcaatacttc   3300
ctgccaggta aagcgattgt tcagctggaa gatggtactc agatccactc tggtgacacc   3360
ctggcgcgta ttcctcagga atccggcggt accaaggaca tcaccggtgg tctgccacgc   3420
gttgctgacc tgttcgaagc acgtcgtccg aaagagcctg caatccttgc tgaaatcagc   3480
gggatcatct ccttcggtaa agaaaccaaa ggcaaacgtc gtctggtaat ttctccgtta   3540
gatggcagcg atgcttacga agaaatgatc cctaaatggc gtcagctgaa cgtgttcgaa   3600
ggcgaagttg tggaacgtgg tgacgtcgta tccgacggcc ctgagtctcc gcacgacatc   3660
ttgcgtttac gtggtgttca cgcggttacc cgctacatca ccaacgaagt gcaggaagtt   3720
taccgtctgc aaggcgttaa gattaacgat aagcacatcg aagttatcgt tcgtcagatg   3780
ttgcgtaaag gcaccatcgt tagcgctggt ggcactgact tcctggaagg cgagcaggca   3840
gaaatgtctc gcgttaaaat cgctaaccgt aagctggaag ctgaaggcaa aatcacggca   3900
```

```
acattcagcc gtgacctgct cggtatcacc aaggcatccc tggcgaccga atccttcatc   3960

tctgcagcgt cgttccagga aaccacgcgt gttcttaccg aagcggctgt tgccggtaaa   4020

cgtgatgaac tgcgtggcct gaaagagaac gttatcgttg gccgtctgat cccagccggt   4080

accggttacg cttatcatca ggatcgtgca cgccgtaaag cacaaggcga agtgccagtt   4140

gtaccgcaag tcagcgcgga tgaagcaacg gctaacctgg ctgaactgct gaacgcaggt   4200

ttcggtaaca gcgacgatta a                                             4221
```

<210> SEQ ID NO 102
<211> LENGTH: 1668
<212> TYPE: DNA
<213> ORGANISM: Unknown
<220> FEATURE:
<223> OTHER INFORMATION: Description of Unknown:
DP67 Glutamine--tRNA ligase microbial sequence

<400> SEQUENCE: 102

```
atgagtgagg ctgaagcccg cccaactaac tttattcgtc agattatcga cgaagatctg     60

gcgaacggta agcacagttc agtgcacacc cgcttcccgc ctgagccgaa tggctatctg    120

catattggcc atgcgaaatc aatctgcctg aactttggta tcgctcagga ttatcagggg    180

cagtgtaacc tgcgctttga tgacactaac ccggtgaaag aagatctgga gtttgttgaa    240

tcaatcaagc gtgatgtgca gtggctgggc tttaagtgga gtggtgacgt acgctactca    300

tctgactatt tcgagcaact gcacaattat gccgttgagc tgattagtaa agggctggcg    360

tacgttgatg aactgtcacc ggagcagatc cgtgaatacc gtggcagcct gacctcagcg    420

ggtaaaaaca gccccttccg cgatcgcagc gtggacgaaa accttgcgct ctttgcaaaa    480

atgcgcgcgg gcggctttgc cgagggcacc gcgtgtttac gagccaaaat tgatatggct    540

tccaacttta tcgttctgcg cgatccggtg atctaccgca tcaaatttgc cgaacatcat    600

cagaccggca ataagtggtg catctatccg atgtatgact ttacccactg catctctgat    660

gcgctggaag gcattactca ctcactgtgt acgctggaat tccaggataa ccgtcgcctg    720

tacgactggg tgctggataa catcaccatt ccggttcatc cgcgtcagta tgaattctct    780

cgcctgaatc ttgaatatgc catcatgtcc aagcgtaagt tgagtcagtt ggtgaccgag    840

aacgtggtgg aaggttggga tgatccccgt atgctgactg tttcgggttt gcgccgccgt    900

ggctacactg cggaatccat ccgtgaattc tgccgccgca ttggggtgac caagcaggac    960

aatattgttg aaatggccgc tctggaatcc tgtatccgtg acgacctcaa tgagaatgcc   1020

ccgcgtgcca tggcagtgat ggatccggta aaagtggtga tagaaaatct gcctgcgcat   1080

cacgatgagg tgatcaccat gccgaatcat ccgagcaagc cggaaatggg tacccgcgaa   1140

gtcccgttca gtcgtgagat ctacatcgat cgtgctgact tccgtgagga agcaaacaag   1200

cagtacaagc ggctggtgct gggcaaagaa gtgcgtctgc gtaacgctta tgtgatcaaa   1260

gccgagcgcg tggcaaagga cgatgaaggc aacattacct gcctgttctg tacctgtgat   1320

gtggatactc tgagcaagga tccggccgac gggcgtaaag tgaagggcgt tatccactgg   1380

gtgtcagctg ttcatgccct tccggcagag ttccgtctgt acgatcggct gttcagcgta   1440

ccgaatccgg gggcggcaga agacttcctg gccagcatca acccggaatc tctggtgatc   1500

cgtcagggct tcgtggagcc cgggatgcag caggcggagg cgtcagcccc gtatcagttt   1560

gagcgtgaag gctacttctg cgctgacagt gtctactcca gtgccagcaa tctggtgttc   1620

aaccgcaccg ttggcctgcg tgacacctgg gcgaaagtcg gcgagtaa                1668
```

<210> SEQ ID NO 103
<211> LENGTH: 2409
<212> TYPE: DNA
<213> ORGANISM: Unknown
<220> FEATURE:
<223> OTHER INFORMATION: Description of Unknown:
DP67 DNA gyrase subunit B microbial sequence

<400> SEQUENCE: 103

```
atgtcgaatt cttatgactc ctccagtatc aaagttctga aagggctcga tgctgtacgc     60
aaacgcccgg gtatgtatat cggcgatacg gatgacggta ccggtctgca tcacatggta    120
tttgaggtcg tggataacgc cattgacgaa gcgctcgccg gtcactgttc cgatattctt    180
gtcactattc atgccgataa ctctgtttcc gttgtggatg atggccgtgg tattccgacc    240
ggtattcacg aagaagaagg catctcagcc gctgaagtga tcatgaccgt gctgcacgcc    300
ggcggtaagt tcgacgataa ctcttataaa gtctccggcg gcctgcacgg cgtgggcgtg    360
tcagtggtga acgccctgtc ggaaaaactg gagctgacca ttcgtcgcga agggaaagtt    420
caccagcaga cttacgtcca cggcgtgcca caggccccgt tgagtgtgag cggtgaaact    480
gacctgacgg gaacgcgcgt gcgtttctgg cccagccatc agacgttcac taacgtcgtg    540
gagttcgagt acgaaatttt ggcaaagcgc ctgcgtgagc tgtcgttcct gaactccggt    600
gtatcaatca agctggaaga taagcgcgac ggtaaaagcg accattacca ctatgaaggt    660
ggtatcaagg cgtttgttga gtacctcaac aagaacaaaa ccccgatcca cccgaatgtg    720
ttctatttct caaccgagaa agacggcatt ggtgtggaag tggcgctgca gtggaacgat    780
ggtttccagg aaaatatcta ctgctttacc aacaacatcc cacagcggga tgggggcacg    840
cacctcgttg gtttccgtac cgcgatgacc cgtaccctga atgcctacat ggataaagaa    900
ggctacagca agaaagccaa agtcagcgcc accggtgacg acgcgcgtga aggcctgatt    960
gctgtggtgt cggtgaaagt gccggatccg aaattctctt cacagaccaa agataaactg   1020
gtctcttctg aagtgaaaac cgccgttgag cagcagatga acgagctgct ggcagaatac   1080
ctgctggaaa acccgaccga tgccaaaatc gtcgtcggta aaatcattga tgcggcccgc   1140
gcccgtgaag cggcccgtcg tgcacgtgaa atgacccgcc gtaaaggcgc gctggatctg   1200
gcaggcctgc cgggcaaact ggcggactgc caggagcgtg atccggctct gtccgaaatt   1260
tacctggtgg aaggggactc tgcgggcggc tctgccaagc agggacgtaa ccgtaaaaac   1320
caggccatcc tgccgctgaa gggtaaaatc ctcaacgtcg agaaggcgcg ctttgacaag   1380
atgctcgcgt cgcaggaagt cgctacgctg atcaccgcgc tgggctgtgg tatcggtcgt   1440
gatgagtaca accccgacaa actgcgctat cacagcatca ttatcatgac cgatgccgac   1500
gtggatggct cgcatatccg taccctgctg ctgaccttct tctaccgtca gatgccagaa   1560
atcattgagc gtggtcatgt ctatattgcc cagccaccgc tgtacaaggt gaaaaaaggc   1620
aagcaggagc agtatattaa agacgacgat gcgatggatc agtaccagat cgccatcgcg   1680
ctggacggtg ccacgctgca tgcgaacgcc agcgccccgg cccttggcgg taagccactg   1740
gaagatctgg tgtctgagtt caacagcacg cgcaagatga tcaagcgcat ggagcgccgt   1800
tacccggtgg ccttgctgaa tgcgctggtc tacaacccga ccctgagcga tttgaccgcc   1860
gaagcgccgg tacagagctg gatggatgtg ctggtgaagt atctgaacga caacgaccag   1920
cacggcagca cctacagcgg tctggtacgc gaaaatctgg agctgcatat ctttgagccg   1980
gtactgcgta tcaaaaccca cggcgtggat accgattatc cgctcgacag cgagtttatg   2040
```

-continued

```
ctcggcggcg aataccgtaa gctctgcgcg ctgggtgaga agctgcgtgg cctgatcgaa   2100
gaagacgcgt tcatcgaacg tggtgagcgg cgtcagccga ttgccagctt tgagcaggcg   2160
atggagtggc tggttaaaga gtcacgccgt ggcctgacgg ttcagcgtta taaaggtctg   2220
ggcgagatga acccggatca gctgtgggaa accaccatgg atccggacag ccgccgtatg   2280
ctgcgcgtga ccatcaaaga tgccgtggcc gccgaccagc tgttcaccac cctgatgggg   2340
gatgcggtag agccccgtcg tgcctttatt gaagagaacg ccctgcgcgc ggcaaacatc   2400
gatatctga                                                           2409
```

```
<210> SEQ ID NO 104
<211> LENGTH: 2817
<212> TYPE: DNA
<213> ORGANISM: Unknown
<220> FEATURE:
<223> OTHER INFORMATION: Description of Unknown:
      DP67 Isoleucine--tRNA ligase microbial sequence

<400> SEQUENCE: 104
```

```
atgagtgact ataaatctac cctgaatttg ccggaaacgg ggttcccgat gcgtggcgat     60
ctggccaaac gcgaaccggg tatgctgcaa cgttggtatg atgacaagct gtacggcatc    120
attcgcgaag ccaagaaagg gaaaaaaacc tttatcctgc acgatggccc tccttacgcc    180
aacggcagca ttcatattgg tcactccgtt aacaagattc tgaaagacat tatcgttaag    240
tcgaaaggca tggcgggcta tgactcgcct tatgtaccgg gttgggactg ccacggtctg    300
cctatcgagc ataaagttga gcagatgatc ggtaagccgg gagagaaagt cagcgccgct    360
gagttccgtg ctgcctgccg caaatacgct gccgagcagg tggaagggca gaaagccgac    420
tttatccgtc tgggtgtgtt gggtgactgg gatcgtccgt atctgacaat gaacttccag    480
accgaagcca atattatccg tgcgctgggt aaaatcatcg gtaacgggca cctgcacaaa    540
ggggccaagc cggtacactg gtgcctggac tgccgttctg ccctggctga ggcggaagtg    600
gagtactacg ataaaacctc tccgtctatc gatgtcatgt tcaatgcgac tgataaagag    660
ggggtacagg ccaaatttgc ggcaacgaat gttgacggcc cgatctcgct ggtgatctgg    720
actaccacgc cgtggaccat gccggctaac cgcgctatct cactgcatcc tgaattcgac    780
taccagctgg tacagattga aggccgtgct ctgatcctcg ccaaagagat ggttgagagc    840
gtgatgcagc gcgttggtgt tgccgcctgg accgtgctgg gcgaagcgaa aggggcagac    900
ctggagctga tgggcttcca gcatccgttc ctcgaccata cctctccggt tgtgctgggt    960
gagcatgtca cgctggaagc cggtaccggt gcggtccata ccgcaccagg ccatggcccg   1020
gacgactatg ttatcggtca gaaatacggt atcgaagtgg ctaacccggt cggcccggat   1080
ggctgctacc tgccgggaac ctacccgacg ctggatggtg tgaacgtctt taaagccaac   1140
gatatgatcg ttgaactgct gcgtgaaaag ggtgctctgc tgcacgttga gaaactgttc   1200
cacagctatc cacactgctg gcgtcataaa acgcccatca tcttccgcgc tacgccacag   1260
tggtttatca gcatggatca gaagggcctg cgtgcgcagt cgctgaaaga gatcaagggc   1320
gtgcagtgga tcccggactg ggtcaggca cgtattgaat cgatggtcgc gaaccgtcct    1380
gactggtgta tttcccgtca gcgtacctgg ggcgtgccga tggcgctgtt cgtccataaa   1440
gacaccgaac agctgcaccc ggattcgctg gagctgatgg agaaagtggc gaagcgggtt   1500
gagcaggacg gcattcaggc atggtgggat cttgatgccc gcgacctgat gggcgccgat   1560
gctgacaact acgttaaagt cccggatacc ctggacgtct ggtttgactc cggttcaacc   1620
```

agctactcgg tcgtcgatgc ccgccctgaa tttgacggca atgcccctga cctgtatctg 1680
gaaggatcgg atcagcaccg cggctggttt atgtcctcac tgatgatctc gaccgcgatg 1740
aaaggcaaag cgccttaccg tcaggtactg acgcacggct tcaccgtcga tggtcagggc 1800
cgtaagatgt ccaagtcact gggcaatact gtcagcccgc aggatgtgat gaacaaactg 1860
ggcgccgata ttctgcgcct gtgggtcgcc tctacggact actccggtga gatcgccgta 1920
tccgacgaga tccttaaacg ctctgccgac agctatcgcc gcatccgtaa caccgcacgt 1980
ttcctgctgg caaaccttgc cggttttaat ccggaaaccg atagggtgaa accggaagag 2040
atggtggtgg tggatcgctg ggccgttggc cgtgcgctgg cggcacagaa tgatatcgta 2100
gcctcgtatg aagcttatga cttccatgaa gtcgtgcagc gtctgatgca gttctgttcg 2160
gttgagatgg gctccttcta cctggatatc atcaaggatc gtcagtacac cgcgaaggcc 2220
gatggcctgg cgcgtcgcag ctgtcagacg gcgctgtggt atatcgtgga agcgctggtg 2280
cgctggatgg caccgattat gtccttcact gccgatgaaa tctggggtta cctgccgggt 2340
aaacgcagcc agtatgtctt taccgaagag tggtttgacg ggctgttcag cctggaggac 2400
aatcagccga tgaacgacag ttactgggca gaactgctga aagtacgcgg tgaagtcaac 2460
aaggtgatcg agcaggcccg cgctgataag cggattggcg ggtctctgga agccagcgtg 2520
acgctgtatg ctgacgcaga cctggccgcg aagctgacca gcctgggtga ggagctgcgc 2580
tttgtgttgc tgacttccgg ggcgcaggtt gcggattatg cgcaggccac cgctgatgca 2640
cagcaaagcg aaggggtaaa aggtctgaaa attgccctga gcaaagcgga aggcgagaag 2700
tgcccgcgct gctggcatta cactaacgat atcggccaga atgctgaaca cgctgacgtg 2760
tgcggccgtt gtgtcactaa cgtcgcgggc agcggcgaac agcgtaagtt tgcatga 2817

<210> SEQ ID NO 105
<211> LENGTH: 1731
<212> TYPE: DNA
<213> ORGANISM: Unknown
<220> FEATURE:
<223> OTHER INFORMATION: Description of Unknown:
DP67 NADH-quinone oxidoreductase subunit C/D
microbial sequence

<400> SEQUENCE: 105
gtgatcggcg agctgcgtaa tcgttttggg cctgatgcct ttacagtaca agcgacccgt 60
accggcgtgc cggtggtctg ggtaaaacgt gagcagttgc ttgagattat tgagttcctg 120
cgcaagctgc ctaaacccta tgtgatgctg tatgacctgc atggcatgga tgagcgcctg 180
cgtactcacc gtgccggttt accggcggcg gatttttccg ttttctatca cttcatctcc 240
attgaacgta accgcgacat catgctcaag gtggcgttgt ctgaaaacga tttgaatgtg 300
cccaccatca ccaaaatttt cccgaatgcc aactggtatg agcgtgaaac ctgggagatg 360
tttggtatca atgttgaagg ccacccgcac ctgacgcgca ttatgatgcc gcagagctgg 420
gaagggcatc cgctgcgcaa agattaccct gcgcgtgcga ccgagttcga tccgtttgaa 480
ctgaccaagc agaaagaaga tctggagatg gaatctctga ccttcaagcc tgaagactgg 540
ggcatgaagc gttcgaccaa caatgaggac ttcatgttcc tcaacctggg cccgaaccac 600
ccttctgcgc acggcgcgtt ccgtatcatc ctgcaactgg acggtgaaga gatcgtcgac 660
tgcgtgccgg atatcggata ccaccatcgt ggtgccgaaa aaatgggtga acgccagtcc 720
tggcacagct acattccgta taccgaccgt attgagtatc tcggcggctg cgtaaacgaa 780
atgccgtacg tgctggcggt agaaaagctg gctggtatca aagtccctga gcgcgtggaa 840
gtcattcgcg tgatgctatc agagctgttc cgtataaaca gccacctgct gtacatctct 900
acgtttatcc aggacgtcgg tgctatgtcc ccggtgttct ttgcctttac tgaccgccag 960
aaaatttacg acgtggtaga agccattacc ggcttccgta tgcatccggc ctggttccgc 1020
attggtggcg tggcgcatga tctgcctaaa ggctgggagc gcctgctgcg tgagttcctg 1080
gattggatgc ctaagcgtct gaaagcctat gagcagaccg cactgaaaaa ctccgtgctt 1140
attgcccgtt ccaaaggggt ttctgcctat aacatggaag aagcactggc ctggggcacg 1200
acgggggctg gcctgcgtgg taccggtctg gactttgatg tgcgtaaatg gcgtccatat 1260
tccggttatg aaaacttcga tttcgaagtg ccaatcggag atggcgtaag ctgtgcttac 1320
acccgtgtca tgctgaagat ggaagagatg cgccagagta tgcgcatcct ggaacagtgc 1380
ctgaagaaca tgccagcagg cccgttcaag gctgaccatc cgctgaccac gccgccgccg 1440
aaagagcgca cgctgcagca tatcgaaacc ctgatcactc acttcctgca ggtttcgtgg 1500
ggcccggtaa tgccggcaaa cgaatccttc cagatgattg aagcgaccaa agggatcaac 1560
agttactacc tgaccagtga tggcagcacg atgagctacc gcacccgcgt gcgtacgccg 1620
agcttcccgc atttgcaaca gatcccatcg gtgatcaacg gcagcctggt atccgatctg 1680
atcgtatacc tcggtagtat cgattttgtt atgtcagacg tggaccgcta a 1731

<210> SEQ ID NO 106
<211> LENGTH: 1062
<212> TYPE: DNA
<213> ORGANISM: Unknown
<220> FEATURE:
<223> OTHER INFORMATION: Description of Unknown:
DP67 Protein RecA microbial sequence

<400> SEQUENCE: 106
atggctatcg acgaaaacaa gcaaaaagca ctggcagcag cgctgggcca gattgaaaag 60
cagtttggta aaggctccat catgcgcctg ggtgaagacc gcaccatgga tgtggaaacc 120
atctcaaccg gttctttatc actggatatc gcgctgggtg ccggtggttt accaatgggc 180
cgtatcgttg aaatctatgg cccggagtct tccggtaaaa ccacccctgac gctgcaggtt 240 atcgcttctg cacagcgtaa agggaaaacc tgtgcattta tcgatgccga gcatgctctg 300
gacccggtct acgctaaaaa actgggcgtg gatatcgata acttgctgtg ttctcagccg 360
gataccggtg agcaggcgct ggaaatctgt gatgcgctgg cccgttccgg tgcggttgac 420
gtcatcatcg tcgactccgt agcggcgttg acaccaaaag cagaaatcga aggtgaaatc 480
ggtgactctc atatgggcct tgcggcacgt atgatgagcc aggcgatgcg taagctggcc 540
ggtaacctga agaactccgg tacgctgctg atctttatca accagatccg tatgaaaatt 600
ggcgtgatgt tcggtaaccc ggaaaccact accggtggta acgctctgaa attctacgct 660
tctgtccgtc tggatattcg ccgcatcggc gcgatcaaag agggtgatga agtggtgggt 720
agcgaaaccc gcgttaaagt ggtgaaaaac aaaatcgcag caccgtttaa acaggctgag 780
ttccagatca tgtacggcga aggtatcaac gtttacggtg agctggtcga cctgggcgtg 840
aagcacaagc tgatcgaaaa agccggtgcc tggtacagct ataacggtga caagattggt 900
cagggtaaag ccaactcagg taacttcctg aaagagaacc cggctatcgc taacgaaatc 960
gaagcaaaac tgcgtgaaat gctgttgaac agcccggacg ataagcctga ttttgttccg 1020
gctccgcatg aagccgatag tgaagttaac gaagatatct aa 1062

<210> SEQ ID NO 107
<211> LENGTH: 1842
<212> TYPE: DNA
<213> ORGANISM: Unknown
<220> FEATURE:
<223> OTHER INFORMATION: Description of Unknown:
RNA polymerase sigma factor RpoD microbial sequence

<400> SEQUENCE: 107

```
atggagcaaa acccgcagtc acagcttaag ctacttgtca cccgtggtaa ggagcaaggc     60
tatctgacct atgccgaggt caatgaccat ctgccggaag atatcgtcga ctccgatcag    120
attgaagaca tcattcagat gatcaacgac atgggcattc aggttgtaga agaagcgcct    180
gatgccgatg atttgatgct gaatgagaac aacaacgaca cggacgaaga cgctgccgaa    240
gcggctgctc aggtattatc cagcgtagaa tctgaaatcg gacgtaccac cgacccggtg    300
cgcatgtaca tgcgcgaaat ggggacggtt gaactgctga cgcgtgaagg cgagatcgat    360
atcgccaaac gcatcgaaga gggtatcaac caggtacagt gttccgttgc tgaatatcct    420
gaagcgatta cttacctgct tgagcaatat gaccgtgttg aagcgggcga agcgcgcctg    480
tcggatctga tcaccggttt tgtcgacccg aatgccgaag cagagatcgc ccctactgcg    540
actcacgtgg gttcagaact ttccgctgaa gagcgtgatg acgaagaaga agacgaagag    600
tctgacgacg acagctcgga tgatgacaac agcatcgatc cggaactggc gcgggaaaaa    660
ttcaacgacc tgcgcgttca gtacgaaacc acccgtaccg ttatcaaagc gaaaagccgc    720
agccacgctg atgccatcgc tgagatccag aatctgtccg acgtgttcaa gcagttccgc    780
ctggtgccga agcagttcga cttcctggtg aacagcatgc gcaccatgat ggatcgcgtc    840
cgtactcagg aacgcctgat cctcaagctg tgcgtagaaa tctgtaagat gccgaagaag    900
aacttcatta ccctgttcac cggtaatgaa accagcgaaa cctggttcaa agcggcactg    960
gcaatgaata agccgtggtc agagaagctg aacgatgtgt cagatgacgt acaccgtagc   1020
ctgatgaagc tgcagcagat cgaaacggaa actggcctga cgattgaaca ggtaaaagac   1080
atcaaccgtc gtatgtcgat cggcgaagcg aaagcgcgcc gtgcgaagaa agagatggtt   1140
gaggctaacc tgcgtctggt tatctctatc gccaagaagt acaccaaccg tggcctgcag   1200
ttcctggatc tgattcagga aggtaacatc ggtctgatga aagcggtgga taagtttgaa   1260
tatcgccgtg gttataagtt ctcgacttat gccacctggt ggatccgtca ggcgatcacc   1320
cgttcaatcg ctgaccaggc gcgtaccatc cgtattccgg tgcacatgat tgagacgatt   1380
aacaagctca accgtatttc ccgccagatg ctgcaagaga tgggccgtga gccgacgccg   1440
gaagagctgg ccgagcgtat gctgatgccg gaagataaga tccgtaaggt gctgaaaatt   1500
gccaaagagc cgatctctat ggagacgccg attggtgatg atgaagattc acatctgggt   1560
gattttatcg aagacaccac gctggagctg ccgctggact ccgcgacgtc agagagcctg   1620
cgttctgcca cgcacgacgt gctggccggt ctgaccgcgc gtgaagccaa agtactgcgt   1680
atgcgtttcg gtatcgatat gaataccgac cacacgctgg aagaagtggg caaacagttc   1740
gacgtaacgc gtgagcgtat tcgtcagatt gaggcgaaag cgctgcgtaa gctgcgtcac   1800
ccaagccgct ctgaagtgct gcgcagcttc ctcgacgatt aa                      1842
```

<210> SEQ ID NO 108
<211> LENGTH: 4029
<212> TYPE: DNA
<213> ORGANISM: Unknown
<220> FEATURE:
<223> OTHER INFORMATION: Description of Unknown:

DNA-directed RNA polymerase subunit beta microbial sequence

<400> SEQUENCE: 108

```
atggtttact cctataccga gaaaaaacgt attcgtaagg attttggaaa gcgtccacaa     60
gttctggaca ttccatatct cctttctatc cagcttgact cgttccagaa gttcatcgag    120
caagatccgg aaggtcaata tggtctggaa gcagcattcc gctccgtatt tccaatccaa    180
agctatagcg gtaattctga gctgcagtac gtcagctacc gtttaggcga acccgtcttt    240
gatgtgaaag agtgtcagat tcgtggcgtc acgtattctg ctcctctgcg cgtaaaactg    300
cgcctggtga tctacgagcg cgaagcgccg gaaggcaccg ttaaagacat caaagaacaa    360
gaagtttaca tgggcgaaat tccgctcatg acggataacg gtacctttgt tatcaacggt    420
actgagcgcg ttatcgtttc tcagctccac cgtagtcctg gtgtcttctt cgacagcgat    480
aagggtaaaa cccactcgtc cggtaaagtg ctgtataacg cacgtatcat cccttaccgt    540
ggttcatggc tggacttcga gttcgacccg aaagacaacc tgttcgtccg tattgaccgt    600
cgccgtaaac tgccagcgac catcattctg cgcgcgttga attacaccac tgaacagatc    660
ctcgacctgt tcttcgataa agtggtttac caaattcgcg acaacaagct gcagatggag    720
cttattcctg agcgcctgcg tggtgagacc gcttcatttg atattgaagc gaacggcacc    780
gtttacgtcg aaaaaggccg ccgtattact gcgcgccata ttcgccagct tgagaaagat    840
gctgttgccc acatcgaagt gccggttgag tatattgccg gtaaagtggt cgctaaagac    900
tacgttgatg agagcaccgg tgaactgctg atcgcagcga acatggaact gtcactggat    960
ctgctggcta aactcagcca gtccggtcac aagcgcattg aaaccctgtt caccaacgat   1020
ctggatcacg gtgcgtacat gtctgagacg gtacgtgtcg acccaaccag cgatcgcctg   1080
agcgctctgg ttgagatcta ccgcatgatg cgtcctggtg agccaccaac gcgtgaagcg   1140
gctgaaaacc tgtttgagaa cctgttcttc tctgaagacc gctatgatct gtctgcggtt   1200
ggtcgtatga agttcaaccg ttctctgctg cgcgacgaga tcgaaggttc cggtatcctg   1260
agcaaagacg acatcattca ggtgatgaag aagctcatcg gtatccgtaa cggtattggc   1320
gaagtggatg atatcgacca cctcggcaac cgtcgtatcc gttccgttgg cgaaatggct   1380
gaaaaccagt tccgtgttgg ccttgtgcgc gtagagcgtg cggtgaaaga gcgtctgtcc   1440
ctgggcgatc tggataccct gatgccacag gacatgatca acgccaagcc aatttctgcg   1500
gcagtgaaag agttcttcgg ctccagccag ctgtcacagt ttatggacca gaacaacccg   1560
ttgtctgaga tcacgcataa gcgtcgtatc tctgcactgg gtccgggcgg tctgacgcgt   1620
gagcgtgcag gcttcgaagt tcgagacgta cacccgacgc actacggtcg cgtatgtcca   1680
atcgaaacgc cggaaggtcc aaacatcggt ctgatcaact ccttgtctgt gtatgcacag   1740
accaatgagt acggtttcct ggaaacccca taccgtcgcg ttcgcgaagg cgtggtgacc   1800
gacgaaattc attacctctc tgctattgaa gagggtaact acgttatcgc tcaggcaaac   1860
accaatctcg acgacgaagg tcacttcgta gacgacctgg tcacctgccg tagcaaaggc   1920
gaatcgagtc tcttcaaccg cgatcaagtt gactacatgg acgtttccac ccagcaggtg   1980
gtttccgtcg gtgcgtcact gatcccgttc ctggagcacg atgacgccaa ccgcgcattg   2040
atgggtgcaa acatgcaacg tcaggcggtt cctactctgc gtgctgataa gccgctggta   2100
ggtaccggta tggagcgtgc ggttgcggtt gactccggtg ttactgccgt agcgaaacgt   2160
ggtggtaccg tgcagtacgt ggatgcatcc cgtatcgtta ttaaagttaa cgaagacgaa   2220
atgtatccgg gcgaagccgg tatcgacatt tacaacctga ccaaatatac ccgttctaac   2280
```

cagaacacct gcatcaacca gatgccttgc gtgaacctgg gtgagccaat cgaacgtggt 2340
gatgtgctgg ctgatggccc ttcaaccgat ctcggcgaac tggcactcgg tcagaacatg 2400
cgcgtcgcgt tcatgccgtg gaacggctac aacttcgaag actccattct ggtctcggag 2460
cgcgttgttc aggaagatcg cttcaccact atccacattc aggaactggc gtgtgtgtct 2520
cgtgacacca agctggggcc agaagagatc accgctgaca tccctaacgt gggtgaagct 2580
gcgctctcta aactggatga gtccggtatc gtgtatatcg gtgcggaagt gaccggtggg 2640
gacattctgg ttggtaaggt aacacctaaa ggtgaaaccc agctgacgcc agaagagaaa 2700
ctgctgcgtg cgatcttcgg tgaaaaagcg tctgacgtta aagactcttc tctgcgcgta 2760
ccaaacggtg tgtcagggac aatcatcgac gttcaggtct ttacccgcga tggcgtggaa 2820
aaagacaagc gtgcgctgga aatcgaagag atgcagctga agcaggcgaa gaaagacctg 2880
tctgaagaat tgcagatcct cgaagccggc ttgttcagcc gtattaacta cctgctggtt 2940
gccggcggtg ttgaagcgga aaaactggag aagctgccac gtgagcgctg gctcgaactg 3000
ggcctgaccg acgaagagaa gcaaaatcag ctggaacagc tggccgagca gtacgacgag 3060
ctgaagcacg agtttgagaa aaaacttgaa gccaagcgcc gtaaaatcac tcagggcgat 3120
gacctggcac ctggcgtgct gaaaatcgtg aaagtgtatc tggccgttaa acgtcagatc 3180
cagcctggtg acaaaatggc aggtcgtcac gggaacaaag gtgttatctc caagatcaac 3240
ccgatcgaag atatgccata cgatgagttc ggtacgccgg tcgacatcgt actgaacccg 3300
ctgggcgttc catcacgtat gaacattggt cagattcttg aaacccacct gggtatggct 3360
gcgaaaggca ttggcgagaa aattaacgct atgcttaaga agcaggaaga agtgtccaag 3420
ctgcgtgaat tcattcagcg tgcttacgat ctgggcagcg atctgcgtca gaaagttgac 3480
ctgaacacct tcaccgatga cgaagtgctg cgcctggcag agaatctgaa aaaaggtatg 3540
ccaattgcaa caccagtgtt tgacggcgcg aaagagagcg aaatcaaaga gctgttacag 3600
ctcggcggcc tgccttcttc tggccagatc acgctgtttg atggtcgtac cggtgagcag 3660
ttcgaacgtc aggttaccgt tggctacatg tacatgctga agctgaacca cctggttgat 3720
gacaaaatgc atgcgcgttc taccggttct tacagcctcg ttactcagca gccgctgggt 3780
ggtaaggcgc agttcggtgg tcagcgcttc ggtgagatgg aagtgtgggc actggaagca 3840
tacggtgccg cgtataccct gcaggaaatg ctgaccgtga agtctgatga cgttaacggc 3900
cgtaccaaga tgtataaaaa catcgttgac ggcaaccatc agatggaacc gggcatgccg 3960
gaatctttca acgtactgtt gaaagagatc cgctcgctgg gtatcaacat cgagctggaa 4020
gacgagtaa 4029

<210> SEQ ID NO 109
<211> LENGTH: 1700
<212> TYPE: DNA
<213> ORGANISM: Unknown
<220> FEATURE:
<223> OTHER INFORMATION: Description of Unknown:
DP68 Glutamine--tRNA ligase microbial sequence

<400> SEQUENCE: 109
atgagcaagc ccactgtcga ccctacctcg aattccaagg ccggacctgc cgtcccggtc 60
aatttcctgc gcccgatcat ccaggcggac ctggattcgg gcaagcacac gcagatcgtc 120
acccgcttcc cgccagagcc caacggctac ctgcacatcg gtcacgccaa gtcgatctgt 180
gtgaacttcg gcctggccca ggagttcggt ggcgtcacgc acctgcgttt cgacgacacc 240

```
aacccggcca aggaagacca ggaatacatc gacgccatcg aaagcgacat caagtggctg    300
ggcttcgaat ggtccggtga agtgcgctat gcgtccaagt atttcgacca gttgttcgac    360
tgggccgtcg agctgatcaa ggccggcaag gcctacgtcg acgacctgac cccggagcag    420
gccaaggaat accgtggcac gctgaccgag ccgggcaaga acagcccgtt ccgtgaccgt    480
tcggtagaag agaacctcga ctggttcaac cgcatgcgcg ccggtgagtt cccggacggc    540
gcccgcgtgc tgcgcgccaa gatcgacatg gcctcgccga acatgaacct gcgcgacccg    600
atcatgtacc gcatccgcca cgcccatcac caccagaccg gtgacaagtg gtgcatctac    660
ccgaactatg acttcaccca cggtcagtcg gacgccatcg aaggcatcac ccactccatc    720
tgcaccctgg agttcgaaag ccatcgcccg ctgtatgagt ggttcctcga cagcctgccg    780
gttccggcgc acccgcgtca gtacgagttc agccgcctga acctgaacta caccatcacc    840
agcaagcgca agctcaagca gttggtggac gaaaagcacg tgcatggctg ggatgacccg    900
cgcatgtcca ccctgtcggg tttccgccgt cgcggctaca ccccggcgtc gatccgcagc    960
ttctgcgaca tggtcggcac caaccgctcc gacggcgtgg tcgattacgg catgctcgag   1020
ttcagcatcc gtcaggacct ggacgccaac gcgccgcgtg ccatgtgcgt attgcgcccg   1080
ttgaaagtcg tgatcaccaa ctatccggaa gacaaggtcg accacctcga actgccgcgt   1140
cacccgcaga aagaagaact tggcgtgcgc aagctgccgt tcgcgcgtga aatctacatc   1200
gaccgtgatg acttcatgga agagccgccg aaaggctaca agcgcctgga gcctaacggc   1260
gaagtgcgcc tgcgcggcag ctacgtgatc cgtgccgatg aagcgatcaa ggacgccgat   1320
ggcaacatcg tcgaactgcg atgctcctac gacccggaaa ccctgggcaa gaaccctgaa   1380
ggccgcaagg tcaaaggcgt cgttcactgg gtgccggctg ctgccagcat cgagtgcgaa   1440
gtgcgcctgt acgatcgtct gttccgttcg ccgaaccctg agaaggctga agacagcgcc   1500
agcttcctgg acaacatcaa ccctgactcc ctgcaagttc tcacgggttg tcgtgccgag   1560
ccatcgcttg gcgacgcaca gccggaagac cgtttccagt tcgagcgcga aggttacttc   1620
tgcgcggata tcaaggactc caaacctggt catccggtct tcaaccgtac cgtgaccttg   1680
cgtgattcgt ggggccagtg                                               1700
```

<210> SEQ ID NO 110
<211> LENGTH: 2418
<212> TYPE: DNA
<213> ORGANISM: Unknown
<220> FEATURE:
<223> OTHER INFORMATION: Description of Unknown:
DP68 DNA gyrase subunit B microbial sequence

<400> SEQUENCE: 110

```
atgagcgaag aaaacacgta cgactcgacc agcattaaag tgctgaaagg tttggatgcc     60
gtacgcaaac gtcccggtat gtacatcggc gacaccgatg atggtagcgg tctgcaccac    120
atggtgttcg aggtggtcga caactccatc gacgaagctt tggccggtca ctgcgacgac    180
atcagcatta tcatccaccc ggatgagtcc atcaccgtgc gcgacaacgg tcgcggtatt    240
ccggtcgatg tgcacaaaga agaaggcgta tcggcggcag aggtcatcat gaccgtgctt    300
cacgccggcg gtaagttcga cgacaactcc tataaagttt ccggcggttt gcacggtgta    360
ggtgtgtcgg tggtgaacgc tctgtccgaa gagcttatcc tgactgttcg ccgtagcggc    420
aagatctggg aacagaccta cgtgcatggt gttccacaag aaccgatgaa aatcgttggc    480
gacagtgaat ccaccggtac gcagatccac ttcaagcctt cggcagaaac cttcaagaat    540
```

```
atccacttca gttgggacat cctggccaag cgtattcgtg aactgtcgtt ccttaactcc    600
ggtgtgggta tcgtcctcaa ggacgagcgc agcggcaagg aagagttgtt caagtacgaa    660
ggcggcttgc gtgcgttcgt tgagtacctg aacaccaaca agactgcggt caaccaggtg    720
ttccacttca acatccagcg tgaagacggt atcggcgttg aaatcgccct gcagtggaac    780
gacagcttca acgagaacct gttgtgcttc accaacaaca ttccacagcg cgacggcggt    840
actcacttgg tgggtttccg ttccgcactg acgcgtaacc tgaacaccta catcgaagcg    900
gaaggcttgg ccaagaagca caaagtggcc actaccggtg acgatgcgcg tgaaggcctg    960
acggcgatta tctcggtgaa agtgccggat ccaaagttca gctcccagac caaagacaag   1020
ctggtgtctt ccgaagtgaa gaccgcagtg gaacaggaga tgggcaagta cttctccgac   1080
ttcctgctgg aaaacccgaa cgaagccaag ttggttgtcg gcaagatgat cgacgcggcg   1140
cgtgcccgtg aagcggcgcg taaagcccgt gagatgaccc gccgtaaagg cgcgttggat   1200
atcgccggcc tgccgggcaa actggctgac tgccaggaga aggaccctgc cctctccgaa   1260
ctgtacctgg tggaaggtga ctctgctggc ggttccgcca agcagggtcg taaccgtcgc   1320
acccaggcta tcctgccgtt gaagggtaag atcctcaacg tcgagaaggc ccgcttcgac   1380
aagatgattt cctctcagga agtcggcacc ttgatcacgg cgttgggctg cggtattggc   1440
cgcgatgagt acaacatcga caaactgcgt taccacaaca tcatcatcat gaccgatgct   1500
gacgtcgacg gttcgcacat ccgtaccctg ctgctgacct tcttcttccg tcagttgccg   1560
gagctgatcg agcgtggcta catctacatc gctcagccgc cgttgtacaa agtgaaaaag   1620
ggcaagcaag agcagtacat caaagacgac gacgccatgg aagagtacat gacgcagtcg   1680
gccctggaag atgccagcct gcacttgaac gacgaagccc cgggcatttc cggtgaggcg   1740
ctggagcgtt tggttaacga cttccgcatg gtaatgaaga ccctcaagcg tctgtcgcgc   1800
ctgtaccctc aggagctgac cgagcacttc atctacctgc cttccgtgag cctggagcag   1860
ttgggcgatc acgcccacat gcagaattgg ctggctcagt acgaagtacg tctgcgcacc   1920
gtcgagaagt ctggcctggt ttacaaagcc agcttgcgtg aagaccgtga acgtaacgtg   1980
tggctgccgg aggttgaact gatctcccac ggcctgtcga actacgtcac cttcaaccgc   2040
gacttcttcg gcagcaacga ctacaagacc gtggttaccc tcggcgcgca attgagcacc   2100
ctgttggacg acggtgctta catccagcgt ggcgagcgta agaaagcggt caaggagttc   2160
aaggaagccc tggactggtt gatggctgaa agcaccaagc gccacaccat ccagcgatac   2220
aaaggtctgg gcgagatgaa cccggatcaa ctgtgggaaa ccaccatgga tcctgctcag   2280
cgtcgcatgc tacgcgtgac catcgaagac gccattggcg cagaccagat cttcaacacc   2340
ctgatgggtg atgcggtcga gcctcgccgt gacttcatcg agagcaacgc cttggcggtg   2400
tctaacctgg atttctga                                                 2418
```

<210> SEQ ID NO 111
<211> LENGTH: 2832
<212> TYPE: DNA
<213> ORGANISM: Unknown
<220> FEATURE:
<223> OTHER INFORMATION: Description of Unknown:
      DP68 Isoleucine--tRNA ligase microbial sequence

<400> SEQUENCE: 111

```
atgaccgact ataaagccac gctaaacctt ccggacaccg ccttcccaat gaaggccggc     60
ctgccacagc gcgaaccgca gatcctgcag cgctgggaca gtattggcct gtacggaaag    120
```

```
ttgcgcgaaa ttggcaagga tcgtccgaag ttcgtcctgc acgacggccc tccttatgcc    180
aacggcacga ttcacatcgg tcatgcgctg aacaaaattc tcaaggacat gatcctgcgt    240
tcgaaaaccc tgtcgggctt cgacgcgcct tatgttccgg gctgggactg ccacggcctg    300
ccgatcgaac acaaagtcga agtgacctac ggcaagaacc tgggcgcgga taaaacccgc    360
gaactgtgcc gtgcctacgc caccgagcag atcgaagggc agaagtccga attcatccgc    420
ctgggcgtgc tgggcgagtg ggacaacccg tacaagacca tgaacttcaa gaacgaggcc    480
ggtgaaatcc gtgccttggc tgaaatcgtc aaaggcggtt tcgtgttcaa gggcctcaag    540
cccgtgaact ggtgcttcga ctgcggttcg gccctggctg aagcggaagt cgagtacgaa    600
gacaagaagt cctcgaccat cgacgtggcc ttcccgatcg ccgacgacga caagctggct    660
caagcctttg gcctgtccag cctgccaaag cctgcagcca tcgtgatctg gaccaccacc    720
ccgtggacca tcccggccaa ccaggcgctg aacgtgcacc cggaattcac ctacgccctg    780
gtggacgtcg gtgatcgcct gctggtgctg gctgaagaaa tggtcgaggc ctgcctggcg    840
cgctacgagc tgcaaggttc ggtcatcgcc accaccaccg gcactgcgct ggagctgatc    900
aatttccgtc acccgttcta tgaccgtctg tcgccggtgt acctggctga ctacgtagag    960
ctgggttcgg gtactggtgt ggttcactcc gcgccggcct acggcgttga tgactttgtg   1020
acctgcaaag cctacggcat ggtcaacgat gacatcctca acccggtgca gagcaatggc   1080
gtgtacgcgc cgtcgctgga gttctttggc ggccagttca tcttcaaggc caacgagccg   1140
atcatcgaca aactgcgtga agtcggttcg ctgctgcaca ccgaaaccat caagcacagc   1200
tacatgcact gctggcgtca caagaccccg ctgatctacc gcgctaccgc gcagtggttt   1260
atcggcatgg acaaagagcc gaccagcggc gacaccctgc gtgtgcgctc gctcaaagcg   1320
atcgaagaga ccaagtttgt cccggcctgg ggccaggcgc gcctgcactc gatgatcgcc   1380
aaccgcccgg actggtgcat ctcccgccag cgcaactggg gcgtgccgat tccgttcttc   1440
ctgaacaagg aaagcggcga gctgcaccca cgtaccgttg aactgatgga agcagtggcg   1500
ctgcgcgttg agcaggaagg catcgaagcc tggttcaagc tggacgccgc cgaactgctg   1560
ggcgacgaag cgccgctgta cgacaagatc agcgacaccc tcgacgtgtg gttcgactcg   1620
ggtaccaccc actggcacgt gctgcgcggt tcgcacccga tgggtcacgc caccggcccg   1680
cgtgccgacc tgtacctgga aggctcggac caacaccgtg gctggttcca ctcgtcgttg   1740
ctgaccggct gcgccatcga caaccacgcg ccgtaccgcg aactgctgac ccacggcttc   1800
accgtcgacg agacgggccg caagatgtcc aagtcgctga aaaacgtgat cgagccgaaa   1860
aagatcaacg acaccctggg cgccgatatc atgcgtctgt gggtcgcctc gaccgattac   1920
tcgggcgaaa tcgccgtgtc ggaccagatc ctggcccgta gcgccgatgc ctaccgccgt   1980
atccgtaata ccgcacgctt cctgctgtcg aacctgaccg gtttcaaccc ggccaccgac   2040
atcctgccgg ccgaggacat gctcgccctg gaccgttggg ccgtggaccg tacgctgttg   2100
ctgcagcgcg agttgcagga acactacggc gaataccgtt tctggaacgt gtactccaag   2160
atccacaact tctgcgtgca ggagctgggt ggtttctacc tcgatatcat caaggaccgc   2220
cagtacacca ccggcgccaa cagcaaggcg cgccgctcgg cgcagaccgc gctgtaccac   2280
atctctgaag cgctggtgcg ctggatcgca ccgatcctgg ccttcaccgc tgacgaactg   2340
tgggaatacc tgccgggcga gcgtaacgaa tcggtgatgc tcaacacctg gtacgaaggc   2400
ctgaccgaat tgccggccaa cttcgaactg ggccgcgagt actgggaagg cgtgatggcc   2460
```

```
gtcaaggttg cggtgaacaa ggagctggaa gttcagcgcg cggccaaggc cgtcggtggc   2520

aacctgcaag ccgaagtcac cctgtttgcc gaggaaggcc tgaccgccga cctggccaag   2580

ctgagcaacg aactgcgctt cgtactgatc acctcgaccg cgagcctggc accgtttgcc   2640

caggcacctg cggacgcagt ggccaccgaa gtgccgggcc tcaagctcaa agtggtcaag   2700

tcggcctttc ctaagtgcgc ccgttgctgg cactgccgtg aagacgtcgg cgtgaaccca   2760

gagcatccgg aaatctgcgg tcgttgcgtc gacaacatca gcggtgctgg cgaggttcgc   2820

cactatgcct aa                                                       2832
```

```
<210> SEQ ID NO 112
<211> LENGTH: 1785
<212> TYPE: DNA
<213> ORGANISM: Unknown
<220> FEATURE:
<223> OTHER INFORMATION: Description of Unknown:
      DP68 NADH-quinone oxidoreductase subunit C/D
      microbial sequence

<400> SEQUENCE: 112

atgactacag gcagtgctct gtacatcccg ccttacaagg cagacgacca ggatgtggtt     60

gtcgaactca ataaccgttt tggccctgac gccttcaccg cccaggccac acgcaccggt    120

atgccggtgc tgtgggtggc gcgcgccaag ctcgtcgaag tcctgagctt cctgcgcaac    180

ctgcccaagc cgtacgtcat gctttatgac ctgcatggcg tggacgagcg tctgcgcacc    240

aagcgtcaag gtttgccgag cggtgccgat ttcaccgtgt tctaccactt gatgtcgctg    300

gaacgtaaca gcgacgtgat gatcaaggtc gcgctgtccg aaagcgactt gagcatcccg    360

accgtcaccg gtatctggcc gaatgccagc tggtacgagc gcgaagtttg ggacatgttc    420

ggtatcgact tcccgggcca cccgcacctg acgcgcatca tgatgccgcc gacctgggaa    480

ggtcacccgc tgcgcaagga ctttcctgcc cgcgcaaccg aattcgaccc gttcagcctc    540

aacctcgcca agcagcagct tgaagaagaa gctgcacgct tccgtccgga agactggggc    600

atgaaacgct ccggcaccaa cgaggactac atgttcctca acctgggccc gaaccaccct    660

tcggctcacg gtgccttccg tatcatcctg caactggacg gcgaagaaat cgtcgactgt    720

gtgccggaca tcggttacca ccaccgtggt gccgagaaga tggccgagcg ccagtcctgg    780

cacagcttca tcccgtacac cgaccgtatc gactacctcg gcggcgtgat gaacaacctg    840

ccgtacgtgc tgtcggtcga gaagctggcc ggtatcaagg tgccggaccg cgtcgacacc    900

atccgcatca tgatggccga gttcttccgc atcaccagcc acctgctgtt cctgggtacc    960

tatatccagg acgttggcgc catgaccccg gtgttcttca ccttcaccga ccgtcaacgc   1020

gcctacaagg tgatcgaagc catcaccggt ttccgcctgc acccggcctg gtatcgcatc   1080

ggcggcgtgg cgcacgacct gccgaacggc tgggagcgcc tggtcaagga attcatcgac   1140

tggatgccca agcgtctgga cgagtaccaa aaggctgcgc tggacaacag catcctcaag   1200

ggtcgtacca tcggcgtcgc gcagtacaac accaaagaag ccctggaatg gggcgtcact   1260

ggtgccggcc tgcgttcgac cggctgcgac ttcgacctgc gtaaagcacg gccgtactcg   1320

ggctacgaga acttcgagtt cgaagtgccg ctggccgcca atggcgatgc ctacgaccgg   1380

tgcatcgtgc gcgttgaaga aatgcgccag agcctgaaga tcatcgagca gtgcatgcgc   1440

aacatgccgg ctggcccgta caaggcggat catccgctga ccacaccgcc gccgaaagag   1500

cgcacgctgc agcacatcga aaccctgatc acgcacttcc tgcaagtttc gtggggcccg   1560

gtgatgccgg ccaacgaatc cttccagatg atcgaagcga ccaagggtat caacagttat   1620
```

tacctgacga gcgatggcgg caccatgagc taccgcaccc ggattcgtac cccaagcttt 1680
gcccacttgc agcagatccc ttcggtgatc aaaggcgaga tggtcgcgga cttgattgcg 1740
tacctgggta gtatcgattt cgttatggcc gacgtggacc gctaa 1785

<210> SEQ ID NO 113
<211> LENGTH: 1059
<212> TYPE: DNA
<213> ORGANISM: Unknown
<220> FEATURE:
<223> OTHER INFORMATION: Description of Unknown:
DP68 Protein RecA microbial sequence

<400> SEQUENCE: 113
atggacgaca acaagaagaa agccttggct gcggccctgg gtcagatcga acgtcaattc 60
ggcaagggtg ccgtaatgcg tatgggcgat cacgaccgtc aggcgatccc ggctatttcc 120
actggctctc tgggtctgga catcgcactc ggcattggcg gcctgccaaa aggccgtatc 180
gttgaaatct acggtcctga atcttccggt aaaaccaccc tgaccctgtc ggtgattgcc 240
caggcgcaaa aaatgggcgc cacctgtgcg ttcgtcgacg ccgagcacgc cctggacccg 300
gaatacgccg gtaagctggg cgtcaacgtt gacgacctgc tggtttccca gccggacacc 360
ggtgagcaag ccctggaaat caccgacatg ctggtgcgct ccaacgccat cgacgtgatc 420
gtggtcgact ccgtggctgc cctggtaccg aaagctgaaa tcgaaggcga aatgggcgac 480
atgcacgtgg gcctgcaagc ccgcctgatg tcccaggcgc tgcgtaaaat taccggtaac 540
atcaagaacg ccaactgcct ggtgatcttc atcaaccaga tccgtatgaa gatcggcgta 600
atgttcggca gcccggaaac cactaccggt ggtaacgcgc tgaagttcta cgcttcggtc 660
cgtctggaca tccgccgtac cggcgcggtg aaggaaggtg acgaagttgt tggtagcgaa 720
actcgcgtta aagtcgtgaa gaacaaggtc gctccgcctt tccgtcaggc agagttccag 780
attctctacg gcaagggtat ctacctgaac ggcgagatga ttgacctggg cgtactgcac 840
ggtttcgtcg agaagtccgg tgcctggtat gcctacaacg gcagcaagat cggtcagggc 900
aaggccaact cggccaagtt cctggcagac aacccggata tcgctgccac gcttgagaag 960
cagattcgcg acaagctgct gaccccagcg ccagacgtga aagctgccgc caaccgcgag 1020
ccggttgaag aagtggaaga agctgacact gatatctga 1059

<210> SEQ ID NO 114
<211> LENGTH: 1851
<212> TYPE: DNA
<213> ORGANISM: Unknown
<220> FEATURE:
<223> OTHER INFORMATION: Description of Unknown:
DP68 RNA polymerase sigma factor RpoD microbial sequence

<400> SEQUENCE: 114
atgtccggaa aagcgcaaca acagtctcgt attaaagagt tgatcaccct tggtcgtgag 60
cagaaatatc tgacttacgc agaggtcaac gatcacctgc ctgaggatat ttcagatcct 120
gagcaggtgg aagacatcat ccgcatgatt aatgacatgg ggatccccgt acacgagagt 180
gctccggatg cggacgccct tatgttggcc gactccgata ccgacgaggc agctgctgaa 240
gaagcggctg ctgcgctggc agcggtggag accgacatcg gtcgtacgac tgaccctgtg 300
cgcatgtata tgcgtgaaat gggtaccgtc gagctgctga cacgtgaagg cgaaatcgaa 360
atcgccaaac gtattgaaga gggtatccgt gaagtgatgg gcgcaatcgc gcacttccct 420
ggcacggttg accacattct ctccgagtac actcgcgtca ccaccgaagg tggccgcctg 480
tctgacgttc tgagcggcta catcgacccg gacgacggca ttgcgccgcc tgccgccgaa 540
gtaccgccgc ccgtcgatgc gaaagccgcg aaggctgacg acgacaccga agacgacgat 600
gctgaagcca gcagcgacga cgaagatgaa gttgaaagcg gcccggaccc gatcatcgca 660
gcccagcgtt tcggtgcggt ttccgatcaa atggaaatca cccgcaaggc cctgaaaaag 720
cacggtcgct ccaacaagct ggcgattgcc gagctggtgg ccctggctga gctgttcatg 780
ccgatcaagc tggtaccgaa gcaattcgaa ggcttggttg agcgtgttcg cagtgccctt 840
gaacgtctgc gtgcgcaaga acgcgcaatc atgcagctgt gtgtacgtga tgcacgtatg 900
ccgcgggctg acttcctgcg ccagttcccg ggcaacgaag tagacgaaag ctggaccgac 960
gcactggcca aaggcaaggc gaaatacgcc gaagccattg gtcgcctgca gccggacatc 1020
atccgttgcc agcagaagct gaccgcgctt gagaccgaaa ccggtctgac gattgctgaa 1080
atcaaagaca tcaaccgtcg catgtcgatc ggtgaggcca aggcccgccg cgcgaagaaa 1140
gagatggttg aagcgaactt gcgtctggtg atctcgatcg ccaagaagta caccaaccgt 1200
ggtctgcaat tcctcgatct gatccaggaa ggcaacatcg gcttgatgaa ggcggtggac 1260
aagttcgaat accgtcgcgg ctacaagttc tcgacttatg ccacctggtg gatccgtcag 1320
gcgatcactc gctcgatcgc cgaccaggct cgcaccatcc gtattccggt gcacatgatc 1380
gagacgatca acaagctcaa ccgtatttcc cggcagatgt tgcaggaaat gggtcgcgaa 1440
ccgaccccgg aagagctggg cgaacgcatg gaaatgcctg aggataaaat ccgcaaggta 1500
ttgaagatcg ctaaagagcc gatctccatg gaaacgccga ttggtgatga cgaagactcc 1560
cacctgggtg acttcatcga agactcgacc atgcagtcgc caatcgatgt cgccactgtt 1620
gagagcctta aagaagcgac tcgcgacgta ctgtccggcc tcactgcccg tgaagccaag 1680
gtactgcgca tgcgtttcgg catcgacatg aataccgacc acacccttga ggaagtcggt 1740
aagcagtttg acgtgacccg cgagcggatc cgtcagatcg aagccaaggc gctgcgcaag 1800
ttgcgccacc cgacgcgaag cgagcatctg cgctccttcc tcgacgagtg a 1851

<210> SEQ ID NO 115
<211> LENGTH: 4074
<212> TYPE: DNA
<213> ORGANISM: Unknown
<220> FEATURE:
<223> OTHER INFORMATION: Description of Unknown:
DP68 DNA-directed RNA polymerase subunit beta
microbial sequence

<400> SEQUENCE: 115
atggcttact catatactga gaaaaaacgt atccgcaagg actttagcaa gttgccggac 60
gtcatggatg tcccgtacct tctggctatc cagctggatt cgtatcgtga attcttgcag 120
gcgggagcga ccaaagatca gttccgcgac gtgggcctgc atgcggcctt caaatccgtt 180
ttcccgatca tcagctactc cggcaatgct gcgctggagt acgtgggtta tcgcctgggc 240
gaaccggcat ttgatgtcaa agaatgcgtg ttgcgcggtg ttacgtacgc cgtacctttg 300
cgggtaaaag tccgcctgat cattttcgac aaagaatcgt cgaacaaagc gatcaaggac 360
atcaaagagc aagaagtcta catgggcgaa atcccactga tgactgaaaa cggtaccttc 420
gtaatcaacg gtaccgagcg tgttattgtt tcccagctgc accgttcccc gggcgtgttc 480
ttcgaccacg accgcggcaa gacgcacagc tccggtaaac tcctgtactc cgcgcggatc 540
attccgtacc gcggttcgtg gttggacttc gagttcgacc cgaaagactg cgtgttcgtg 600

```
cgtatcgacc gtcgtcgcaa gctgccggcc tcggtactgc tgcgcgcgct cggttacacc    660
actgagcagg tgctggacgc tttctacacc accaacgtat tcagcctgaa ggatgaaacc    720
ctcagcctgg agctgattgc ttcgcgtctg cgtggtgaaa ttgccgttct ggacattcag    780
gacgaaaacg gcaaagtgat cgttgaagcg ggtcgtcgta ttactgcgcg ccacatcaac    840
cagatcgaaa aagccggcat caagtcgctg gaagtgcctc tggactacgt cctgggtcgc    900
accaccgcca aggttatcgt tcacccggct acaggcgaaa tcctggctga gtgcaacacc    960
gagctgaaca ccgaaatcct ggcaaaaatc gccaaggccc aggttgttcg catcgagacc   1020
ctgtacacca acgacatcga ctgcggtccg ttcatctccg acacactgaa gatcgactcc   1080
accagcaacc aattggaagc gctggtcgag atctatcgca tgatgcgtcc tggtgagcca   1140
ccgaccaaag acgctgccga gaccctgttc aacaacctgt tcttcagccc tgagcgttat   1200
gacctgtctg cggtcggccg gatgaagttc aaccgtcgta tcggtcgtac cgagatcgaa   1260
ggttcgggcg tgctgtgcaa ggaagatatc gtcgcggtac tgaagactct ggtcgacatc   1320
cgtaacggta aaggcatcgt cgatgacatc gaccacctgg gtaaccgtcg tgttcgctgc   1380
gtaggcgaaa tggccgaaaa ccagttccgc gttggccttg tgcgtgttga acgtgcggtc   1440
aaagagcgtc tgtcgatggc tgaaagcgaa ggcctgatgc cgcaagacct gatcaacgcc   1500
aagccagtgg ctgcggcagt gaaagagttc ttcggttcca gccagctttc ccagttcatg   1560
gaccagaaca acccgctctc cgagatcacc cacaagcgcc gtgtttctgc actgggcccg   1620
ggcggtctga cccgtgagcg tgctggcttt gaagttcgtg acgtacaccc gacgcactac   1680
ggtcgtgttt gcccgatcga aacgccggaa ggtccgaaca tcggtctgat caactccctg   1740
gccgcttatg cgcgcaccaa ccagtacggc ttcctcgaga gcccgtaccg cgtggtgaaa   1800
gacgctctgg tcaccgacga gatcgtattc ctgtccgcca tcgaagaagc tgatcacgtg   1860
atcgctcagg cttcggccac gatgaacgac aagaaagtcc tgatcgacga gctggtagct   1920
gttcgtcact tgaacgagtt caccgtcaag gcgccggaag acgtcacctt gatggacgtt   1980
tcgccgaagc aggtagtttc ggttgcagcg tcgctgatcc cgttcctgga acacgatgac   2040
gccaaccgtg cgttgatggg ttccaacatg cagcgtcaag ctgtaccaac cctgcgcgct   2100
gacaagccgc tggtaggtac cggcatggag cgtaacgtag cccgtgactc cggcgtttgc   2160
gtcgtagccc gtcgtggcgg cgtgatcgac tccgttgatg ccagccgtat cgtggttcgt   2220
gttgccgatg atgaagttga aactggcgaa gccggtgtcg acatctacaa cctgaccaaa   2280
tacacccgct cgaaccagaa cacctgcatc aaccagcgtc cgctggtgag caagggtgac   2340
cgcgttcagc gtagcgacat catggccgac ggcccgtcca ctgacatggg tgaactggct   2400
ctgggtcaga acatgcgcat cgcgttcatg gcatggaacg gcttcaactt cgaagactcc   2460
atctgcctgt ccgagcgtgt tgttcaagaa gaccgtttca ccacgatcca cattcaggaa   2520
ctgacctgtg tggcacgtga taccaagctt gggccagagg aaatcactgc agacatcccg   2580
aacgtgggtg aagctgcact gaacaagctg gacgaagccg gtatcgttta cgtaggtgct   2640
gaagttggcg caggcgacat cctggtaggt aaggtcactc cgaaaggcga gacccaactg   2700
actccggaag agaagctgct gcgtgccatc ttcggtgaaa aagccagcga cgttaaagac   2760
acctccctgc gtgtacctac cggtaccaag ggtactgtta tcgacgtaca ggtcttcacc   2820
cgtgacggcg ttgagcgtga tgctcgtgca ctgtccatcg agaagactca actcgacgag   2880
atccgcaagg acctgaacga agagttccgt atcgttgaag gcgcgacctt cgaacgtctg   2940
```

```
cgttccgctc tggtaggcca caaggctgaa ggcggcgcag gtctgaagaa aggtcaggac   3000

atcaccgacg aagtactcga cggtcttgag cacggccagt ggttcaaact gcgcatggct   3060

gaagatgctc tgaacgagca gctcgagaag gcccaggcct acatcgttga tcgccgtcgt   3120

ctgctggacg acaagttcga agacaagaag cgcaaactgc agcagggcga tgacctggct   3180

ccaggcgtgc tgaaaatcgt caaggtttac ctggcaatcc gtcgccgcat ccagccgggc   3240

gacaagatgg ccggtcgtca cggtaacaaa ggtgtggtct ccgtgatcat gccggttgaa   3300

gacatgccgc acgatgccaa tggcaccccg gtcgacgtcg tcctcaaccc gttgggcgta   3360

ccttcgcgta tgaacgttgg tcagatcctc gaaacccacc tgggcctcgc ggccaaaggt   3420

ctgggcgaga agatcaaccg tatgatcgaa gagcagcgca aggttgctga cctgcgtaag   3480

ttcctgcacg agatctacaa cgagatcggc ggtcgcaacg aagagctgga caccttctcc   3540

gaccaggaaa tcctggactt ggcgaagaac ctgcgcggcg gcgttccaat ggctaccccg   3600

gtgttcgacg gtgccaagga aagcgaaatc aaggccatgc tgaaactggc agacctgccg   3660

gaaagcggcc agatgcagct gttcgacggc cgtaccggca acaagtttga gcgcccggtt   3720

actgttggct acatgtacat gctgaagctg aaccacttgg tagacgacaa gatgcacgct   3780

cgttctaccg gttcgtacag cctggttacc cagcagccgc tgggtggtaa ggctcagttc   3840

ggtggtcagc gtttcgggga gatggaggtc tgggcactgg aagcatacgg tgctgcatac   3900

actctgcaag aaatgctcac agtgaagtcg gacgatgtga acggtcggac caagatgtac   3960

aaaaacatcg tggacggcga tcaccgtatg gagccgggca tgcccgagtc cttcaacgtg   4020

ttgatcaaag aaattcgttc cctcggcatc gatatcgatc tggaaaccga ataa         4074
```

```
<210> SEQ ID NO 116
<211> LENGTH: 1674
<212> TYPE: DNA
<213> ORGANISM: Unknown
<220> FEATURE:
<223> OTHER INFORMATION: Description of Unknown:
      DP69 Glutamine--tRNA ligase microbial sequence

<400> SEQUENCE: 116
```

```
gtgcgcgagg acctggccag cggaaagcac caggcgatca agacccgctt cccgccggag     60

ccgaacggct acctgcacat cggccacgcc aagtcgatct gcctgaactt cggcatcgcc    120

ggtgagttca gcggcgtctg caacctgcgt ttcgacgaca ccaatccggc caaggaagac    180

ccggagtacg tggccgcgat ccaggacgac gtgcgctggc tgggctttga atggaacgag    240

ctgcgccacg cctcggacta cttccagacc tattacctgg ccgccgagaa gctgatcgaa    300

cagggcaagg cctacgtctg cgacctgtcg gccgaggaag tgcgcgccta ccgcggcacc    360

ctgaccgagc cgggccgccc gtcgccgtgg cgtgaccgca gcgtcgagga gaacctcgac    420

ctgttccgcc gcatgcgtgc cggtgaattc cccgatggcg cgcgcaccgt gcgcgccaag    480

atcgacatgg ccagcggcaa catcaacctg cgtgatccgg cgctgtaccg catcaagcac    540

gtcgagcacc agaacaccgg caacgcgtgg ccgatctacc cgatgtacga cttcgcccat    600

gcgctgggcg attcgatcga gggcatcacc cactcgctgt gcacgctgga attcgaagac    660

caccgcccgc tgtacgactg gtgcgtggac aacgtcgact tcgcccacga tgacgcgctg    720

acccagccgc tggtcgacgc cggcctgccg cgcgaagcgg ccaaaccgcg ccagatcgag    780

ttctcgcgcc tgaacatcaa ctacacggtg atgagcaagc gcaagctgat ggcgctggtc    840

accgaacagc tggtggacgg ctgggaagac ccgcgcatgc cgaccctgca gggcctgcgt    900
```

```
cgccgtggct acaccccggc agcgatgcgc ctgttcgccg agcgcgtggg catcagcaag    960

cagaattcgc tgatcgattt cagcgtgctg gaaggcgcgc tgcgcgaaga cctggacagc   1020

gccgcaccgc gccgcatggc cgtggtcgac ccggtcaagc tggtgctgac caacctggcc   1080

gaaggccacg aagagcagct gaccttcagc aaccacccga aggacgagag cttcggtacc   1140

cgcgaagtgc cgttcgcacg tgaagtgtgg atcgaccgcg aggacttcgc cgaagtgccg   1200

ccgaagggct ggaagcgcct ggttcccggt ggtgaagtgc gcctgcgcgg cgccggcatc   1260

atccgctgcg acgacgtgat caaggatgcc gacggcacca tcaccgagct gcgcggctgg   1320

ctggatccgg aatcgcgccc gggcatggaa ggcgccaacc gcaaggtcaa gggcaccatc   1380

cactgggtca gcgcggtgca cggtgtgccg gccgagatcc gcctgtatga ccgcctgttc   1440

tcggtgccga acccggacga tgaatcggaa ggcaagacct accgcgacta cctcaatccg   1500

gactcgcgcc gcaccgtcac cggctatgtc gagccggcgg ctgccagcgc tgcgccggaa   1560

cagtcgttcc agttcgagcg caccggctac ttcgttgccg accgccgcga ccacaccgaa   1620

gccaagccgg tgttcaaccg cagcgtgacc ctgcgcgaca cctggtcggc ctga         1674
```

<210> SEQ ID NO 117
<211> LENGTH: 2460
<212> TYPE: DNA
<213> ORGANISM: Unknown
<220> FEATURE:
<223> OTHER INFORMATION: Description of Unknown:
DP69 DNA gyrase subunit B microbial sequence

<400> SEQUENCE: 117

```
atgaccgacg aacagaacac cccggcaaac aacggcaact acgacgccaa cagcattacg     60

gccctggaag gcctggaggc tgtccgcaag cgcccaggca tgtacatcgg cgacgtccat    120

gacggcaccg gcctgcatca catggtgttc gaggtcgtcg acaactcaat cgacgaagcc    180

ctcgccggcc atgccgacca cgtctcggtg acgatccatg ccgatggctc ggtaggcgtg    240

tccgacaacg gtcgcggcat cccgacgggc aagcacgagc agatgagcaa gaagctcgac    300

cgcgatgtgt ctgcagccga agtggtgatg acggtcctgc acgcaggcgg caagttcgac    360

gacaacagct acaaggtttc cggcggcctg cacggcgtgg gcgtcagcgt ggtcaacgcg    420

ctgtcgcaga agctggtcct ggatatctac cagggtggct tccactacca gcaggagtac    480

gccgacggcg cagcactgca tccgctgaag cagatcggcc ccagcaccaa gcgcgggacc    540

accctgcgct tctggccctc ggtaaaggct ttccacgaca acgtggaatt ccactacgac    600

atcctggccc ggcgcctgcg cgaactgtcc ttcctcaatt ccggcgtcaa gatcgtgctg    660

gtggacgagc gtggtgatgg ccgccgcgac gacttccatt acgagggcgg catccgcagc    720

ttcgtggagc atctggcgca gttgaagacg ccgttgcacc cgaacgtgat ctcggtgacc    780

ggcgaatcca atggcatcac cgtggaagtg gcgctgcagt ggaccgactc ctaccaggag    840

acgatgtact gcttcaccaa caacattccg cagaaggacg gcggtaccca cctggccggc    900

ttccgtggcg cattgacccg cgtgctcaac aactacatcg agcagaacgg catcgccaag    960

caggccaaga tcaacctgac cggcgatgac atgcgcgaag gcatgatcgc ggtgctgtcg   1020

gtgaaggtgc cggatcccag cttctccagc cagaccaagg aaaagctggt cagctcggat   1080

gtgcgcccgg ccgtggaaag cgcgttcggc cagcgcctgg aagagttcct gcaggaaaac   1140

ccgaacgaag ccaaggccat cgccggcaag atcgtcgacg ctgcccgtgc ccgcgaagcg   1200

gcgcgcaagg cccgcgacct gacccgccgc aagggtgcgc tggatatcgc cggcctgccg   1260
```

ggcaagctgg ccgactgcca ggaaaaggat ccggcgctgt ccgaactgtt catcgtcgag 1320
ggtgactcgg caggtggttc ggccaagcag ggtcgcaacc gcaagaacca ggcggtgctg 1380
ccgctgcgcg gcaagatcct caacgtggaa cgtgcgcgct tcgaccgcat gctggcgtcc 1440
gaccaggtgg gtacgctgat caccgcgctg ggtaccggca tcggtcgtga cgagtacaac 1500
ccggacaagc tgcggtacca caagatcatc atcatgaccg acgccgacgt cgacggcgcg 1560
cacatccgca ccctgctgct gacgttcttc taccgtcaga tgccggagct gatcgagcgc 1620
ggttatgtct atatcggcct gccgccgttg tacaagatca agcagggcaa gcaggagctg 1680
tacctgaagg acgacccggc gctggacagc tatctggcca gcagcgcggt ggagaacgct 1740
gggctggtgc cggccagcgg cgagccgccg atcgacggcg tggcactgga aaagctgctg 1800
ctcgcctacg ctgccgcgca ggacacgatc aaccgcaata cccaccgcta cgaccgcaac 1860
ctgctcgaag cgctggtcga cttcatgccg ctggagctgg aaaacctgcg cactgcaggt 1920
cctggcgaag gtctggacgc gttggccaag cacctcaacc agggcaacct cggcagcgcc 1980
cgcttcaccc tggaactgca ggaacccaac gagcagcgtc cggcggccgt actggtgacc 2040
cgcagccaca tgggcgaaca gcacatccag gtgctgccgc tgtccgcgct ggaaagcggc 2100
gaactgcgcg gcatccatca ggcagcgcag ctgctgcacg gtctggtccg cgaaggcgcg 2160
gtcatcaccc gtggcgccaa gtcgatcgag atcgactcgt tcgcacaggc ccgcaactgg 2220
ctgttggacg aagccaagcg cggccggcag atccagcgat tcaagggtct gggcgaaatg 2280
aatccggaac agctgtggga taccaccgtc aatcccgata cccgtcgcct gctgcaggtg 2340
cgcatcgaag acgcggtggc cgctgaccag atcttcagca ccctgatggg tgatgtggtc 2400
gaaccgcgtc gtgacttcat cgaagacaac gcgttgaagg tcgccaacct ggatatctga 2460

<210> SEQ ID NO 118
<211> LENGTH: 2835
<212> TYPE: DNA
<213> ORGANISM: Unknown
<220> FEATURE:
<223> OTHER INFORMATION: Description of Unknown:
DP69 Isoleucine--tRNA ligase microbial sequence

<400> SEQUENCE: 118
gtgagccagg actacaagac caccctcaac ctgccggcca ccgaattccc gatgcgcggc 60
gacctgccca agcgcgagcc gggcattctg gcgcgctggg aagagcaggg gctctaccag 120
cagctgcgcg acaacgccgc cggccgcccg ctgttcgtgc tgcatgacgg cccgccgtac 180
gccaatgcgc gcatccacct gggccatgcg gtcaacaaga tcctcaagga catcatcgtc 240
aagtcgcgct acctggccgg cttcgatgcg ccctacgtgc cgggctggga ctgccatggc 300
ctgccgatcg aaatcgcggt ggaaaagaag tggggcaagg tcggggtgaa gctcgatgcg 360
gtcgagttcc ggcagaagtg ccgcgagttc gccgaagaac agatcgacat ccagcgtgcc 420
gacttcaagc gcctgggcgt caccggcgac tgggacaacc cgtacaagac cctaagcttc 480
gatttcgagg ccaacgagat ccgtgcgctg tccaagatcg tggccaacgg ccatctgctg 540
cgtggcgcca agccggtcta ctggtgcttc gactgcggct cggcactggc cgaggccgag 600
atcgagtacc acgagaagac ctcgccggcg atcgacgtgg cctacaccgc gcgtgatccg 660
caggcggtgg cgcaggcgtt cggcgtcagc ctgccggccg atgtcgaagt ggcggtgccg 720
atctggacca ccactccgtg gacgctgccg gcttcgctgg cggtgtcgct gggcgcggac 780
atccgctacg tgctggccga aggcccggcg cacaacggca agcgccgttg gctggtgctg 840
gctgctgcgc tggccgaacg gtcgctgcag cgctacggcg tggacgcggt ggtgctgcac 900
ggtgaagccg aaggttcggc gctggaaaac cagctgctgg cgcacccgtt ctacccggag 960
cgcgagatcc ccgtgctcaa cggcgaacac gtgtccgacg aggacggtac cggtgcggtg 1020
cacactgccc ccggccacgg ccaggaagac tacgtggtca gccagaagta cggcctgctg 1080
gagaagtaca acgccggcca gatcaatccg gtcgacggtg cgggcgtgta cctggcgtcc 1140
accccgcccg ccggtgacct ggtgctggcc ggtacccaca tctggaaggc gcagcagccg 1200
atcatcgaag tgctggccgc cagcggcgcg ctgctcaagg ccgtggagat cgtgcacagt 1260
tatccgcatt gttggcgcca caagaagacc ccgctggtgt tccgcgccac cccgcagtgg 1320
ttcatttcga tggacaaggc caacctgcgc aacgatgcgc tggccgcgat cgataccgtc 1380
ggctggttcc cgagctgggg caaggcgcgc atccaaagca tgatcgacgg ccgcccggac 1440
tggaccatct cgcgccagcg cacctggggc gtgccgatcg cgctgttcac ccaccgccag 1500
accggcgaga tccacccgcg ttcggtggag ctgatgcagc aggtggccga ccgcgttgaa 1560
gccgaaggca tcgacgtgtg gtactcgctg gatgcggctg aactgctggg cgctgaagcg 1620
gccgactacg agaaggtcac cgacatcctc gatgtctggt tcgattccgg cgtgacccac 1680
gaagccgtgc tggctgcccg tggcttcggc aagccggccg atctgtacct ggaaggttcg 1740
gaccagcatc gcggctggtt ccagtcctcg ctgctgaccg gcgtggccat cgacaagcgc 1800
gcgccgtaca agcagtgcct cacccacggt ttcaccgtgg acgagcacgg ccgcaagatg 1860
tccaagtcgc tgggcaacgg catcgaaccg caggaaatca tgaacaagct gggcgcggac 1920
atcctgcgcc tgtggatcgc ctcggccgac tacagcaacg agatgtcgct gtcgcaggaa 1980
atcctcaagc gcaccgccga cgcctaccgc cgcctgcgca acaccgcccg cttcctgctg 2040
ggcaacctgg acggtttcga tccggcccag cacctgcgcc cgctcaacga gatggtcgcg 2100
ctggaccgct ggatcgtgca tcgcgcctgg gagctgcagg agaagatcaa ggcggcgtat 2160
gacaactacg acatggccga gatcgtgcag ttgctgctga acttctgcag cgtggacctg 2220
ggctcgctgt acctggacgt gaccaaggat cgcctgtata cgatgccgac cgattcggat 2280
ggtcgtcgtt cggcgcagag cgcgatgtac cacatcgccg aagcgttcac ccgctgggtg 2340
gcgccgatcc tgaccttcac cgccgacgag ctgtggggct acctgccggg cgatcgtgcc 2400
ggccacgtgc tgttcactac ctggtacgag ggcctggcac cgctgccgac cgatgcacag 2460
ctcaacgctg ccgacttcga tcagctgctg gccgtgcgcg agcaggtggc caaggtgctg 2520
gagccgatgc gcgccaatgg tgcgatcggt gccgcgctgg aagcggagat caccatcgcc 2580
gccagcgaag agcaggccgc gcgctggcag ccgctggccg atgaactgcg tttcctgttc 2640
atcagtggtg acgtgcaggt gcgtccggcg accaccgacg aggtgttcgt cagcgcgcag 2700
ccgacgcaga agtccaagtg cgtgcgctgc tggcaccacc gtgccgacgt tggcagcaat 2760
gccgaccacc cggaactgtg cggccgctgc gtgaccaaca tcgccggtgc cggcgaagcg 2820
cggagctggt tctga 2835

<210> SEQ ID NO 119
<211> LENGTH: 2076
<212> TYPE: DNA
<213> ORGANISM: Unknown
<220> FEATURE:
<223> OTHER INFORMATION: Description of Unknown:
DP69 Glycine--tRNA ligase beta subunit microbial sequence

<400> SEQUENCE: 119

-continued

```
atgagccact tgtctcccct gctgattgaa ctgggcaccg aagagttgcc ggtcaaggcg     60
ctgccgggcc tggcccaggc cttcttcgac ggtgttgtcg atggcctgcg caagcgcggc    120
gtcgaactgg agctgggcga tgcccgcccg ctgtcgaccc cgcgccgcct ggccgtgctg    180
ctgccgggcg ttggcctgga acagccggaa caacacagcg aagtgctggg cccgtacctg    240
aacatcgcgc tggacgccga aggccagccg accaaggcgc tgcagggttt cgcggccaag    300
gccgggatcg actggaccgc gctggagaag accaccgaca acaagggtga gcgcttcgtg    360
caccgtgcgg tgactccggg cgcgcgcacc gctgcgctgc tgccggagat cctgcgcgag    420
gccatcgccg gcatgccgat tcccaagccg atgcgctggg gcgaccacag ctggggcttc    480
gcccgcccgg tgcactggct ggtgctgctg catggcggcg acgtggtcga ggccgaactg    540
tttggcctga aggccgaccg catgagccgc ggccaccgct tcctgcacga caagaccgtg    600
tggctgaccc agccgcagga ctatgtcgaa tcgctgcgcg ccgccttcgt gctggtcgat    660
ccggccgagc gccgccggcg catcgttgcc gaagtggaag ccgctgccgc caccgccggt    720
ggcagcgcac gcatcaccga ggacaacctg gagcaggtgg tgaacctggt cgagtggccg    780
gcggcagtgt tgtgcagctt cgagcgcgcg ttcctggcgg taccgcagga agcgctgatc    840
gagacgatgg agatcaacca gaagttcttc ccggtgctgg atgacggcgg caagctgacc    900
gagaagttca tcggcatcgc caacatcgag tccaaggacg tggccgaagt ggccaagggc    960
tacgagcgcg tgatccgccc gcgcttcgcc gatgccaagt tcttcttcga cgaagacctg   1020
aagcagggcc tgcaggcgat gggcgagggc ctgaagacgg tgacctacca ggccaagctg   1080
ggcagcgtgg ccgacaaggt cgcgcgcgtg gcggcgctgg ccgaggtgat cgctgcgcag   1140
gtgggggccg acccggtgct ggccaagcgt gccgcgcagc tggccaagaa cgacctgcag   1200
tcgcgcatgg tcaatgagtt cccggaactg cagggcatcg ctggccgcca ctacgcggtg   1260
gccggtggcg agtcgccgga ggtggcgctg gccatcgacg aggcctacca gccgcgcttc   1320
ggtggcgatg acatcgcgct gtcgccgctg ggcaaggtgc tggcgatcgc cgagcgtgtg   1380
gacacgctgg ccggcggttt cgccgcgggc ctgaagccga ccggcaacaa ggacccgttc   1440
gccctgcgcc gcaacgcgct gggcctggcc cgcacgatta tcgaaagtgg cttcgagctg   1500
gacctgcgcg cgctgctggc cagcgccaat gccgggctga ccgtgcgcaa cgtgcaggcc   1560
gacgtggctg agctgtacga cttcatcctc gaccgcctga agggctacta cagcgacaag   1620
ggcgtgccgg ccagccactt caatgcggtg gctgagctga agccggtctc gctgtacgat   1680
ttcgaccgtc gcctggacgc catcggtatc ttcgcggcgc tgccggaggc cgaggcgctg   1740
gcagcggcca acaagcgcat ccgcaacatc ctgcgcaagg ccgaaggcga tattccgggc   1800
cagatcgatg cggccctgtt gcaggaagat gccgagcgcg cgctggcgga agccgtgact   1860
gcagccatcg acgacaccgg cgccagcctg caccagaagg actacgtggc cgtgctggcg   1920
cgcctggccc gcctgcgtcc gcaggtcgat gcgttcttcg atggggtgat ggtcaatgcc   1980
gaggatccgg cactgcgcgg caaccgcctg gcgctgctga cgatgctggg cgagcgcttg   2040
ggcaaggtcg cggcgatcga gcatctgtcg agctga                              2076
```

<210> SEQ ID NO 120
<211> LENGTH: 1410
<212> TYPE: DNA
<213> ORGANISM: Unknown
<220> FEATURE:
<223> OTHER INFORMATION: Description of Unknown:
DP69 Glutamine synthetase microbial sequence

<400> SEQUENCE: 120
atgtccgtgg aaaccgtaga gaagctgatc aaggacaacc agatcgagtt cgtcgatctg 60
cgcttcgtcg acatgcgtgg tgtcgaacag catgtgacct tcccggtcag catcgtcgag 120
ccgtcgctgt ttgaagaagg caagatgttc gatggcagct cgatcgccgg ctggaagggc 180
atcaacgagt cggacatggt gctgctgccg gacaccgcca gcgcctacgt cgacccgttc 240
tacgccgatc cgaccatcgt gatcagctgc gacatcctcg acccggccac catgcagccg 300
tatggccgtt gcccgcgcgg catcgccaag cgcgccgagt cctacctgaa gtcctcgggc 360
atcgccgaaa ccgcgttctt cggcccggag ccggagttct tcatcttcga ctcggtgcgt 420
ttcgccaatg aaatgggcaa caccttcttc aaggtcgact cggaagaagc ggcgtggaac 480
agcggcgcca agtacgacgg cgccaacagc ggctaccgtc cgggcgtgaa gggcggttat 540
ttccccgttc cgccgaccga caccctgcac gacctgcgtg cggagatgtg caagaccctg 600
gaacaggtcg gcatcgaagt ggaagtgcag caccacgaag tggccaccgc cggccagtgc 660
gagatcggca ccaagttcag caccctggtg cagaaggccg acgaactgct gcggatgaag 720
tacgtcatca agaacgtcgc ccaccgcaac ggcaagaccg tcaccttcat gcccaagccg 780
atcgtcggcg acaacggcag cggcatgcac gtgcaccagt cgctgtccaa gggcggcacc 840
aacctgttct ccggtgacgg ctacggtggc ctgagccaga tggcgctgtg gtacatcggc 900
ggcatcttca agcatgccaa ggcgatcaac gcctttgcca actcgggtac caacagctac 960
aagcgcctgg tgccgggctt cgaagccccg gtgatgctgg cctactcggc gcgcaaccgt 1020
tcggcctcgt gccgcattcc gtgggtgtcc aacccgaagg cgcgtcgcat tgaaatgcgc 1080
ttccccgatc cgatccagtc gggctacctg accttcaccg cgctgatgat ggccggcctg 1140
gacggcatca agaaccagat cgacccgggc gcaccgagcg acaaggatct gtacgacctg 1200
ccgccggaag aagagaagct gattccgcag gtctgctcct cgctggacca ggccctggaa 1260
gcgctggaca aggaccgtga gttcctcaag gccggtggcg tgatgagcga tgacttcatc 1320
gacggctaca tcgcgctgaa gatgcaggaa gtgaccaagt tccgcgcggc gacccacccg 1380
ctggaatacc agttgtacta cgccagctga 1410

<210> SEQ ID NO 121
<211> LENGTH: 1515
<212> TYPE: DNA
<213> ORGANISM: Unknown
<220> FEATURE:
<223> OTHER INFORMATION: Description of Unknown:
DP69 Glucose-6-phosphate isomerase microbial sequence

<400> SEQUENCE: 121
atgacaacga acaacggatt cgactcgctg cattcccacg cccagcgcct gaagggcgca 60
agcatcccca gcctgctcgc cgccgaaccc ggccgcgtac aggacctggc gctgcgggtc 120
ggtccgttgt atgtcaactt cgcccggcag aaatacgatg ccgcggcgtt gcaggcgctg 180
ttggcgctgg ctgccgaacg tgatgtcggc ggcgccatca cgcgcctgtt ccgtggcgag 240
caggtcaatc tgaccgaagg ccgcgccgca ctgcacaccg cactgcgcgg cgacgtggtc 300
gatgcgccgg ttgccgccga ggcctatgcc acggcccgcg aaatccgcca gcgcatgggc 360
gtgctggtgc gcgcactgga agacagtggc gtgaccgatg tggtcagtgt cggcatcggc 420
ggttccgatc tcggtccgcg tctggtcgcc gacgcactgc gtccagtcac tggcgctcgc 480
ctgcgcgtgc atttcgtgtc taacgtggac ggcgctgcca tgcagcgcac gctggccacg 540

-continued

```
ctggatccgg cgaagaccgc cggcatcctc atttccaaga ccttcggtac ccaggaaacc    600

ctgctcaacg gccagatcct gcacgattgg ctgggtggca gcgagcgcct gtacgcggtc    660

agcgccaatc cggaacgcgc cgccaaggcc ttcgccatcg ccgccgagcg cgtgctgccg    720

atgtgggact gggtaggggg gcgctattcg ctgtggtcgg ccgtcggttt cccgatcgca    780

ctggccatcg gcttcgagcg tttcgagcag ttgctggaag gcgccgcgca gatggatgcg    840

catgcgctgg acgcgccgct ggagcgcaac ctgccggtgc tgcacggcct gaccgacatc    900

tggaaccgca atctgctggg ctctgccacg catgcggtga tgacctacga ccagcgcttg    960

gcgctgctgc cggcctacct gcagcagctg gtgatggaaa gcctgggcaa gcgcgtgcag   1020

cgcgatggcc agccggtcac caccgacacc gtgccggtgt ggtggggcgg tgccggcacc   1080

gatgtgcagc acagcttctt ccaggccctg caccagggca ccagcatcat tccggccgat   1140

ttcatcggct gcgtgcacaa cgacgatccg tatacggtca accaccaggc gttgatggcc   1200

aacctgctgg cgcagaccga agcgctggcc aacggccagg gcagtgacga tccgcaccgc   1260

gattatccgg gtggccgccc gagcacgatg atcctgctcg acgcgctcac cccgcaggcg   1320

ctgggcgcct tgatcgcgat gtacgaacac gccgtgtacg tgcagtcggt gatctggaac   1380

atcaacgcct tcgaccagtt cggtgtcgag ctgggcaagc agctggccag tggcctgctg   1440

cccgctctgc agggtgagga tgtcgaggtc aacgacccgc tgacccgtga gctgctggcc   1500

cagctgaagg gctga                                                    1515
```

<210> SEQ ID NO 122
<211> LENGTH: 2640
<212> TYPE: DNA
<213> ORGANISM: Unknown
<220> FEATURE:
<223> OTHER INFORMATION: Description of Unknown:
DP69 Leucine--tRNA ligase microbial sequence

<400> SEQUENCE: 122

```
atgaccagcg tcgaacccaa cgtttacgat ccgcagcagg ttgaatccgc cgcccagaag     60

tactgggacg ctacccgtgc cttcgaggtc gatgaagcct cggacaagcc gaagtactac    120

tgcctgtcga tgcttccgta tccgtccggt gcgctgcaca tgggccacgt gcgcaattac    180

acgatcggcg acgtgatcag ccgctacaag cgcatgaccg gccacaacgt gctgcagccg    240

atgggctggg acgcgtttgg cctgccggcg gaaaacgctg cgatcaagaa caagaccgcg    300

ccggccgcct ggacctacaa gaacatcgac cacatgcgca gccagctgca gtcgctgggc    360

tatgccatcg actggtcgcg cgagttcgcc acctgccgcc cggactatta cgtccacgag    420

cagcgcatgt tcacccgcct gatgcgcaag ggcctggcct accgccgcaa cgcggtggtg    480

aactgggacc cggtcgacca gaccgtgctg gccaacgagc aggtcatcga cggccgtggc    540

tggcgctccg gcgcgcttgt ggaaaagcgc gagatcccgc agtggttcct gcgcatcacc    600

gactacgccc aggaactgct ggacggcctg gatgagctgg acggctggcc ggagtcggtc    660

aagaccatgc agcgcaactg gatcggccgc tccgaagggc tggaaatcca gttcgacgtg    720

cgcgacgtcg atggtgccgc actggatccg ctgcgcgtgt tcaccacccg cccggacacc    780

gtgatgggcg tgactttcgt gtcgatcgcg gccgaacatc cgctggcgct gcatgccgcg    840

aagaacaacc cggaactggc tgcgctgctg tcggaaatga agcagggcgg cgtgtccgag    900

gccgagctgg agacccagga aaagcgcggc atggataccg gcctgcgcgc cgtgcatccg    960

gttaccggtg cccaggtgcc ggtgtgggtc gccaacttcg tgctgatggg ctacggcact   1020
```

ggcgcggtga tggccgtacc gggccacgac cagcgcgaca atgaattcgc caacaagtac 1080
aacctgccga tccgccaggt catcgcgctg aagtcgctgc gcaaggacga aggcgcctac 1140
gacgcgacgc gctggcagga ctggtacggc gacaagaccc gcgagaccga actggtcaac 1200
tccgaagagt tcgacggcct ggacttccag ggcgctttcg aggcgctggc cgaacggttc 1260
gagcgcaagg cccagggaca gcgccgggtg aactaccgcc tgcgcgactg gggcgtgagc 1320
cgccagcgct actggggctg cccgattccg gtgatctact gcgacaagtg tggcgcggta 1380
ccggtgccgg aagaccagct gccggtggtg ctgccggaag acgtggcgtt cgccggtacc 1440
ggttcgccga tcaagaccga tccggaatgg cgcaagacca cctgcccgga ctgcggcggt 1500
gcggccgagc gtgagaccga caccttcgac accttcatgg agtcgagctg gtactacgcc 1560
cgctacacct cgccgggcgc ccgcgatgcg gtcgacaagc gcggcaacta ctggctgccg 1620
gtggaccagt acatcggtgg catcgaacac gcgatcctgc acctgatgta tttccgcttc 1680
taccacaagc tgctgcgcga cgcgcggatg gtggacagca acgaacccgc gcggaacctg 1740
ctgtgccagg gcatggtgat cgctgagacc tactaccgcc cgaacccgga cggctcgaag 1800
gactggatca acccggccga tgtggaagtg cagcgcgacg agcgcggccg catcaccggc 1860
gccaccctga tcgccgacgg tcagccggtg gtggtcggtg gtaccgagaa gatgtccaag 1920
tcgaagaaca acggcgtgga cccgcaggcg atggtcggca agtacggcgc cgataccgtg 1980
cgcctgttct cgatgttcgc tgcaccgccg gaacagtcgc tggaatggaa cgaagccggc 2040
gtggacggca tggcccgctt cctgcgccgc ctgtgggcac aggtgcagaa gcacgctgcc 2100
gagggtgccg caccggcgct cgacgcggcc gcgctggatg ccggccagaa ggccctgcgc 2160
cgcaagaccc acgagaccat cggcaaggtc ggcgacgact acggccgccg ccacagcttc 2220
aacaccgcca ttgccgcggt gatggagctg atgaacgcgc tggccaagtt cgaggacggc 2280
agtgaacagg ggcgcgccgt gcgccaggaa gcactgcagg ccatcgtgct gctgctcaac 2340
ccgatcaccc cgcatgccag ccacgccctg tggcaggtac tgggccatgg cgaaacgctg 2400
ctggaagatc agccgttccc gcaggccgac agcagtgcgc tggtgcgcga tgcgctgact 2460
ttggccgtgc aggtcaatgg caagctgcgt ggcaccatcg aggtcgccgc cgatgccgcg 2520
cgcgagcaga tcgaagcgct ggccctggcc gagccgaacg cggccaagtt cctggaaggc 2580
ctgacggtgc gcaagatcat catcgttccc ggcaagatcg tgaacatcgt cgctgcctga 2640

<210> SEQ ID NO 123
<211> LENGTH: 2070
<212> TYPE: DNA
<213> ORGANISM: Unknown
<220> FEATURE:
<223> OTHER INFORMATION: Description of Unknown:
DP70 Glycine--tRNA ligase beta subunit microbial sequence

<400> SEQUENCE: 123
atgtctaaac atacagtatt gttcgaattg ggctgtgaag aacttccacc taaaagcctc 60
aaaaaattac gtgatgcact gcatgctgaa acggtaaaag gcttaaaaga tgcaggctta 120
gcattcgact caatcgaagc ttatgcagca ccgcgtcgtt tggcacttaa aattgtgaat 180
atcgatggcg ctcagcctga tacacaaaaa cgctttgacg gccctgcaaa agaagcggct 240
tatgatgctg aaggcaaacc aagcaaagca ttagaaggct ttatgcgtgg tcaaggcatc 300
actgcggatc aagtcaccac gttccaagcg ggtaaagttg aaaaggtttg ctatttaaaa 360
gatgttaaag gtcaaagcct tgaggtttta ctgccacaaa ttctacaagc agctttggac 420

-continued

```
aatcttccaa ttgcaaaacg tatgcgttca gcggcaagcc gtactgaatt cgtgcgtcct    480

gtaaaatggg tggtgttgct caaagacaat gatgtgattg cagccactat tcaagatcac    540

aaagcaggca atgtgactta tggtcatcgt ttccatgccc ctgaagcgat tactttggct    600

catgcagatg aatatcttgc caagttaaaa gcggcttatg tggttgctga ctttgcagaa    660

cgccaagcca tcattgacca acaagtcaaa gcgttggctg atgaagttaa tgcgattgcg    720

attgtaccaa gcgacctgcg tgatgaagtg accgcattgg tggaatggcc tgttgcgcta    780

cgtgccagct ttgaggagcg tttccttgct gtaccgcaag aagctttgat taccacgatg    840

caagacaacc aaaaatactt ctgtttggtg aatagtgata acaagctaca gccttatttc    900

attactgttt caaatattga gtctaaagat ccgattcaaa ttattgaagg caatgaaaaa    960

gtggttcgtc cacgtttgtc ggatgctgaa ttcttcttct tgcaagatca aaagcaacca   1020

ctagcttctc gtaaagaaaa actggctaac atggtgttcc aagcacaatt gggtacgctg   1080

tgggataagt cacaacgtat tgcaaaattg gctgtggctt tatcgaacat cacgggtgca   1140

actgcggctg atgctgaaaa agcagcattg ctggcaaaat gtgacttaac ctctgaattg   1200

gtgggtgaat tccctgaact tcaaggcatt gcgggaacct attacgcacg cattgaaggt   1260

gaaaaccatg aagtggctga agctttaggc gaacagtatt tacctaaatt tgcaggcgat   1320

gttttaccgc aaacaaaaac aggcacaacc attgcccttg ccgaccgttt agacacgctc   1380

acgggtattt ttggtattgg tcaagcacct acaggttcta aagatccgtt tgcattacgt   1440

cgttctgcaa tcggtatttt acgtttggtg actgaaaaca atcttgatgt gtcgattgaa   1500

gatttaatcc agctggcatt aaacgcttat ggcgatgttg tagcggatca tgcgaagact   1560

ttagcggatg ctgttgcatt ccttgaaggt cgttaccgtg ccaagtatga agaccaaggc   1620

gttgcagttg atgtgattca agcggttcaa gcattatcac caaaatcacc tttagatttt   1680

gataagcgtg tgactgcggt aaatcatttc cgtgcattgc ctgaagctgc tgcactggct   1740

gctgcaaata agcgtgttgc caacattctt gccaaagaag cagaactaac aggcgcagtg   1800

gttgaagcaa acttggttga agaggctgaa aaagcattat tcgctgtact tgctaaaatt   1860

acgcctgaag ttgaaccatt atttgctgcc aaagattaca ccactgcatt gtctaagctt   1920

gctgctttac gtgcgcctgt ggatgcattc tttgaaggcg tcatggtcat ggcagatgat   1980

gcagaattga aagccaaccg tttacgttta ttggctcaat tacgtggttt gtttacaagt   2040

gttgcggata tttcggtgtt gcagcactaa                                  2070
```

<210> SEQ ID NO 124
<211> LENGTH: 2472
<212> TYPE: DNA
<213> ORGANISM: Unknown
<220> FEATURE:
<223> OTHER INFORMATION: Description of Unknown:
DP70 DNA gyrase subunit B microbial sequence

<400> SEQUENCE: 124

```
atgagttcag aagatcaagc tgcttctcaa acagaacaaa ccaatgaaaa ggcttatgat     60

tcctctagta tcaaagtatt acgtggccta gatgctgttc gtaagcgtcc gggtatgtat    120

attggtgata cggacgatgg ttcaggttta catcacatgg tgtttgaggt ggtcgataat    180

gcgattgatg aagccttagc gggtcactgt gatgaaatct tagtcaccat ccatgaagat    240

gagtctgtaa gtgttgcaga taacggtcgt gggattccaa cggatattca ccctgaagaa    300

ggggtatctg ccgctgaagt gattttaacc attttgcatg ctggcggtaa gtttgatgat    360
```

-continued

```
aatagctata aagtttccgg tggtttacac ggggtaggtg tttctgttgt aaatgccttg    420
tcgagtaaat tattactaaa tattcgtcgt gcaggaaaag tatatgaaca ggaatatcac    480
catggtgatc ctgtctatcc attacgcgcg attggtgata ctgaagaaac cggtaccacc    540
gttcgtttct atccgagtga attaaccttc tctcaaacga tttttaatgt tgatatttta    600
gcgcgtcgtt tgcgcgaact ttcattctta aatgcagggg ttcgtattgt attacgtgat    660
gaacgtatca atgctgaaca tgtatttgat tatgaaggtg gtttgtctga atttgtaaaa    720
tatatcaatc aaggtaaaac ccacttgaat gagatttttc attttaccag tgaagttgtg    780
gaaacaggaa ttactgttga agtagcatta cagtggaatg atacttatca agaaaatgtc    840
cgttgcttta ccaataacat cccacaaaaa gatggtggta cgcatttagc cggtttccgt    900
gccgcgttaa cacggggttt aaaccagtat cttgatagtg aaaatattct taagaaagaa    960
aaagttgctg tcacaggtga tgatgcccgt gaaggtttaa cggcgattgt ttcagtgaaa   1020
gtgcctgatc caaaattctc atcacaaacc aaagaaaaat tggtttccag tgaagtgaaa   1080
actgctgtag agcaggcgat gaacaagtct ttttctgaat atcttttaga aaatccacaa   1140
gcggctaaat cgattgccgg caaaattatt gatgctgcac gtgcacgtga tgctgcgcgt   1200
aaagcacgtg aaatgacacg tcgtaagagt gcattagata ttgctggtct gcctggtaaa   1260
ctggcggatt gccaagaaaa agatccagca ttgtctgaac tttacttggt cgaaggtgac   1320
tcggcgggcg gttctgcaaa acagggtcgt aaccgtaaga tgcaagctat tctgccgctt   1380
aaaggtaaaa tcttaaacgt agaacgtgca cgttttgaca aaatgatttc atcgcaagaa   1440
gtgggcacgc tgattactgc actgggctgt ggtattggtc gtgaggaata caatcctgat   1500
aaattgcgtt atcacaaaat cattatcatg accgatgccg acgtcgatgg ttcgcacatt   1560
cgtacgctcc tgttgacctt cttcttccgt caaatgccag aacttgtgga acgtggttat   1620
atttatattg cacagccacc gttgtataag ttgaaaaaag gtaagcaaga gcaatatctt   1680
aaagataatg atgctttaga aacctatctt atttcgaatg ccattgatga gcttgaactg   1740
catattagtg ctgaggcacc tgcgattcgt ggtgaatctt tggctaaagt gattgctgat   1800
tatcaaacct cacaaaaaag tttaaatcgt ttaacgctac gttatcctgc aagcttgctg   1860
gatggtttac ttggtttgga tgcatttaaa cttgatcaaa atcatgatga agattatgta   1920
aaacaatggt ctgaacaatt gcgtgcagca attgaacaac accaaccaag tttgcgtcct   1980
gaaatcacct tagaagcttt tgaaaaagag catgcagatg gtgagaaagt gacgcattat   2040
tggccacgtg taacggtcta tgtacataac ttgccgcatc attatttact tgattctgga   2100
ttattggctt caagtgaata caagcgttta ctgcaaaatt cgaagagttg gttcacattg   2160
cttgaagatg gcgcttattt gcaaaaaggt gagcgtaaaa ttcatgtcgc cactttccat   2220
caagtttggc aacatatttt atccgactcg cgtcgtggca tgatgatcca gcgctataaa   2280
ggtttgggtg agatgaacgc ggaacagctt tgggaaacca ccatggatcc tgaaaaccgt   2340
aacatgttgc aagtcaccat taatgatgcg attgaagcgg atcgtatgtt ctcttgtttg   2400
atgggagatg atgtggaacc acgtcgtgcc ttcattgaag aaaatgcttt aaatgcggat   2460
attgacgctt aa                                                        2472
```

<210> SEQ ID NO 125
<211> LENGTH: 2625
<212> TYPE: DNA
<213> ORGANISM: Unknown
<220> FEATURE:
<223> OTHER INFORMATION: Description of Unknown:

DP70 Leucine--tRNA ligase microbial sequence

<400> SEQUENCE: 125

```
atgactactt ctcacattga ccctgaatat caagcgagcg cgattgaatc cactgtccaa     60
caagactggg aaactcgcaa agcctttaaa gttgccgaca ctgtagaagg taaacatcgt    120
tatatcctct cgatgttccc ttatccaagt ggcaagctgc atatgggtca tgtgcgtaac    180
tacaccattg gcgacgtgat tagccgtttc caccgtctca aaggtgaaac tgtcctacaa    240
ccgatgggtt gggatgcttt tggtctgcct gcggaaaatg cagcgattgc acaccaagtt    300
gcccctgcaa aatggacctt tgaaaacatc gcgtacatgc gtgaccagtt aaaaaaattg    360
ggtctgtcag tcgattggga tcgtgaattt gcgacctgta cgccagagta ttatcactgg    420
gaacaatggt tatttgtaca gctgtataaa aaagggctga tttatcgcaa actttcaacg    480
gtaaactggg atcctgtcga tcagactgta cttgctaatg aacaagttga aaatggtcgt    540
ggttggcgtt cgggtgcatt ggttgaaaaa cgtgatattc caatgtatta cttccgtatt    600
accgattatg cacaagaatt attagacgat ttagattcgc ttaaagatgg ttggccgcaa    660
caagtcttga ccatgcaacg caactggatt ggtcgttcac aaggcatgga aatcaccttt    720
ccatctgcga accctgaaat ctatgcagat gatttaacgg tttataccac acgtggtgac    780
accttgatgg gcgtgacgta tgttgcggtt gccgctgaac atccaatggc gcttaaagcg    840
gctgaaacaa atcccgaatt ggctgcattt attgaagaat gccgtatggg ttcagtggct    900
gaagcagatc ttgccactgc cgagaaaaaa ggcatggcca ctggtttgtc tgtgaagcat    960
cctgtaacgg gtgaagtggt tccagtgtgg attgcgaact atgtattgat gtcatacggt   1020
tcaggtgcgg tgatggcagt tccagcacac gacgaacgtg atttcgaatt tgccaacaaa   1080
tatggtttaa ccctccagca agtgattgat gccaaaggtg cagacgatgc tgaattttct   1140
gcaactgaat ggcaggaatg gtatggctcg aaagaaggca aactggttaa ttctggcgaa   1200
tttgacggtt tagacttcca agctgcattt gatgcattca ttgcaaaatt agaaccacaa   1260
aaactggcaa atacgaaagt tcagttccgt ctacgtgact ggggtgtttc gcgtcagcgt   1320
tattggggtt gtccaattcc aatgatcaac tgtgaaactt gtggtcaagt acctgtacct   1380
gaagaacaac ttccagtaat tttaccaact gacgtggtgc cagatggttc aggcaatccg   1440
ttaaataaaa tgcctgaatt ttatgaaacc caatgtccat gttgtggtgc aggtgcacgc   1500
cgtgaaaccg atactttgga tacgttcgta gagtcatctt ggtactatgc acgttatgca   1560
tctccagatt tcactggcgg tttagttaaa cctgaagctg caaaatcatg gctaccagtc   1620
aaccaatata ttggcggtgt ggaacatgca attttgcatt tattgtatgc ccgtttcttc   1680
cataaattga tgcgtgatga aggcgtcgtt gaaggcaatg aacctttcgc taacttactg   1740
actcaaggta tggttttagc tgataccttc taccgtgaag ccgaatcagg taagaaaaca   1800
tggtttaatc ctgcggatat tgaattagaa aaagacgaaa aaggtcgtgt tctttctgct   1860
aaatacacag gtgatggcca agaagttgtg gttggcggtc aagaaaaaat gtcgaaatcg   1920
aaaaataatg gcatcgaccc gcaatcgatt attgatcaat acggcgcaga tactgcacgt   1980
gtatttatga tgtttgcggc ccccacccgat caatcgcttg aatggtctga tgccggtgtg   2040
gaaggtgcaa accgtttctt gaaacgtgta tggcgtttaa ccacaggttt cttagaaaaa   2100
ggcaaccatg ctgctgtaat tgatgttgcg aatttgtcat cagcggcaca agacttacgt   2160
cgtaaaaccc acgaaaccat tcaaaaagtc ggtgatgaca ttgaacgtcg tcatgccttc   2220
aatactgcca ttgcagcgca aatggaatta ttgaatgctt gcaataaatt tgaagccaaa   2280
```

```
gatgataatg acgttgcggt tgaacgcgat gctattgtta gcttactcac tttacttgca   2340

ccatttgcac cacatttaag tcagacccta ttggctcaat tcggtattga gttaactgaa   2400

accttgttcc ctactgtgga tgagtctgcg ctaacccgca acacacaaac tattgtggta   2460

caggtcaatg gtaaacttcg tggcaagttg gaagtgtctg ttgatctctc taaagaagat   2520

attttggatc aagccaaagc attgcctgaa gtacaacaat tcttaaccgg tccaaccaag   2580

aaagaaattg tggtgccgaa taaattggtc aatttggtgg tttaa                   2625
```

<210> SEQ ID NO 126
<211> LENGTH: 1671
<212> TYPE: DNA
<213> ORGANISM: Unknown
<220> FEATURE:
<223> OTHER INFORMATION: Description of Unknown:
DP70 Glucose-6-phosphate isomerase microbial sequence

<400> SEQUENCE: 126

```
atgaatagta ttgaaaaatt tcccttgcat gatacggatc tgattcagga aaaactaaaa     60

agttttgccc aacaagagca agagattaat ttaaattatt tatttaaaaa aaataaaaaa    120

cgttttgatg aatattccgt tcatgcgggt cagttatgtt ttgattatag taagcaccgt    180

gttgatgagc gtattattaa cgagcttatt tgttatgcgg aatcacaaca tttgggtaac    240

tggattcagc gcttattttc tttagaaaaa attaattaca ctgaaaatcg cgcagcgatg    300

cattgggctt tgcgtttgcc gaagcaagat agtacacatg cagatttggc agcgcaggta    360

catagtcagc ttgatcgtat gtatcaattg gtcgagaaaa ttcatcaggg gcagtatcga    420

ggagctacag gtgaggtcat ccatgatgtg gtcaatattg gtgtcggtgg atcagatctt    480

ggtcctttaa tggtgtctca agcgctgact gattttaaag ttcaaacggc tcaaaaatta    540

aaagtccatt ttgtttcgac gatggatggc agccaacttt cagatctttt acatcagttt    600

cgcccagaaa ccaccttgtt tattatttca tccaagtctt ttggcaccat tgatacgctt    660

tccaatgcac aaacggcaaa atgctggctt gagcaatctt taggaacgtc gaaatcagtt    720

ctaagatgtc actttgttgg tgtttcaacc aagcccgata agatgaccga gtggggaatc    780

agcactgaaa atcaattctt attgtgggat tgggtcggtg ggcgctattc actatggtcg    840

tgtattggtt tgcctattgc attaagtatt ggggtcgagg gctttaaaca gttgcttgct    900

ggtgcttatg aaatggatca gcattttcag aacacaccac ttgaacaaaa tattcctgtg    960

ttgatgggtt tactgggaat atggaataac aacttcctga atattcaaac tcatgcggta   1020

cttccttatg atggtcggct gaaatatttt gcggcttatt tacagcaatt ggaaatggag   1080

tcgaatggta agtcgattca gcgttctggt gaaaaagtcg tattagatac ctgcccaatt   1140

ttatggggtg aagttggacc aaatgcacaa catgcttttt atcagctgct gcatcaaggt   1200

acacatgctg tgagttgtga ctttattgca cctgtgaaac gctataatgc caatcaattt   1260

acctatgttg aaaatgcaga ggctttagtt gaacaacacc atttagcctt atcgaattgt   1320

ttggcacaat cacgtctatt ggcctttggt aatcatgttc tagatccgaa agaagtagaa   1380

agttcaccga aatataaaca atatgcaggc aaccaaccga ccacaacaat tttgttaaaa   1440

gagttgaatc cgcgcagttt aggtatgctc attgcgatgt atgagcacaa ggtatttgtg   1500

caatccgtga tgtggaatat taatccattt gaccaatggg gcgtagaaaa aggtaaagaa   1560

attgccaatc aactgttacc gattctcaat caagagcaag ctgatgtttc tgatcttgat   1620

tcttcaacgc aaggtctatt aagaatttta ctgggaaaag ctgatggcta a            1671
```

<210> SEQ ID NO 127
<211> LENGTH: 1788
<212> TYPE: DNA
<213> ORGANISM: Unknown
<220> FEATURE:
<223> OTHER INFORMATION: Description of Unknown:
DP70 NADH-quinone oxidoreductase subunit C/D
microbial sequence

<400> SEQUENCE: 127

```
atggctgaaa ctgacattgc tatgccagaa tcaacgcctg ttgattcacg cccagcattt     60
gcaattgtag aagagctcaa agccaaattt ggtgagaact tctatgtgca agcgactttt    120
gaagattttc caacggtctg ggttgagcgc gcgcgcgtac aagatgtttt aatgttcttg    180
cgtaaagtat cacgtccata cgtgatgctg ttcgacttgt ctgcggtaga tgagcgttta    240
cgtacccacc gtgacggttt acctgcatca gacttcactg tgttttatca tttgttgtcg    300
ctagagcgca acagtgatat tcgtattaaa gttgcgttga gtgagagtga tctcaatctt    360
ccaaccgcaa ccaacatttg gccaaatgcc aactggtacg aacgtgaagc ttacgatatg    420
ttcgggatca atttcgaagg gcatccaatg ctccgtcgta ttttgttgcc aacctattgg    480
gaaggtcacc cactgcgtaa agaatattct gcacgtgcga ctgaatatac accgtatatg    540
cagaaccaag cgaagcagga tttcgagcaa gaacatttac gttttgttcc tgaagattgg    600
ggtctatcac gcggtaatgc cgatgaagat ttcatgttct tgaacttagg tccaaaccat    660
ccatctgcgc acggtgcatt ccgtatcatt ttgcagttgg acggtgaaga agtgaaagac    720
tgtgtgcctg atattggcta tcaccaccgt ggtgtggaaa agatggctga acgtcaaact    780
tggcattcat tcattccata taccgaccgt gttgactact tgggtggttg tgcgcaaaac    840
atgccttatg tgatgggtgt ggagcaaatg gcaggaatta ctgttcctga ccgtgcacaa    900
tgtatccgtg tcatgatgtc tgaattattc cgtatcaata accatttatt gtttattggt    960
actgcaattc aagatgccgg cggtatgacg ccagtcttct atatgtttgc cgatcgtcaa   1020
aagatctatg atgcgattga agcgattaca ggctaccgta tgcatccagc atggttccgt   1080
attggcggga ctgcgcacga ccttccaaac aattggcaac atctgattcg tgaaattctc   1140
gaatggatgc cgaagcgtat gaatgaatac tatacagctg cactacgcaa ctcagtattt   1200
attggtcgta cccgtaatgt tgcacaatac gatgcaaaat ctgcattggc ttggggtgta   1260
acaggtacag gtctacgcgc gacagggatt gatttcgacg tgcgtaaata ccgtccgtat   1320
agcggttatg aaaactacga cttcgacgtg cctttagaat acgaaggcga tgcttacgct   1380
cgtgtgatgg ttcacttccg tgaaattgaa gaatcactga aaattgtgaa gcagtgcttg   1440
gataacatgc catctggtcc atataaagcg gatcatcctt tggctgttcc accaccaaaa   1500
gacaagacat tacaagatat tgaaactttg attacgcact tcttgagcgt gtcatggggt   1560
cctgtgatgc ctgcgggtga agcgtctgta atggctgaag tggtaaaagg tgcatcgaac   1620
tactacttga cttcagacaa gtcaaccatg agttatcgta cccgtattcg tacaccaact   1680
ttcacgcact tacagcaaat gccttctgtg attaatggca gtcttgtatc tgacttgatc   1740
atttatttag cgaccattga cgtcgtaatg gctgacgtgg atcgctag                1788
```

<210> SEQ ID NO 128
<211> LENGTH: 1044
<212> TYPE: DNA
<213> ORGANISM: Unknown
<220> FEATURE:

<223> OTHER INFORMATION: Description of Unknown:
DP70 Protein RecA microbial sequence

<400> SEQUENCE: 128
atggatgata ataaaagtaa ggcgcttaat gctgccctaa gccagattga aaaacaattt 60
ggtaaaaata ccgtaatgcg tcttggtgat aataccgtat tggccgttga agcggtctct 120
acaggttctt taacactaga cattgcactt ggtattggtg gcttaccaaa aggtcgtatc 180
gttgaaattt acggtcctga atcttctggt aaaaccacaa tgacattgca agcgattgca 240
caatgtcaaa aagccggtgg tacttgtgct tttatcgatg cagaacatgc actcgatcct 300
cagtatgcac gtaagcttgg tgtcgacctt gacaacctgt tggtttctca accagaccac 360
ggtgaacaag cccttgaaat tgcagacatg ttagtccgct ctggtgctat tgacatgatc 420
gttgtcgatt ccgtggctgc actgacacct cgcgctgaaa ttgaaggtga aatgggcgac 480
tcacatatgg gcttacaagc acgtttgatg agtcaggcat tacgtaaaat tactggtaat 540
gcaaaacgct caaactgtat ggtgatcttc attaaccaaa tccgtatgaa gattggtgta 600
atgtttggta gccctgaaac cacaacaggt ggtaatgcac tcaaattcta cgcttctgta 660
cgtttggata tccgtcgtat tggtcaagtg aaagaaggcg atgaaattgt cggttcagaa 720
acccgcgtta aagtcgtaaa aaataaaatg gcacctcctt ttaaggaagc gttattccaa 780
attttatatg gcaaaggtgt caatcaactg ggtgaactgg ttgatcttgc tgttgcgcaa 840
gaactggtac aaaaagcagg tgcttggtat tcatatcaag gcaataaaat tggtcaaggt 900
aaaaacaacg tgatccgcca tttagaggaa aatcctcaaa ttgcacaaga acttgatcgc 960
ctgattcgtg aaaaattgtt gacaccaacg accacgccta ttgaagaaaa agatgaagta 1020
gaaccagact ttctagatgc ttaa 1044

<210> SEQ ID NO 129
<211> LENGTH: 1887
<212> TYPE: DNA
<213> ORGANISM: Unknown
<220> FEATURE:
<223> OTHER INFORMATION: Description of Unknown:
DP70 RNA polymerase sigma factor RpoD microbial sequence

<400> SEQUENCE: 129
atgagcgata tgacttcccc tacttcgcaa gtagcggctc tgattagccg aggcaaagag 60
caaggttact taacttacgc tgaggttaac gatcatctcc cagactcgat cacggaaagc 120
gaacagattg aagacattat tcaaatgctt caagatgtcg gcattccagt gcatgaacgt 180
gcgcctgaat ctgatgacac catgttcgac ggtaacaatg cagaagcaac cgatgaagtc 240
gctgaagaag aagcggcagc tgttcttgct tcagttgaaa gcgaacctgg tcgtaccacc 300
gatccagtac gtatgtacat gcgtgaaatg ggaacggttg aactattaac gcgtgaaggc 360
gaaattagca ttgcaaaacg cattgaagaa ggtattcgtg acgttcttca ttcgattgcg 420
tactggccaa atgcagttga agttgtatta aaagaatata gcgatgttgc tgaaggcgaa 480
cgtcgtcttg ctgatatttt atctggttat ttagacccag aatctgacga agaaattcca 540
gaagttttag aagaagaagc tgaaattgtt gaagatgatg aagcgacgac taaaaccact 600
aaagatgtaa aattggacga tgacgaagaa gaagaatctg aaagtgatga tgattctgaa 660
ggtgagtctg gtccagatcc agaaattgca cgtgttcgtt tcactgaatt agaagatgcg 720
tggaaagtaa ccaaagccac cattgaaaag catggccgta acagcaaaca agcagatgaa 780
gcgcttgaag ctcttgcaac tgtgtttatg atgttcaaat ttacaccacg tttatttgaa 840

-continued atcatttcag aaatgattcg tggcacgcat gaacaaattc gtacagcaga acgtgaagtg 900
atgcgttacg cagttcgtcg tggtcgtatg gaccgtaccc aattccgtac atcgttccca 960
ggccaagagt caaatccagc ttggttagat gaacaaattg ctaaagcacc tgcggatcaa 1020
aaaggttatt tagaaaaagt acgtccagat gttgttgcat tccagcaaaa gattgccgat 1080
atcgaaaaag aattgggctt agatgttaaa gacatcaaag acatttctaa acgtatggct 1140
gtgggtgaag cgaaagcacg tcgcgcgaaa aaagaaatgg ttgaagcaaa cttacgtttg 1200
gtgatttcga ttgcgaaaaa atataccaac cgtggtttac aattccttga cttgattcaa 1260
gaaggtaaca tcggtttgat gaaagccgta gacaagtttg aataccgtcg tggttataaa 1320
ttctcgactt atgcaacttg gtggattcgt caggcgatta cccgttcgat tgccgatcaa 1380
gcacgtacca tccgtattcc agtacacatg atcgaaacca ttaacaagat caaccgtgta 1440
tctcgtcaac ttcttcaaga aatgggccgt gagcctaccc ctgaagaatt aggcgaacgt 1500
ctggaaatgg acgaagttaa agtacgtaaa gtgctgaaaa ttgccaaaga accgatttcg 1560
atggaaacac cgattggtga tgacgaagat tcgcatcttg gtgacttcat tgaagatggt 1620
aacattacct ctccaattga tgccgcgact tctgaaggct taaaagaagc aacacgtgaa 1680
gtgctggaaa acttgaccga acgtgaagcg aaagtcttaa aaatgcgttt tggtattgat 1740
atgccaaccg accatacttt agaagaagtg ggtaaacaat ttgatgtaac acgtgaacgt 1800
attcgtcaga ttgaagccaa agctttacgt aaattacgtc acccttctcg ttctgaacac 1860
ttacgttcat tcctagaaaa tgactaa 1887

<210> SEQ ID NO 130
<211> LENGTH: 1671
<212> TYPE: DNA
<213> ORGANISM: Unknown
<220> FEATURE:
<223> OTHER INFORMATION: Description of Unknown:
DP71 Glutamine--tRNA ligase microbial sequence

<400> SEQUENCE: 130
atgagtgagg ctgaagcccg cccaacaaat tttatccgtc agattattga tgaagatctg 60
gcgaccggga aacacaatac cgttcacacc cgtttcccgc ctgagcctaa tggctatttg 120
catatcggcc atgcgaagtc tatctgcctg aatttcggca ttgcgcaaga ctaccagggt 180
cagtgcaatc tgcgttttga cgatactaac ccggcaaaag aagacatcga attcgttgag 240
tcgatcaaat acgacgtcca gtggctgggc ttcgactgga gcggtgatat tcactactcc 300
tcagactatt tcgatcaact gcacgcatac gcgctggagc taatcaacaa aggtctggcg 360
tacgttgacg aactgtctcc cgatcaaatt cgcgaatacc gtggttcgct gaccgcaccg 420
ggcaaaaaca gcccgtatcg cgatcgcagc gtggaagaaa atatcgcgct gtttgaaaaa 480
atgcgtaacg gtgaattcgc cgaaggtgcc gcttgcctgc gtgccaaaat cgatatggcg 540
tcgccattct tcgtgatgcg cgatccggtc atctaccgta ttaagtttgc cgaacatcat 600
cagactggca caaaatggtg catctacccg atgtacgatt tcactcactg catttccgat 660
gcgctggaag ggatcaccca ttcactgtgt acgctggaat tccaggacaa ccgccgtctg 720
tacgactggg tactggataa catcactatt ccatgccatc cgcgtcagta tgagttctcc 780
cgtctgaatc ttgaatactc catcatgtcc aagcgtaagc tgaacctgct ggtgacggat 840
aagattgtag aaggttggga cgatccgcgt atgccgacgg tttccggtct gcgtcgccgt 900
ggttataccg ccgcgtctat ccgcgaattc tgccgtcgta tcggcgtgac caagcaggac 960
aacaacgttg aaatgatggc gctggaatcc tgtattcgtg acgatctgaa cgaaaacgca 1020
ccgcgcgcca tggccgttat taacccggtt aaagttgtca ttgagaactt caccggtgat 1080
gacgtgcaaa tggtgaaaat gccgaatcat ccgagcaaac cggaaatggg cacccgcgaa 1140
gtgccgttca cccgtgagat ttacatcgat caggctgatt tccgcgaaga agcgaacaaa 1200
cagtacaaac gtctggtgct gggcaaagaa gttcgcctgc gcaatgcgta tgtgatcaaa 1260
gcggaacaca tcgagaaaga cgcggaaggg aatatcacca ccatcttctg ttcttacgat 1320
atcgatacgc tgagcaaaga tcccgctgat ggccgtaagg tgaaaggcgt gattcactgg 1380
gtttctgctt ctgaaggtaa accggcagaa tttcgcctgt atgaccgtct gttcagtgtt 1440
gcgaaccctg gccaggctga agatttcctg accaccatca acccggaatc tctggtgatt 1500
gctcagggct tcgttgagcc gtctctggtc gctgctcagg cagaagtcag tgtgcagttc 1560
gaacgtgaag gttacttctg tgccgacagc cgctattcaa gtgctgagca tctggtgttc 1620
aaccgcaccg tcggccttcg cgacacctgg gaaagcaaac ccgtcgcctg a 1671

<210> SEQ ID NO 131
<211> LENGTH: 2415
<212> TYPE: DNA
<213> ORGANISM: Unknown
<220> FEATURE:
<223> OTHER INFORMATION: Description of Unknown:
DP71 DNA gyrase subunit B microbial sequence

<400> SEQUENCE: 131
atgtcgaatt cttatgactc ctcaagtatc aaggtattaa aagggctgga cgcggtgcgt 60
aagcgccccg gcatgtatat cggcgatacc gatgacggca ctggtctgca ccacatggta 120
ttcgaggttg tggacaacgc tatcgacgaa gccctcgcgg gccactgtaa agagattcag 180
gtcacgatcc atgcggataa ctctgtttcc gtacaggatg atggtcgtgg tattcctacc 240
ggcattcacg aagaagaggg cgtttctgct gctcaggtca tcatgaccgt acttcatgcc 300
ggcggtaaat ttgacgataa ctcgtacaaa gtctccggcg gtctgcatgg cgtgggtgtt 360
tccgtcgtta acgccctgtc ggaaaaactg gagctggtta tccgccgtga aggcaaagtg 420
cacacccaga cttacgtcca cggtgagccg caggatccgc tgaaagtggt tggcgatacc 480
gaggcgaccg gtacgaccgt gcgcttctgg ccaagctacg ccaccttcac caatcaaaca 540
gaattcgagt atgacattct ggcgaaacgc ctccgtgagc tgtcattcct gaactctggt 600
gtggcgatcc gcctgctcga caaacgcgat ggcaagaacg atcacttcca ttatgaaggc 660
ggtatcaaag ctttcgtgga atacctgaac aaaaacaaaa ccccaatcca cccaaccgtg 720
ttctatttct ccaccgtgaa agacgatatc ggtgtggaag tggcgttgca gtggaatgat 780
ggtttccagg aaaatattta ctgctttacc aacaatatcc ctcagcgcga cggcggcacc 840
catctggtag gcttccgttc tgcgatgacc cgtacgctta acgcgtatat ggataaagaa 900
ggctacagca agaaatccaa aatcagcgcc accggtgatg atgcccgtga aggcctgatc 960
gccgtggttt cggtaaaagt gccggatcct aagttctcct ctcagaccaa agacaaactg 1020
gtttcttccg aagtgaagac cgccgttgag tctctgatga acgagaagct ggttgattat 1080
ctgatggaaa acccggccga cgcgaaaatc gttgtcggta aaatcatcga tgcagcccgt 1140
gcgcgtgaag ccgcgcgtaa agcacgtgaa atgacccgtc gtaaaggcgc gctcgatctg 1200
gccggtctgc caggcaaact ggctgactgt caggaacgcg acccggcaca ttccgaactg 1260
tacttagtgg aaggggactc agcgggcggc tctgcaaaac aaggccgtaa ccgtaagaac 1320

```
caggcgattc tgccgttgaa agggaaaatc ctcaacgttg agaaagcgcg cttcgacaaa   1380

atgctctctt ctcaggaagt ggcgacgctg attaccgcgc tcggttgcgg tatcggccgt   1440

gacgaataca acccggataa actgcgttat cacagcatca tcatcatgac cgatgccgac   1500

gtcgatggtt cgcacatccg taccctgtta ctgacattct tctaccgtca gatgcctgaa   1560

attgtagagc gtggccacgt gtttatcgcg cagcctccgc tgtacaaagt gaaaaaaggc   1620

aaacaggaac agtacattaa agatgatgaa gcgatggatc agtatcaaat ctctatcgcg   1680

atggacgggg caacgttaca cgccaacgcc catgcaccag cactggcggg cgaaccgctg   1740

gagaaactgg tggctgaaca tcacagcgtg cagaaaatga ttggccgtat ggaacgtcgt   1800

tatccgcgtg cgctgctgaa taatctggtc tatcagccaa cgctggcggg tgctgaactt   1860

gccgacgaag cgaaagtgaa ggaatggatt gaaacgctgg tgtctcgtct gaacgagaaa   1920

gagcagcacg gcagcagcta cagtgcgatc gtgcgcgaaa atcttgaaca ccagctgttc   1980

gagccaatcc tgcgcattcg tactcacggt gtggataccg actacgatct cgatgcagac   2040

ttcattcagg gcggcgaata ccgcaaaatc tgtaccctgg gtgaaaaact gcgcggcctg   2100

atcgaagaag atgcttacat cgaacgtggc gaacgccgtc agccagtgac cagcttcgag   2160

caggcgctgg aatggctggt gaaagagtcg cgtcgcggtc tgtcgattca gcgttataaa   2220

ggtctgggtg aaatgaaccc tgagcaattg tgggaaacca cgatggatcc gacacaacgc   2280

cgcatgctgc gcgtgacggt gaaagatgct atcgcggcgg accagctgtt caccacgctg   2340

atgggcgatg cggttgaacc gcgccgcgcc ttcatcgaag agaacgccct taaagctgcc   2400

aatatcgata tctga                                                     2415
```

<210> SEQ ID NO 132
<211> LENGTH: 2817
<212> TYPE: DNA
<213> ORGANISM: Unknown
<220> FEATURE:
<223> OTHER INFORMATION: Description of Unknown:
DP71 Isoleucine--tRNA ligase microbial sequence

<400> SEQUENCE: 132

```
atgagtgact acaagaacac cctgaatttg ccggaaacag ggttcccgat gcgtggcgat     60

ctggccaagc gtgaacctga catgctgaag aattggtatg accaggatct gtacgggatt    120

attcgtgctg ccaagaaagg caagaaaacc tttatcttgc atgacggccc tccgtatgcg    180

aacggcagca ttcatattgg tcactcagta aacaaaattc ttaaagacat gatcgttaag    240

tccaaaggac tggcgggctt tgatgcgccg tatgttccgg gctgggattg tcatggtctg    300

ccgattgaac tgaaagttga acagctgatc ggtaagccgg gcgaaaaagt cacggcggcg    360

gaattccgtg aagcctgccg caagtacgct gctgaacagg ttgaaggtca gaagaaagac    420

ttcatccgtc tgggcgtgct cggtgactgg gatcatccgt acctgaccat ggacttcaaa    480

acagaagcca acatcattcg tgccctgggt aaaatcatcg gcaacggtca cctgcataaa    540

ggtgcgaaac ctgttcactg gtgtaccgat tgcggatctt cactggctga agccgaagtc    600

gaatattacg acaaagtgtc tccgtctatc gacgtgacgt ttaatgcgac ggatgccgcc    660

gctgttgctg cgaaattcgg tgccactgct ttcaatggcc cggtttctct ggtcatctgg    720

accaccaccc cgtggaccat gccagctaac cgcgcgattt cactcaacgc tgagttctct    780

tatcagctgg tgcagattga aggtcagtgc ctgatcctgg ctaccgatct ggtagaaagc    840

gtgatgaatc gcgccggtat cgctgagtgg actgtgctgg gcgaatgtaa aggtgcggat    900
```

```
cttgaattgc ttcgattcca gcatccgttc ctcggtttcg atgttccggc gatcctcggc    960
gatcacgtta ctctcgatgc cggtaccggt gctgtacata ccgcacctgg ccacggtcct   1020
gatgactttg tcattggcca gaaatacggt ctggaagtcg caaacccggt tggaccgaac   1080
ggctgctacc tgccgggcac ttatccgacg ctggatggca aattcgtctt taaagcgaat   1140
gatctgatcg ttgaattgct gcgtgagaag ggcgcactgc tgcacgttga gaaaatgaac   1200
cacagctatc cgtgctgctg gcgtcacaaa acgccgatca tcttccgcgc tacgccacaa   1260
tggttcatca gcatggatca gaaaggtttg cgtcagaagt ctctggaaga gatcaaaggc   1320
gtgcagtgga tccctgactg ggtcaggcg cgtatcgaaa acatggtcgc taaccgtcct   1380
gactggtgta tctcccgcca gcgtacgtgg ggcgtaccga tgtctctgtt cgtgcataaa   1440
gataccgaac agcttcatcc gcgcagcctt gagctgatgg aagaagtggc aaaacgcgtg   1500
gaagccgatg gcattcaggc atggtgggat ctgaaccctg aagagatttt gggtgcagac   1560
gctgccgatt acgtcaaagt gccggatacg ctggacgtct ggtttgactc cggttccacg   1620
cactcctccg ttgtggatgt gcgccctgag ttcaacggtc attcaccgga tctgtatctg   1680
gaaggttctg accagcatcg cggctggttc atgtcttctc tgatgatttc tacggcgatg   1740
aaaggcaaag cgccttacaa acaagtactg actcacggtt tcaccgtcga tggtcagggc   1800
cgtaaaatgt ctaaatccat cggtaacacc atcgcgcctc aggatgtgat gaataagctg   1860
ggtggcgaca tcctgcgttt gtgggtggca tctacggatt acaccggcga aatcgccgtg   1920
tccgacgaaa tcctcaaacg tgctgccgat tcttatcgcc gtatccgtaa caccgcgcgc   1980
ttcctgctgg cgaaccttaa cggtttcgat ccggcgctgc acagcgtggc accggaagag   2040
atggttgtgc tggatcgctg ggcggttggc cgcgcgaaag ctgcacaaga cgagatcatt   2100
gctgcgtacg aagcctatga tttccacggc gttgttcagc gtctgatgca gttctgctcg   2160
atcgaaatgg gttcgttcta tctggatatc attaaagatc gccagtacac cgcgaagagc   2220
gacagcgttg cgcgccgcag ctgccagacc gcgctgtatc acatctgcga agcactggtt   2280
cgctggatgg cgccaatcat gtccttcact gccgatgaaa tctgggctga actgccaggt   2340
catcgcgaga agttcgtctt tactgaagaa tggtacgacg gtctgtttgg cctgatcggt   2400
aacgaatcca tgaacgatgc gttctgggat gagctgctga aagtgcgtgg tgaagtgaac   2460
aaagtgatcg aacaggcgcg tgctgataaa cgtctgggcg gttctctgga agcagccgtg   2520
accttatatg cagacgacgc gctggcaaca gacctgcgtt ctctgggtaa cgaactgcgc   2580
tttgtgctcc tgacttccgg tgcgaaagtc gccgcgctgt ctgaagctga tgactcagcg   2640
caggccagcg aattgttgaa aggactgaaa attggtctgg cgaaagcaga aggcgagaag   2700
tgcccgcgct gctggcattt caccactgat atcggccaga atgcggaaca cagtgacatc   2760
tgtggccgtt gtgtgactaa cattgccggt gacggcgaag agcgtaagtt tgcataa      2817
```

<210> SEQ ID NO 133
<211> LENGTH: 1560
<212> TYPE: DNA
<213> ORGANISM: Unknown
<220> FEATURE:
<223> OTHER INFORMATION: Description of Unknown:
DP71 NADH-quinone oxidoreductase subunit C/D
microbial sequence

<400> SEQUENCE: 133

```
atgtcagaac ttactcatat taatgcttcc ggcgacgccc acatggtgga tgtctccggt     60
```

-continued aaagacgaca ccgttcgtga agcccgtgcc gaagcctttg ttgaaatggc cgaaagcacg 120
ctggcgatga tcatcggcgg taatcaccat aagggtgacg tgttcgcgac cgcgcggatt 180
gccggtattc aggcagcgaa gaaaacctgg gatctgatcc cgctgtgtca tccgctgttg 240
ctgaccaagg tggaagtgaa tcttgaagcg cagccagaat ttaatcgtgt acgtattgaa 300
tcccgctgcc gcctgagcgg taaaaccggc gtcgagatgg aagcgctgac cttcaagcct 360
gaagactggg gaatgaagcg cggcaccgaa aacgaggact tcatgttcct caacctcgga 420
cctaaccatc cgtctgcgca cggtgcgttc cgcatcatcc tgcagcttga tggcgaagaa 480
attgtcgact gtgtaccgga cgtcggttac caccaccgtg gtgctgagaa gatgggcgag 540
cgccagtcat ggcacagcta cattccatac acggaccgta tcgaatacct cggcggttgc 600
gttaacgaga tgccatacgt actggctgtt gaaaaactgg cgggtatcgt cgtgccggat 660
cgcgttaaca ccatccgcgt gatgctgtct gaactgttcc gtatcaacag ccacctgctg 720
tacatctcta cgtttattca ggacgtgggc gcgatgacgc cagtgttctt cgcctttacc 780
gatcgtcaga aaatttacga tctggtggaa gcgatcaccg gtttccgtat gcacccggcc 840
tggttccgta ttggtggcgt tgcacacgac ctgccgaaag gctgggagcg tctgctgcgt 900
gaattccttg actggatgcc agcccgtctg gattcctacg tcaaggcagc gctgaaaaac 960
accattctga ttggacgttc caaaggcgta gcagcataca acgccgatga tgcgctggcg 1020
tggggcacca ccggtgctgg cctgcgtgcg accgggatcg acttcgatgt ccgcaaatgg 1080
cgtccatatt caggttacga aaacttcgat tttgaagtgc cggtcggcga tggcgtcagt 1140
gattgctatt cccgcgtgat gctaaaagtg gaagagcttc gtcagagcct gcgcattctg 1200
gaacagtgct acaaaaacat gccggaaggc ccgttcaagg cggatcaccc gctgaccacg 1260
ccgccaccga aagagcgtac gctgcaacac atcgaaaccc tgatcactca cttcctgcaa 1320
gtgtcgtggg gtccgatcat gcctgcgcaa gaatctttcc agatggttga agccaccaaa 1380
gggatcaaca gctactacct gaccagtgac ggcagcacca tgagctaccg cacgcgcgtc 1440
cgtacgccaa gcttcccgca tttgcagcag atcccgtccg taatccgtgg cagcctggta 1500
tccgacctga tcgtgtatct gggcagtatc gattttgtaa tgtcagatgt ggaccgctaa 1560

<210> SEQ ID NO 134
<211> LENGTH: 1065
<212> TYPE: DNA
<213> ORGANISM: Unknown
<220> FEATURE:
<223> OTHER INFORMATION: Description of Unknown:
DP71 Protein RecA microbial sequence

<400> SEQUENCE: 134
atggctattg atgagaacaa gcaaaaagcg ttagctgcag cactgggcca gattgaaaag 60
caattcggta aaggctccat catgcgtctg ggtgaagatc gctctatgga cgtggaaacg 120
atctctaccg gctctttgtc tctggatatc gcgttaggcg ccggtggttt gccgatgggc 180
cgtatcgttg agatttatgg cccggaatcc tccggtaaaa ctacgctgac ccttcaggtt 240
attgctgccg cacagcgcga aggcaaaacc tgtgcgttca tcgatgcgga acatgcactt 300
gaccctatct acgcgaagaa attgggcgta gatatcgaca acctgttgtg ttctcagccg 360
gataccggcg aacaggctct ggaaatctgt gacgcgctga cccgttcagg cgcggtcgac 420
gttatcatcg tcgactccgt tgctgcactg acgccaaaag cagaaatcga aggcgaaatc 480
ggtgactctc acatgggcct tgcggcacgt atgatgagcc aggcaatgcg taagcttgcc 540

```
ggtaacctga aaaacgccaa caccttgctg atcttcatca accagatccg tatgaaaatc    600

ggtgtgatgt tcggtaaccc ggaaaccacc accggtggta acgccctgaa attctacgcc    660

tctgtgcgtc tggatatccg ccgcatcggc gctatcaaag aaggcgacgt ggtgatcggc    720

agtgaaacgc gcgtgaaagt tgtgaagaac aaaatcgctg cgcctttcaa acaggctgaa    780

ttccagatcc tatacggcga aggcatcaac attaacggcg agctgatcga tttgggcgtt    840

aagcacaaac tggtcgaaaa agccggtgca tggtacagct acaacggcga gaagattggt    900

cagggtaaat ctaactcctg caactatctg aaagaaaacc cgaaaatcgc tgctgaactg    960

gataaaaaac tgcgtgatat gttgttgagt ggcactggtg aactggccgc tgcaaccaca   1020

gcagaacttg cagacgacga tatggaaacc agcgaagagt tttaa                   1065
```

<210> SEQ ID NO 135
<211> LENGTH: 1794
<212> TYPE: DNA
<213> ORGANISM: Unknown
<220> FEATURE:
<223> OTHER INFORMATION: Description of Unknown:
      DP71 RNA polymerase sigma factor RpoD microbial sequence

<400> SEQUENCE: 135

```
ggtaaggagc aaggctatct gacctttgct gaggtcaatg accatctgcc ggaagatatc     60

gtcgactccg accagatcga agacatcatc cagatgatta acgacatggg catccaggtt    120

cttgaagaag cgccggacgc cgatgatttg atgctggccg aaaaccgccc tgataccgat    180

gaagatgctg cagaagcagc ggctcaggtg ctttccagcg ttgaatctga aattggccgt    240

accaccgacc ctgtgcgtat gtatatgcgc gaaatgggta ccgttgagct cctgacccgt    300

gaaggcgaaa tcgacatcgc caaacgtatc gaagacggta tcaatcaggt ccagtgctcc    360

gttgctgaat atcctgaagc tatcacctat ttgttagagc aatatgaccg tgttgaagca    420

ggcgaagcac gtctgtctga tttgatcacc ggttttgttg atccgaacgc cgaagaagaa    480

atcgcgccga ctgcgactca cgtgggttct gaactgacca ctgaagagca aaatgatacc    540

gacgacgatg aagaagacga cgacgatgct gaagacgaca acagcatcga cccggaactg    600

gcgcgtcaga agttcaccga tctgcgtgag caacatgaag cgacccgtgc cgtcatcaag    660

aaaaatggcc gtagccacaa aagcgccgca gaagaaattc tgaagctgtc cgatgtgttt    720

aaacagttcc gtctggtacc aaaacagttc gatttcctgg tgaacagcat gcgctccatg    780

atggatcgcg tccgtactca ggaacgtctg atcatgaaag tgtgcgttga acagtgcaaa    840

atgccgaaga aaaacttcgt caatctgttc gccggtaacg aaaccagcag tacctggttt    900

gatgctgctc tggcaatggg taaaccatgg tctgagaagc tgaaagaagt gaccgaagac    960

gtgcagcgcg gcctgatgaa actgcgccaa atcgaagaag aaactggcct gactatcgaa   1020

caggtaaaag acattaaccg tcgcatgtcg atcggcgaag cgaaagcacg ccgcgcgaag   1080

aaagagatgg ttgaagcgaa cttacgtctg gttatctcta tcgcgaagaa atacaccaac   1140

cgtggcttgc agttccttga cctgattcag gaaggtaaca tcggcctgat gaaagccgtt   1200

gataagtttg aatatcgccg tggttataag ttctctactt atgcgacctg gtggatccgt   1260

caggctatca cccgctccat cgccgaccag gcacgtacca tccgtattcc ggtgcatatg   1320

attgagacca tcaacaaact caaccgtatt tcgcgccaga tgttgcagga gatgggccgt   1380

gagccgacgc cggaagagct ggctgaacgc atgctgatgc cggaagacaa gatccgtaaa   1440

gtgctgaaaa ttgctaaaga gccaatctcc atggaaacgc caatcggcga cgatgaagat   1500
```

-continued

```
tcgcatctgg gtgatttcat cgaggatact accctcgagc tgccgctgga ttctgcgacc   1560

tctgaaagcc tgcgttctgc aacgcacgac gttctggctg gcctgaccgc acgtgaagcg   1620

aaagttctgc gtatgcgttt cggtatcgat atgaacactg accacactct ggaagaagtg   1680

ggcaaacagt tcgacgtaac ccgtgaacgt atccgtcaga tcgaagccaa agcgttgcgt   1740

aaactacgcc acccaagccg ctccgaagtg ctgcgcagct tcctcgacga ctag          1794
```

<210> SEQ ID NO 136
<211> LENGTH: 2487
<212> TYPE: DNA
<213> ORGANISM: Unknown
<220> FEATURE:
<223> OTHER INFORMATION: Description of Unknown:
DP71 DNA-directed RNA polymerase subunit beta
microbial sequence

<400> SEQUENCE: 136

```
atggaccaga acaacccgtt gtctgagatc acgcacaaac gtcgtatctc tgcactgggc     60

ccgggcggtt tgacccgtga acgtgctggc tttgaagttc gagacgtaca cccgacgcac    120

tacggtcgcg tatgtccaat cgaaacgcca gaaggtccaa acatcggtct gatcaactca    180

ttatctgtct atgcacagac aaatgagtat ggtttcctgg aaacccctta ccgccgtgtg    240

cgtgaaggta tggttaccga tgaaattaac tacctgtctg ccatcgaaga aggcaacttt    300

gttatcgctc aggcgaactc caacctggat gacgaaggcc acttcctgga agatttagtc    360

acttgtcgta gcaaaggcga atcaagcctg ttcagccgcg accaggttga ctacatggac    420

gtttctaccc agcagatcgt atccgttggt gcttcactga ttccattcct ggaacacgat    480

gacgccaacc gtgcattgat gggtgcgaac atgcaacgtc aggcagttcc tactctgcgt    540

gctgataagc cgctggtagg tactggtatg gaacgtgctg ttgcggttga ctccggtgtt    600

actgccgttg ccaaacgtgg tggtactgtt cagtacgtag atgcatcccg tatcgttatt    660

cgtgttaacg aagaagagat gaatccaggc gaagcaggta tcgacattta taacctgact    720

aagtacaccc gttctaacca gaacacctgc atcaaccaga tgccgtgtgt gaatctgggc    780

gagccaatcg agcgcggcga cgtgctggca gatggtccgt caacagatct gggcgaactg    840

gcactgggtc agaacatgcg tgtcgcgttc atgccttgga acggttacaa cttcgaagac    900

tccatcttgg tctccgaacg tgttgtgcag gaagatcgct tcacgaccat ccatatccag    960

gaactggcat gtgtgtcccg tgacacaaag ttagggcctg aagagatcac tgctgatatc   1020

cctaacgtgg gtgaagctgc gctctccaaa ctggatgagt ccggtattgt gtatatcggt   1080

gctgaagtga ccggtggtga cattctggtc ggtaaagtta cgcctaaagg cgaaacccag   1140

ctgactccag aagagaaact gctgcgtgcg atcttcggtg agaaagcgtc tgacgttaaa   1200

gattcttctc tgcgtgtacc aaacggcgtt tccggtacga ttattgacgt gcaagtcttt   1260

acccgcgatg gcgtggaaaa agataagcgt gcgttagaaa tcgaagaaat gcagctgaaa   1320

caggctaaga aagacctgac tgaagagctg caaattctgg aagctggtct gtttgcacgt   1380

atccagtccg cgctggttgc tggcggtgtt gaagccgata agctgggcaa attgccacgc   1440

gatcgttggc ttgaactgtc actgactgac gaagacaaac agaatcagtt ggaacagctt   1500

gctgaacagt acgacgaact gaaatccgag tttgagaaaa aactcgaagc taaacgtcgt   1560

aaaatcactc agggcgatga cctagcacca ggtgtgctga aaatcgttaa agtgtacctg   1620

gccgttaaac gtcagatcca acctggtgac aaaatggcag gccgccacgg taacaaaggt   1680

gttatctcca agatcaaccc gatcgaagat atgccttacg atgaaaacgg gactcctgtt   1740
```

-continued

```
gacatcgtac tgaacccgct gggcgttcca tcacgtatga acattggtca gattttagaa   1800

acccacctgg gtatggccgc gaaaggtatt ggtgaaaaaa tcaatgccat gcttaagaaa   1860

catgaagaag tttctaagct gcgcgagttc atccagcgtg cctatgatct gggcgacgac   1920

gtacgtcaga aagttgatct gaccaccttc accgatgatg aagtattgcg tttggctgaa   1980

aacctgaaaa agggtatgcc aattgcaaca ccagtcttcg acggtgcgaa agagacagag   2040

atcaagcaac tgcttgaaat gggcggcgtc ccaacctctg gccagatcac actgtttgac   2100

ggccgtaccg gcgagcaatt cgagcgccag gttaccgtcg gctacatgta catgctgaaa   2160

ctgaaccacc tggttgacga taagatgcat gcgcgttcta ccggttctta cagccttgtt   2220

actcagcagc cgctgggtgg taaagctcag ttcggtggtc agcgcttcgg tgagatggaa   2280

gtgtgggcac tggaagcata cggtgccgct tataccctgc aggaaatgct gactgttaag   2340

tccgatgacg tgaacggccg tactaagatg tataaaaaca tcgtagatgg cgatcaccgg   2400

atggaaccag gcatgccgga atcattcaac gtactgttga aagaaatccg ctctctgggt   2460

atcaacatcg agctggaaga cgagtaa                                       2487
```